US012383615B2

(12) United States Patent
Kotin et al.

(10) Patent No.: US 12,383,615 B2
(45) Date of Patent: Aug. 12, 2025

(54) PROTOPARVOVIRUS COMPOSITIONS COMPRISING A PROTOPARVOVIRUS VARIANT VP1 CAPSID POLYPEPTIDE AND RELATED METHODS

(71) Applicant: Carbon Biosciences, Inc., Waltham, MA (US)

(72) Inventors: Robert Kotin, Cambridge, MA (US); Sebastian Aguirre Kozlouski, Cambridge, MA (US); Carolyn Pelletier, Salem, MA (US)

(73) Assignee: Carbon Biosciences, Inc., Waltham, MA (US)

( * ) Notice: Subject to any disclaimer, the term of this patent is extended or adjusted under 35 U.S.C. 154(b) by 0 days.

(21) Appl. No.: 18/614,158

(22) Filed: Mar. 22, 2024

(65) Prior Publication Data

US 2024/0358820 A1 Oct. 31, 2024

Related U.S. Application Data

(60) Provisional application No. 63/545,449, filed on Oct. 24, 2023, provisional application No. 63/454,259, filed on Mar. 23, 2023.

(51) Int. Cl.
*A61K 39/23* (2006.01)
*A61K 39/00* (2006.01)

(52) U.S. Cl.
CPC ...... *A61K 39/23* (2013.01); *A61K 2039/5256* (2013.01); *C12N 2750/14322* (2013.01); *C12N 2750/14334* (2013.01); *C12N 2750/14362* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Merigan et al. |
| 4,845,205 | A | 7/1989 | Huynh Dinh et al. |
| 4,981,957 | A | 1/1991 | Lebleu et al. |
| 4,987,071 | A | 1/1991 | Cech et al. |
| 5,116,742 | A | 5/1992 | Cech et al. |
| 5,118,800 | A | 6/1992 | Smith et al. |
| 5,122,458 | A | 6/1992 | Post et al. |
| 5,130,302 | A | 7/1992 | Spielvogel et al. |
| 5,134,066 | A | 7/1992 | Rogers et al. |
| 5,168,062 | A | 12/1992 | Stinski |

(Continued)

FOREIGN PATENT DOCUMENTS

| | | |
|---|---|---|
| EP | 1275658 A1 | 1/2003 |
| JP | 2020-062045 A | 4/2020 |

(Continued)

OTHER PUBLICATIONS

Alignment of SEQ 89 with PIR_80 db access No. VCPVCD by Parrish et al. 1990.*

(Continued)

*Primary Examiner* — Shanon A. Foley
(74) *Attorney, Agent, or Firm* — Choate, Hall & Stewart LLP; Margo R. Monroe; Stephany Foster

(57) ABSTRACT

The present disclosure provides technologies comprising compositions, preparations, constructs, and methods comprising a protoparvovirus variant VP1 capsid polypeptide.

21 Claims, 25 Drawing Sheets

Specification includes a Sequence Listing.

(56) References Cited

U.S. PATENT DOCUMENTS

| | | | |
|---|---|---|---|
| 5,175,273 | A | 12/1992 | Bischofberger et al. |
| 5,319,080 | A | 6/1994 | Leumann |
| 5,359,044 | A | 10/1994 | Cook et al. |
| 5,367,066 | A | 11/1994 | Urdea et al. |
| 5,432,272 | A | 7/1995 | Benner |
| 5,457,187 | A | 10/1995 | Gmeiner et al. |
| 5,457,191 | A | 10/1995 | Cook et al. |
| 5,459,255 | A | 10/1995 | Cook et al. |
| 5,478,745 | A | 12/1995 | Samulski et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,157 | A | 9/1996 | Yagi et al. |
| 5,552,540 | A | 9/1996 | Haralambidis |
| 5,565,213 | A | 10/1996 | Nakamori et al. |
| 5,567,434 | A | 10/1996 | Szoka, Jr. |
| 5,580,703 | A | 12/1996 | Kotin et al. |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,656,016 | A | 8/1997 | Ogden |
| 5,681,941 | A | 10/1997 | Cook et al. |
| 5,697,899 | A | 12/1997 | Hillman et al. |
| 5,738,868 | A | 4/1998 | Shinkarenko |
| 5,741,516 | A | 4/1998 | Webb et al. |
| 5,750,692 | A | 5/1998 | Cook et al. |
| 5,770,219 | A | 6/1998 | Chiang et al. |
| 5,779,708 | A | 7/1998 | Wu |
| 5,783,208 | A | 7/1998 | Venkateshwaran et al. |
| 5,795,587 | A | 8/1998 | Gao et al. |
| 5,797,898 | A | 8/1998 | Santini, Jr. et al. |
| 6,015,886 | A | 1/2000 | Dale et al. |
| 6,147,200 | A | 11/2000 | Manoharan et al. |
| 6,166,197 | A | 12/2000 | Cook et al. |
| 6,222,025 | B1 | 4/2001 | Cook et al. |
| 6,235,887 | B1 | 5/2001 | Froehler et al. |
| 6,380,368 | B1 | 4/2002 | Froehler et al. |
| 6,503,717 | B2 | 1/2003 | Case et al. |
| 6,528,640 | B1 | 3/2003 | Beigelman et al. |
| 6,534,261 | B1 | 3/2003 | Cox, III et al. |
| 6,599,692 | B1 | 7/2003 | Case et al. |
| 6,617,438 | B1 | 9/2003 | Beigelman et al. |
| 6,639,062 | B2 | 10/2003 | Manoharan et al. |
| 6,689,558 | B2 | 2/2004 | Case |
| 6,723,551 | B2 | 4/2004 | Kotin et al. |
| 6,855,314 | B1 | 2/2005 | Chiorini et al. |
| 7,045,610 | B2 | 5/2006 | Dempcy et al. |
| 7,067,317 | B2 | 6/2006 | Rebar et al. |
| 7,252,997 | B1 * | 8/2007 | Hallek .................. C12N 15/86 435/5 |
| 7,262,054 | B2 | 8/2007 | Jamieson et al. |
| 7,271,002 | B2 | 9/2007 | Kotin et al. |
| 7,427,672 | B2 | 9/2008 | Imanishi et al. |
| 7,495,088 | B1 | 2/2009 | Brakel et al. |
| 7,951,925 | B2 | 5/2011 | Ando et al. |
| 8,021,867 | B2 | 9/2011 | Smith et al. |
| 8,110,379 | B2 | 2/2012 | DeKelver et al. |
| 8,119,381 | B2 | 2/2012 | Smith et al. |
| 8,124,369 | B2 | 2/2012 | Smith et al. |
| 8,129,134 | B2 | 3/2012 | Smith et al. |
| 8,133,697 | B2 | 3/2012 | Smith et al. |
| 8,143,015 | B2 | 3/2012 | Smith et al. |
| 8,143,016 | B2 | 3/2012 | Smith et al. |
| 8,148,098 | B2 | 4/2012 | Smith et al. |
| 8,163,514 | B2 | 4/2012 | Smith et al. |
| 8,304,222 | B1 | 11/2012 | Smith et al. |
| 8,507,267 | B2 | 8/2013 | Chiorini et al. |
| 8,586,526 | B2 | 11/2013 | Gregory et al. |
| 8,697,359 | B1 | 4/2014 | Zhang |
| 8,771,945 | B1 | 7/2014 | Zhang |
| 8,771,985 | B2 | 7/2014 | Cui et al. |
| 8,795,965 | B2 | 8/2014 | Zhang |
| 8,865,406 | B2 | 10/2014 | Zhang et al. |
| 8,871,445 | B2 | 10/2014 | Cong et al. |
| 10,266,850 | B2 | 4/2019 | Doudna et al. |
| 10,793,835 | B2 | 10/2020 | Yan et al. |
| 2006/0166363 | A1 * | 7/2006 | Zolotukhin ............ C12N 15/86 435/456 |
| 2010/0218264 | A1 | 8/2010 | Cui et al. |
| 2011/0059502 | A1 | 3/2011 | Chalasani |
| 2011/0091502 | A1 | 4/2011 | Delwart et al. |
| 2011/0265198 | A1 | 10/2011 | Gregory et al. |
| 2013/0122591 | A1 | 5/2013 | Cost et al. |
| 2013/0137104 | A1 | 5/2013 | Cost et al. |
| 2013/0177960 | A1 | 7/2013 | Rebar |
| 2013/0177983 | A1 | 7/2013 | Rebar |
| 2013/0189265 | A1 | 7/2013 | Salome et al. |
| 2014/0068797 | A1 | 3/2014 | Doudna et al. |
| 2014/0170753 | A1 | 6/2014 | Zhang |
| 2015/0056705 | A1 | 2/2015 | Conway et al. |
| 2015/0159172 | A1 | 6/2015 | Miller et al. |
| 2017/0191078 | A1 | 7/2017 | Zhang et al. |
| 2017/0356008 | A1 | 12/2017 | Lubelski et al. |
| 2019/0203229 | A1 | 7/2019 | Engelhardt et al. |
| 2019/0382452 | A1 | 12/2019 | Samulski et al. |
| 2021/0079421 | A1 | 3/2021 | Yan et al. |
| 2024/0002882 | A1 | 1/2024 | Yan et al. |
| 2024/0066080 | A1 | 2/2024 | Kotin et al. |
| 2024/0358820 | A1 * | 10/2024 | Kotin ..................... C12N 15/86 |

FOREIGN PATENT DOCUMENTS

| | | | |
|---|---|---|---|
| WO | WO-98/10088 | A1 | 3/1998 |
| WO | WO-05/073384 | A2 | 8/2005 |
| WO | WO-06/12414 | A2 | 2/2006 |
| WO | WO-2012/030683 | A2 | 3/2012 |
| WO | WO-2013/163628 | A2 | 10/2013 |
| WO | WO-2015/070083 | A1 | 5/2015 |
| WO | WO-2015/138510 | A1 | 9/2015 |
| WO | WO-2016/073990 | A2 | 5/2016 |
| WO | WO-2017/079673 | A1 | 5/2017 |
| WO | WO-2017/152149 | A1 | 9/2017 |
| WO | WO-2019/169233 | A1 | 9/2019 |
| WO | WO-2022/140683 | A1 | 6/2022 |
| WO | WO-2024/196965 | A1 | 9/2024 |
| WO | WO-2024/197242 | A1 | 9/2024 |

OTHER PUBLICATIONS

Alignment of SEQ 91 with UniProt db access No. A0A1S5VGK8_9VIRU by Mollerup et al. 2017.*

Alignment of SEQ 93 with PIR_80 db access No. VCPVCD by Parrish et al. 1990.*

Alignment of SEQ 94 with PIR_80 db access No. VCPVCD by Parrish et al. 1990.*

Alignment of SEQ 89 with geneseq db access No. AZH07203 by Delwart et al. 2011.*

Parrish et al. (Virology. 1988; 166: 293-307.*

Ilyas et al. (Viruses. 2018; 10, 22; doi:10.3390/v10010022).*

Martella et al. (Emerging Infectious Diseases. 2018; 24 (6): 1061-1068).*

Aach, J. et al., CasFinder: Flexible algorithm for identifying specific Cas9 targets in genomes, bioRxiv, 8 pages, (2014).

Agbandje-McKenna, M. et al., Functional implications of the structure of the murine parvovirus, minute virus of mice, Structure, 6(11):1369-1381 (1998).

Airenne, K.J. et al., Baculovirus: an Insect-derived Vector for Diverse Gene Transfer Applications, Mol. Ther., 21(4):739-749, (2013).

Allison, A.B. et al., Single Mutations in the VP2 300 Loop Region of the Three-Fold Spike of the Carnivore Parvovirus Capsid Can Determine Host Range, J. Virol., 90(2):753-767 (2015).

Altschul, S.F. et al., Basic local alignment search tool, J. Mol. Biol., 215(3):403-410 (1990).

Ame, J.C. et al., A bidirectional promoter connects the poly(ADP-ribose) polymerase 2 (PARP-2) gene to the gene for RNase P RNA. structure and expression of the mouse PARP-2 gene, J. Biol. Chem., 276(14):11092-11099 (2001).

(56) References Cited

OTHER PUBLICATIONS

Angelova, A.L. et al., Immunotherapeutic Potential of Oncolytic H-1 Parvovirus: Hints of Glioblastoma Microenvironment Conversion towards Immunogenicity, Viruses, 9(12):382 (2017).
Antoniou, M.N. et al., Optimizing retroviral gene expression for effective therapies, Hum. Gene. Ther., 24(4):363-374 (2013).
Ardestani, S. et al., Membrane versus soluble isoforms of TNF-a exert opposing effects on tumor growth and survival of tumor-associated myeloid cells, Cancer Res., 73(13):3938-3950 (2013).
Bacon, B.R. et al., Molecular medicine and hemochromatosis: at the crossroads, Gastroenterology, 116(1):193-207 (1999).
Bae, S. et al., Cas-OFFinder: a fast and versatile algorithm that searches for potential off-target sites of Cas9 RNA-guided endonucleases, Bioinformatics, 30(10):1473-1475 (2014).
Bagella, L. et al., Cloning of murine CDK9/PITALRE and its tissue-specific expression in development, J. Cell. Physiol, 177(2):206-213 (1998).
Baggio, L.L. and Drucker, D.J., Biology of incretins: GLP-1 and GIP, Gastroenterology, 132(6):131-157 (2007).
Bar, S. et al., Vesicular egress of non-enveloped lytic parvoviruses depends on gelsolin functioning, PLoS Pathog., 4(8):e1000126 (2008).
Bar, S. et al., Vesicular transport of progeny parvovirus particles through ER and Golgi regulates maturation and cytolysis, PLoS Pathog., 9(9):e1003605 (2013).
Bartel, D.P. and Szostak, Isolation of new ribozymes from a large pool of random sequences, J.W., Science, 261(5127):1411-1418 (1993).
Batt, D. and Carmichael, G., Characterization of the polyomavirus late polyadenylation signal, Mol Cell Biol., 15(9):4783-4790 (1995).
Beirwaltes, W.H., Endocrine imaging in the management of goiter and thyroid nodules: Part I, J. Nucl. Med., 32(7):1455-1461 (1991).
Benner, S.A. and Sismour, A.M., Synthetic biology, Nat. Rev. Genet., 6(7):533-543 (2005).
Berns, K.I., The Unusual Properties of the AAV Inverted Terminal Repeat, Hum. Gene Ther., 31(9-10):518-523 (2020).
Bernstein, E. et al., Role for a bidentate ribonuclease in the initiation step of RNA interference, Nature, 409(6818):363-366 (2001).
Bodendorf, U. et al., Nuclear export factor CRM1 interacts with nonstructural proteins NS2 from parvovirus minute virus of mice, J. Virol., 73(9):7769-7779 (1999).
Boeda, B. et al., A specific promoter of the sensory cells of the inner ear defined by transgenesis, Hum. Mol. Genet., 10(15):1581-1589 (2001).
Bohringer, M. et al., Warum Pentose- und nicht Hexose-Nucleinsauren ??. Teil II. Oligonucleotide aus 2',3'-Dideoxy-beta-D-glucopyranosyl-Bausteinen ('Homo-DNS'): Herstellung., Helv. Chim. Acta., 75(5):1416-1477 (1992).
Boissel, S. and Scharenberg, A.M., Assembly and characterization of megaTALs for hyperspecific genome engineering applications, Methods Mol. Biol., 1239:171-196 (2015).
Boissel, S. et al., megaTALs: a rare-cleaving nuclease architecture for therapeutic genome engineering, Nucleic Acids Res., 42(4):2591-2601 (2014).
Borner, K. et al., Pre-arrayed Pan-AAV Peptide Display Libraries for Rapid Single-Round Screening, Mol. Ther., 28(4):1016-1032 (2020).
Boshart, M. et al., A very strong enhancer is located upstream of an immediate early gene of human cytomegalovirus, Cell, 41(2):521-530 (1985).
Bourlais, C.L. et al., Ophthalmic drug delivery systems—recent advances, Prog. Retin. Eye Res., 17(1):33-58 (1998).
Brockhaus, K. et al., Nonstructural proteins NS2 of minute virus of mice associate in vivo with 14-3-3 protein family members, J. Virol., 70(11):7527-7534 (1996).
Brummelkamp, T.R. et al., A system for stable expression of short interfering RNAs in mammalian cells, Science, 296(5567):550-553 (2002).
Bull, P.C. et al., The Wilson disease gene is a putative copper transporting P-type ATPase similar to the Menkes gene, Nat. Genet., 5(4):327-337 (1993).
Buning, H. and Srivastava, A., Capsid Modifications for Targeting and Improving the Efficacy of AAV Vectors, Mol. Ther. Methods Clin. Dev., 12:248-265 (2019).
Callaway, H.M. et al., Parvovirus Capsid Structures Required for Infection: Mutations Controlling Receptor Recognition and Protease Cleavages, J. Virol., 91(2):e01871-16 (2017).
Candotti, D. et al., Identification and characterization of persistent human erythrovirus infection in blood donor samples, J. Virol., 78(22):12169-12178, (2004).
Canuti, M. et al., Two novel parvoviruses in frugivorous New and Old World bats, PLoS One, 6(12):e29140 (2011).
Carillo, H. and Lipman, D., The Multiple Sequence Alignment Problem in Biology, SIAM J. Appl. Math., 48(5):1073-1082 (1988).
Carrasco, C. et al., DNA-mediated anisotropic mechanical reinforcement of a virus, PNAS USA, 103(37):13706-13711 (2006).
Carrasco, C. et al., Manipulation of the mechanical properties of a virus by protein engineering, PNAS USA, 105(11):4150-4155 (2008).
Cater, M.A. et al., Copper binding to the N-terminal metal-binding sites or the CPC motif is not essential for copper-induced trafficking of the human Wilson protein (ATP7B), Biochem. J., 401(1):143-153 (2007).
Cecchini, S. et al., Reproducible High Yields of Recombinant Adeno-Associated Virus Produced Using Invertebrate Cells in 0.02- to 200-Liter Cultures, Hum. Gene. Ther., 22(8):1021-1030, (2011).
Cecchini, S. et al., Toward exascale production of recombinant adeno-associated virus for gene transfer applications, Gene Ther., 15(11):823-830, (2008).
Certo, M.T. et al., Coupling endonucleases with DNA end-processing enzymes to drive gene disruption, Nat. Methods, 9(10):973-975 (2012).
Chapman, M.S. and Rossmann, M.G., Single-stranded DNA-protein interactions in canine parvovirus, Structure, 3(2):151-162 (1995).
Chejanovsky, N. and Carter, B.J., Mutation of a consensus purine nucleotide binding site in the adeno-associated virus rep gene generates a dominant negative phenotype for DNA replication, J. Virol., 64(4):1764-1770 (1990).
Chen, C.Y. et al., mRNA decay mediated by two distinct AU-rich elements from c-fos and granulocyte-macrophage colony-stimulating factor transcripts: different deadenylation kinetics and uncoupling from translation, Mol. Cell. Biol., 15(10):5777-5788 (1995).
Chen, Q. et al., An AU-rich element in the 3' untranslated region of the spinach chloroplast petD gene participates in sequence-specific RNA-protein complex formation, Mol. Cell. Biol., 15(4):2010-2018 (1995).
Chiu, Y. and Rana, T.M., siRNA function in RNAi: a chemical modification analysis, RNA, 9(9):1034-1048 (2003).
Choi, E.Y. et al., Replication of minute virus of mice DNA is critically dependent on accumulated levels of NS2, J. Virol., 79(19):12375-12381 (2005).
Choi, J.H. et al., Optimization of AAV expression cassettes to improve packaging capacity and transgene expression in neurons, Mol. Brain., 7:17 (2014).
Choi, S.H. et al., Detargeting Lentiviral-Mediated CFTR Expression in Airway Basal Cells Using miR-106b, Genes (Basel), 11(10):1169 (2020).
Christensen, J. et al., Minute virus of mice initiator protein NS1 and a host KDWK family transcription factor must form a precise ternary complex with origin DNA for nicking to occur, J. Virol., 75(15):7009-7017 (2001).
Christensen, J. et al., Minute virus of mice transcriptional activator protein NS1 binds directly to the transactivation region of the viral P38 promoter in a strictly ATP-dependent manner, J. Virol., 69(9):5422-5430 (1995).
Chu, G. and Sharp, P.A., SV40 Dna transfection of cells in suspension: analysis of efficiency of transcription and translation of T-antigen, Gene, 13(2):197-202 (1981).
Clevers, H., The intestinal crypt, a prototype stem cell compartment, Cell, 154(2):274-284 (2013).

(56) References Cited

OTHER PUBLICATIONS

Cong, L. et al., Multiplex genome engineering using CRISPR/Cas systems, Science, 339(6121):819-823 (2013).
Cotmore, S.F. and Tattersall, P. et al., Encapsidation of minute virus of mice DNA: aspects of the translocation mechanism revealed by the structure of partially packaged genomes, Virology, 336(1):100-112 (2005).
Cotmore, S.F. and Tattersall, P., Mutations at the base of the icosahedral five-fold cylinders of minute virus of mice induce 3'-to-5' genome uncoating and critically impair entry functions, J. Virol., 86(1):69-80 (2012).
Cotmore, S.F. et al., Depletion of virion-associated divalent cations induces parvovirus minute virus of mice to eject its genome in a 3'-to-5' direction from an otherwise intact viral particle, J. Virol., 84(4):1945-1956 (2010).
Cotmore, S.F. et al., The family Parvoviridae, Arch. Virol., 159(5):1239-1247 (2014).
Cotmore, S.F. et al., The NS1 polypeptide of the murine parvovirus minute virus of mice binds to DNA sequences containing the motif [ACCA]2-3, J. Virol., 69(3):1652-1660 (1995).
Cotmore, S.F. et al., The NS2 polypeptide of parvovirus MVM is required for capsid assembly in murine cells, Virology, 231(2):267-280 (1997).
Cotmore, S.F. et al., Two widely spaced initiator binding sites create an HMG1-dependent parvovirus rolling-hairpin replication origin, J. Virol., 74(3):1332-1341 (2000).
Cunningham, S.C. et al., Gene delivery to the juvenile mouse liver using AAV2/8 vectors, Mol. Ther., 16(6):1081-1088 (2008).
Davis, L. and Maizels, N., Homology-directed repair of DNA nicks via pathways distinct from canonical double-strand break repair, PNAS USA, 111(10):E924-E932 (2014).
Davit-Spraul, A. et al., The spectrum of liver diseases related to ABCB4 gene mutations: pathophysiology and clinical aspects, Semin. Liver. Dis., 30(2):134-146 (2010).
De Almeida, S.F. and De Sousa, M., The unfolded protein response in hereditary haemochromatosis, J. Cell. Mol. Med., 12(2):421-434 (2008).
Dekelver, R.C. et al., Functional genomics, proteomics, and regulatory DNA analysis in isogenic settings using zinc finger nuclease-driven transgenesis into a safe harbor locus in the human genome, Genome Res., 20(8):1133-1142 (2010).
Demirci, S. et al., Gene therapy for sickle cell disease: An update, Cytotherapy, 20(7):899-910 (2018).
Deng, X. et al., DNA Damage Signaling Is Required for Replication of Human Bocavirus 1 DNA in Dividing HEK293 Cells, J. Virol., 91(1):e01831-16 (2016).
Deng, X. et al., Establishment of a Recombinant AAV2/HBoV1 Vector Production System in Insect Cells, Genes (Basel), 11(4):439, (2020).
Deng, X. et al., Human Parvovirus Infection of Human Airway Epithelia Induces Pyroptotic Cell Death by Inhibiting Apoptosis, J. Virol., 91(24):e01533-17 (2017).
Deng, X. et al., In vitro modeling of human bocavirus 1 infection of polarized primary human airway epithelia, J. Virol., 87(7):4097-4102 (2013).
Deng, X. et al., Replication of an Autonomous Human Parvovirus in Non-dividing Human Airway Epithelium is Facilitated through the DNA Damage and Repair Pathways, PLoS Pathog., 12(1):e1005399 (2016).
Devereux, J. et al., A comprehensive set of sequence analysis programs for the VAX, Nucleic Acids Res., 12(1 Pt 1):387-395 (1984).
Ding, W. et al., rAAV2 traffics through both the late and the recycling endosomes in a dose-dependent fashion, Mol. Ther., 13(4):671-682 (2006).
Ding, W. et al., Second-strand genome conversion of adeno-associated virus type 2 (AAV-2) and AAV-5 is not rate limiting following apical infection of polarized human airway epithelia, J. Virol., 77(13):7361-7366 (2003).
Doench, J.G. et al., Optimized sgRNA design to maximize activity and minimize off-target effects of CRISPR-Cas9, Nat. Biotechnol., 34(2):184-191 (2016).
Doerschug, K. et al., First-generation adenovirus vectors shorten survival time in a murine model of sepsis, J. Immunol., 169(11):6539-6545 (2002).
Domingo, E., Molecular basis of genetic variation of viruses, Viruses as Populations, 2020:35-71 (2020).
Donze, O. and Picard, D., RNA interference in mammalian cells using siRNAs synthesized with T7 RNA polymerase, Nucleic Acids Res., 30(10):e46 (2002).
Driskell, R.A. and Engelhardt, J.F., Current status of gene therapy for inherited lung diseases, Annu. Rev. Physiol., 65:585-612 (2003).
Duan, D. et al., Consequences of DNA-dependent protein kinase catalytic subunit deficiency on recombinant adeno-associated virus genome circularization and heterodimerization in muscle tissue, J. Virol., 77(8):4751-4759 (2003).
Duan, D. et al., Dual vector expansion of the recombinant AAV packaging capacity, Methods Mol. Biol., 219:29-51 (2003).
Duan, D. et al., Trans-splicing vectors expand the packaging limits of adeno-associated virus for gene therapy applications, Methods Mol. Med., 76:287-307 (2003).
Duclert, A. et al., An 83-nucleotide promoter of the acetylcholine receptor epsilon-subunit gene confers preferential synaptic expression in mouse muscle, PNAS USA, 90(7):3043-3047 (1993).
Earley, L.F. et al., Adeno-Associated Virus Serotype-Specific Inverted Terminal Repeat Sequence Role in Vector Transgene Expression, Hum. Gene Ther., 31(3-4):151-162 (2020).
Egli, M. et al., Crystal structure of homo-DNA and nature's choice of pentose over hexose in the genetic system, J. Am. Chem. Soc., 128(33):10847-10856 (2006).
Eichwald, V. et al., The NS2 proteins of parvovirus minute virus of mice are required for efficient nuclear egress of progeny virions in mouse cells, J. Virol., 76(20):10307-10319 (2002).
Elbashir, S.M. et al., Duplexes of 21-nucleotide RNAs mediate RNA interference in cultured mammalian cells, Nature, 411(6836):494-498 (2001).
Elbashir, S.M. et al., RNA interference is mediated by 21- and 22-nucleotide RNAs, Genes. Dev., 15(2):188-200 (2001).
Engelhardt, J.F., AAV hits the genomic bull's-eye, Nat. Biotechnol., 24(8):949-950 (2006).
Engelhardt, J.F., The lung as a metabolic factory for gene therapy, J. Clin. Invest., 110(4):429-432 (2002).
Engelsma, D. et al., A supraphysiological nuclear export signal is required for parvovirus nuclear export, Mol. Biol. Cell., 19(6):2544-2552 (2008).
Eschenmoser, A. and Dobler, M., Warum Pentose- und nicht Hexose-Nucleinsauren?? Teil I. Einleitung und Problemstellung, Konformationsanalyse fur Oligonucleotid-Ketten aus 2',3'-Dideoxyglucopyranosyl-Bausteinen ('Homo-DNS') sowie Betrachtungen zur Konformation von A- und B-DNS., Helv. Chim. Acta., 75(1):218-259 (1992).
Eschenmoser, A., Chemical etiology of nucleic acid structure, Science, 284(5423):2118-2124 (1999).
Ezquer, F. et al., Hereditary hemochromatosis: an opportunity for gene therapy, Biol. Res., 39(1):113-124 (2006).
Fakhiri, J. and Grimm, D., Best of most possible worlds: Hybrid gene therapy vectors based on parvoviruses and heterologous viruses, Mol.Ther., 29(12):3359-3382 (2021).
Fakhiri, J. et al., Novel Chimeric Gene Therapy Vectors Based on Adeno-Associated Virus and Four Different Mammalian Bocaviruses, Mol. Ther. Methods Clin. Dev., 12:202-222, (2019).
Feder, J.N. et al., A novel MHC class I-like gene is mutated in patients with hereditary haemochromatosis, Nat. Genet., 13(4):399-408 (1996).
Feder, J.N. et al., The hemochromatosis founder mutation in HLA-H disrupts beta2-microglobulin interaction and cell surface expression, J. Biol. Chem., 272(22):14025-14028 (1997).
Fisher, K. et al., Transduction with recombinant adeno-associated virus for gene therapy is limited by leading-strand synthesis, J Virol., 70(1):520-532 (1996).

(56) References Cited

OTHER PUBLICATIONS

Flotte, T.R. et al., Dual reporter comparative indexing of rAAV pseudotyped vectors in chimpanzee airway, Mol. Ther., 18(3):594-600 (2010).
Fox, L.E. et al., Screen for dominant behavioral mutations caused by genomic insertion of P-element transposons in *Drosophila*: an examination of the integration of viral vector sequences, J. Neurogenet., 21(1-2):31-43 (2007).
Frit, P. et al., Alternative end-joining pathway(s): bricolage at DNA breaks, DNA Repair (Amst)., 17:81-97 (2014).
Fu, Y. et al., Improving CRISPR-Cas nuclease specificity using truncated guide RNAs, Nat. Biotechnol., 32(3):279-284 (2014).
Gaj, T. et al., Enhancing the specificity of recombinase-mediated genome engineering through dimer interface redesign, J. Am. Chem. Soc., 136(13):5047-5056 (2014).
Geletneky, K. et al., Oncolytic H-1 Parvovirus Shows Safety and Signs of Immunogenic Activity in a First Phase I/IIa Glioblastoma Trial, Mol. Ther., 25(12):2620-2634 (2017).
GenBank Accession No. J04617.1, Human elongation factor EF-1-alpha gene, complete cds, 3 pages, (1994).
Gilham, D.E. et al., Cytokine stimulation and the choice of promoter are critical factors for the efficient transduction of mouse T cells with HIV-1 vectors, J. Gene. Med., 12(2):129-136 (2010).
Gill, D.R. et al., Increased persistence of lung gene expression using plasmids containing the ubiquitin C or elongation factor 1alpha promoter, Gene. Ther., 8(20):1539-1546 (2001).
Gil-Ranedo, J. et al., The Mammalian Cell Cycle Regulates Parvovirus Nuclear Capsid Assembly, PLoS Pathog., 11(6):e1004920 (2015).
Gochee, P.A. et al., A population-based study of the biochemical and clinical expression of the H63D hemochromatosis mutation, Gastroenterology, 122(3):646-651 (2002).
Goodman, L.B. et al., Binding site on the transferrin receptor for the parvovirus capsid and effects of altered affinity on cell uptake and infection, J. Virol., 84(10):4969-4978 (2010).
Gossen, M. et al., Tight control of gene expression in mammalian cells by tetracycline-responsive promoters., Proc. Natl. Acad. Sci. USA, 89:5547-5551 (1992).
Gossen, M. et al., Transcriptional activation by tetracyclines in mammalian cells, Science, 268:1766-1769 (1995).
Graham, F.L. and Van Der Eb, A.J., A new technique for the assay of infectivity of human adenovirus 5 DNA, Virology, 52(2):456-467 (1973).
Gray, S.J. et al., Optimizing promoters for recombinant adeno-associated virus-mediated gene expression in the peripheral and central nervous system using self-complementary vectors, Hum. Gene. Ther., 22(9):1143-1153 (2011).
Grekova, S. et al., Activation of an antiviral response in normal but not transformed mouse cells: a new determinant of minute virus of mice oncotropism, J. Virol., 84(1):516-531 (2010).
Grieger, J.C. et al., Production of Recombinant Adeno-associated Virus Vectors Using Suspension HEK293 Cells and Continuous Harvest of Vector From the Culture Media for GMP FIX and FLT1 Clinical Vector, Mol. Ther., 24(2):287-297 (2016).
Groebke, K. et al., Warum Pentose-und nicht Hexose-Nucleinsauren??. Teil V. (Purin-Purin)-Basenpaarung in der homo-DNS-Reihe: Guanin, Isoguanin, 2,6-Diaminopurin und Xanthin, Helv. Chim. Acta., 81(3-4):375-474 (1998).
Gu, Z. et al., NF-Y controls transcription of the minute virus of mice P4 promoter through interaction with an unusual binding site, J. Virol., 69(1):239-246 (1995).
Guggino, W.B. et al., A Preclinical Study in Rhesus Macaques for Cystic Fibrosis to Assess Gene Transfer and Transduction by AAV1 and AAV5 with a Dual-Luciferase Reporter System, Hum. Gene. Ther. Clin. Dev., 28(3):145-156 (2017).
Halder, S. et al., Structural characterization of H-1 parvovirus: comparison of infectious virions to empty capsids, J. Virol., 87(9):5128-5140 (2013).
Hammond, S.M. et al., Post-transcriptional gene silencing by double-stranded RNA, Nat. Rev. Genet., 2(2):110-119 (2001).
Harper, S.Q. et al., Modular flexibility of dystrophin: implications for gene therapy of Duchenne muscular dystrophy, Nat. Med., 8(3):253-261 (2002).
Harraz, M.M. et al., MKK6 phosphorylation regulates production of superoxide by enhancing Rac GTPase activity, Antioxid. Redox. Signal., 9(11):1803-1813 (2007).
Harvey, D. M. and Caskey, C. T., Inducible Control of Gene Expression: Prospects for Gene Therapy, Curr. Opin. Chem. Biol., 2:512-518 (1998).
Haseloff, J. and Gerlach, W.L., Simple RNA enzymes with new and highly specific endoribonuclease activities, Nature, 334(6183):585-591 (1988).
Haut, D.D. and Pintel, D.J., Inclusion of the NS2-specific exon in minute virus of mice mRNA is facilitated by an intronic splicing enhancer that affects definition of the downstream small intron, Virology, 258(1):84-94 (1999).
Havens, M.A. and Hastings, M.L., Splice-switching antisense oligonucleotides as therapeutic drugs, Nucleic Acids Res., 44(14):6549-6563 (2016).
Hayakawa, J. et al., Busulfan produces efficient human cell engraftment in NOD/LtSz-Scid IL2Rgamma(null) mice, Stem Cells, 27(1):175-182 (2009).
Heigwer, F. et al., E-CRISP: fast CRISPR target site identification, Nat. Methods, 11(2):122-123 (2014).
Hendrickson, B.A. et al., Clinical aspects and pathophysiology of inflammatory bowel disease, Clin. Microbiol. Rev., 15(1):79-94 (2002).
Henry, A.A. and Romesberg, F.E., Beyond A, C, G and T: augmenting nature's alphabet, Curr. Opin. Chem. Biol., 7(6):727-733 (2003).
Heuberger, B.D. et al., A pre-RNA candidate revisited: both enantiomers of flexible nucleoside triphosphates are DNA polymerase substrates, J. Am. Chem. Soc., 130(2):412-413 (2008).
Hingtgen, S.D. et al., Nox2-containing NADPH oxidase and Akt activation play a key role in angiotensin II-induced cardiomyocyte hypertrophy, Physiol. Genomics, 26(3):180-191 (2006).
Hirao, I., Unnatural base pair systems for DNA/RNA-based biotechnology, Curr. Opin. Chem. Biol., 10(6):622-627 (2006).
Hsu, M.Y. et al., Aggressive melanoma cells escape from BMP7-mediated autocrine growth inhibition through coordinated Noggin upregulation, Lab. Invest., 88(8):842-855 (2008).
Huang, Q. et al., Establishment of a reverse genetics system for studying human bocavirus in human airway epithelia, PLoS Pathog., 8(8):e1002899 (2012).
Hueffer, K. et al., Combinations of two capsid regions controlling canine host range determine canine transferrin receptor binding by canine and feline parvoviruses, J. Virol., 77(18):10099-10105 (2003).
Hueffer, K. et al., The natural host range shift and subsequent evolution of canine parvovirus resulted from virus-specific binding to the canine transferrin receptor, J. Virol., 77(3):1718-1726 (2003).
Hunziker, J. et al., Warum pentose-und nicht hexose-nucleinsauren? Teil III. Oligo(2',3'-dideoxy-beta-D-glucopyranosyl) nucleotide ('homo-DNS'): Paarungesigenschaften., Helv. Chim. Acta., 76(1):259-352 (1993).
Husain, T. et al., Long-term AAV vector gene and protein expression in mouse brain from a small pan-cellular promoter is similar to neural cell promoters, Gene. Ther., 16(7):927-932 (2009).
Ikeda, Y. et al., Gene transduction efficiency in cells of different species by HIV and EIAV vectors, Gene. Ther., 9(14):932-938 (2002).
International Search Report for PCT/US2021/065108, filed Dec. 23, 2021, 3 pages, (mailed Apr. 11, 2022).
Iyama, T. and Wilson, D.M., Dna repair mechanisms in dividing and non-dividing cells, DNA Repair (Amst)., 12(8):620-636 (2013).
Jinek, M. et al., A programmable dual-RNA-guided DNA endonuclease in adaptive bacterial immunity, Science, 337(6096):816-821 (2012).
Jones, M.S. et al., New DNA viruses identified in patients with acute viral infection syndrome, J. Virol., 79(13):8230-8236 (2005).
Joyce, G.F. et al., The case for an ancestral genetic system involving simple analogues of the nucleotides, PNAS USA, 84(13):4398-4402 (1987).
Kailasan, S. et al., Parvovirus Family Conundrum: What Makes a Killer? Annu. Rev. Virol., 2(1):425-450 (2015).

(56) References Cited

OTHER PUBLICATIONS

Kajigaya, S. et al., Self-assembled B19 parvovirus capsids, produced in a baculovirus system, are antigenically and immunogenically similar to native virions, Proc. Natl. Acad. Sci. USA, 88(11):4646-4650, (1991).
Kallunki, T. et al., How to Choose the Right Inducible Gene Expression System for Mammalian Studies? Cells, 8(8):796 (2019).
Kawasaki, A.M et al., Uniformly modified 2'-deoxy-2'-fluoro phosphorothioate oligonucleotides as nuclease-resistant antisense compounds with high affinity and specificity for RNA targets, J. Med. Chem., 36(7):831-841 (1993).
Keiser, N.W. et al., Unique characteristics of AAV1, 2, and 5 viral entry, intracellular trafficking, and nuclear import define transduction efficiency in Hela cells, Hum. Gene. Ther., 22(11):1433-1444 (2011).
Kilham, L. and Oliver, L.J., A latent virus of rats isolated in tissue culture, Virology, 7(4):428-437 (1959).
King, J.A. et al., DNA helicase-mediated packaging of adeno-associated virus type 2 genomes into preformed capsids, EMBO J., 20(12):3282-3291 (2001).
Klein, R.L. et al., Dose and promoter effects of adeno-associated viral vector for green fluorescent protein expression in the rat brain, Exp. Neurol., 176(1):66-74 (2002).
Komor, A.C. et al., Programmable editing of a target base in genomic DNA without double-stranded DNA cleavage, Nature, 533(7603):420-424 (2016).
Kool, E.T., Replacing the nucleobases in DNA with designer molecules, Acc. Chem. Res., 35(11):936-943 (2002).
Kotin, R.M. and Berns, K.I., Organization of adeno-associated virus DNA in latently infected Detroit 6 cells, Virology, 170(2):460-467 (1989).
Kotin, R.M. and Snyder, R.O., Manufacturing Clinical Grade Recombinant Adeno-Associated Virus Using Invertebrate Cell Lines, Hum. Gene. Ther., 28(4):350-260, (2017).
Kotin, R.M et al., Characterization of a preferred site on human chromosome 19q for integration of adeno-associated virus DNA by non-homologous recombination, 11(13):5071-5078 (1992).
Kotin, R.M. et al., Mapping and direct visualization of a region-specific viral DNA integration site on chromosome 19913-qter, Genomics, 10(3):831-834 (1991).
Kotin, R.M. et al., Site-specific integration by adeno-associated virus, PNAS USA, 87(6):2211-2215 (1990).
Kotin, R.M., Large-scale recombinant adeno-associated virus production, Hum. Mol. Genet., 20(R1):R2-R6, (2011).
Kriegler, M. et al., A novel form of TNF/cachectin is a cell surface cytotoxic transmembrane protein: ramifications for the complex physiology of TNF, Cell, 53(1):45-53 (1988).
Krueger, A.T. et al., Synthesis and properties of size-expanded DNAs: toward designed, functional genetic systems, Acc. Chem. Res., 40(2):141-150 (2007).
Lahtinen, A. et al., Serodiagnosis of primary infections with human parvovirus 4, Finland, Emerg. Infect. Dis., 17(1):79-82 (2011).
Lai, Y. et al., Efficient in vivo gene expression by trans-splicing adeno-associated viral vectors, Nat. Biotechnol., 23(11):1435-1439 (2005).
Lau, S.K.P. et al., Identification of novel porcine and bovine parvoviruses closely related to human parvovirus 4, J. Gen. Virol., 89(Pt 8)1840-1848 (2008).
Lee, H. et al., Transferrin receptor binds virus capsid with dynamic motion, Proc. Natl. Acad. Sci. USA., 116(41):20462-20471 (2019).
Lee, N.S. et al., Expression of small interfering RNAs targeted against HIV-1 rev transcripts in human cells, Nat Biotechnol., 20(5):500-505 (2002).
Levine, B. et al., Development of autophagy inducers in clinical medicine, J. Clin. Invest., 125(1):14-24 (2015).
Levitt, N. el al, Definition of an efficient synthetic poly(A) site, Genes Dev. 3(7):1019-1025 (1989).
Li, A. et al., A Self-Deleting AAV-CRISPR System for In Vivo Genome Editing, Mol. Ther. Methods Clin. Dev., 12:111-122 (2018).
Limanskiy, V. et al., Harnessing the potential of gene editing technology using CRISPR in inflammatory bowel disease, World. J. Gastroenterol., 25(18):2177-2187 (2019).
Limbach, P.A. et al., Summary: the modified nucleosides of RNA, Nucleic Acids Res., 22(12):2183-2196 (1994).
Liu, X. et al., Analysis of adeno-associated virus progenitor cell transduction in mouse lung, Mol. Ther., 17(2):285-293 (2009).
Liu, X. et al., Biological Differences in rAAV Transduction of Airway Epithelia in Humans and in Old World Non-human Primates, Mol. Ther., 15(12):2114-2123 (2007).
Liu, X. et al., Partial correction of endogenous DeltaF508 CFTR in human cystic fibrosis airway epithelia by spliceosome-mediated RNA trans-splicing, Nat. Biotechnol., 20(1):47-52 (2002).
Liu, X. et al., Species-specific differences in mouse and human airway epithelial biology of recombinant adeno-associated virus transduction, Am. J. Respir. Cell. Mol. Biol., 34(1):56-64 (2006).
Liu, X et al., Spliceosome-mediated RNA trans-splicing with recombinant adeno-associated virus partially restores cystic fibrosis transmembrane conductance regulator function to polarized human cystic fibrosis airway epithelial cells, Hum. Gene. Ther., 16(9):1116-1123 (2005).
Liu, X. et al., Targeted correction of single-base-pair mutations with adeno-associated virus vectors under nonselective conditions, J. Virol., 78(8):4165-4175 (2004).
Liu, Y. et al., Mutant HFE H63D protein is associated with prolonged endoplasmic reticulum stress and increased neuronal vulnerability, J. Biol. Chem., 286(15):13161-13170 (2011).
Liu, Y. et al., Promoter effects of adeno-associated viral vector for transgene expression in the cochlea in vivo, Experimental and Molecular Medicine, 39(2):170-175 (2007).
Lofling, J. et al., Canine and feline parvoviruses preferentially recognize the non-human cell surface sialic acid N-glycolylneuraminic acid, Virology, 440(1):89-96 (2013).
Lombardo, E. et al., A beta-stranded motif drives capsid protein oligomers of the parvovirus minute virus of mice into the nucleus for viral assembly, J. Virol., 74(8):3804-3814 (2000).
Lopez-Astacio, R.A. et al., Viral Capsid, Antibody, and Receptor Interactions: Experimental Analysis of the Antibody Escape Evolution of Canine Parvovirus, J. Virol., 97(6):e00090-23 (2023).
Lopez-Bueno, A. et al., Enhanced cytoplasmic sequestration of the nuclear export receptor CRM1 by NS2 mutations developed in the host regulates parvovirus fitness, J. Virol., 78(19):10674-10684 (2004).
Lorson, C. et al., Efficient transactivation of the minute virus of mice P38 promoter requires upstream binding of NS1, J. Virol., 70(2):834-842 (1996).
Lou, S. et al., Molecular characterization of the newly identified human parvovirus 4 in the family Parvoviridae, Virology, 422(1):59-69 (2012).
Lusby, E. et al., Nucleotide sequence of the inverted terminal repetition in adeno-associated virus DNA, J. Virol., 34(2):402-409 (1980).
Lyi, S.M. et al., Parvovirus particles and movement in the cellular cytoplasm and effects of the cytoskeleton, Virology, 456-457:342-353 (2014).
Magari, S. R. et al., Pharmacologic control of a humanized gene therapy system implanted into nude mice., J. Clin. Invest., 100:2865-2872 (1997).
Makarova, K.S. et al., Evolution and classification of the CRISPR-Cas systems, Nat. Rev. Microbiol., 9(6):467-477 (2011).
Mantyla, E. et al., Cytoplasmic Parvovirus Capsids Recruit Importin Beta for Nuclear Delivery, J. Virol., 94(4):e01532-19 (2020).
Maroto, B. et al., Nuclear export of the nonenveloped parvovirus virion is directed by an unordered protein signal exposed on the capsid surface, J. Virol., 78(19):10685-10694 (2004).
Mattei, L.M. et al., Parvovirus evades interferon-dependent viral control in primary mouse embryonic fibroblasts, Virology, 442(1):20-27 (2013).
Matthews, P.C. et al., Human parvovirus 4 'PARV4' remains elusive despite a decade of study, F1000Res., 6:82 (2017).

(56) References Cited

OTHER PUBLICATIONS

Mcintosh, B.E. et al., Nonirradiated NOD, B6.SCID Il12ry-/- Kit(W41/W41) (NBSGW) mice support multilineage engraftment of human hematopoietic cells, Stem Cell Reports, 4(2):171-180 (2015).
Mcmanus, M.T. et al., Gene silencing using micro-RNA designed hairpins, RNA, 8(6):842-850 (2002).
Meriluoto, M. et al., Association of Human Bocavirus 1 Infection with Respiratory Disease in Childhood Follow-up Study, Finland, Emerg. Infect. Dis., 18(2):264-271, (2012).
Meszaros, I. et al., Biology of Porcine Parvovirus (Ungulate parvovirus 1), Viruses, 9(12):393 (2017).
Meszaros, I. et al., The SAT Protein of Porcine Parvovirus Accelerates Viral Spreading through Induction of Irreversible Endoplasmic Reticulum Stress, J. Virol., 91(16):e00627-17 (2017).
Mietzsch, M. et al., Twenty-Five Years of Structural Parvovirology, Viruses, 11(4):362 (2019).
Miller, C.L. and Pintel, D.J., Interaction between parvovirus NS2 protein and nuclear export factor Crm1 is important for viral egress from the nucleus of murine cells, J. Virol., 76(7):3257-3266 (2002).
Miyagishi, M. and Taira, K., U6 promoter-driven siRNAs with four uridine 3' overhangs efficiently suppress targeted gene expression in mammalian cells, Nat. Biotechnol., 20(5):497-500 (2002).
Mollerup, S. et al., Cutavirus in Cutaneous Malignant Melanoma, Emerg. Infect. Dis., 23(2):363-365 (2017).
Morales-Rojas, H. and Kool, E.T., A porphyrin C-nucleoside incorporated into DNA, 4(25):4377-4380 (2002).
Mueller, C. et al., Sustained miRNA-mediated Knockdown of Mutant AAT With Simultaneous Augmentation of Wild-type AAT Has Minimal Effect on Global Liver miRNA Profiles, Mol. Ther., 20(3):590-600 (2012).
Naeger, L.K. et al., The small nonstructural protein (NS2) of the parvovirus minute virus of mice is required for efficient DNA replication and infectious virus production in a cell-type- specific manner, J. Virol., 64(12):6166-6175 (1990).
Naito, Y. et al., CRISPRdirect: software for designing CRISPR/Cas guide RNA with reduced off-target sites, Bioinformatics, 31(7):1120-1123 (2015).
Nasir, W. et al., Parvovirus B19 VLP recognizes globoside in supported lipid bilayers, Virology, 456-457:364-369, (2014).
Navone, S.E. et al., Human and mouse brain-derived endothelial cells require high levels of growth factors medium for their isolation, in vitro maintenance and survival, Vasc. Cell., 5(1):10 (2013).
Negrete, A. and Kotin, R.M., Production of recombinant adeno-associated vectors using two bioreactor configurations at different scales, J. Virol. Methods, 145(2):155-161, (2007).
Negrete, A. and Kotin, R.M., Strategies for manufacturing recombinant adeno-associated virus vectors for gene therapy applications exploiting baculovirus technology, Brief Funct. Genomic Proteomic, 7(4):303-311, (2008).
Nemeth, E. et al., Hepcidin is decreased in TFR2 hemochromatosis, Blood, 105(4):1803-1806 (2005).
Nemeth, E. et al., Hepcidin regulates cellular iron efflux by binding to ferroportin and inducing its internalization, Science, 306(5704):2090-2093 (2004).
No, D. et al., Ecdysone-inducible gene expression in mammalian cells and transgenic mice, Proc. Natl. Acad. Sci. USA, 93:3346-3351 (1996).
Nozoe, M. et al., Inhibition of Rac1-derived reactive oxygen species in nucleus tractus solitarius decreases blood pressure and heart rate in stroke-prone spontaneously hypertensive rats, Hypertension, 50(1):62-68 (2007).
Ochi, K. et al., Multicolor staining of globin subtypes reveals impaired globin switching during erythropoiesis in human pluripotent stem cells, Stem Cells Transl. Med., 3(7):792-800 (2014).
Ohlfest, J.R. et al., Phenotypic correction and long-term expression of factor VIII in hemophilic mice by immunotolerization and nonviral gene transfer using the Sleeping Beauty transposon system, Blood, 105(7):2691-2698 (2005).
Orkin, S. et al., Thalassemia due to a mutation in the cleavage-polyadenylation signal of the human beta-globin gene, EMBO J., 4(2):453-456 (1985).
Ostedgaard, L.S. et al., A shortened adeno-associated virus expression cassette for CFTR gene transfer to cystic fibrosis airway epithelia, PNAS USA, 102(8):2952-2957 (2005).
Otting, G. et al., Warum Pentose- und nicht Hexose-Nucleinsauren??. Teil VI. 'Homo-DNS': 1H-, 13C-, 31P- und 15N-NMR-spektroskopische Untersuchung von ddGlc(A-A-A-A-A-T-T-T- T-T) in wassriger Losung, Helv. Chim. Acta., 76(8):2701-2756 (1993).
Paddison, P.J. et al., Short hairpin RNAs (shRNAs) induce sequence-specific silencing in mammalian cells, Genes Dev., 16(8):948-958 (2002).
Panning, M. et al., Novel human parvovirus 4 genotype 3 in infants, Ghana, Emerg. Infect. Dis., 16(7):1143-1146 (2010).
Parker, J.S. et al., Canine and feline parvoviruses can use human or feline transferrin receptors to bind, enter, and infect cells, J. Virol., 75(8):3896-3902 (2001).
Paul, C.P. et al., Effective expression of small interfering RNA in human cells, Nat Biotechnol., 20(5):505-508 (2002).
Pearson, W.R. and Lipman, D.J., Improved tools for biological sequence comparison, PNAS USA, 85(8):2444-2448 (1988).
Peng, X. et al., The draft genome sequence of the ferret (*Mustela putorius furo*) facilitates study of human respiratory disease, Nat. Biotechnol., 32(12):1250-1255 (2014).
Peterson, J.R. et al., Longitudinal noninvasive monitoring of transcription factor activation in cardiovascular regulatory nuclei using bioluminescence imaging, Physiol. Genomics, 33(2):292-299 (2008).
Phan, T.G. et al., A new protoparvovirus in human fecal samples and cutaneous T cell lymphomas (mycosis fungoides), Virology, 496:299-305 (2016).
Phan, T.G. et al., Acute diarrhea in West African children: diverse enteric viruses and a novel *Parvovirus* genus, J. Virol., 86(20):11024-11030 (2012).
Phan, T.G. et al., New parvovirus in child with unexplained diarrhea, Tunisia, Emerg. Infect. Dis., 20(11):1911-1913 (2014).
Pillay, S. et al., Adeno-associated Virus (AAV) Serotypes Have Distinctive Interactions with Domains of the Cellular AAV Receptor, J. Virol., 91(18):e00391-17 (2017).
Pintel, D. et al., The genome of minute virus of mice, an autonomous parvovirus, encodes two overlapping transcription units, Nucleic Acids Res., 11(4):1019-1038 (1983).
Ponnazhagan, S. et al., Recombinant human parvovirus B19 vectors: erythroid cell-specific delivery and expression of transduced genes, J. Virol., 72(6):5224-5230, (1998).
Porro, F. et al., Promoterless gene targeting without nucleases rescues lethality of a Crigler-Najjar syndrome mouse model, EMBO Mol. Med., 9(10):1346-1355 (2017).
Powell, S.K. et al., Viral expression cassette elements to enhance transgene target specificity and expression in gene therapy, Discov. Med., 19(102):49-57 (2015).
Proudfoot, N.J. et al., Integrating mRNA processing with transcription, Cell, 108(4):501-512 (2002).
Qi, L.S. et al., Repurposing CRISPR as an RNA-guided platform for sequence-specific control of gene expression, Cell, 152(5):1173-1183 (2013).
Qin, J.Y. et al., Systematic comparison of constitutive promoters and the doxycycline-inducible promoter, PLoS One, 5(5):e10611 (2010).
Qiu, J. et al., Human Parvoviruses, Clin. Microbiol. Rev., 30(1):43-113 (2017).
Ran, F.A. et al., Double nicking by RNA-guided CRISPR Cas9 for enhanced genome editing specificity, Cell, 154(6):1380-1389 (2013).
Rangarajan, S. et al., AAV5-Factor VIII Gene Transfer in Severe Hemophilia A, N. Engl. J. Med., 377(26):2519-2530 (2017).
Riolobos, L. et al., Viral oncolysis that targets Raf-1 signaling control of nuclear transport, J. Virol., 84(4):2090-2099 (2010).
Rivera, S. et al., Hepcidin excess induces the sequestration of iron and exacerbates tumor-associated anemia, Blood., 105(4):1797-1802 (2005).

(56) References Cited

OTHER PUBLICATIONS

Roetto, A. et al., Mutant antimicrobial peptide hepcidin is associated with severe juvenile hemochromatosis, Nat. Genet., 33(1):21-22 (2003).
Rogers, C.S. et al., Production of CFTR-null and CFTR-DeltaF508 heterozygous pigs by adeno-associated virus-mediated gene targeting and somatic cell nuclear transfer, J. Clin. Invest., 118(4):1571-1577 (2008).
Ros, C. et al., Protoparvovirus Cell Entry, Viruses, 9(11):313, (2017).
Ruiz, Z. et al., Differential roles for the C-terminal hexapeptide domains of NS2 splice variants during MVM infection of murine cells, Virology, 349(2):382-395 (2006).
Sadelain, M. et al., Safe harbours for the integration of new DNA in the human genome, Nature Reviews Cancer, 12:51-58 (2012).
Sandberg, H. et al., Structural and functional characteristics of the B-domain-deleted recombinant factor VIII protein, r-VIII SQ, Thromb. Haemost., 85(1):93-100 (2001).
Sanglioglu, A.D. et al., Novel approaches to augment adeno-associated virus type-2 endocytosis and transduction, Virus Res., 104(1):51-59 (2004).
Santosh, V. et al., The Cryo-EM structure of AAV2 Rep68 in complex with ssDNA reveals a malleable AAA+ machine that can switch between oligomeric states, Nucleic Acids Res., 48(22):12983-12999 (2020).
Sather, B.D. et al., Efficient modification of CCR5 in primary human hematopoietic cells using a megaTAL nuclease and AAV donor template, Sci. Transl. Med., 7(307):307ra156 (2015).
Schambach, A. et al., Improving transcriptional termination of self-inactivating gamma-retroviral and lentiviral vectors, Mol. Ther., 15(6):1167-1173 (2007).
Schek, N. et al., Definition of the Upstream Efficiency Element of the Simian Virus 40 Late Polyadenylation Signal by Using in Vitro Analyses, Mol. Cell Biol., 12(12):5386-5393 (1992).
Schoning, K. et al., Chemical etiology of nucleic acid structure: the alpha-threofuranosyl-(3'-->2') oligonucleotide system, Science, 290(5495):1347-1351 (2000).
Seth, P.P. et al., An exocyclic methylene group acts as a bioisostere of the 2'-oxygen atom in LNA, J. Am. Chem. Soc., 132(42):14942-14950 (2010).
Sharp, C.P. et al., High frequencies of exposure to the novel human parvovirus PARV4 in hemophiliacs and injection drug users, as detected by a serological assay for PARV4 antibodies, J. Infect. Dis., 200(7):1119-1125 (2009).
Sharp, P.A., RNAi and double-strand RNA, Genes. Dev., 13(2):139-141 (1999).
Shen, W. et al., Analysis of cis and trans Requirements for DNA Replication at the Right-End Hairpin of the Human Bocavirus 1 Genome, J. Virol., 90(17):7761-7777 (2016).
Shen, W. et al., Hairpin Transfer—Independent Parvovirus DNA Replication Produces Infectious Virus, J. Virol., 95(20):e0110821 (2021).
Shen, W. et al., Identification and Functional Analysis of Novel Nonstructural Proteins of Human Bocavirus 1, J. Virol., 89(19):10097-10109 (2015).
Shmakov, S. et al., Discovery and Functional Characterization of Diverse Class 2 CRISPR-Cas Systems, Mol. Cell., 60(3):385-397 (2015).
Slavov, S.N. et al., Human parvovirus 4 prevalence among HTLV-1/2 infected individuals in Brazil, J. Med. Virol., 89(4):748-752 (2017).
Smith, R.H. et al., A simplified baculovirus-AAV expression vector system coupled with one-step affinity purification yields high-titer rAAV stocks from insect cells, Mol. Ther., 17(11):1888-1896, (2009).
Spooner, B.S. et al., The development of the dorsal and ventral mammalian pancreas in vivo and in vitro, J. Cell. Biol., 47(1):235-246 (1970).
Srivastava, A. et al., A Tribute to Barrie J. Carter, Hum. Gene. Ther., 31(9-10):491-493 (2020).
Srivastava, C.H. et al., Construction of a recombinant human parvovirus B19: adeno-associated virus 2 (AAV) DNA inverted terminal repeats are functional in an AAV-B19 hybrid virus, Proc. Natl. Acad. Sci. USA, 86(20):8078-8082, (1989).
Steines, B. et al., CFTR gene transfer with AAV improves early cystic fibrosis pig phenotypes, JCI Insight, 1(14):e88728 (2016).
Stone, I.M. et al., Adeno-associated virus-mediated gene transfer to hair cells and support cells of the murine cochlea, Mol. Ther., 11(6):843-848 (2005).
Subramanian, S. et al., Cryo-EM maps reveal five-fold channel structures and their modification by gatekeeper mutations in the parvovirus minute virus of mice (MVM) capsid, Virology, 10:216-223 (2017).
Sui, G. et al., A DNA vector-based RNAi technology to suppress gene expression in mammalian cells, PNAS USA, 99(8):5515-5520 (2002).
Sun, X. et al., Adeno-associated virus-targeted disruption of the CFTR gene in cloned ferrets, J. Clin. Invest., 118(4):1578-1583 (2008).
Sun, X. et al., In utero and postnatal VX-770 administration rescues multiorgan disease in a ferret model of cystic fibrosis, Sci. Transl. Med., 11(485):eaau7531, (2019).
Szymanski, P. et al., Development and validation of a robust and versatile one-plasmid regulated gene expression system, Mol Ther., 15(7):1340-1347 (2007).
Tang, Y. et al., Repeat Dosing of AAV2.5T to Ferret Lungs Elicits an Antibody Response That Diminishes Transduction in an Age-Dependent Manner, Mol. Ther. Methods Clin. Dev., 19:186-200, (2020).
Tang, Y. et al., Viral Vectors, Animal Models, and Cellular Targets for Gene Therapy of Cystic Fibrosis Lung Disease, Hum. Gene. Ther., 31(9-10):524-537 (2020).
Tanzi, R.E. et al., The Wilson disease gene is a copper transporting ATPase with homology to the Menkes disease gene, Nat. Genet., 5(4):344-350 (1993).
Terui, K. et al., Stat3 confers resistance against hypoxia/reoxygenation-induced oxidative injury in hepatocytes through upregulation of Mn-SOD, J. Hepatol., 41(6):957-965 (2004).
Thein, S. et al., The polyadenylation site mutation in the alpha-globin gene cluster, Blood, 71(2):313-319 (1988).
Tsai, C. et al., Enzymatic synthesis of DNA on glycerol nucleic acid templates without stable duplex formation between product and template, PNAS USA, 104(37):14598-14603 (2007).
Tse, H. et al., Discovery and genomic characterization of a novel ovine partetravirus and a new genotype of bovine partetravirus, PLoS One, 6(9):e25619 (2011).
Tseng, Y.S. and Agbandje-McKenna, M., Mapping the AAV Capsid Host Antibody Response toward the Development of Second Generation Gene Delivery Vectors, Front. Immunol., 5:9 (2014).
Tuschl, T., Expanding small RNA interference, Nat. Biotechnol., 20(5)446-448 (2002).
Tuschl, T., RNA interference and small interfering RNAs, Chembiochem., 2(4):239-245 (2001).
Tyson, J.J. et al., Analysis of the kinetic hairpin transfer model for parvoviral DNA replication, J. Theor. Biol., 144(2):155-169 (1990).
Urabe, M. et al., Scalable generation of high-titer recombinant adeno-associated virus type 5 in insect cells, J. Virol., 80(4):1874-1885 (2006).
Urcelay, E. et al., Asymmetric replication in vitro from a human sequence element is dependent on adeno-associated virus Rep protein, J. Virol., 69(4):2038-2046 (1995).
Urnov, F.D. et al., Highly efficient endogenous human gene correction using designed zinc-finger nucleases, Nature, 435(7042):646-651 (2005).
Vaisanen, E. et al., Global Distribution of Human Protoparvoviruses, Emerg. Infect. Dis., 24(7):1292-2199 (2018).
Vaisanen, E. et al., Human Protoparvoviruses, Viruses, 9(11):354 (2017).
Van Linthout, S. et al., Effect of promoters and enhancers on expression, transgene DNA persistence, and hepatotoxicity after adenoviral gene transfer of human apolipoprotein A-I, Hum. Gene. Ther., 13(7):829-840 (2002).

(56) References Cited

OTHER PUBLICATIONS

Van Regenmortel, M. and Mahy, B., Emerging Issues in Virus Taxonomy, Emerging Infectious Diseases, 10(1):8-13 (2004).
Van Vliet, K.M. et al., The role of the adeno-associated virus capsid in gene transfer, Methods Mol. Biol., 437:51-91 (2008).
Verma, S. and Eckstein, F., Modified oligonucleotides: synthesis and strategy for users, Annu. Rev. Biochem., 67:99-134 (1998).
Virag, T. et al., Producing Recombinant Adeno-Associated Virus in Foster Cells: Overcoming Production Limitations Using a Baculovirus—Insect Cell Expression Strategy, Hum. Gene. Ther., 20(8):807-817, (2009).
Visboll, T. et al., Incretin secretion in relation to meal size and body weight in healthy subjects and people with type 1 and type 2 diabetes mellitus, J. Clin. Endocrinol. Metab., 88(6):2706-2713 (2003).
Visboll, T. et al., Similar elimination rates of glucagon-like peptide-1 in obese type 2 diabetic patients and healthy subjects, J. Clin. Endocrinol. Metab., 88(1):220-224 (2003).
Waheed, A. et al., Hereditary hemochromatosis: effects of C282Y and H63D mutations on association with beta2-microglobulin, intracellular processing, and cell surface expression of the HFE protein in COS-7 cells, PNAS USA, 94(23):12384-12390 (1997).
Wang, X. et al., Cellular Cleavage and Polyadenylation Specificity Factor 6 (CPSF6) Mediates Nuclear Import of Human Bocavirus 1 NP1 Protein and Modulates Viral Capsid Protein Expression, J. Virol., 94(2):e01444-19 (2020).
Wang, Y. et al., Genome editing of human embryonic stem cells and induced pluripotent stem cells with zinc finger nucleases for cellular imaging, Circ. Res., 111(12):1494-1503 (2012).
Wang, Y. et al., Ligand-inducible and liver-specific target gene expression in transgenic mice, Nat. Biotech., 15:239-243 (1997).
Wang, Y. et al., Positive and negative regulation of gene expression in eukaryotic cells with an inducible transcriptional regulator, Gene Ther., 4:432-441 (1997).
Wang, Z. et al., Development of a Novel Recombinant Adeno-Associated Virus Production System Using Human Bocavirus 1 Helper Genes, Mol. Ther. Methods Clin. Dev., 11:40-51 (2018).
Wang, Z. et al., Human Bocavirus 1 is a Novel Helper for Adeno-associated Virus Replication, J. Virol., 91(18):e00710-e00717, (2017).
Wang, Z. et al., Parvovirus Expresses a Small Noncoding RNA That Plays an Essential Role in Virus Replication, J. Virol., 91(8):e02375-16 (2017).
Wengel, J. et al., Synthesis of 3'-C- and 4'-C-Branched Oligodeoxynucleotides and the Development of Locked Nucleic Acid (LNA), Acc. Chem. Res., 32(4):301-310 (1999).
Whitfield, J. et al., The ER Fusion System in Mouse Models: A Reversible Switch, Cold Spring Harb. Protoc., 2015(3):227-234 (2015).
Wojcik, J.P. et al., Natural history of C282Y homozygotes for hemochromatosis, Can. J. Gastroenterol., 16(5):297-302 (2002).
Woychick, R.P. et al., Requirement for the 3' flanking region of the bovine growth hormone gene for accurate polyadenylylation, PNAS USA, 81(13):3944-3948 (1984).
Written Opinion for PCT/US2021/065108, filed Dec. 23, 2021, 5 pages, (mailed Apr. 11, 2022).
Wu, Z. et al., Optimization of self-complementary AAV vectors for liver-directed expression results in sustained correction of hemophilia B at low vector dose, Mol. Ther., 16(2):280-289 (2008).
Xia, X.G. et al., An enhanced U6 promoter for synthesis of short hairpin RNA, Nucleic Acids Res., 31(17):e100 (2003).
Xiao, A. et al., CasOT: a genome-wide Cas9/gRNA off-target searching tool, Bioinformatics, 30(8):1180-1182 (2014).
Xie, Q. and Chapman, M.S., Canine parvovirus capsid structure, analyzed at 2.9 A resolution, J. Mol. Biol., 264(3):497-520 (1996).
Xu, L. et al., CMV-beta-actin promoter directs higher expression from an adeno-associated viral vector in the liver than the cytomegalovirus or elongation factor 1 alpha promoter and results in therapeutic levels of human factor X in mice, Hum. Gene. Ther., 12(5):563-573 (2001).
Xu, M. et al., Persistence of Human Bocavirus 1 in Tonsillar Germinal Centers and Antibody-Dependent Enhancement of Infection, mBio, 12(1):e03132-20, (2021).
Xu, R. et al., Quantitative comparison of expression with adeno-associated virus (AAV-2) brain-specific gene cassettes, Gene. Ther., 8(17):1323-1332 (2001).
Yahiro, T. et al., Novel human bufavirus genotype 3 in children with severe diarrhea, Bhutan, Emerg. Infect. Dis., 20(6):1037-1039 (2014).
Yamaguchi, Y. et al., Mass screening for Wilson's disease: Results and recommendations, Pediatrics International, 41(4):405-408 (1999).
Yan, X. et al., Human Bocavirus 1 Infection of Well-Differentiated Human Airway Epithelium, Curr. Protoc. Microbiol., 58(1):e107, (2020).
Yan, Z. et al., A novel chimeric adenoassociated virus 2/human bocavirus 1 parvovirus vector efficiently transduces human airway epithelia, Mol. Ther., 21(12):2181-2194, (2013).
Yan, Z. et al., AAV-mediated gene editing lights up the lung, Mol. Ther., 30(1):7-9 (2022).
Yan, Z. et al., Distinct classes of proteasome-modulating agents cooperatively augment recombinant adeno-associated virus type 2 and type 5-mediated transduction from the apical surfaces of human airway epithelia, J. Virol., 78(6):2863-2874 (2004).
Yan, Z. et al., Establishment of a High-Yield Recombinant Adeno-Associated Virus/Human Bocavirus Vector Production System Independent of Bocavirus Nonstructural Proteins, Hum. Gen. Ther., 30(5):556-570 (2019).
Yan, Z. et al., Human Bocavirus Type-1 Capsid Facilitates the Transduction of Ferret Airways by Adeno-Associated Virus Genomes, Hum. Gene. Ther., 28(8):612-625, (2017).
Yan, Z. et al., Hybrid adeno-associated virus bearing nonhomologous inverted terminal repeats enhances dual-vector reconstruction of minigenes in vivo, Hum. Gene. Ther., 18(1):81-87 (2007).
Yan, Z. et al., Indexing TNF-alpha gene expression using a gene-targeted reporter cell line, BMC Biol., 7:8 (2009).
Yan, Z. et al., Inverted terminal repeat sequences are important for intermolecular recombination and circularization of adeno-associated virus genomes, J. Virol., 79(1):364-379 (2005).
Yan, Z. et al., Optimization of Recombinant Adeno-Associated Virus-Mediated Expression for Large Transgenes, Using a Synthetic Promoter and Tandem Array Enhancers, Hum. Gene. Ther., 26(6):334-346 (2015).
Yan, Z. et al., Postentry processing of recombinant adeno-associated virus type 1 and transduction of the ferret lung are altered by a factor in airway secretions, Hum. Gene. Ther., 24(9):786-796 (2013).
Yan, Z. et al., Recombinant AAV-mediated gene delivery using dual vector heterodimerization, Methods Enzymol., 346:334-357 (2002).
Yan, Z. et al., Ubiquitination of both adeno-associated virus type 2 and 5 capsid proteins affects the transduction efficiency of recombinant vectors, J. Virol., 76(5):2043-2053 (2002).
Yan, Z. et al., Unique biologic properties of recombinant AAV1 transduction in polarized human airway epithelia, J.Biol. Chem., 281(40):29684-29692 (2006).
Yang, G.S. et al., Virus-mediated transduction of murine retina with adeno-associated virus: effects of viral capsid and genome size, J. Virol., 76(15):7651-7660 (2002).
Yang, J. et al., Genetic redox preconditioning differentially modulates AP-1 and NF kappa B responses following cardiac ischemia/reperfusion injury and protects against necrosis and apoptosis, Mol. Ther., 7(3):341-353 (2003).
Yang, J. et al., Model system for developing gene therapy approaches for myocardial ischemia-reperfusion injury, Methods Enzymol., 353:321-336 (2002).
Yew, N.S. et al., Optimization of plasmid vectors for high-level expression in lung epithelial cells, Hum. Gene Ther., 8(5):575-584 (1997).
Yokobayashi, Y., Aptamer-based and aptazyme-based riboswitches in mammalian cells, Curr. Opin. Chem. Biol., 52:72-78 (2019).
Yu, J. et al., RNA interference by expression of short-interfering RNAs and hairpin RNAs in mammalian cells, PNAS USA, 99(9):6047-6052 (2002).
Yuan, W. and Parrish, C.R., Canine parvovirus capsid assembly and differences in mammalian and insect cells, Virology, 279(2):546-557 (2001).

(56) References Cited

OTHER PUBLICATIONS

Zadori, Z. et al., SAT: a late NS protein of porcine parvovirus, J. Virol., 79(20):13129-13138 (2005).
Zarate-Perez, F. et al., Oligomeric properties of adeno-associated virus Rep68 reflect its multifunctionality, J. Virol., 87(2):1232-1241 (2013).
Zeng, Y. et al., Both natural and designed micro RNAs can inhibit the expression of cognate mRNAs when expressed in human cells, Mol. Cell., 9(6):1327-1333 (2002).
Zhang, J.P. et al., Efficient precise knockin with a double cut HDR donor after CRISPR/Cas9-mediated double-stranded DNA cleavage, Genome Biol., 18(1):35 (2017).
Zhang, L. et al., A simple glycol nucleic acid, J. Am. Chem. Soc., 127(12):4174-4175 (2005).
Zhang, L.N. et al., Dual therapeutic utility of proteasome modulating agents for pharmaco-gene therapy of the cystic fibrosis airway, Mol. Ther., 10(6):990-1002 (2004).
Zhang, R.S. et al., Synthesis of two mirror image 4-helix junctions derived from glycerol nucleic acid, J. Am. Chem. Soc., 130(18):5846-5847 (2008).
Zimmerman, M.C. et al., Requirement for Rac1-dependent NADPH oxidase in the cardiovascular and dipsogenic actions of angiotensin II in the brain, Circ. Res., 95(5):532-539 (2004).
Zou, J. et al., Oxidase-deficient neutrophils from X-linked chronic granulomatous disease iPS cells: functional correction by zinc finger nuclease-mediated safe harbor targeting, Blood, 117(21):5561-5572 (2011).
Zou, W. et al., A Comprehensive RNA-seq Analysis of Human Bocavirus 1 Transcripts in Infected Human Airway Epithelium, Viruses, 11(1):33 (2019).
Zou, W. et al., Nonstructural Protein NP1 of Human Bocavirus 1 Plays a Critical Role in the Expression of Viral Capsid Proteins, J. Virol., 90(9):4658-4669 (2016).
International Search Report for PCT/US2024/021126, 5 pages, (mailed Jul. 24, 2024).
Liu, P. et al., The role of nuclear localization signal in parvovirus life cycle, Virol. J., 14(1):80 (2017).
Written Opinion for PCT/US2024/021126, 10 pages, (mailed Jul. 24, 2024).
International Search Report for PCT/US2024/020608, 5 pages, (mailed Aug. 5, 2024).
Written Opinion for PCT/US2024/020608, 7 pages, (mailed Aug. 5, 2024).
Geiss, C. et al., Preclinical Testing of an Oncolytic Parvovirus: Standard Protoparvovirus H-1PV Efficiently Induces Osteosarcoma Cell Lysis In Vitro, Viruses, 9(10):301 (2017).
Gilbert, L. et al., Assembly of fluorescent chimeric virus-like particles of canine parvovirus in insect cells, Biochem. Biophys. Res. Commun., 313(4):878-887 (2004).
Haag, A. et al., Highly efficient transduction and expression of cytokine genes in human tumor cells by means of autonomous parvovirus vectors; generation of antitumor responses in recipient mice, Hum. Gene. Ther., 11(4):597-609 (2000).
Spitzer, A.L. et al., Tropic determinant for canine parvovirus and feline panleukopenia virus functions through the capsid protein VP2, J. Gen. Virol., 78(Pt 4):925-928 (1997).

* cited by examiner

```
                                       Putative NLS                aa_del   PLA2 Motif
SEQ ID NO: 160 BuV_AFN44271        --MPAIR------------------------KARGWVPPGYNYLGPFNQDFSKKPTNPSD   34
SEQ ID NO: 161 CuV_AQN78782.1      --MPAIR------------------------KARGWVPPGYNFLGPFNQDFNKEPTNPSD   34
SEQ ID NO: 161 CuV_YP_009508805    --MPAIR------------------------KARGWVPPGYNFLGPFNQDFNKEPTNPSD   34
SEQ ID NO: 162 TuV_AIT18930        MAP-AARPR------------------------KGWVPPGYNYLGPGNDLDAGEPTNKSD   35
SEQ ID NO: 163 MVM_J02275.1        MAPPAKRAKR------------------------GWVPPGYKYLGPGNSLDQGEPTNPSD   36
SEQ ID NO: 164 CPV_AXQ00350        MAPPAKRARR------------------------GLVPPGYKYLGPGNSLDQGEPTNPSD   36
SEQ ID NO: 165 CPV_M19296.1        MAPPAKRARRGKGVLVKWGEGKDLITXLSMCFFIGLVPPGYKYLGPGNSLDQGEPTNPSD   60
SEQ ID NO: 164 FPV_ACD37389.1      MAPPAKRARR------------------------GLVPPGYKYLGPGNSLDQGEPTNPSD   36
SEQ ID NO: 164 FPV_AKI88071        MAPPAKRARR------------------------GLVPPGYKYLGPGNSLDQGEPTNPSD   36
                                       * *                           * *****::*** *.    :*** **
```

FIG. 1

| | | | | | | | |
|---|---|---|---|---|---|---|---|
| SEQ ID NO: 166 | *Gm* DNV | 177 | : | LTVPGYKYLGPGNSLN---RGQPINQIDEDAKEHDEAYDKVKT-----SQEVSRADNTFVNK | : | 230 | (AAA66966) |
| SEQ ID NO: 167 | *Ml* DNV | 177 | : | LTVPGYKYLGPGNSLN---RGQPTNQIDEDAKEHDEAYDKAKT-----SQEVSEADNTFVNK | : | 230 | |
| SEQ ID NO: 168 | *Jc DNV* | 177 | : | LTVPGYKYLGPGNSLN---RGQPTNQIDEDAKEHDEAYDKAKT-----SQEVSQADNTFVNK | : | 230 | (Q90053) |
| SEQ ID NO: 169 | *Pi* DNV | 177 | : | LTVPGYKYLGPGNSLD---RGEPVNQIDADAKEHDEAYDKAKT-----SQEVSDADSKFVSK | : | 230 | |
| SEQ ID NO: 170 | *Ds* DNV | 177 | : | LTVPGYKYLGPGNSLN---RGPPTNEIDADAKEHDEAYSQSKT-----AQEVSKADNTFVNK | : | 230 | (AAC18002) |
| SEQ ID NO: 171 | *Cp* DNV | 140 | : | LVPAPYKYAGPGNSLN---RGPAYDLVDESARQHDIAYDKAKS-----PEDIHKADRQFLTE | : | 193 | |
| SEQ ID NO: 172 | *Pf* DNV | 149 | : | LTYPFHHYLGPGNPLD---NNEPVDRDDAIAEEHDKAYANAKS-----SIDVINADKKAIDH | : | 202 | (AAF04300) |
| SEQ ID NO: 173 | *Ad* DNV | 178 | : | AVLPGTDFVGPGNPID---PKPARSETDQIAKEHDLGYEDLLHRA--KSQYFTEEDFKTEVY | : | 234 | |
| SEQ ID NO: 174 | *Ce* DNV | 4 | : | IHFPYHNYLGPGSDNF---KKQPVDEDDAIARAHDLDYDKASSDKDIFKADKQARDEFFSSF | : | 62 | (AF375296) |
| SEQ ID NO: 175 | *Bm* DNV | 4 | : | IHFPYHNYLGPGTDNF---EKNPVDEDDAIARSHDLAYDKVTNHKEVFQADKQARDEFFTSF | : | 62 | (AY033435) |
| SEQ ID NO: 176 | Canine PV | 33 | : | LVPPGYKYLGPGNSLD---QGEPTNPSDAAAKEHDEAYAAYLRSGKNPYLYFSPADQRFIDQ | : | 91 | (VCPVCP) |
| SEQ ID NO: 176 | Mink PV | 7 | : | LVPPGYKYLGPGNSLD---QGEPTNPSDAAAKEHDEAYAAYLRSGKNPYLYFSPADQRFVDQ | : | 65 | (VCPVME) |
| SEQ ID NO: 176 | Mouse1 PV | 7 | : | LVPPGYKYLGPGNSLD---QGEPTNPSDAAAKEHDEAYAAYLRSGKNPYLYFSPADQRFIDQ | : | 65 | (AAA61406) |
| SEQ ID NO: 176 | Feline PV | 12 | : | LVPPGYKYLGPGNSLD---QGEPTNPSDAAAKEHDEAYAAYLRSGKNPYLYFSPADQRFIDQ | : | 70 | (AAC37928) |
| SEQ ID NO: 177 | MVM PV | 1 | : | MVPPGYKYLGPGNSLD---QGEPTNPSDAAAKEHDEAYDQYIKSGKNPYLYFSAADQRFIDQ | : | 59 | (VCPVIM) |
| SEQ ID NO: 178 | LuIII PV | 12 | : | WVPPGYKYLGPGNSLN---QGEPTNPSDAAAKEHDEAYDQYIKSGKNPYLYFSPADQRFIDQ | : | 70 | (M81888) |
| SEQ ID NO: 179 | H1 PV | 12 | : | WVPPGYKYLGPGNSLD---QGEPTNPSDAAAKEHDEAYDQYIKSGKNPYLYFSPADQRFIDQ | : | 70 | (PO3136) |
| SEQ ID NO: 180 | K. Rat PV | 12 | : | CVPPGYKYLGPGNSLD---QGEPTNPSDAAAKEHDLAYDEYIKSGKNPYLYFSPADQRFIDQ | : | 70 | (AAB38327) |
| SEQ ID NO: 181 | Porcine PV | 11 | : | LTLPGYKYLGPGNSLD---QGEPTNPSDAAAKEHDEAYDKYIKSGKNPYFYFSAADEKFIKE | : | 69 | (VCPVNA) |
| SEQ ID NO: 182 | MDuck PV | 53 | : | FVLPGYKYVGPGNGLD---KGPPVNKADSVALEHDKAYDQQLKAGDNPYIKFKHADQEFIDN | : | 111 | (CAA52984) |
| SEQ ID NO: 183 | Goose PV | 53 | : | FVLPGYKYLGPGNGLD---KGPPVNKADSVALEHDKAYDQQLKAGDNPYIKFNHADQDFIDS | : | 111 | (AAAA3230) |

FIG. 2

Figure 1. Sequencing Alignments of Parvovirus $PLA_2$ Motifs and $sPLA_2$ Representatives CPV-VP1u consensus aa sequence:

MAPPAKRARRGLVPPGYKYLGPGNSLDQGEPTNPS
DAAAKEHDEAYAAYLRSGKNPYLYFSPADQRFIDQTK     SEQ ID NO:218
DAKDWGGKIGHYFFRAKKAIAPVLTDTPDHPSTSRP
TKPTKRSKPPPHIFINLAKKKKAGAGQVKRDNLAP

| VP1u | VP2 |

Toxic in insect cells

SEQ ID NO: 1
LVPPG deletion

| VP1u | VP2 |

- Reduced tox in insect cells
- High VP yield
- Approach applied to other Protoparvoviruses

| Common features | Elements |
| --- | --- |
| Promoter | -Polyhedrin (strong, late)<br>-P10 (strong, late)<br>-OpiE1(weak, early)** Currently used for NS proteins |
| 5'UTR | -spacer sequence (original)<br>-alt initiation depleted (ATT, ATA, ATC)<br>- No spacer sequence |
| Kozak | -Eukaryotic conventional (GCCGCC---G)<br>-Viral-derived (CCTGTTAAG)<br>-Alternative (AAA) |
| VP1 initiation codon | CTG, TTG, ACG, ATC |

FIG. 11

Transduction of HEK293T cells with Exemplary CPV Construct 5 at different MOIs.
Imaging at 2 days 6 hours Transduction of HEK293T cells with Exemplary CPV Construct 5 at different MOIs

SEQUENCE LISTING

```
Sequence total quantity: 221
SEQ ID NO: 1            moltype = AA  length = 5
FEATURE                 Location/Qualifiers
source                  1..5
                        mol_type = protein
                        organism = synthetic construct
SEQUENCE: 1
LVPPG                                                              5

SEQ ID NO: 2            moltype = AA  length = 5
FEATURE                 Location/Qualifiers
source                  1..5
                        mol_type = protein
                        organism = synthetic construct
SEQUENCE: 2
WVPPG                                                              5

SEQ ID NO: 3            moltype = AA  length = 10
FEATURE                 Location/Qualifiers
source                  1..10
                        mol_type = protein
                        organism = synthetic construct
SEQUENCE: 3
WVPPGYNFLG                                                         10

SEQ ID NO: 4            moltype = AA  length = 668
FEATURE                 Location/Qualifiers
source                  1..668
                        mol_type = protein
                        organism = synthetic construct
SEQUENCE: 4
MSGNQYTEEV MEGVNWLKKH AENEAFSFVF KCDNVQLNGK DVRWNNYTKP IQNEELTSLI  60
RGAQTAMDQT EEEEMDWESE VDSLAKKQVQ TFDALIKKCL FEVFVSKNIE PNECVWFIQH  120
EWGKDQGWHC HVLLHSKNLQ QATGKWLRRQ MNMYWSRWLV TLCSVNLTPT EKIKLREIAE  180
DSEWVTILTY RHKQTKKDYV KMVHFGNMIA YYFLTKKKIV HMTKESGYFL STDSGWKFNF  240
MKYQDRQIVS TLYTEQMKPE TVETTVTTAQ ETKRGRIQTK KEVSIKCTLR DLVSKRVTSP  300
EDWMMLQPDS YIEMMAQPGG ENLLKNTLEI CTLTLARTKT AFELILEKAD NTKLTNFDLA  360
NSRTCQIFRM HGWNWIKVCH AIACVLNRQG GKRNTVLFHG PASTGKSIIA QAIAQAVGNV  420
GCYNAANVNF PFNDCTNKNL IWIEEAGNFG QQVNQFKAIC SGQTIRIDQK GKGSKQIEPT  480
PVIMTTNENI TIVRIGCEER PEHTQPIRDR MLNIKLVCKL PGDFGLVDKE EWPLICAWLV  540
KHGFVSTMAN YTHHWGKVPE WDENWAEPKI QEGINSPGCK DLKTQAASNP QSQDQVLTPL  600
TPDVVDLALE PWSTPDTPIA ETANQQSNQL GVTHKDVQAS PTWSEIEADL RAIFTSEQLE  660
EDFRDDLD                                                           668

SEQ ID NO: 5            moltype = AA  length = 14
FEATURE                 Location/Qualifiers
source                  1..14
                        mol_type = protein
                        organism = synthetic construct
SEQUENCE: 5
QAGTFALRGD NPQG                                                    14

SEQ ID NO: 6            moltype = AA  length = 6
FEATURE                 Location/Qualifiers
source                  1..6
                        mol_type = protein
                        organism = synthetic construct
SEQUENCE: 6
NGRAHA                                                             6

SEQ ID NO: 7            moltype = AA  length = 7
```

-continued

```
FEATURE                 Location/Qualifiers
source                  1..7
                        mol_type = protein
                        organism = synthetic construct
SEQUENCE: 7
RGDAVGV                                                        7

SEQ ID NO: 8            moltype = AA  length = 7
FEATURE                 Location/Qualifiers
source                  1..7
                        mol_type = protein
                        organism = synthetic construct
SEQUENCE: 8
RGDTPTS                                                        7

SEQ ID NO: 9            moltype = AA  length = 7
FEATURE                 Location/Qualifiers
source                  1..7
                        mol_type = protein
                        organism = synthetic construct
SEQUENCE: 9
GENQARS                                                        7

SEQ ID NO: 10           moltype = AA  length = 7
FEATURE                 Location/Qualifiers
source                  1..7
                        mol_type = protein
                        organism = synthetic construct
SEQUENCE: 10
RSNAVVP                                                        7

SEQ ID NO: 11           moltype = AA  length = 9
FEATURE                 Location/Qualifiers
source                  1..9
                        mol_type = protein
                        organism = synthetic construct
SEQUENCE: 11
CDCRGDCFC                                                      9

SEQ ID NO: 12           moltype = AA  length = 7
FEATURE                 Location/Qualifiers
source                  1..7
                        mol_type = protein
                        organism = synthetic construct
SEQUENCE: 12
PRGTNGP                                                        7

SEQ ID NO: 13           moltype = AA  length = 7
FEATURE                 Location/Qualifiers
source                  1..7
                        mol_type = protein
                        organism = synthetic construct
SEQUENCE: 13
SRGATTT                                                        7

SEQ ID NO: 14           moltype = AA  length = 7
FEATURE                 Location/Qualifiers
source                  1..7
                        mol_type = protein
                        organism = synthetic construct
SEQUENCE: 14
SIGYPLP                                                        7

SEQ ID NO: 15           moltype = AA  length = 12
FEATURE                 Location/Qualifiers
source                  1..12
                        mol_type = protein
                        organism = synthetic construct
SEQUENCE: 15
MTPFPTSNEA NL                                                  12

SEQ ID NO: 16           moltype = AA  length = 7
FEATURE                 Location/Qualifiers
source                  1..7
                        mol_type = protein
                        organism = synthetic construct
SEQUENCE: 16
QPEHSST                                                        7
```

-continued

```
SEQ ID NO: 17           moltype = AA  length = 7
FEATURE                 Location/Qualifiers
source                  1..7
                        mol_type = protein
                        organism = synthetic construct
SEQUENCE: 17
VNTANST                                                                    7

SEQ ID NO: 18           moltype = AA  length = 9
FEATURE                 Location/Qualifiers
source                  1..9
                        mol_type = protein
                        organism = synthetic construct
SEQUENCE: 18
CNHRYMQMC                                                                  9

SEQ ID NO: 19           moltype = AA  length = 9
FEATURE                 Location/Qualifiers
source                  1..9
                        mol_type = protein
                        organism = synthetic construct
SEQUENCE: 19
CAPGPSKSG                                                                  9

SEQ ID NO: 20           moltype = AA  length = 7
FEATURE                 Location/Qualifiers
source                  1..7
                        mol_type = protein
                        organism = synthetic construct
SEQUENCE: 20
EYHHYNK                                                                    7

SEQ ID NO: 21           moltype = AA  length = 7
FEATURE                 Location/Qualifiers
source                  1..7
                        mol_type = protein
                        organism = synthetic construct
SEQUENCE: 21
ASSLNIA                                                                    7

SEQ ID NO: 22           moltype = AA  length = 7
FEATURE                 Location/Qualifiers
source                  1..7
                        mol_type = protein
                        organism = synthetic construct
SEQUENCE: 22
TQVGQKT                                                                    7

SEQ ID NO: 23           moltype = AA  length = 7
FEATURE                 Location/Qualifiers
source                  1..7
                        mol_type = protein
                        organism = synthetic construct
SEQUENCE: 23
LPSSLQK                                                                    7

SEQ ID NO: 24           moltype = AA  length = 7
FEATURE                 Location/Qualifiers
source                  1..7
                        mol_type = protein
                        organism = synthetic construct
SEQUENCE: 24
WPFYGTP                                                                    7

SEQ ID NO: 25           moltype = AA  length = 7
FEATURE                 Location/Qualifiers
source                  1..7
                        mol_type = protein
                        organism = synthetic construct
SEQUENCE: 25
DSPAHPS                                                                    7

SEQ ID NO: 26           moltype = AA  length = 7
FEATURE                 Location/Qualifiers
source                  1..7
                        mol_type = protein
                        organism = synthetic construct
SEQUENCE: 26
GWTLHNK                                                                    7
```

-continued

```
SEQ ID NO: 27           moltype = AA  length = 7
FEATURE                 Location/Qualifiers
source                  1..7
                        mol_type = protein
                        organism = synthetic construct
SEQUENCE: 27
GMNAFRA                                                       7

SEQ ID NO: 28           moltype = AA  length = 7
FEATURE                 Location/Qualifiers
source                  1..7
                        mol_type = protein
                        organism = synthetic construct
SEQUENCE: 28
LGETTRP                                                       7

SEQ ID NO: 29           moltype = AA  length = 7
FEATURE                 Location/Qualifiers
source                  1..7
                        mol_type = protein
                        organism = synthetic construct
SEQUENCE: 29
RGDTATL                                                       7

SEQ ID NO: 30           moltype = AA  length = 7
FEATURE                 Location/Qualifiers
source                  1..7
                        mol_type = protein
                        organism = synthetic construct
SEQUENCE: 30
PRGDLAP                                                       7

SEQ ID NO: 31           moltype = AA  length = 7
FEATURE                 Location/Qualifiers
source                  1..7
                        mol_type = protein
                        organism = synthetic construct
SEQUENCE: 31
RGDQQSL                                                       7

SEQ ID NO: 32           moltype = AA  length = 10
FEATURE                 Location/Qualifiers
source                  1..10
                        mol_type = protein
                        organism = synthetic construct
SEQUENCE: 32
EQLSISEEDL                                                    10

SEQ ID NO: 33           moltype = AA  length = 35
FEATURE                 Location/Qualifiers
source                  1..35
                        mol_type = protein
                        organism = synthetic construct
VARIANT                 35
                        note = X can be any amino acid
SEQUENCE: 33
FNMQCQRRFY EALHDPNLNE EQRNAKIKSI RDDCX                        35

SEQ ID NO: 34           moltype = AA  length = 15
FEATURE                 Location/Qualifiers
source                  1..15
                        mol_type = protein
                        organism = synthetic construct
SEQUENCE: 34
GLNDIFEAQK IEWHE                                              15

SEQ ID NO: 35           moltype = AA  length = 13
FEATURE                 Location/Qualifiers
source                  1..13
                        mol_type = protein
                        organism = synthetic construct
SEQUENCE: 35
LCTPSRAALL TGR                                                13

SEQ ID NO: 36           moltype = AA  length = 15
FEATURE                 Location/Qualifiers
source                  1..15
                        mol_type = protein
```

```
                          organism = synthetic construct
SEQUENCE: 36
QVSHWVSGLA EGSFG                                                            15

SEQ ID NO: 37             moltype = AA  length = 15
FEATURE                   Location/Qualifiers
source                    1..15
                          mol_type = protein
                          organism = synthetic construct
SEQUENCE: 37
LSHTSGRVEG SVSLL                                                            15

SEQ ID NO: 38             moltype = AA  length = 7
FEATURE                   Location/Qualifiers
source                    1..7
                          mol_type = protein
                          organism = synthetic construct
SEQUENCE: 38
VTAGRAP                                                                     7

SEQ ID NO: 39             moltype = AA  length = 7
FEATURE                   Location/Qualifiers
source                    1..7
                          mol_type = protein
                          organism = synthetic construct
SEQUENCE: 39
APVTRPA                                                                     7

SEQ ID NO: 40             moltype = AA  length = 7
FEATURE                   Location/Qualifiers
source                    1..7
                          mol_type = protein
                          organism = synthetic construct
SEQUENCE: 40
DLSNLTR                                                                     7

SEQ ID NO: 41             moltype = AA  length = 7
FEATURE                   Location/Qualifiers
source                    1..7
                          mol_type = protein
                          organism = synthetic construct
SEQUENCE: 41
NQVGSWS                                                                     7

SEQ ID NO: 42             moltype = AA  length = 7
FEATURE                   Location/Qualifiers
source                    1..7
                          mol_type = protein
                          organism = synthetic construct
SEQUENCE: 42
EARVRPP                                                                     7

SEQ ID NO: 43             moltype = AA  length = 7
FEATURE                   Location/Qualifiers
source                    1..7
                          mol_type = protein
                          organism = synthetic construct
SEQUENCE: 43
NSVSLYT                                                                     7

SEQ ID NO: 44             moltype = AA  length = 7
FEATURE                   Location/Qualifiers
source                    1..7
                          mol_type = protein
                          organism = synthetic construct
SEQUENCE: 44
NDVRSAN                                                                     7

SEQ ID NO: 45             moltype = AA  length = 7
FEATURE                   Location/Qualifiers
source                    1..7
                          mol_type = protein
                          organism = synthetic construct
SEQUENCE: 45
NESRVLS                                                                     7

SEQ ID NO: 46             moltype = AA  length = 7
FEATURE                   Location/Qualifiers
source                    1..7
```

```
                        mol_type = protein
                        organism = synthetic construct
SEQUENCE: 46
NRTWEQQ                                                          7

SEQ ID NO: 47           moltype = AA  length = 7
FEATURE                 Location/Qualifiers
source                  1..7
                        mol_type = protein
                        organism = synthetic construct
SEQUENCE: 47
NSVQSSW                                                          7

SEQ ID NO: 48           moltype = AA  length = 7
FEATURE                 Location/Qualifiers
source                  1..7
                        mol_type = protein
                        organism = synthetic construct
SEQUENCE: 48
RGDLGLS                                                          7

SEQ ID NO: 49           moltype = AA  length = 7
FEATURE                 Location/Qualifiers
source                  1..7
                        mol_type = protein
                        organism = synthetic construct
SEQUENCE: 49
RGDMSRE                                                          7

SEQ ID NO: 50           moltype = AA  length = 7
FEATURE                 Location/Qualifiers
source                  1..7
                        mol_type = protein
                        organism = synthetic construct
SEQUENCE: 50
ESGLSQS                                                          7

SEQ ID NO: 51           moltype = AA  length = 7
FEATURE                 Location/Qualifiers
source                  1..7
                        mol_type = protein
                        organism = synthetic construct
SEQUENCE: 51
EYRDSSG                                                          7

SEQ ID NO: 52           moltype = AA  length = 7
FEATURE                 Location/Qualifiers
source                  1..7
                        mol_type = protein
                        organism = synthetic construct
SEQUENCE: 52
DLGSARA                                                          7

SEQ ID NO: 53           moltype = AA  length = 7
FEATURE                 Location/Qualifiers
source                  1..7
                        mol_type = protein
                        organism = synthetic construct
SEQUENCE: 53
GPQGKNS                                                          7

SEQ ID NO: 54           moltype = AA  length = 7
FEATURE                 Location/Qualifiers
source                  1..7
                        mol_type = protein
                        organism = synthetic construct
SEQUENCE: 54
NSSRDLG                                                          7

SEQ ID NO: 55           moltype = AA  length = 7
FEATURE                 Location/Qualifiers
source                  1..7
                        mol_type = protein
                        organism = synthetic construct
SEQUENCE: 55
NDVRAVS                                                          7

SEQ ID NO: 56           moltype = AA  length = 7
FEATURE                 Location/Qualifiers
```

```
source                1..7
                      mol_type = protein
                      organism = synthetic construct
SEQUENCE: 56
PRSTSDP                                                                   7

SEQ ID NO: 57         moltype = AA  length = 5
FEATURE               Location/Qualifiers
source                1..5
                      mol_type = protein
                      organism = synthetic construct
SEQUENCE: 57
DIIRA                                                                     5

SEQ ID NO: 58         moltype = AA  length = 12
FEATURE               Location/Qualifiers
source                1..12
                      mol_type = protein
                      organism = synthetic construct
SEQUENCE: 58
SYENVASRRP EG                                                             12

SEQ ID NO: 59         moltype = AA  length = 12
FEATURE               Location/Qualifiers
source                1..12
                      mol_type = protein
                      organism = synthetic construct
SEQUENCE: 59
PENSVRRYGL EE                                                             12

SEQ ID NO: 60         moltype = AA  length = 12
FEATURE               Location/Qualifiers
source                1..12
                      mol_type = protein
                      organism = synthetic construct
SEQUENCE: 60
LSLASNRPTA TS                                                             12

SEQ ID NO: 61         moltype = AA  length = 19
FEATURE               Location/Qualifiers
source                1..19
                      mol_type = protein
                      organism = synthetic construct
SEQUENCE: 61
NDVWNRDNSS KRGGTTEAS                                                      19

SEQ ID NO: 62         moltype = AA  length = 19
FEATURE               Location/Qualifiers
source                1..19
                      mol_type = protein
                      organism = synthetic construct
SEQUENCE: 62
NRTYSSTSNS TSRSEWDNS                                                      19

SEQ ID NO: 63         moltype = AA  length = 7
FEATURE               Location/Qualifiers
source                1..7
                      mol_type = protein
                      organism = synthetic construct
SEQUENCE: 63
ESGHGYF                                                                   7

SEQ ID NO: 64         moltype = AA  length = 7
FEATURE               Location/Qualifiers
source                1..7
                      mol_type = protein
                      organism = synthetic construct
SEQUENCE: 64
GQHPRPG                                                                   7

SEQ ID NO: 65         moltype = AA  length = 7
FEATURE               Location/Qualifiers
source                1..7
                      mol_type = protein
                      organism = synthetic construct
SEQUENCE: 65
PSVSPRP                                                                   7

SEQ ID NO: 66         moltype = AA  length = 7
```

-continued

```
FEATURE                Location/Qualifiers
source                 1..7
                       mol_type = protein
                       organism = synthetic construct
SEQUENCE: 66
VNSTRLP                                                                 7

SEQ ID NO: 67          moltype = AA  length = 7
FEATURE                Location/Qualifiers
source                 1..7
                       mol_type = protein
                       organism = synthetic construct
SEQUENCE: 67
LSPVRPG                                                                 7

SEQ ID NO: 68          moltype = AA  length = 12
FEATURE                Location/Qualifiers
source                 1..12
                       mol_type = protein
                       organism = synthetic construct
SEQUENCE: 68
MSSDPRRPPR DG                                                           12

SEQ ID NO: 69          moltype = AA  length = 12
FEATURE                Location/Qualifiers
source                 1..12
                       mol_type = protein
                       organism = synthetic construct
SEQUENCE: 69
GARPSEVTTR PG                                                           12

SEQ ID NO: 70          moltype = AA  length = 12
FEATURE                Location/Qualifiers
source                 1..12
                       mol_type = protein
                       organism = synthetic construct
SEQUENCE: 70
GNEVLGTKPR AP                                                           12

SEQ ID NO: 71          moltype = AA  length = 19
FEATURE                Location/Qualifiers
source                 1..19
                       mol_type = protein
                       organism = synthetic construct
SEQUENCE: 71
KMRPGAMGTT GEGTRVTRE                                                    19

SEQ ID NO: 72          moltype = AA  length = 7
FEATURE                Location/Qualifiers
source                 1..7
                       mol_type = protein
                       organism = synthetic construct
SEQUENCE: 72
MNVRGDL                                                                 7

SEQ ID NO: 73          moltype = AA  length = 7
FEATURE                Location/Qualifiers
source                 1..7
                       mol_type = protein
                       organism = synthetic construct
SEQUENCE: 73
ENVRGDL                                                                 7

SEQ ID NO: 74          moltype = AA  length = 7
FEATURE                Location/Qualifiers
source                 1..7
                       mol_type = protein
                       organism = synthetic construct
SEQUENCE: 74
KTLLPTP                                                                 7

SEQ ID NO: 75          moltype = AA  length = 12
FEATURE                Location/Qualifiers
source                 1..12
                       mol_type = protein
                       organism = synthetic construct
SEQUENCE: 75
HLNILSTLWK YR                                                           12
```

```
SEQ ID NO: 76           moltype = AA  length = 7
FEATURE                 Location/Qualifiers
source                  1..7
                        mol_type = protein
                        organism = synthetic construct
SEQUENCE: 76
SKAGRSP                                                           7

SEQ ID NO: 77           moltype =   length =
SEQUENCE: 77
000

SEQ ID NO: 78           moltype = AA  length = 9
FEATURE                 Location/Qualifiers
source                  1..9
                        mol_type = protein
                        organism = synthetic construct
SEQUENCE: 78
PERTAMSLP                                                         9

SEQ ID NO: 79           moltype = AA  length = 7
FEATURE                 Location/Qualifiers
source                  1..7
                        mol_type = protein
                        organism = synthetic construct
SEQUENCE: 79
ESGLSOS                                                           7

SEQ ID NO: 80           moltype = AA  length = 7
FEATURE                 Location/Qualifiers
source                  1..7
                        mol_type = protein
                        organism = synthetic construct
SEQUENCE: 80
SEGLKNL                                                           7

SEQ ID NO: 81           moltype = AA  length = 7
FEATURE                 Location/Qualifiers
source                  1..7
                        mol_type = protein
                        organism = synthetic construct
SEQUENCE: 81
SLRSPPS                                                           7

SEQ ID NO: 82           moltype = AA  length = 7
FEATURE                 Location/Qualifiers
source                  1..7
                        mol_type = protein
                        organism = synthetic construct
SEQUENCE: 82
RGDLRVS                                                           7

SEQ ID NO: 83           moltype = AA  length = 7
FEATURE                 Location/Qualifiers
source                  1..7
                        mol_type = protein
                        organism = synthetic construct
SEQUENCE: 83
TLAVPFK                                                           7

SEQ ID NO: 84           moltype = AA  length = 7
FEATURE                 Location/Qualifiers
source                  1..7
                        mol_type = protein
                        organism = synthetic construct
SEQUENCE: 84
YTLSQGW                                                           7

SEQ ID NO: 85           moltype = AA  length = 671
FEATURE                 Location/Qualifiers
source                  1..671
                        mol_type = protein
                        organism = synthetic construct
SEQUENCE: 85
MPPIKRQPRG WVLPGYRYLG PFNPLDNGEP VNNADRAAQL HDHAYSELIK SGKNPYLYFN  60
KADEKFIDDL KDDWSIGGII GSSFFKIKRA VAPALGNKER AQKRHFYFAN SNKGAKKTKK  120
SEPKPGTSKM SDTDIQDQQP DTVDAPQNAS GGGTGSIGGG KGSGVGISTG GWVGGSHFSD  180
KYVVTKNTRQ FITTIQNGHL YKTEAIETTN QSGKSQRCVT TPWTYFNFNQ YSCHFSPQDW  240
QRLTNEYKRF RPKAMQVKIY NLQIKQILSN GADTTYNNDL TAGVHIFCDG EHAYPNASHP  300
```

-continued

```
WDEDVMPDLP YKTWKLFQYG YIPIENELAD LDGNAAGGNA TEKALLYQMP FFLLENSDHQ  360
VLRTGESTEF TFNFDCEWVN NERAYIPPGL MFNPKVPTRR VQYIRQNGST AASTGRIQPY  420
SKPTSWMTGP GLLSAQRVGP QSSDTAPFMV CTNPEGTHIN TGAAGFGSGF DPPSGCLAPT  480
NLEYKLQWYQ TPEGTGNNGN IIANPSLSML RDQLLYKGNQ TTYNLVGDIW MFPNQVWDRF  540
PITRENPIWC KKPRADKHTI MDPFDGSIAM DHPPGTIFIK MAKIPVPTAT NADSYLNIYC  600
TGQVSCEIVW EVERYATKNW RPERRHTALG MSLGGESNYT PTYHVDPTGA YIQPTSYDQC  660
MPVKTNINKV L                                                     671

SEQ ID NO: 86          moltype = DNA  length = 2256
FEATURE                Location/Qualifiers
source                 1..2256
                       mol_type = other DNA
                       note = Canine parvovirus
                       organism = unidentified
SEQUENCE: 86
atggcacctc cggcaaagag agccaggaga ggtaagggtg tgttagtaaa gtggggggag  60
gggaaagatt taataactta actaagtatg tgttttttta taggacttgt gcctccaggt  120
tataaatatc ttgggcctgg gaacagtctt gaccaaggag aaccaactaa cccttctgac  180
gccgctgcaa aagaacacga cgaagcttac gctgcttatc ttcgctctgg taaaaaccca  240
tacttatatt tctcgccagc agatcaacgc tttatagatc aaactaagga cgctaaagat  300
tgggggggga aaataggaca ttattttttt agagctaaaa aggcaattgc tccagtatta  360
actgatacac cagatcatcc atcaacatca agaccaacaa aaccaactaa aagaagtaaa  420
ccaccacctc atattttcat caatcttgca aaaaaaaaaa aagccggtgc aggacaagta  480
aaaagagaca atcttgcacc aatgagtgat ggagcagttc aaccagacgg tggtcagcct  540
gctgtcagaa atgaaagagc tacaggatct gggaacgggt ctggaggcgg gggtggtggt  600
ggttctgggg gtgtggggat ttctacgggt actttcaata atcagacgga atttaaattt  660
ttggaaaacg gatgggtgga aatcacagca aactcaagca gacttgtaca tttaaatatg  720
ccagaaagtg aaaattatag aagagtggtt gtaaataatt tggataaaac tgcagttaac  780
ggaaacatgg ctttagatga tactcatgca caaattgtaa caccttggtc attggttgat  840
gcaaatgctt ggggagtttg gtttaatcca ggagattggc aactaattgt taatactatg  900
agtgagttgc atttagttag ttttgaacaa gaaattttta atgttgtttt aaagactgtt  960
tcagagtctg ctactcagcc accaacaaaa gtttataata atgatttaac tgcatcattg  1020
atggttgcat tagatagtaa taatactatg ccatttactc cagcagctat gagatctgag  1080
acattgggtt tttatccatg gaaaccaacc ataccaactc catggagata ttattttcaa  1140
tgggatagaa cattaatacc atctcatact ggaactagtg gcacaccaac aaatatatac  1200
catggtacag atccagatga cgttcaattt tatactattg aaaattctgt gccagtacac  1260
ttactaagaa caggagatga atttgctaca ggaacatttt tttttgattg taaaccatgt  1320
agactaacac atacatggca aacaaataga gcattgggct taccaccatt tctaaattct  1380
ttgcctcaag ctgaaggagg tactaacttt ggttatatag gagttcaaca agataaaaga  1440
cgtggtgtaa ctcaaatggg aaatacaaac tatattactg aagctactat tatgagacca  1500
gctgaggttg gttatagtgc accatattat tcttttgagg cgtctacaca agggccattt  1560
aaaacaccta ttgcagcagg acggggggga gcgcaaacag atgaaaatca agcagcagat  1620
ggtgatccaa gatatgcatt tggtagacaa catggtcaaa aaactaccac aacaggagaa  1680
acacctgaga gatttacata tatagcacat caagatacag gaagatatcc agaaggagat  1740
tggattcaaa atattaactt taaccttcct gtaacaaatg ataatgtatt gctaccaaca  1800
gatccaattg gaggtaaagc aggaattaac tataccaata tatttaatac ttatggtcct  1860
ttaactgcat taaataatgt accaccagtt tatccaaatg gtcaaatttg ggataaagaa  1920
tttgatactg atttaaaacc aagacttcat gtaaatgcac catttgtttg tcaaaataat  1980
tgtcctggtc aattatttgt aaaagttgcg cctaatttaa caaatgaata tgatcctgat  2040
gcatctgcta atatgtcaag aattgtaact tactcagatt tttggtggaa aggtaaatta  2100
gtatttaaag ctaaactaag agcctctcat acttggaatc caattcaaca aatgagtatt  2160
aatgtagata accaatttaa ctatgtacca agtaatattg gaggtatgaa aattgtatat  2220
gaaaaatctc aactagcacc tagaaaatta tattaa                          2256

SEQ ID NO: 87          moltype = DNA  length = 1764
FEATURE                Location/Qualifiers
source                 1..1764
                       mol_type = other DNA
                       note = Minute virus of mice
                       organism = unidentified
SEQUENCE: 87
atgagtgatg gcaccagcca acctgacagc ggaaacgctg tccactcagc tgcaagagtt  60
gaacgagcag ctgacggccc tggaggctct gggggtgggg gctctggcgg gggtggggtt  120
ggtgtttcta ctgggtctta tgataatcaa acgcattata gattcttggg tgacggctgg  180
gtagaaatta ctgcactagc aactagacta gtacatttaa acatgcctaa atcagaaaac  240
tattgcagaa tcagagttca caatacaaca gacacatcag tcaaaggcaa catggcaaaa  300
gatgatgctc atgagcaaat ttggacacca tggagcttgg tggatgctaa tgcttgggga  360
gtttggctcc agccaagtga ctggcaatac atttgcaaca ccatgagcca gcttaacttg  420
gtatcacttg atcaagaaat attcaatgta gtgctgaaaa ctgttacaga gcaagactta  480
ggaggtcaag ctataaaaat atacaacaat gaccttacag cttgcatgat ggttgcagta  540
gactcaaaca acattttgcc atacacacct gcagcaaact caatggaaac acttggtttc  600
taccccctgga aaccaaccat agcatcacca tacaggtact atttttgcgt tgacagagat  660
ctttcagtga cctacgaaaa tcaagaaggc acagttgaac ataatgtgat gggaacacca  720
aaaggaatga attctcaatt ttttaccatt gagaacacac aacaaatcac attgctcaga  780
acaggggacg aatttgccac aggtacttac tactttgaca caaattcagt taaactcaca  840
cacacgtggc aaaccaaccg tcaacttgga cagcctccac tgctgtcaac ctttcctgaa  900
gctgacactg atgcaggtac acttactgct caagggagca gacatggaac aacacaaatg  960
gggggttaact gggtgagtga agcaatcaga accagacctg ctcaagtagg attttgtcaa  1020
ccacacaatg actttgaagc cagcagagct ggaccatttg ctgccccaaa agttccagca  1080
```

-continued

```
gatattactc aaggagtaga caaagaagcc aatggcagtg ttagatacag ttatggcaaa  1140
cagcatggtg aaaattgggc ttcacatgga ccagcaccag agcgctacac atgggatgaa  1200
acaagctttg gttcaggtag agacaccaaa gatggtttta ttcaatcagc accactagtt  1260
gttccaccac cactaaatgg cattcttaca aatgcaaacc ctattgggac taaaaatgac  1320
attcattttt caaatgtttt taacagctat ggtccactaa ctgcattttc acacccaagt  1380
cctgtatacc ctcaaggaca aatatgggac aaagaactag atcttgaaca caaacctaga  1440
cttcacataa ctgctccatt tgtttgtaaa aacaatgcac ctggacaaat gttggttaga  1500
ttaggaccaa acctaactga ccaatatgat ccaaacggag ccacactttc tagaattgtt  1560
acatacggta catttttctg gaaaggaaaa ctaaccatga gagcaaaact tagagctaac  1620
accacttgga acccagtgta ccaagtaagt gctgaagaca atggcaactc atacatgagt  1680
gtaactaaat ggttaccaac tgctactgga aacatgcagt ctgtgccgct tataacaaga  1740
cctgttgcta gaaatactta ctaa                                         1764

SEQ ID NO: 88          moltype = AA  length = 707
FEATURE                Location/Qualifiers
source                 1..707
                       mol_type = protein
                       note = Bufavirus-1
                       organism = unidentified
SEQUENCE: 88
MPAIRKARGW VPPGYNYLGP FNQDFSKKPT NPSDNAARKH DLEYNKLIKQ GHNPYWNYNH  60
ADEDFIKETD QATDWGGKFG NFVFRAKRAL APELAPPAKK KTKTKHTEPE YSHKHIKAGT  120
KRGKPFYLFV NLARKKARMT DTQDVSEQQS DQPSVASTSA KAGGGGGGGG SGVGHSTGNY  180
NNRTEFYYHG DEVTIVCHSS RHIHLNMSES EEYKIYDTDR GPTFPTDQTL QGRDTINDSY  240
HAQVETPWFL INPNSWGTWM NPADFQQLTT TCREVTLEHL DQTLDNIVIK TVSKQGSGAE  300
ETTQYNNDLT ALLQVALDKS NQLPWVADNM YLDSLGYIPW RPCKLKQYSY HVNFWNTIDI  360
ISGPQQNQWQ QVKKEIKWDD LQFTPIETTT EIDLLRTGDS WTSGPYKFNT KPTQLSYHWQ  420
STRHTGSVHP TEPPNAIGQQ GRNIIDINGW QWGDRSNPMS AATRVSNFHI GYSWPEWRIH  480
YGSGGPAINP GAPFSQAPWS TDPQVRLTQG ASEKAIFDYN HGDDDPAHRD QWWQNNLPMT  540
GQTDWAPKNA HQTNVSNNIP SRQEFWTQDY HNTFGPFTAV DDVGIQYPWG AIWTKTPDTT  600
HKPMMSAHAP FICKDGPPGQ LLVKLAPNYT ENLQTDGLGN NRIVTYATFW WTGKLVLKGK  660
LRLPRQFNLY NLPGRPRGTE AKKFLPNEIG HFELPFMPGR CMPNYTI                707

SEQ ID NO: 89          moltype = AA  length = 751
FEATURE                Location/Qualifiers
source                 1..751
                       mol_type = protein
                       organism = synthetic construct
VARIANT                27
                       note = X can be any amino acid
SEQUENCE: 89
MAPPAKRARR GKGVLVKWGE GKDLITXLSM CFFIGLVPPG YKYLGPGNSL DQGEPTNPSD  60
AAAKEHDEAY AAYLRSGKNP YLYFSPADQR FIDQTKDAKD WGGKIGHYFF RAKKAIAPVL  120
TDTPDHPSTS RPTKPTKRSK PPPHIFINLA KKKKAGAGQV KRDNLAPMSD GAVQPDGGQP  180
AVRNERATGS GNGSGGGGGG GSGGVGISTG TFNNQTEFKF LENGWVEITA NSSRLVHLNM  240
PESENYRRVV VNNMDKTAVN GNMALDDIHA QIVTPWSLVD ANAWGVWFNP GDWQLIVNTM  300
SELHLVSFEQ EIFNVVLKTV SESATQPPTK VYNNDLTASL MVALDSNNTM PFTPAAMRSE  360
TLGFYPWKPT IPTPWRYYFQ WDRTLIPSHT GTSGTPTNIY HGTDPDDVQF YTIENSVPVH  420
LLRTGDEFAT GTFFFDCKPC RLTHTWQTNR ALGLPPFLNS LPQSEGATNF GDIGVQQDKR  480
RGVTQMGNTN YITEATIMRP AEVGYSAPYY SFEASTQGPF KTPIAAGRGG AQTYENQAAD  540
GDPRYAFGRQ HGQKTTTTGE TPERFTYIAH QDTGRYPEGD WIQNINFNLP VTNDNVLLPT  600
DPIGGKTGIN YTNIFNTYGP LTALNNVPPV YPNGQIWDKE FDTDLKPRLH VNAPFVCQNN  660
CPGQLFVKVA PNLTNEYDPD ASANMSRIVT YSDFWWKGKL VFKAKLRASH TWNPIQQMSI  720
NVDNQFNYVP SNIGGMKIVY EKSQLAPRKL Y                                 751

SEQ ID NO: 90          moltype = AA  length = 727
FEATURE                Location/Qualifiers
source                 1..727
                       mol_type = protein
                       note = Canine parvovirus
                       organism = unidentified
SEQUENCE: 90
MAPPAKRARR GLVPPGYKYL GPGNSLDQGE PTNPSDAAAK EHDEAYAAYL RSGKNPYLYF  60
SPADQRFIDQ TKDAKDWGGK IGHYFFRAKK AIAPVLTDTP DHPSTSRPTK PTKRSKPPPH  120
IFINLAKKKK AGAGQVKRDN LAPMSDGGVQ PDGGQPAVRN ERATGSGNGS GGGGGGGSGG  180
VGISTGTFNN QTEFKFLENG WVEITANSSR LVHLNMPESE NYRRVVVNNL DKTAVNGNMA  240
LDDTHAQIVT PWSLVDANAW GVWFNPGDWQ LIVNTMSELH LVSFEQEIFN VVLKTVSESA  300
TQPPTKVYNN DLTASLMVAL DSNNTMPFTP AAMRSETLGF YPWKPTIPTP WRYYFQWDRT  360
LIPSHTGTSG TPTNIYHGTD PDDVQFYTIE NSVPVHLLRT GDEFATGTFY FDCKPCRLTH  420
TWQTNRALGL PPFLNSLPQA EGGTNFGYIG VQQDKRRGVT QMGNTNIITE ATIMRPAEVG  480
YSAPYYSFEA STQGPFKTPI AAGRGGAQTD ENRAADGDPR YAFGRQHGQK TTTTGETPER  540
FTYIAHQDTG RYPEGDWIQN INFNLPVTED NVLLPTDPIG GKTGINYTNI FNTYGPLTAL  600
NNVPPVYPNG QIWDKEFDTD LKPRLHVNAP FVCQNNCPGQ LFVKVAPNLT NEYDPDASAN  660
MSRIVTYSDF WWKGKLVFKA KLRASHTWNP IQQMSINVDN QFNYVPSNIG GMKIVYEKSQ  720
LAPRKLY                                                            727

SEQ ID NO: 91          moltype = AA  length = 707
FEATURE                Location/Qualifiers
source                 1..707
```

```
                         mol_type = protein
                         note = Cutavirus
                         organism = unidentified
SEQUENCE: 91
MPAIRKARGW VPPGYNFLGP FNQDFNKEPT NPSDNAAKQH DLEYNKLINQ GHNPYWYYNK  60
ADEDFIKATD QAPDWGGKFG NFIFRAKKHI APELAPPAKK KSKTKHPEPE FSHKHIKPGT  120
KRGKPFHIFV NLARKRARMS EPAENTNDQP NDSPVEQGAG QIGGGGGGGG SGVGHSTGDY  180
NNRTEFIYHG DEVTIICHST RLVHINMSDR EDYIIYETDR GQLFPTTQDL QGRDTLNDSY  240
HAKVETPWKL LHANSWGCWF SPADFQQMIT TCRDIAPIQM HQKIENIVIK TVSKTGTGET  300
ETTNYNNDLT ALLQIAQDNS NLLPWAADNF YIDSVGYVPW RACKLPTYCY HVDTWNTIDI  360
NQADAPNRWR EIKKGIQWDN IQFTPLETMI NIDLLRTGDA WQSGNYNFHT KPTNLAYHWQ  420
SQRHTGSCHP TVAPLVERGQ GTNIQSVNCW QWGDRNNPSS ASTRVSNMHI GYSFPEWQIH  480
YSTGGPVINP GSAFSQAPWG STTEGTRLTQ GASEKAIYDW AHGDDQPGAR ETWWQNNQHV  540
TGQTDWAPKN AHTSELNNNV PAATHFWKNS YHNTFSPFTA VDDHGPQYPW GAIWGKYPDT  600
THKPMMSAHA PFLLHGPPGQ LFVKLAPNYT DTLDNGGVTH PRIVTYGTFW WSGKLIFKGK  660
LRTPRQWNTY NLPSLDKRET MKNTVPNEVG HFELPYMPGR CLPNYTL                707

SEQ ID NO: 92            moltype = AA  length = 707
FEATURE                  Location/Qualifiers
source                   1..707
                         mol_type = protein
                         note = Cutavirus
                         organism = unidentified
SEQUENCE: 92
MPAIRKARGW VPPGYNFLGP FNQDFNKEPT NPSDNAAKQH DLEYNKLINQ GHNPYWYYNK  60
ADEDFIKATD QAPDWGGKFG NFIFRAKKHI APELAPPAKK KSKTKHSEPE FSHKHIKPGT  120
KRGKPFHIFV NLARKRARMS EPANDTNEQP DNSPVEQGAG QIGGGGGGGG SGVGHSTGDY  180
NNRTEFIYHG DEVTIICHST RLVHINMSDR EDYIIYETDR GPLFPTTQDL QGRDTLNDSY  240
HAKVETPWKL LHANSWGCWF SPADFQQMIT TCRDIAPIKM HQKIENIVIK TVSKTGTGET  300
ETTNYNNDLT ALLQIAQDNS NLLPWAADNF YIDSVGYVPW RACKLPTYCY HVDTWNTIDI  360
NQADTPNQWR EIKKGIQWDN IQFTPLETMI NIDLLRTGDA WESGNYNFHT KPTNLAYHWQ  420
SQRHTGSCHP TVAPLVERGQ GTNIQSVNCW QWGDRNNPSS ASTRVSNIHI GYSFPEWQIH  480
YSTGGPVINP GSAFSQAPWG STTEGTRLTQ GASEKAIYDW SHGDDQPGAR ETWWQNNQHV  540
TGQTDWAPKN AHTSELNNNV PAATHFWKNS YHNTFSPFTA VDDHGPQYPW GAIWGKYPDT  600
THKPMMSAHA PFLLHGPPGQ LFVKLAPNYT DTLDNGGVTH PRIVTYGTFW WSGQLIFKGK  660
LRTPRQWNTY NLPSLDKRET MKNTVPNEVG HFELPYMPGR CLPNYTL                707

SEQ ID NO: 93            moltype = AA  length = 727
FEATURE                  Location/Qualifiers
source                   1..727
                         mol_type = protein
                         note = Feline panleukopenia virus
                         organism = unidentified
SEQUENCE: 93
MAPPAKRARR GLVPPGYKYL GPGNSLDQGE PTNPSDAAAK EHDEAYAAYL RSGKNPYLYF  60
SPADQRFIDQ TKDAKDWGGK IGHYFFRAKK AIAPVLTDTP DHPSTSRPTK PTKRSKPPPH  120
IFINLAKKKK AGAGQVKRDN LAPMSDGAVQ PDGGQPAVRN ERATGSGNGS GGGGGGGSGG  180
VGISTGTFNN QTEFKFLENG WVEITANSSR LVHLNMPESE NYKRVVVNNM DKTAVKGNMA  240
LDDIHVQIVT PWSLVDANAW GVWFNPGDWQ LIVNTMSELH LVSFEQEIFN VVLKTVSESA  300
TQPPTKVYNN DLTASLMVAL DSNNTMPFTP AAMRSETLGF YPWKPTIPTP WRYYFQWDRT  360
LIPSHTGTSG TPTNVYHGTD PDDVQFYTIE NSVPVHLLRT GDEFATGTFF FDCKPCRLTH  420
TWQTNRALGL PPFLNSLPQS EGATNYGDIG VQQDKRRGVT QMGNTDYITE ATIMRPAEVG  480
YSAPYYSFEA STQGPFKTPI AAGRGGAQTD ENQAADGDPR YAFGRQHGQK TTTTGETPER  540
FTYIAHQDTG RYPEGDWIQN INFNLPVTND NVLLPTDPIG GKTGINYTNI FNTYGPLTAL  600
NNVPPVYPNG QIWDKEFDTD LKPRLHVNAP FVCQNNCPGQ LFVKVAPNLT NEYDPDASAN  660
MSRIVTYSDF WWKGKLVFKA KLRASHTWNP IQQMSINVDN QFNYVPNNIG AMKIVYEKSQ  720
LAPRKLY                                                            727

SEQ ID NO: 94            moltype = AA  length = 727
FEATURE                  Location/Qualifiers
source                   1..727
                         mol_type = protein
                         note = Feline panleukopenia virus
                         organism = unidentified
SEQUENCE: 94
MAPPAKRARR GLVPPGYKYL GPGNSLDQGE PTNPSDAAAK EHDEAYAAYL RSGKNPYLYF  60
SPADQRFIDQ TKDAKDWGGK IGHYFFRAKK AIAPVLTDTP DHPSTSRPTK PTKRSKPPPH  120
IFINLAKKKK AGAGQVKRDN LAPMSDGAVQ PDGGQPAVRN ERATGSGNGS GGGGGGGSGG  180
VGISTGTFNN QTEFKFLENG WVEITANSSR LVHLNMPESE NYKRVVVNNM DKTAVKGNMA  240
LDDTHVQIVT PWSLVDANAW GVWFNPGDWQ LIVNTMSELH LVSFEQEIFN VVLKTVSESA  300
TQPPTKVYNN DLTASLMVAL DSNNTMPFTP AAMRSETLGF YPWKPTIPTP WRYYFQWDRT  360
LIPSHTGTSG TPTNVYHGTD PDDVQFYTIE NSVPVHLLRT GDEFATGTFF FDCKPCRLTH  420
TWQTNRALGL PPFLNSLPQS EGATNFGDIG VQQDKRRGVT QMGNTDYITE ATIMRPAEVG  480
YSAPYYSFEA STQGPFKTPI AAGRGGAQTD ENQAADGDPR YAFGRQHGQK TTTTGETPER  540
FTYIAHQDTG RYPEGDWIQN INFNLPVTND NVLLPTDPIG GKTGINYTNI FNTYGPLTAL  600
NNVPPVYPNG QIWDKEFDTD LKPRLHVNAP FVCQNNCPGQ LFVKVAPNLT NEYDPDASAN  660
MSRIVTYSDF WWKGKLVFKA KLRASHTWNP IQQMSINVDN QFNYVPNNIG AMKIVYEKSQ  720
LAPRKLY                                                            727
```

-continued

```
SEQ ID NO: 95          moltype = AA  length = 729
FEATURE                Location/Qualifiers
source                 1..729
                       mol_type = protein
                       note = Minute virus of mice
                       organism = unidentified
SEQUENCE: 95
MAPPAKRAKR GWVPPGYKYL GPGNSLDQGE PTNPSDAAAK EHDEAYDQYI KSGKNPYLYF  60
SAADQRFIDQ TKDAKDWGGK VGHYFFRTKR AFAPKLATDS EPGTSGVSRA GKRTRPPAYI  120
FINQARAKKK LTSSAAQQSS QTMSDGTSQP DSGNAVHSAA RVERAADGPG GSGGGGSGGG  180
GVGVSTGSYD NQTHYRFLGD GWVEITALAT RLVHLNMPKS ENYCRIRVHN TTDTSVKGNM  240
AKDDAHEQIW TPWSLVDANA WGVWLQPSDW QYICNTMSQL NLVSLDQEIF NVVLKTVTEQ  300
DLGGQAIKIY NNDLTACMMV AVDSNNILPY TPAANSMETL GFYPWKPTIA SPYRYYFCVD  360
RDLSVTYENQ EGTVEHNVMG TPKGMNSQFF TIENTQQITL LRTGDEFATG TYYFDTNSVK  420
LTHTWQTNRQ LGQPPLLSTF PEADTDAGTL TAQGSRHGTT QMGVNWVSEA IRTRPAQVGF  480
CQPHNDFEAS RAGPFAAPKV PADITQGVDK EANGSVRYSY GKQHGENWAS HGPAPERYTW  540
DETSFGSGRD TKDGFIQSAP LVVPPPLNGI LTNANPIGTK NDIHFSNVFN SYGPLTAFSH  600
PSPVYPQGQI WDKELDLEHK PRLHITAPFV CKNNAPGQML VRLGPNLTDQ YDPNGATLSR  660
IVTYGTFFWK GKLTMRAKLR ANTTWNPVYQ VSAEDNGNSY MSVTKWLPTA TGNMQSVPLI  720
TRPVARNTY                                                        729

SEQ ID NO: 96          moltype = AA  length = 715
FEATURE                Location/Qualifiers
source                 1..715
                       mol_type = protein
                       note = Tusavirus 1
                       organism = unidentified
SEQUENCE: 96
MAPAARPRKG WVPPGYNYLG PGNDLDAGEP TNKSDAAARK HDFAYSAYLK QGLDPYWNFN  60
KADEKFIRDT EGATDWGGRL GHWIFRAKKH ILPHLKEPTL AGRKRPAPAH IFVNLANKRK  120
KGLPTRKDQQ KDTLDSNAQQ PVREADQPDG MAASSSDSGP SSSGGGARAG GVGVSTGDFD  180
NTTLWDFHED GTATITCNST RLVHLTRPDS LDYKIIPTQN NTAVQTVGHM MDDDNHTQVL  240
TPWSLVDCNA WGVWLSPHDW QHIMNIGEEL ELLSLEQEVF NVTLKTATET GPPESRITMY  300
NNDLTAVMMI TTDTNNQLPY TPAAIRSETL GFYPWRPTVV PRWRYYFDWD RFLSVTSSSD  360
QSTSIINHSS TQSAIGQFFV IETQLPIALL RTGDSYATGG YKFDCNKVNL GRHWQTTRSL  420
GLPPKIEPPT SESALGTINQ NARLGWRWGI NDVHETNVVR PCTAGYNHPE WFYTHTLEGP  480
AIDPAPPTSI PSNWGGGTPP DTRASSHNQQ RITYNYNHGN KDENLNNFSL NPNIELGSII  540
NQGNFLSYEG NGQQINTTAG VGKNGETATS DPNLVRYMPN TYGVYTAVDH QGPVYPHGQI  600
WDKQIHTDKK PELHCLAPFT CKNNPPGQMF VRIAPNLTDT FNATPTFSEI ITYADFWWKG  660
TLKMKIKLRP PHQWNIATVL GAAVNIGDAA RFVPNRLGQL EFPVINGRIV PSTVY       715

SEQ ID NO: 97          moltype = DNA  length = 2169
FEATURE                Location/Qualifiers
source                 1..2169
                       mol_type = other DNA
                       organism = synthetic construct
SEQUENCE: 97
ctggcacctc cggcaaagag agccaggaga ggatataaat atcttgggcc tgggaacagt  60
cttgaccaag gagaaccaac taacccttct gacgccgctg caaaagaaca cgacgaagct  120
tacgctgctt atcttcgctc tggtaaaaac ccatacttat atttctcgcc agcagatcaa  180
cgctttatag atcaaactaa ggacgctaaa gattgggggg ggaaaatagg acattatttt  240
tttagagcta aaaaggcaat tgctccagta ttaactgata caccagatca tccatcaaca  300
tcaagaccaa caaaaccaac taaaagaagt aaaccaccac ctcatatttt catcaatctt  360
gcaaaaaaaa aaaaagccgg tgcaggacaa gtaaaaagag acaatcttgc accaatgagt  420
gatggagcag ttcaaccaga cggtggtcaa cctgctgtca gaaatgaaag agctacagga  480
tctgggaacg ggtctggagg cgggggtggt ggtggttctg gggtgtggg gatttctacg  540
ggtactttca ataatcagac ggaatttaaa tttttggaaa acggatgggt ggaaatcaca  600
gcaaactcaa gcagacttgt acatttaaat atgccagaaa gtgaaaatta tagaagagtg  660
gttgtaaata atatggataa aactgcagtt aacggaaaca tggctttaga tgatattcat  720
gcacaaattg taacaccttg gtcattggtt gatgcaaatg cttggggagt ttggtttaat  780
ccaggagatt ggcaactaat tgttaatact atgagtgagt tgcatttagt tagttttgaa  840
caagaaattt ttaatgttgt tttaaagact gtttcagaat ctgctactca gccaccaact  900
aaagtttata ataatgattt aactgcatca ttgatggttg cattagatag taataatact  960
atgccattta ctccagcagc tatgagatct gagacattgg gtttttatcc atggaaacca  1020
accataccaa ctccatggag atattatttt caatgggata gaacattaat accatctcat  1080
actggaacta gtggcacacc aacaaatata taccatggta cagatccaga tgatgttcaa  1140
ttttatacta ttgaaaattc tgtgccagta cacttactaa gaacaggtga tgaatttgct  1200
acaggaacat tttttttga ttgtaaacca tgtagactaa cacatacatg gcaaacaaat  1260
agagcattgg gcttaccacc atttctaaat tctttgcctc aatctgaagg agctactaac  1320
tttggtgata taggagttca acaagataaa agacgtggtg taactcaaat gggaaataca  1380
aactatatta ctgaagctac tattatgaga ccagctgagg ttggttatag tgcaccatat  1440
tattcttttg aggcgtctac acaagggcca tttaaaacac ctattgcagc aggacggggg  1500
ggagcgcaaa catatgaaaa tcaagcagca gatggtgatc caagatatgc atttggtaga  1560
caacatggtc aaaaaactac cacaacagga gaaacacctg agagatttac atatatagca  1620
catcaagata caggaagata tccagaagga gattggattc aaaatattaa ctttaacctt  1680
cctgtaacga atgataatgt attgctacca acagatccaa ttggaggtaa aacaggaatt  1740
aactatacta atatatttaa tacttatggt cctttaactg cattaaataa tgtaccacca  1800
gtttatccaa atggtcaaat ttgggataaa gaatttgata ctgacttaaa accaagactt  1860
catgtaaatg caccatttgt ttgtcaaaat aattgtcctg gtcaattatt tgtaaaagtt  1920
```

```
gcgcctaatt taacaaatga atatgatcct gatgcatctg ctaatatgtc aagaattgta  1980
acttactcag atttttggtg gaaaggtaaa ttagtattta aagctaaact aagagcctct  2040
catacttgga atccaattca acaaatgagt attaatgtag ataaccaatt taactatgta  2100
ccaagtaata ttggaggtat gaaaattgta tatgaaaaat ctcaactagc acctagaaaa  2160
ttatattaa                                                          2169

SEQ ID NO: 98          moltype = DNA  length = 402
FEATURE                Location/Qualifiers
source                 1..402
                       mol_type = other DNA
                       organism = synthetic construct
SEQUENCE: 98
ctggctccag ctattagaaa agccagaggt tacaacttcc taggaccctt caatcaagac  60
ttcaacaaag aaccaactaa tccatcagac aacgctgcaa aacaacacga tttggaatac  120
aacaaactaa tcaaccaagg acacaatcct tattggtact acaacaaagc tgacgaagac  180
ttcatcaaag caacagatca agcaccagac tggggaggaa aatttggcaa cttcatcttc  240
agagccaaaa aacacatcgc tccagaactg gcaccaccag caaaaaagaa aagcaaaacc  300
aaacacagtg aaccagaatt cagccacaaa cacatcaaac caggcaccaa aagaggtaag  360
ccttttcata tttttgtaaa ccttgctaga aaaagagccc gc                    402

SEQ ID NO: 99          moltype = DNA  length = 2094
FEATURE                Location/Qualifiers
source                 1..2094
                       mol_type = other DNA
                       organism = synthetic construct
SEQUENCE: 99
acgccagcta ttagaaaagc cagaggaccc ttcaatcaag acttcaacaa agaaccaact  60
aatccatcag acaacgctgc aaaacaacac gatttggaat acaacaaact aatcaaccaa  120
ggacacaatc cttattggta ctacaacaaa gctgacgaag acttcatcaa agcaacagat  180
caagcaccag actggggagg aaaatttggc aacttcatct tcagagccaa aaaacacatc  240
gctccagaac tggcaccacc agcaaaaaag aaaagcaaaa ccaaacacag tgaaccagaa  300
ttcagccaca aacacatcaa accaggcacc aaaagaggta agccttttca tatttttgta  360
aaccttgcta gaaaaagagc ccgcatgtca gaaccagcta atgatacaaa tgaacaacca  420
gacaactccc ctgttgaaca gggtgctggt caaattggag gaggtggagg tggaggtgga  480
agcggtgtcg ggcacagcac tggtgattat aataatagga ctgagtttat ttatcatggt  540
gatgaagtca caattatttg ccactctaca agactggttc acatcaatat gtcagacagg  600
gaagactaca tcatctatga aacagacaga ggaccactct ttcctaccac tcaggacctg  660
cagggtagag acactctaaa tgactcttac catgccaaag tagaaacacc atggaaacta  720
ctccatgcaa acagctgggg ctgctggttt tcaccagcag acttccaaca aatgatcacc  780
acatgcagag acatagcacc aataaaaatg caccaaaaaa tagaaaacat tgtcatcaaa  840
acagtcagta aaacaggcac aggagaaaca gaaacaacca actacaacaa tgacctcaca  900
gcactcctac aaattgcaca agacaacagt aacctactac catgggctgc agataacttt  960
tatatagact cagtaggtta cgttccatgg agagcatgca aactaccaac ctactgctac  1020
cacgtagaca cttggaatac aattgacata aaccaagcag acacaccaaa ccaatggaga  1080
gaaatcaaaa aaggcatcca atgggacaat atccaattca caccactaga aactatgata  1140
aacattgact tactaagaac aggagatgcc tgggaatctg gtaactacaa tttccacaca  1200
aaaccaacaa acctagctta ccattggcaa tcacaaagac acacaggcag ctgtcaccca  1260
acagtagcac ctctagttga aagaggacaa ggaaccaaca tacaatcagt aaactgttgg  1320
caatggggag acagaaacaa tccaagctct gcatcaacca gagtatccaa tatacatatt  1380
ggatactcat ttccagaatg gcaaatccac tactcaacag gaggaccagt aattaatcca  1440
ggcagtgcat tctcacaagc accatggggc tcaacaactg aaggcaccag actaacccaa  1500
ggtgcatctg aaaaagccat ctatgactgg tcccatggag atgaccaacc aggagccaga  1560
gaaacctggt ggcaaaacaa ccaacatgta acaggacaaa ctgactgggc accaaaaaat  1620
gcacacacct cagaactcaa caacaatgta ccagcagcca cacacttctg gaaaaacagc  1680
tatcacaaca ccttctcacc attcactgca gtagatgatc atggaccaca atatccatgg  1740
ggagccatct ggggaaaata cccagacacc acacacaaac caatgatgtc agctcacgca  1800
ccattcctac ttcatggacc acctggacaa ctctttgtaa aactagcacc aaactataca  1860
gacacacttg acaacggagg tgtaacacat cccagaatcg tcacatatgg aaccttctgg  1920
tggtcaggac aactcatctt taaaggaaaa ctacgcactc caagacaatg gaatacctac  1980
aacctaccaa gcctagacaa aagagaaacc atgaaaaaca cagtaccaaa tgaagttggt  2040
cactttgaac taccatacat gccaggaaga tgtctaccaa actacacatt gtaa        2094

SEQ ID NO: 100         moltype = DNA  length = 2169
FEATURE                Location/Qualifiers
source                 1..2169
                       mol_type = other DNA
                       organism = synthetic construct
SEQUENCE: 100
ctggcacctc cggcaaagag agccaggaga ggatataaat atcttgggcc tgggaacagt  60
cttgaccaag gagaaccaac taacccttct gacgccgctg caaaagaaca cgacgaagct  120
tacgctgctt atcttcgctc tggtaaaaac ccatacttat atttctcgcc agcagatcaa  180
cgctttatag atcaaactaa ggacgctaaa gattgggggg ggaaaatagg acattatttt  240
tttagagcta aaaaggcaat tgctccagta ttaactgata caccagatca tccatcaaca  300
tcaagaccaa caaaaccaac taaaagaagt aaaccaccac ctcatatttt catcaatctt  360
gcaaaaaaaa aaaaagccgg tgcaggacaa gtaaaaagag acaatcttgc accaatgagt  420
gatggagcag ttcaaccaga cggtggtcaa cctgctgtca gaaatgaaag agctacagga  480
tctgggaacg ggtctggagg cgggggtggt ggtggttctg ggggtgtggg gatttctacg  540
ggtactttca ataatcagac ggaatttaaa tttttggaaa acggatgggt ggaaatcaca  600
gcaaactcaa gcagacttgt acatttaaat atgccagaaa gtgaaaatta taaaagagta  660
```

```
gttgtaaata atatggataa aactgcagtt aaaggaaaca tggctttaga tgatattcat  720
gtacaaattg taacaccttg gtcattggtt gatgcaaatg cttggggagt ttggtttaat  780
ccaggagatt ggcaactaat tgttaatact atgagtgagt tgcatttagt tagttttgaa  840
caagaaattt ttaatgttgt tttaaagact gtttcagaat ctgctactca gccaccaact  900
aaagtttata ataatgattt aactgcatca ttgatggttg cattagatag taataatact  960
atgccattta ctccagcagc tatgagatct gagacattgg gtttttatcc atggaaacca  1020
accataccaa ctccatggag atattatttt caatgggata gaacattaat accatctcat  1080
actggaacta gtggcacacc aacaaatata taccatggta cagatccaga tgatgttcaa  1140
ttttatacta ttgaaaattc tgtgccagta cacttactaa gaacaggtga tgaatttgct  1200
acaggaacat ttttttttga ttgtaaacca tgtagactaa cacatacatg gcaaacaaat  1260
agagcattgg gcttaccacc atttttaaat tctttgcctc aatctgaagg agctactaac  1320
tttggtgata taggagttca acaagataaa agacgtggtg taactcaaat gggaaataca  1380
aactatatta ctgaagctac tattatgaga ccagctgagg ttggttatag tgcaccatat  1440
tattcttttg aggcgtctac acaagggcca tttaaaacac ctattgcagc aggacggggg  1500
ggagcgcaaa cagatgaaaa tcaagcagca gatggtgatc caagatatgc atttggtaga  1560
caacatggtc aaaaaactac cacaacagga gaaacacctg agagatttac atatatagca  1620
catcaagata caggaagata tccagaagga gattggattc aaaatattaa ctttaacctt  1680
cctgtaacaa atgataatgt attgctacca acagatccaa ttggaggtaa aacaggaatt  1740
aactatacta atatatttaa tacttatggt cctttaactg cattaaataa tgtaccacca  1800
gtttatccaa atggtcaaat ttgggataaa gaatttgata ctgacttaaa accaagactt  1860
catgtaaatg caccatttgt ttgtcaaaat aattgtcctg gtcaattatt tgtaaaagtt  1920
gcgcctaatt taacaaatga atatgatcct gatgcatctg ctaatatgtc aagaattgta  1980
acttactcag atttttggtg gaaaggtaaa ttagtattta aagctaaact aagagcctct  2040
catacttgga atccaattca acaaatgagt attaatgtag ataaccaatt taactatgta  2100
ccaagtaata ttggagctat gaaaattgta tatgaaaaat ctcaactagc acctagaaaa  2160
ttatattaa                                                          2169

SEQ ID NO: 101          moltype = DNA  length = 2175
FEATURE                 Location/Qualifiers
source                  1..2175
                        mol_type = other DNA
                        organism = synthetic construct
SEQUENCE: 101
acggcgcctc cagctaaaag agctaaaaga ggctacaagt acctgggacc agggaacagc  60
cttgaccaag gagaaccaac caatccatct gacgccgctg ccaaagagca cgacgaggcc  120
tacgatcaat acatcaaatc tggaaaaaat ccttacctgt acttctctgc tgctgatcaa  180
cgctttattg accaaaccaa ggacgccaaa gactggggag gcaaggttgg tcactacttt  240
tttagaacca agcgcgcttt tgcacctaag cttgctactg actctgaacc tggaacttct  300
ggtgtaagca gagctggtaa acgcactaga ccacctgctt acatttttat taaccaagcc  360
agagctaaaa aaaaacttac ttcttctgct gcacagcaaa gcagtcaaac catgagtgat  420
ggcaccagcc aacctgacag cggaaacgct gtccactcag ctgcaagagt tgaacgagca  480
gctgacggcc ctggaggctc tgggggtggg ggctctggcg ggggtggggt tggtgtttct  540
actgggtctt atgataatca aacgcattat agattcttgg gtgacggctg ggtagaaatt  600
actgcactag caactagact agtacattta aacatgccta aatcagaaaa ctattgcaga  660
atcagagttc acaatacaac agacacatca gtcaaaggca acatggcaaa agatgatgct  720
catgagcaaa tttggacacc atggagcttg gtggatgcta atgcttgggg agtttggctc  780
cagccaagtg actggcaata catttgcaac accatgagcc agcttaactt ggtatcactt  840
gatcaagaaa tattcaatgt agtgctgaaa actgttacag agcaagactt aggaggtcaa  900
gctataaaaa tatacaacaa tgaccttaca gcttgcatga tggttgcagt agactcaaac  960
aacattttgc catacacacc tgcagcaaac tcaatggaaa cacttggttt ctacccctgg  1020
aaaccaacca tagcatcacc atacaggtac tatttttgcg ttgacagaga tctttcagtg  1080
acctacgaaa atcaagaagg cacagttgaa cataatgtga tgggaacacc aaaaggaatg  1140
aattctcaat tttttaccat tgagaacaca caacaaatca cattgctcag aacaggggac  1200
gaatttgcca caggtactta ctactttgac acaaattcag ttaaactcac acacacgtgg  1260
caaaccaacc gtcaacttgg acagcctcca ctgctgtcaa cctttcctga agctgacact  1320
gatgcaggta cacttactgc tcaagggagc agacatggaa caacacaaat gggggttaac  1380
tgggtgagtg aagcaatcag aaccagacct gctcaagtag gattttgtca accacacaat  1440
gactttgaag ccagcagagc tggaccattt gctgccccaa aagttccagc agatattact  1500
caaggagtag acaaagaagc caatggcagt gttagataca gttatggcaa acagcatggt  1560
gaaaattggg cttcacatgg accagcacca gagcgctaca catgggatga aacaagcttt  1620
ggttcaggta gagacaccaa agatggtttt attcaatcag caccactagt tgttccacca  1680
ccactaaatg gcattcttac aaatgcaaac cctattggga ctaaaaatga cattcatttt  1740
tcaaatgttt ttaacagcta tggtccacta actgcatttt cacacccaag tcctgtatac  1800
cctcaaggac aaatatggga caaagaacta gatcttgaac acaaacctag acttcacata  1860
actgctccat ttgtttgtaa aaacaatgca cctggacaaa tgttggttag attaggacca  1920
aacctaactg accaatatga tccaaacgga gccacacttt ctagaattgt tacatacggt  1980
acatttttct ggaaaggaaa actaaccatg agagcaaaac ttagagctaa caccacttgg  2040
aacccagtgt accaagtaag tgctgaagac aatggcaact catacatgag tgtaactaaa  2100
tggttaccaa ctgctactgg aaacatgcag tctgtgccgc ttataacaag acctgttgct  2160
agaaatactt actaa                                                   2175

SEQ ID NO: 102          moltype = DNA  length = 2193
FEATURE                 Location/Qualifiers
source                  1..2193
                        mol_type = other DNA
                        organism = synthetic construct
SEQUENCE: 102
acggcacctc cagctaaaag agctaaaaga ggctacaagt acctgggacc agggaacagc  60
cttgaccaag gagaaccaac caacccttct gacgccgctg ccaaagaaca cgacgaagcc  120
```

-continued

```
tacgaccaat acatcaaatc tggaaaaaat ccttacctgt acttctctcc tgctgatcaa  180
cgcttcattg accaaaccaa agacgccaag gactggggcg gcaaggttgg tcactacttt  240
tttagaacca agcgagcttt tgcacctaag ctttctactg actctgaacc tggcacttct  300
ggtgtgagca gacctggtaa acgaactaaa ccacctgctc acatttttgt aaatcaagcc  360
agagctaaaa aaaaacgcgc ttctcttgct gcacagcaga ggactctgac aatgagtgat  420
ggcaccgaaa caaaccaacc agacactgga atcgctaatg ctagagttga gcgatcagct  480
gacggaggtg gaagctctgg gggtgggggc tctggcgggg gtgggattgg tgtttctact  540
gggacttatg ataatcaaac gacttataag tttttgggag atggatgggt agaaataact  600
gcacatgctt ctagactttt gcacttggga atgcctcctt cagaaaacta ctgccgcgtc  660
accgttcaca ataatcaaac aacaggacac ggaactaagg taaagggaaa catggcctat  720
gatgacacac atcaacaaat ttggacacca tggagcttgg tagatgctaa tgcttgggga  780
gtttggttcc aaccaagtga ctggcagttc attcaaaaca gcatggaatc gctgaatctt  840
gactcattga gccaagaact atttaatgta gtagtcaaaa cagtcactga acaacaagga  900
gctggccaag atgccattaa agtctataat aatgacttga cggcctgtat gatggttgct  960
ctggatagta acaacatact gccttacaca cctgcagctc aaacatcaga aacacttggt  1020
ttctacccat ggaaaccaac cgcaccagct ccttacagat actacttttt catgcctaga  1080
caactcagtg taacctctag caactctgct gaaggaactc aaatcacaga caccattgga  1140
gagccacagg cactaaactc tcaatttttt actattgaga acaccttgcc tattactctc  1200
ctgcgcacag gtgatgagtt tacaactggc acctacatct ttaacactga cccacttaaa  1260
cttactcaca catggcaaac caacagacac ttgggcatgc ctccaagaat aactgaccta  1320
ccaacatcag atacagcaac agcatcacta actgcaaatg gagacagatt tggatcaaca  1380
caaacacaga atgtgaacta tgtcacagag gctttgcgca ccaggcctgc tcagattggc  1440
ttcatgcaac ctcatgacaa ctttgaagca aacagaggtg gcccatttaa ggttccagtg  1500
gtaccgctag acataacagc tggcgaggac catgatgcaa acggagccat acgatttaac  1560
tatggcaaac aacatggcga agattgggcc aaacaaggag cagcaccaga aaggtacaca  1620
tgggatgcaa ttgatagtgc agctgggagg gacacagcta gatgctttgt acaaagtgca  1680
ccaatatcta ttccaccaaa ccaaaaccag atcttgcagc gagaagacgc catagctggc  1740
agaactaaca tgcattatac taatgttttt aacagctatg gtccacttag tgcatttcct  1800
catccagatc ccatttatcc aaatggacaa atttgggaca aagaattgga cctggaacac  1860
aaacctagac tacacgtaac tgcaccattt gtttgtaaaa acaacccacc aggtcaacta  1920
tttgttcgct tggggcctaa tctgactgac caatttgacc caaacagcac aactgtttct  1980
cgcattgtta catatagcac tttttactgg aagggtattt tgaaattcaa agccaaacta  2040
agaccaaatc tgacctggaa tcctgtatac caagcaacca cagactctgt tgccaattct  2100
tacatgaatg ttaagaaatg gctcccatct gcaactggca acatgcactc tgatccattg  2160
atttgtagac ctgtgcctca catgacatac taa                              2193
```

```
SEQ ID NO: 103          moltype = AA  length = 702
FEATURE                 Location/Qualifiers
source                  1..702
                        mol_type = protein
                        organism = synthetic construct
SEQUENCE: 103
MPAIRKARGY NYLGPFNQDF SKKPTNPSDN AARKHDLEYN KLIKQGHNPY WNYNHADEDF  60
IKETDQATDW GGKFGNFVFR AKRALAPELA PPAKKKTKTK HTEPEYSHKH IKAGTKRGKP  120
FYLFVNLARK KARMTDTQDV SEQQSDQPSV ASTSAKAGGG GGGGGSGVGH STGNYNNRTE  180
FYYHGDEVTI VCHSSRHIHL NMSESEEYKI YDTDRGPTFP TDQTLQGRDT INDSYHAQVE  240
TPWFLINPNS WGTWMNPADF QQLTTTCREV TLEHLDQTLD NIVIKTVSKQ GSGAEETTQY  300
NNDLTALLQV ALDKSNQLPW VADNMYLDSL GYIPWRPCKL KQYSYHVNFW NTIDIISGPQ  360
QNQWQQVKKE IKWDDLQFTP IETTTEIDLL RTGDSWTSGP YKFNTKPTQL SYHWQSTRHT  420
GSVHPTEPPN AIGQQGRNII DINGWQWGDR SNPMSAATRV SNFHIGYSWP EWRIHYGSGG  480
PAINPGAPFS QAPWSTDPQV RLTQGASEKA IFDYNHGDDD PAHRDQWWQN NLPMTGQTDW  540
APKNAHQTNV SNNIPSRQEF WTQDYHNTFG PFTAVDDVGI QYPWGAIWTK TPDTTHKPMM  600
SAHAPFICKD GPPGQLLVKL APNYTENLQT DGLGNNRIVT YATFWWTGKL VLKGKLRLPR  660
QFNLYNLPGR PRGTEAKKFL PNEIGHFELP FMPGRCMPNY TI                    702
```

```
SEQ ID NO: 104          moltype = AA  length = 722
FEATURE                 Location/Qualifiers
source                  1..722
                        mol_type = protein
                        organism = synthetic construct
SEQUENCE: 104
LAPPAKRARR GYKYLGPGNS LDQGEPTNPS DAAAKEHDEA YAAYLRSGKN PYLYFSPADQ  60
RFIDQTKDAK DWGGKIGHYF FRAKKAIAPV LTDTPDHPST SRPTKPTKRS KPPPHIFINL  120
AKKKKAGAGQ VKRDNLAPMS DGAVQPDGGQ PAVRNERATG SGNGSGGGGG GGSGGVGIST  180
GTFNNQTEFK FLENGWVEIT ANSSRLVHLN MPESENYRRV VVNNMDKTAV NGNMALDDIH  240
AQIVTPWSLV DANAWGVWFN PGDWQLIVNT MSELHLVSFE QEIFNVVLKT VSESATQPPT  300
KVYNNDLTAS LMVALDSNNT MPFTPAAMRS ETLGFYPWKP TIPTPWRYYF QWDRTLIPSH  360
TGTSGTPTNI YHGTDPDDVQ FYTIENSVPV HLLRTGDEFA TGTFFFDCKP CRLTHTWQTN  420
RALGLPPFLN SLPQSEGATN FGDIGVQQDK RRGVTQMGNT NYITEATIMR PAEVGYSAPY  480
YSFEASTQGP FKTPIAAGRG GAQTYENQAA DGDPRYAFGR QHGQKTTTTG ETPERFTYIA  540
HQDTGRYPEG DWIQNINFNL PVTNDNVLLP TDPIGGKTGI NYTNIFNTYG PLTALNNVPP  600
VYPNGQIWDK EFDTDLKPRL HVNAPFVCQN NCPGQLFVKV APNLTNEYDP DASANMSRIV  660
TYSDFWWKGK LVFKAKLRAS HTWNPIQQMS INVDNQFNYV PSNIGGMKIV YEKSQLAPRK  720
LY                                                                722
```

```
SEQ ID NO: 105          moltype = AA  length = 702
FEATURE                 Location/Qualifiers
source                  1..702
                        mol_type = protein
```

-continued

```
                          organism = synthetic construct
SEQUENCE: 105
MPAIRKARGY NFLGPFNQDF NKEPTNPSDN AAKQHDLEYN KLINQGHNPY WYYNKADEDF  60
IKATDQAPDW GGKFGNFIFR AKKHIAPELA PPAKKKSKTK HPEPEFSHKH IKPGTKRGKP  120
FHIFVNLARK RARMSEPAEN TNDQPNDSPV EQGAGQIGGG GGGGGSGVGH STGDYNNRTE  180
FIYHGDEVTI ICHSTRLVHI NMSDREDYII YETDRGQLFP TTQDLQGRDT LNDSYHAKVE  240
TPWKLLHANS WGCWFSPADF QQMITTCRDI APIQMHQKIE NIVIKTVSKT GTGETETTNY  300
NNDLTALLQI AQDNSNLLPW AADNFYIDSV GYVPWRACKL PTYCYHVDTW NTIDINQADA  360
PNRWREIKKG IQWDNIQFTP LETMINIDLL RTGDAWQSGN YNFHTKPTNL AYHWQSQRHT  420
GSCHPTVAPL VERGQGTNIQ SVNCWQWGDR NNPSSASTRV SNMHIGYSFP EWQIHYSTGG  480
PVINPGSAFS QAPWGSTTEG TRLTQGASEK AIYDWAHGDD QPGARETWWQ NNQHVTGQTD  540
WAPKNAHTSE LNNNVPAATH FWKNSYHNTF SPFTAVDDHG PQYPWGAIWG KYPDTTHKPM  600
MSAHAPFLLH GPPGQLFVKL APNYTDTLDN GGVTHPRIVT YGTFWWSGKL IFKGKLRTPR  660
QWNTYNLPSL DKRETMKNTV PNEVGHFELP YMPGRCLPNY TL                    702

SEQ ID NO: 106            moltype = AA  length = 697
FEATURE                   Location/Qualifiers
source                    1..697
                          mol_type = protein
                          organism = synthetic construct
SEQUENCE: 106
TPAIRKARGP FNQDFNKEPT NPSDNAAKQH DLEYNKLINQ GHNPYWYYNK ADEDFIKATD  60
QAPDWGGKFG NFIFRAKKHI APELAPPAKK KSKTKHSEPE FSHKHIKPGT KRGKPFHIFV  120
NLARKRARMS EPANDTNEQP DNSPVEQGAG QIGGGGGGGG SGVGHSTGDY NNRTEFIYHG  180
DEVTIICHST RLVHINMSDR EDYIIYETDR GPLFPTTQDL QGRDTLNDSY HAKVETPWKL  240
LHANSWGCWF SPADFQQMIT TCRDIAPIKM HQKIENIVIK TVSKTGTGET ETTNYNNDLT  300
ALLQIAQDNS NLLPWAADNF YIDSVGYVPW RACKLPTYCY HVDTWNTIDI NQADTPNQWR  360
EIKKGIQWDN IQFTPLETMI NIDLLRTGDA WESGNYNFHT KPTNLAYHWQ SQRHTGSCHP  420
TVAPLVERGQ GTNIQSVNCW QWGDRNNPSS ASTRVSNIHI GYSFPEWQIH YSTGGPVINP  480
GSAFSQAPWG STTEGTRLTQ GASEKAIYDW SHGDDQPGAR ETWWQNNQHV TGQTDWAPKN  540
AHTSELNNNV PAATHFWKNS YHNTFSPFTA VDDHGPQYPW GAIWGKYPDT THKPMMSAHA  600
PFLLHGPPGQ LFVKLAPNYT DTLDNGGVTH PRIVTYGTFW WSGQLIFKGK LRTPRQWNTY  660
NLPSLDKRET MKNTVPNEVG HFELPYMPGR CLPNYTL                          697

SEQ ID NO: 107            moltype = AA  length = 722
FEATURE                   Location/Qualifiers
source                    1..722
                          mol_type = protein
                          organism = synthetic construct
SEQUENCE: 107
LAPPAKRARR GYKYLGPGNS LDQGEPTNPS DAAAKEHDEA YAAYLRSGKN PYLYFSPADQ  60
RFIDQTKDAK DWGGKIGHYF FRAKKAIAPV LTDTPDHPST SRPTKPTKRS KPPPHIFINL  120
AKKKKAGAGQ VKRDNLAPMS DGAVQPDGGQ PAVRNERATG SGNGSGGGGG GGSGGVGIST  180
GTFNNQTEFK FLENGWVEIT ANSSRLVHLN MPESENYKRV VVNNMDKTAV KGNMALDDIH  240
VQIVTPWSLV DANAWGVWFN PGDWQLIVNT MSELHLVSFE QEIFNVVLKT VSESATQPPT  300
KVYNNDLTAS LMVALDSNNT MPFTPAAMRS ETLGFYPWKP TIPTPWRYYF QWDRTLIPSH  360
TGTSGTPTNI YHGTDPDDVQ FYTIENSVPV HLLRTGDEFA TGTFFFDCKP CRLTHTWQTN  420
RALGLPPFLN SLPQSEGATN FGDIGVQQDK RRGVTQMGNT NYITEATIMR PAEVGYSAPY  480
YSFEASTQGP FKTPIAAGRG GAQTDENQAA DGDPRYAFGR QHGQKTTTTG ETPERFTYIA  540
HQDTGRYPEG DWIQNINFNL PVTNDNVLLP TDPIGGKTGI NYTNIFNTYG PLTALNNVPP  600
VYPNGQIWDK EFDTDLKPRL HVNAPFVCQN NCPGQLFVKV APNLTNEYDP DASANMSRIV  660
TYSDFWWKGK LVFKAKLRAS HTWNPIQQMS INVDNQFNYV PSNIGAMKIV YEKSQLAPRK  720
LY                                                                722

SEQ ID NO: 108            moltype = AA  length = 724
FEATURE                   Location/Qualifiers
source                    1..724
                          mol_type = protein
                          organism = synthetic construct
SEQUENCE: 108
TAPPAKRAKR GYKYLGPGNS LDQGEPTNPS DAAAKEHDEA YDQYIKSGKN PYLYFSAADQ  60
RFIDQTKDAK DWGGKVGHYF FRTKRAFAPK LATDSEPGTS GVSRAGKRTR PPAYIFINQA  120
RAKKKLTSSA AQQSSQTMSD GTSQPDSGNA VHSAARVERA ADGPGGSGGG GSGGGGVGVS  180
TGSYDNQTHY RFLGDGWVEI TALATRLVHL NMPKSENYCR IRVHNTTDTS VKGNMAKDDA  240
HEQIWTPWSL VDANAWGVWL QPSDWQYICN TMSQLNLVSL DQEIFNVVLK TVTEQDLGGQ  300
AIKIYNNDLT ACMMVAVDSN NILPYTPAAN SMETLGFYPW KPTIASPYRY YFCVDRDLSV  360
TYENQEGTVE HNVMGTPKGM NSQFFTIENT QQITLLRTGD EFATGTYYFD TNSVKLTHTW  420
QTNRQLGQPP LLSTFPEADT DAGTLTAQGS RHGTTQMGVN WVSEAIRTRP AQVGFCQPHN  480
DFEASRAGPF AAPKVPADIT QGVDKEANGS VRYSYGKQHG ENWASHGPAP ERYTWDETSF  540
GSGRDTKDGF IQSAPLVVPP PLNGILTNAN PIGTKNDIHF SNVFNSYGPL TAFSHPSPVY  600
PQGQIWDKEL DLEHKPRLHI TAPFVCKNNA PGQMLVRLGP NLTDQYDPNG ATLSRIVTYG  660
TFFWKGKLTM RAKLRANTTW NPVYQVSAED NGNSYMSVTK WLPTATGNMQ SVPLITRPVA  720
RNTY                                                              724

SEQ ID NO: 109            moltype = AA  length = 710
FEATURE                   Location/Qualifiers
source                    1..710
                          mol_type = protein
                          organism = synthetic construct
```

```
SEQUENCE: 109
MAPAARPRKG YNYLGPGNDL DAGEPTNKSD AAARKHDFAY SAYLKQGLDP YWNFNKADEK  60
FIRDTEGATD WGGRLGHWIF RAKKHILPHL KEPTLAGRKR PAPAHIFVNL ANKRKKGLPT  120
RKDQQKDTLD SNAQQPVREA DQPDGMAASS SDSGPSSSGG GARAGGVGVS TGDFDNTTLW  180
DFHEDGTATI TCNSTRLVHL TRPDSLDYKI IPTQNNTAVQ TVGHMMDDDN HTQVLTPWSL  240
VDCNAWGVWL SPHDWQHIMN IGEELELLSL EQEVFNVTLK TATETGPPES RITMYNNDLT  300
AVMMITTDTN NQLPYTPAAI RSETLGFYPW RPTVVPRWRY YFDWDRFLSV TSSSDQSTSI  360
INHSSTQSAI GQFFVIETQL PIALLRTGDS YATGGYKFDC NKVNLGRHWQ TTRSLGLPPK  420
IEPPTSESAL GTINQNARLG WRWGINDVHE TNVVRPCTAG YNHPEWFYTH TLEGPAIDPA  480
PPTSIPSNWG GGTPPDTRAS SHNQQRITYN YNHGNKDENL NNFSLNPNIE LGSIINQGNF  540
LSYEGNGQQI NTTAGVGKNG ETATSDPNLV RYMPNTYGVY TAVDHQGPVY PHGQIWDKQI  600
HTDKKPELHC LAPFTCKNNP PGQMFVRIAP NLTDTFNATP TFSEIITYAD FWWKGTLKMK  660
IKLRPPHQWN IATVLGAAVN IGDAARFVPN RLGQLEFPVI NGRIVPSTVY            710

SEQ ID NO: 110          moltype = AA  length = 730
FEATURE                 Location/Qualifiers
source                  1..730
                        mol_type = protein
                        organism = synthetic construct
SEQUENCE: 110
TAPPAKRAKR GYKYLGPGNS LDQGEPTNPS DAAAKEHDEA YDQYIKSGKN PYLYFSPADQ  60
RFIDQTKDAK DWGGKVGHYF FRTKRAFAPK LSTDSEPGTS GVSRPGKRTK PPAHIFVNQA  120
RAKKKRASLA AQQRTLTMSD GTETNQPDTG IANARVERSA DGGGSSGGGG SGGGGIGVST  180
GTYDNQTTYK FLGDGWVEIT AHASRLLHLG MPPSENYCRV TVHNNQTTGH GTKVKGNMAY  240
DDTHQQIWTP WSLVDANAWG VWFQPSDWQF IQNSMESLNL DSLSQELFNV VVKTVTEQQG  300
AGQDAIKVYN NDLTACMMVA LDSNNILPYT PAAQTSETLG FYPWKPTAPA PYRYYFFMPR  360
QLSVTSSNSA EGTQITDTIG EPQALNSQFF TIENTLPITL LRTGDEFTTG TYIFNTDPLK  420
LTHTWQTNRH LGMPPRITDL PTSDTATASL TANGDRFGST QTQNVNYVTE ALRTRPAQIG  480
FMQPHDNFEA NRGGPFKVPV VPLDITAGED HDANGAIRFN YGKQHGEDWA KQGAAPERYT  540
WDAIDSAAGR DTARCFVQSA PISIPPNQNQ ILQREDAIAG RTNMHYTNVF NSYGPLSAFP  600
HPDPIYPNGQ IWDKELDLEH KPRLHVTAPF VCKNNPPGQL FVRLGPNLTD QFDPNSTTVS  660
RIVTYSTFYW KGILKFKAKL RPNLTWNPVY QATTDSVANS YMNVKKWLPS ATGNMHSDPL  720
ICRPVPHMTY                                                        730

SEQ ID NO: 111          moltype = AA  length = 569
FEATURE                 Location/Qualifiers
source                  1..569
                        mol_type = protein
                        organism = synthetic construct
SEQUENCE: 111
MTDTQDVSEQ QSDQPSVAST SAKAGGGGGG GGSGVGHSTG NYNNRTEFYY HGDEVTIVCH  60
SSRHIHLNMS ESEEYKIYDT DRGPTFPTDQ TLQGRDTIND SYHAQVETPW FLINPNSWGT  120
WMNPADFQQL TTTCREVTLE HLDQTLDNIV IKTVSKQGSG AEETTQYNND LTALLQVALD  180
KSNQLPWVAD NMYLDSLGYI PWRPCKLKQY SYHVNFWNTI DIISGPQQNQ WQQVKKEIKW  240
DDLQFTPIET TTEIDLLRTG DSWTSGPYKF NTKPTQLSYH WQSTRHTGSV HPTEPPNAIG  300
QQGRNIIDIN GWQWGDRSNP MSAATRVSNF HIGYSWPEWR IHYGSGGPAI NPGAPFSQAP  360
WSTDPQVRLT QGASEKAIFD YNHGDDDPAH RDQWWQNNLP MTGQTDWAPK NAHQTNVSNN  420
IPSRQEFWTQ DYHNTFGPFT AVDDVGIQYP WGAIWTKTPD TTHKPMMSAH APFICKDGPP  480
GQLLVKLAPN YTENLQTDGL GNNRIVTYAT FWWTGKLVLK GKLRLPRQFN LYNLPGRPRG  540
TEAKKFLPNE IGHFELPFMP GRCMPNYTI                                   569

SEQ ID NO: 112          moltype = AA  length = 584
FEATURE                 Location/Qualifiers
source                  1..584
                        mol_type = protein
                        organism = synthetic construct
SEQUENCE: 112
MSDGAVQPDG GQPAVRNERA TGSGNGSGGG GGGGSGGVGI STGTFNNQTE FKFLENGWVE  60
ITANSSRLVH LNMPESENYR RVVVNNLDKT AVNGNMALDD THAQIVTPWS LVDANAWGVW  120
FNPGDWQLIV NTMSELHLVS FEQEIFNVVL KTVSESATQP PTKVYNNDLT ASLMVALDSN  180
NTMPFTPAAM RSETLGFYPW KPTIPTPWRY YFQWDRTLIP SHTGTSGTPT NIYHGTDPDD  240
VQFYTIENSV PVHLLRTGDE FATGTFFFDC KPCRLTHTWQ TNRALGLPPF LNSLPQSEGG  300
TNFGYIGVQQ DKRRGVTQMG NTNYITEATI MRPAEVGYSA PYYSFEASTQ GPFKTPIAAG  360
RGGAQTDENQ AADGDPRYAF GRQHGQKTTT TGETPERFTY IAHQDTGRYP EGDWIQNINF  420
NLPVTDDNVL LPTDPIGGKT GINYTNIFNT YGPLTALNNV PPVYPNGQIW DKEFDTDLKP  480
RLHVNAPFVC QNNCPGQLFV KVAPNLTNEY DPDASANMSR IVTYSDFWWK GKLVFKAKLR  540
ASHTWNPIQQ MSINVDNQFN YVPSNIGGMK IVYEKSQLAP RKLY                  584

SEQ ID NO: 113          moltype = DNA  length = 1752
FEATURE                 Location/Qualifiers
source                  1..1752
                        mol_type = other DNA
                        organism = synthetic construct
SEQUENCE: 113
atgagcgacg gcgccgtgca gcccgacggc ggccagcccg ccgtgcgcaa cgagcgcgcc  60
accggcagcg gcaacggcag cggcggcggc ggcggcggcg gcagcggcgg cgtgggcatc  120
agcaccggca ccttcaacaa ccagaccgag ttcaagttcc tggagaacgg ctgggtggag  180
atcaccgcca acagcagccg cctggtgcac ctgaacatgc ccgagagcga gaactaccgc  240
cgcgtggtgg tgaacaacat ggacaagacc gccgtgaacg gcaacatggc cctggacgac  300
```

-continued

```
atccacgccc agatcgtgac cccctggagc ctggtggacg ccaacgcctg gggcgtgtgg  360
ttcaaccccg gcgactggca gctgatcgtg aacaccatga gcgagctgca cctggtgagc  420
ttcgagcagg agatcttcaa cgtggtgctg aagaccgtga gcgagagcgc cacccagccc  480
cccaccaagg tgtacaacaa cgacctgacc gccagcctga tggtggccct ggacagcaac  540
aacaccatgc ccttcacccc cgccgccatg cgcagcgaga ccctgggctt ctacccctgg  600
aagcccacca tccccaccc ctggcgctac tacttccagt gggaccgcac cctgatcccc  660
agccacaccg gcaccagcgg cacccccacc aacatctacc acggcaccga ccccgacgac  720
gtgcagttct acaccatcga gaacagcgtg cccgtgcacc tgctgcgcac cggcgacgag  780
ttcgccaccg gcaccttctt cttcgactgc aagccctgcc gcctgaccca cacctggcag  840
accaaccgcg ccctgggcct gcccccttc ctgaacagcc tgccccagag cgagggcgcc  900
accaacttcg gcgacatcgg cgtgcagcag gacaagcgcc gcggcgtgac ccagatgggc  960
aacaccaact acatcaccga ggccaccatc atgcgccccg ccgaggtggg ctacagcgcc  1020
ccctactaca gcttcgaggc cagcacccag ggcccttca agaccccat cgccgccggc  1080
cgcggcggcg cccagaccta cgagaaccag gccgccgacg gcgacccccg ctacgccttc  1140
ggccgccagc acggccagaa gaccaccacc accggcgaga cccccgagcg cttcacctac  1200
atcgcccacc aggacaccgg ccgctacccc gagggcgact ggatccagaa catcaacttc  1260
aacctgcccg tgaccaacga caacgtgctg ctgcccaccg accccatcgg cggcaagacc  1320
ggcatcaact acaccaacat cttcaacacc tacggccccc tgaccgccct gaacaacgtg  1380
ccccccgtgt accccaacgg ccagatctgg gacaaggagt tcgacaccga cctgaagccc  1440
cgcctgcacg tgaacgcccc cttcgtgtgc cagaacaact gccccggcca gctgttcgtg  1500
aaggtggccc ccaacctgac caacgagtac gaccccgacg ccagcgccaa catgagccgc  1560
atcgtgacct acagcgactt ctggtggaag ggcaagctgg tgttcaaggc caagctgcgc  1620
gccagccaca cctggaaccc catccagcag atgagcatca acgtggacaa ccagttcaac  1680
tacgtgccca gcaacatcgg cggcatgaag atcgtgtacg agaagagcca gctggccccc  1740
cgcaagctgt ac                                                     1752

SEQ ID NO: 114         moltype = AA  length = 569
FEATURE                Location/Qualifiers
source                 1..569
                       mol_type = protein
                       organism = synthetic construct
SEQUENCE: 114
MSEPANDTNE QPDNSPVEQG AGQIGGGGGG GGSGVGHSTG DYNNRTEFIY HGDEVTIICH  60
STRLVHINMS DREDYIIYET DRGPLFPTTQ DLQGRDTLND SYHAKVETPW KLLHANSWGC  120
WFSPADFQQM ITTCRDIAPI KMHQKIENIV IKTVSKTGTG ETETTNYNND LTALLQIAQD  180
NSNLLPWAAD NFYIDSVGYV PWRACKLPTY CYHVDTWNTI DINQADTPNQ WREIKKGIQW  240
DNIQFTPLET MINIDLLRTG DAWESGNYNF HTKPTNLAYH WQSQRHTGSC HPTVAPLVER  300
GQGTNIQSVN CWQWGDRNNP SSASTRVSNI HIGYSFPEWQ IHYSTGGPVI NPGSAFSQAP  360
WGSTTEGTRL TQGASEKAIY DWSHGDDQPG ARETWWQNNQ HVTGQTDWAP KNAHTSELNN  420
NVPAATHFWK NSYHNTFSPF TAVDDHGPQY PWGAIWGKYP DTTHKPMMSA HAPFLLHGPP  480
GQLFVKLAPN YTDTLDNGGV THPRIVTYGT FWWSGQLIFK GKLRTPRQWN TYNLPSLDKR  540
ETMKNTVPNE VGHFELPYMP GRCLPNYTL                                   569

SEQ ID NO: 115         moltype = DNA  length = 1707
FEATURE                Location/Qualifiers
source                 1..1707
                       mol_type = other DNA
                       organism = synthetic construct
SEQUENCE: 115
atgagcgagc ccgccaacga caccaacgag cagcccgaca acagccccgt ggagcagggc  60
gccggccaga tcggcggcgg cggcggcggc ggcggcagcg gcgtgggcca cagcaccggc  120
gactacaaca accgcaccga gttcatctac cacggcgacg aggtgaccat catctgccac  180
agcacccgcc tggtgcacat caacatgagc gaccgcgagg actacatcat ctacgagacc  240
gaccgcggcc ccctgttccc caccacccag gacctgcagg gccgcgacac cctgaacgac  300
agctaccacg ccaaggtgga gacccctgg aagctgctgc acgccaacag ctggggctgc  360
tggttcagcc ccgccgactt ccagcagatg atcaccacct gccgcgacat cgcccccatc  420
aagatgcacc agaagatcga gaacatcgtg atcaagaccg tgagcaagac cggcaccggc  480
gagaccgaga ccaccaacta caacaacgac ctgaccgccc tgctgcagat cgcccaggac  540
aacagcaacc tgctgccctg ggccgccgac aacttctaca tcgacagcgt gggctacgtg  600
ccctggcgcg cctgcaagct gcccacctac tgctaccacg tggacacctg gaacaccatc  660
gacatcaacc aggccgacac ccccaaccag tggcgcgaga tcaagaaggg catccagtgg  720
gacaacatcc agttcacccc cctggagacc atgatcaaca tcgacctgct gcgcaccggc  780
gacgcctggg agagcggcaa ctacaacttc cacaccaagc ccaccaacct ggcctaccac  840
tggcagagcc agcgccacac cggcagctgc caccccaccg tggccccct ggtggagcgc  900
ggccagggca ccaacatcca gagcgtgaac tgctggcagt ggggcgaccg caacaacccc  960
agcagcgcca gcacccgcgt gagcaacatc cacatcggct acagcttccc cgagtggcag  1020
atccactaca gcaccggcgg ccccgtgatc aaccccggca gcgccttcag ccaggccccc  1080
tggggcagca ccaccgaggg cacccgcctg acccagggcg ccagcgagaa ggccatctac  1140
gactggagcc acggcgacga ccagcccggc gcccgcgaga cctggtggca gaacaaccag  1200
cacgtgaccg gccagaccga ctgggccccc aagaacgccc acaccagcga gctgaacaac  1260
aacgtgcccg ccgccaccca cttctggaag aacagctacc acaacacctt cagccccttc  1320
accgccgtgg acgaccacgg cccccagtac ccctggggcg ccatctgggg caagtacccc  1380
gacaccaccc acaagcccat gatgagcgcc cacgccccct tcctgctgca cggccccccc  1440
ggccagctgt tcgtgaagct ggcccccaac tacaccgaca ccctggacaa cggcggcgtg  1500
acccaccccc gcatcgtgac ctacggcacc ttctggtgga gcggccagct gatcttcaag  1560
ggcaagctgc gcacccccg ccagtggaac acctacaacc tgcccagcct ggacaagcgc  1620
gagaccatga agaacaccgt gcccaacgag gtgggccact tcgagctgcc ctacatgccc  1680
ggccgctgcc tgcccaacta caccctg                                     1707
```

-continued

```
SEQ ID NO: 116         moltype = AA  length = 584
FEATURE                Location/Qualifiers
source                 1..584
                       mol_type = protein
                       organism = synthetic construct
SEQUENCE: 116
MSDGAVQPDG GQPAVRNERA TGSGNGSGGG GGGGSGGVGI STGTFNNQTE FKFLENGWVE  60
ITANSSRLVH LNMPESENYK RVVVNNMDKT AVKGNMALDD IHVQIVTPWS LVDANAWGVW  120
FNPGDWQLIV NTMSELHLVS FEQEIFNVVL KTVSESATQP PTKVYNNDLT ASLMVALDSN  180
NTMPFTPAAM RSETLGFYPW KPTIPTPWRY YFQWDRTLIP SHTGTSGTPT NIYHGTDPDD  240
VQFYTIENSV PVHLLRTGDE FATGTFFFDC KPCRLTHTWQ TNRALGLPPF LNSLPQSEGA  300
TNFGDIGVQQ DKRRGVTQMG NTNYITEATI MRPAEVGYSA PYYSFEASTQ GPFKTPIAAG  360
RGGAQTDENQ AADGDPRYAF GRQHGQKTTT TGETPERFTY IAHQDTGRYP EGDWIQNINF  420
NLPVTNDNVL LPTDPIGGKT GINYTNIFNT YGPLTALNNV PPVYPNGQIW DKEFDTDLKP  480
RLHVNAPFVC QNNCPGQLFV KVAPNLTNEY DPDASANMSR IVTYSDFWWK GKLVFKAKLR  540
ASHTWNPIQQ MSINVDNQFN YVPSNIGAMK IVYEKSQLAP RKLY                  584

SEQ ID NO: 117         moltype = AA  length = 565
FEATURE                Location/Qualifiers
source                 1..565
                       mol_type = protein
                       organism = synthetic construct
SEQUENCE: 117
MAASSSDSGP SSSGGGARAG GVGVSTGDFD NTTLWDFHED GTATITCNST RLVHLTRPDS  60
LDYKIIPTQN NTAVQTVGHM MDDDNHTQVL TPWSLVDCNA WGVWLSPHDW QHIMNIGEEL  120
ELLSLEQEVF NVTLKTATET GPPESRITMY NNDLTAVMMI TTDTNNQLPY TPAAIRSETL  180
GFYPWRPTVV PRWRYYFDWD RFLSVTSSSD QSTSIINHSS TQSAIGQFFV IETQLPIALL  240
RTGDSYATGG YKFDCNKVNL GRHWQTTRSL GLPPKIEPPT SESALGTINQ NARLGWRWGI  300
NDVHETNVVR PCTAGYNHPE WFYTHTLEGP AIDPAPPTSI PSNWGGGTPP DTRASSHNQQ  360
RITYNYNHGN KDENLNNFSL NPNIELGSII NQGNFLSYEG NGQQINTTAG VGKNGETATS  420
DPNLVRYMPN TYGVYTAVDH QGPVYPHGQI WDKQIHTDKK PELHCLAPFT CKNNPPGQMF  480
VRIAPNLTDT FNATPTFSEI ITYADFWWKG TLKMKIKLRP PHQWNIATVL GAAVNIGDAA  540
RFVPNRLGQL EFPVINGRIV PSTVY                                       565

SEQ ID NO: 118         moltype = DNA  length = 89
FEATURE                Location/Qualifiers
source                 1..89
                       mol_type = other DNA
                       organism = synthetic construct
SEQUENCE: 118
catggagata attaaaatga taaccatctc gcaaataaat aagtatttta ctgttttcgt  60
aacagttttg taataaaaaa acctataaa                                   89

SEQ ID NO: 119         moltype = DNA  length = 580
FEATURE                Location/Qualifiers
source                 1..580
                       mol_type = other DNA
                       organism = synthetic construct
SEQUENCE: 119
ggtacctctg gtcgttacat aacttacggt aaatggcccg cctggctgac cgcccaacga  60
ccccgcccat tgacgtcaat aatgacgtat gttcccatag taacgccaat agggactttc  120
cattgacgtc aatgggtgga gtatttacgg taaactgccc acttggcagt acatcaagtg  180
tatcatatgc caagtacgcc ccctattgac gtcaatgacg gtaaatggcc cgcctggcat  240
tatgcccagt acatgacctt atgggacttt cctacttggc agtacatcta ctcgaggcca  300
cgttctgctt cactctcccc atctcccccc cctccccacc cccaattttg tatttattta  360
ttttttaatt attttgtgca gcgatggggg cggggggggg gggggggcgc gcgccaggcg  420
gggcggggcg gggcgagggg cggggcgggg cgaggcggag aggtgcggcg gcagccaatc  480
agagcggcgc gctccgaaag tttcctttta tggcgaggcg gcggcggcgg cggccctata  540
aaaagcgaag cgcgcggcgg gcgggagcgg gatcagccac                        580

SEQ ID NO: 120         moltype = DNA  length = 292
FEATURE                Location/Qualifiers
source                 1..292
                       mol_type = other DNA
                       organism = synthetic construct
SEQUENCE: 120
gcgaaacacg cacggcgcgc gcacgcagct tagcacaaac gcgtcgttgc acgcgcccac  60
cgctaaccgc aggccaatcg gtcggccggc ctcatatccg ctcaccagcc gcgtcctatc  120
gggcgcggct tccgcgccca ttttgaataa ataaacgata acgccgttgg tggcgtgagg  180
catgtaaaag gttacatcat tatcttgttc gccatccggt tggtataaat agacgttcat  240
gttggttttt gtttcagttg caagttggct gcggcgcgcg cagcaccttt gc          292

SEQ ID NO: 121         moltype = DNA  length = 110
FEATURE                Location/Qualifiers
source                 1..110
                       mol_type = other DNA
                       organism = synthetic construct
SEQUENCE: 121
gacctttaat tcaacccaac acaatatatt atagttaaat aagaattatt atcaaatcat  60
```

-continued

```
ttgtatatta attaaaatac tatactgtaa attacatttt atttacaatc           110

SEQ ID NO: 122         moltype = DNA  length = 40
FEATURE                Location/Qualifiers
source                 1..40
                       mol_type = other DNA
                       organism = synthetic construct
SEQUENCE: 122
ctcgacgaag acttgatcac ccgggggatc ccctgttaag                      40

SEQ ID NO: 123         moltype = DNA  length = 42
FEATURE                Location/Qualifiers
source                 1..42
                       mol_type = other DNA
                       organism = synthetic construct
SEQUENCE: 123
attccggatt attcataccg tcccaccatc gggcgcggat ct                   42

SEQ ID NO: 124         moltype = DNA  length = 42
FEATURE                Location/Qualifiers
source                 1..42
                       mol_type = other DNA
                       organism = synthetic construct
SEQUENCE: 124
actccggact actgataccg tcccactttc gggcgcttac ct                   42

SEQ ID NO: 125         moltype = DNA  length = 132
FEATURE                Location/Qualifiers
source                 1..132
                       mol_type = other DNA
                       organism = synthetic construct
SEQUENCE: 125
ttgtttattg cagcttataa tggttacaaa taaagcaata gcatcacaaa tttcacaaat  60
aaagcatttt tttcactgca ttctagttgt ggtttgtcca aactcatcaa tgtatcttat  120
catgtctgga tc                                                      132

SEQ ID NO: 126         moltype = DNA  length = 2591
FEATURE                Location/Qualifiers
source                 1..2591
                       mol_type = other DNA
                       organism = synthetic construct
SEQUENCE: 126
catggagata attaaaatga taaccatctc gcaaataaat aagtatttta ctgttttcgt  60
aacagttttg taataaaaaa acctataaaa ttccggatta ttcataccgt cccaccatcg  120
ggcgcggatc tcctgttaag ctggcacctc cggcaaagag agccaggaga ggatataaat  180
atcttgggcc tgggaacagt cttgaccaag gagaaccaac taacccttct gacgccgctg  240
caaaagaaca cgacgaagct tacgctgctt atcttcgctc tggtaaaaac ccatacttat  300
atttctcgcc agcagatcaa cgctttatag atcaaactaa ggacgctaaa gattgggggg  360
ggaaaatagg acattatttt tttagagcta aaaaggcaat tgctccagta ttaactgata  420
caccagatca tccatcaaca tcaagaccaa caaaaccaac taaaagaagt aaaccaccac  480
ctcatatttt catcaatctt gcaaaaaaaa aaaaagccgg tgcaggacaa gtaaaaagag  540
acaatcttgc accaatgagt gatggagcag ttcaaccaga cggtggtcaa cctgctgtca  600
gaaatgaaag agctacagga tctgggaacg ggtctggagg cgggggtggt ggtggttctg  660
gggtgtgggg gatttctacg ggtactttca ataatcagac ggaatttaaa tttttggaaa  720
acggatgggt ggaaatcaca gcaaactcaa gcagacttgt acatttaaat atgccagaaa  780
gtgaaaatta tagaagagtg gttgtaaata atatggataa aactgcagtt aacggaaaca  840
tggctttaga tgatattcat gcacaaattg taacaccttg gtcattggtt gatgcaaatg  900
cttggggagt ttggtttaat ccaggagatt ggcaactaat tgttaatact atgagtgagt  960
tgcatttagt tagttttgaa caagaaattt ttaatgttgt tttaaagact gtttcagaat  1020
ctgctactca gccaccaact aaagtttata ataatgattt aactgcatca ttgatggttg  1080
cattagatag taataatact atgccattta ctccagcagc tatgagatct gagacattgg  1140
gtttttatcc atggaaacca accataccaa ctccatggag atattatttt caatgggata  1200
gaacattaat accatctcat actggaacta gtggcacacc aacaaatata taccatggta  1260
cagatccaga tgatgttcaa ttttatacta ttgaaaattc tgtgccagta cacttactaa  1320
gaacaggtga tgaatttgct acaggaacat tttttttga ttgtaaacca tgtagactaa  1380
cacatacatg gcaaacaaat agagcattgg gcttaccacc atttctaaat tctttgcctc  1440
aatctgaagg agctactaac tttggtgata taggagttca acaagataaa agacgtggtg  1500
taactcaaat gggaaataca aactatatta ctgaagctac tattatgaga ccagctgagg  1560
ttggttatag tgcaccatat tattcttttg aggcgtctac acaagggcca tttaaaacac  1620
ctattgcagc aggacggggg ggagcgcaaa catatgaaaa tcaagcagca gatggtgatc  1680
caagatatgc atttggtaga caacatggtc aaaaaactac cacaacagga gaaacacctg  1740
agagatttac atatatagca catcaagata caggaagata tccagaagga gattggattc  1800
aaaatattaa ctttaacctt cctgtaacga atgataatgt attgctacca acagatccaa  1860
ttggaggtaa aacaggaatt aactatacta atatatttaa tacttatggt cctttaactg  1920
cattaaataa tgtaccacca gtttatccaa atggtcaaat ttgggataaa gaatttgata  1980
ctgacttaaa accaagactt catgtaaatg caccatttgt ttgtcaaaat aattgtcctg  2040
gtcaattatt tgtaaaagtt gcgcctaatt taacaaatga atatgatcct gatgcatctg  2100
ctaatatgtc aagaattgta acttactcag atttttggtg gaaaggtaaa ttagtattta  2160
aagctaaact aagagcctct catacttgga atccaattca acaaatgagt attaatgtag  2220
```

```
ataaccaatt taactatgta ccaagtaata ttggaggtat gaaaattgta tatgaaaaat  2280
ctcaactagc acctagaaaa ttatattaac tcgaggcatg cggtaccaag cttgtcgaga  2340
agtactagag gatcataatc agccatacca catttgtaga ggttttactt gctttaaaaa  2400
acctcccaca cctccccctg aacctgaaac ataaaatgaa tgcaattgtt gttgttaact  2460
tgtttattgc agcttataat ggttacaaat aaagcaatag catcacaaat ttcacaaata  2520
aagcattttt ttcactgcat tctagttgtg gtttgtccaa actcatcaat gtatcttatc  2580
atgtctggat c                                                       2591

SEQ ID NO: 127         moltype = DNA  length = 2540
FEATURE                Location/Qualifiers
source                 1..2540
                       mol_type = other DNA
                       organism = synthetic construct
SEQUENCE: 127
catggagata attaaaatga taaccatctc gcaaataaat aagtatttta ctgttttcgt  60
aacagttttg taataaaaaa acctataaac tggcacctcc ggcaaagaga gccaggagag  120
gatataaata tcttgggcct gggaacagtc ttgaccaagg agaaccaact aacccttctg  180
acgccgctgc aaaagaacac gacgaagctt acgctgctta tcttcgctct ggtaaaaacc  240
catacttata tttctcgcca gcagatcaac gctttataga tcaaactaag gacgctaaag  300
attggggggg gaaaatagga cattattttt ttagagctaa aaaggcaatt gctccagtat  360
taactgatac accagatcat ccatcaacat caagaccaac aaaaccaact aaaagaagta  420
aaccaccacc tcatattttc atcaatcttg caaaaaaaaa aaaagccggt gcaggacaag  480
taaaaagaga caatcttgca ccaatgagtg atggagcagt tcaaccagac ggtggtcaac  540
ctgctgtcag aaatgaaaga gctacaggat ctgggaacgg gtctggaggc gggggtggtg  600
gtggttctgg gggtgtgggg atttctacgg gtactttcaa taatcagacg gaatttaaat  660
ttttggaaaa cggatgggtg gaaatcacag caaactcaag cagacttgta catttaaata  720
tgccagaaag tgaaaattat agaagagtgg ttgtaaataa tatggataaa actgcagtta  780
acggaaacat ggctttagat gatattcatg cacaaattgt aacaccttgg tcattggttg  840
atgcaaatgc ttggggagtt tggtttaatc caggagattg gcaactaatt gttaatacta  900
tgagtgagtt gcatttagtt agttttgaac aagaaatttt taatgttgtt ttaaagactg  960
tttcagaatc tgctactcag ccaccaacta aagtttataa taatgattta actgcatcat  1020
tgatggttgc attagatagt aataatacta tgccatttac tccagcagct atgagatctg  1080
agacattggg tttttatcca tggaaaccaa ccataccaac tccatggaga tattattttc  1140
aatgggatag aacattaata ccatctcata ctggaactag tggcacacca acaaatatat  1200
accatggtac agatccagat gatgttcaat tttatactat tgaaaattct gtgccagtac  1260
acttactaag aacaggtgat gaatttgcta caggaacatt ttttttttgat tgtaaaccat  1320
gtagactaac acatacatgg caaacaaata gagcattggg cttaccacca tttctaaatt  1380
ctttgcctca atctgaagga gctactaact ttggtgatat aggagttcaa caagataaaa  1440
gacgtggtgt aactcaaatg ggaaatacaa actatattac tgaagctact attatgagac  1500
cagctgaggt tggttatagt gcaccatatt attcttttga ggcgtctaca caagggccat  1560
ttaaaacacc tattgcagca ggacgggggg gagcgcaaac atatgaaaat caagcagcag  1620
atggtgatcc aagatatgca tttggtagac aacatggtca aaaaactacc acaacaggag  1680
aaacacctga gagatttaca tatatagcac atcaagatac aggaagatat ccagaaggag  1740
attggattca aaatattaac tttaaccttc ctgtaacgaa tgataatgta ttgctaccaa  1800
cagatccaat tggaggtaaa acaggaatta actatactaa tatatttaat acttatggtc  1860
ctttaactgc attaaataat gtaccaccag tttatccaaa tggtcaaatt tgggataaag  1920
aatttgatac tgacttaaaa ccaagacttc atgtaaatgc accatttgtt tgtcaaaata  1980
attgtcctgg tcaattattt gtaaaagttg cgcctaattt aacaaatgaa tatgatcctg  2040
atgcatctgc taatatgtca agaattgtaa cttactcaga tttttggtgg aaaggtaaat  2100
tagtatttaa agctaaacta agagcctctc atacttggaa tccaattcaa caaatgagta  2160
ttaatgtaga taaccaattt aactatgtac caagtaatat tggaggtatg aaaattgtat  2220
atgaaaaatc tcaactagca cctagaaaat tatattaact cgaggcatgc ggtaccaagc  2280
ttgtcgagaa gtactagagg atcataatca gccataccac atttgtagag gttttacttg  2340
ctttaaaaaa cctcccacac ctccccctga acctgaaaca taaaatgaat gcaattgttg  2400
ttgttaactt gtttattgca gcttataatg gttacaaata aagcaatagc atcacaaatt  2460
tcacaaataa agcatttttt tcactgcatt ctagttgtgg tttgtccaaa ctcatcaatg  2520
tatcttatca tgtctggatc                                              2540

SEQ ID NO: 128         moltype = DNA  length = 2540
FEATURE                Location/Qualifiers
source                 1..2540
                       mol_type = other DNA
                       organism = synthetic construct
SEQUENCE: 128
catggagata attaaaatga taaccatctc gcaaataaat aagtatttta ctgttttcgt  60
aacagttttg taataaaaaa acctataaaa cggcacctcc ggcaaagaga gccaggagag  120
gatataaata tcttgggcct gggaacagtc ttgaccaagg agaaccaact aacccttctg  180
acgccgctgc aaaagaacac gacgaagctt acgctgctta tcttcgctct ggtaaaaacc  240
catacttata tttctcgcca gcagatcaac gctttataga tcaaactaag gacgctaaag  300
attggggggg gaaaatagga cattattttt ttagagctaa aaaggcaatt gctccagtat  360
taactgatac accagatcat ccatcaacat caagaccaac aaaaccaact aaaagaagta  420
aaccaccacc tcatattttc atcaatcttg caaaaaaaaa aaaagccggt gcaggacaag  480
taaaaagaga caatcttgca ccaatgagtg atggagcagt tcaaccagac ggtggtcaac  540
ctgctgtcag aaatgaaaga gctacaggat ctgggaacgg gtctggaggc gggggtggtg  600
gtggttctgg gggtgtgggg atttctacgg gtactttcaa taatcagacg gaatttaaat  660
ttttggaaaa cggatgggtg gaaatcacag caaactcaag cagacttgta catttaaata  720
tgccagaaag tgaaaattat agaagagtgg ttgtaaataa tatggataaa actgcagtta  780
acggaaacat ggctttagat gatattcatg cacaaattgt aacaccttgg tcattggttg  840
atgcaaatgc ttggggagtt tggtttaatc caggagattg gcaactaatt gttaatacta  900
```

-continued

```
tgagtgagtt gcatttagtt agttttgaac aagaaatttt taatgttgtt ttaaagactg  960
tttcagaatc tgctactcag ccaccaacta aagtttataa taatgattta actgcatcat  1020
tgatggttgc attagatagt aataatacta tgccatttac tccagcagct atgagatctg  1080
agacattggg tttttatcca tggaaaccaa ccataccaac tccatggaga tattattttc  1140
aatgggatag aacattaata ccatctcata ctggaactag tggcacacca acaaatatat  1200
accatggtac agatccagat gatgttcaat tttatactat tgaaaattct gtgccagtac  1260
acttactaag aacaggtgat gaatttgcta caggaacatt ttttttgat tgtaaaccat  1320
gtagactaac acatacatgg caaacaaata gagcattggg cttaccacca tttctaaatt  1380
ctttgcctca atctgaagga gctactaact ttggtgatat aggagttcaa caagataaaa  1440
gacgtggtgt aactcaaatg ggaaatacaa actatattac tgaagctact attatgagac  1500
cagctgaggt tggttatagt gcaccatatt attcttttga ggcgtctaca caagggccat  1560
ttaaaacacc tattgcagca ggacgggggg gagcgcaaac atatgaaaat caagcagcag  1620
atggtgatcc aagatatgca tttggtagac aacatggtca aaaaactacc acaacaggag  1680
aaacacctga gagatttaca tatatagcac atcaagatac aggaagatat ccagaaggag  1740
attggattca aaatattaac tttaaccttc ctgtaacgaa tgataatgta ttgctaccaa  1800
cagatccaat tggaggtaaa acaggaatta actatactaa tatatttaat acttatggtc  1860
ctttaactgc attaaataat gtaccaccag tttatccaaa tggtcaaatt tgggataaag  1920
aatttgatac tgacttaaaa ccaagacttc atgtaaatgc accatttgtt tgtcaaaata  1980
attgtcctgg tcaattattt gtaaaagttg cgcctaattt aacaaatgaa tatgatcctg  2040
atgcatctgc taatatgtca agaattgtaa cttactcaga tttttggtgg aaaggtaaat  2100
tagtatttaa agctaaacta agagcctctc atacttggaa tccaattcaa caaatgagta  2160
ttaatgtaga taaccaattt aactatgtac caagtaatat tggaggtatg aaaattgtat  2220
atgaaaaatc tcaactagca cctagaaaat tatattaact cgaggcatgc ggtaccaagc  2280
ttgtcgagaa gtactagagg atcataatca gccataccac atttgtagag gttttacttg  2340
ctttaaaaaa cctcccacac ctccccctga acctgaaaca taaaatgaat gcaattgttg  2400
ttgttaactt gtttattgca gcttataatg gttacaaata aagcaatagc atcacaaatt  2460
tcacaaataa agcatttttt tcactgcatt ctagttgtgg tttgtccaaa ctcatcaatg  2520
tatcttatca tgtctggatc                                              2540

SEQ ID NO: 129          moltype = DNA  length = 2540
FEATURE                 Location/Qualifiers
source                  1..2540
                        mol_type = other DNA
                        organism = synthetic construct
SEQUENCE: 129
catggagata attaaaatga taaccatctc gcaaataaat aagtatttta ctgttttcgt  60
aacagttttg taataaaaaa acctataaat tggcacctcc ggcaaagaga gccaggagag  120
gatataaata tcttgggcct gggaacagtc ttgaccaagg agaaccaact aacccttctg  180
acgccgctgc aaaagaacac gacgaagctt acgctgctta tcttcgctct ggtaaaaacc  240
catacttata tttctcgcca gcagatcaac gctttataga tcaaactaag gacgctaaag  300
attggggggg gaaaatagga cattattttt ttagagctaa aaaggcaatt gctccagtat  360
taactgatac accagatcat ccatcaacat caagaccaac aaaaccaact aaaagaagta  420
aaccaccacc tcatattttc atcaatcttg caaaaaaaaa aaaagccggt gcaggacaag  480
taaaaagaga caatcttgca ccaatgagtg atggagcagt tcaaccagac ggtggtcaac  540
ctgctgtcag aaatgaaaga gctacaggat ctgggaacgg gtctggaggc gggggtggtg  600
gtggttctgg gggtgtgggg atttctacgg gtactttcaa taatcagacg gaatttaaat  660
ttttggaaaa cggatgggtg gaaatcacag caaactcaag cagacttgta catttaaata  720
tgccagaaag tgaaaattat agaagagtgg ttgtaaataa tatggataaa actgcagtta  780
acggaaacat ggctttagat gatattcatg cacaaattgt aacaccttgg tcattggttg  840
atgcaaatgc ttggggagtt tggtttaatc caggagattg gcaactaatt gttaatacta  900
tgagtgagtt gcatttagtt agttttgaac aagaaatttt taatgttgtt ttaaagactg  960
tttcagaatc tgctactcag ccaccaacta aagtttataa taatgattta actgcatcat  1020
tgatggttgc attagatagt aataatacta tgccatttac tccagcagct atgagatctg  1080
agacattggg tttttatcca tggaaaccaa ccataccaac tccatggaga tattattttc  1140
aatgggatag aacattaata ccatctcata ctggaactag tggcacacca acaaatatat  1200
accatggtac agatccagat gatgttcaat tttatactat tgaaaattct gtgccagtac  1260
acttactaag aacaggtgat gaatttgcta caggaacatt ttttttgat tgtaaaccat  1320
gtagactaac acatacatgg caaacaaata gagcattggg cttaccacca tttctaaatt  1380
ctttgcctca atctgaagga gctactaact ttggtgatat aggagttcaa caagataaaa  1440
gacgtggtgt aactcaaatg ggaaatacaa actatattac tgaagctact attatgagac  1500
cagctgaggt tggttatagt gcaccatatt attcttttga ggcgtctaca caagggccat  1560
ttaaaacacc tattgcagca ggacgggggg gagcgcaaac atatgaaaat caagcagcag  1620
atggtgatcc aagatatgca tttggtagac aacatggtca aaaaactacc acaacaggag  1680
aaacacctga gagatttaca tatatagcac atcaagatac aggaagatat ccagaaggag  1740
attggattca aaatattaac tttaaccttc ctgtaacgaa tgataatgta ttgctaccaa  1800
cagatccaat tggaggtaaa acaggaatta actatactaa tatatttaat acttatggtc  1860
ctttaactgc attaaataat gtaccaccag tttatccaaa tggtcaaatt tgggataaag  1920
aatttgatac tgacttaaaa ccaagacttc atgtaaatgc accatttgtt tgtcaaaata  1980
attgtcctgg tcaattattt gtaaaagttg cgcctaattt aacaaatgaa tatgatcctg  2040
atgcatctgc taatatgtca agaattgtaa cttactcaga tttttggtgg aaaggtaaat  2100
tagtatttaa agctaaacta agagcctctc atacttggaa tccaattcaa caaatgagta  2160
ttaatgtaga taaccaattt aactatgtac caagtaatat tggaggtatg aaaattgtat  2220
atgaaaaatc tcaactagca cctagaaaat tatattaact cgaggcatgc ggtaccaagc  2280
ttgtcgagaa gtactagagg atcataatca gccataccac atttgtagag gttttacttg  2340
ctttaaaaaa cctcccacac ctccccctga acctgaaaca taaaatgaat gcaattgttg  2400
ttgttaactt gtttattgca gcttataatg gttacaaata aagcaatagc atcacaaatt  2460
tcacaaataa agcatttttt tcactgcatt ctagttgtgg tttgtccaaa ctcatcaatg  2520
tatcttatca tgtctggatc                                              2540
```

-continued

```
SEQ ID NO: 130          moltype = DNA  length = 3321
FEATURE                 Location/Qualifiers
source                  1..3321
                        mol_type = other DNA
                        organism = synthetic construct
SEQUENCE: 130
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggactatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtgatgcggt tttggcagta catcaatggg cgtggatagc  420
ggtttgactc acggggattt ccaagtctcc accccattga cgtcaatggg agtttgtttt  480
ggcaccaaaa tcaacgggac tttccaaaat gtcgtaacaa ctccgcccca ttgacgcaaa  540
tgggcggtag gcgtgtacgg tgggaggtct atataagcag agctctctgg ctaactagag  600
aacccactgc ttactggctt atcgaaatta atacgactca ctatagggag acccaagctt  660
ggtaccggac tctagaggat ccggtactcg aggaactgaa aaaccagaaa gttaactggt  720
aagtttagtc tttttgtctt ttatttcagg tcccggatcc ggtggtggtg caaatcaaag  780
aactgctcct cagtggatgt tgcctttact tctaggcctg tacggaagtg ttacttctgc  840
tctaaaagct gcggaattgt acccgcggaa gcttcctagg ccgccaccat ggcccccccc  900
gccaagcgcg cccgccgcgg ctacaagtac ctgggccccg gcaacagcct ggaccagggc  960
gagcccacca accccagcga cgccgccgcc aaggagcacg acgaggccta cgccgcctac  1020
ctgcgcagcg gcaagaaccc ctacctgtac ttcagccccg ccgaccagcg cttcatcgac  1080
cagaccaagg acgccaagga ctggggcggc aagatcggcc actacttctt ccgcgccaag  1140
aaggccatcg cccccgtgct gaccgacacc cccgaccacc ccagcaccag ccgcccccacc  1200
aagcccacca agcgcagcaa gccccccccc cacatcttca tcaacctggc caagaagaag  1260
aaggccggcg ccggccaggt gaagcgcgac aacctggccc ccatgagcga cggcgccgtg  1320
cagcccgacg gcggccagcc cgccgtgcgc aacgagcgcg ccaccggcag cggcaacggc  1380
agcggcggcg gcggcggcgg cggcagcggc ggcgtgggca tcagcaccgg caccttcaac  1440
aaccagaccg agttcaagtt cctggagaac ggctgggtgg agatcaccgc caacagcagc  1500
cgcctggtgc acctgaacat gcccgagagc gagaactacc gccgcgtggt ggtgaacaac  1560
atggacaaga ccgccgtgaa cggcaacatg gccctggacg acatccacgc ccagatcgtg  1620
accccctgga gcctggtgga cgccaacgcc tggggcgtgt ggttcaaccc cggcgactgg  1680
cagctgatcg tgaacaccat gagcgagctg cacctggtga gcttcgagca ggagatcttc  1740
aacgtggtgc tgaagaccgt gagcgagagc gccacccagc cccccaccaa ggtgtacaac  1800
aacgacctga ccgccagcct gatggtggcc ctggacagca acaacaccat gcccttcacc  1860
cccgccgcca tgcgcagcga gaccctgggc ttctacccct ggaagcccac catccccacc  1920
ccctggcgct actacttcca gtgggaccgc accctgatcc ccagccacac cggcaccagc  1980
ggcaccccca ccaacatcta ccacggcacc gaccccgacg acgtgcagtt ctacaccatc  2040
gagaacagcg tgcccgtgca cctgctgcgc accggcgacg agttcgccac cggcaccttc  2100
ttcttcgact gcaagccctg ccgcctgacc cacacctggc agaccaaccg cgccctgggc  2160
ctgccccccct tcctgaacag cctgccccag agcgagggcg ccaccaactt cggcgacatc  2220
ggcgtgcagc aggacaagcg ccgcggcgtg acccagatgg gcaacaccaa ctacatcacc  2280
gaggccacca tcatgcgccc cgccgaggtg ggctacagcg ccccctacta cagcttcgag  2340
gccagcaccc agggcccctt caagaccccc atcgccgccg gccgcggcgg cgcccagacc  2400
tacgagaacc aggccgccga cggcgacccc cgctacgcct tcggccgcca gcacggccag  2460
aagaccacca ccaccggcga gacccccgag cgcttcacct acatcgccca ccaggacacc  2520
ggccgctacc ccgagggcga ctggatccag aacatcaact tcaacctgcc cgtgaccaac  2580
gacaacgtgc tgctgcccac cgaccccatc ggcggcaaga ccggcatcaa ctacaccaac  2640
atcttcaaca cctacggccc cctgaccgcc ctgaacaacg tgccccccgt gtaccccaac  2700
ggccagatct gggacaagga gttcgacacc gacctgaagc cccgcctgca cgtgaacgcc  2760
cccttcgtgt gccagaacaa ctgcccccggc cagctgttcg tgaaggtggc ccccaacctg  2820
accaacgagt acgaccccga cgccagcgcc aacatgagcc gcatcgtgac ctacagcgac  2880
ttctggtgga agggcaagct ggtgttcaag gccaagctgc gcgccagcca cacctggaac  2940
cccatccagc agatgagcat caacgtggac aaccagttca actacgtgcc cagcaacatc  3000
ggcggcatga agatcgtgta cgagaagagc cagctggccc cccgcaagct gtactaataa  3060
ctcgagcatg catctagagg tacatctaga tagagctcgc tgatcagcct cgactgtgcc  3120
ttctagttgc cagccatctg ttgtttgccc ctcccccgtg ccttccttga ccctggaagg  3180
tgccactccc actgtccttt cctaataaaa tgaggaaatt gcatcgcatt gtctgagtag  3240
gtgtcattct attctggggg gtggggtggg gcaggacagc aagggggagg attgggaaga  3300
caatagcagg catgctgggg a                                            3321

SEQ ID NO: 131          moltype = DNA  length = 2531
FEATURE                 Location/Qualifiers
source                  1..2531
                        mol_type = other DNA
                        organism = synthetic construct
SEQUENCE: 131
atcatggaga taattaaaat gataaccatc tcgcaaataa ataagtattt tactgttttc  60
gtaacagttt tgtaataaaa aaacctataa atattccctc gacgaagact tgatcacccg  120
ggggatcccc tgttaagctg gctccagcta ttagaaaagc cagaggttac aacttcctag  180
gacccttcaa tcaagacttc aacaaagaac caactaatcc atcagacaac gctgcaaaac  240
aacacgattt ggaatacaac aaactaatca accaaggaca caatccttat tggtactaca  300
acaaagctga cgaagacttc atcaaagcaa cagatcaagc accagactgg ggaggaaaat  360
ttggcaactt catcttcaga gccaaaaaac acatcgctcc agaactggca ccaccagcaa  420
aaaagaaaag caaaaccaaa cacagtgaac cagaattcag ccacaaacac atcaaaccag  480
gcaccaaaag aggtaagcct tttcatattt ttgtaaacct tgctagaaaa agagcccgca  540
tgtcagaacc agctaatgat acaaatgaac aaccagacaa ctcccctgtt gaacagggtg  600
```

-continued

```
ctggtcaaat tggaggaggt ggaggtggag gtggaagcgg tgtcgggcac agcactggtg  660
attataataa taggactgag tttatttatc atggtgatga agtcacaatt atttgccact  720
ctacaagact ggttcacatc aatatgtcag acagggaaga ctacatcatc tatgaaacag  780
acagaggacc actctttcct accactcagg acctgcaggg tagagacact ctaaatgact  840
cttaccatgc caaagtagaa acaccatgga aactactcca tgcaaacagc tggggctgct  900
ggttttcacc agcagacttc caacaaatga tcaccacatg cagagacata gcaccaataa  960
aaatgcacca aaaaatagaa aacattgtca tcaaaacagt cagtaaaaca ggcacaggag  1020
aaacagaaac aaccaactac aacaatgacc tcacagcact cctacaaatt gcacaagaca  1080
acagtaacct actaccatgg gctgcagata acttttatat agactcagta ggttacgttc  1140
catggagagc atgcaaacta ccaacctact gctaccacgt agacacttgg aatacaattg  1200
acataaacca agcagacaca ccaaaccaat ggagagaaat caaaaaaggc atccaatggg  1260
acaatatcca attcacacca ctagaaacta tgataaacat tgacttacta agaacaggag  1320
atgcctggga atctggtaac tacaatttcc acacaaaacc aacaaaccta gcttaccatt  1380
ggcaatcaca aagacacaca ggcagctgtc acccaacagt agcacctcta gttgaaagag  1440
gacaaggaac caacatacaa tcagtaaact gttggcaatg ggagacagaa aacaatccaa  1500
gctctgcatc aaccagagta tccaatatac atattggata ctcatttcca gaatggcaaa  1560
tccactactc aacaggagga ccagtaatta atccaggcag tgcattctca caagcaccat  1620
ggggctcaac aactgaaggc accagactaa cccaaggtgc atctgaaaaa gccatctatg  1680
actggtccca tggagatgac caaccaggag ccagagaaac ctggtggcaa aacaaccaac  1740
atgtaacagg acaaactgac tgggcaccaa aaaatgcaca cacctcagaa ctcaacaaca  1800
atgtaccagc agccacacac ttctggaaaa acagctatca caacaccttc tcaccattca  1860
ctgcagtaga tgatcatgga ccacaatatc catggggagc catctgggga aaatacccag  1920
acaccacaca caaaccaatg atgtcagctc acgcaccatt cctacttcat ggaccacctg  1980
gacaactctt tgtaaaacta gcaccaaact atacagacac acttgacaac ggaggtgtaa  2040
cacatcccag aatcgtcaca tatggaacct tctggtggtc aggacaactc atctttaaag  2100
gaaaactacg cactccaaga caatggaata cctacaacct accaagccta gacaaaagag  2160
aaaccatgaa aaacacagta ccaaatgaag ttggtcactt tgaactacca tacatgccag  2220
gaagatgtct accaaactac acattgtaac tcgaggcatg cggtaccaag cttgtcgaga  2280
agtactagag gatcataatc agccatacca catttgtaga ggttttactt gctttaaaaa  2340
acctcccaca cctccccctg aacctgaaac ataaaatgaa tgcaattgtt gttgttaact  2400
tgtttattgc agcttataat ggttacaaat aaagcaatag catcacaaat ttcacaaata  2460
aagcattttt ttcactgcat tctagttgtg gtttgtccaa actcatcaat gtatcttatc  2520
atgtctggat c                                                      2531

SEQ ID NO: 132          moltype = DNA  length = 2531
FEATURE                 Location/Qualifiers
source                  1..2531
                        mol_type = other DNA
                        organism = synthetic construct
SEQUENCE: 132
atcatggaga taattaaaat gataaccatc tcgcaaataa ataagtattt tactgttttc  60
gtaacagttt tgtaataaaa aaacctataa atactccgga ctactgatac cgtcccactt  120
tcgggcgctt acctgccgcc acgccagcta ttagaaaagc cagaggatac aacttcctag  180
gacccttcaa tcaagacttc aacaaagaac caactaatcc atcagacaac gctgcaaaac  240
aacacgattt ggaatacaac aaactaatca accaaggaca caatccttat tggtactaca  300
acaaagctga cgaagacttc atcaaagcaa cagatcaagc accagactgg ggaggaaaat  360
ttggcaactt catcttcaga gccaaaaaac acatcgctcc agaactggca ccaccagcaa  420
aaaagaaaag caaaaccaaa cacagtgaac cagaattcag ccacaaacac atcaaaccag  480
gcaccaaaag aggtaagcct tttcatattt ttgtaaacct tgctagaaaa agagcccgca  540
tgtcagaacc agctaatgat acaaatgaac aaccagacaa ctcccctgtt gaacagggtg  600
ctggtcaaat tggaggaggt ggaggtggag gtggaagcgg tgtcgggcac agcactggtg  660
attataataa taggactgag tttatttatc atggtgatga agtcacaatt atttgccact  720
ctacaagact ggttcacatc aatatgtcag acagggaaga ctacatcatc tatgaaacag  780
acagaggacc actctttcct accactcagg acctgcaggg tagagacact ctaaatgact  840
cttaccatgc caaagtagaa acaccatgga aactactcca tgcaaacagc tggggctgct  900
ggttttcacc agcagacttc caacaaatga tcaccacatg cagagacata gcaccaataa  960
aaatgcacca aaaaatagaa aacattgtca tcaaaacagt cagtaaaaca ggcacaggag  1020
aaacagaaac aaccaactac aacaatgacc tcacagcact cctacaaatt gcacaagaca  1080
acagtaacct actaccatgg gctgcagata acttttatat agactcagta ggttacgttc  1140
catggagagc atgcaaacta ccaacctact gctaccacgt agacacttgg aatacaattg  1200
acataaacca agcagacaca ccaaaccaat ggagagaaat caaaaaaggc atccaatggg  1260
acaatatcca attcacacca ctagaaacta tgataaacat tgacttacta agaacaggag  1320
atgcctggga atctggtaac tacaatttcc acacaaaacc aacaaaccta gcttaccatt  1380
ggcaatcaca aagacacaca ggcagctgtc acccaacagt agcacctcta gttgaaagag  1440
gacaaggaac caacatacaa tcagtaaact gttggcaatg ggagacagaa aacaatccaa  1500
gctctgcatc aaccagagta tccaatatac atattggata ctcatttcca gaatggcaaa  1560
tccactactc aacaggagga ccagtaatta atccaggcag tgcattctca caagcaccat  1620
ggggctcaac aactgaaggc accagactaa cccaaggtgc atctgaaaaa gccatctatg  1680
actggtccca tggagatgac caaccaggag ccagagaaac ctggtggcaa aacaaccaac  1740
atgtaacagg acaaactgac tgggcaccaa aaaatgcaca cacctcagaa ctcaacaaca  1800
atgtaccagc agccacacac ttctggaaaa acagctatca caacaccttc tcaccattca  1860
ctgcagtaga tgatcatgga ccacaatatc catggggagc catctgggga aaatacccag  1920
acaccacaca caaaccaatg atgtcagctc acgcaccatt cctacttcat ggaccacctg  1980
gacaactctt tgtaaaacta gcaccaaact atacagacac acttgacaac ggaggtgtaa  2040
cacatcccag aatcgtcaca tatggaacct tctggtggtc aggacaactc atctttaaag  2100
gaaaactacg cactccaaga caatggaata cctacaacct accaagccta gacaaaagag  2160
aaaccatgaa aaacacagta ccaaatgaag ttggtcactt tgaactacca tacatgccag  2220
gaagatgtct accaaactac acattgtaac tcgaggcatg cggtaccaag cttgtcgaga  2280
agtactagag gatcataatc agccatacca catttgtaga ggttttactt gctttaaaaa  2340
```

-continued

```
acctcccaca cctccccctg aacctgaaac ataaaatgaa tgcaattgtt gttgttaact  2400
tgtttattgc agcttataat ggttacaaat aaagcaatag catcacaaat ttcacaaata  2460
aagcattttt ttcactgcat tctagttgtg gtttgtccaa actcatcaat gtatcttatc  2520
atgtctggat c                                                       2531

SEQ ID NO: 133          moltype = DNA  length = 3261
FEATURE                 Location/Qualifiers
source                  1..3261
                        mol_type = other DNA
                        organism = synthetic construct
SEQUENCE: 133
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggactatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtgatgcggt tttggcagta catcaatggg cgtggatagc  420
ggtttgactc acggggattt ccaagtctcc accccattga cgtcaatggg agtttgtttt  480
ggcaccaaaa tcaacgggac tttccaaaat gtcgtaacaa ctccgcccca ttgacgcaaa  540
tgggcggtag gcgtgtacgg tgggaggtct atataagcag agctctctgg ctaactagag  600
aacccactgc ttactggctt atcgaaatta atacgactca ctatagggag acccaagctt  660
ggtaccggac tctagaggat ccggtactcg aggaactgaa aaaccagaaa gttaactggt  720
aagtttagtc tttttgtctt ttatttcagg tcccggatcc ggtggtggtg caaatcaaag  780
aactgctcct cagtggatgt tgcctttact tctaggcctg tacggaagtg ttacttctgc  840
tctaaaagct gcggaattgt acccgcggaa gcttcctagg ccgccaccat gcccgccatc  900
cgcaaggccc gcggctacaa cttcctgggc cccttcaacc aggacttcaa caaggagccc  960
accaacccca gcgacaacgc cgccaagcag cacgacctgg agtacaacaa gctgatcaac  1020
cagggccaca accccctactg gtactacaac aaggccgacg aggacttcat caaggccacc  1080
gaccaggccc ccgactgggg cggcaagttc ggcaacttca tcttccgcgc caagaagcac  1140
atcgcccccg agctggcccc ccccgccaag aagaagagca agaccaagca cagcgagccc  1200
gagttcagcc acaagcacat caagcccggc accaagcgcg gcaagccctt ccacatcttc  1260
gtgaacctgg cccgcaagcg cgcccgcatg agcgagcccg ccaacgacac caacgagcag  1320
cccgacaaca gccccgtgga gcagggcgcc ggccagatcg gcggcggcgg cggcggcggc  1380
ggcagcggcg tgggccacag caccggcgac tacaacaacc gcaccgagtt catctaccac  1440
ggcgacgagg tgaccatcat ctgccacagc acccgcctgg tgcacatcaa catgagcgac  1500
cgcgaggact acatcatcta cgagaccgac cgcggccccc tgttccccac cacccaggac  1560
ctgcagggcc gcgacaccct gaacgacagc taccacgcca aggtggagac cccctggaag  1620
ctgctgcacg ccaacagctg ggctgctgg ttcagccccg ccgacttcca gcagatgatc  1680
accacctgcc gcgacatcgc ccccatcaag atgcaccaga agatcgagaa catcgtgatc  1740
aagaccgtga gcaagaccgg caccggcgag accgagacca ccaactacaa caacgacctg  1800
accgccctgc tgcagatcgc ccaggacaac agcaacctgc tgccctgggc cgccgacaac  1860
ttctacatcg acagcgtggg ctacgtgccc tggcgcgcct gcaagctgcc cacctactgc  1920
taccacgtgg acacctggaa caccatcgac atcaaccagg ccgacacccc caaccagtgg  1980
cgcgagatca agaagggcat ccagtgggac aacatccagt tcaccccct ggagaccatg  2040
atcaacatcg acctgctgcg caccggcgac gcctgggaga gcggcaacta caacttccac  2100
accaagccca ccaacctggc ctaccactgg cagagccagc gccacaccgg cagctgccac  2160
cccaccgtgg ccccccctggt ggagcgcggc cagggcacca acatccagag cgtgaactgc  2220
tggcagtggg gcgaccgcaa caaccccagc agcgccagca cccgcgtgag caacatccac  2280
atcggctaca gcttccccga gtggcagatc cactacagca ccggcggccc cgtgatcaac  2340
cccggcagcg ccttcagcca ggcccccctgg ggcagcacca ccgagggcac ccgcctgacc  2400
cagggcgcca gcgagaaggc catctacgac tggagccacg gcgacgacca gcccggcgcc  2460
cgcgagacct ggtggcagaa caaccagcac gtgaccggcc agaccgactg ggcccccaag  2520
aacgcccaca ccagcgagct gaacaacaac gtgcccgccg ccacccactt ctggaagaac  2580
agctaccaca acaccttcag ccccttcacc gccgtggacg accacggccc ccagtacccc  2640
tggggcgcca tctggggcaa gtaccccgac accacccaca agcccatgat gagcgcccac  2700
gccccttcc tgctgcacgg cccccccggc cagctgttcg tgaagctggc ccccaactac  2760
accgacaccc tggacaacgg cggcgtgacc cacccccgca tcgtgaccta cggcaccttc  2820
tggtggagcg gccagctgat cttcaagggc aagctgcgca ccccccgcca gtggaacacc  2880
tacaacctgc ccagcctgga caagcgcgag accatgaaga acaccgtgcc caacgaggtg  2940
ggccacttcg agctgcccta catgcccggc cgctgcctgc ccaactacac cctgtaataa  3000
ctcgagcatg catctagagg tacatctaga tagagctcgc tgatcagcct cgactgtgcc  3060
ttctagttgc cagccatctg ttgtttgccc ctcccccgtg ccttccttga ccctggaagg  3120
tgccactccc actgtccttt cctaataaaa tgaggaaatt gcatcgcatt gtctgagtag  3180
gtgtcattct attctggggg gtggggtggg gcaggacagc aagggggagg attgggaaga  3240
caatagcagg catgctgggg a                                            3261

SEQ ID NO: 134          moltype = DNA  length = 2516
FEATURE                 Location/Qualifiers
source                  1..2516
                        mol_type = other DNA
                        organism = synthetic construct
SEQUENCE: 134
atcatggaga taattaaaat gataaccatc tcgcaaataa ataagtattt tactgttttc  60
gtaacagttt tgtaataaaa aaacctataa atactccgga ctactgatac cgtcccactt  120
tcgggcgctt acctgccgcc acgccagcta ttagaaaagc cagaggaccc ttcaatcaag  180
acttcaacaa agaaccaact aatccatcag acaacgctgc aaaacaacac gatttggaat  240
acaacaaact aatcaaccaa ggacacaatc cttattggta ctacaacaaa gctgacgaag  300
acttcatcaa agcaacagat caagcaccag actggggagg aaaatttggc aacttcatct  360
```

-continued

```
tcagagccaa aaaacacatc gctccagaac tggcaccacc agcaaaaaag aaaagcaaaa  420
ccaaacacag tgaaccagaa ttcagccaca aacacatcaa accaggcacc aaaagaggta  480
agccttttca tatttttgta aaccttgcta gaaaaagagc ccgcatgtca gaaccagcta  540
atgatacaaa tgaacaacca gacaactccc ctgttgaaca gggtgctggt caaattggag  600
gaggtggagg tggaggtgga agcggtgtcg ggcacagcac tggtgattat aataatagga  660
ctgagtttat ttatcatggt gatgaagtca caattatttg ccactctaca agactggttc  720
acatcaatat gtcagacagg gaagactaca tcatctatga aacagacaga ggaccactct  780
ttcctaccac tcaggacctg cagggtagag acactctaaa tgactcttac catgccaaag  840
tagaaacacc atggaaacta ctccatgcaa acagctgggg ctgctggttt tcaccagcag  900
acttccaaca aatgatcacc acatgcagag acatagcacc aataaaaatg caccaaaaaa  960
tagaaaacat tgtcatcaaa acagtcagta aaacaggcac aggagaaaca gaaacaacca  1020
actacaacaa tgacctcaca gcactcctac aaattgcaca agacaacagt aacctactac  1080
catgggctgc agataacttt tatatagact cagtaggtta cgttccatgg agagcatgca  1140
aactaccaac ctactgctac cacgtagaca cttggaatac aattgacata aaccaagcag  1200
acacaccaaa ccaatggaga gaaatcaaaa aaggcatcca atgggacaat atccaattca  1260
caccactaga aactatgata aacattgact tactaagaac aggagatgcc tgggaatctg  1320
gtaactacaa tttccacaca aaaccaacaa acctagctta ccattggcaa tcacaaagac  1380
acacaggcag ctgtcaccca acagtagcac ctctagttga aagaggacaa ggaaccaaca  1440
tacaatcagt aaactgttgg caatggggag acagaaacaa tccaagctct gcatcaacca  1500
gagtatccaa tatacatatt ggatactcat ttccagaatg gcaaatccac tactcaacag  1560
gaggaccagt aattaatcca ggcagtgcat tctcacaagc accatggggc tcaacaactg  1620
aaggcaccag actaacccaa ggtgcatctg aaaaagccat ctatgactgg tcccatggag  1680
atgaccaacc aggagccaga gaaacctggt ggcaaaacaa ccaacatgta acaggacaaa  1740
ctgactgggc accaaaaaat gcacacacct cagaactcaa caacaatgta ccagcagcca  1800
cacacttctg gaaaaacagc tatcacaaca ccttctcacc attcactgca gtagatgatc  1860
atggaccaca atatccatgg ggagccatct ggggaaaata cccagacacc acacacaaac  1920
caatgatgtc agctcacgca ccattcctac ttcatggacc acctggacaa ctctttgtaa  1980
aactagcacc aaactataca gacacacttg acaacggagg tgtaacacat cccagaatcg  2040
tcacatatgg aaccttctgg tggtcaggac aactcatctt taaaggaaaa ctacgcactc  2100
caagacaatg gaatacctac aacctaccaa gcctagacaa aagagaaacc atgaaaaaca  2160
cagtaccaaa tgaagttggt cactttgaac taccatacat gccaggaaga tgtctaccaa  2220
actacacatt gtaactcgag gcatgcggta ccaagcttgt cgagaagtac tagaggatca  2280
taatcagcca taccacattt gtagaggttt tacttgcttt aaaaaacctc ccacacctcc  2340
ccctgaacct gaaacataaa atgaatgcaa ttgttgttgt taacttgttt attgcagctt  2400
ataatggtta caaataaagc aatagcatca caaatttcac aaataaagca tttttttcac  2460
tgcattctag ttgtggtttg tccaaactca tcaatgtatc ttatcatgtc tggatc      2516

SEQ ID NO: 135         moltype = DNA  length = 3246
FEATURE                Location/Qualifiers
source                 1..3246
                       mol_type = other DNA
                       organism = synthetic construct
SEQUENCE: 135
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggactatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtgatgcggt tttggcagta catcaatggg cgtggatagc  420
ggtttgactc acggggattt ccaagtctcc accccattga cgtcaatggg agtttgtttt  480
ggcaccaaaa tcaacgggac tttccaaaat gtcgtaacaa ctccgcccca ttgacgcaaa  540
tgggcggtag gcgtgtacgg tgggaggtct atataagcag agctctctgg ctaactagag  600
aacccactgc ttactggctt atcgaaatta atacgactca ctatagggag acccaagctt  660
ggtaccggac tctagaggat ccggtactcg aggaactgaa aaaccagaaa gttaactggt  720
aagtttagtc tttttgtctt ttatttcagg tcccggatcc ggtggtggtg caaatcaaag  780
aactgctcct cagtggatgt tgcctttact tctaggcctg tacggaagtg ttacttctgc  840
tctaaaagct gcggaattgt acccgcggaa gcttcctagg ccgccaccat gcccgccatc  900
cgcaaggccc gcggcccctt caaccaggac ttcaacaagg agcccaccaa ccccagcgac  960
aacgccgcca agcagcacga cctggagtac aacaagctga tcaaccaggg ccacaacccc  1020
tactggtact acaacaaggc cgacgaggac ttcatcaagg ccaccgacca ggcccccgac  1080
tggggcggca agttcggcaa cttcatcttc cgcgccaaga agcacatcgc cccccgagctg  1140
gcccccccg ccaagaagaa gagcaagacc aagcacagcg agcccgagtt cagccacaag  1200
cacatcaagc ccggcaccaa gcgcggcaag cccttccaca tcttcgtgaa cctggcccgc  1260
aagcgcgccc gcatgagcga gcccgccaac gacaccaacg agcagcccga caacagcccc  1320
gtggagcagg gcgccggcca gatcggcggc ggcggcggcg gcggcggcag cggcgtgggc  1380
cacagcaccg gcgactacaa caaccgcacc gagttcatct accacggcga cgaggtgacc  1440
atcatctgcc acagcacccg cctggtgcac atcaacatga gcgaccgcga ggactacatc  1500
atctacgaga ccgaccgcgg cccccctgttc cccaccaccc aggacctgca gggccgcgac  1560
accctgaacg acagctacca cgccaaggtg gagacccccct ggaagctgct gcacgccaac  1620
agctggggct gctggttcag ccccgccgac ttccagcaga tgatcaccac ctgccgcgac  1680
atcgccccca tcaagatgca ccagaagatc gagaacatcg tgatcaagac cgtgagcaag  1740
accggcaccg gcgagaccga gaccaccaac tacaacaacg acctgaccgc cctgctgcag  1800
atcgcccagg acaacagcaa cctgctgccc tgggccgccg acaacttcta catcgacagc  1860
gtgggctacg tgccctggcg cgcctgcaag ctgcccacct actgctacca cgtggacacc  1920
tggaacacca tcgacatcaa ccaggccgac accccccaacc agtggcgcga gatcaagaag  1980
ggcatccagt gggacaacat ccagttcacc cccctggaga ccatgatcaa catcgacctg  2040
ctgcgcaccg gcgacgcctg ggagagcggc aactacaact tccacaccaa gcccaccaac  2100
ctggcctacc actggcagag ccagcgccac accggcagct gccaccccac cgtggccccc  2160
```

-continued

```
ctggtggagc gcggccaggg caccaacatc cagagcgtga actgctggca gtggggcgac  2220
cgcaacaacc ccagcagcgc cagcacccgc gtgagcaaca tccacatcgg ctacagcttc  2280
cccgagtggc agatccacta cagcaccggc ggccccgtga tcaaccccgg cagcgccttc  2340
agccaggccc cctggggcag caccaccgag ggcacccgcc tgacccaggg cgccagcgag  2400
aaggccatct acgactggag ccacggcgac gaccagcccg gcgcccgcga gacctggtgg  2460
cagaacaacc agcacgtgac cggccagacc gactgggccc ccaagaacgc ccacaccagc  2520
gagctgaaca acaacgtgcc cgccgccacc cacttctgga agaacagcta ccacaacacc  2580
ttcagcccct tcaccgccgt ggacgaccac ggcccccagt accccctgggg cgccatctgg  2640
ggcaagtacc ccgacaccac ccacaagccc atgatgagcg cccacgcccc cttcctgctg  2700
cacggccccc ccggccagct gttcgtgaag ctggccccca actacaccga caccctggac  2760
aacggcggcg tgacccaccc ccgcatcgtg acctacggca ccttctggtg gagcggccag  2820
ctgatcttca agggcaagct gcgcaccccc cgccagtgga acacctacaa cctgcccagc  2880
ctggacaagc gcgagaccat gaagaacacc gtgcccaacg aggtgggcca cttcgagctg  2940
ccctacatgc ccggccgctg cctgcccaac tacaccctgt aataactcga gcatgcatct  3000
agaggtacat ctagatagag ctcgctgatc agcctcgact gtgccttcta gttgccagcc  3060
atctgttgtt tgcccctccc ccgtgccttc cttgaccctg gaaggtgcca ctcccactgt  3120
cctttcctaa taaaatgagg aaattgcatc gcattgtctg agtaggtgtc attctattct  3180
ggggggtggg gtggggcagg acagcaaggg ggaggattgg gaagacaata gcaggcatgc  3240
tgggga                                                            3246
```

```
SEQ ID NO: 136          moltype = DNA  length = 2591
FEATURE                 Location/Qualifiers
source                  1..2591
                        mol_type = other DNA
                        organism = synthetic construct
SEQUENCE: 136
catggagata attaaaatga taaccatctc gcaaataaat aagtatttta ctgttttcgt  60
aacagttttg taataaaaaa acctataaaa ttccggatta ttcataccgt cccaccatcg  120
ggcgcggatc tcctgttaag ctggcacctc cggcaaagag agccaggaga ggatataaat  180
atcttgggcc tgggaacagt cttgaccaag gagaaccaac taacccttct gacgccgctg  240
caaaagaaca cgacgaagct tacgctgctt atcttcgctc tggtaaaaac ccatacttat  300
atttctcgcc agcagatcaa cgctttatag atcaaactaa ggacgctaaa gattgggggg  360
ggaaaatagg acattatttt tttagagcta aaaaggcaat tgctccagta ttaactgata  420
caccagatca tccatcaaca tcaagaccaa caaaaccaac taaaagaagt aaaccaccac  480
ctcatatttt catcaatctt gcaaaaaaaa aaaaagccgg tgcaggacaa gtaaaaagag  540
acaatcttgc accaatgagt gatggagcag ttcaaccaga cggtggtcaa cctgctgtca  600
gaaatgaaag agctacagga tctgggaacg ggtctggagg cgggggtggt ggtggttctg  660
ggggtgtggg gatttctacg ggtactttca ataatcagac ggaatttaaa tttttggaaa  720
acggatgggt ggaaatcaca gcaaactcaa gcagacttgt acatttaaat atgccagaaa  780
gtgaaaatta taaaagagta gttgtaaata atatggataa aactgcagtt aaaggaaaca  840
tggctttaga tgatattcat gtacaaattg taacaccttg gtcattggtt gatgcaaatg  900
cttggggagt ttggtttaat ccaggagatt ggcaactaat tgttaatact atgagtgagt  960
tgcatttagt tagttttgaa caagaaattt ttaatgttgt tttaaagact gtttcagaat  1020
ctgctactca gccaccaact aaagtttata ataatgattt aactgcatca ttgatggttg  1080
cattagatag taataatact atgccattta ctccagcagc tatgagatct gagacattgg  1140
gtttttatcc atggaaacca accataccaa ctccatggag atattatttt caatgggata  1200
gaacattaat accatctcat actggaacta gtggcacacc aacaaatata taccatggta  1260
cagatccaga tgatgttcaa ttttatacta ttgaaaattc tgtgccagta cacttactaa  1320
gaacaggtga tgaatttgct acaggaacat tttttttga ttgtaaacca tgtagactaa  1380
cacatacatg gcaaacaaat agagcattgg gcttaccacc atttttaaat tctttgcctc  1440
aatctgaagg agctactaac tttggtgata taggagttca acaagataaa agacgtggtg  1500
taactcaaat gggaaataca aactatatta ctgaagctac tattatgaga ccagctgagg  1560
ttggttatag tgcaccatat tattcttttg aggcgtctac acaagggcca tttaaaacac  1620
ctattgcagc aggacggggg ggagcgcaaa cagatgaaaa tcaagcagca gatggtgatc  1680
caagatatgc atttggtaga caacatggtc aaaaaactac cacaacagga gaaacacctg  1740
agagatttac atatatagca catcaagata caggaagata tccagaagga gattggattc  1800
aaaatattaa ctttaacctt cctgtaacaa atgataatgt attgctacca acagatccaa  1860
ttggaggtaa aacaggaatt aactatacta atatatttaa tacttatggt cctttaactg  1920
cattaaataa tgtaccacca gtttatccaa atggtcaaat ttgggataaa gaatttgata  1980
ctgacttaaa accaagactt catgtaaatg caccatttgt ttgtcaaaat aattgtcctg  2040
gtcaattatt tgtaaaagtt gcgcctaatt taacaaatga atatgatcct gatgcatctg  2100
ctaatatgtc aagaattgta acttactcag atttttggtg gaaaggtaaa ttagtattta  2160
aagctaaact aagagcctct catacttgga atccaattca acaaatgagt attaatgtag  2220
ataaccaatt taactatgta ccaagtaata ttggagctat gaaaattgta tatgaaaaat  2280
ctcaactagc acctagaaaa ttatattaac tcgaggcatg cggtaccaag cttgtcgaga  2340
agtactagag gatcataatc agccatacca catttgtaga ggttttactt gctttaaaaa  2400
acctcccaca cctccccctg aacctgaaac ataaaatgaa tgcaattgtt gttgttaact  2460
tgtttattgc agcttataat ggttacaaat aaagcaatag catcacaaat ttcacaaata  2520
aagcattttt ttcactgcat tctagttgtg gtttgtccaa actcatcaat gtatcttatc  2580
atgtctggat c                                                      2591
```

```
SEQ ID NO: 137          moltype = DNA  length = 2597
FEATURE                 Location/Qualifiers
source                  1..2597
                        mol_type = other DNA
                        organism = synthetic construct
SEQUENCE: 137
atcatggaga taattaaaat gataaccatc tcgcaaataa ataagtattt tactgttttc  60
gtaacagttt tgtaataaaa aaacctataa atactccgga ctactgatac cgtcccactt  120
```

```
tcgggcgctt acctgccgcc acggcgcctc cagctaaaag agctaaaaga ggctacaagt  180
acctgggacc agggaacagc cttgaccaag gagaaccaac caatccatct gacgccgctg  240
ccaaagagca cgacgaggcc tacgatcaat acatcaaatc tggaaaaaat ccttacctgt  300
acttctctgc tgctgatcaa cgctttattg accaaaccaa ggacgccaaa gactggggag  360
gcaaggttgg tcactacttt tttagaacca agcgcgcttt tgcacctaag cttgctactg  420
actctgaacc tggaacttct ggtgtaagca gagctggtaa acgcactaga ccacctgctt  480
acatttttat taaccaagcc agagctaaaa aaaaacttac ttcttctgct gcacagcaaa  540
gcagtcaaac catgagtgat ggcaccagcc aacctgacag cggaaacgct gtccactcag  600
ctgcaagagt tgaacgagca gctgacggcc ctggaggctc tgggggtggg ggctctggcg  660
ggggtggggt tggtgtttct actgggtctt atgataatca aacgcattat agattcttgg  720
gtgacggctg ggtagaaatt actgcactag caactagact agtacattta aacatgccta  780
aatcagaaaa ctattgcaga atcagagttc acaatacaac agacacatca gtcaaaggca  840
acatggcaaa agatgatgct catgagcaaa tttggacacc atggagcttg gtggatgcta  900
atgcttgggg agtttggctc cagccaagtg actggcaata catttgcaac accatgagcc  960
agcttaactt ggtatcactt gatcaagaaa tattcaatgt agtgctgaaa actgttacag  1020
agcaagactt aggaggtcaa gctataaaaa tatacaacaa tgaccttaca gcttgcatga  1080
tggttgcagt agactcaaac aacattttgc catacacacc tgcagcaaac tcaatggaaa  1140
cacttggttt ctacccctgg aaaccaacca tagcatcacc atacaggtac tatttttgcg  1200
ttgacagaga tctttcagtg acctacgaaa atcaagaagg cacagttgaa cataatgtga  1260
tgggaacacc aaaaggaatg aattctcaat tttttaccat tgagaacaca caacaaatca  1320
cattgctcag aacaggggac gaatttgcca caggtactta ctactttgac acaaattcag  1380
ttaaactcac acacacgtgg caaaccaacc gtcaacttgg acagcctcca ctgctgtcaa  1440
cctttcctga agctgacact gatgcaggta cacttactgc tcaagggagc agacatggaa  1500
caacacaaat gggggttaac tgggtgagtg aagcaatcag aaccagacct gctcaagtag  1560
gattttgtca accacacaat gactttgaag ccagcagagc tggaccattt gctgccccaa  1620
aagttccagc agatattact caaggagtag acaaagaagc caatggcagt gttagataca  1680
gttatggcaa acagcatggt gaaaattggg cttcacatgg accagcacca gagcgctaca  1740
catgggatga aacaagcttt ggttcaggta gagacaccaa agatggtttt attcaatcag  1800
caccactagt tgttccacca ccactaaatg gcattcttac aaatgcaaac cctattggga  1860
ctaaaaatga cattcatttt tcaaatgttt ttaacagcta tggtccacta actgcatttt  1920
cacacccaag tcctgtatac cctcaaggac aaatatggga caaagaacta gatcttgaac  1980
acaaacctag acttcacata actgctccat ttgtttgtaa aaacaatgca cctggacaaa  2040
tgttggttag attaggacca aacctaactg accaatatga tccaaacgga gccacacttt  2100
ctagaattgt tacatacggt acatttttct ggaaaggaaa actaaccatg agagcaaaac  2160
ttagagctaa caccacttgg aacccagtgt accaagtaag tgctgaagac aatggcaact  2220
catacatgag tgtaactaaa tggttaccaa ctgctactgg aaacatgcag tctgtgccgc  2280
ttataacaag acctgttgct agaaatactt actaactcga ggcatgcggt accaagcttg  2340
tcgagaagta ctagaggatc ataatcagcc ataccacatt tgtagaggtt ttacttgctt  2400
taaaaaacct cccacacctc cccctgaacc tgaaacataa aatgaatgca attgttgttg  2460
ttaacttgtt tattgcagct tataatggtt acaaataaag caatagcatc acaaatttca  2520
caaataaagc attttttca ctgcattcta gttgtggttt gtccaaactc atcaatgtat  2580
cttatcatgt ctggatc                                                 2597
```

```
SEQ ID NO: 138         moltype = DNA  length = 2615
FEATURE                Location/Qualifiers
source                 1..2615
                       mol_type = other DNA
                       organism = synthetic construct
SEQUENCE: 138
atcatggaga taattaaaat gataaccatc tcgcaaataa ataagtattt tactgttttc  60
gtaacagttt tgtaataaaa aaacctataa atactccgga ctactgatac cgtcccactt  120
tcgggcgctt acctgccgcc acggcacctc cagctaaaag agctaaaaga ggctacaagt  180
acctgggacc agggaacagc cttgaccaag gagaaccaac caacccttct gacgccgctg  240
ccaaagaaca cgacgaagcc tacgaccaat acatcaaatc tggaaaaaat ccttacctgt  300
acttctctcc tgctgatcaa cgcttcattg accaaaccaa agacgccaag gactggggcg  360
gcaaggttgg tcactacttt tttagaacca agcgagcttt tgcacctaag ctttctactg  420
actctgaacc tggcacttct ggtgtgagca gacctggtaa acgaactaaa ccacctgctc  480
acatttttgt aaatcaagcc agagctaaaa aaaaacgcgc ttctcttgct gcacagcaga  540
ggactctgac aatgagtgat ggcaccgaaa caaaccaacc agacactgga atcgctaatg  600
ctagagttga gcgatcagct gacggaggtg gaagctctgg gggtgggggc tctggcgggg  660
gtgggattgg tgtttctact gggacttatg ataatcaaac gacttataag tttttgggag  720
atggatgggt agaaataact gcacatgctt ctagactttt gcacttggga atgcctcctt  780
cagaaaacta ctgccgcgtc accgttcaca ataatcaaac aacaggacac ggaactaagg  840
taaagggaaa catggcctat gatgacacac atcaacaaat ttggacacca tggagcttgg  900
tagatgctaa tgcttgggga gtttggttcc aaccaagtga ctggcagttc attcaaaaca  960
gcatggaatc gctgaatctt gactcattga gccaagaact atttaatgta gtagtcaaaa  1020
cagtcactga acaacaagga gctggccaag atgccattaa agtctataat aatgacttga  1080
cggcctgtat gatggttgct ctggatagta acaacatact gccttacaca cctgcagctc  1140
aaacatcaga aacacttggt ttctacccat ggaaaccaac cgcaccagct ccttacagat  1200
actacttttt catgcctaga caactcagtg taacctctag caactctgct gaaggaactc  1260
aaatcacaga caccattgga gagccacagg cactaaactc tcaatttttt actattgaga  1320
acaccttgcc tattactctc ctgcgcacag gtgatgagtt tacaactggc acctacatct  1380
ttaacactga cccacttaaa cttactcaca catggcaaac caacagacac ttgggcatgc  1440
ctccaagaat aactgaccta ccaacatcag atacagcaac agcatcacta actgcaaatg  1500
gagacagatt tggatcaaca caaacacaga atgtgaacta tgtcacagag gctttgcgca  1560
ccaggcctgc tcagattggc ttcatgcaac ctcatgacaa ctttgaagca aacagaggtg  1620
gcccatttaa ggttccagtg gtaccgctag acataacagc tggcgaggac catgatgcaa  1680
acggagccat acgatttaac tatggcaaac aacatggcga agattgggcc aaacaaggag  1740
cagcaccaga aaggtacaca tgggatgcaa ttgatagtgc agctgggagg gacacagcta  1800
```

```
gatgctttgt acaaagtgca ccaatatcta ttccaccaaa ccaaaaccag atcttgcagc  1860
gagaagacgc catagctggc agaactaaca tgcattatac taatgttttt aacagctatg  1920
gtccacttag tgcatttcct catccagatc ccatttatcc aaatggacaa atttgggaca  1980
aagaattgga cctggaacac aaacctagac tacacgtaac tgcaccattt gtttgtaaaa  2040
acaacccacc aggtcaacta tttgttcgct tggggcctaa tctgactgac caatttgacc  2100
caaacagcac aactgtttct cgcattgtta catatagcac tttttactgg aagggtattt  2160
tgaaattcaa agccaaacta agaccaaatc tgacctggaa tcctgtatac caagcaacca  2220
cagactctgt tgccaattct tacatgaatg ttaagaaatg gctcccatct gcaactggca  2280
acatgcactc tgatccattg atttgtagac ctgtgcctca catgacatac taactcgagg  2340
catgcggtac caagcttgtc gagaagtact agaggatcat aatcagccat accacatttg  2400
tagaggtttt acttgcttta aaaaacctcc cacacctccc cctgaacctg aaacataaaa  2460
tgaatgcaat tgttgttgtt aacttgttta ttgcagctta taatggttac aaataaagca  2520
atagcatcac aaatttcaca aataaagcat ttttttcact gcattctagt tgtggtttgt  2580
ccaaactcat caatgtatct tatcatgtct ggatc                             2615

SEQ ID NO: 139          moltype = DNA  length = 2546
FEATURE                 Location/Qualifiers
source                  1..2546
                        mol_type = other DNA
                        organism = synthetic construct
SEQUENCE: 139
atcatggaga taattaaaat gataaccatc tcgcaaataa ataagtattt tactgttttc  60
gtaacagttt tgtaataaaa aaacctataa atactccgga ctactgatac cgtcccactt  120
tcgggcgctt acctgccgcc acgccagcta ttagaaaagc cagaggttgg gtaccacctg  180
gatacaactt cctaggaccc ttcaatcaag acttcaacaa agaaccaact aatccatcag  240
acaacgctgc aaaacaacac gatttggaat acaacaaact aatcaaccaa ggacacaatc  300
cttattggta ctacaacaaa gctgacgaag acttcatcaa agcaacagat caagcaccag  360
actggggagg aaaatttggc aacttcatct tcagagccaa aaaacacatc gctccagaac  420
tggcaccacc agcaaaaaag aaaagcaaaa ccaaacacag tgaaccagaa ttcagccaca  480
aacacatcaa accaggcacc aaaagaggta agccttttca tatttttgta aaccttgcta  540
gaaaaagagc ccgcatgtca gaaccagcta atgatacaaa tgaacaacca gacaactccc  600
ctgttgaaca gggtgctggt caaattggag gaggtggagg tggaggtgga agcggtgtcg  660
ggcacagcac tggtgattat aataatagga ctgagtttat ttatcatggt gatgaagtca  720
caattatttg ccactctaca agactggttc acatcaatat gtcagacagg gaagactaca  780
tcatctatga aacagacaga ggaccactct ttcctaccac tcaggacctg cagggtagag  840
acactctaaa tgactcttac catgccaaag tagaaacacc atggaaacta ctccatgcaa  900
acagctgggg ctgctggttt tcaccagcag acttccaaca aatgatcacc acatgcagag  960
acatagcacc aataaaaatg caccaaaaaa tagaaaacat tgtcatcaaa acagtcagta  1020
aaacaggcac aggagaaaca gaaacaacca actacaacaa tgacctcaca gcactcctac  1080
aaattgcaca agacaacagt aacctactac catgggctgc agataacttt tatatagact  1140
cagtaggtta cgttccatgg agagcatgca aactaccaac ctactgctac cacgtagaca  1200
cttggaatac aattgacata aaccaagcag acacaccaaa ccaatggaga gaaatcaaaa  1260
aaggcatcca atgggacaat atccaattca caccactaga aactatgata aacattgact  1320
tactaagaac aggagatgcc tgggaatctg gtaactacaa tttccacaca aaaccaacaa  1380
acctagctta ccattggcaa tcacaaagac acacaggcag ctgtcaccca acagtagcac  1440
ctctagttga aagaggacaa ggaaccaaca tacaatcagt aaactgttgg caatggggag  1500
acagaaacaa tccaagctct gcatcaacca gagtatccaa tatacatatt ggatactcat  1560
ttccagaatg gcaaatccac tactcaacag gaggaccagt aattaatcca ggcagtgcat  1620
tctcacaagc accatggggc tcaacaactg aaggcaccag actaacccaa ggtgcatctg  1680
aaaaagccat ctatgactgg tcccatggag atgaccaacc aggagccaga gaaacctggt  1740
ggcaaaaacaa ccaacatgta acaggacaaa ctgactgggc accaaaaaat gcacacacct  1800
cagaactcaa caacaatgta ccagcagcca cacacttctg gaaaaacagc tatcacaaca  1860
ccttctcacc attcactgca gtagatgatc atggaccaca atatccatgg ggagccatct  1920
ggggaaaata cccagacacc acacacaaac caatgatgtc agctcacgca ccattcctac  1980
ttcatggacc acctggacaa ctctttgtaa aactagcacc aaactataca gacacacttg  2040
acaacggagg tgtaacacat cccagaatcg tcacatatgg aaccttctgg tggtcaggac  2100
aactcatctt taaaggaaaa ctacgcactc caagacaatg gaatacctac aacctaccaa  2160
gcctagacaa aagagaaacc atgaaaaaca cagtaccaaa tgaagttggt cactttgaac  2220
taccatacat gccaggaaga tgtctaccaa actacacatt gtaactcgag gcatgcggta  2280
ccaagcttgt cgagaagtac tagaggatca taatcagcca taccacattt gtagaggttt  2340
tacttgcttt aaaaaacctc ccacacctcc ccctgaacct gaaacataaa atgaatgcaa  2400
ttgttgttgt taacttgttt attgcagctt ataatggtta caaataaagc aatagcatca  2460
caaatttcac aaataaagca ttttttttcac tgcattctag ttgtggtttg tccaaactca  2520
tcaatgtatc ttatcatgtc tggatc                                      2546

SEQ ID NO: 140          moltype = DNA  length = 2612
FEATURE                 Location/Qualifiers
source                  1..2612
                        mol_type = other DNA
                        organism = synthetic construct
SEQUENCE: 140
atcatggaga taattaaaat gataaccatc tcgcaaataa ataagtattt tactgttttc  60
gtaacagttt tgtaataaaa aaacctataa atactccgga ctactgatac cgtcccactt  120
tcgggcgctt acctgccgcc acggcgcctc cagctaaaag agctaaaaga ggttgggtgc  180
ctcctggcta caagtacctg ggaccaggga acagccttga ccaaggagaa cccaaccaatc  240
catctgacgc cgctgccaaa gagcacgacg aggcctacga tcaatacatc aaatctggaa  300
aaaatcctta cctgtacttc tctgctgctg atcaacgctt tattgaccaa accaaggacg  360
ccaaagactg ggaggcaag gttggtcact actttttag aaccaagcgc gcttttgcac  420
ctaagcttgc tactgactct gaacctggaa cttctggtgt aagcagagct ggtaaacgca  480
```

```
ctagaccacc tgcttacatt tttattaacc aagccagagc taaaaaaaaa cttacttctt  540
ctgctgcaca gcaaagcagt caaaccatga gtgatggcac cagccaacct gacagcggaa  600
acgctgtcca ctcagctgca agagttgaac gagcagctga cggccctgga ggctctgggg  660
gtgggggctc tggcgggggt ggggttggtg tttctactgg gtcttatgat aatcaaacgc  720
attatagatt cttgggtgac ggctgggtag aaattactgc actagcaact agactagtac  780
atttaaacat gcctaaatca gaaaactatt gcagaatcag agttcacaat acaacagaca  840
catcagtcaa aggcaacatg gcaaaagatg atgctcatga gcaaatttgg acaccatgga  900
gcttggtgga tgctaatgct tggggagttt ggctccagcc aagtgactgg caatacattt  960
gcaacaccat gagccagctt aacttggtat cacttgatca agaaatattc aatgtagtgc  1020
tgaaaactgt tacagagcaa gacttaggag gtcaagctat aaaaatatac aacaatgacc  1080
ttacagcttg catgatggtt gcagtagact caaacaacat tttgccatac acacctgcag  1140
caaactcaat ggaaacactt ggtttctacc cctggaaacc aaccatagca tcaccataca  1200
ggtactattt ttgcgttgac agagatcttt cagtgaccta cgaaaatcaa gaaggcacag  1260
ttgaacataa tgtgatggga acaccaaaag gaatgaattc tcaatttttt accattgaga  1320
acacacaaca aatcacattg ctcagaacag gggacgaatt tgccacaggt acttactact  1380
ttgacacaaa ttcagttaaa ctcacacaca cgtggcaaac caaccgtcaa cttggacagc  1440
ctccactgct gtcaaccttt cctgaagctg acactgatgc aggtacactt actgctcaag  1500
ggagcagaca tggaacaaca caaatggggg ttaactgggt gagtgaagca atcagaacca  1560
gacctgctca agtaggattt tgtcaaccac acaatgactt tgaagccagc agagctggac  1620
catttgctgc cccaaaagtt ccagcagata ttactcaagg agtagacaaa gaagccaatg  1680
gcagtgttag atacagttat ggcaaacagc atggtgaaaa ttgggcttca catggaccag  1740
caccagagcg ctacacatgg gatgaaacaa gctttggttc aggtagagac accaaagatg  1800
gtttttattca atcagcacca ctagttgttc caccaccact aaatggcatt cttacaaatg  1860
caaaccctat tgggactaaa aatgacattc atttttcaaa tgtttttaac agctatggtc  1920
cactaactgc attttcacac ccaagtcctg tataccctca aggacaaata tgggacaaag  1980
aactagatct tgaacacaaa cctagacttc acataactgc tccatttgtt tgtaaaaaca  2040
atgcacctgg acaaatgttg gttagattag gaccaaacct aactgaccaa tatgatccaa  2100
acggagccac actttctaga attgttacat acggtacatt tttctggaaa ggaaaactaa  2160
ccatgagagc aaaacttaga gctaacacca cttggaaccc agtgtaccaa gtaagtgctg  2220
aagacaatgg caactcatac atgagtgtaa ctaaatggtt accaactgct actggaaaca  2280
tgcagtctgt gccgcttata acaagacctg ttgctagaaa tacttactaa ctcgaggcat  2340
gcggtaccaa gcttgtcgag aagtactaga ggatcataat cagccatacc acatttgtag  2400
aggttttact tgctttaaaa aacctcccac acctccccct gaacctgaaa cataaaatga  2460
atgcaattgt tgttgttaac ttgtttattg cagcttataa tggttacaaa taaagcaata  2520
gcatcacaaa tttcacaaat aaagcatttt tttcactgca ttctagttgt ggtttgtcca  2580
aactcatcaa tgtatcttat catgtctgga tc                                2612

SEQ ID NO: 141         moltype = DNA  length = 2630
FEATURE                Location/Qualifiers
source                 1..2630
                       mol_type = other DNA
                       organism = synthetic construct
SEQUENCE: 141
atcatggaga taattaaaat gataaccatc tcgcaaataa ataagtattt tactgttttc  60
gtaacagttt tgtaataaaa aaacctataa atactccgga ctactgatac cgtcccactt  120
tcgggcgctt acctgccgcc acggcacctc cagctaaaag agctaaaaga ggttgggtgc  180
ctcctggcta caagtacctg ggaccaggga acagccttga ccaaggagaa ccaaccaacc  240
cttctgacgc cgctgccaaa gaacacgacg aagcctacga ccaatacatc aaatctggaa  300
aaaatcctta cctgtacttc tctcctgctg atcaacgctt cattgaccaa accaaagacg  360
ccaaggactg gggcggcaag gttggtcact actttttttag aaccaagcga gcttttgcac  420
ctaagctttc tactgactct gaacctggca cttctggtgt gagcagacct ggtaaacgaa  480
ctaaaccacc tgctcacatt tttgtaaatc aagccagagc taaaaaaaaa cgcgcttctc  540
ttgctgcaca gcagaggact ctgacaatga gtgatggcac cgaaacaaac caaccagaca  600
ctggaatcgc taatgctaga gttgagcgat cagctgacgg aggtggaagc tctgggggtg  660
ggggctctgg cgggggtggg attggtgttt ctactgggac ttatgataat caaacgactt  720
ataagttttt gggagatgga tgggtagaaa taactgcaca tgcttctaga cttttgcact  780
tgggaatgcc tccttcagaa aactactgcc gcgtcaccgt tcacaataat caaacaacag  840
gacacggaac taaggtaaag ggaaacatgg cctatgatga cacacatcaa caaatttgga  900
caccatggag cttggtagat gctaatgctt ggggagtttg gttccaacca agtgactggc  960
agttcattca aaacagcatg gaatcgctga atcttgactc attgagccaa gaactattta  1020
atgtagtagt caaaacagtc actgaacaac aaggagctgg ccaagatgcc attaaagtct  1080
ataataatga cttgacggcc tgtatgatgg ttgctctgga tagtaacaac atactgcctt  1140
acacacctgc agctcaaaca tcagaaacac ttggtttcta cccatggaaa ccaaccgcac  1200
cagctcctta cagatactac tttttcatgc ctagacaact cagtgtaacc tctagcaact  1260
ctgctgaagg aactcaaatc acagacacca ttggagagcc acaggcacta aactctcaat  1320
tttttactat tgagaacacc ttgcctatta ctctcctgcg cacaggtgat gagtttacaa  1380
ctggcaccta catctttaac actgacccac ttaaacttac tcacacatgg caaaccaaca  1440
gacacttggg catgcctcca agaataactg acctaccaac atcagataca gcaacagcat  1500
cactaactgc aaatggagac agatttggat caacacaaac acagaatgtg aactatgtca  1560
cagaggcttt gcgcaccagg cctgctcaga ttggcttcat gcaacctcat gacaactttg  1620
aagcaaacag aggtggccca tttaaggttc cagtggtacc gctagacata acagctggcg  1680
aggaccatga tgcaaacgga gccatacgat ttaactatgg caaacaacat ggcgaagatt  1740
gggccaaaca aggagcagca ccagaaaggt acacatggga tgcaattgat agtgcagctg  1800
ggagggacac agctagatgc tttgtacaaa gtgcaccaat atctattcca ccaaaccaaa  1860
accagatctt gcagcggagaa gacgccatag ctggcagaac taacatgcat tatactaatg  1920
tttttaacag ctatggtcca cttagtgcat ttcctcatcc agatcccatt tatccaaatg  1980
gacaaatttg ggacaaagaa ttggacctgg aacacaaacc tagactacac gtaactgcac  2040
catttgtttg taaaaacaac ccaccaggtc aactatttgt tcgcttgggg cctaatctga  2100
ctgaccaatt tgacccaaac agcacaactg tttctcgcat tgttacatat agcacttttt  2160
```

-continued

```
actggaaggg tattttgaaa ttcaaagcca aactaagacc aaatctgacc tggaatcctg  2220
tataccaagc aaccacagac tctgttgcca attcttacat gaatgttaag aaatggctcc  2280
catctgcaac tggcaacatg cactctgatc cattgatttg tagacctgtg cctcacatga  2340
catactaact cgaggcatgc ggtaccaagc ttgtcgagaa gtactagagg atcataatca  2400
gccataccac atttgtagag gttttacttg ctttaaaaaa cctcccacac ctccccctga  2460
acctgaaaca taaaatgaat gcaattgttg ttgttaactt gtttattgca gcttataatg  2520
gttacaaata aagcaatagc atcacaaatt tcacaaataa agcatttttt tcactgcatt  2580
ctagttgtgg tttgtccaaa ctcatcaatg tatcttatca tgtctggatc             2630

SEQ ID NO: 142          moltype = DNA  length = 2900
FEATURE                 Location/Qualifiers
source                  1..2900
                        mol_type = other DNA
                        organism = synthetic construct
SEQUENCE: 142
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggactatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtgatgcggt tttggcagta catcaatggg cgtggatagc  420
ggtttgactc acggggattt ccaagtctcc accccattga cgtcaatggg agtttgtttt  480
ggcaccaaaa tcaacgggac tttccaaaat gtcgtaacaa ctccgcccca ttgacgcaaa  540
tgggcggtag gcgtgtacgg tgggaggtct atataagcag agctctctgg ctaactagag  600
aacccactgc ttactggctt atcgaaatta atacgactca ctatagggag acccaagctt  660
ggtaccggac tctagaggat ccggtactcg aggaactgaa aaaccagaaa gttaactggt  720
aagtttagtc tttttgtctt ttatttcagg tcccggatcc ggtggtggtg caaatcaaag  780
aactgctcct cagtggatgt tgcctttact tctaggcctg tacggaagtg ttacttctgc  840
tctaaaagct gcggaattgt acccgcggtt gaggaacctg ttaagatgag cgacggcgcc  900
gtgcagcccg acggcggcca gcccgccgtg cgcaacgagc gcgccaccgg cagcggcaac  960
ggcagcggcg gcggcggcgg cggcggcagc ggcggcgtgg gcatcagcac cggcaccttc  1020
aacaaccaga ccgagttcaa gttcctggag aacggctggg tggagatcac cgccaacagc  1080
agccgcctgg tgcacctgaa catgcccgag agcgagaact accgccgcgt ggtggtgaac  1140
aacatggaca agaccgccgt gaacggcaac atggccctgg acgacatcca cgcccagatc  1200
gtgacccccct ggagcctggt ggacgccaac gcctggggcg tgtggttcaa ccccggcgac  1260
tggcagctga tcgtgaacac catgagcgag ctgcacctgg tgagcttcga gcaggagatc  1320
ttcaacgtgg tgctgaagac cgtgagcgag agcgccaccc agccccccac caaggtgtac  1380
aacaacgacc tgaccgccag cctgatggtg gccctggaca gcaacaacac catgcccttc  1440
accccccgccg ccatgcgcag cgagaccctg ggcttctacc cctggaagcc caccatcccc  1500
acccccctggc gctactactt ccagtgggac cgcaccctga tccccagcca caccggcacc  1560
agcggcaccc ccaccaacat ctaccacggc accgaccccg acgacgtgca gttctacacc  1620
atcgagaaca gcgtgcccgt gcacctgctg cgcaccggcg acgagttcgc caccggcacc  1680
ttcttcttcg actgcaagcc ctgccgcctg acccacacct ggcagaccaa ccgcgccctg  1740
ggcctgcccc ccttcctgaa cagcctgccc cagagcgagg gcgccaccaa cttcggcgac  1800
atcggcgtgc agcaggacaa gcgccgcggc gtgacccaga tgggcaacac caactacatc  1860
accgaggcca ccatcatgcg ccccgccgag gtgggctaca gcgcccccta ctacagcttc  1920
gaggccagca cccagggccc cttcaagacc cccatcgccg ccggccgcgg cggcgcccag  1980
acctacgaga accaggccgc cgacggcgac ccccgctacg ccttcggccg ccagcacggc  2040
cagaagacca ccaccaccgg cgagaccccc gagcgcttca cctacatcgc ccaccaggac  2100
accggccgct accccgaggg cgactggatc cagaacatca acttcaacct gcccgtgacc  2160
aacgacaacg tgctgctgcc caccgacccc atcggcggca agaccggcat caactacacc  2220
aacatcttca acacctacgg cccccctgacc gccctgaaca acgtgccccc cgtgtacccc  2280
aacggccaga tctgggacaa ggagttcgac accgacctga agccccgcct gcacgtgaac  2340
gccccccttcg tgtgccagaa caactgcccc ggccagctgt tcgtgaaggt ggcccccaac  2400
ctgaccaacg agtacgaccc cgacgccagc gccaacatga gccgcatcgt gacctacagc  2460
gacttctggt ggaagggcaa gctggtgttc aaggccaagc tgcgcgccag ccacacctgg  2520
aaccccatcc agcagatgag catcaacgtg gacaaccagt tcaactacgt gcccagcaac  2580
atcggcggca tgaagatcgt gtacgagaag agccagctgg ccccccgcaa gctgtactaa  2640
taactcgagc atgcatctag agatctagat agagctcgct gatcagcctc gactgtgcct  2700
tctagttgcc agccatctgt tgtttgcccc tcccccgtgc cttccttgac cctggaaggt  2760
gccactccca ctgtcctttc ctaataaaat gaggaaattg catcgcattg tctgagtagg  2820
tgtcattcta ttctgggggg tggggtgggg caggacagca agggggagga ttgggaagac  2880
aatagcaggc atgctgggga                                              2900

SEQ ID NO: 143          moltype = DNA  length = 2855
FEATURE                 Location/Qualifiers
source                  1..2855
                        mol_type = other DNA
                        organism = synthetic construct
SEQUENCE: 143
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggactatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtgatgcggt tttggcagta catcaatggg cgtggatagc  420
ggtttgactc acggggattt ccaagtctcc accccattga cgtcaatggg agtttgtttt  480
```

```
ggcaccaaaa tcaacgggac tttccaaaat gtcgtaacaa ctccgcccca ttgacgcaaa  540
tgggcggtag gcgtgtacgg tgggaggtct atataagcag agctctctgg ctaactagag  600
aacccactgc ttactggctt atcgaaatta atacgactca ctatagggag acccaagctt  660
ggtaccggac tctagaggat ccggtactcg aggaactgaa aaaccagaaa gttaactggt  720
aagtttagtc tttttgtctt ttatttcagg tcccggatcc ggtggtggtg caaatcaaag  780
aactgctcct cagtggatgt tgcctttact tctaggcctg tacggaagtg ttacttctgc  840
tctaaaagct gcggaattgt acccgcggtt gaggaacctg ttaagatgag cgagcccgcc  900
aacgacacca acgagcagcc cgacaacagc cccgtggagc agggcgccgg ccagatcggc  960
ggcggcggcg gcggcggcgg cagcggcgtg ggccacagca ccggcgacta caacaaccgc  1020
accgagttca tctaccacgg cgacgaggtg accatcatct gccacagcac ccgcctggtg  1080
cacatcaaca tgagcgaccg cgaggactac atcatctacg agaccgaccg cggcccccctg  1140
ttccccacca cccaggacct gcagggccgc gacaccctga acgacagcta ccacgccaag  1200
gtggagaccc cctggaagct gctgcacgcc aacagctggg gctgctggtt cagccccgcc  1260
gacttccagc agatgatcac cacctgccgc gacatcgccc ccatcaagat gcaccagaag  1320
atcgagaaca tcgtgatcaa gaccgtgagc aagaccggca ccggcgagac cgagaccacc  1380
aactacaaca acgacctgac cgccctgctg cagatcgccc aggacaacag caacctgctg  1440
ccctgggccg ccgacaactt ctacatcgac agcgtgggct acgtgccctg gcgcgcctgc  1500
aagctgccca cctactgcta ccacgtggac acctggaaca ccatcgacat caaccaggcc  1560
gacaccccca accagtggcg cgagatcaag aagggcatcc agtgggacaa catccagttc  1620
acccccctgg agaccatgat caacatcgac ctgctgcgca ccggcgacgc ctgggagagc  1680
ggcaactaca acttccacac caagcccacc aacctggcct accactggca gagccagcgc  1740
cacaccggca gctgccaccc caccgtggcc cccctggtgg agcgcggcca gggcaccaac  1800
atccagagcg tgaactgctg gcagtggggc gaccgcaaca accccagcag cgccagcacc  1860
cgcgtgagca acatccacat cggctacagc ttccccgagt ggcagatcca ctacagcacc  1920
ggcggccccg tgatcaaccc cggcagcgcc ttcagccagg cccccctgggg cagcaccacc  1980
gagggcaccc gcctgaccca gggcgccagc gagaaggcca tctacgactg gagccacggc  2040
gacgaccagc ccggcgcccg cgagacctgg tggcagaaca accagcacgt gaccggccag  2100
accgactggg cccccaagaa cgcccacacc agcgagctga acaacaacgt gcccgccgcc  2160
acccacttct ggaagaacag ctaccacaac accttcagcc ccttcaccgc cgtggacgac  2220
cacggccccc agtaccccctg gggcgccatc tggggcaagt accccgacac cacccacaag  2280
cccatgatga gcgcccacgc cccccttcctg ctgcacggcc cccccggcca gctgttcgtg  2340
aagctggccc ccaactacac cgacaccctg gacaacggcg gcgtgaccca cccccgcatc  2400
gtgacctacg gcaccttctg gtggagcggc cagctgatct tcaagggcaa gctgcgcacc  2460
ccccgccagt ggaacaccta caacctgccc agcctggaca agcgcgagac catgaagaac  2520
accgtgccca acgaggtggg ccacttcgag ctgccctaca tgcccggccg ctgcctgccc  2580
aactacaccc tgtaataact cgagcatgca tctagagatc tagatagagc tcgctgatca  2640
gcctcgactg tgccttctag ttgccagcca tctgttgttt gcccctcccc cgtgccttcc  2700
ttgaccctgg aaggtgccac tcccactgtc ctttcctaat aaaatgagga aattgcatcg  2760
cattgtctga gtaggtgtca ttctattctg gggggtgggg tggggcagga cagcaagggg  2820
gaggattggg aagacaatag caggcatgct gggga                            2855
```

```
SEQ ID NO: 144          moltype = DNA  length = 42
FEATURE                 Location/Qualifiers
source                  1..42
                        mol_type = other DNA
                        organism = synthetic construct
SEQUENCE: 144
gcccgggcaa agcccgggcg tcgggcgacc tttggtcgcc cg                    42

SEQ ID NO: 145          moltype = AA  length = 6
FEATURE                 Location/Qualifiers
source                  1..6
                        mol_type = protein
                        organism = synthetic construct
SEQUENCE: 145
KRARRG                                                            6

SEQ ID NO: 146          moltype = AA  length = 6
FEATURE                 Location/Qualifiers
source                  1..6
                        mol_type = protein
                        organism = synthetic construct
SEQUENCE: 146
KRAKRG                                                            6

SEQ ID NO: 147          moltype = AA  length = 4
FEATURE                 Location/Qualifiers
source                  1..4
                        mol_type = protein
                        organism = synthetic construct
SEQUENCE: 147
KARG                                                              4

SEQ ID NO: 148          moltype = DNA  length = 3336
FEATURE                 Location/Qualifiers
source                  1..3336
                        mol_type = other DNA
                        organism = synthetic construct
SEQUENCE: 148
```

-continued

```
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggactatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtgatgcggt tttggcagta catcaatggg cgtggatagc  420
ggtttgactc acggggattt ccaagtctcc accccattga cgtcaatggg agtttgtttt  480
ggcaccaaaa tcaacgggac tttccaaaat gtcgtaacaa ctccgcccca ttgacgcaaa  540
tgggcggtag gcgtgtacgg tgggaggtct atataagcag agctctctgg ctaactagag  600
aacccactgc ttactggctt atcgaaatta atacgactca ctatagggag acccaagctt  660
ggtaccggac tctagaggat ccggtactcg aggaactgaa aaaccagaaa gttaactggt  720
aagtttagtc tttttgtctt ttatttcagg tcccggatcc ggtggtggtg caaatcaaag  780
aactgctcct cagtggatgt tgcctttact tctaggcctg tacggaagtg ttacttctgc  840
tctaaaagct gcggaattgt acccgcggaa gcttcctagg ccgccaccat ggcccccccc  900
gccaagcgcg cccgccgcgg cctggtgccc cccggctaca agtacctggg ccccggcaac  960
agcctggacc agggcgagcc caccaacccc agcgacgccg ccgccaagga gcacgacgag  1020
gcctacgccg cctacctgcg cagcggcaag aacccctacc tgtacttcag ccccgccgac  1080
cagcgcttca tcgaccagac caaggacgcc aaggactggg gcggcaagat cggccactac  1140
ttcttccgcg ccaagaaggc catcgccccc gtgctgaccg acacccccga ccaccccagc  1200
accagccgcc ccaccaagcc caccaagcgc agcaagcccc cccccacat cttcatcaac  1260
ctggccaaga agaagaaggc cggcgccggc caggtgaagc gcgacaacct ggcccccatg  1320
agcgacggcg ccgtgcagcc cgacggcggc cagcccgccg tgcgcaacga gcgcgccacc  1380
ggcagcggca acggcagcgg cggcggcggc ggcggcggca gcggcggcgt gggcatcagc  1440
accggcacct tcaacaacca gaccgagttc aagttcctgg agaacggctg ggtggagatc  1500
accgccaaca gcagccgcct ggtgcacctg aacatgcccg agagcgagaa ctaccgccgc  1560
gtggtggtga acaacatgga caagaccgcc gtgaacggca acatggccct ggacgacatc  1620
cacgcccaga tcgtgacccc ctggagcctg gtggacgcca acgcctgggg cgtgtggttc  1680
aaccccggcg actggcagct gatcgtgaac accatgagcg agctgcacct ggtgagcttc  1740
gagcaggaga tcttcaacgt ggtgctgaag accgtgagcg agagcgccac ccagcccccc  1800
accaaggtgt acaacaacga cctgaccgcc agcctgatgg tggccctgga cagcaacaac  1860
accatgccct tcacccccgc cgccatgcgc agcgagaccc tgggcttcta cccctggaag  1920
cccaccatcc ccacccccctg gcgctactac ttccagtggg accgcaccct gatccccagc  1980
cacaccggca ccagcggcac ccccaccaac atctaccacg gcaccgaccc cgacgacgtg  2040
cagttctaca ccatcgagaa cagcgtgccc gtgcacctgc tgcgcaccgg cgacgagttc  2100
gccaccggca ccttcttctt cgactgcaag ccctgccgcc tgacccacac ctggcagacc  2160
aaccgcgccc tgggcctgcc ccccttcctg aacagcctgc cccagagcga gggcgccacc  2220
aacttcggcg acatcggcgt gcagcaggac aagcgccgcg gcgtgaccca gatgggcaac  2280
accaactaca tcaccgaggc caccatcatg cgccccgccg aggtgggcta cagcgccccc  2340
tactacagct tcgaggccag cacccagggc cccttcaaga cccccatcgc cgccggccgc  2400
ggcggcgccc agacctacga gaaccaggcc gccgacggcg acccccgcta cgccttcggc  2460
cgccagcacg gccagaagac caccaccacc ggcgagaccc ccgagcgctt cacctacatc  2520
gcccaccagg acaccggccg ctaccccgag ggcgactgga tccagaacat caacttcaac  2580
ctgcccgtga ccaacgacaa cgtgctgctg cccaccgacc ccatcggcgg caagaccggc  2640
atcaactaca ccaacatctt caacacctac ggccccctga ccgccctgaa caacgtgccc  2700
cccgtgtacc ccaacggcca gatctgggac aaggagttcg acaccgacct gaagccccgc  2760
ctgcacgtga acgccccctt cgtgtgccag aacaactgcc ccggccagct gttcgtgaag  2820
gtggccccca acctgaccaa cgagtacgac cccgacgcca gcgccaacat gagccgcatc  2880
gtgacctaca gcgacttctg gtggaagggc aagctggtgt tcaaggccaa gctgcgcgcc  2940
agccacacct ggaaccccat ccagcagatg agcatcaacg tggacaacca gttcaactac  3000
gtgcccagca acatcggcgg catgaagatc gtgtacgaga agagccagct ggccccccgc  3060
aagctgtact aataactcga gcatgcatct agaggtacat ctagatagag ctcgctgatc  3120
agcctcgact gtgccttcta gttgccagcc atctgttgtt tgcccctccc ccgtgccttc  3180
cttgaccctg gaaggtgcca ctcccactgt cctttcctaa taaaatgagg aaattgcatc  3240
gcattgtctg agtaggtgtc attctattct ggggggtggg gtggggcagg acagcaaggg  3300
ggaggattgg gaagacaata gcaggcatgc tgggga                            3336
```

```
SEQ ID NO: 149         moltype = DNA  length = 2588
FEATURE                Location/Qualifiers
source                 1..2588
                       mol_type = other DNA
                       organism = synthetic construct
SEQUENCE: 149
catggagata attaaaatga taaccatctc gcaaataaat aagtatttta ctgttttcgt  60
aacagttttg taataaaaaa acctataaaa ttccggatta ttcataccgt cccaccatcg  120
ggcgcggatc tgccgccctg gcacctccgg caaagagagc caggagagga tataaatatc  180
ttgggcctgg gaacagtctt gaccaaggag aaccaactaa cccttctgac gccgctgcaa  240
aagaacacga cgaagcttac gctgcttatc ttcgctctgg taaaaaccca tacttatatt  300
tctcgccagc agatcaacgc tttatagatc aaactaagga cgctaaagat tggggggggga  360
aaataggaca ttattttttt agagctaaaa aggcaattgc tccagtatta actgatacac  420
cagatcatcc atcaacatca agaccaacaa aaccaactaa aagaagtaaa ccaccacctc  480
atattttcat caatcttgca aaaaaaaaaa aagccggtgc aggacaagta aaaagagaca  540
atcttgcacc aatgagtgat ggagcagttc aaccagacgg tggtcaacct gctgtcagaa  600
atgaaagagc tacaggatct gggaacgggt ctggaggcgg gggtggtggt ggttctgggg  660
gtgtggggat ttctacgggt actttcaata atcagacgga atttaaattt ttggaaaacg  720
gatgggtgga aatcacagca aactcaagca gacttgtaca tttaaatatg ccagaaagtg  780
aaaattatag aagagtggtt gtaaataata tggataaaac tgcagttaac ggaaacatgg  840
ctttagatga tattcatgca caaattgtaa caccttggtc attggttgat gcaaatgctt  900
ggggagtttg gtttaatcca ggagattggc aactaattgt taatactatg agtgagttgc  960
```

-continued

```
atttagttag ttttgaacaa gaaattttta atgttgtttt aaagactgtt tcagaatctg  1020
ctactcagcc accaactaaa gtttataata atgatttaac tgcatcattg atggttgcat  1080
tagatagtaa taatactatg ccatttactc cagcagctat gagatctgag acattgggtt  1140
tttatccatg gaaaccaacc ataccaactc catggagata ttattttcaa tgggatagaa  1200
cattaatacc atctcatact ggaactagtg gcacaccaac aaatatatac catggtacag  1260
atccagatga tgttcaattt tatactattg aaaattctgt gccagtacac ttactaagaa  1320
caggtgatga atttgctaca ggaacatttt tttttgattg taaaccatgt agactaacac  1380
atacatggca aacaaataga gcattgggct taccaccatt tctaaattct ttgcctcaat  1440
ctgaaggagc tactaacttt ggtgatatag gagttcaaca agataaaaga cgtggtgtaa  1500
ctcaaatggg aaatacaaac tatattactg aagctactat tatgagacca gctgaggttg  1560
gttatagtgc accatattat tcttttgagg cgtctacaca agggccattt aaaacaccta  1620
ttgcagcagg acgggggga gcgcaaacat atgaaaatca agcagcagat ggtgatccaa  1680
gatatgcatt tggtagacaa catggtcaaa aaactaccac aacaggagaa acacctgaga  1740
gatttacata tatagcacat caagatacag gaagatatcc agaaggagat tggattcaaa  1800
atattaactt taaccttcct gtaacgaatg ataatgtatt gctaccaaca gatccaattg  1860
gaggtaaaac aggaattaac tatactaata tatttaatac ttatggtcct ttaactgcat  1920
taaataatgt accaccagtt tatccaaatg gtcaaatttg ggataaagaa tttgatactg  1980
acttaaaacc aagacttcat gtaaatgcac catttgtttg tcaaaataat tgtcctggtc  2040
aattatttgt aaaagttgcg cctaatttaa caaatgaata tgatcctgat gcatctgcta  2100
atatgtcaag aattgtaact tactcagatt tttggtggaa aggtaaatta gtatttaaag  2160
ctaaactaag agcctctcat acttggaatc caattcaaca aatgagtatt aatgtagata  2220
accaatttaa ctatgtacca agtaatattg gaggtatgaa aattgtatat gaaaaatctc  2280
aactagcacc tagaaaatta tattaactcg aggcatgcgg taccaagctt gtcgagaagt  2340
actagaggat cataatcagc cataccacat ttgtagaggt tttacttgct ttaaaaaacc  2400
tcccacacct ccccctgaac ctgaaacata aaatgaatgc aattgttgtt gttaacttgt  2460
ttattgcagc ttataatggt tacaaataaa gcaatagcat cacaaatttc acaaataaag  2520
catttttttc actgcattct agttgtggtt tgtccaaact catcaatgta tcttatcatg  2580
tctggatc                                                             2588

SEQ ID NO: 150          moltype = DNA  length = 2588
FEATURE                 Location/Qualifiers
source                  1..2588
                        mol_type = other DNA
                        organism = synthetic construct
SEQUENCE: 150
catggagata attaaaatga taaccatctc gcaaataaat aagtatttta ctgttttcgt  60
aacagttttg taataaaaaa acctataaaa ttccggatta ttcataccgt cccaccatcg  120
ggcgcggatc tgccgccacg gcacctccgg caaagagagc caggagagga tataaatatc  180
ttgggcctgg gaacagtctt gaccaaggag aaccaactaa cccttctgac gccgctgcaa  240
aagaacacga cgaagcttac gctgcttatc ttcgctctgg taaaaaccca tacttatatt  300
tctcgccagc agatcaacgc tttatagatc aaactaagga cgctaaagat tgggggggga  360
aaataggaca ttattttttt agagctaaaa aggcaattgc tccagtatta actgatacac  420
cagatcatcc atcaacatca agaccaacaa aaccaactaa aagaagtaaa ccaccacctc  480
atattttcat caatcttgca aaaaaaaaaa aagccggtgc aggacaagta aaaagagaca  540
atcttgcacc aatgagtgat ggagcagttc aaccagacgg tggtcaacct gctgtcagaa  600
atgaaagagc tacaggatct gggaacgggt ctggaggcgg gggtggtggt ggttctgggg  660
gtgtggggat ttctacgggt actttcaata atcagacgga atttaaattt ttggaaaacg  720
gatgggtgga aatcacagca aactcaagca gacttgtaca tttaaatatg ccagaaagtg  780
aaaattatag aagagtggtt gtaaataata tggataaaac tgcagttaac ggaaacatgg  840
ctttagatga tattcatgca caaattgtaa caccttggtc attggttgat gcaaatgctt  900
ggggagtttg gtttaatcca ggagattggc aactaattgt taatactatg agtgagttgc  960
atttagttag ttttgaacaa gaaattttta atgttgtttt aaagactgtt tcagaatctg  1020
ctactcagcc accaactaaa gtttataata atgatttaac tgcatcattg atggttgcat  1080
tagatagtaa taatactatg ccatttactc cagcagctat gagatctgag acattgggtt  1140
tttatccatg gaaaccaacc ataccaactc catggagata ttattttcaa tgggatagaa  1200
cattaatacc atctcatact ggaactagtg gcacaccaac aaatatatac catggtacag  1260
atccagatga tgttcaattt tatactattg aaaattctgt gccagtacac ttactaagaa  1320
caggtgatga atttgctaca ggaacatttt tttttgattg taaaccatgt agactaacac  1380
atacatggca aacaaataga gcattgggct taccaccatt tctaaattct ttgcctcaat  1440
ctgaaggagc tactaacttt ggtgatatag gagttcaaca agataaaaga cgtggtgtaa  1500
ctcaaatggg aaatacaaac tatattactg aagctactat tatgagacca gctgaggttg  1560
gttatagtgc accatattat tcttttgagg cgtctacaca agggccattt aaaacaccta  1620
ttgcagcagg acgggggga gcgcaaacat atgaaaatca agcagcagat ggtgatccaa  1680
gatatgcatt tggtagacaa catggtcaaa aaactaccac aacaggagaa acacctgaga  1740
gatttacata tatagcacat caagatacag gaagatatcc agaaggagat tggattcaaa  1800
atattaactt taaccttcct gtaacgaatg ataatgtatt gctaccaaca gatccaattg  1860
gaggtaaaac aggaattaac tatactaata tatttaatac ttatggtcct ttaactgcat  1920
taaataatgt accaccagtt tatccaaatg gtcaaatttg ggataaagaa tttgatactg  1980
acttaaaacc aagacttcat gtaaatgcac catttgtttg tcaaaataat tgtcctggtc  2040
aattatttgt aaaagttgcg cctaatttaa caaatgaata tgatcctgat gcatctgcta  2100
atatgtcaag aattgtaact tactcagatt tttggtggaa aggtaaatta gtatttaaag  2160
ctaaactaag agcctctcat acttggaatc caattcaaca aatgagtatt aatgtagata  2220
accaatttaa ctatgtacca agtaatattg gaggtatgaa aattgtatat gaaaaatctc  2280
aactagcacc tagaaaatta tattaactcg aggcatgcgg taccaagctt gtcgagaagt  2340
actagaggat cataatcagc cataccacat ttgtagaggt tttacttgct ttaaaaaacc  2400
tcccacacct ccccctgaac ctgaaacata aaatgaatgc aattgttgtt gttaacttgt  2460
ttattgcagc ttataatggt tacaaataaa gcaatagcat cacaaatttc acaaataaag  2520
catttttttc actgcattct agttgtggtt tgtccaaact catcaatgta tcttatcatg  2580
tctggatc                                                             2588
```

```
SEQ ID NO: 151          moltype = DNA  length = 2588
FEATURE                 Location/Qualifiers
source                  1..2588
                        mol_type = other DNA
                        organism = synthetic construct
SEQUENCE: 151
catggagata attaaaatga taaccatctc gcaaataaat aagtatttta ctgttttcgt  60
aacagttttg taataaaaaa acctataaaa ttccggatta ttcataccgt cccaccatcg  120
ggcgcggatc tgccgccttg gcacctccgg caaagagagc caggagagga tataaatatc  180
ttgggcctgg gaacagtctt gaccaaggag aaccaactaa cccttctgac gccgctgcaa  240
aagaacacga cgaagcttac gctgcttatc ttcgctctgg taaaaaccca tacttatatt  300
tctcgccagc agatcaacgc tttatagatc aaactaagga cgctaaagat tggggggga  360
aaataggaca ttattttttt agagctaaaa aggcaattgc tccagtatta actgatacac  420
cagatcatcc atcaacatca agaccaacaa aaccaactaa aagaagtaaa ccaccacctc  480
atattttcat caatcttgca aaaaaaaaaa aagccggtgc aggacaagta aaaagagaca  540
atcttgcacc aatgagtgat ggagcagttc aaccagacgg tggtcaacct gctgtcagaa  600
atgaaagagc tacaggatct gggaacgggt ctggaggcgg gggtggtggt ggttctgggg  660
gtgtggggat ttctacgggt actttcaata atcagacgga atttaaattt ttggaaaacg  720
gatgggtgga aatcacagca aactcaagca gacttgtaca tttaaatatg ccagaaagtg  780
aaaattatag aagagtggtt gtaaataata tggataaaac tgcagttaac ggaaacatgg  840
ctttagatga tattcatgca caaattgtaa caccttggtc attggttgat gcaaatgctt  900
ggggagtttg gtttaatcca ggagattggc aactaattgt taatactatg agtgagttgc  960
atttagttag ttttgaacaa gaaattttta atgttgtttt aaagactgtt tcagaatctg  1020
ctactcagcc accaactaaa gtttataata atgatttaac tgcatcattg atggttgcat  1080
tagatagtaa taatactatg ccatttactc cagcagctat gagatctgag acattgggtt  1140
tttatccatg gaaaccaacc ataccaactc catggagata ttattttcaa tgggatagaa  1200
cattaatacc atctcatact ggaactagtg gcacaccaac aaatatatac catggtacag  1260
atccagatga tgttcaattt tatactattg aaaattctgt gccagtacac ttactaagaa  1320
caggtgatga atttgctaca ggaacatttt tttttgattg taaaccatgt agactaacac  1380
atacatggca aacaaataga gcattgggct taccaccatt tctaaattct ttgcctcaat  1440
ctgaaggagc tactaacttt ggtgatatag gagttcaaca agataaaaga cgtggtgtaa  1500
ctcaaatggg aaatacaaac tatattactg aagctactat tatgagacca gctgaggttg  1560
gttatagtgc accatattat tcttttgagg cgtctacaca agggccattt aaaacaccta  1620
ttgcagcagg acggggggga gcgcaaacat atgaaaatca agcagcagat ggtgatccaa  1680
gatatgcatt tggtagacaa catggtcaaa aaactaccac aacaggagaa acacctgaga  1740
gatttacata tatagcacat caagatacag gaagatatcc agaaggagat tggattcaaa  1800
atattaactt taaccttcct gtaacgaatg ataatgtatt gctaccaaca gatccaattg  1860
gaggtaaaac aggaattaac tatactaata tatttaatac ttatggtcct ttaactgcat  1920
taaataatgt accaccagtt tatccaaatg gtcaaatttg ggataaagaa tttgatactg  1980
acttaaaacc aagacttcat gtaaatgcac catttgtttg tcaaaataat tgtcctggtc  2040
aattatttgt aaaagttgcg cctaatttaa caaatgaata tgatcctgat gcatctgcta  2100
atatgtcaag aattgtaact tactcagatt tttggtggaa aggtaaatta gtatttaaag  2160
ctaaactaag agcctctcat acttggaatc caattcaaca aatgagtatt aatgtagata  2220
accaatttaa ctatgtacca agtaatattg gaggtatgaa aattgtatat gaaaaatctc  2280
aactagcacc tagaaaatta tattaactcg aggcatgcgg taccaagctt gtcgagaagt  2340
actagaggat cataatcagc cataccacat ttgtagaggt tttacttgct ttaaaaaacc  2400
tcccacacct ccccctgaac ctgaaacata aaatgaatgc aattgttgtt gttaacttgt  2460
ttattgcagc ttataatggt tacaaataaa gcaatagcat cacaaatttc acaaataaag  2520
catttttttc actgcattct agttgtggtt tgtccaaact catcaatgta tcttatcatg  2580
tctggatc                                                           2588

SEQ ID NO: 152          moltype = DNA  length = 2588
FEATURE                 Location/Qualifiers
source                  1..2588
                        mol_type = other DNA
                        organism = synthetic construct
SEQUENCE: 152
catggagata attaaaatga taaccatctc gcaaataaat aagtatttta ctgttttcgt  60
aacagttttg taataaaaaa acctataaaa ttccggatta ttcataccgt cccaccatcg  120
ggcgcggatc tgccgccatc gcacctccgg caaagagagc caggagagga tataaatatc  180
ttgggcctgg gaacagtctt gaccaaggag aaccaactaa cccttctgac gccgctgcaa  240
aagaacacga cgaagcttac gctgcttatc ttcgctctgg taaaaaccca tacttatatt  300
tctcgccagc agatcaacgc tttatagatc aaactaagga cgctaaagat tggggggga  360
aaataggaca ttattttttt agagctaaaa aggcaattgc tccagtatta actgatacac  420
cagatcatcc atcaacatca agaccaacaa aaccaactaa aagaagtaaa ccaccacctc  480
atattttcat caatcttgca aaaaaaaaaa aagccggtgc aggacaagta aaaagagaca  540
atcttgcacc aatgagtgat ggagcagttc aaccagacgg tggtcaacct gctgtcagaa  600
atgaaagagc tacaggatct gggaacgggt ctggaggcgg gggtggtggt ggttctgggg  660
gtgtggggat ttctacgggt actttcaata atcagacgga atttaaattt ttggaaaacg  720
gatgggtgga aatcacagca aactcaagca gacttgtaca tttaaatatg ccagaaagtg  780
aaaattatag aagagtggtt gtaaataata tggataaaac tgcagttaac ggaaacatgg  840
ctttagatga tattcatgca caaattgtaa caccttggtc attggttgat gcaaatgctt  900
ggggagtttg gtttaatcca ggagattggc aactaattgt taatactatg agtgagttgc  960
atttagttag ttttgaacaa gaaattttta atgttgtttt aaagactgtt tcagaatctg  1020
ctactcagcc accaactaaa gtttataata atgatttaac tgcatcattg atggttgcat  1080
tagatagtaa taatactatg ccatttactc cagcagctat gagatctgag acattgggtt  1140
tttatccatg gaaaccaacc ataccaactc catggagata ttattttcaa tgggatagaa  1200
cattaatacc atctcatact ggaactagtg gcacaccaac aaatatatac catggtacag  1260
```

```
atccagatga tgttcaattt tatactattg aaaattctgt gccagtacac ttactaagaa  1320
caggtgatga atttgctaca ggaacatttt tttttgattg taaaccatgt agactaacac  1380
atacatggca aacaaataga gcattgggct taccaccatt tctaaattct ttgcctcaat  1440
ctgaaggagc tactaacttt ggtgatatag gagttcaaca agataaaaga cgtggtgtaa  1500
ctcaaatggg aaatacaaac tatattactg aagctactat tatgagacca gctgaggttg  1560
gttatagtgc accatattat tcttttgagg cgtctacaca agggccattt aaaacaccta  1620
ttgcagcagg acggggggga gcgcaaacat atgaaaatca agcagcagat ggtgatccaa  1680
gatatgcatt tggtagacaa catggtcaaa aaactaccac aacaggagaa acacctgaga  1740
gatttacata tatagcacat caagatacag gaagatatcc agaaggagat tggattcaaa  1800
atattaactt taaccttcct gtaacgaatg ataatgtatt gctaccaaca gatccaattg  1860
gaggtaaaac aggaattaac tatactaata tatttaatac ttatggtcct ttaactgcat  1920
taaataatgt accaccagtt tatccaaatg gtcaaatttg ggataaagaa tttgatactg  1980
acttaaaacc aagacttcat gtaaatgcac catttgtttg tcaaaataat tgtcctggtc  2040
aattatttgt aaaagttgcg cctaatttaa caaatgaata tgatcctgat gcatctgcta  2100
atatgtcaag aattgtaact tactcagatt tttggtggaa aggtaaatta gtatttaaag  2160
ctaaactaag agcctctcat acttggaatc caattcaaca aatgagtatt aatgtagata  2220
accaatttaa ctatgtacca agtaatattg gaggtatgaa aattgtatat gaaaaatctc  2280
aactagcacc tagaaaatta tattaactcg aggcatgcgg taccaagctt gtcgagaagt  2340
actagaggat cataatcagc cataccacat ttgtagaggt tttacttgct ttaaaaaacc  2400
tcccacacct ccccctgaac ctgaaacata aaatgaatgc aattgttgtt gttaacttgt  2460
ttattgcagc ttataatggt tacaaataaa gcaatagcat cacaaatttc acaaataaag  2520
cattttttc actgcattct agttgtggtt tgtccaaact catcaatgta tcttatcatg  2580
tctggatc                                                           2588
```

```
SEQ ID NO: 153          moltype = DNA  length = 1206
FEATURE                 Location/Qualifiers
source                  1..1206
                        mol_type = other DNA
                        organism = synthetic construct
SEQUENCE: 153
gtatactccg gaatattaat agatgcgaaa cacgcacggc gcgcgcacgc agcttagcac  60
aaacgcgtcg ttgcacgcgc ccaccgctaa ccgcaggcca atcggtcggc cggcctcata  120
tccgctcacc agccgcgtcc tatcgggcgc ggcttccgcg cccattttga ataaataaac  180
gataacgccg ttggtggcgt gaggcatgta aaaggttaca tcattatctt gttcgccatc  240
cggttggtat aaatagacgt tcatgttggt ttttgtttca gttgcaagtt ggctgcggcg  300
cgcgcagcac ctttgctatt ccggattatt cataccgtcc caccatcggg cgcggatctg  360
cctccatgtc tggcaaccag tatactgagg aagttatgga gggagtaaat tggttaaaga  420
aacatgcaga aaatgaagca ttttcgtttg tttttaaatg tgacaacgtc caactaaatg  480
gaaaggatgt tcgctggaac aactatacca aaccaattca aaatgaagaa ctaacatctt  540
taattagagg agcacaaaca gcaatggatc aaaccgaaga agaagaaatg gactgggaat  600
cggaagttga tagtctcgcc aaaaagttgc aaagacttag agacacaagc ggcaagcaat  660
cctcagagtc aagaccaagt tctaactcct ctgactccgg acgtagtgga ccttgcactg  720
gaaccgtgga gtactccaga tacgcctatt gcagaaactg caaatcaaca atcaaaccaa  780
cttggcgtta ctcacaaaga cgtgcaagcg agtccgacgt ggtccgaaat agaggcagac  840
ctgagagcca tctttacttc catcatcacc atcaccactg agagctcact agtcgcggcc  900
gctttcgaat ctagagcctg cagtctcgag gcatgcggta ccaagcttgt cgagaagtac  960
tagaggatca taatcagcca taccacattt gtagaggttt tacttgcttt aaaaaacctc  1020
ccacacctcc ccctgaacct gaaacataaa atgaatgcaa ttgttgttgt taacttgttt  1080
attgcagctt ataatggtta caaataaagc aatagcatca caaatttcac aaataaagca  1140
tttttttcac tgcattctag ttgtggtttg tccaaactca tcaatgtatc ttatcatgtc  1200
tggatc                                                             1206
```

```
SEQ ID NO: 154          moltype = DNA  length = 1188
FEATURE                 Location/Qualifiers
source                  1..1188
                        mol_type = other DNA
                        organism = synthetic construct
SEQUENCE: 154
gtatactccg gaatattaat agatgcgaaa cacgcacggc gcgcgcacgc agcttagcac  60
aaacgcgtcg ttgcacgcgc ccaccgctaa ccgcaggcca atcggtcggc cggcctcata  120
tccgctcacc agccgcgtcc tatcgggcgc ggcttccgcg cccattttga ataaataaac  180
gataacgccg ttggtggcgt gaggcatgta aaaggttaca tcattatctt gttcgccatc  240
cggttggtat aaatagacgt tcatgttggt ttttgtttca gttgcaagtt ggctgcggcg  300
cgcgcagcac ctttgctatt ccggattatt cataccgtcc caccatcggg cgcggatctg  360
cctccctgtc tggcaaccag tatactgagg aagttatgga gggagtaaat tggttaaaga  420
aacatgcaga aaatgaagca ttttcgtttg tttttaaatg tgacaacgtc caactaaatg  480
gaaaggatgt tcgctggaac aactatacca aaccaattca aaatgaagaa ctaacatctt  540
taattagagg agcacaaaca gcaatggatc aaaccgaaga agaagaaatg gactgggaat  600
cggaagttga tagtctcgcc aaaaagttgc aaagacttag agacacaagc ggcaagcaat  660
cctcagagtc aagaccaagt tctaactcct ctgactccgg acgtagtgga ccttgcactg  720
gaaccgtgga gtactccaga tacgcctatt gcagaaactg caaatcaaca atcaaaccaa  780
cttggcgtta ctcacaaaga cgtgcaagcg agtccgacgt ggtccgaaat agaggcagac  840
ctgagagcca tctttacttc tgagagctca ctagtcgcgg ccgctttcga atctagagcc  900
tgcagtctcg aggcatgcgg taccaagctt gtcgagaagt actagaggat cataatcagc  960
cataccacat ttgtagaggt tttacttgct ttaaaaaacc tcccacacct ccccctgaac  1020
ctgaaacata aaatgaatgc aattgttgtt gttaacttgt ttattgcagc ttataatggt  1080
tacaaataaa gcaatagcat cacaaatttc acaaataaag cattttttc actgcattct  1140
agttgtggtt tgtccaaact catcaatgta tcttatcatg tctggatc              1188
```

```
SEQ ID NO: 155          moltype = DNA  length = 3066
FEATURE                 Location/Qualifiers
source                  1..3066
                        mol_type = other DNA
                        organism = synthetic construct
SEQUENCE: 155
cgcgtggcct ccgcgccggg ttttggcgcc tcccgcgggc gcccccctcc tcacggcgag  60
cgctgccacg tcagacgaag ggcgcaggag cgttcctgat ccttccgccc ggacgctcag  120
gacagcggcc cgctgctcat aagactcggc cttagaaccc cagtatcagc agaaggacat  180
tttaggacgg gacttgggtg actctagggc actggttttc tttccagaga gcggaacagg  240
cgaggaaaag tagtcccttc tcggcgattc tgcggaggga tctccgtggg gcggtgaacg  300
ccgatgatta tataaggacg cgccgggtgt ggcacagcta gttccgtcgc agccgggatt  360
tgggtcgcgg ttcttgtttg tggatcgctg tgatcgtcac ttggtggtac cggactctag  420
aggatccggt actcgaggaa ctgaaaaacc agaaagttaa ctggtaagtt tagtcttttt  480
gtcttttatt tcaggtcccg gatccggtgg tggtgcaaat caaagaactg ctcctcagtg  540
gatgttgcct ttacttctag gcctgtaggg aagtgttact tctgctctaa aagctgcgga  600
attgtagccg ttgaagcttc ctaggccgcc accatggccc cccccgccaa gcgcgcccgc  660
cgcggctaca agtacctggg ccccggcaac agcctggacc agggcgagcc caccaacccc  720
agcgacgccg ccgccaagga gcacgacgag gcctacgccg cctacctgcg cagcggcaag  780
aacccctacc tgtacttcag ccccgccgac cagcgcttca tcgaccagac caaggacgcc  840
aaggactggg gcggcaagat cggccactac ttcttccgcg ccaagaaggc catcgccccc  900
gtgctgaccg acacccccga ccaccccagc accagccgcc ccaccaagcc caccaagcgc  960
agcaagcccc ccccccacat cttcatcaac ctggccaaga agaagaaggc cggcgccggc  1020
caggtgaagc gcgacaacct ggcccccatg agcgacggcg ccgtgcagcc cgacggcggc  1080
cagcccgccg tgcgcaacga gcgcgccacc ggcagcggca acggcagcgg cggcggcggc  1140
ggcggcggca gcggcggcgt gggcatcagc accggcacct tcaacaacca gaccgagttc  1200
aagttcctgg agaacggctg ggtggagatc accgccaaca gcagccgcct ggtgcacctg  1260
aacatgcccg agagcgagaa ctaccgccgc gtggtggtga acaacatgga caagaccgcc  1320
gtgaacggca acatggccct ggacgacatc cacgcccaga tcgtgacccc ctggagcctg  1380
gtggacgcca acgcctgggg cgtgtggttc aaccccggcg actggcagct gatcgtgaac  1440
accatgagcg agctgcacct ggtgagcttc gagcaggaga tcttcaacgt ggtgctgaag  1500
accgtgagcg agagcgccac ccagcccccc accaaggtgt acaacaacga cctgaccgcc  1560
agcctgatgg tggccctgga cagcaacaac accatgccct tcaccccccgc cgccatgcgc  1620
agcgagaccc tgggcttcta cccctggaag cccaccatcc ccacccccctg gcgctactac  1680
ttccagtggg accgcaccct gatccccagc cacaccggca ccagcggcac ccccaccaac  1740
atctaccacg gcaccgaccc cgacgacgtg cagttctaca ccatcgagaa cagcgtgccc  1800
gtgcacctgc tgcgcaccgg cgacgagttc gccaccggca ccttcttctt cgactgcaag  1860
ccctgccgcc tgacccacac ctggcagacc aaccgcgccc tgggcctgcc ccccttcctg  1920
aacagcctgc cccagagcga gggcgccacc aacttcggcg acatcggcgt gcagcaggac  1980
aagcgccgcg gcgtgaccca gatgggcaac accaactaca tcaccgaggc caccatcatg  2040
cgccccgccg aggtgggcta cagcgccccc tactacagct tcgaggccag cacccagggc  2100
cccttcaaga cccccatcgc cgccggccgc ggcggcgccc agacctacga gaaccaggcc  2160
gccgacggcg acccccgcta cgccttcggc cgccagcacg gccagaagac caccaccacc  2220
ggcgagaccc ccgagcgctt cacctacatc gcccaccagg acaccggccg ctaccccgag  2280
ggcgactgga tccagaacat caacttcaac ctgcccgtga ccaacgacaa cgtgctgctg  2340
cccaccgacc ccatcggcgg caagaccggc atcaactaca ccaacatctt caacacctac  2400
ggccccctga ccgccctgaa caacgtgccc cccgtgtacc ccaacggcca gatctgggac  2460
aaggagttcg acaccgacct gaagccccgc ctgcacgtga acgccccctt cgtgtgccag  2520
aacaactgcc ccggccagct gttcgtgaag gtggccccca acctgaccaa cgagtacgac  2580
cccgacgcca gcgccaacat gagccgcatc gtgacctaca gcgacttctg gtggaagggc  2640
aagctggtgt tcaaggccaa gctgcgcgcc agccacacct ggaaccccat ccagcagatg  2700
agcatcaacg tggacaacca gttcaactac gtgcccagca acatcggcgg catgaagatc  2760
gtgtacgaga agagccagct ggccccccgc aagctgtact aataactcga gcatgcatct  2820
agaggtacat ctagatagag ctcgctgatc agcctcgact gtgccttcta gttgccagcc  2880
atctgttgtt tgcccctccc ccgtgccttc cttgaccctg gaaggtgcca ctcccactgt  2940
cctttcctaa taaaatgagg aaattgcatc gcattgtctg agtaggtgtc attctattct  3000
ggggggtggg gtggggcagg acagcaaggg ggaggattgg gaagacaata gcaggcatgc  3060
tgggga                                                             3066

SEQ ID NO: 156          moltype = DNA  length = 2890
FEATURE                 Location/Qualifiers
source                  1..2890
                        mol_type = other DNA
                        organism = synthetic construct
SEQUENCE: 156
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggagtatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtgatgcggt tttggcagta catcaatggg cgtggatagc  420
ggtttgactc acggggattt ccaagtctcc accccattga cgtcaatggg agtttgtttt  480
ggcaccaaaa tcaacgggac tttccaaaat gtcgtaacaa ctccgcccca ttgacgcaaa  540
tgggcggtag gcgtgtacgg tgggaggtct atataagcag agctctctgg ctaactagag  600
aacccactgc ttactggctt atcgaaatta atacgactca ctatagggag acccaagctt  660
ggtaccggac tctagaggat ccggtactcg aggaactgaa aaaccagaaa gttaactggt  720
aagtttagtc tttttgtctt ttatttcagg tcccggatcc ggtggtggtg caaatcaaag  780
aactgctcct cagtggatgt tgcctttact tctaggcctg tacggaagtg ttacttctgc  840
```

```
tctaaaagct tgattaatta aggccgccac catgagcgac ggcgccgtgc agcccgacgg  900
cggccagccc gccgtgcgca acgagcgcgc caccggcagc ggcaacggca gcggcggcgg  960
cggcggcggc ggcagcggcg gcgtgggcat cagcaccggc accttcaaca accagaccga  1020
gttcaagttc ctggagaacg gctgggtgga gatcaccgcc aacagcagcc gcctggtgca  1080
cctgaacatg cccgagagcg agaactaccg ccgcgtggtg gtgaacaaca tggacaagac  1140
cgccgtgaac ggcaacatgg ccctggacga catccacgcc cagatcgtga ccccctggag  1200
cctggtggac gccaacgcct ggggcgtgtg gttcaacccc ggcgactggc agctgatcgt  1260
gaacaccatg agcgagctgc acctggtgag cttcgagcag gagatcttca acgtggtgct  1320
gaagaccgtg agcgagagcg ccacccagcc ccccaccaag gtgtacaaca acgacctgac  1380
cgccagcctg atggtggccc tggacagcaa caacaccatg cccttcaccc ccgccgccat  1440
gcgcagcgag accctgggct tctacccctg gaagcccacc atccccaccc cctggcgcta  1500
ctacttccag tgggaccgca ccctgatccc cagccacacc ggcaccagcg gcacccccac  1560
caacatctac cacggcaccg accccgacga cgtgcagttc tacaccatcg agaacagcgt  1620
gcccgtgcac ctgctgcgca ccggcgacga gttcgccacc ggcaccttct tcttcgactg  1680
caagccctgc cgcctgaccc acacctggca gaccaaccgc gccctgggcc tgcccccctt  1740
cctgaacagc ctgccccaga gcgagggcgc caccaacttc ggcgacatcg gcgtgcagca  1800
ggacaagcgc cgcggcgtga cccagatggg caacaccaac tacatcaccg aggccaccat  1860
catgcgcccc gccgaggtgg gctacagcgc cccctactac agcttcgagg ccagcaccca  1920
gggccccttc aagaccccca tcgccgccgg ccgcggcggc gcccagacct acgagaacca  1980
ggccgccgac ggcgaccccc gctacgcctt cggccgccag cacggccaga agaccaccac  2040
caccggcgag acccccgagc gcttcaccta catcgcccac caggacaccg gccgctaccc  2100
cgagggcgac tggatccaga acatcaactt caacctgccc gtgaccaacg acaacgtgct  2160
gctgcccacc gaccccatcg gcggcaagac cggcatcaac tacaccaaca tcttcaacac  2220
ctacggcccc ctgaccgccc tgaacaacgt gccccccgtg taccccaacg gccagatctg  2280
ggacaaggag ttcgacaccg acctgaagcc ccgcctgcac gtgaacgccc ccttcgtgtg  2340
ccagaacaac tgccccggcc agctgttcgt gaaggtggcc cccaacctga ccaacgagta  2400
cgaccccgac gccagcgcca acatgagccg catcgtgacc tacagcgact tctggtggaa  2460
gggcaagctg gtgttcaagg ccaagctgcg cgccagccac acctggaacc ccatccagca  2520
gatgagcatc aacgtggaca accagttcaa ctacgtgccc agcaacatcg gcggcatgaa  2580
gatcgtgtac gagaagagcc agctggcccc ccgcaagctg tactaatgac tcgagcatgc  2640
atctagaggt acatctagat agagctcgct gatcagcctc gactgtgcct tctagttgcc  2700
agccatctgt tgtttgcccc tcccccgtgc cttccttgac cctggaaggt gccactccca  2760
ctgtcctttc ctaataaaat gaggaaattg catcgcattg tctgagtagg tgtcattcta  2820
ttctgggggg tggggtgggg caggacagca agggggagga ttgggaagac aatagcaggc  2880
atgctgggga                                                         2890
```

```
SEQ ID NO: 157          moltype = DNA  length = 189
FEATURE                 Location/Qualifiers
source                  1..189
                        mol_type = other DNA
                        organism = synthetic construct
SEQUENCE: 157
gggcggagtt agggcggagc caatcagcgt gcgccgttcc gaaagttgcc ttttatggct  60
gggcggagaa tgggcggtga acgccgatga ttatataagg acgcgccggg tgtggcacag  120
ctagttccgt cgcagccggg atttgggtcg cggttcttgt ttgtggatcc ctgtgatcgt  180
cacttgaca                                                          189
```

```
SEQ ID NO: 158          moltype = DNA  length = 400
FEATURE                 Location/Qualifiers
source                  1..400
                        mol_type = other DNA
                        organism = synthetic construct
SEQUENCE: 158
ggcctccgcg ccgggttttg gcgcctcccg cgggcgcccc cctcctcacg gcgagcgctg  60
ccacgtcaga cgaagggcgc aggagcgttc ctgatccttc cgcccggacg ctcaggacag  120
cggcccgctg ctcataagac tcggccttag aaccccagta tcagcagaag gacattttag  180
gacgggactt gggtgactct agggcactgg ttttctttcc agagagcgga acaggcgagg  240
aaaagtagtc ccttctcggc gattctgcgg agggatctcc gtggggcggt gaacgccgat  300
gattatataa ggacgcgccg ggtgtggcac agctagttcc gtcgcagccg ggatttgggt  360
cgcggttctt gtttgtggat cgctgtgatc gtcacttggt                        400
```

```
SEQ ID NO: 159          moltype = DNA  length = 376
FEATURE                 Location/Qualifiers
source                  1..376
                        mol_type = other DNA
                        organism = synthetic construct
SEQUENCE: 159
ggtaaactgc ccacttggca gtacatcaag tgtatcatat gccaagtacg cccccctattg  60
acgtcaatga cggtaaatgg cccgcctggc attatgccca gtacatgacc ttatgggact  120
ttcctacttg gcagtacatc tacgtattag tcatcgctat taccatggtg atgcggtttt  180
ggcagtacat caatgggcgt ggatagcggt ttgactcacg gggatttcca agtctccacc  240
ccattgacgt caatgggagt ttgttttggc accaaaatca acgggacttt ccaaaatgtc  300
gtaacaactc cgccccattg acgcaaatgg gcggtaggcg tgtacggtgg gaggtctata  360
taagcagagc tctctg                                                  376
```

```
SEQ ID NO: 160          moltype = AA  length = 34
FEATURE                 Location/Qualifiers
source                  1..34
                        mol_type = protein
```

```
                        note = Bufavirus-1
                        organism = unidentified
SEQUENCE: 160
MPAIRKARGW VPPGYNYLGP FNQDFSKKPT NPSD                               34

SEQ ID NO: 161          moltype = AA  length = 34
FEATURE                 Location/Qualifiers
source                  1..34
                        mol_type = protein
                        note = Cutavirus
                        organism = unidentified
SEQUENCE: 161
MPAIRKARGW VPPGYNFLGP FNQDFNKEPT NPSD                               34

SEQ ID NO: 162          moltype = AA  length = 35
FEATURE                 Location/Qualifiers
source                  1..35
                        mol_type = protein
                        note = Tusavirus 1
                        organism = unidentified
SEQUENCE: 162
MAPAARPRKG WVPPGYNYLG PGNDLDAGEP TNKSD                              35

SEQ ID NO: 163          moltype = AA  length = 36
FEATURE                 Location/Qualifiers
source                  1..36
                        mol_type = protein
                        note = Minute virus of mice
                        organism = unidentified
SEQUENCE: 163
MAPPAKRAKR GWVPPGYKYL GPGNSLDQGE PTNPSD                             36

SEQ ID NO: 164          moltype = AA  length = 36
FEATURE                 Location/Qualifiers
source                  1..36
                        mol_type = protein
                        note = Canine parvovirus
                        organism = unidentified
SEQUENCE: 164
MAPPAKRARR GLVPPGYKYL GPGNSLDQGE PTNPSD                             36

SEQ ID NO: 165          moltype = AA  length = 60
FEATURE                 Location/Qualifiers
source                  1..60
                        mol_type = protein
                        organism = synthetic construct
VARIANT                 27
                        note = X can be any amino acid
SEQUENCE: 165
MAPPAKRARR GKGVLVKWGE GKDLITXLSM CFFIGLVPPG YKYLGPGNSL DQGEPTNPSD  60

SEQ ID NO: 166          moltype = AA  length = 54
FEATURE                 Location/Qualifiers
source                  1..54
                        mol_type = protein
                        organism = synthetic construct
SEQUENCE: 166
LTVPGYKYLG PGNSLNRGQP INQIDEDAKE HDEAYDKVKT SQEVSRADNT FVNK        54

SEQ ID NO: 167          moltype = AA  length = 54
FEATURE                 Location/Qualifiers
source                  1..54
                        mol_type = protein
                        organism = synthetic construct
SEQUENCE: 167
LTVPGYKYLG PGNSLNRGQP TNQIDEDAKE HDEAYDKAKT SQEVSEADNT FVNK        54

SEQ ID NO: 168          moltype = AA  length = 54
FEATURE                 Location/Qualifiers
source                  1..54
                        mol_type = protein
                        organism = synthetic construct
SEQUENCE: 168
LTVPGYKYLG PGNSLNRGQP TNQIDEDAKE HDEAYDKAKT SQEVSQADNT FVNK        54

SEQ ID NO: 169          moltype = AA  length = 54
FEATURE                 Location/Qualifiers
source                  1..54
                        mol_type = protein
```

```
                        organism = synthetic construct
SEQUENCE: 169
LTVPGYKYLG PGNSLDRGEP VNQIDADAKE HDEAYDKAKT SQEVSDADSK FVSK        54

SEQ ID NO: 170          moltype = AA  length = 54
FEATURE                 Location/Qualifiers
source                  1..54
                        mol_type = protein
                        organism = synthetic construct
SEQUENCE: 170
LTVPGYKYLG PGNSLNRGPP TNEIDADAKE HDEAYSQSKT AQEVSKADNT FVNK        54

SEQ ID NO: 171          moltype = AA  length = 54
FEATURE                 Location/Qualifiers
source                  1..54
                        mol_type = protein
                        organism = synthetic construct
SEQUENCE: 171
LVPAPYKYAG PGNSLNRGPA YDLVDESARQ HDIAYDKAKS PEDIHKADRQ FLTE        54

SEQ ID NO: 172          moltype = AA  length = 54
FEATURE                 Location/Qualifiers
source                  1..54
                        mol_type = protein
                        organism = synthetic construct
SEQUENCE: 172
LTYPFHHYLG PGNPLDNNEP VDRDDAIAEE HDKAYANAKS SIDVINADKK AIDH        54

SEQ ID NO: 173          moltype = AA  length = 57
FEATURE                 Location/Qualifiers
source                  1..57
                        mol_type = protein
                        organism = synthetic construct
SEQUENCE: 173
AVLPGTDFVG PGNPIDPKPA RSETDQIAKE HDLGYEDLLH RAKSQYFTEE DFKTEVY     57

SEQ ID NO: 174          moltype = AA  length = 59
FEATURE                 Location/Qualifiers
source                  1..59
                        mol_type = protein
                        organism = synthetic construct
SEQUENCE: 174
IHFPYHNYLG PGSDNFKKQP VDEDDAIARA HDLDYDKASS DKDIFKADKQ ARDEFFSSF   59

SEQ ID NO: 175          moltype = AA  length = 59
FEATURE                 Location/Qualifiers
source                  1..59
                        mol_type = protein
                        organism = synthetic construct
SEQUENCE: 175
IHFPYHNYLG PGTDNFEKNP VDEDDAIARS HDLAYDKVTN HKEVFQADKQ ARDEFFTSF   59

SEQ ID NO: 176          moltype = AA  length = 59
FEATURE                 Location/Qualifiers
source                  1..59
                        mol_type = protein
                        organism = synthetic construct
SEQUENCE: 176
LVPPGYKYLG PGNSLDQGEP TNPSDAAAKE HDEAYAAYLR SGKNPYLYFS PADQRFIDQ   59

SEQ ID NO: 177          moltype = AA  length = 59
FEATURE                 Location/Qualifiers
source                  1..59
                        mol_type = protein
                        organism = synthetic construct
SEQUENCE: 177
MVPPGYKYLG PGNSLDQGEP TNPSDAAAKE HDEAYDQYIK SGKNPYLYFS AADQRFIDQ   59

SEQ ID NO: 178          moltype = AA  length = 59
FEATURE                 Location/Qualifiers
source                  1..59
                        mol_type = protein
                        organism = synthetic construct
SEQUENCE: 178
WVPPGYKYLG PGNSLNQGEP TNPSDAAAKE HDEAYDQYIK SGKNPYLYFS PADQRFIDQ   59

SEQ ID NO: 179          moltype = AA  length = 59
FEATURE                 Location/Qualifiers
source                  1..59
```

-continued

```
                        mol_type = protein
                        organism = synthetic construct
SEQUENCE: 179
WVPPGYKYLG PGNSLDQGEP TNPSDAAAKE HDEAYDQYIK SGKNPYLYFS PADQRFIDQ   59

SEQ ID NO: 180          moltype = AA  length = 59
FEATURE                 Location/Qualifiers
source                  1..59
                        mol_type = protein
                        organism = synthetic construct
SEQUENCE: 180
CVPPGYKYLG PGNSLDQGEP TNPSDAAAKE HDLAYDEYIK SGKNPYLYFS PADQRFIDQ   59

SEQ ID NO: 181          moltype = AA  length = 59
FEATURE                 Location/Qualifiers
source                  1..59
                        mol_type = protein
                        organism = synthetic construct
SEQUENCE: 181
LTLPGYKYLG PGNSLDQGEP TNPSDAAAKE HDEAYDKYIK SGKNPYFYFS AADEKFIKE   59

SEQ ID NO: 182          moltype = AA  length = 59
FEATURE                 Location/Qualifiers
source                  1..59
                        mol_type = protein
                        organism = synthetic construct
SEQUENCE: 182
FVLPGYKYVG PGNGLDKGPP VNKADSVALE HDKAYDQQLK AGDNPYIKFK HADQEFIDN   59

SEQ ID NO: 183          moltype = AA  length = 58
FEATURE                 Location/Qualifiers
source                  1..58
                        mol_type = protein
                        organism = synthetic construct
SEQUENCE: 183
FVLPGYKYLP GNGLDKGPPV NKADSVALEH DKAYDQQLKA GDNPYIKFNH ADQDFIDS    58

SEQ ID NO: 184          moltype = AA  length = 59
FEATURE                 Location/Qualifiers
source                  1..59
                        mol_type = protein
                        organism = synthetic construct
SEQUENCE: 184
LVLPGYKYLG PFNGLDKGEP VNEADAAALE HDKAYDRQLD SGDNPYLKYN HADAEFQER   59

SEQ ID NO: 185          moltype = AA  length = 59
FEATURE                 Location/Qualifiers
source                  1..59
                        mol_type = protein
                        organism = synthetic construct
SEQUENCE: 185
LVLPGYKYLG PGNGLDKGEP VNEADAAALE HDKAYDQQLK AGDNPYLKYN HADAEFQER   59

SEQ ID NO: 186          moltype = AA  length = 59
FEATURE                 Location/Qualifiers
source                  1..59
                        mol_type = protein
                        organism = synthetic construct
SEQUENCE: 186
LVLPGYKYLG PGNGLDKGEP VNAADAAALE HDKAYDQQLK AGDNPYLKYN HADAEFQQR   59

SEQ ID NO: 187          moltype = AA  length = 59
FEATURE                 Location/Qualifiers
source                  1..59
                        mol_type = protein
                        organism = synthetic construct
SEQUENCE: 187
LVLPGYKYLG PFNGLDKGEP VNAADAAALE HDKAYDQQLK AGDNPYLRYN HADAEFQER   59

SEQ ID NO: 188          moltype = AA  length = 59
FEATURE                 Location/Qualifiers
source                  1..59
                        mol_type = protein
                        organism = synthetic construct
SEQUENCE: 188
LTLPGYNYLG PFNSLFAGAP VNKADAAARK HDFGYSDLLK EGKNPYLYFN THDQNLIDE   59

SEQ ID NO: 189          moltype = AA  length = 59
FEATURE                 Location/Qualifiers
```

```
source                  1..59
                        mol_type = protein
                        organism = synthetic construct
SEQUENCE: 189
LTLPFSNYIG PGNQLQAGNP QSVVDAAARI HDFRYSELIK LGINPYTHWS VADDELLHN   59

SEQ ID NO: 190          moltype = AA  length = 59
FEATURE                 Location/Qualifiers
source                  1..59
                        mol_type = protein
                        organism = synthetic construct
SEQUENCE: 190
LTLPLTHYIG PGNPLQAGSP TDVVDAAARI HDYRYSELIK LGINPYTHWT VADDELLHN   59

SEQ ID NO: 191          moltype = AA  length = 59
FEATURE                 Location/Qualifiers
source                  1..59
                        mol_type = protein
                        organism = synthetic construct
SEQUENCE: 191
IHLPADRYLG PGNPLENGPP VDPVDAVARI HDFRYADLEK QGINPYTTYT IADEELLKN   59

SEQ ID NO: 192          moltype = AA  length = 59
FEATURE                 Location/Qualifiers
source                  1..59
                        mol_type = protein
                        organism = synthetic construct
SEQUENCE: 192
VQLPGTNYVG PGNELQAGPP QSAVDSAARI HDFRYSQLAK LGINPYTHWT VADEELLKN   59

SEQ ID NO: 193          moltype = AA  length = 47
FEATURE                 Location/Qualifiers
source                  1..47
                        mol_type = protein
                        organism = synthetic construct
SEQUENCE: 193
DFADYGCYCG RGGSGTPVDD LDRCCQVHDN CYNEAAVCDC DRLAAIC               47

SEQ ID NO: 194          moltype = AA  length = 47
FEATURE                 Location/Qualifiers
source                  1..47
                        mol_type = protein
                        organism = synthetic construct
SEQUENCE: 194
EYNNYGCYCG LGGSGTPVDE LDKCCQTHDN CYDQAFICNC DRNAAIC               47

SEQ ID NO: 195          moltype = AA  length = 47
FEATURE                 Location/Qualifiers
source                  1..47
                        mol_type = protein
                        organism = synthetic construct
SEQUENCE: 195
SYGFYGCHCG VGGRGSPKDA TDRCCVTHDC CYKRLQLCEC DKAAATC               47

SEQ ID NO: 196          moltype = AA  length = 48
FEATURE                 Location/Qualifiers
source                  1..48
                        mol_type = protein
                        organism = synthetic construct
SEQUENCE: 196
DYIYYGCYCG WGGKGKPIDA TDRCCFVHDC CYGKMELCEC EDRVAAIC              48

SEQ ID NO: 197          moltype = AA  length = 47
FEATURE                 Location/Qualifiers
source                  1..47
                        mol_type = protein
                        organism = synthetic construct
SEQUENCE: 197
SYYGYGCYCG LGGRGIPVDA TDRCCWAHDC CYHKLKACEC DKLSVYC               47

SEQ ID NO: 198          moltype = AA  length = 52
FEATURE                 Location/Qualifiers
source                  1..52
                        mol_type = protein
                        organism = synthetic construct
SEQUENCE: 198
IIYPGTLWCG HGNKSSGPNE LGRFKHTDAC CRTHDMCPDV MLSCDCDKFY DC         52

SEQ ID NO: 199          moltype = AA  length = 47
```

```
FEATURE                 Location/Qualifiers
source                  1..47
                        mol_type = protein
                        organism = synthetic construct
SEQUENCE: 199
NYGFYGCYCG WGGRGTPKDG TDWCCWAHDH CYGRLNLCAC DRKLVYC               47

SEQ ID NO: 200          moltype = AA  length = 47
FEATURE                 Location/Qualifiers
source                  1..47
                        mol_type = protein
                        organism = synthetic construct
SEQUENCE: 200
AYMKYGCFCG LGGHGQPRDA IDWCCHGHDC CYTRALLCKC DQEIANC               47

SEQ ID NO: 201          moltype = DNA  length = 180
FEATURE                 Location/Qualifiers
source                  1..180
                        mol_type = other DNA
                        organism = synthetic construct
SEQUENCE: 201
agaagatttt cgagacgact tggattaagg tacgatggca cctccggcaa agagagccag  60
gagaggtaag ggtgtgttag taaagtgggg ggaggggaaa gatttaataa cttaactaag  120
tatgtgtttt tttataggac ttgtgcctcc aggttataaa tatcttgggc ctgggaacag  180

SEQ ID NO: 202          moltype = DNA  length = 180
FEATURE                 Location/Qualifiers
source                  1..180
                        mol_type = other DNA
                        organism = synthetic construct
SEQUENCE: 202
tcttctaaaa gctctgctga acctaattcc atgctaccgt ggaggccgtt tctctcggtc  60
ctctccattc ccacacaatc atttcacccc cctccccttt ctaaattatt gaattgattc  120
atacacaaaa aaatatcctg aacacggagg tccaatattt atagaacccg gacccttgtc  180

SEQ ID NO: 203          moltype = AA  length = 86
FEATURE                 Location/Qualifiers
source                  1..86
                        mol_type = protein
                        organism = synthetic construct
SEQUENCE: 203
RRFSRRLGLR YDGTSGKESQ ERGCVSKVGE DFRDDLDGTM APPAKRARRG KGVLVKWGKK  60
IFETTWIKVR WHLRQREPGE VRVCSG                                      86

SEQ ID NO: 204          moltype = AA  length = 79
FEATURE                 Location/Qualifiers
source                  1..79
                        mol_type = protein
                        organism = synthetic construct
SEQUENCE: 204
GGERFNNLTK YVFFYRTCAS RLISWAWEQE GKDLITLSMC FFIGLVPPGY KYLGPGNSLN  60
VCVFLDLCLQ VINILGLGT                                              79

SEQ ID NO: 205          moltype = DNA  length = 180
FEATURE                 Location/Qualifiers
source                  1..180
                        mol_type = other DNA
                        organism = synthetic construct
SEQUENCE: 205
acttcagcga gccgctgaac ttggactaag gtacgatggc gcctccagct aaaagagcta  60
aaagaggtaa gggtttaagg gatggttggt tggtggggta ttaatgttta attacctgtt  120
ttacaggcct gaaatcactt ggttttaggt tgggtgcctc ctggctacaa gtacctggga  180

SEQ ID NO: 206          moltype = DNA  length = 177
FEATURE                 Location/Qualifiers
source                  1..177
                        mol_type = other DNA
                        organism = synthetic construct
SEQUENCE: 206
tgaagtcgct cggcgacttg aacctgattc catgctaccg cggaggtcga ttttctcgat  60
tttctccatt cccaaattcc ctaccaacca accaccccat aattacaaat taatggacaa  120
aatgtccgga ctttagtgaa ccaaaatcca acccacggac cgatgttcat ggaccct     177

SEQ ID NO: 207          moltype = AA  length = 84
FEATURE                 Location/Qualifiers
source                  1..84
                        mol_type = protein
                        organism = synthetic construct
SEQUENCE: 207
```

```
TSASRTWTKV RWRLQLKELK EVRVGMVGLQ RAAELGLRYD GASSKSKRGF KGWLVDFSEP  60
LNLDGTMAPP AKRAKRGKGL RDGW                                         84

SEQ ID NO: 208          moltype = AA  length = 80
FEATURE                 Location/Qualifiers
source                  1..80
                        mol_type = protein
                        organism = synthetic construct
SEQUENCE: 208
WWGINVLPVL QANHLVLGWV PPGYKYLGGG VLMFNYLFYR PEITWFVGCL LATSTWDITC  60
FTGLKSLGFR LGASWLQVPG                                              80

SEQ ID NO: 209          moltype = DNA  length = 180
FEATURE                 Location/Qualifiers
source                  1..180
                        mol_type = other DNA
                        organism = synthetic construct
SEQUENCE: 209
acttcaacga ggagctgacc ttggactaag gtacaatggc acctccagct aaaagagcta  60
aaagaggtaa ggggctaagg gatggttggt tggtggggta ctaatgtatg actacctgtt  120
ttacaggcct gaaatcactt ggttctaggt tgggtgcctc ctggctacaa gtacctggga  180

SEQ ID NO: 210          moltype = DNA  length = 180
FEATURE                 Location/Qualifiers
source                  1..180
                        mol_type = other DNA
                        organism = synthetic construct
SEQUENCE: 210
tgaagttgct cctcgactgg aacctgattc catgttaccg tggaggtcga ttttctcgat  60
tttctccatt ccccgattcc ctaccaacca accaccccat gattacatac tgatggacaa  120
aatgtccgga ctttagtgaa ccaagatcca acccacggag gaccgatgtt catggaccct  180

SEQ ID NO: 211          moltype = AA  length = 84
FEATURE                 Location/Qualifiers
source                  1..84
                        mol_type = protein
                        organism = synthetic construct
SEQUENCE: 211
TSTRSPWTKV QWHLQLKELK EVRGGMVGLQ RGADLGLRYN GTSSKSKRGA KGWLVDFNEE  60
LTLDGTMAPP AKRAKRGKGL RDGW                                         84

SEQ ID NO: 212          moltype = AA  length = 80
FEATURE                 Location/Qualifiers
source                  1..80
                        mol_type = protein
                        organism = synthetic construct
SEQUENCE: 212
WWGTNVLPVL QANHLVLGWV PPGYKYLGGG VLMYDYLFYR PEITWFVGCL LATSTWDTTC  60
FTGLKSLGSR LGASWLQVPG                                              80

SEQ ID NO: 213          moltype = DNA  length = 270
FEATURE                 Location/Qualifiers
source                  1..270
                        mol_type = other DNA
                        organism = synthetic construct
SEQUENCE: 213
cctgaagaaa caactaacac agaagaacta gctgcaacag gatatggcca accactgata  60
tccggaacgg atgtgaatgc cagctattag aaaagccaga ggtaagtaaa tatttcatta  120
tacactacac aatgcaaact acagaaaatc ttctaaaagc tctaccttgc ttacttggat  180
ccatccaacc aatataggtt gggtaccacc tggatacaac ttcctaggac ccttcaatca  240
agacttcaac aaagaaccaa ctaatccatc                                   270

SEQ ID NO: 214          moltype = DNA  length = 270
FEATURE                 Location/Qualifiers
source                  1..270
                        mol_type = other DNA
                        organism = synthetic construct
SEQUENCE: 214
ggacttcttt gttgattgtg tcttcttgat cgacgttgtc ctataccggt tggtgactat  60
aggccttgcc tacacttacg gtcgataatc ttttcggtct ccattcattt ataaagtaat  120
atgtgatgtg ttacgtttga tgtcttttag aagattttcg agatggaacg aatgaaccta  180
ggtaggttgg ttatatccaa cccatggtgg acctatgttg aaggatcctg ggaagttagt  240
tctgaagttg tttcttggtt gattaggtag                                   270

SEQ ID NO: 215          moltype = AA  length = 84
FEATURE                 Location/Qualifiers
source                  1..84
                        mol_type = protein
                        organism = synthetic construct
```

-continued

```
SEQUENCE: 215
PEETTNTEEL AATGYGQPLI SGTDVNASYL KKQLTQKNLQ QDMANHYPER MMPAIRPRNN  60
HRRTSCNRIW PTTDIRNGCE CQLL                                         84

SEQ ID NO: 216         moltype = AA  length = 87
FEATURE                Location/Qualifiers
source                 1..87
                       mol_type = protein
                       organism = synthetic construct
SEQUENCE: 216
KSQRVNISLY TTQCKLQKIF KLYLAYLDKA RGKIFHYTLH NANYRKSSKS STLLTWIEKP  60
EVSKYFIIHY TMQTTENLLK ALPCLLG                                      87

SEQ ID NO: 217         moltype = AA  length = 87
FEATURE                Location/Qualifiers
source                 1..87
                       mol_type = protein
                       organism = synthetic construct
SEQUENCE: 217
PSNQYRLGTT WIQLPRTLQS RLQQRTNSIH PTNIGWVPPG YNFLGPFNQD FNKEPTNPST  60
IQPIVGYHLD TTSDPSIKTS TKNQLIH                                      87

SEQ ID NO: 218         moltype = AA  length = 143
FEATURE                Location/Qualifiers
source                 1..143
                       mol_type = protein
                       organism = synthetic construct
SEQUENCE: 218
MAPPAKRARR GLVPPGYKYL GPGNSLDQGE PTNPSDAAAK EHDEAYAAYL RSGKNPYLYF  60
SPADQRFIDQ TKDAKDWGGK IGHYFFRAKK AIAPVLTDTP DHPSTSRPTK PTKRSKPPPH  120
IFINLAKKKK AGAGQVKRDN LAP                                          143

SEQ ID NO: 219         moltype = AA  length = 6
FEATURE                Location/Qualifiers
source                 1..6
                       mol_type = protein
                       organism = synthetic construct
VARIANT                1
                       note = K can be replaced by I
SEQUENCE: 219
KRARRG                                                             6

SEQ ID NO: 220         moltype = AA  length = 4
FEATURE                Location/Qualifiers
source                 1..4
                       mol_type = protein
                       organism = synthetic construct
SEQUENCE: 220
LGPF                                                               4

SEQ ID NO: 221         moltype = DNA  length = 12
FEATURE                Location/Qualifiers
source                 1..12
                       mol_type = other DNA
                       organism = synthetic construct
SEQUENCE: 221
tggttggttg gt                                                      12
```

PROTOPARVOVIRUS COMPOSITIONS COMPRISING A PROTOPARVOVIRUS VARIANT VP1 CAPSID POLYPEPTIDE AND RELATED METHODS

CROSS REFERENCE TO RELATED APPLICATIONS

This application claims the benefit of U.S. Application Ser. No. 63/454,259 filed on Mar. 23, 2023, and U.S. Application Ser. No. 63/545,449 filed on Oct. 24, 2023, the disclosures of each of which are hereby incorporated by reference in their entireties.

SEQUENCE LISTING

This application contains a Sequence Listing, which has been submitted electronically through USPTO Patent Center in XML format and is hereby incorporated by reference in its entirety. Said XML copy, created on May 1, 2024, is named "2017359-0074.xml" and is 308,234 bytes in size.

BACKGROUND

Viral particles (or virions) are commonly utilized for gene therapy. The present disclosure provides technologies relating to protoparvovirus variant VP1 capsid polypeptides, their production and use, including in gene therapy.

SUMMARY

The present disclosure recognizes a need for improvements in gene therapy technologies. For example, among other things, the present disclosure recognizes a need for improved compositions, preparations, constructs, virions, populations of virions, host cells, etc. Furthermore, the present disclosure specifically recognizes a need for improved production and manufacturing of virions that comprise or otherwise utilize a protoparvovirus VP1 capsid polypeptide.

Among other things, the present disclosure provides an insight that improving retention of a protoparvovirus VP1 capsid polypeptide in cytoplasm of a cell can provide a variety of benefits. Alternatively or additionally, the present disclosure recognizes a need for reduced toxicity of virions comprising a protoparvovirus VP1 capsid polypeptide in cytoplasm of a cell. For example, in some embodiments, retention of a protoparvovirus VP1 capsid polypeptide can lead to cell toxicity, thereby reducing protoparvovirus VP1 capsid polypeptide yield.

Among other things, in some embodiments, the present disclosure recognizes that one or more characteristic sequence elements of a protoparvovirus VP1 capsid polypeptide surprisingly affects internalization of virions into a host cell. Among other things, in some embodiments, the present disclosure recognizes that one or more characteristic sequence elements of a protoparvovirus VP1 capsid polypeptide surprisingly affects virion transit into a nucleus of a cell. Among other things, the present disclosure recognizes that one or more characteristic sequence elements of a protoparvovirus VP1 capsid polypeptide surprisingly affects protoparvovirus VP1 capsid polypeptide expression in a host cell. Among other things, the present disclosure recognizes that one or more characteristic sequence elements of a protoparvovirus VP1 capsid polypeptide surprisingly affects protoparvovirus VP1 capsid polypeptide toxicity in a host cell.

In some embodiments, a characteristic sequence element comprises one or more stretches of amino acid residues within a protoparvovirus VP1 capsid polypeptide. In some embodiments, a characteristic sequence element comprises one or more stretches of amino acid residues within a protoparvovirus VP1 unique region (VP1u). In some embodiments, a characteristic sequence element comprises a protoparvovirus nuclear localization signal sequence (NLS) within a protoparvovirus VP1 capsid polypeptide. In some embodiments, a characteristic sequence element comprises a phospholipase A2 (PLA2) motif within a protoparvovirus VP1 capsid polypeptide. In some embodiments, a characteristic sequence element comprises a stretch of amino acid residues between a NLS and a PLA2 motif within a protoparvovirus VP1 capsid polypeptide. In some embodiments, a characteristic sequence element between a NLS and a PLA2 motif within a protoparvovirus VP1 capsid polypeptide comprises at least one sequence variation that improves characteristic features of compositions, preparations, constructs, virions, population of virions, and host cells for gene therapy and related methods described herein, relative to a protoparvovirus reference VP1 capsid polypeptide. In some embodiments, at least one sequence variation comprises one or more deletions of a stretch of amino acid residues between a NLS and a PLA2 motif of a protoparvovirus VP1capsid polypeptide as described herein.

For example, in some embodiments, the present disclosure recognizes a splicing event that occurs in a protoparvovirus VP1 capsid polypeptide which eliminates a characteristic sequence element between a NLS and a PLA2 motif within a protoparvovirus VP1 capsid polypeptide. Surprisingly, it is an insight of the present disclosure that such splicing event is not guaranteed to occur during infection and/or production of a virion in a host cell. Moreover, surprisingly, it is an insight of the present disclosure that such splicing event is dependent on a type of host cell that is being infected and/or used to produce a virion.

Therefore, in some embodiments, the present disclosure describes that deletion of one or more amino acid residues of a characteristic sequence element between a NLS and a PLA2 motif within a protoparvovirus VP1 capsid polypeptide resulted in a significant increase of expression of a protoparvovirus variant VP1 capsid polypeptide in a host cell, relative to a protoparvovirus reference VP1 capsid polypeptide. In some embodiments, deletion of five amino acid residues between a NLS and a PLA2 motif within a protoparvovirus VP1 capsid polypeptide resulted in significant reduced toxicity of a protoparvovirus variant VP1 capsid polypeptide in a host cell, relative to a protoparvovirus reference VP1 capsid polypeptide. In some embodiments, deletion of five amino acid residues between a NLS and a PLA2 motif within a protoparvovirus VP1 capsid polypeptide resulted in significant improvement of VP1 capsid polypeptide expression, relative to a protoparvovirus reference VP1 capsid polypeptide in a host cell.

Among other things, is an insight of the present disclosure that a VP1 capsid coding sequence encoding a protoparvovirus reference VP1 capsid polypeptide may comprise an unwanted out-of-frame ATG which can affect protoparvovirus VP1 capsid polypeptide expression and/or formation. Among other things, in some embodiments, constructs described herein comprise one or more nucleotide modifications to remove out-of-frame ATG in a protoparvovirus VP1 capsid polypeptide (e.g., a protoparvovirus VP1u capsid polypeptide).

Among other things, in some embodiments, the present disclosure provides compositions, preparations, constructs, virions, population of virions, and host cells comprising a protoparvovirus variant VP1 capsid polypeptide for gene therapy. In some embodiments, a protoparvovirus variant VP1 capsid polypeptide is characterized by reduced toxicity in a host cell, relative to a protoparvovirus reference VP1 capsid polypeptide. In some embodiments, a protoparvovirus variant VP1 capsid polypeptide is characterized by improved production of a protoparvovirus variant VP1 capsid polypeptide in a host cell, relative to a protoparvovirus reference VP1 capsid polypeptide. In some embodiments, a protoparvovirus variant VP1 capsid polypeptide is characterized by increased retention of a protoparvovirus variant VP1 capsid polypeptide in a host cell, relative to a protoparvovirus reference VP1 capsid polypeptide. In some embodiments, a host cell is an insect cell. In some embodiments, a protoparvovirus variant VP1 capsid polypeptide is characterized by increased expression of a protoparvovirus variant VP1 capsid polypeptide in a host cell, relative to a protoparvovirus reference VP1 capsid polypeptide. In some embodiments, deletion of five amino acid residues between a NLS and a PLA2 motif within a protoparvovirus VP1 resulted in significant improvement of increased capsid polypeptide yield, relative to a protoparvovirus reference VP1 capsid polypeptide. In some embodiments, an insect cell is a Sf9 cell. In some embodiments, a host cell is a mammalian cell.

Among other things, in some embodiments, the present disclosure provides a construct comprising a VP1 capsid coding sequence operably linked to an expression control sequence, wherein the VP1 capsid coding sequence encodes a protoparvovirus variant VP1 capsid polypeptide wherein the protoparvovirus variant VP1 capsid polypeptide comprises at least one sequence variation relative to the protoparvovirus reference VP1 capsid polypeptide. In some embodiments, a protoparvovirus variant VP1 capsid polypeptide comprises a deletion of one or more amino acid residues downstream of a NLS sequence. In some embodiments, an expression control sequence is a promoter that improves protoparvovirus variant VP1 capsid polypeptide initiation. In some embodiments, a construct comprises a 5' untranslated region (UTR). In some embodiments, a 5' UTR sequence improves protoparvovirus variant VP1 capsid polypeptide initiation. For example, in some embodiments, a 5' UTR sequence comprises a nucleotide spacer sequence. In some embodiments, a 5' UTR sequence comprises a nucleotide spacer sequence that does not comprise an alternative translation initiation sequence (e.g., ATT, ATA, ATC). In some embodiments, a 5' UTR sequence comprises a Kozak consensus sequence, or portion thereof. In some embodiments, such portion of a Kozak consensus sequence comprises a single nucleotide. In some embodiments, such portion of a Kozak consensus sequence comprises one to three nucleotides. In some embodiments, such portion of a Kozak consensus sequence comprises one to five nucleotides. In some embodiments, a 5' UTR sequence comprises a nucleotide spacer sequence and a Kozak consensus sequence. In some embodiments, a 5' UTR sequence does not comprise a nucleotide spacer sequence. In some embodiments, at least one Kozak residue may be within a translated region of a construct described herein. In some embodiments, a Kozak residue may be within a translated region of a construct described herein. In some embodiments, a 5' UTR sequence comprises a stretch of nucleotides between an expression control sequence and a VP1 capsid coding sequence. In some embodiments, a Kozak consensus sequence comprises a eukaryotic sequence (GCCGCC - - - G). In some embodiments, a Kozak consensus sequence comprises a viral-derived Kozak consensus sequence (CCTGTTAAG). In some embodiments, a Kozak consensus sequence comprises an alternative Kozak consensus sequence (AAA). In some embodiments a construct comprises a VP1 translation initiation codon sequence of CTG. In some embodiments a construct comprises a VP1 translation initiation codon sequence of TTG. In some embodiments a construct comprises a VP1 translation initiation codon sequence of ACG. In some embodiments a construct comprises a VP1 translation initiation codon sequence of ATC. In some embodiments a construct comprises a VP1 translation initiation codon sequence of ATG.

Moreover, among other things, in some embodiments, the present disclosure provides that protoparvovirus is not as prevalent as AAV. Thus, among other things, administration (e.g., systemic administration) of compositions (e.g., pharmaceutical compositions), preparations, constructs, virions, population of virions comprising a protoparvovirus VP1 capsid polypeptide to a subject would not trigger an extensive anti-viral immune reaction that precludes efficient gene delivery. Accordingly, in some embodiments, prescreening a subject for anti-protoparvovirus antibodies is not required prior to administering (e.g., systemically) compositions (e.g., pharmaceutical compositions), preparations, constructs, virions, population of virions described herein.

Moreover, among other things, in some embodiments, the present disclosure describes that the provided compositions (e.g., pharmaceutical compositions), preparations, constructs, virions, population of virions can be administered (e.g., systemically) to a subject to achieve expression of a heterologous nucleic acid (or payload) in specific target cells, tissues, and/or organs as described herein. Importantly, unlike AAV for example, the provided compositions (e.g., pharmaceutical compositions), preparations, constructs, virions, population of virions can be administered (e.g., systemically) to a subject to achieve expression of a heterologous nucleic acid (or payload) in specific target cells, tissues, and/or organs as described herein, with minimal targeting to liver cells.

In some embodiments, provided compositions, preparations, constructs, virions, population of virions, and host cells are for use in methods of treatment, delivery, producing polypeptides, or delaying/arresting progression of a disease or disorder.

In some embodiments, provided compositions, preparations, constructs, virions, population of virions, and host cells are for use in methods of manufacturing.

In some embodiments, provided compositions, preparations, constructs, virions, population of virions, and host cells are for use in methods of characterization.

In some embodiments, provided compositions, preparations, constructs, virions, population of virions, and host cells are for use in methods of purification.

Elements of embodiments involving one aspect of the invention (e.g., systems) can be applied in embodiments involving other aspects of the invention, and vice versa.

Elements of embodiments involving one aspect of the invention (e.g., methods) can be applied in embodiments involving other aspects of the invention, and vice versa.

Definitions

The scope of the present disclosure is defined by the claims appended hereto and is not limited by certain embodiments described herein. Those skilled in the art, reading the present specification, will be aware of various modifications that may be equivalent to such described embodiments, or otherwise within the scope of the claims. In general, terms used herein are in accordance with their understood meaning in the art, unless clearly indicated otherwise. Explicit definitions of certain terms are provided below; meanings of these and other terms in particular instances throughout this specification will be clear to those skilled in the art from context.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an," as used herein, should be understood to include plural referents unless clearly indicated to the contrary. Claims or descriptions that include "or" between one or more members of a group are considered satisfied if one, more than one, or all of the group members are present in, employed in, or otherwise relevant to a given product or process unless indicated to the contrary or otherwise evident from the context. In some embodiments, exactly one member of a group is present in, employed in, or otherwise relevant to a given product or process. In some embodiments, more than one, or all group members are present in, employed in, or otherwise relevant to a given product or process. It is to be understood that the present disclosure encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists (e.g., in Markush group or similar format), it is to be understood that each subgroup of the elements is also disclosed, and any element(s) can be removed from the group. It should be understood that, in general, where embodiments or aspects are referred to as "comprising" particular elements, features, etc., certain embodiments or aspects "consist," or "consist essentially of," such elements, features, etc. For purposes of simplicity, those embodiments have not in every case been specifically set forth in so many words herein. It should also be understood that any embodiment or aspect can be explicitly excluded from the claims, regardless of whether the specific exclusion is recited in the specification.

Throughout the specification, whenever a polynucleotide or polypeptide is represented by a sequence of letters (e.g., A, C, G, and T, which denote adenosine, cytidine, guanosine, and thymidine, respectively, in the case of a polynucleotide), such polynucleotides or polypeptides are presented in 5' to 3' or N-terminus to C-terminus order, from left to right.

Administration: As used herein, the term "administration" typically refers to administration of a composition to a subject or system to achieve delivery of an agent to a subject or system. In some embodiments, an agent is, or is included in, a composition; in some embodiments, an agent is generated through metabolism of a composition or one or more components thereof. Those of ordinary skill in the art will be aware of a variety of routes that may, in appropriate circumstances, be utilized for administration to a subject, for example a human. For example, in some embodiments, administration may be systematic or local. In some embodiments, a systematic administration can be intravenous. In some embodiments, administration can be local. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Amelioration: As used herein, the term "amelioration" refers to prevention, reduction or palliation of a state, or improvement of a state of a subject. Amelioration may include, but does not require, complete recovery or complete prevention of a disease, disorder or condition.

Amino acid: In its broadest sense, as used herein, the term "amino acid" refers to any compound and/or substance that can be incorporated into a polypeptide chain, e.g., through formation of one or more peptide bonds. In some embodiments, an amino acid has a general structure, e.g., $H_2N$—C(H)(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than standard amino acids, regardless of whether it is prepared synthetically or obtained from a natural source. In some embodiments, an amino acid, including a carboxy- and/or amino-terminal amino acid in a polypeptide can contain a structural modification as compared with general structure as shown above. For example, in some embodiments, an amino acid may be modified by methylation, amidation, acetylation, pegylation, glycosylation, phosphorylation, and/or substitution (e.g., of an amino group, a carboxylic acid group, one or more protons, and/or a hydroxyl group) as compared with a general structure. In some embodiments, such modification may, for example, alter circulating half-life of a polypeptide containing a modified amino acid as compared with one containing an otherwise identical unmodified amino acid. In some embodiments, such modification does not significantly alter a relevant activity of a polypeptide containing a modified amino acid, as compared with one containing an otherwise identical unmodified amino acid.

Approximately or About: As used herein, the terms "approximately" or "about" may be applied to one or more values of interest, including a value that is similar to a stated reference value. In some embodiments, the term "approximately" or "about" refers to a range of values that fall within +10% (greater than or less than) of a stated reference value unless otherwise stated or otherwise evident from context (except where such number would exceed 100% of a possible value). For example, in some embodiments, the term "approximately" or "about" may encompass a range of values that within 10%, 9%, 8%, 7%, 6%, 5%, 4%, 3%, 2%, 1%, or less of a reference value.

Associated: As used herein, the term "associated" describes two events or entities as "associated" with one another, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: As used herein, the term "biologically active" refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Characteristic portion: As used herein, the term "characteristic portion," in the broadest sense, refers to a portion of a substance whose presence (or absence) correlates with presence (or absence) of a particular feature, attribute, or activity of the substance. In some embodiments, a characteristic portion of a substance is a portion that is found in a given substance and in related substances that share a particular feature, attribute or activity, but not in those that do not share the particular feature, attribute or activity. In some embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to a sequence and/or structural identity specified above, shares at least one functional characteristic with the relevant intact substance. In some embodiments, a characteristic portion may be biologically active.

Characteristic sequence: As used herein, the term "characteristic sequence" is a sequence that is found in all members of a family of polypeptides or nucleic acids, and therefore can be used by those of ordinary skill in the art to define members of the family.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of a polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share a sequence element.

Cleavage: As used herein, the term "cleavage" refers to generation of a break in DNA. For example, in some embodiments, cleavage could refer to either a single-stranded break or a double-stranded break depending on a type of nuclease that may be employed to cause such a break.

Combination therapy: As used herein, the term "combination therapy" refers to those situations in which a subject is simultaneously exposed to two or more therapeutic regimens (e.g., two or more therapeutic agents). In some embodiments, two or more agents may be administered simultaneously. In some embodiments, two or more agents may be administered sequentially. In some embodiments, two or more agents may be administered in overlapping dosing regimens.

Comparable: As used herein, the term "comparable" refers to two or more agents, entities, situations, sets of conditions, subjects, populations, etc., that may not be identical to one another but that are sufficiently similar to permit comparison therebetween so that one skilled in the art will appreciate that conclusions may reasonably be drawn based on differences or similarities observed. In some embodiments, comparable sets of agents, entities, situations, sets of conditions, subjects, populations, etc. are characterized by a plurality of substantially identical features and one or a small number of varied features. Those of ordinary skill in the art will understand, in context, what degree of identity is required in any given circumstance for two or more such agents, entities, situations, sets of conditions, subjects, populations, etc. to be considered comparable. For example, those of ordinary skill in the art will appreciate that sets of agents, entities, situations, sets of conditions, subjects, populations, etc. are comparable to one another when characterized by a sufficient number and type of substantially identical features to warrant a reasonable conclusion that differences in results obtained or phenomena observed under or with different sets of circumstances, stimuli, agents, entities, situations, sets of conditions, subjects, populations, etc. are caused by or indicative of the variation in those features that are varied.

Construct: As used herein, the term "construct" refers to a composition including a polynucleotide capable of carrying at least one heterologous polynucleotide. In some embodiments, a construct can be a plasmid, a transposon, a cosmid, an artificial chromosome (e.g., a human artificial chromosome (HAC), a yeast artificial chromosome (YAC), a bacterial artificial chromosome (BAC), or a P1-derived artificial chromosome (PAC)) or a viral construct, and any Gateway® plasmids. A construct can, e.g., include sufficient cis-acting elements for expression; other elements for expression can be supplied by the host primate cell or in an in vitro expression system. A construct may include any genetic element (e.g., a plasmid, a transposon, a cosmid, an artificial chromosome, or a viral construct, etc.) that is capable of replicating when associated with proper control elements. Thus, in some embodiments, "construct" may include a cloning and/or expression construct and/or a viral construct (e.g., an adeno-associated virus (AAV) construct, an adenovirus construct, a lentivirus construct, or a retrovirus construct).

Conservative: As used herein, the term "conservative" refers to instances describing a conservative amino acid substitution, including a substitution of an amino acid residue by another amino acid residue having a side chain R group with similar chemical properties (e.g., charge or hydrophobicity). In general, a conservative amino acid substitution will not substantially change functional properties of interest of a protein, for example, ability of a receptor to bind to a ligand. Examples of groups of amino acids that have side chains with similar chemical properties include: aliphatic side chains such as glycine (Gly, G), alanine (Ala, A), valine (Val, V), leucine (Leu, L), and isoleucine (Ile, I); aliphatic-hydroxyl side chains such as serine (Ser, S) and threonine (Thr, T); amide-containing side chains such as asparagine (Asn, N) and glutamine (Gln, Q); aromatic side chains such as phenylalanine (Phe, F), tyrosine (Tyr, Y), and tryptophan (Trp, W); basic side chains such as lysine (Lys, K), arginine (Arg, R), and histidine (His, H); acidic side chains such as aspartic acid (Asp, D) and glutamic acid (Glu, E); and sulfur-containing side chains such as cysteine (Cys, C) and methionine (Met, M). Conservative amino acids substitution groups include, for example, valine/leucine/isoleucine (Val/Leu/Ile, V/L/I), phenylalanine/tyrosine (Phe/Tyr, F/Y), lysine/arginine (Lys/Arg, K/R), alanine/valine (Ala/Val, A/V), glutamate/aspartate (Glu/Asp, E/D), and asparagine/glutamine (Asn/Gln, N/Q). In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al., 1992, Science 256:1443-1445, which is incorporated herein by reference in its entirety. In some embodiments, a substitution is a moderately conservative substitution wherein the substitution has a nonnegative value in the PAM250 log-likelihood matrix. One skilled in the art would appreciate that a change (e.g., substitution, addition, deletion, etc.) of amino acids that are not conserved between the same protein from different species is less likely to have an effect on the function of a protein and therefore, these amino acids should be selected for mutation. Amino acids that are conserved between the same protein from different species should not be changed (e.g., deleted, added, substituted, etc.), as these mutations are more likely to result in a change in function of a protein.

CONSERVATIVE AMINO ACID SUBSTITUTIONS

| For Amino Acid | Code | Replace With |
|---|---|---|
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, B-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. 4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Control: As used herein, the term "control" refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. For example, in one experiment, a "test" (i.e., a variable being tested) is applied. In a second experiment, a "control," the variable being tested is not applied. In some embodiments, a control is a historical control (e.g., of a test or assay performed previously, or an amount or result that is previously known). In some embodiments, a control is or comprises a printed or otherwise saved record. In some embodiments, a control is a positive control. In some embodiments, a control is a negative control.

Determining, measuring, evaluating, assessing, assaying and analyzing: As used herein, the terms "determining," "measuring," "evaluating," "assessing," "assaying," and "analyzing" may be used interchangeably to refer to any form of measurement, and include determining if an element is present or not. These terms include both quantitative and/or qualitative determinations. Assaying may be relative or absolute. For example, in some embodiments, "Assaying for the presence of" can be determining an amount of something present and/or determining whether or not it is present or absent.

Editing: As used herein, the term "edit," "editing," or "edited" refers to a method of altering a nucleic acid sequence of a polynucleotide (e.g., a wild type naturally occurring nucleic acid sequence or a mutated naturally occurring sequence) by selective deletion of a specific nucleic acid sequence (e.g., a genomic target sequence), a given specific inclusion of new sequence through use of an exogenous nucleic acid sequence, or a replacement of nucleic acid sequence with an exogenous nucleic acid sequence. In some embodiments, such a specific genomic target includes, but may be not limited to, a chromosomal region, mitochondrial DNA, a gene, a promoter, an open reading frame or any nucleic acid sequence.

Engineered: In general, as used herein, the term "engineered" refers to an aspect of having been manipulated by the hand of man. For example, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Excipient: As used herein, the term "excipient" refers to an inactive (e.g., non-therapeutic) agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: As used herein, the term "expression" of a nucleic acid sequence refers to generation of any gene product (e.g., transcript, e.g., mRNA, e.g., polypeptide, etc.) from a nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, the term "functional" describes something that exists in a form in which it exhibits a property and/or activity by which it is characterized. For example, in some embodiments, a "functional" biological molecule is a biological molecule in a form in which it exhibits a property and/or activity by which it is characterized. In some such embodiments, a functional biological molecule is characterized relative to another biological molecule which is non-functional in that the "non-functional" version does not exhibit the same or equivalent property and/or activity as the "functional" molecule. A biological molecule may have one function, two functions (i.e., bifunctional) or many functions (i.e., multifunctional).

Gene: As used herein, the term "gene" refers to a DNA sequence in a chromosome that codes for a gene product (e.g., an RNA product, e.g., a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). As used herein, the term "gene" generally refers to a portion of a nucleic acid that encodes a polypeptide or fragment thereof; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid. In some embodiments, a gene may encode a polypeptide, but that polypeptide may not be functional, e.g., a gene variant may encode a polypeptide that does not function in the same way, or at all, relative to the wild-type gene. In some embodiments, a gene may encode a transcript which, in some embodiments, may be toxic beyond a threshold level. In some embodiments, a gene may encode a polypeptide, but that polypeptide may not be functional and/or may be toxic beyond a threshold level.

Genome Editing System: As used herein, the term "genome editing system" refers to any system having DNA editing activity. Among other things, DNA editing activity can include deleting, replacing, or inserting a DNA sequence in a genome. In some embodiments, a genome editing system comprises RNA-guided DNA editing activity. In some embodiments, a genome editing system of the present disclosure includes more than one component. In some embodiments, a genome editing system includes at least two components adapted from naturally occurring CRISPR systems: a guide RNA (gRNA) and an RNA-guided nuclease. In certain embodiments, these two components form a complex that is capable of associating with a specific nucleic acid sequence and editing DNA in or around that nucleic acid sequence, for instance by making one or more of a single-strand break (an SSB or nick), a double-strand break (a DSB) and/or a point mutation. In some embodiments, genome editing systems of the present disclosure lack a component having cleavage activity but maintain a component(s) having DNA binding activity. In some such embodiments, a genome editing system of the present disclosure comprises a component(s) that functions as an inhibitor of DNA activity, e.g., transcription, translation, etc. In some embodiments, a genome editing system of the present disclosure comprises a component(s) fused to modulators to modulate target DNA expression.

Genomic modification: As used herein, the term "genomic modification" refers to a change made in a genomic region of a cell that permanently alters a genome (e.g., an endogenous genome) of that cell. In some embodiments, such changes are in vitro, ex vivo, or in vivo. In some embodiments, every cell in a living organism is modified. In some embodiments, only a particular set of cells such as, e.g., in a specific organ, is modified. For example, in some embodiments, a genome is modified by deletion, substitution, or addition of one or more nucleotides from one or more genomic regions. In some embodiments, a genomic modification is performed in a stem cell or undifferentiated cell. In some such embodiments, progeny of a genomically modified cell or organism will also be genomically modified, relative to a parental genome prior to modification. In some embodiments, a genomic modification is performed on a mature or post-mitotic cell such that no progeny will be generated and thus, no genomic modifications propagated other than in a particular cell.

Heterologous: As used herein, the term “heterologous” may be used in reference to one or more regions of a particular molecule as compared to another region and/or another molecule. For example, in some embodiments, heterologous polypeptide domains, refers to the fact that polypeptide domains do not naturally occur together (e.g., in the same polypeptide). For example, in fusion proteins generated by the hand of man, a polypeptide domain from one polypeptide may be fused to a polypeptide domain from a different polypeptide. In such a fusion protein, two polypeptide domains would be considered “heterologous” with respect to each other, as they do not naturally occur together.

Identity: As used herein, the term “identity” refers to overall relatedness between polymeric molecules, e.g., between nucleic acid molecules (e.g., DNA molecules and/or RNA molecules) and/or between polypeptide molecules. In some embodiments, polymeric molecules are considered to be “substantially identical” to one another if their sequences are at least 25%, 30%, 35%, 40%, 45%, 50%, 55%, 60%, 65%, 70%, 75%, 80%, 85%, 90%, 95%, or 99% identical. Calculation of percent identity of two nucleic acid or polypeptide sequences, for example, can be performed by aligning two sequences for optimal comparison purposes (e.g., gaps can be introduced in one or both of a first and a second sequences for optimal alignment and non-identical sequences can be disregarded for comparison purposes). In some embodiments, a length of a sequence aligned for comparison purposes is at least 30%, at least 40%, at least 50%, at least 60%, at least 70%, at least 80%, at least 90%, at least 95%, or substantially 100% of length of a reference sequence; nucleotides at corresponding positions are then compared. When a position in the first sequence is occupied by the same residue (e.g., nucleotide or amino acid) as a corresponding position in the second sequence, then the two molecules (i.e., first and second) are identical at that position. Percent identity between two sequences is a function of the number of identical positions shared by the two sequences being compared, taking into account the number of gaps, and the length of each gap, which needs to be introduced for optimal alignment of the two sequences. Comparison of sequences and determination of percent identity between two sequences can be accomplished using a mathematical algorithm. For example, percent identity between two nucleotide sequences can be determined using the algorithm of Meyers and Miller (CABIOS, 1989, 4:11-17, which is herein incorporated by reference in its entirety), which has been incorporated into the ALIGN program (version 2.0). In some embodiments, nucleic acid sequence comparisons made with the ALIGN program use a PAM120 weight residue table, a gap length penalty of 12 and a gap penalty of 4.

Inhibitory nucleic acid: As used herein, the term “inhibitory nucleic acid” refers to a nucleic acid sequence that hybridizes specifically to a target gene, including target DNA or RNA (e.g., a target mRNA). Thereby, in some embodiments, an inhibitory nucleic acid inhibits expression and/or activity of a target gene. In some embodiments, an inhibitory nucleic acid is a short interfering RNA (siRNA), a short hairpin RNA (shRNA), a microRNA (or “miRNA”), an antisense oligonucleotide, a guide RNA (gRNA), or a ribozyme. In some embodiments, an inhibitory nucleic acid is between about 10 nucleotides to about 30 nucleotides in length (e.g., about 10 nucleotides to about 28 nucleotides, about 10 nucleotides to about 26 nucleotides, about 10 nucleotides to about 24 nucleotides, about 10 nucleotides to about 22 nucleotides, about 10 nucleotides to about 20 nucleotides, about 10 nucleotides to about 18 nucleotides, about 10 nucleotides to about 16 nucleotides, about 10 nucleotides to about 14 nucleotides, about 10 nucleotides to about 12 nucleotides, about 12 nucleotides to about 30 nucleotides, about 12 nucleotides to about 28 nucleotides, about 12 nucleotides to about 26 nucleotides, about 12 nucleotides to about 24 nucleotides, about 12 nucleotides to about 22 nucleotides, about 12 nucleotides to about 20 nucleotides, about 12 nucleotides to about 18 nucleotides, about 12 nucleotides to about 16 nucleotides, about 12 nucleotides to about 14 nucleotides, about 16 nucleotides to about 30 nucleotides, about 16 nucleotides to about 28 nucleotides, about 16 nucleotides to about 26 nucleotides, about 16 nucleotides to about 24 nucleotides, about 16 nucleotides to about 22 nucleotides, about 16 nucleotides to about 20 nucleotides, about 16 nucleotides to about 18 nucleotides, about 18 nucleotides to about 30 nucleotides, about 18 nucleotides to about 28 nucleotides, about 18 nucleotides to about 26 nucleotides, about 18 nucleotides to about 24 nucleotides, about 18 nucleotides to about 22 nucleotides, about 18 nucleotides to about 20 nucleotides, about 20 nucleotides to about 30 nucleotides, about 20 nucleotides to about 28 nucleotides, about 20 nucleotides to about 26 nucleotides, about 20 nucleotides to about 24 nucleotides, about 20 nucleotides to about 22 nucleotides, about 22 nucleotides to about 30 nucleotides, about 22 nucleotides to about 28 nucleotides, about 22 nucleotides to about 26 nucleotides, about 22 nucleotides to about 24 nucleotides, about 24 nucleotides to about 30 nucleotides, about 24 nucleotides to about 28 nucleotides, about 24 nucleotides to about 26 nucleotides, about 26 nucleotides to about 30 nucleotides, about 26 nucleotides to about 28 nucleotides, about 28 nucleotides to about 30 nucleotides, or 11, 12, 13, 14, 15, 16, 17, 18, 19, 20, 21, 22, 23, 24, 25, 26, 27, 28, 29 or 30 nucleotides Improve, increase, enhance, inhibit or reduce: As used herein, the terms “improve,” “increase,” “enhance,” “inhibit,” “reduce,” or grammatical equivalents thereof, indicate values that are relative to a baseline or other reference measurement. In some embodiments, a value is statistically significantly difference that a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment. In some embodiments, an appropriate reference is a negative reference; in some embodiments, an appropriate reference is a positive reference.

Knockdown: As used herein, the term “knockdown” refers to a decrease in expression of one or more gene products. In some embodiments, an inhibitory nucleic acid achieve knockdown. In some embodiments, a genome editing system described herein achieves knockdown.

Knockout: As used herein, the term “knockout” refers to ablation of expression of one or more gene products. In some embodiments, a genome editing system described herein achieve knockout.

Modulating: As used herein, the term “modulating,” means mediating a detectable increase or decrease in a level of a response in a subject compared with a level of a response in a subject in absence of a treatment or compound, and/or compared with a level of a response in an otherwise identical but untreated subject. The term encompasses perturbing and/or affecting a native signal or response thereby mediating a beneficial therapeutic response in a subject, preferably, a human.

Nuclease: As used herein, the term "nuclease" refers to an agent, for example a protein or a small molecule, capable of cleaving a phosphodiester bond connecting nucleotide residues in a nucleic acid molecule. In some embodiments, a nuclease is a protein, e.g., an enzyme that can bind a nucleic acid molecule and cleave a phosphodiester bond connecting nucleotide residues within a nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease is a RNA-guided (i.e., RNA-programmable) nuclease, which complexes with (e.g., binds with) an RNA having a sequence that complements a target site, thereby providing the sequence specificity of a nuclease. In some embodiments, a nuclease recognizes a single stranded target site, while in some embodiments, a nuclease recognizes a double-stranded target site, for example a double-stranded DNA target site. Target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within a target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target sites asymmetrically, i.e., cutting each strand at a different position so that the ends comprise unpaired nucleotides. Unpaired nucleotides at an end of a double-stranded DNA molecule are also referred to as "overhangs," e.g., as "5'-overhang" or as "3'-overhang," depending on whether unpaired nucleotide(s) form(s) the 5' or the 3' end of a given DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates interaction of a protein with a nucleic acid substrate, and also, in some cases, specifically binds to a target site, and a "cleavage domain" that catalyzes the cleavage of a phosphodiester bond within a nucleic acid backbone. In some embodiments, a nuclease protein can bind and cleave a nucleic acid molecule in a monomeric form, while, in some embodiments, a nuclease protein has to dimerize or multimerize in order to cleave a target nucleic acid molecule. Binding domains and cleavage domains of naturally occurring nucleases, as well as modular binding domains and cleavage domains that can be fused to create nucleases binding specific target sites, are well known to those of skill in the art.

Nucleic acid: As used herein, the term "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments, a nucleic acid has a nucleotide sequence comprising at least one element that encodes, or is complementary to a sequence that encodes, a polypeptide. In some embodiments, a nucleic acid has enzymatic activity.

Operably linked: As used herein, refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with coding elements of interest; in some embodiments, control elements act in trans to or otherwise at a from the functional element of interest. In some embodiments, "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. In some embodiments, for example, a functional linkage may include transcriptional control. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

Pharmaceutical composition: As used herein, the term "pharmaceutical composition" refers to a composition in which an active agent is formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for, e.g., administration, for example, an injectable formulation that is, e.g., an aqueous or non-aqueous solution or suspension or a liquid drop designed to be administered into an ear canal. In some embodiments, a pharmaceutical composition may be formulated for administration via injection either in a particular organ or compartment, e.g., directly into an ear, or systemic, e.g., intravenously. In some embodiments, a formulation may be or comprise drenches (aqueous or non-aqueous solutions or suspensions), tablets, boluses, powders, granules, pastes, capsules, powders, etc. In some embodiments, an active agent may be or comprise an isolated, purified, or pure compound.

Pharmaceutically acceptable: As used herein, the term "pharmaceutically acceptable" which, for example, may be used in reference to a carrier, diluent, or excipient used to formulate a pharmaceutical composition as disclosed herein, means that a carrier, diluent, or excipient is compatible with other ingredients of a composition and not deleterious to a recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting a subject compound from one organ, or portion of a body, to another organ, or portion of a body. Each carrier must be is "acceptable" in the sense of being compatible with other ingredients of a formulation and not injurious to a patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polypeptide: As used herein, the term "polypeptide" refers to any polymeric chain of residues (e.g., amino acids) that are typically linked by peptide bonds. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may include one or more pendant groups or other modifications, e.g., modifying or attached to one or more amino acid side chains, at a polypeptide's N-terminus, at a polypeptide's C-terminus, or any combination thereof. In some embodiments, such pendant groups or modifications may be acetylation, amidation, lipidation, methylation, pegylation, etc., including combinations thereof. In some embodiments, polypeptides may contain L-amino acids, D-amino acids, or both and may contain any of a variety of amino acid modifications or analogs known in the art. In some embodiments, useful modifications may be or include, e.g., terminal acetylation, amidation, methylation, etc. In some embodiments, a protein may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, a protein is antibodies, antibody fragments, biologically active portions thereof, and/or characteristic portions thereof.

Polynucleotide: As used herein, the term "polynucleotide" refers to any polymeric chain of nucleic acids. In some embodiments, a polynucleotide is or comprises RNA; in some embodiments, a polynucleotide is or comprises DNA. In some embodiments, a polynucleotide is, comprises, or consists of one or more natural nucleic acid residues. In some embodiments, a polynucleotide is, comprises, or consists of one or more nucleic acid analogs. In some embodiments, a polynucleotide analog differs from a nucleic acid in that it does not utilize a phosphodiester backbone. Alternatively or additionally, in some embodiments, a polynucleotide has one or more phosphorothioate and/or 5'-N-phosphoramidite linkages rather than phosphodiester bonds. In some embodiments, a polynucleotide is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a polynucleotide is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a polynucleotide comprises one or more modified sugars (e.g., 2'-fluororibose, ribose, 2'-deoxyribose, arabinose, and hexose) as compared with those in natural nucleic acids. In some embodiments, a polynucleotide has a nucleotide sequence that encodes a functional gene product such as an RNA or protein. In some embodiments, a polynucleotide includes one or more introns. In some embodiments, a polynucleotide is prepared by one or more of isolation from a natural source, enzymatic synthesis by polymerization based on a complementary template (in vivo or in vitro), reproduction in a recombinant cell or system, and chemical synthesis. In some embodiments, a polynucleotide is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a polynucleotide is partly or wholly single stranded; in some embodiments, a polynucleotide is partly or wholly double stranded. In some embodiments, a polynucleotide has a nucleotide sequence comprising at least one element that encodes, or is the complement of a sequence that encodes, a polypeptide. In some embodiments, a polynucleotide has enzymatic activity.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a genotypic variant thereof. Those of ordinary skill will appreciate that a protein can sometimes include more than one polypeptide chain, for example linked by one or more disulfide bonds or associated by other means.

Recombinant: As used herein, the term "recombinant" is intended to refer to polypeptides that are designed, engineered, prepared, expressed, created, manufactured, and/or or isolated by recombinant means, such as polypeptides expressed using a recombinant expression construct transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of a polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Reference: As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is a negative control reference; in some embodiments, a reference is a positive control reference.

Regulatory Element: As used herein, the term "regulatory element" or "regulatory sequence" refers to non-coding regions of DNA that regulate, in some way, expression of one or more particular genes. In some embodiments, such genes are apposed or "in the neighborhood" of a given regulatory element. In some embodiments, such genes are located quite far from a given regulatory element. In some embodiments, a regulatory element impairs or enhances transcription of one or more genes. In some embodiments, a regulatory element may be located in cis to a gene being regulated. In some embodiments, a regulatory element may be located in trans to a gene being regulated. For example, in some embodiments, a regulatory sequence refers to a nucleic acid sequence which is regulates expression of a gene product operably linked to a regulatory sequence. In some such embodiments, this sequence may be an enhancer sequence and other regulatory elements which regulate expression of a gene product.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe (e.g., virus), a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., bronchioalveolar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

Subject: As used herein, the term "subject" refers an organism, typically a mammal (e.g., a human, in some embodiments including prenatal human forms). In some embodiments, a subject is a non-human primate. In some embodiments a non-human primate is a cynomolgus macaque. In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to a qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result. The term "substantially" is therefore used herein to capture a potential lack of completeness inherent in many biological and chemical phenomena.

Target site: As used herein, the term "target site" means a portion of a nucleic acid to which a binding molecule, e.g., a microRNA, an siRNA, a guide RNA ("gRNA") or a guide RNA: Cas complex, will bind, provided sufficient conditions for binding exist. In some embodiments, a nucleic acid comprising a target site is double stranded. In some embodiments, a nucleic acid comprising a target site is single stranded. Typically, a target site comprises a nucleic acid sequence to which a binding molecule, e.g., a gRNA or a gRNA: Cas complex described herein, binds and/or that is cleaved as a result of such binding. In some embodiments, a target site comprises a nucleic acid sequence (also referred to herein as a target sequence or protospacer) that is complementary to a DNA sequence to which the targeting sequence (also referred to herein as the spacer) of a gRNA described herein binds. In some embodiments in the context of RNA-guided nucleases, e.g., CRISPR/Cas nucleases, a target site typically comprises a nucleotide sequence (also referred to herein as a target sequence or a protospacer) that is complementary to a sequence comprised in a gRNA (also referred to herein as the targeting sequence or the spacer) of an RNA-programmable nuclease. In some such embodiments, a target site further comprises a protospacer adjacent motif (PAM) at the 3' end or 5' end adjacent to the gRNA-complementary sequence. For an RNA-guided nuclease Cas9, a target sequence may be, in some embodiments, 16-24 base pairs plus a 3-6 base pair PAM (e.g., NNN, wherein N represents any nucleotide). Exemplary PAM sequences for RNA-guided nucleases, such as Cas9, are known to those of skill in the art and include, without limitation, NNG, NGN, NAG, NGA, NGG, NGAG and NGCG wherein N represents any nucleotide. In addition, Cas9 nucleases from different species have been described, e.g., *S. thermophilus* recognizes a PAM that comprises the sequence NGGNG, and Cas9 from *S. aureus* recognizes a PAM that comprises the sequence NNGRRT. In some embodiments, Cas9 from *S. aureus* recognizes a PAM that comprises the sequence NNNRRT. Additional PAM sequences are known in the art, including, but not limited to NNAGAAW and NAAR (see, e.g., Esvelt and Wang, Molecular Systems Biology, 9:641 (2013), the entire content of which is incorporated herein by reference). For example, the target site of an RNA-guided nuclease, such as, e.g., Cas9, may comprise a structure [Nz]-[PAM], where each Nis, independently, any nucleotide, and z is an integer between 1 and 50. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20.

Treatment: As used herein, the term "treatment" (also "treat" or "treating") refers to any administration of a therapy that partially or completely alleviates, ameliorates, eliminates, reverses, relieves, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively, or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of a given disease, disorder, and/or condition.

Variant: As used herein, the term "variant" refers to a version of something, e.g., a gene sequence, that is different, in some way, from another version. To determine if something is a variant, a reference version is typically chosen and a variant is different relative to that reference version. In some embodiments, a variant can have the same or a different (e.g., increased or decreased) level of activity or functionality than a wild type sequence. For example, in some embodiments, a variant can have improved functionality as compared to a wild-type sequence if it is, e.g., mutated to confer reduced toxicity in a cell. As another example, in some embodiments, a variant can have improved functionality as compared to a wild-type sequence if it is, e.g., mutated to confer improved protein production in a cell.

BRIEF DESCRIPTION OF THE DRAWING

FIG. 1 shows alignments of an N-terminus region of exemplary protoparvovirus VP1u within a VP1 capsid polypeptide. Alignments depicted by FIG. 1 reveal significant conservation of a stretch of amino acid residues (or amino acid motif) within exemplary protoparvovirus species including bufavirus (BuV), cutavirus (CuV), tusavirus (TuV), minute virus of mice (MVM), canine parvovirus (CPV), and feline panleukopenia virus (FPV). Alignments depicted by FIG. 1 also show significant conservation of a putative nuclear localization signal (NLS) upstream of a five amino acid motif. Alignments depicted by FIG. 1 also show highly conserved PLA2 motif residues downstream of an amino acid motif.

FIG. 11 depicts exemplary protoparvovirus construct elements that can improve production and/or reduce toxicity of a protoparvovirus variant VP1 capsid polypeptide in host cells, according to an embodiment of the present disclosure.

DETAILED DESCRIPTION OF CERTAIN EMBODIMENTS

Among other things, the present disclosure recognizes that compositions, preparations, constructs, virions, population of virions, and host cells comprising a protoparvovirus variant VP1 capsid polypeptide are particularly advantageous as a vehicle for gene therapy.

First, due to a larger virion genome size, a protoparvovirus (~5.3 kb (e.g., canine parvovirus) compared with ~4.7 kb of AAV) can package a nucleic acid at least 0.6 kb greater than AAV, thereby allowing delivery of a therapeutic gene(s) whose size exceeds the capacity of AAV. A larger virion genome size also allows delivery of a therapeutic transgene(s) together with genomic safe harbor (GSH) sequences that accommodate site-specific recombination of the transgene(s) at a desired genomic location. Such site-specific recombination allows integration of the transgene at an inert location in the genome, as opposed to random integration that could disrupt an essential gene and its expression.

Second, unlike AAV, protoparvovirus is not as prevalent as AAV. Thus, administration of a virion comprising a protoparvovirus variant VP1 capsid polypeptide would not trigger an extensive anti-viral immune reaction that precludes efficient gene delivery. That is, in some embodiments, no prescreening of a subject for anti-parvovirus antibodies is required prior to administering (e.g., systemically) compositions (e.g., pharmaceutical compositions), preparations, constructs, virions, population of virions described herein. Accordingly, a virion comprising a protoparvovirus variant VP1 capsid polypeptide can achieve gene delivery with the efficiency unparalleled to AAV.

Figure 19:
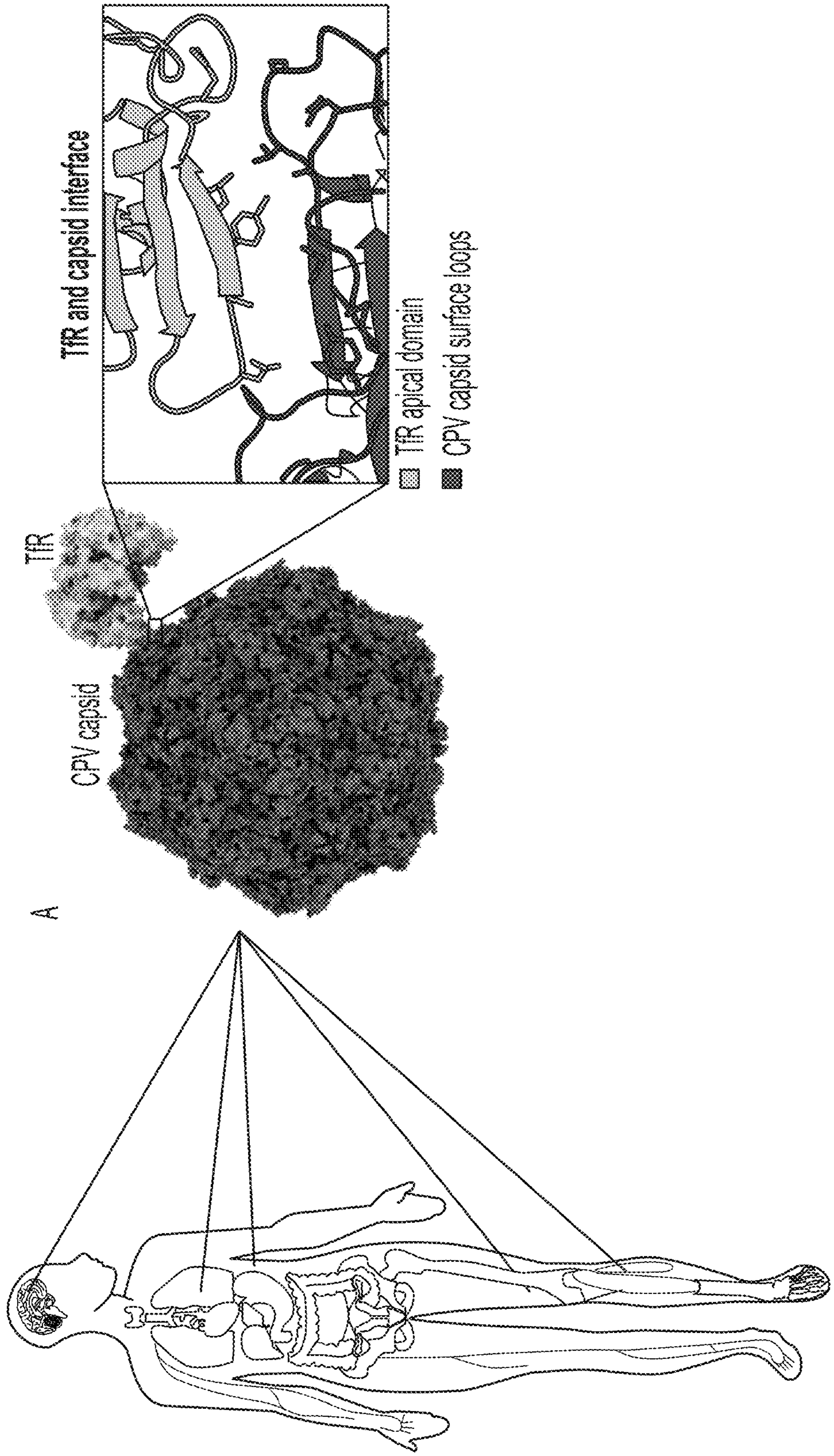
FIG. 19 shows a schematic depicting a structural model of interaction between a virion comprising a protoparvovirus VP1 capsid polypeptide encoded by a VP1 capsid coding sequence described herein and a transferrin receptor (TfR).

Third, protoparvovirus has an extraordinary tropism for specific tissues. For example, protoparvovirus has a tropism for hematopoietic stem cells and is particularly useful for treatment or prevention of hematologic diseases such as hemoglobinopathies, anemia, myeloproliferative disorders, coagulopathies, and cancer. In addition, protoparvovirus can efficiently transcytose across the cells via its interaction with a transferrin receptor. Thus, protoparvovirus can cross a blood-brain barrier (BBB) and deliver therapeutic genes to nerve cells that are hidden behind an endothelial barrier (see, e.g., FIG. 19, see also, e.g., Lopez-Atacio, et al., J. Virol. (2023), the contents of which are incorporated by reference herein in its entirety). It is an insight of the present disclosure that a model of capsid: TfR interaction and capsid: TfR binding (e.g., as described by Lopez-Atacio, et al., J. Virol. (2023) can be extended to a protoparvovirus described herein. It is an insight of the present disclosure that a model of capsid: TfR interaction and capsid: TfR binding (e.g., as described by Lopez-Atacio, et al., J. Virol. (2023)) can be extended to a canine protoparvovirus described herein. Further, it is an insight of the present disclosure that a VP1 capsid polypeptide encoded by a VP1 capsid coding sequence described herein exhibits a capsid: TfR interaction and capsid: TfR interaction binding (see, e.g., FIG. 19). Among other things, in some embodiments, interaction with a TfR receptor results in cell-specific tropism. Also, as described herein, TfR is a receptor of interest for blood-brain barrier (BBB)-transcytosis-mediated CNS delivery. For example, in some embodiments, virions comprising a VP1 capsid polypeptide encoded by a VP1 capsid coding sequence described herein exhibit cell-specific tropism for central nervous system (CNS) cells. As another example, in some embodiments, virions comprising a VP1 capsid polypeptide encoded by a VP1 capsid coding sequence described herein exhibit cell-specific tropism for kidney cells. As another example, in some embodiments, virions comprising a VP1 capsid polypeptide encoded by a VP1 capsid coding sequence described herein exhibit cell-specific tropism for lung cells. As another example, in some embodiments, virions comprising a VP1 capsid polypeptide encoded by a VP1 capsid coding sequence described herein exhibit cell-specific tropism for bone marrow cells. As another example, in some embodiments, virions comprising a VP1 capsid polypeptide encoded by a VP1 capsid coding sequence described herein exhibit cell-specific tropism for muscle cells. Accordingly, a virion comprising a capsid protein of protoparvovirus provides a novel means of gene therapy for patients afflicted with e.g., neurodegenerative or neuromuscular diseases. Accordingly, a virion comprising protoparvovirus capsid protein(s) provides a new modality for gene therapy that can target specific cells/tissues/organs for treatment or prevention of a wide range of human diseases.

Protoparvovirus capsid polypeptides comprise two main structural polypeptides, VP1, with an approximate MW of 81 KDa, and VP2 with an approximate MW of 58 to 62 KDa. In some embodiments, viral capsid polypeptide stoichiometry is VP1: VP2 (from about 1:10 to about 1:20, e.g., about 1:10, 1:11, 1:12, 1:13, 1:14, 1:15, 1:16, 1:17, 1:18, 1:19, 1:20).

For example, in some embodiments, the present disclosure recognizes that a protoparvovirus VP1 capsid polypeptide (e.g., within a VP1 unique region (VP1u)) harbors amino acid residues that are useful for virion internalization. Moreover, among other things, the present disclosure recognizes that a protoparvovirus VP1 harbors amino acid motifs that are useful for transit to a cell nucleus. Additionally, among other things, the present disclosure recognizes that a protoparvovirus VP1 harbors amino acid motifs that are useful for productive virus infection. Moreover, among other things, the present disclosure recognizes that a protoparvovirus phospholipase A (PLA) motif allows for endosomal escape early during infection. For different protoparvovirus species, for example, a N-termini of a protoparvovirus VP1 also harbors stretches of basic amino acids that function as nuclear localization sites (also referred to as nuclear localization signals) (NLS) which can be recognized by importin proteins (alpha, and beta) in host cells. In some embodiments, recognition by importin proteins mediate nuclear delivery (Mantyla et al. 2020, Lyi et al. 2014, each of which is hereby incorporated by reference herein in its entirety).

For example, as described herein, in some embodiments, expression of protoparvovirus full capsid polypeptides (composed of VP1 and VP2) in baculovirus-Sf9 systems has been reported to be challenging, for example, due to cell toxicity. Without wishing to be bound to any theory, it is believed that cell toxicity is presumably a result of protoparvovirus VP1 capsid polypeptide retention in cell cytoplasm, ultimately resulting in protein aggregation and subsequent toxicity (Yuan et al. 2001, the contents of which is hereby incorporated by reference herein in its entirety). Moreover, in some embodiments, differential phosphorylation of MVM capsid (VP1) by host Raf1 kinase led to VP1 capsid polypeptide retention in the cytoplasm (Riobolos et al. 2009, the contents of which is hereby incorporated by reference herein in its entirety). Without wishing to be bound to any theory, it is believed that phosphorylation does not occur in insect cells due to a different sequence and structure from mammalian Raf1.

Moreover, in some embodiments, the present disclosure recognizes splicing events found in a protoparvovirus VP1 capsid polypeptide (e.g., within a VP1u) that eliminates five amino acid residues downstream of an NLS. It is an insight of the present disclosure that these five amino acid residues are conserved across protoparvovirus species. Surprisingly, in some embodiments, the present disclosure describes that this deletion resulted in significant improvement of protoparvovirus VP1 capsid polypeptide expression in a host cell. In some embodiments, a host cell is an insect cell. In some embodiments, an insect cell is a Sf9 cell. In some embodiments, a host cell is a mammalian cell.

1. Protoparvovirus

Among other things, the present disclosure describes compositions, preparations, constructs, virions, population of virions, and host cells comprising a protoparvovirus variant VP1 capsid polypeptide relative to a protoparvovirus reference VP1 capsid polypeptide. As described herein, protoparvovirus is of particular interest as a gene therapy composition. For example, neutralizing antibodies against human protoparvovirus, including bufavirus, tusavirus, and cutavirus have low prevalence in many Western countries (Vaisanen, Mohanraj et al. 2018, the entire contents of which are hereby incorporated by reference herein). While circulation of human protoparvovirus, inferred by the prevalence of virus-specific antibodies, has shown to be greater than 50% in the Middle East or Africa, circulation in European countries and in the United States is strikingly low, varying between 0% and 5% (Vaisanen, Mohanraj et al. 2018, the entire contents of which are hereby incorporated by reference herein). This is a feature that makes protoparvovirus particularly attractive for gene therapy as compared to AAV-derived vectors, which has a human IgG prevalence of 40-70%.

Moreover, protoparvovirus has capacity to encapsulate and deliver a larger nucleic acid molecule as compared to AAV-derived vectors. For example, bufavirus can incorporate DNA molecules of ~5.1 Kb, allowing design and delivery of genomes that encode larger proteins or contain cis-acting regulatory elements in these vectors (when compared to AAV), while tusavirus and cutavirus can incorporate a genome similar to AAV (~4.6 Kb).

Further, protoparvovirus can target certain cell types, tissues, and/or organs. Human bufavirus and tusavirus have been isolated from respiratory and gastrointestinal (GI) tracks (or stool) in humans, and studies performed in non-human primates suggest that bufavirus can elicit a systemic infection (Vaisanen, Mohanraj et al. 2018, the entire contents of which are hereby incorporated by reference herein). Accordingly, in some embodiments, bufavirus can be used for gene therapy targeting different human organs including but not limited to small intestine, liver, heart, lung, brain, and muscle. In addition, parvovirus capsid polypeptides can tolerate harsh environmental conditions such as low pH levels or physiological conditions found in stomach. Such tolerance makes a virion comprising a protoparvovirus capsid polypeptide(s) suitable for transducing cells of gastrointestinal track, including intestinal stem cells. The small intestine epithelium is organized into two fundamental structures: villi and crypts. Villi form functional absorptive units populated by a diverse group of differentiated cells, including enterocytes, goblet, enteroendocrine, tuft, and microfold cells. Each villus is supported by at least six invaginations, or crypts of Lieberkuhn (Clevers 2013, the entire contents of which are hereby incorporated by reference herein). Crypts are occupied mainly by undifferentiated cells, including transit-amplifying cells; however, differentiated enteroendocrine and Paneth cells also reside in crypts. Wedged between Paneth cells are crypt base columnar cells, which maintain homeostasis through both self-renewal and continuous replacement of differentiated cells that are constantly turned-over. Targeting intestinal stem cells with a virion comprising a protoparvovirus variant capsid(s) of the present disclosure, therefore, opens a possibility to prevent or treat different GI related complications including hereditary hemochromatosis, or inflammatory bowel disease. Use of validated genomic safe harbors for targeting a transgene in intestinal stem cells is substantially beneficial for providing a long-term expression and avoiding any differentiation effect that is often associated with random genomic insertion.

In some embodiments, a protoparvovirus is of a species selected from Carnivore protoparvovirus, Carnivore protoparvovirus 1, Chiropteran protoparvovirus 1, Eulipotyphla protoparvovirus 1, Primate protoparvovirus 1, Primate protoparvovirus 2, Primate protoparvovirus 3, Primate protoparvovirus 4, Rodent protoparvovirus 1, Rodent protoparvovirus 2, Rodent protoparvovirus 3, Ungulate protoparvovirus 1, and Ungulate protoparvovirus 2. In some embodiments, the protoparvovirus is selected from canine parvovirus, feline panleukopenia virus, human bufavirus 1, human bufavirus 2, human bufavirus 3, human tusavirus, human cutavirus, Wuharv parvovirus, porcine parvovirus, minute virus of mice, megabat bufavirus, and a genotypic variant thereof.

a. Characteristic Sequence Elements

Among other things, in some embodiments, the present disclosure recognizes that one or more characteristic sequence elements of a protoparvovirus variant VP1 capsid polypeptide surprisingly affects virion internalization into a host cell, relative to a protoparvovirus reference VP1 capsid polypeptide. Among other things, in some embodiments, the present disclosure recognizes that one or more characteristic sequence elements of a protoparvovirus variant VP1 capsid polypeptide surprisingly affects virion transit into a nucleus of a cell, relative to a protoparvovirus reference VP1 capsid polypeptide. Among other things, the present disclosure recognizes that one or more characteristic sequence elements of a protoparvovirus variant VP1 capsid polypeptide surprisingly affects productive virus infection, relative to a protoparvovirus reference VP1 capsid polypeptide.

i. VP1 Sequence Elements

Among other things, the present disclosure recognizes that a protoparvovirus reference VP1 capsid polypeptide comprises at least three characteristic sequence elements within a protoparvovirus VP1 capsid polypeptide (e.g., within a VP1 unique region (VP1u)). In some embodiments, a protoparvovirus reference VP1 capsid polypeptide comprises a VP1 Sequence Element 1, a VP1 Sequence Element 2, a VP1 Sequence Element 3, or any combination thereof. In some embodiments, a characteristic sequence element is a VP1 Sequence Element 1 as described herein. In some embodiments, a characteristic sequence element is a VP1 Sequence Element 2 as described herein. In some embodiments, a characteristic sequence element is a VP1 Sequence Element 3 as described herein.

In some embodiments, a VP1 Sequence Element 1 functions as a nuclear localization signal sequence (NLS). In some embodiments, a VP1 Sequence Element 2 comprises a stretch of one or more amino acids downstream of a NLS. In some embodiments, a VP1 Sequence Element 3 comprises a PLA2 motif. In some embodiments, a VP1 Sequence Element 2 comprises a stretch of one or more amino acids upstream of a VP1 Sequence Element 3. In some embodiments, a VP1 Sequence Element 2 is between a VP1 Sequence Element 1 and a VP1 Sequence Element 3.

In some embodiments, VP1 Sequence Element 1 comprises a stretch of amino acids that function as a nuclear localization signal sequence (NLS). In some embodiments, Sequence Element 1 comprises a basic structure: (K/I) RARRG. In some embodiments, Sequence Element 1 comprises a basic structure: KARG. In some embodiments, Sequence Element 1 comprises one or more of a K residue, an A residue, an R residue, a G residue, or a combination thereof.

In some embodiments, VP1 Sequence Element 2 comprises a stretch of five amino acids downstream of Sequence Element 1. In some embodiments, VP1 Sequence Element 2 comprises a stretch of five amino acids immediately downstream of Sequence Element 1. In some embodiments, VP1 Sequence Element 2 comprises a stretch of more than five amino acids downstream of Sequence Element 1. In some embodiments, VP1 Sequence Element 2 comprises a stretch of more than five amino acids immediately downstream of Sequence Element 1. In some embodiments, Sequence Element 2 comprises a basic structure: LVPPG (SEQ ID NO: 1). In some embodiments, Sequence Element 2 comprises one or more of an L residue, a V residue, a P residue, a G residue, or a combination thereof. In some embodiments, Sequence Element 2 comprises a basic structure: WVPPG (SEQ ID NO: 2). In some embodiments, Sequence Element 2 comprises a basic structure: WVPPGYNFLG (SEQ ID NO: 3). In some embodiments, Sequence Element 2 comprises one or more of a W residue, a V residue, a P residue, a G residue, or a combination thereof.

In some embodiments, VP1 Sequence Element 3 comprises a PLA2 motif. In some embodiments, a PLA2 motif comprises a Ca2+ binding loop. In some embodiments, VP1 Sequence Element 3 is downstream VP1 Sequence Element 2. In some embodiments, VP1 Sequence Element 3 is immediately downstream VP1 Sequence Element 2. In some embodiment, Sequence Element 3 has a basic structure: LGPF. In some embodiments, Sequence Element 2 comprises one or more of an L residue, a G residue, a P residue, or a combination thereof.

ii. NS1 Sequence Elements

Among other things, the present disclosure recognizes that members of the genus protoparvovirus encode NS1 proteins that are generally greater than 30% identical to each other at the amino acid sequence level as determined by pairwise sequence alignments (Cotmore S. F., et al. Nov. 9, 2013). Among other things, a member of a genus protoparvovirus encodes an NS1 protein that has greater than 30% identity to an exemplary NS1 amino acid sequence according to SEQ ID NO: 4.

```
Exemplary Canine Parvovirus (CPV) NS1 Amino Acid
Sequence
                                        (SEQ ID NO: 4)
MSGNQYTEEVMEGVNWLKKHAENEAFSFVFKCDNVQLNGKDVRWNNYTK

PIQNEELTSLIRGAQTAMDQTEEEEMDWESEVDSLAKKQVQTFDALIKK

CLFEVFVSKNIEPNECVWFIQHEWGKDQGWHCHVLLHSKNLQQATGKWL

RRQMNMYWSRWLVTLCSVNLTPTEKIKLREIAEDSEWVTILTYRHKQTK

KDYVKMVHFGNMIAYYFLTKKKIVHMTKESGYFLSTDSGWKFNFMKYQD

RQIVSTLYTEQMKPETVETTVTTAQETKRGRIQTKKEVSIKCTLRDLVS

KRVTSPEDWMMLQPDSYIEMMAQPGGENLLKNTLEICTLTLARTKTAFE

LILEKADNTKLTNFDLANSRTCQIFRMHGWNWIKVCHAIACVLNRQGGK

RNTVLFHGPASTGKSIIAQAIAQAVGNVGCYNAANVNFPFNDCTNKNLI

WIEEAGNFGQQVNQFKAICSGQTIRIDQKGKGSKQIEPTPVIMTTNENI

TIVRIGCEERPEHTQPIRDRMLNIKLVCKLPGDFGLVDKEEWPLICAWL

VKHGFVSTMANYTHHWGKVPEWDENWAEPKIQEGINSPGCKDLKTQAAS

NPQSQDQVLTPLTPDVVDLALEPWSTPDTPIAETANQQSNQLGVTHKDV

QASPTWSEIEADLRAIFTSEQLEEDFRDDLD
```

Among other things, the present disclosure recognizes that members of a species within genus protoparvovirus can be characterized by encoding an NS1 protein that shares at least 85% identity with a NS1 protein encoded by other members of the species (Cotmore S. F., et al. Nov. 9, 2013, the entire contents of which are hereby incorporated by reference herein). Among other things, the present disclosure recognizes that members of genus protoparvovirus are monophyletic.

The present disclosure also recognizes that genomes of founder protoparvoviruses are distinctive because they contain many reiterations of a tetranucleotide sequence 5'-TGGT-3' (or its complement 5'-ACCA-3'), which is a modular binding motif of the NS1 duplex DNA recognition site, generally depicted as $(TGGT)_{2-3}$ (Cotmore et al., 1995, the entire contents of which are hereby incorporated by reference herein). Minute virus of mice NS1 recognizes variably spaced, tandem and inverted, clusters of TGGT motif, allowing it to bind to a wide variety of sequences distributed throughout replicative-form viral DNA. TGGT/ACCA tetranucleotide clusters are also dispersed throughout genomes of new viruses, suggesting significant biological similarities with founder members. For example, in a 4822 nt sequence of bufavirus 1a (human) (JX027296) there are 95 copies of ACCA or TGGT, while in a 4452 nt sequence of a melanoma-associated human cutavirus (KX685945) there are 105 separate copies.

b. Virions

Among other things, the present disclosure describes a virion comprising a protoparvovirus variant VP1 capsid polypeptide comprising at least one sequence variation relative to a protoparvovirus reference VP1 capsid polypeptide. In some embodiments, a virion comprises a protoparvovirus variant VP1 capsid polypeptide and a heterologous nucleic acid sequence.

X-ray reconstructions indicate that first ordered VP residues in protoparvovirus capsid polypeptides are located inside a particle at a base of the 5-fold pore, leaving unresolved VP1 and VP2 N-termini of ~180 and 37 residues, respectively (Halder et al., 2013, Agbandje-McKenna et al., 1998, Xie and Chapman 1996, the contents of which are hereby incorporated by reference herein in its entirety). A C-terminal region of this unresolved sequence forms a slender glycine-rich chain, present in both VP1 and VP2, which in minute virus of mice (MVM) variant VLPs can be modeled into claw-like densities positioned inside the capsid below the 5-fold channels in some cryoEM reconstructions (Subramanian et al., 2017, the entire contents of which are hereby incorporated by reference herein). However, in X-ray structures of MVM virions, but not empty particles, a first 10 amino acids from a single copy of this sequence (VP2 G37-G28) can be modeled into submolar density that occupies a central pore of most 5-fold cylinders. Although all VP1 and VP2 N-terminal peptides are sequestered in empty particles, a subset of MVM VP2 N-termini become exposed at a virion surface early during genome encapsidation (Cotmore and Tattersall 2005, the entire contents of which are hereby incorporated by reference herein), presumably via a poorly understood conformational shift that involves expansion of the 5-fold cylinders. These externalized VP2 N-termini contain a nuclear export signal (Maroto et al., 2004, the entire contents of which are hereby incorporated by reference herein) that in some cells effectively converts a trafficking-neutral capsid into a nuclear export-competent particle. Virions are released from infected cells in this form (Cotmore and Tattersall 2005, the entire contents of which are hereby incorporated by reference herein), but both in an extracellular environment and during cell entry, exposed N-termini undergo proteolytic cleavage, which removes ~25 amino acids and converts VP2 to a form called VP3. Because X-ray structures show slightly less than one polyglycine tract threaded through each cylinder, it is significant that ~90% of the ~50 MVM VP2 termini eventually become surface exposed and cleaved. X-ray structures of cleaved, predominantly VP3, virions indicate that this proteolysis allows the polyglycine tract of cleaved proteins to be retracted into the capsid interior, where it folds back and assumes additional icosahedral ordering extending to residue G30, while being replaced in cylinders by a new cluster of VP2 N-termini (Govindasamy L, Gurda B L, Halder S, Van Vliet K, McKenna R, Cotmore S F, Tattersall P, Agbandje-McKenna M. 2010, unpublished observations). Externalized VP2 N-termini also serve an important structural role, stabilizing the cylinders prior to cell entry and preventing premature exposure of VP1 N-termini and ultimately the genome (Cotmore and Tattersall 2012). Thus, in members of genus Protoparvovirus, 5-fold cylinders serve as portals for three different forms of cargo, mediating 1) genome translocation into and out of an intact particle, 2) VP1SR extrusion prior to bilayer transit, and 3) early externalization of some VP2 N-termini concomitant with genome encapsidation. This is in sharp contrast to viruses in many other parvovirus genera, which rely on just one or two of these portal functions.

A second distinctive feature of protoparvovirus virions is that in X-ray structures not only is a capsid icosahedrally ordered, but so is ~11-34% of the single-stranded DNA genome, forming patches in each asymmetric unit that are positioned below a cavity on an interior capsid surface. This ordered DNA comprises 2-3 short (8-11 nt) single-strands, which adopt an inverted-loop configuration with phosphates chelated in interior by two Mg++ ions while bases point outwards towards a capsid shell where they establish non-covalent interactions with specific amino acid side chains (Halder et al., 2013, Agbandje-McKenna et al., 1998, Chapman and Rossmann 1995, the contents of which are hereby incorporated by reference herein in its entirety). For example, atomic force microscopy has been used to probe rigidity of individual MVM particles along their 5-fold, 3-fold and 2-fold symmetry axes, which showed that in empty particles, but not in DNA-containing virions, two-fold axes can be easily distorted by nanoindentation, suggesting that a genome has a major influence on capsid rigidity of this region (Carrasco et al., 2006, the entire contents of which are hereby incorporated by reference herein). Single alanine mutations that did not compromise intracapsid interactions but did disrupt major interactions between a capsid and bound DNA patches, had no effect on empty particles but abrogated a genome-enhanced 2-fold rigidity seen in full particles, indicating that it derives predominantly from these ordered DNA: capsid interactions (Carrasco et al., 2008, the entire contents of which are hereby incorporated by reference herein). This perhaps indicates an importance of a full-length, 5 kb genome in establishing wild-type capsid dynamics, as also suggested by in vitro uncoating studies (Cotmore et al., 2010, the entire contents of which are hereby incorporated by reference herein).

c. Genome Organization and Replication

Protoparvoviruses have heterotelomeric genomes of around 5 kb, flanked by hairpin telomeres of ~120 nt at their left-end, generally in a single sequence orientation, while a right-end hairpin is ~250 nt and can be present as either of two inverted-complementary sequences dubbed "flip" and "flop." Right-end of protoparvovirus genomes can be excised from replication intermediates in a hairpin configuration by hairpin transfer, which in MVM involves binding of NS1 complexes to two separate clusters of $(TGGT)_{2-3}$ binding sites, one that positions NS1 over a cleavage site (5'-CTATCA-3') and a second that is ~120 bp away, at a hairpin axis. For cleavage to occur, NS1 complexes at these two sites must be coordinated, and a origin refolded, by recruiting DNA bending proteins from a host HMGB family, which bind to NS1 and create an essential ~30 bp double-helical loop in the intervening G-rich origin DNA (Cotmore et al., 2000, the entire contents of which are hereby incorporated by reference herein).

In contrast, origin sequences generated from a left end of this virus are not cleaved in a hairpin configuration because there is a critical TC/GAA mismatch in a hairpin stem. To create an active origin, a left hairpin must be unfolded and copied to form a base-paired junction region that spans adjacent genomes in dimer RF, in which two arms of a hairpin are effectively segregated on either side of a symmetry axis. However, only a TC arm gives rise to an active origin because a dinucleotide serves as a spacer element that is positioned between a NS1 binding site and a binding site for an essential co-factor, called parvovirus initiation factor (PIF, also known as glucocorticoid modulatory element binding protein GMEB). PIF is a heterodimeric host complex that binds to two spaced 5'-ACGT-3' half sites positioned near an axis of a DNA palindrome. In an active origin, PIF is able to interact with NS1 across a TC dinucleotide, stabilizing its binding to a relatively weak NS1 binding site, but it cannot stabilize NS1 binding to an identical binding site across a GAA trinucleotide in an inactive (GAA) arm (Christensen et al., 2001, the entire contents of which are hereby incorporated by reference herein). In consequence, sequences in the hairpin configuration or perfectly-duplex hairpin arms carrying a GAA sequence are not cleaved, making them potentially available for alternative roles such as driving transcription from an adjacent P4 promoter (Gu et al., 1995, the entire contents of which are hereby incorporated by reference herein). Due to major disparities in cleavage efficiency between a left- and right-end origins, progeny negative-sense single-strands are preferentially displaced from a right end of a genome, with the result that protoparvoviruses typically displace and package predominantly (~99%) negative-sense progeny ssDNA.

Viruses in this genus use two transcriptional promoters at map units (mu) 4 and 38, and a single polyadenylation site corresponding to mu 95, to create 3 major size classes of mRNAs, all of which have a short intron sequence between 46-48 mu removed (Pintel et al., 1983, the entire contents of which are hereby incorporated by reference herein). In MVM this splice has alternative donors (D1 and D2) and acceptors (A1 and A2) of different strengths, which are positioned within a region of 120 nt so that a potential D2:A1 splice is eliminated by minimal intron size constraints. Splicing therefore creates 3 forms of each mRNA size class that are expressed with different stoichiometry (Haut and Pintel 1999, the entire contents of which are hereby incorporated by reference herein). Transcripts arising from P4 that have just this central intron removed encode a single form of NS1, translation of which terminates upstream of D1. In some P4 transcripts however, a second, long intron between 10-40 mu is also excised, creating mRNAs that encode NS2 proteins of ~25 kDa. These share 85 amino acids of N-terminal sequence with NS1, but are then spliced into a different reading frame and finally reach a short central intron where 2 disparate C-terminal hexapeptides can be added. This generates variants called NS2P and NS2Y that are expressed in a ~5:1 ratio. P38 transcription is strongly transactivated by the C-terminal domain of NS1, mediated by NS1 binding to upstream 5'-TGGT-3' repeat sequences (Christensen et al., 1995, Lorson et al., 1996, the contents of which are hereby incorporated by reference herein in its entirety). Alternative splicing at a short intron also causes two size variants of a capsid polypeptide to be expressed with ~1:5 stoichiometry, with VP1 (~83 kDa) initiating at an ATG codon positioned between the two acceptor sites while VP2 (~64 kDa) initiates downstream of the splice.

During infection, newly synthesized capsid polypeptides assemble as two types of trimers (VP2-only and 1×VP1+2×VP2) in the cytoplasm, and are transported into the nucleus for capsid-assembly using a non-conventional, structure-dependent trafficking motif (Lombardo et al., 2000). However, this translocation is restricted to S-phase (Gil-Ranedo et al., 2015, the contents of which are hereby incorporated by reference herein in its entirety), and is dependent upon trimer phosphorylation by the cellular Raf-1 kinase (Riolobos et al., 2010, the contents of which are hereby incorporated by reference herein in its entirety).

Ancillary polypeptides encoded by protoparvoviruses include the NS2 variants, which appear to have multiple functions that are mostly mediated by interactions with host proteins, and a small alternatively translated (SAT) protein (Zádori et al., 2005, the contents of which are hereby incorporated by reference herein in its entirety). MVM NS2 is not essential in transformed human cell lines, but its absence in murine cells leads to rapid cessation of duplex DNA amplification early in the infectious cycle by an unknown mechanism (Naeger et al., 1990, Ruiz et al., 2006, the contents of which are hereby incorporated by reference herein in its entirety). This early defect can be abrogated by relatively low levels of NS2 expression, but much higher levels of NS2 are required later in a cycle to enable efficient capsid assembly (Cotmore et al., 1997, the contents of which are hereby incorporated by reference herein in its entirety), which is a pre-requisite for the subsequent accumulation of progeny DNA single-strands, and for virion release. In a late capsid defect, VP polypeptides are expressed, but most fail to assemble into capsid polypeptides and are rapidly degraded, perhaps reflecting inadequacies in nuclear translocation of precursor subunits linked to a severe dislocation in normal nuclear/cytoplasmic protein trafficking, as discussed below. During MVM infection NS2 associates with proteins from a cellular 14-3-3 family (Brockhaus et al., 1996, the contents of which are hereby incorporated by reference herein in its entirety) and with the nuclear export factor CRM1 (Bodendorf et al., 1999, the contents of which are hereby incorporated by reference herein in its entirety). Significantly, a NS2 nuclear export signal (NES) engages CRM1 with "supraphysiological" affinity, which is independent of presence of RanGTP and thus can potentially resist cytoplasmic release (Engelsma et al., 2008, the contents of which are hereby incorporated by reference herein in its entirety). During wildtype MVM infection CRM1 can be detected in perinuclear cytoplasm, but this redistribution is exacerbated in infections with mutant viruses that carry point mutations close to the NS2 NES that cause CRM1 to bind at even higher affinity (López-Bueno et al., 2004, the contents of which are hereby incorporated by reference herein in its entirety). These mutations also accelerate onset of a late step in infection, which is characterized by a cytoplasmic accumulation of large, typically nuclear structures including NS1 and empty capsid polypeptides, again suggesting major disruptions in normal nuclear/cytoplasmic trafficking pathways. Following transfection into A9 fibroblasts, wildtype MVMi genomes express low levels of NS2, but when genomes were engineered to express one of a NS2-NES mutations, resulting low levels of mutant NS2 were able to drive wildtype levels of virus progeny accumulation, confirming that cumulative late infection blocks seen in cells expressing insufficient NS2 result from a stoichiometric limitation of NS2: CRM1 interactions (Choi et al., 2005, the contents of which are hereby incorporated by reference herein in its entirety). Studies with mutant viruses in which NS2: CRM1 binding was impaired, rather than enhanced, similarly indicate that during infection this interaction is required for the efficient release of virions (Eichwald et al., 2002, Miller and Pintel 2002, the contents of which are hereby incorporated by reference herein in its entirety).

A second protoparvovirus ancillary polypeptide, SAT, is encoded within a capsid gene and is expressed late, from the same mRNA as VP2. SAT accumulates in endoplasmic reticulum (ER) of a infected cell (Zádori et al., 2005, the contents of which are hereby incorporated by reference herein in its entirety). Like NS2, it enhances the rate at which virus spreads through cultures but it acts via a different mechanism that involves induction of irreversible ER-stress and is linked to enhanced cell necrosis (Mészáros et al., 2017b, the contents of which are hereby incorporated by reference herein in its entirety). Although both SAT and a dependoparvovirus ancillary polypeptide, AAP, occupy similar positions in a capsid gene and contain essential N-terminal hydrophobic domains, these polypeptides are not known to exhibit functional homology. Thus, in protoparvoviruses early virion export is a distinctive feature that can be driven by multiple mechanisms, either occurring prior to cell lysis and mediated by VP2 signals or Crm1 interactions that vary with cell type, or linked to enhanced cell necrosis and driven by SAT. During export, some virions can be internalized in COPII vesicles in a endoplasmic reticulum and undergo gelsolin-dependent trafficking to a Golgi, where they undergo tyrosine phosphorylation, and perhaps by other modifications that enhance their subsequent particle-to-infectivity ratios (Bär et al., 2008, Bär et al., 2013, the contents of which are hereby incorporated by reference herein in its entirety). Release at early times in a cycle allows infection to spread rapidly, potentially enhancing overall progeny production from infected tissues and prior to accumulation of neutralizing antibodies.

d. Exemplary Protoparvovirus

Among other things, the present disclosure provides exemplary protoparvovirus that can be used in accordance with embodiments described herein.

Exemplary Protoparvovirus species include human bufavirus genotypes 1, 2 and 3, human tusavirus, human cutavirus, canine parvovirus, porcine parvovirus, minute virus of mice and megabat bufavirus (see also Table 1 for nomenclature designated by International Committee on Taxonomy of Viruses (ICTV); world wide web at talk.ictvonline.org/taxonomy/, the entire contents of which are hereby incorporated by reference herein).

i. Kilham Rat Virus (KRV) and Minute Virus of Mice (MVM)

Kilham rat virus (KRV), one of the original viruses used to establish family Parvoviridae, was isolated in 1959 from lysates of an experimental rat tumor (Kilham and Olivier 1959, the contents of which are hereby incorporated by reference herein in its entirety). Over the next decade, a succession of similar single-stranded DNA viruses were discovered in transplantable tumors, tissue culture cell lines, or laboratory stocks of other viruses. Some of these, such as MVM, closely resemble viruses now known to infect wild rodents, while other members of the same species (Rodent protoparvovirus 1), such as LuIII (M81888), appear to be distant recombinants of viruses found in nature. Studied extensively in the intervening years, these viruses have served as important model systems for defining the basic characteristics and underlying biology of the family. In rodents, viruses from species Rodent protoparvovirus 1 exhibit a range of pathologies, from asymptomatic viremia to teratogenesis and fetal or neonatal cell death. While these viruses fail to infect normal human cells, host restrictions are often relaxed when human cells undergo oncogenic transformation, allowing viruses to become preferentially oncolytic, and suggesting their potential for use in clinical cancer virotherapy. To this end, Phase I/IIa clinical trials were recently completed using virus H-1 (X01457) to target advanced glioblastoma, which provided evidence that a virus was well tolerated and could partially disrupt the local immune suppression commonly associated with cancer (Geletneky et al., 2017, Angelova et al., 2017, the contents of which are hereby incorporated by reference herein in its entirety).

In some cells parvovirus infection results in delayed but significant type 1 IFN release, whereas pretreatment with exogenous IFN-beta strongly inhibits the viral life cycle (Grekova et al., 2010, Mattei et al., 2013, the contents of which are hereby incorporated by reference herein in its entirety). During MVMp infection of mouse embryonic fibroblasts (MEFs) the IFN response did not involve mitochondrial antiviral signaling protein (MAVS) and RIG-I sensing and did not conspicuously inhibit viral DNA replication (Mattei et al., 2013), although pretreatment of cells with IFN-beta-neutralizing antibody did enhance infection in another study (Grekova et al., 2010, the contents of which are hereby incorporated by reference herein in its entirety). However, infected MEFs become unresponsive to Poly (I:C) stimulation, suggesting that a virus is able to inactivate antiviral immune mechanisms elicited by type I IFNs.

ii. Feline Panleukopenia Virus (FPV)

Feline panleukopenia virus (FPV) is also known as feline parvovirus, and is closely related to mink and raccoon parvoviruses, which have existed for over 100 years, and canine parvovirus (CPV), which arose as a variant in the mid-1970s and in 1978 spread worldwide, causing a disease pandemic among dogs, wolves and coyotes. These variants all belong to a single species, Carnivore protoparvovirus 1. In adult animals, viruses in this species predominantly infect lymphoid tissues, leading to leukopenia or lymphopenia, and intestinal epithelia, resulting in severe diarrhea, dehydration and fever. In contrast, infection of neonates is characterized by cerebellar lesions in kittens or ferrets, potentially leading to ataxia, or by myocarditis in puppies. Disease is well controlled by vaccination, but mortality in affected litters varies between 20 and 100 percent (reviewed in (Kailasan et al., 2015a, the contents of which are hereby incorporated by reference herein in its entirety)).

iii. Porcine Parvovirus (PPV)

Porcine parvovirus (PPV), a member of the species Ungulate protoparvovirus 1, is a major cause of fetal death and infertility in pigs worldwide, although PPV infection alone rarely causes disease in non-pregnant pigs or piglets. However, when seronegative pregnant sows are exposed to a virulent PPV strain during first 70 days of gestation, transplacental infection can lead to a syndrome called SMEDI (stillbirths, mummification, embryonic death, and infertility) (Mészáros et al., 2017a, the contents of which are hereby incorporated by reference herein in its entirety). Weakly pathogenic and vaccine strains of PPV exist (e.g., NADL-2), which are lethal if injected into amniotic fluid but they do not cross a placental barrier as efficiently as pathogenic strains (e.g., Kresse), so disease is rare. Widespread vaccination programs are in place to prevent SMEDI, but some newly emerging virulent PPV variants cannot be neutralized by antibodies raised by exposure to current vaccine strains (Mészáros et al., 2017a, the contents of which are hereby incorporated by reference herein in its entirety). Co-infection with PPV can also potentiate the effect of porcine circovirus type 2 (PCV-2, Porcine circovirus 2, family Circoviridae) in the development of post-weaning multisystemic wasting syndrome (PMWS).

iv. Bufavirus (BuV)

Most newly discovered viruses segregate to species in a new branch of the Protoparvovirus tree, established for bufavirus 1a (human). Two genotypes of this virus, BuV1 and BuV2, were identified in 2012 in viral metagenomic analysis of fecal samples from diarrheic children in Burkina Faso and Tunisia (hence the name "bufavirus") (Phan et al., 2012, the contents of which are hereby incorporated by reference herein in its entirety), while a third genotype, BuV3, was later discovered in the diarrheal feces of Bhutanese children (Yahiro et al., 2014, the contents of which are hereby incorporated by reference herein in its entirety). To date, BuV DNA has been detected in diarrhea of children from Burkina Faso, Tunisia, Bhutan, Thailand, Turkey, China, and Finland, and of adults from Finland, the Netherlands, Thailand, and China, but has not been found in non-diarrheal feces, suggesting a causal relationship (Väisänen et al., 2017, the contents of which are hereby incorporated by reference herein in its entirety). When analyzed for the presence of anti-BuV1 capsid IgG, the seroprevalences of adults from Finland and the USA were low (~2-4%), but much higher rates were found for adults in Iraq (~85%), Iran (~56%) and Kenya (~72%) (Väisänen et al., 2018, the contents of which are hereby incorporated by reference herein in its entirety).

v. Cutavirus (CuV)

A second human protoparvovirus in a bufavirus branch, called cutavirus (CuV), was detected in a small number of diarrheal samples from Brazilian and Botswanan children, and in four French skin biopsies of cutaneous T-cell lymphomas, from which the virus derives its name (Phan et al., 2016, the contents of which are hereby incorporated by reference herein in its entirety), and in malignant skin lesions from a Danish melanoma patient (Mollerup et al., 2017). Etiological significance of CuV in human disease has yet to be determined.

Prevalence rates for IgG against CuV were evenly low (0-~ 6%) in the same sample series mentioned above for bufavirus, confirming that CuV is widely distributed through human populations (Väisänen et al., 2018, the contents of which are hereby incorporated by reference herein in its entirety). In contrast, IgG directed against a third new, as yet unclassified protoparvovirus that was detected in a Tunisian human fecal sample (hence tusavirus, TuV) (Phan et al., 2014) was not present in the same panels of sera, and its DNA has yet to be detected in other fecal samples (Väisänen et al., 2017, Väisänen et al., 2018, the contents of which are hereby incorporated by reference herein in its entirety), so evidence for TuV being a human virus is thus, so far, insufficient. It segregates phylogenetically with viruses occupying the original branch of the protoparvovirus phylogenetic tree, discussed previously.

vi. Canine Parvovirus (CPV)

Canine parvovirus (CPV) is a well-studied species of protoparvovirus. CPV infects wild and domestic dogs. CPV has a genome size of ~5.3 kb, 600 bp larger than AAV. The large genome makes CPV particularly attractive for the transfer of genes in human cells that cannot be accommodated in AAV derived vectors. Because CPV does not normally infect humans, there is no humoral immunity pre-existing against CPV in human population, i.e., humans are seronegative for CPV capsid antigens. This is in stark contrast to AAV; humans are seropositive for AAV capsid antigen such that presence of neutralizing AAV antibodies excludes a large percentage of patients eligible for AAV gene therapy. Therefore, a lack of neutralizing antibodies against CPV antigen in humans makes the CPV viral particles, or a virion comprising a capsid polypeptide of CPV or a variant thereof, particularly useful for highly potent gene therapy applications to prevent or treat different human genetic diseases that cannot be treated efficiently with AAV-derived vectors. Without wishing to be bound to any theory, CPV uses a canine transferrin receptor (TfR or CD71) as a cellular receptor to enter the cell, a protein expressed in the external membrane of a canine host cells (Goodman, Lyi et al. 2010). CPV also can interact with a human TfR counterpart and therefore internalize and transduce human cells. In addition, as described above, a VP2 capsid polypeptide of CPV can be engineered to comprise at least one sequence variation that alter tropism and the specificity/affinity of target cell interaction and eventually the efficiency of target cell transduction.

TABLE 1

Exemplary Isolates of Protoparvovirus

| | |
|---|---|
| Species of Protoparvovirus | Carnivore protoparvovirus<br>Carnivore protoparvovirus 1<br>Chiropteran protoparvovirus 1<br>Eulipotyphla protoparvovirus 1<br>Primate protoparvovirus 1<br>Primate protoparvovirus 2<br>Primate protoparvovirus 3<br>Primate protoparvovirus 4<br>Rodent protoparvovirus 1<br>Rodent protoparvovirus 2<br>Rodent protoparvovirus 3<br>Ungulate protoparvovirus 1<br>Ungulate protoparvovirus 2 |

| Exemplary Viruses | Accession No. | Ref Seq No. |
|---|---|---|
| Sea otter parvovirus | KU561552 | NC_030837 |
| Canine parvovirus | M19296 | NC_001539 |
| Megabat bufavirus 1 | LC085675 | NC_029797 |
| Mpulungu (shrew) bufavirus | AB937988 | NC_026815 |
| Bufavirus 1a (human) | JX027296 | NC_038544 |
| Wuharv (rhesus) parvovirus 1 | JX627576 | NC_039049 |
| Cutavirus (human); Human Cutavirus 1 | KT868811 | NC_039050 |
| Tusavirus; Human tusavirus | KJ495710 | — |
| Minute virus of mice | J02275 | NC_001510 |
| Rat parvovirus 1 | AF036710 | NC_038545 |
| Rat bufavirus SY-2015 | KT716186 | NC_028650 |
| Porcine parvovirus; Porcine parvovirus 5 | L23427 | NC_001718 |
| Porcine bufavirus; Protoparvovirus (porcine) | KT965075 | NC_043446 |
| Porcine parvovirus 2 | — | NC_025965 |
| Porcine parvovirus 6 | — | NC_023860 |
| Feline panleukopeniavirus | FJ231389; KP769859 | — |
| Human bufavirus 1 | JQ918261 | — |
| Human bufavirus 2 | JX027297 | — |
| Human bufavirus 3 | AB847989 | — |

e. Genotypic Variants of Viruses

An ordinarily skilled artisan appreciates that a species of virus comprises clusters of genetic variants (Van Regenmortel MHV (2000) Virus Taxonomy-Seventh Report of the International Committee on Taxonomy of Viruses). Genetic variants may comprise mutations (that encompasses point mutations and insertions-deletions of different lengths), hypermutations, several types of recombination, and genome segment reassortments. Mutation is observed in all viruses, with no known exceptions (Domingo (2019) Virus as Populations 2020:35-71). Recombination is also widespread, and its occurrence was soon accepted for DNA viruses as well as RNA viruses. Genome segment reassortment, a type of variation close to chromosomal exchanges in sexual reproduction, is an adaptive asset of segmented viral genomes, as continuously evidenced by the ongoing evolution of the influenza viruses. Three modes of virus genome variation are compatible, and reassortant-recombinant-mutant genomes are continuously arising in present-day viruses.

Accordingly, a genetic variant of viruses described herein may comprise a polypeptide described herein or those belonging to a virus or virion described herein (e.g., a capsid polypeptide (e.g., VP1 capsid polypeptide, VP2 capsid polypeptide, or variant thereof), NS1 polypeptide, etc.) with a polypeptide sequence that is at least, about, or no more than 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to a polypeptide sequence of the exemplary sequences presented herein or a polypeptide sequence of the polypeptide of exemplary viruses referenced herein.

f. Marker and/or Reporter Genes

Exemplary marker genes include but not limited to any of fluorescent reporter genes, e.g., GFP, RFP and the like, as well as bioluminescence reporter genes. Exemplary marker genes include, but are not limited to, glutathione-S-transferase (GST), horseradish peroxidase (HRP), chloramphenicol acetyltransferase (CAT) beta-galactosidase, beta-glucuronidase, luciferase, green fluorescent proteins (e.g., GFP, GFP-2, tagGFP, turboGFP, sfGFP, EGFP, Emerald, Azami Green, Monomeric Azami Green, CopGFP, AceGFP, ZsGreenl), HcRed, DsRed, cyan fluo-rescent protein (CFP), yellow fluorescent proteins (e.g., YFP, EYFP, Citrine, Venus YPet, PhiYFP, ZsYellowl), cyan fluorescent proteins (e.g., ECFP, Cerulean, CyPet AmCyanl, Midoriishi-Cyan) red fluorescent proteins (e.g., mKate, mKate2, mPlum, DsRed monomer, mCherry, mRFPI, DsRed-Express, DsRed2, HcRed-Tandem, HcRed 1, AsRed2, eqFP6l 1, mRaspberry, mStrawberry, Jred), orange fluorescent proteins (e.g., mOrange, mKO, Kusabira-Orange, monomeric Kusabira-Orange, mTangerine, tdTomato) and autofluorescent proteins including blue fluorescent protein (BFP).

Marker genes may also include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where a marker sequence is the LacZ gene, a presence of a construct carrying a signal is detected by assays for β-galactosidase activity. In some embodiments, where a marker gene is green fluorescent protein or luciferase, a construct carrying a signal may be measured colorimetrically based on visible light absorbance or light production in a luminometer, respectively. Such reporters can, for example, be useful in verifying tissue-specific targeting capabilities and tissue specific promoter regulatory activity(ies) of a nucleic acid.

Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate cellular metabolism resulting in enhanced cell growth rates and/or gene amplification (e.g., dihydrofolate reductase).

2. Compositions

Among other things, the present disclosure provides compositions. In some embodiments, a composition comprises a construct as described herein. In some embodiments, a composition comprises one or more constructs as described herein. In some embodiments, a composition comprises a plurality of constructs as described herein. In some embodiments, when more than one construct is included in the composition, the constructs are different from one another.

In some embodiments, a composition comprises a polynucleotide encoding a protoparvovirus variant VP1 capsid polypeptide. In some embodiments, a composition comprises a polynucleotide encoding a protoparvovirus VP2 capsid polypeptide.

In some embodiments, a composition comprises a virion as described herein. In some embodiments, a composition comprises one or more virions as described herein. In some embodiments, a composition comprises a plurality of virions. In some embodiments, when more than one type of virion is included in a composition, the more than one type of virions are each different types of virions.

In some embodiments, a composition comprises a cell. In some embodiments, a composition comprises a host cell. In some embodiments, a composition comprises an insect cell. In some embodiments, a composition comprises a mammalian cell. In some embodiments, a composition comprises a target cell.

In some embodiments, a composition is or comprises a pharmaceutical composition.

Among other things, in some embodiments, the present disclosure provides at least one sequence modification to a protoparvovirus VP1 capsid polypeptide that alters affinity and/or specificity of a virion to a cellular receptor involved in internalization of a virion, optionally wherein a cellular receptor is a transferrin receptor. In some embodiments, the at least one sequence modification of a protoparvovirus VP1 capsid polypeptide comprise: (a) at least one sequence variation that reduces toxicity of the virion in a host cell; (b) at least one sequence variation that increases virion production and/or virion production in a host cell; (c) at least one sequence variation that increases capsid polypeptide yield; or (d) any combination thereof.

In some embodiments, further provided herein is a virion comprising a protoparvovirus variant VP1 capsid polypeptide comprising a heterologous peptide tag. In some embodiments, a heterologous peptide tag allows affinity purification using an antibody, an antigen-binding fragment of an antibody, or a nanobody. In some embodiments, a heterologous peptide tag comprises an epitope/tag selected from hemagglutinin, His (e.g., 6X-His), FLAG, E-tag, TK15, Strep-tag II, AU1, AU5, Myc, Glu-Glu, KT3, and IRS.

Among other things, the present disclosure provides polynucleotides, e.g., polynucleotides comprising a VP1 capsid coding sequence operably linked to an expression control sequence, wherein the VP1 capsid coding sequence encodes a protoparvovirus variant VP1 capsid polypeptide. The present disclosure also provides methods utilizing such polynucleotides, e.g., in a composition (e.g., a pharmaceutical composition).

In some embodiments, a polynucleotide of the present disclosure may be or comprise DNA or RNA. In some embodiments, DNA can be genomic DNA or cDNA. In some embodiments, RNA can be an mRNA, an miRNA, a shRNA/siRNA, a gRNA, etc.

In some embodiments, a gene product is expressed from a polynucleotide comprising a VP1 capsid coding sequence operably linked to an expression control sequence, wherein the coding sequence encodes a protoparvovirus variant VP1 capsid polypeptide. In some embodiments, expression of such a polynucleotide can utilize one or more control elements (e.g., promoters, enhancers, splice sites, polyadenylation sites, translation initiation sites, etc.). Thus, in some embodiments, a polynucleotide provided herein can comprise one or more control elements.

In some embodiments, a VP1 gene is a protoparvovirus VP1 gene. In some embodiments, a protoparvovirus VP1 gene is a bufavirus VP1 gene as described herein. In some embodiments, a protoparvovirus VP1 gene is a canine parvovirus VP1 gene as described herein. In some embodiments, a protoparvovirus VP1 gene is a cutavirus VP1 gene as described herein. In some embodiments, a protoparvovirus VP1 gene is a feline panleukopenia VP1 gene as described herein. In some embodiments, a protoparvovirus VP1 gene is a minute virus of mice VP1 gene as described herein. In some embodiments, a protoparvovirus VP1 gene is a tusavirus VP1 gene described herein.

In some embodiments, a protoparvovirus VP1 capsid polypeptide is a bufavirus VP1 gene described herein. In some embodiments, a protoparvovirus VP1 capsid polypeptide is a canine parvovirus VP1 capsid polypeptide as described herein. In some embodiments, a protoparvovirus VP1 capsid polypeptide is a cutavirus VP1 capsid polypeptide as described herein. In some embodiments, a protoparvovirus VP1 capsid polypeptide is a feline panleukopenia VP1 capsid polypeptide as described herein. In some embodiments, a protoparvovirus VP1 capsid polypeptide is a minute virus of mice VP1 capsid polypeptide as described herein. In some embodiments, a protoparvovirus VP1 capsid polypeptide is a tusavirus VP1 capsid polypeptide as described herein.

Among other things, in some embodiments, the present disclosure describes exemplary constructs that have been engineered (e.g., see Exemplary Variant VP1 Capsid Sequences, see also, e.g., Table 4) to improve protoparvovirus VP1 capsid polypeptide production of a protoparvovirus VP1 capsid polypeptide in a host cell. Among other things, in some embodiments, the present disclosure describes exemplary constructs that have been engineered (e.g., see Exemplary Variant VP1 Capsid Sequences, see also, e.g., Table 4) to reduce toxicity of protoparvovirus VP1 capsid polypeptide in a host cell.

One skilled in the art would appreciate that a change (e.g., substitution, addition, deletion, etc.) of amino acids that are not conserved between a same polypeptide from different species is less likely to have an effect on the function of a protein and therefore, these amino acids should be selected for mutation. Amino acids that are conserved between a same polypeptide from different species should not be changed (e.g., deleted, added, substituted, etc.), as these mutations are more likely to result in a change in function of a polypeptide.

In some embodiments, a polynucleotide in accordance with the present disclosure comprises a protoparvovirus variant VP1 capsid polypeptide that is at least 85%, at least 90%, at least 95%, at least 98%, or at least 99% identical to a sequence of SEQ ID NOs: 103-110.

In some embodiments, a polypeptide provided herein comprises post-translational modifications. In some embodiments, a protoparvovirus variant VP1 capsid polypeptide provided herein comprises post-translational modifications. In some embodiments, post-translational modifications can comprise but is not limited to glycosylation (e.g., N-linked glycosylation, O-linked glycosylation), phosphorylation, acetylation, amidation, hydroxylation, methylation, ubiquitylation, sulfation, and/or a combination thereof.

a. Constructs

Among other things, the present disclosure provides that some polynucleotides as described herein are polynucleotide constructs. Polynucleotide constructs according to the present disclosure include all those known in the art, including cosmids, plasmids (e.g., naked or contained in liposomes) and constructs (e.g., protoparvovirus-related constructs) that incorporate a polynucleotide comprising a VP1 capsid coding sequence operably linked to an expression control sequence, wherein the VP1 capsid coding sequence encodes a protoparvovirus variant VP1 capsid polypeptide. Those of skill in the art will be capable of selecting suitable constructs, as well as cells, for making any of a nucleic acids described herein. In some embodiments, a construct is a plasmid (i.e., a circular DNA molecule that can autonomously replicate inside a cell). In some embodiments, a construct can be a cosmid (e.g., pWE or sCos series).

Constructs provided herein can be of different sizes. In some embodiments, a construct is a plasmid and can include a total length of up to about 1 kb, up to about 2 kb, up to about 3 kb, up to about 4 kb, up to about 5 kb, up to about 6 kb, up to about 7 kb, up to about 8 kb, up to about 9 kb, up to about 10 kb, up to about 11 kb, up to about 12 kb, up to about 13 kb, up to about 14 kb, or up to about 15 kb. In some embodiments, a construct is a plasmid and can have a total length in a range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 1 kb to about 11 kb, about 1 kb to about 12 kb, about 1 kb to about 13 kb, about 1 kb to about 14 kb, or about 1 kb to about 15 kb.

In some embodiments, a construct is a viral construct and can have a total number of nucleotides of up to 10 kb. In some embodiments, a viral construct can have a total number of nucleotides in the range of about 1 kb to about 2 kb, 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 2 kb to about 9 kb, about 2 kb to about 10 kb, about 3 kb to about 4 kb, about 3 kb to about 5 kb, about 3 kb to about 6 kb, about 3 kb to about 7 kb, about 3 kb to about 8 kb, about 3 kb to about 9 kb, about 3 kb to about 10 kb, about 4 kb to about 5 kb, about 4 kb to about 6 kb, about 4 kb to about 7 kb, about 4 kb to about 8 kb, about 4 kb to about 9 kb, about 4 kb to about 10 kb, about 5 kb to about 6 kb, about 5 kb to about 7 kb, about 5 kb to about 8 kb, about 5 kb to about 9 kb, about 5 kb to about 10 kb, about 6 kb to about 7 kb, about 6 kb to about 8 kb, about 6 kb to about 9 kb, about 6 kb to about 10 kb, about 7 kb to about 8 kb, about 7 kb to about 9 kb, about 7 kb to about 10 kb, about 8 kb to about 9 kb, about 8 kb to about 10 kb, or about 9 kb to about 10 kb.

In some embodiments, a construct is a protoparvovirus construct and can have a total number of nucleotides of up to 6 kb in a single construct. In some embodiments, a construct can have a total number of nucleotides in the range of about 1 kb to about 2 kb, 1 kb to about 3 kb, about 1 kb to about 4 kb, about 1 kb to about 6 kb, about 2 kb to about 3 kb, about 2 kb to about 4 kb, about 2 kb to about 5 kb, about 3 kb to about 4 kb, about 3 kb to about 6 kb, about 4 kb to about 6 kb.

Any of constructs described herein can further include a control sequence, e.g., a control sequence selected from the group of a transcription initiation sequence, a transcription termination sequence, a promoter sequence, an enhancer sequence, an RNA splicing sequence, a polyadenylation (polyA) sequence, a Kozak consensus sequence, and/or additional untranslated regions which may house pre- or post-transcriptional regulatory and/or control elements. In some embodiments, a promoter can be a native promoter, a constitutive promoter, an inducible promoter, and/or a tissue-specific promoter. Non-limiting examples of control sequences are described herein. The foregoing methods for producing recombinant constructs are not meant to be limiting, and other suitable methods will be apparent to the skilled artisan.

b. Capsid Modifications

Among other things, the present disclosure describes insertion of one or more heterologous peptides into one or more residues of a protoparvovirus VP1 capsid polypeptide, or variant thereof, as described herein. In some embodiments, insertion of one or more heterologous peptides is at one or more residues of a protoparvovirus VP1 capsid polypeptide that map(s) onto a structural overlay of one or more residues within a variable region (e.g., VR (e.g., VR-IV, VR-V, VR-VIII)) of a parvovirus VP1 capsid (e.g., AAV capsid, e.g., AAV2 capsid, e.g., AAV5 capsid, e.g., AAV8 capsid, e.g., AAV9 capsid, or any variant thereof). In some embodiments, a heterologous peptide comprises or is a heterologous targeting peptide.

AAV VRs differ between serotypes and are responsible for serotype-specific variations in antibody and receptor binding (see Tseng and Agbandje-McKenna, 2014, the entire contents of which are hereby incorporated by reference herein). In some embodiments, one or more heterologous peptides increases cell specificity and/or viral transduction efficiency and/or increases virion performance of a protoparvovirus variant VP1 capsid polypeptide.

Adenovirus capsid modifications are described by Buning and Srivastava, 2019, the entire contents of which are hereby incorporated by reference herein. It is an insight of the present disclosure that, in some embodiments, one or more modifications introduced into one or more residues of an AAV capsid can be introduced into one or more corresponding residues of a variant VP1 protoparvovirus, as described herein. In some embodiments, one or more modifications described by Buning and Srivastava, 2019 are introduced into one or more residues of a protoparvovirus variant VP1 capsid polypeptide.

Among other things, the present disclosure describes insertion of one or more heterologous peptides into one or more residues along a 3-fold axis of symmetry of a protoparvovirus variant VP1 capsid polypeptide. Residues in regions along a 3-fold axis of symmetry of a capsid can be responsible for serotype-specific variations in antibody and/or receptor binding (see, Callaway et al., 2017, the entire contents of which are hereby incorporated by reference herein).

It is also an insight of the present disclosure that one or more modifications at one or more residues along a 3-fold axis of symmetry of a protoparvovirus VP1 capsid polypeptide, or variant thereof, can help re-direct or expand tropism (e.g., cell surface targeting) of viral-based gene therapies described herein.

Adenovirus capsid modifications are described by Buning and Srivastava, 2019, the entire contents of which are hereby incorporated by reference herein. It is an insight of the present disclosure that, in some embodiments, one or more modifications introduced in a variable region of an AAV capsid can be introduced into one or more residues along the 3-fold axis of symmetry of a variant VP1 protoparvovirus, as described herein. In some embodiments, one or more modifications described by Buning and Srivastava, 2019 are introduced into corresponding residues (e.g., along a 3-fold axis of symmetry) of a protoparvovirus VP1 capsid polypeptide. In some embodiments, one or more modifications are introduced into one or more residues along the 3-fold axis of symmetry of a protoparvovirus VP1 capsid polypeptide. In some embodiments a capsid modification is a peptide insertion. In some embodiments a capsid modification is a peptide insertion into a residue of a protoparvovirus VP1 capsid polypeptide that corresponds to a residue described by Buning and Srivastava, 2019. In some embodiments, one or more heterologous peptides is inserted into one or more residues along the 3-fold axis of symmetry of a common VP1 region of a protoparvovirus VP3 capsid polypeptide. In some embodiments, one or more heterologous peptides is inserted into one or more residues along a 3-fold axis of symmetry of a common VP2 region of a protoparvovirus VP1 capsid polypeptide.

In some embodiments, a heterologous peptide is inserted into one or more residues of a protoparvovirus variant VP1 capsid polypeptide corresponding to residue 587 of a common VP3 region of AAV2. In some embodiments, a heterologous peptide is inserted into one or more residues of a protoparvovirus variant VP1 capsid polypeptide corresponding to residue 588 of a common VP3 Region of AAV2. In some embodiments, a heterologous peptide is inserted into one or more residues of a protoparvovirus variant VP1 capsid polypeptide corresponding to residues other than 587 or 588 of a common VP3 region of AAV2. For example, in some embodiments, a heterologous peptide is inserted into one or more residues of a protoparvovirus variant VP1 capsid polypeptide corresponding to residue 453 of a common VP3 region of AAV2. In some embodiments, a heterologous peptide is inserted into one or more residues of a protoparvovirus variant VP1 capsid polypeptide corresponding to residue 585 of a common VP3 Region of AAV2. In some embodiments, a heterologous peptide is inserted into one or more residues of a protoparvovirus variant VP1 capsid polypeptide corresponding to residue 520 of a common VP3 Region of AAV2. In some embodiments, a heterologous peptide is inserted into one or more residues of a protoparvovirus variant VP1 capsid polypeptide corresponding to residue 584 of a common VP3 Region of AAV2.

In some embodiments, a heterologous peptide is inserted into one or more residues of a protoparvovirus variant VP1 capsid polypeptide corresponding to a common VP3 region of AAV1. For example, in some embodiments, a heterologous peptide is inserted into one or more residues of a protoparvovirus variant VP1 capsid polypeptide corresponding to residue 590 of a common VP3 Region of AAV1.

In some embodiments, a heterologous peptide is inserted into one or more residues of a protoparvovirus variant VP1 capsid polypeptide corresponding to a common VP3 Region of AAV3. For example, in some embodiments, a heterologous peptide is inserted into one or more residues of a protoparvovirus variant VP1 capsid polypeptide corresponding to residue 586 of a common VP3 Region of AAV3.

In some embodiments, a heterologous peptide is inserted into one or more residues of a protoparvovirus variant VP1 capsid polypeptide corresponding to a common VP3 Region of AAV4. For example, in some embodiments, a heterologous peptide is inserted into one or more residues of a protoparvovirus variant VP1 capsid polypeptide corresponding to residue 586 of a common VP3 Region of AAV4.

In some embodiments, a heterologous peptide is inserted into one or more residues of a protoparvovirus variant VP1 capsid polypeptide corresponding to a common VP3 Region of AAV5. For example, in some embodiments, a heterologous peptide is inserted into one or more residues of a protoparvovirus variant VP1 capsid polypeptide corresponding to residue 575 of a common VP3 Region of AAV5.

In some embodiments, a heterologous peptide is inserted into one or more residues of a protoparvovirus variant VP1 capsid polypeptide corresponding to a common VP3 Region of AAV6. For example, in some embodiments, a heterologous peptide is inserted into one or more residues of a protoparvovirus variant VP1 capsid polypeptide corresponding to residue 585 of a common VP3 Region of AAV6. In some embodiments, a heterologous peptide is inserted into one or more residues of a protoparvovirus variant VP1 capsid polypeptide corresponding to residue 585 in combination with mutation of a tyrosine to phenylalanine at residues 705 and 731 and mutation of threonine to valine at residue 492 of a common VP3 Region of AAV6. In some embodiments, a heterologous peptide is inserted into one or more residues of a protoparvovirus variant VP1 capsid polypeptide corresponding to residue 585 in combination with mutation of a tyrosine to phenylalanine at residues 705 and 731 and mutation of threonine to valine at residue 492 and mutation of lysine to glutamic acid at residue 531 of a common VP3 Region of AAV6.

In some embodiments, a heterologous peptide is inserted into one or more residues of a protoparvovirus variant VP1 capsid polypeptide corresponding to a common VP3 Region of AAV8. For example, in some embodiments, a heterologous peptide is inserted into one or more residues of a protoparvovirus variant VP1 capsid polypeptide corresponding to residue 585 of a common VP3 Region of AAV8. In some embodiments, a heterologous peptide is inserted into one or more residues of a protoparvovirus variant VP1 capsid polypeptide corresponding to residue 590 of a common VP3 Region of AAV8.

In some embodiments, a heterologous peptide is inserted into one or more residues of a protoparvovirus variant VP1 capsid polypeptide corresponding to a common VP3 Region of AAV9. For example, in some embodiments, a heterologous peptide is inserted into one or more residues of a protoparvovirus variant VP1 capsid polypeptide corresponding to residue 588 of a common VP3 Region of AAV9. In some embodiments, a heterologous peptide is inserted into one or more residues of a protoparvovirus variant VP1 capsid polypeptide corresponding to residue 589 of a common VP3 Region of AAV9.

In some embodiments, a heterologous peptide is inserted into one or more residues of a protoparvovirus variant VP1 capsid polypeptide corresponding to a common VP3 Region of AAV9P1.

In some embodiments, a heterologous peptide is inserted into one or more residues of a protoparvovirus variant VP1 capsid polypeptide corresponding to a common VP3 Region of AAV-PHP.B. For example, in some embodiments, a heterologous peptide is inserted into one or more residues of a protoparvovirus variant VP1 capsid polypeptide corresponding to residue 588 of a common VP3 Region of AAV-PHP.B. In some embodiments, a heterologous peptide is inserted into one or more residues of a protoparvovirus variant VP1 capsid polypeptide corresponding to residue 589 of a common VP3 Region of AAV-PHP.B.

Table 2 shows exemplary heterologous peptide sequences that can be inserted into one or more residues of a protoparvovirus variant VP1 capsid polypeptide described herein.

TABLE 2

| Exemplary Sequence Name | Amino Acid Sequence | SEQ ID NO: |
|---|---|---|
| Exemplary Heterologous Peptide 1 | QAGTFALRGDNPQG | SEQ ID NO: 5 |
| Exemplary Heterologous Peptide 2 | NGRAHA | SEQ ID NO: 6 |
| Exemplary Heterologous Peptide 3 | RGDAVGV | SEQ ID NO: 7 |
| Exemplary Heterologous Peptide 4 | RGDTPTS | SEQ ID NO: 8 |
| Exemplary Heterologous Peptide 5 | GENQARS | SEQ ID NO: 9 |
| Exemplary Heterologous Peptide 6 | RSNAVVP | SEQ ID NO: 10 |
| Exemplary Heterologous Peptide 7 | CDCRGDCFC | SEQ ID NO: 11 |
| Exemplary Heterologous Peptide 8 | PRGTNGP | SEQ ID NO: 12 |
| Exemplary Heterologous Peptide 9 | SRGATTT | SEQ ID NO: 13 |
| Exemplary Heterologous Peptide 10 | SIGYPLP | SEQ ID NO: 14 |
| Exemplary Heterologous Peptide 11 | MTPFPTSNEANL | SEQ ID NO: 15 |
| Exemplary Heterologous Peptide 12 | QPEHSST | SEQ ID NO: 16 |
| Exemplary Heterologous Peptide 13 | VNTANST | SEQ ID NO: 17 |

TABLE 2-continued

| Exemplary Sequence Name | Amino Acid Sequence | SEQ ID NO: |
|---|---|---|
| Exemplary Heterologous Peptide 14 | CNHRYMQMC | SEQ ID NO: 18 |
| Exemplary Heterologous Peptide 15 | CAPGPSKSG | SEQ ID NO: 19 |
| Exemplary Heterologous Peptide 16 | EYHHYNK | SEQ ID NO: 20 |
| Exemplary Heterologous Peptide 17 | ASSLNIA | SEQ ID NO: 21 |
| Exemplary Heterologous Peptide 18 | TQVGQKT | SEQ ID NO: 22 |
| Exemplary Heterologous Peptide 19 | LPSSLQK | SEQ ID NO: 23 |
| Exemplary Heterologous Peptide 20 | WPFYGTP | SEQ ID NO: 24 |
| Exemplary Heterologous Peptide 21 | DSPAHPS | SEQ ID NO: 25 |
| Exemplary Heterologous Peptide 22 | GWTLHNK | SEQ ID NO: 26 |
| Exemplary Heterologous Peptide 23 | GMNAFRA | SEQ ID NO: 27 |
| Exemplary Heterologous Peptide 24 | LGETTRP | SEQ ID NO: 28 |
| Exemplary Heterologous Peptide 25 | RGDTATL | SEQ ID NO: 29 |
| Exemplary Heterologous Peptide 26 | PRGDLAP | SEQ ID NO: 30 |
| Exemplary Heterologous Peptide 27 | RGDQQSL | SEQ ID NO: 31 |
| Exemplary Heterologous Peptide 28 | EQLSISEEDL | SEQ ID NO: 32 |
| Exemplary Heterologous Peptide 29 | FNMQCQRRFYEALHDP NLNEEQRNAKIKSIRDD CX | SEQ ID NO: 33 |
| Exemplary Heterologous Peptide 30 | GLNDIFEAQKIEWHE | SEQ ID NO: 34 |
| Exemplary Heterologous Peptide 31 | LCTPSRAALLTGR | SEQ ID NO: 35 |
| Exemplary Heterologous Peptide 32 | QVSHWVSGLAEGSFG | SEQ ID NO: 36 |
| Exemplary Heterologous Peptide 33 | LSHTSGRVEGSVSLL | SEQ ID NO: 37 |
| Exemplary Heterologous Peptide 34 | VTAGRAP | SEQ ID NO: 38 |
| Exemplary Heterologous Peptide 35 | APVTRPA | SEQ ID NO: 39 |
| Exemplary Heterologous Peptide 36 | DLSNLTR | SEQ ID NO: 40 |
| Exemplary Heterologous Peptide 37 | NQVGSWS | SEQ ID NO: 41 |
| Exemplary Heterologous Peptide 38 | EARVRPP | SEQ ID NO: 42 |
| Exemplary Heterologous Peptide 39 | NSVSLYT | SEQ ID NO: 43 |
| Exemplary Heterologous Peptide 40 | NDVRSAN | SEQ ID NO: 44 |
| Exemplary Heterologous Peptide 41 | NESRVLS | SEQ ID NO: 45 |
| Exemplary Heterologous Peptide 42 | NRTWEQQ | SEQ ID NO: 46 |
| Exemplary Heterologous Peptide 43 | NSVQSSW | SEQ ID NO: 47 |
| Exemplary Heterologous Peptide 44 | RGDLGLS | SEQ ID NO: 48 |
| Exemplary Heterologous Peptide 45 | RGDMSRE | SEQ ID NO: 49 |
| Exemplary Heterologous Peptide 46 | ESGLSQS | SEQ ID NO: 50 |
| Exemplary Heterologous Peptide 47 | EYRDSSG | SEQ ID NO: 51 |
| Exemplary Heterologous Peptide 48 | DLGSARA | SEQ ID NO: 52 |
| Exemplary Heterologous Peptide 49 | GPQGKNS | SEQ ID NO: 53 |
| Exemplary Heterologous Peptide 50 | NSSRDLG | SEQ ID NO: 54 |
| Exemplary Heterologous Peptide 51 | NDVRAVS | SEQ ID NO: 55 |

TABLE 2-continued

| Exemplary Sequence Name | Amino Acid Sequence | SEQ ID NO: |
|---|---|---|
| Exemplary Heterologous Peptide 52 | PRSTSDP | SEQ ID NO: 56 |
| Exemplary Heterologous Peptide 53 | DIIRA | SEQ ID NO: 57 |
| Exemplary Heterologous Peptide 54 | SYENVASRRPEG | SEQ ID NO: 58 |
| Exemplary Heterologous Peptide 55 | PENSVRRYGLEE | SEQ ID NO: 59 |
| Exemplary Heterologous Peptide 56 | LSLASNRPTATS | SEQ ID NO: 60 |
| Exemplary Heterologous Peptide 57 | NDVWNRDNSSKRGGTT EAS | SEQ ID NO: 61 |
| Exemplary Heterologous Peptide 58 | NRTYSSTSNSTSRSEWD NS | SEQ ID NO: 62 |
| Exemplary Heterologous Peptide 59 | ESGHGYF | SEQ ID NO: 63 |
| Exemplary Heterologous Peptide 60 | GQHPRPG | SEQ ID NO: 64 |
| Exemplary Heterologous Peptide 61 | PSVSPRP | SEQ ID NO: 65 |
| Exemplary Heterologous Peptide 62 | VNSTRLP | SEQ ID NO: 66 |
| Exemplary Heterologous Peptide 63 | LSPVRPG | SEQ ID NO: 67 |
| Exemplary Heterologous Peptide 64 | MSSDPRRPPRDG | SEQ ID NO: 68 |
| Exemplary Heterologous Peptide 65 | GARPSEVTTRPG | SEQ ID NO: 69 |
| Exemplary Heterologous Peptide 66 | GNEVLGTKPRAP | SEQ ID NO: 70 |
| Exemplary Heterologous Peptide 67 | KMRPGAMGTTGEGTRV TRE | SEQ ID NO: 71 |
| Exemplary Heterologous Peptide 68 | MNVRGDL | SEQ ID NO: 72 |
| Exemplary Heterologous Peptide 69 | ENVRGDL | SEQ ID NO: 73 |
| Exemplary Heterologous Peptide 70 | KTLLPTP | SEQ ID NO: 74 |
| Exemplary Heterologous Peptide 71 | HLNILSTLWKYR | SEQ ID NO: 75 |
| Exemplary Heterologous Peptide 72 | SKAGRSP | SEQ ID NO: 76 |
| Exemplary Heterologous Peptide 73 | RGD | SEQ ID NO: 77 |
| Exemplary Heterologous Peptide 74 | PERTAMSLP | SEQ ID NO: 78 |
| Exemplary Heterologous Peptide 75 | ESGLSQS | SEQ ID NO: 79 |
| Exemplary Heterologous Peptide 76 | SEGLKNL | SEQ ID NO: 80 |
| Exemplary Heterologous Peptide 77 | SLRSPPS | SEQ ID NO: 81 |
| Exemplary Heterologous Peptide 78 | RGDLRVS | SEQ ID NO: 82 |
| Exemplary Heterologous Peptide 79 | TLAVPFK | SEQ ID NO: 83 |
| Exemplary Heterologous Peptide 80 | YTLSQGW | SEQ ID NO: 84 |

Among other things, in some embodiments, the present disclosure describes compositions, preparations, constructs, virions, population of virions, and host cells comprising a coding sequence that encodes a protoparvovirus variant VP1 capsid polypeptide further comprise an insertion of one or more heterologous peptides as described by Borner et al., 2020, the contents of which are hereby incorporated by reference in its entirety. In some embodiments, a heterologous peptide comprises a length of from 10 amino acids to 20 amino acids. In some embodiments, an insertion of one or more heterologous peptides is at one or more residues along a 3-fold axis of symmetry of a VP1 capsid polypeptide. In some embodiments, a protoparvovirus variant VP1 capsid polypeptide confers increased infectivity compared to the infectivity by a reference virion comprising the corresponding protoparvovirus reference VP1 capsid polypeptide. In some embodiments, the heterologous peptide alters cell specificity and/or viral transduction efficiency. In some embodiments the heterologous peptide increases virion performance.

In some embodiments, a protoparvovirus variant VP1 capsid polypeptide comprises a threonine to serine mutation at a residue corresponding to residue 590 of a HBoV reference VP1 capsid polypeptide (SEQ ID NO: 85), relative to a protoparvovirus reference VP1 capsid polypeptide. In some embodiments, a protoparvovirus variant VP1 capsid polypeptide comprises an aspartic acid to asparagine mutation at a residue corresponding to residue 86 of a HBoV reference VP1 capsid polypeptide (SEQ ID NO: 85), relative to a protoparvovirus reference VP1 capsid polypeptide. In some embodiments, a protoparvovirus variant VP1 capsid polypeptide comprises a serine to asparagine mutation at a residue corresponding to residue 474 of a HBoV reference VP1 capsid polypeptide (SEQ ID NO: 85), relative to a protoparvovirus reference VP1 capsid polypeptide. In some embodiments, a protoparvovirus variant VP1 capsid polypeptide comprises an alanine to threonine mutation at a residue corresponding to residue 149 of a HBoV reference VP1 capsid polypeptide (SEQ ID NO: 85), relative to a protoparvovirus reference VP1 capsid polypeptide. In some embodiments, a protoparvovirus variant VP1 capsid polypeptide comprises a threonine to serine mutation at a residue corresponding to residue 590, an aspartic acid to asparagine mutation at a residue corresponding to residue 86, a serine to asparagine mutation at a residue corresponding to residue 474, an alanine to threonine mutation at a residue corresponding to residue 149, or any combination thereof, of a HBoV reference VP1 capsid polypeptide (SEQ ID NO: 85), relative to a protoparvovirus reference VP1 capsid polypeptide.

```
Exemplary HBOV reference VP1 capsid polypeptide
                                      (SEQ ID NO: 85)
MPPIKRQPRGWVLPGYRYLGPFNPLDNGEPVNNADRAAQLHDHAYSELI

KSGKNPYLYFNKADEKFIDDLKDDWSIGGIIGSSFFKIKRAVAPALGNK

ERAQKRHFYFANSNKGAKKTKKSEPKPGTSKMSDTDIQDQQPDTVDAPQ

NASGGGTGSIGGGKGSGVGISTGGWVGGSHFSDKYVVTKNTRQFITTIQ

NGHLYKTEAIETTNQSGKSQRCVTTPWTYFNFNQYSCHFSPQDWQRLTN

EYKRFRPKAMQVKIYNLQIKQILSNGADTTYNNDLTAGVHIFCDGEHAY

PNASHPWDEDVMPDLPYKTWKLFQYGYIPIENELADLDGNAAGGNATEK
```

-continued

```
ALLYQMPFFLLENSDHQVLRTGESTEFTFNFDCEWVNNERAYIPPGLMF

NPKVPTRRVQYIRQNGSTAASTGRIQPYSKPTSWMTGPGLLSAQRVGPQ

SSDTAPFMVCTNPEGTHINTGAAGFGSGFDPPSGCLAPTNLEYKLQWYQ

TPEGTGNNGNIIANPSLSMLRDQLLYKGNQTTYNLVGDIWMFPNQVWDR

FPITRENPIWCKKPRADKHTIMDPFDGSIAMDHPPGTIFIKMAKIPVPT

ATNADSYLNIYCTGQVSCEIVWEVERYATKNWRPERRHTALGMSLGGES

NYTPTYHVDPTGAYIQPTSYDQCMPVKTNINKVL
```

c. Exemplary Capsid Construct Sequences

The present disclosure provides technologies (e.g., compositions, methods, etc.) that are or comprise constructs described herein. In some embodiments, technologies described herein comprise a protoparvovirus variant VP1 capsid polypeptide. In some embodiments, technologies comprising a protoparvovirus variant VP1 capsid polypeptide result in improved characteristics compared to technologies comprising a protoparvovirus reference VP1 capsid polypeptide as described herein.

Among other things, in some embodiments, constructs described herein comprise a VP1 capsid coding sequence and a VP2 capsid coding sequence. In some embodiments, constructs describe herein further comprise a Rep sequence (e.g., AAV Rep protein).

i. Reference VP1 Capsid Sequences

In some embodiments, constructs, compositions, virions, or populations of virions comprise a parvovirus VP1 capsid polypeptide having a VP1 capsid coding sequence that shows at least 70%, at least 80%, at least 85%, at least 90%, at least 91%, at least 92%, at least 93%, at least 94%, at least 95%, at least 96%, at least 97%, at least 98%, at least 99%, at least 100% overall sequence identity with that of a parvovirus reference VP1 capsid selected from the group consisting of those in Table 3A.

Table 3A shows exemplary parvovirus reference VP1 capsid polypeptide sequences described herein.

TABLE 3A

| Reference Sequence Name | GenBank # | Sequence | SEQ ID NO: |
|---|---|---|---|
| Exemplary Canine parvovirus VP1 capsid coding sequence | AJ564427.2 | ATGGCACCTCCGGCAAAGAGAGCCAGGAGAGG<br>TAAGGGTGTGTTAGTAAAGTGGGGGGAGGGGA<br>AAGATTTAATAACTTAACTAAGTATGTGTTTT<br>TTTATAGGACTTGTGCCTCCAGGTTATAAATA<br>TCTTGGGCCTGGGAACAGTCTTGACCAAGGAG<br>AACCAACTAACCCTTCTGACGCCGCTGCAAAA<br>GAACACGACGAAGCTTACGCTGCTTATCTTCG<br>CTCTGGTAAAAACCCATACTTATATTTCTCGC<br>CAGCAGATCAACGCTTTATAGATCAAACTAAG<br>GACGCTAAAGATTGGGGGGGGAAAATAGGACA<br>TTATTTTTTTAGAGCTAAAAAGGCAATTGCTC<br>CAGTATTAACTGATACACCAGATCATCCATCA<br>ACATCAAGACCAACAAAACCAACTAAAAGAAG<br>TAAACCACCACCTCATATTTTCATCAATCTTG<br>CAAAAAAAAAAAAAAGCCGGTGCAGGACAAGTA<br>AAAAGAGACAATCTTGCACCAATGAGTGATGG<br>AGCAGTTCAACCAGACGGTGGTCAGCCTGCTG<br>TCAGAAATGAAAGAGCTACAGGATCTGGGAAC<br>GGGTCTGGAGGCGGGGGTGGTGGTGGTTCTGG<br>GGGTGTGGGGATTTCTACGGGTACTTTCAATA<br>ATCAGACGGAATTTAAATTTTTGGAAAACGGA<br>TGGGTGGAAATCACAGCAAACTCAAGCAGACT<br>TGTACATTTAAATATGCCAGAAAGTGAAAATT<br>ATAGAAGAGTGGTTGTAAATAATTTGGATAAA | SEQ ID NO: 86 |

TABLE 3A-continued

| Reference Sequence Name | GenBank # | Sequence | SEQ ID NO: |
|---|---|---|---|
| | | ACTGCAGTTAACGGAAACATGGCTTTAGATGA<br>TACTCATGCACAAATTGTAACACCTTGGTCAT<br>TGGTTGATGCAAATGCTTGGGGAGTTTGGTTT<br>AATCCAGGAGATTGGCAACTAATTGTTAATAC<br>TATGAGTGAGTTGCATTTAGTTAGTTTTGAAC<br>AAGAAATTTTTAATGTTGTTTTAAAGACTGTT<br>TCAGAGTCTGCTACTCAGCCACCAACAAAAGT<br>TTATAATAATGATTTAACTGCATCATTGATGG<br>TTGCATTAGATAGTAATAATACTATGCCATTT<br>ACTCCAGCAGCTATGAGATCTGAGACATTGGG<br>TTTTTATCCATGGAAACCAACCATACCAACTC<br>CATGGAGATATTATTTTCAATGGGATAGAACA<br>TTAATACCATCTCATACTGGAACTAGTGGCAC<br>ACCAACAAATATATACCATGGTACAGATCCAG<br>ATGACGTTCAATTTTATACTATTGAAAATTCT<br>GTGCCAGTACACTTACTAAGAACAGGAGATGA<br>ATTTGCTACAGGAACATTTTTTTTTGATTGTA<br>AACCATGTAGACTAACACATACATGGCAAACA<br>AATAGAGCATTGGGCTTACCACCATTTCTAAA<br>TTCTTTGCCTCAAGCTGAAGGAGGTACTAACT<br>TTGGTTATATAGGAGTTCAACAAGATAAAAGA<br>CGTGGTGTAACTCAAATGGGAAATACAAACTA<br>TATTACTGAAGCTACTATTATGAGACCAGCTG<br>AGGTTGGTTATAGTGCACCATATTATTCTTTT<br>GAGGCGTCTACACAAGGGCCATTTAAAACACC<br>TATTGCAGCAGGACGGGGGGGAGCGCAAACAG<br>ATGAAAATCAAGCAGCAGATGGTGATCCAAGA<br>TATGCATTTGGTAGACAACATGGTCAAAAAAC<br>TACCACAACAGGAGAAACACCTGAGAGATTTA<br>CATATATAGCACATCAAGATACAGGAAGATAT<br>CCAGAAGGAGATTGGATTCAAAATATTAACTT<br>TAACCTTCCTGTAACAAATGATAATGTATTGC<br>TACCAACAGATCCAATTGGAGGTAAAGCAGGA<br>ATTAACTATACCAATATATTTAATACTTATGG<br>TCCTTTAACTGCATTAAATAATGTACCACCAG<br>TTTATCCAAATGGTCAAATTTGGGATAAAGAA<br>TTTGATACTGATTTAAAACCAAGACTTCATGT<br>AAATGCACCATTTGTTTGTCAAAATAATTGTC<br>CTGGTCAATTATTTGTAAAAGTTGCGCCTAAT<br>TTAACAAATGAATATGATCCTGATGCATCTGC<br>TAATATGTCAAGAATTGTAACTTACTCAGATT<br>TTTGGTGGAAAGGTAAATTAGTATTTAAAGCT<br>AAACTAAGAGCCTCTCATACTTGGAATCCAAT<br>TCAACAAATGAGTATTAATGTAGATAACCAAT<br>TTAACTATGTACCAAGTAATATTGGAGGTATG<br>AAAATTGTATATGAAAAATCTCAACTAGCACC<br>TAGAAAATTATATTAA | |
| Exemplary Minute virus of mince VP1 capsid coding sequence | J02275.1 | ATGAGTGATGGCACCAGCCAACCTGACAGCGG<br>AAACGCTGTCCACTCAGCTGCAAGAGTTGAAC<br>GAGCAGCTGACGGCCCTGGAGGCTCTGGGGGT<br>GGGGGCTCTGGCGGGGGTGGGGTTGGTGTTTC<br>TACTGGGTCTTATGATAATCAAACGCATTATA<br>GATTCTTGGGTGACGGCTGGGTAGAAATTACT<br>GCACTAGCAACTAGACTAGTACATTTAAACAT<br>GCCTAAATCAGAAAACTATTGCAGAATCAGAG<br>TTCACAATACAACAGACACATCAGTCAAAGGC<br>AACATGGCAAAAGATGATGCTCATGAGCAAAT<br>TTGGACACCATGGAGCTTGGTGGATGCTAATG<br>CTTGGGGAGTTTGGCTCCAGCCAAGTGACTGG<br>CAATACATTTGCAACACCATGAGCCAGCTTAA<br>CTTGGTATCACTTGATCAAGAAATATTCAATG<br>TAGTGCTGAAAACTGTTACAGAGCAAGACTTA<br>GGAGGTCAAGCTATAAAAATATACAACAATGA<br>CCTTACAGCTTGCATGATGGTTGCAGTAGACT<br>CAAACAACATTTTGCCATACACACCTGCAGCA<br>AACTCAATGGAAACACTTGGTTTCTACCCCTG<br>GAAACCAACCATAGCATCACCATACAGGTACT<br>ATTTTTGCGTTGACAGAGATCTTTCAGTGACC<br>TACGAAAATCAAGAAGGCACAGTTGAACATAA<br>TGTGATGGGAACACCAAAAGGAATGAATTCTC<br>AATTTTTTACCATTGAGAACACACAACAAATC<br>ACATTGCTCAGAACAGGGGACGAATTTGCCAC<br>AGGTACTTACTACTTTGACACAAATTCAGTTA<br>AACTCACACACACGTGGCAAACCAACCGTCAA<br>CTTGGACAGCCTCCACTGCTGTCAACCTTTCC | SEQ ID NO: 87 |

TABLE 3A-continued

| Reference Sequence Name | GenBank # | Sequence | SEQ ID NO: |
|---|---|---|---|
| | | TGAAGCTGACACTGATGCAGGTACACTTACTG CTCAAGGGAGCAGACATGGAACAACACAAATG GGGGTTAACTGGGTGAGTGAAGCAATCAGAAC CAGACCTGCTCAAGTAGGATTTTGTCAACCAC ACAATGACTTTGAAGCCAGCAGAGCTGGACCA TTTGCTGCCCCAAAAGTTCCAGCAGATATTAC TCAAGGAGTAGACAAAGAAGCCAATGGCAGTG TTAGATACAGTTATGGCAAACAGCATGGTGAA AATTGGGCTTCACATGGACCAGCACCAGAGCG CTACACATGGGATGAAACAAGCTTTGGTTCAG GTAGAGACACCAAAGATGGTTTTATTCAATCA GCACCACTAGTTGTTCCACCACCACTAAATGG CATTCTTACAAATGCAAACCCTATTGGGACTA AAAATGACATTCATTTTTCAAATGTTTTTAAC AGCTATGGTCCACTAACTGCATTTTCACACCC AAGTCCTGTATACCCTCAAGGACAAATATGGG ACAAAGAACTAGATCTTGAACACAAACCTAGA CTTCACATAACTGCTCCATTTGTTTGTAAAAA CAATGCACCTGGACAAATGTTGGTTAGATTAG GACCAAACCTAACTGACCAATATGATCCAAAC GGAGCCACACTTTCTAGAATTGTTACATACGG TACATTTTTCTGGAAAGGAAAACTAACCATGA GAGCAAAACTTAGAGCTAACACCACTTGGAAC CCAGTGTACCAAGTAAGTGCTGAAGACAATGG CAACTCATACATGAGTGTAACTAAATGGTTAC CAACTGCTACTGGAAACATGCAGTCTGTGCCG CTTATAACAAGACCTGTTGCTAGAAATACTTA CTAA | |

In some embodiments, constructs, compositions, virions, or populations of virions comprise a protoparvovirus variant VP1 capsid polypeptide having a polypeptide sequence that shows at least 70%, at least 80%, at least 85%, at least 90%, at least 91%, at least 92%, at least 93%, at least 94%, at least 95%, at least 96%, at least 97%, at least 98%, at least 99%, at least 100% overall sequence identity with that of a protoparvovirus reference VP1 capsid selected from the group consisting of those in Table 3B.

Table 3B shows exemplary protoparvovirus reference VP1 capsid polypeptide sequences described herein.

TABLE 3B

| Reference Sequence Name | GenBank # | Sequence | SEQ ID NO: |
|---|---|---|---|
| Exemplary Bufavirus VP1 polypeptide sequence | AFN44271 | MPAIRKARGWVPPGYNYLGPFNQDFSK KPTNPSDNAARKHDLEYNKLIKQGHNP YWNYNHADEDFIKETDQATDWGGKFGN FVFRAKRALAPELAPPAKKKTKTKHTE PEYSHKHIKAGTKRGKPFYLFVNLARK KARMTDTQDVSEQQSDQPSVASTSAKA GGGGGGGGSGVGHSTGNYNNRTEFYYH GDEVTIVCHSSRHIHLNMSESEEYKIY DTDRGPTFPTDQTLQGRDTINDSYHAQ VETPWFLINPNSWGTWMNPADFQQLTT TCREVTLEHLDQTLDNIVIKTVSKQGS GAEETTQYNNDLTALLQVALDKSNQLP WVADNMYLDSLGYIPWRPCKLKQYSYH VNFWNTIDIISGPQQNQWQQVKKEIKW DDLQFTPIETTTEIDLLRTGDSWTSGP YKFNTKPTQLSYHWQSTRHTGSVHPTE PPNAIGQQGRNIIDINGWQWGDRSNPM SAATRVSNFHIGYSWPEWRIHYGSGGP AINPGAPFSQAPWSTDPQVRLTQGASE KAIFDYNHGDDDPAHRDQWWQNNLPMT GQTDWAPKNAHQTNVSNNIPSRQEFWT QDYHNTFGPFTAVDDVGIQYPWGAIWT KTPDTTHKPMMSAHAPFICKDGPPGQL LVKLAPNYTENLQTDGLGNNRIVTYAT FWWTGKLVLKGKLRLPRQFNLYNLPGR PRGTEAKKFLPNEIGHFELPFMPGRCM PNYTI | SEQ ID NO: 88 |

TABLE 3B-continued

| Reference Sequence Name | GenBank # | Sequence | SEQ ID NO: |
|---|---|---|---|
| Exemplary Canine Parvovirus VP1 polypeptide sequence | M19296.1 | MAPPAKRARRGKGVLVKWGEGKDLITX LSMCFFIGLVPPGYKYLGPGNSLDQGE PTNPSDAAAKEHDEAYAAYLRSGKNPY LYFSPADQRFIDQTKDAKDWGGKIGHY FFRAKKAIAPVLTDTPDHPSTSRPTKP TKRSKPPPHIFINLAKKKKAGAGQVKR DNLAPMSDGAVQPDGGQPAVRNERATG SGNGSGGGGGGGSGGVGISTGTFNNQT EFKFLENGWVEITANSSRLVHLNMPES ENYRRVVVNNMDKTAVNGNMALDDIHA QIVTPWSLVDANAWGVWFNPGDWQLIV NTMSELHLVSFEQEIFNVVLKTVSESA TQPPTKVYNNDLTASLMVALDSNNTMP FTPAAMRSETLGFYPWKPTIPTPWRYY FQWDRTLIPSHTGTSGTPTNIYHGTDP DDVQFYTIENSVPVHLLRTGDEFATGT FFFDCKPCRLTHTWQTNRALGLPPFLN SLPQSEGATNFGDIGVQQDKRRGVTQM GNTNYITEATIMRPAEVGYSAPYYSFE ASTQGPFKTPIAAGRGGAQTYENQAAD GDPRYAFGRQHGQKTTTTGETPERFTY IAHQDTGRYPEGDWIQNINFNLPVTND NVLLPTDPIGGKTGINYTNIFNTYGPL TALNNVPPVYPNGQIWDKEFDTDLKPR LHVNAPFVCONNCPGQLFVKVAPNLTN EYDPDASANMSRIVTYSDFWWKGKLVF KAKLRASHTWNPIQQMSINVDNQFNYV PSNIGGMKIVYEKSQLAPRKLY | SEQ ID NO: 89 |
| Exemplary Canine Parvovirus VP1 polypeptide sequence | AXQ00350 | MAPPAKRARRGLVPPGYKYLGPGNSLD QGEPTNPSDAAAKEHDEAYAAYLRSGK NPYLYFSPADQRFIDQTKDAKDWGGKI GHYFFRAKKAIAPVLTDTPDHPSTSRP TKPTKRSKPPPHIFINLAKKKKAGAGQ VKRDNLAPMSDGGVQPDGGQPAVRNER ATGSGNGSGGGGGGGSGGVGISTGTFN NQTEFKFLENGWVEITANSSRLVHLNM PESENYRRVVVNNLDKTAVNGNMALDD THAQIVTPWSLVDANAWGVWFNPGDWQ LIVNTMSELHLVSFEQEIFNVVLKTVS ESATQPPTKVYNNDLTASLMVALDSNN TMPFTPAAMRSETLGFYPWKPTIPTPW RYYFQWDRTLIPSHTGTSGTPTNIYHG TDPDDVQFYTIENSVPVHLLRTGDEFA TGTFYFDCKPCRLTHTWQTNRALGLPP FLNSLPQAEGGTNFGYIGVQQDKRRGV TQMGNTNIITEATIMRPAEVGYSAPYY SFEASTQGPFKTPIAAGRGGAQTDENR AADGDPRYAFGRQHGQKTTTTGETPER FTYIAHQDTGRYPEGDWIQNINFNLPV TEDNVLLPTDPIGGKTGINYTNIFNTY GPLTALNNVPPVYPNGQIWDKEFDTDL KPRLHVNAPFVCONNCPGQLFVKVAPN LTNEYDPDASANMSRIVTYSDFWWKGK LVFKAKLRASHTWNPIQQMSINVDNQF NYVPSNIGGMKIVYEKSQLAPRKLY | SEQ ID NO: 90 |
| Exemplary Cutavirus VP1u-VP2 polypeptide sequence | AQN78782.1 | MPAIRKARGWVPPGYNFLGPFNQDENK EPTNPSDNAAKQHDLEYNKLINQGHNP YWYYNKADEDFIKATDQAPDWGGKFGN FIFRAKKHIAPELAPPAKKKSKTKHPE PEFSHKHIKPGTKRGKPFHIFVNLARK RARMSEPAENTNDQPNDSPVEQGAGQI GGGGGGGGSGVGHSTGDYNNRTEFIYH GDEVTIICHSTRLVHINMSDREDYIIY ETDRGQLFPTTQDLQGRDTLNDSYHAK VETPWKLLHANSWGCWFSPADFQQMIT TCRDIAPIQMHQKIENIVIKTVSKTGT GETETTNYNNDLTALLQIAQDNSNLLP WAADNFYIDSVGYVPWRACKLPTYCYH VDTWNTIDINQADAPNRWREIKKGIQW DNIQFTPLETMINIDLLRTGDAWQSGN YNFHTKPTNLAYHWQSQRHTGSCHPTV APLVERGQGTNIQSVNCWQWGDRNNPS SASTRVSNMHIGYSFPEWQIHYSTGGP | SEQ ID NO: 91 |

TABLE 3B-continued

| Reference Sequence Name | GenBank # | Sequence | SEQ ID NO: |
|---|---|---|---|
| | | VINPGSAFSQAPWGSTTEGTRLTQGAS<br>EKAIYDWAHGDDQPGARETWWQNNQHV<br>TGQTDWAPKNAHTSELNNNVPAATHFW<br>KNSYHNTFSPFTAVDDHGPQYPWGAIW<br>GKYPDTTHKPMMSAHAPFLLHGPPGQL<br>FVKLAPNYTDTLDNGGVTHPRIVTYGT<br>FWWSGKLIFKGKLRTPRQWNTYNLPSL<br>DKRETMKNTVPNEVGHFELPYMPGRCL<br>PNYTL | |
| Exemplary Cutavirus VP1u-VP2 polypeptide sequence | YP_009508805 | MPAIRKARGWVPPGYNFLGPFNQDENK<br>EPTNPSDNAAKQHDLEYNKLINQGHNP<br>YWYYNKADEDFIKATDQAPDWGGKFGN<br>FIFRAKKHIAPELAPPAKKKSKTKHSE<br>PEFSHKHIKPGTKRGKPFHIFVNLARK<br>RARMSEPANDTNEQPDNSPVEQGAGQI<br>GGGGGGGGSGVGHSTGDYNNRTEFIYH<br>GDEVTIICHSTRLVHINMSDREDYIIY<br>ETDRGPLFPTTQDLQGRDTLNDSYHAK<br>VETPWKLLHANSWGCWFSPADFQQMIT<br>TCRDIAPIKMHQKIENIVIKTVSKTGT<br>GETETTNYNNDLTALLQIAQDNSNLLP<br>WAADNFYIDSVGYVPWRACKLPTYCYH<br>VDTWNTIDINQADTPNQWREIKKGIQW<br>DNIQFTPLETMINIDLLRTGDAWESGN<br>YNFHTKPTNLAYHWQSQRHTGSCHPTV<br>APLVERGQGTNIQSVNCWQWGDRNNPS<br>SASTRVSNIHIGYSFPEWQIHYSTGGP<br>VINPGSAFSQAPWGSTTEGTRLTQGAS<br>EKAIYDWSHGDDQPGARETWWQNNQHV<br>TGQTDWAPKNAHTSELNNNVPAATHFW<br>KNSYHNTFSPFTAVDDHGPQYPWGAIW<br>GKYPDTTHKPMMSAHAPFLLHGPPGQL<br>FVKLAPNYTDTLDNGGVTHPRIVTYGT<br>FWWSGQLIFKGKLRTPRQWNTYNLPSL<br>DKRETMKNTVPNEVGHFELPYMPGRCL<br>PNYTL | SEQ ID NO: 92 |
| Exemplary Feline Panleukopenia Virus VP1 polypeptide sequence | ACD37389.1 | MAPPAKRARRGLVPPGYKYLGPGNSLD<br>QGEPTNPSDAAAKEHDEAYAAYLRSGK<br>NPYLYFSPADQRFIDQTKDAKDWGGKI<br>GHYFFRAKKAIAPVLTDTPDHPSTSRP<br>TKPTKRSKPPPHIFINLAKKKKAGAGQ<br>VKRDNLAPMSDGAVQPDGGQPAVRNER<br>ATGSGNGSGGGGGGGSGGVGISTGTFN<br>NQTEFKFLENGWVEITANSSRLVHLNM<br>PESENYKRVVVNNMDKTAVKGNMALDD<br>IHVQIVTPWSLVDANAWGVWFNPGDWQ<br>LIVNTMSELHLVSFEQEIFNVVLKTVS<br>ESATQPPTKVYNNDLTASLMVALDSNN<br>TMPFTPAAMRSETLGFYPWKPTIPTPW<br>RYYFQWDRTLIPSHTGTSGTPTNVYHG<br>TDPDDVQFYTIENSVPVHLLRTGDEFA<br>TGTFFFDCKPCRLTHTWQTNRALGLPP<br>FLNSLPQSEGATNYGDIGVQQDKRRGV<br>TQMGNTDYITEATIMRPAEVGYSAPYY<br>SFEASTQGPFKTPIAAGRGGAQTDENQ<br>AADGDPRYAFGRQHGQKTTTTGETPER<br>FTYIAHQDTGRYPEGDWIQNINFNLPV<br>TNDNVLLPTDPIGGKTGINYTNIFNTY<br>GPLTALNNVPPVYPNGQIWDKEFDTDL<br>KPRLHVNAPFVCQNNCPGQLFVKVAPN<br>LTNEYDPDASANMSRIVTYSDFWWKGK<br>LVFKAKLRASHTWNPIQQMSINVDNQF<br>NYVPNNIGAMKIVYEKSQLAPRKLY | SEQ ID NO: 93 |
| Exemplary Feline Panleukopenia Virus VP1 polypeptide sequence | AKI88071 | MAPPAKRARRGLVPPGYKYLGPGNSLD<br>QGEPTNPSDAAAKEHDEAYAAYLRSGK<br>NPYLYFSPADQRFIDQTKDAKDWGGKI<br>GHYFFRAKKAIAPVLTDTPDHPSTSRP<br>TKPTKRSKPPPHIFINLAKKKKAGAGQ<br>VKRDNLAPMSDGAVQPDGGQPAVRNER<br>ATGSGNGSGGGGGGGSGGVGISTGTFN<br>NQTEFKFLENGWVEITANSSRLVHLNM<br>PESENYKRVVVNNMDKTAVKGNMALDD<br>THVQIVTPWSLVDANAWGVWFNPGDWQ | SEQ ID NO: 94 |

TABLE 3B-continued

| Reference Sequence Name | GenBank # | Sequence | SEQ ID NO: |
|---|---|---|---|
| | | LIVNTMSELHLVSFEQEIFNVVLKTVS<br>ESATQPPTKVYNNDLTASLMVALDSNN<br>TMPFTPAAMRSETLGFYPWKPTIPTPW<br>RYYFQWDRTLIPSHTGTSGTPTNVYHG<br>TDPDDVQFYTIENSVPVHLLRTGDEFA<br>TGTFFFDCKPCRLTHTWQTNRALGLPP<br>FLNSLPQSEGATNFGDIGVQQDKRRGV<br>TQMGNTDYITEATIMRPAEVGYSAPYY<br>SFEASTQGPFKTPIAAGRGGAQTDENQ<br>AADGDPRYAFGRQHGQKTTTTGETPER<br>FTYIAHQDTGRYPEGDWIQNINFNLPV<br>TNDNVLLPTDPIGGKTGINYTNIFNTY<br>GPLTALNNVPPVYPNGQIWDKEFDTDL<br>KPRLHVNAPFVCQNNCPGQLFVKVAPN<br>LTNEYDPDASANMSRIVTYSDFWWKGK<br>LVFKAKLRASHTWNPIQQMSINVDNQF<br>NYVPNNIGAMKIVYEKSQLAPRKLY | |
| Exemplary Minute Virus of Mice VP1 polypeptide sequence | J02275.1 | MAPPAKRAKRGWVPPGYKYLGPGNSLD<br>QGEPTNPSDAAAKEHDEAYDQYIKSGK<br>NPYLYFSAADQRFIDQTKDAKDWGGKV<br>GHYFFRTKRAFAPKLATDSEPGTSGVS<br>RAGKRTRPPAYIFINQARAKKKLTSSA<br>AQQSSQTMSDGTSQPDSGNAVHSAARV<br>ERAADGPGGSGGGGSGGGGVGVSTGSY<br>DNQTHYRFLGDGWVEITALATRLVHLN<br>MPKSENYCRIRVHNTTDTSVKGNMAKD<br>DAHEQIWTPWSLVDANAWGVWLQPSDW<br>QYICNTMSQLNLVSLDQEIFNVVLKTV<br>TEQDLGGQAIKIYNNDLTACMMVAVDS<br>NNILPYTPAANSMETLGFYPWKPTIAS<br>PYRYYFCVDRDLSVTYENQEGTVEHNV<br>MGTPKGMNSQFFTIENTQQITLLRTGD<br>EFATGTYYFDTNSVKLTHTWQTNRQLG<br>QPPLLSTFPEADTDAGTLTAQGSRHGT<br>TQMGVNWVSEAIRTRPAQVGFCQPHND<br>FEASRAGPFAAPKVPADITQGVDKEAN<br>GSVRYSYGKQHGENWASHGPAPERYTW<br>DETSFGSGRDTKDGFIQSAPLVVPPPL<br>NGILTNANPIGTKNDIHFSNVFNSYGP<br>LTAFSHPSPVYPQGQIWDKELDLEHKP<br>RLHITAPFVCKNNAPGQMLVRLGPNLT<br>DQYDPNGATLSRIVTYGTFFWKGKLTM<br>RAKLRANTTWNPVYQVSAEDNGNSYMS<br>VTKWLPTATGNMQSVPLITRPVARNTY | SEQ ID NO: 95 |
| Exemplary Tusavirus VP1 polypeptide sequence | AIT18930 | MAPAARPRKGWVPPGYNYLGPGNDLDA<br>GEPTNKSDAAARKHDFAYSAYLKQGLD<br>PYWNFNKADEKFIRDTEGATDWGGRLG<br>HWIFRAKKHILPHLKEPTLAGRKRPAP<br>AHIFVNLANKRKKGLPTRKDQQKDTLD<br>SNAQQPVREADQPDGMAASSSDSGPSS<br>SGGGARAGGVGVSTGDFDNTTLWDFHE<br>DGTATITCNSTRLVHLTRPDSLDYKII<br>PTQNNTAVQTVGHMMDDDNHTQVLTPW<br>SLVDCNAWGVWLSPHDWQHIMNIGEEL<br>ELLSLEQEVFNVTLKTATETGPPESRI<br>TMYNNDLTAVMMITTDTNNQLPYTPAA<br>IRSETLGFYPWRPTVVPRWRYYFDWDR<br>FLSVTSSSDQSTSIINHSSTQSAIGQF<br>FVIETQLPIALLRTGDSYATGGYKFDC<br>NKVNLGRHWQTTRSLGLPPKIEPPTSE<br>SALGTINQNARLGWRWGINDVHETNVV<br>RPCTAGYNHPEWFYTHTLEGPAIDPAP<br>PTSIPSNWGGGTPPDTRASSHNQQRIT<br>YNYNHGNKDENLNNFSLNPNIELGSII<br>NQGNFLSYEGNGQQINTTAGVGKNGET<br>ATSDPNLVRYMPNTYGVYTAVDHQGPV<br>YPHGQIWDKQIHTDKKPELHCLAPFTC<br>KNNPPGQMFVRIAPNLTDTFNATPTFS<br>EIITYADFWWKGTLKMKIKLRPPHQWN<br>IATVLGAAVNIGDAARFVPNRLGQLEF<br>PVINGRIVPSTVY | SEQ ID NO: 96 |

ii. Exemplary Variant VP 1 Capsid Sequences

In some embodiments, constructs, compositions, virions, or populations of virions comprise a VP1 capsid coding sequence that encodes a protoparvovirus variant VP1 capsid polypeptide. In some embodiments, a protoparvovirus variant VP1 capsid polypeptide is encoded by a VP1 capsid coding sequence with at least 85%, 90%, 95%, 98% or 99% sequence identity to a VP1 capsid coding sequence described herein. In some embodiments, a protoparvovirus variant VP1 capsid comprises a polypeptide with at least 85%, 90%, 95%, 98% or 99% sequence identity to a polypeptide of a sequence described herein. In some embodiments, constructs described herein comprise fewer ATG sequence(s) across the length of a VP1 capsid coding sequence (e.g., in frame or out of frame) that encodes a protoparvovirus variant VP1 capsid polypeptide. In some embodiments, constructs described herein comprise fewer ATG sequence(s) across the length of a VP1 capsid coding sequence (e.g., in frame or out of frame) that encodes a protoparvovirus variant VP1 capsid polypeptide due to a substitution in one or more of "ATG" relative to a protoparvovirus reference VP1 capsid coding sequence described herein. In some embodiments, constructs described herein comprise fewer ATG sequence(s) across the length of a VP1 capsid coding sequence (e.g., in frame or out of frame) that encodes a protoparvovirus variant VP1 capsid polypeptide due to a deletion in one or more of "ATG" relative to a protoparvovirus reference VP1 capsid coding sequence described herein. In some embodiments, constructs described herein comprise fewer "ATG" sequence(s) across the length of a VP1 capsid coding sequence (e.g., in frame or out of frame, e.g., at position −3 or +4 relative to the first position of a VP1 capsid coding sequence) that encodes a protoparvovirus variant VP1 capsid polypeptide due to a conservative amino acid substitution in one or more of "ATG" relative to a protoparvovirus reference VP1 capsid coding sequence described herein. In some embodiments, constructs described herein comprise fewer "ATG" sequence(s) across the length of a VP1 capsid coding sequence (e.g., in frame or out of frame, e.g., at position −3 or +4 relative to the first position of a VP1 capsid coding sequence) that encodes a protoparvovirus variant VP1 capsid polypeptide due to a conservative amino acid substitution of one or more nucleotides surrounding an "ATG" (e.g., a conservative amino acid substitution within a Kozak consensus sequence) relative to a protoparvovirus reference VP1 capsid coding sequence described herein. In some embodiments, constructs described herein comprise fewer "ATG" sequence(s) across the length of a VP1 capsid coding sequence (e.g., in frame or out of frame) that encodes a protoparvovirus variant VP1 capsid polypeptide due to a conservative amino acid substitution of one or more purines surrounding an "ATG" (e.g., at position −3 or +4 relative to the first position of a VP1 capsid coding sequence, e.g., a conservative amino acid substitution within a Kozak consensus sequence) relative to a protoparvovirus reference VP1 capsid coding sequence described herein. In some embodiments, constructs described herein comprise an alternative translation initiation sequence (e.g., CTG, TTG, ACG, ATC) to improve potency relative to constructs comprising an ATG initiation sequence.

In some embodiments, a protoparvovirus variant VP1 capsid polynucleotide comprises a VP1 capsid coding sequence that is at least about 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to a sequence selected from SEQ ID NOs: 97-102.

In some embodiments, a protoparvovirus variant VP1 capsid polypeptide comprises a polypeptide sequence that is at least about 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to a sequence selected from SEQ ID NOs: 103-110.

Exemplary Variant VP1 Capsid Polypeptide Coding Sequences

Exemplary canine parvovirus (CPV) variant VP1 capsid polypeptide construct sequences may be or comprise a VP1 capsid coding sequence according to SEQ ID NO: 97.

```
CTGGCACCTCCGGCAAAGAGAGCCAGGAGAGGATATAAATATCTTGGGCC
TGGGAACAGTCTTGACCAAGGAGAACCAACTAACCCTTCTGACGCCGCTG
CAAAAGAACACGACGAAGCTTACGCTGCTTATCTTCGCTCTGGTAAAAAC
CCATACTTATATTTCTCGCCAGCAGATCAACGCTTTATAGATCAAACTAA
GGACGCTAAAGATTGGGGGGGGAAAATAGGACATTATTTTTTTAGAGCTA
AAAAGGCAATTGCTCCAGTATTAACTGATACACCAGATCATCCATCAACA
TCAAGACCAACAAAACCAACTAAAAGAAGTAAACCACCACCTCATATTTT
CATCAATCTTGCAAAAAAAAAAAAAAGCCGGTGCAGGACAAGTAAAAAGAG
ACAATCTTGCACCAATGAGTGATGGAGCAGTTCAACCAGACGGTGGTCAA
CCTGCTGTCAGAAATGAAAGAGCTACAGGATCTGGGAACGGGTCTGGAGG
CGGGGGTGGTGGTGGTTCTGGGGGTGTGGGGATTTCTACGGGTACTTTCA
ATAATCAGACGGAATTTAAATTTTTGGAAAACGGATGGGTGGAAATCACA
GCAAACTCAAGCAGACTTGTACATTTAAATATGCCAGAAAGTGAAAATTA
TAGAAGAGTGGTTGTAAATAATATGGATAAAACTGCAGTTAACGGAAACA
TGGCTTTAGATGATATTCATGCACAAATTGTAACACCTTGGTCATTGGTT
GATGCAAATGCTTGGGGAGTTTGGTTTAATCCAGGAGATTGGCAACTAAT
TGTTAATACTATGAGTGAGTTGCATTTAGTTAGTTTTGAACAAGAAATTT
TTAATGTTGTTTTAAAGACTGTTTCAGAATCTGCTACTCAGCCACCAACT
AAAGTTTATAATAATGATTTAACTGCATCATTGATGGTTGCATTAGATAG
TAATAATACTATGCCATTTACTCCAGCAGCTATGAGATCTGAGACATTGG
GTTTTTATCCATGGAAACCAACCATACCAACTCCATGGAGATATTATTTT
CAATGGGATAGAACATTAATACCATCTCATACTGGAACTAGTGGCACACC
AACAAATATATACCATGGTACAGATCCAGATGATGTTCAATTTTATACTA
TTGAAAATTCTGTGCCAGTACACTTACTAAGAACAGGTGATGAATTTGCT
ACAGGAACATTTTTTTTTGATTGTAAACCATGTAGACTAACACATACATG
GCAAACAAATAGAGCATTGGGCTTACCACCATTTCTAAATTCTTTGCCTC
AATCTGAAGGAGCTACTAACTTTGGTGATATAGGAGTTCAACAAGATAAA
AGACGTGGTGTAACTCAAATGGGAAATACAAACTATATTACTGAAGCTAC
```

-continued

TATTATGAGACCAGCTGAGGTTGGTTATAGTGCACCATATTATTCTTTTG

AGGCGTCTACACAAGGGCCATTTAAAACACCTATTGCAGCAGGACGGGGG

GGAGCGCAAACATATGAAAATCAAGCAGCAGATGGTGATCCAAGATATGC

ATTTGGTAGACAACATGGTCAAAAAACTACCACAACAGGAGAAACACCTG

AGAGATTTACATATATAGCACATCAAGATACAGGAAGATATCCAGAAGGA

GATTGGATTCAAAATATTAACTTTAACCTTCCTGTAACGAATGATAATGT

ATTGCTACCAACAGATCCAATTGGAGGTAAAACAGGAATTAACTATACTA

ATATATTTAATACTTATGGTCCTTTAACTGCATTAAATAATGTACCACCA

GTTTATCCAAATGGTCAAATTTGGGATAAAGAATTTGATACTGACTTAAA

ACCAAGACTTCATGTAAATGCACCATTTGTTTGTCAAAATAATTGTCCTG

GTCAATTATTTGTAAAAGTTGCGCCTAATTTAACAAATGAATATGATCCT

GATGCATCTGCTAATATGTCAAGAATTGTAACTTACTCAGATTTTTGGTG

GAAAGGTAAATTAGTATTTAAAGCTAAACTAAGAGCCTCTCATACTTGGA

ATCCAATTCAACAAATGAGTATTAATGTAGATAACCAATTTAACTATGTA

CCAAGTAATATTGGAGGTATGAAAATTGTATATGAAAAATCTCAACTAGC

ACCTAGAAAATTATATTAA

Exemplary cutavirus variant VP1 capsid polypeptide construct sequences may be or comprise a VP1 capsid coding sequence according to SEQ ID NO: 98.

CTGGCTCCAGCTATTAGAAAAGCCAGAGGTTACAACTTCCTAGGACCCTT

CAATCAAGACTTCAACAAAGAACCAACTAATCCATCAGACAACGCTGCAA

AACAACACGATTTGGAATACAACAAACTAATCAACCAAGGACACAATCCT

TATTGGTACTACAACAAAGCTGACGAAGACTTCATCAAAGCAACAGATCA

AGCACCAGACTGGGGAGGAAAATTTGGCAACTTCATCTTCAGAGCCAAAA

AACACATCGCTCCAGAACTGGCACCACCAGCAAAAAAGAAAAGCAAAACC

AAACACAGTGAACCAGAATTCAGCCACAAACACATCAAACCAGGCACCAA

AAGAGGTAAGCCTTTTCATATTTTTGTAAACCTTGCTAGAAAAAGAGCCC

GC

Exemplary cutavirus variant VP1 capsid polypeptide construct sequences may be or comprise a VP1 capsid coding sequence according to SEQ ID NO: 99.

ACGCCAGCTATTAGAAAAGCCAGAGGACCCTTCAATCAAGACTTCAACAA

AGAACCAACTAATCCATCAGACAACGCTGCAAAACAACACGATTTGGAAT

ACAACAAACTAATCAACCAAGGACACAATCCTTATTGGTACTACAACAAA

GCTGACGAAGACTTCATCAAAGCAACAGATCAAGCACCAGACTGGGGAGG

AAAATTTGGCAACTTCATCTTCAGAGCCAAAAAACACATCGCTCCAGAAC

TGGCACCACCAGCAAAAAAGAAAAGCAAAACCAAACACAGTGAACCAGAA

TTCAGCCACAAACACATCAAACCAGGCACCAAAAGAGGTAAGCCTTTTCA

TATTTTTGTAAACCTTGCTAGAAAAAGAGCCCGCATGTCAGAACCAGCTA

ATGATACAAATGAACAACCAGACAACTCCCCTGTTGAACAGGGTGCTGGT

CAAATTGGAGGAGGTGGAGGTGGAGGTGGAAGCGGTGTCGGGCACAGCAC

-continued

TGGTGATTATAATAATAGGACTGAGTTTATTTATCATGGTGATGAAGTCA

CAATTATTTGCCACTCTACAAGACTGGTTCACATCAATATGTCAGACAGG

GAAGACTACATCATCTATGAAACAGACAGAGGACCACTCTTTCCTACCAC

TCAGGACCTGCAGGGTAGAGACACTCTAAATGACTCTTACCATGCCAAAG

TAGAAACACCATGGAAACTACTCCATGCAAACAGCTGGGGCTGCTGGTTT

TCACCAGCAGACTTCCAACAAATGATCACCACATGCAGAGACATAGCACC

AATAAAAATGCACCAAAAAATAGAAAACATTGTCATCAAAACAGTCAGTA

AAACAGGCACAGGAGAAACAGAAACAACCAACTACAACAATGACCTCACA

GCACTCCTACAAATTGCACAAGACAACAGTAACCTACTACCATGGGCTGC

AGATAACTTTTATATAGACTCAGTAGGTTACGTTCCATGGAGAGCATGCA

AACTACCAACCTACTGCTACCACGTAGACACTTGGAATACAATTGACATA

AACCAAGCAGACACACCAAACCAATGGAGAGAAATCAAAAAAGGCATCCA

ATGGGACAATATCCAATTCACACCACTAGAAACTATGATAAACATTGACT

TACTAAGAACAGGAGATGCCTGGGAATCTGGTAACTACAATTTCCACACA

AAACCAACAAACCTAGCTTACCATTGGCAATCACAAAGACACACAGGCAG

CTGTCACCCAACAGTAGCACCTCTAGTTGAAAGAGGACAAGGAACCAACA

TACAATCAGTAAACTGTTGGCAATGGGGAGACAGAAACAATCCAAGCTCT

GCATCAACCAGAGTATCCAATATACATATTGGATACTCATTTCCAGAATG

GCAAATCCACTACTCAACAGGAGGACCAGTAATTAATCCAGGCAGTGCAT

TCTCACAAGCACCATGGGGCTCAACAACTGAAGGCACCAGACTAACCCAA

GGTGCATCTGAAAAAGCCATCTATGACTGGTCCCATGGAGATGACCAACC

AGGAGCCAGAGAAACCTGGTGGCAAAACAACCAACATGTAACAGGACAAA

CTGACTGGGCACCAAAAAATGCACACACCTCAGAACTCAACAACAATGTA

CCAGCAGCCACACACTTCTGGAAAAACAGCTATCACAACACCTTCTCACC

ATTCACTGCAGTAGATGATCATGGACCACAATATCCATGGGGAGCCATCT

GGGGAAAATACCCAGACACCACACACAAACCAATGATGTCAGCTCACGCA

CCATTCCTACTTCATGGACCACCTGGACAACTCTTTGTAAAACTAGCACC

AAACTATACAGACACACTTGACAACGGAGGTGTAACACATCCCAGAATCG

TCACATATGGAACCTTCTGGTGGTCAGGACAACTCATCTTTAAAGGAAAA

CTACGCACTCCAAGACAATGGAATACCTACAACCTACCAAGCCTAGACAA

AAGAGAAACCATGAAAAACACAGTACCAAATGAAGTTGGTCACTTTGAAC

TACCATACATGCCAGGAAGATGTCTACCAAACTACACATTGTAA

Exemplary feline panleukopenia virus variant VP1 capsid polypeptide construct sequences may be or comprise a VP1 capsid coding sequence according to SEQ ID NO: 100.

CTGGCACCTCCGGCAAAGAGAGCCAGGAGAGGATATAAATATCTTGGGCC

TGGGAACAGTCTTGACCAAGGAGAACCAACTAACCCTTCTGACGCCGCTG

CAAAAGAACACGACGAAGCTTACGCTGCTTATCTTCGCTCTGGTAAAAAC

CCATACTTATATTTCTCGCCAGCAGATCAACGCTTTATAGATCAAACTAA

GGACGCTAAAGATTGGGGGGGGAAAATAGGACATTATTTTTTTAGAGCTA

-continued

AAAAGGCAATTGCTCCAGTATTAACTGATACACCAGATCATCCATCAACA

TCAAGACCAACAAAACCAACTAAAAGAAGTAAACCACCACCTCATATTTT

CATCAATCTTGCAAAAAAAAAAAAAAGCCGGTGCAGGACAAGTAAAAAGAG

ACAATCTTGCACCAATGAGTGATGGAGCAGTTCAACCAGACGGTGGTCAA

CCTGCTGTCAGAAATGAAAGAGCTACAGGATCTGGGAACGGGTCTGGAGG

CGGGGGTGGTGGTGGTTCTGGGGGTGTGGGGATTTCTACGGGTACTTTCA

ATAATCAGACGGAATTTAAATTTTTGGAAAACGGATGGGTGGAAATCACA

GCAAACTCAAGCAGACTTGTACATTTAAATATGCCAGAAAGTGAAAATTA

TAAAAGAGTAGTTGTAAATAATATGGATAAAACTGCAGTTAAAGGAAACA

TGGCTTTAGATGATATTCATGTACAAATTGTAACACCTTGGTCATTGGTT

GATGCAAATGCTTGGGGAGTTTGGTTTAATCCAGGAGATTGGCAACTAAT

TGTTAATACTATGAGTGAGTTGCATTTAGTTAGTTTTGAACAAGAAATTT

TTAATGTTGTTTTAAAGACTGTTTCAGAATCTGCTACTCAGCCACCAACT

AAAGTTTATAATAATGATTTAACTGCATCATTGATGGTTGCATTAGATAG

TAATAATACTATGCCATTTACTCCAGCAGCTATGAGATCTGAGACATTGG

GTTTTTATCCATGGAAACCAACCATACCAACTCCATGGAGATATTATTTT

CAATGGGATAGAACATTAATACCATCTCATACTGGAACTAGTGGCACACC

AACAAATATATACCATGGTACAGATCCAGATGATGTTCAATTTTATACTA

TTGAAAATTCTGTGCCAGTACACTTACTAAGAACAGGTGATGAATTTGCT

ACAGGAACATTTTTTTTTGATTGTAAACCATGTAGACTAACACATACATG

GCAAACAAATAGAGCATTGGGCTTACCACCATTTTTAAATTCTTTGCCTC

AATCTGAAGGAGCTACTAACTTTGGTGATATAGGAGTTCAACAAGATAAA

AGACGTGGTGTAACTCAAATGGGAAATACAAACTATATTACTGAAGCTAC

TATTATGAGACCAGCTGAGGTTGGTTATAGTGCACCATATTATTCTTTTG

AGGCGTCTACACAAGGGCCATTTAAAACACCTATTGCAGCAGGACGGGGG

GGAGCGCAAACAGATGAAAATCAAGCAGCAGATGGTGATCCAAGATATGC

ATTTGGTAGACAACATGGTCAAAAAACTACCACAACAGGAGAAACACCTG

AGAGATTTACATATATAGCACATCAAGATACAGGAAGATATCCAGAAGGA

GATTGGATTCAAAATATTAACTTTAACCTTCCTGTAACAAATGATAATGT

ATTGCTACCAACAGATCCAATTGGAGGTAAAACAGGAATTAACTATACTA

ATATATTTAATACTTATGGTCCTTTAACTGCATTAAATAATGTACCACCA

GTTTATCCAAATGGTCAAATTTGGGATAAAGAATTTGATACTGACTTAAA

ACCAAGACTTCATGTAAATGCACCATTTGTTTGTCAAAATAATTGTCCTG

GTCAATTATTTGTAAAAGTTGCGCCTAATTTAACAAATGAATATGATCCT

GATGCATCTGCTAATATGTCAAGAATTGTAACTTACTCAGATTTTTGGTG

GAAAGGTAAATTAGTATTTAAAGCTAAACTAAGAGCCTCTCATACTTGGA

ATCCAATTCAACAAATGAGTATTAATGTAGATAACCAATTTAACTATGTA

CCAAGTAATATTGGAGCTATGAAAATTGTATATGAAAAATCTCAACTAGC

ACCTAGAAAATTATATTAA

Exemplary minute virus of mice variant VP1 capsid polypeptide construct sequences may be or comprise a VP1 capsid coding sequence according to SEQ ID NO: 101.

ACGGCGCCTCCAGCTAAAAGAGCTAAAAGAGGCTACAAGTACCTGGGACC

AGGGAACAGCCTTGACCAAGGAGAACCAACCAATCCATCTGACGCCGCTG

CCAAAGAGCACGACGAGGCCTACGATCAATACATCAAATCTGGAAAAAAT

CCTTACCTGTACTTCTCTGCTGCTGATCAACGCTTTATTGACCAAACCAA

GGACGCCAAAGACTGGGGAGGCAAGGTTGGTCACTACTTTTTTAGAACCA

AGCGCGCTTTTGCACCTAAGCTTGCTACTGACTCTGAACCTGGAACTTCT

GGTGTAAGCAGAGCTGGTAAACGCACTAGACCACCTGCTTACATTTTTAT

TAACCAAGCCAGAGCTAAAAAAAAACTTACTTCTTCTGCTGCACAGCAAA

GCAGTCAAACCATGAGTGATGGCACCAGCCAACCTGACAGCGGAAACGCT

GTCCACTCAGCTGCAAGAGTTGAACGAGCAGCTGACGGCCCTGGAGGCTC

TGGGGGTGGGGGCTCTGGCGGGGGTGGGGTTGGTGTTTCTACTGGGTCTT

ATGATAATCAAACGCATTATAGATTCTTGGGTGACGGCTGGGTAGAAATT

ACTGCACTAGCAACTAGACTAGTACATTTAAACATGCCTAAATCAGAAAA

CTATTGCAGAATCAGAGTTCACAATACAACAGACACATCAGTCAAAGGCA

ACATGGCAAAAGATGATGCTCATGAGCAAATTTGGACACCATGGAGCTTG

GTGGATGCTAATGCTTGGGGAGTTTGGCTCCAGCCAAGTGACTGGCAATA

CATTTGCAACACCATGAGCCAGCTTAACTTGGTATCACTTGATCAAGAAA

TATTCAATGTAGTGCTGAAAACTGTTACAGAGCAAGACTTAGGAGGTCAA

GCTATAAAAATATACAACAATGACCTTACAGCTTGCATGATGGTTGCAGT

AGACTCAAACAACATTTTGCCATACACACCTGCAGCAAACTCAATGGAAA

CACTTGGTTTCTACCCCTGGAAACCAACCATAGCATCACCATACAGGTAC

TATTTTTGCGTTGACAGAGATCTTTCAGTGACCTACGAAAATCAAGAAGG

CACAGTTGAACATAATGTGATGGGAACACCAAAAGGAATGAATTCTCAAT

TTTTTACCATTGAGAACACACAACAAATCACATTGCTCAGAACAGGGGAC

GAATTTGCCACAGGTACTTACTACTTTGACACAAATTCAGTTAAACTCAC

ACACACGTGGCAAACCAACCGTCAACTTGGACAGCCTCCACTGCTGTCAA

CCTTTCCTGAAGCTGACACTGATGCAGGTACACTTACTGCTCAAGGGAGC

AGACATGGAACAACACAAATGGGGGTTAACTGGGTGAGTGAAGCAATCAG

AACCAGACCTGCTCAAGTAGGATTTTGTCAACCACACAATGACTTTGAAG

CCAGCAGAGCTGGACCATTTGCTGCCCCAAAAGTTCCAGCAGATATTACT

CAAGGAGTAGACAAAGAAGCCAATGGCAGTGTTAGATACAGTTATGGCAA

ACAGCATGGTGAAAATTGGGCTTCACATGGACCAGCACCAGAGCGCTACA

CATGGGATGAAACAAGCTTTGGTTCAGGTAGAGACACCAAAGATGGTTTT

ATTCAATCAGCACCACTAGTTGTTCCACCACCACTAAATGGCATTCTTAC

AAATGCAAACCCTATTGGGACTAAAAATGACATTCATTTTTCAAATGTTT

TTAACAGCTATGGTCCACTAACTGCATTTTCACACCCAAGTCCTGTATAC

CCTCAAGGACAAATATGGGACAAAGAACTAGATCTTGAACACAAACCTAG

ACTTCACATAACTGCTCCATTTGTTTGTAAAAACAATGCACCTGGACAAA

TGTTGGTTAGATTAGGACCAAACCTAACTGACCAATATGATCCAAACGGA

GCCACACTTTCTAGAATTGTTACATACGGTACATTTTTCTGGAAAGGAAA

ACTAACCATGAGAGCAAAACTTAGAGCTAACACCACTTGGAACCCAGTGT

-continued

ACCAAGTAAGTGCTGAAGACAATGGCAACTCATACATGAGTGTAACTAAA

TGGTTACCAACTGCTACTGGAAACATGCAGTCTGTGCCGCTTATAACAAG

ACCTGTTGCTAGAAATACTTACTAA

Exemplary rat H-1 parvovirus variant VP1 capsid polypeptide construct sequences may be or comprise a VP1 capsid coding sequence according to SEQ ID NO: 102.

ACGGCACCTCCAGCTAAAAGAGCTAAAAGAGGCTACAAGTACCTGGGACC

AGGGAACAGCCTTGACCAAGGAGAACCAACCAACCCTTCTGACGCCGCTG

CCAAAGAACACGACGAAGCCTACGACCAATACATCAAATCTGGAAAAAAT

CCTTACCTGTACTTCTCTCCTGCTGATCAACGCTTCATTGACCAAACCAA

AGACGCCAAGGACTGGGGCGGCAAGGTTGGTCACTACTTTTTTAGAACCA

AGCGAGCTTTTGCACCTAAGCTTTCTACTGACTCTGAACCTGGCACTTCT

GGTGTGAGCAGACCTGGTAAACGAACTAAACCACCTGCTCACATTTTTGT

AAATCAAGCCAGAGCTAAAAAAAAACGCGCTTCTCTTGCTGCACAGCAGA

GGACTCTGACAATGAGTGATGGCACCGAAACAAACCAACCAGACACTGGA

ATCGCTAATGCTAGAGTTGAGCGATCAGCTGACGGAGGTGGAAGCTCTGG

GGGTGGGGGCTCTGGCGGGGGTGGGATTGGTGTTTCTACTGGGACTTATG

ATAATCAAACGACTTATAAGTTTTTGGGAGATGGATGGGTAGAAATAACT

GCACATGCTTCTAGACTTTTGCACTTGGGAATGCCTCCTTCAGAAAACTA

CTGCCGCGTCACCGTTCACAATAATCAAACAACAGGACACGGAACTAAGG

TAAAGGGAAACATGGCCTATGATGACACACATCAACAAATTTGGACACCA

TGGAGCTTGGTAGATGCTAATGCTTGGGGAGTTTGGTTCCAACCAAGTGA

CTGGCAGTTCATTCAAAACAGCATGGAATCGCTGAATCTTGACTCATTGA

GCCAAGAACTATTTAATGTAGTAGTCAAAACAGTCACTGAACAACAAGGA

GCTGGCCAAGATGCCATTAAAGTCTATAATAATGACTTGACGGCCTGTAT

GATGGTTGCTCTGGATAGTAACAACATACTGCCTTACACACCTGCAGCTC

AAACATCAGAAACACTTGGTTTCTACCCATGGAAACCAACCGCACCAGCT

CCTTACAGATACTACTTTTTCATGCCTAGACAACTCAGTGTAACCTCTAG

CAACTCTGCTGAAGGAACTCAAATCACAGACACCATTGGAGAGCCACAGG

CACTAAACTCTCAATTTTTTACTATTGAGAACACCTTGCCTATTACTCTC

CTGCGCACAGGTGATGAGTTTACAACTGGCACCTACATCTTTAACACTGA

CCCACTTAAACTTACTCACACATGGCAAACCAACAGACACTTGGGCATGC

CTCCAAGAATAACTGACCTACCAACATCAGATACAGCAACAGCATCACTA

ACTGCAAATGGAGACAGATTTGGATCAACACAAACACAGAATGTGAACTA

TGTCACAGAGGCTTTGCGCACCAGGCCTGCTCAGATTGGCTTCATGCAAC

CTCATGACAACTTTGAAGCAAACAGAGGTGGCCCATTTAAGGTTCCAGTG

GTACCGCTAGACATAACAGCTGGCGAGGACCATGATGCAAACGGAGCCAT

ACGATTTAACTATGGCAAACAACATGGCGAAGATTGGGCCAAACAAGGAG

CAGCACCAGAAAGGTACACATGGGATGCAATTGATAGTGCAGCTGGGAGG

GACACAGCTAGATGCTTTGTACAAAGTGCACCAATATCTATTCCACCAAA

-continued

CCAAAACCAGATCTTGCAGCGAGAAGACGCCATAGCTGGCAGAACTAACA

TGCATTATACTAATGTTTTTAACAGCTATGGTCCACTTAGTGCATTTCCT

CATCCAGATCCCATTTATCCAAATGGACAAATTTGGGACAAAGAATTGGA

CCTGGAACACAAACCTAGACTACACGTAACTGCACCATTTGTTTGTAAAA

ACAACCCACCAGGTCAACTATTTGTTCGCTTGGGGCCTAATCTGACTGAC

CAATTTGACCCAAACAGCACAACTGTTTCTCGCATTGTTACATATAGCAC

TTTTTACTGGAAGGGTATTTTGAAATTCAAAGCCAAACTAAGACCAAATC

TGACCTGGAATCCTGTATACCAAGCAACCACAGACTCTGTTGCCAATTCT

TACATGAATGTTAAGAAATGGCTCCCATCTGCAACTGGCAACATGCACTC

TGATCCATTGATTTGTAGACCTGTGCCTCACATGACATACTAA

Exemplary Variant VP1 Capsid Polypeptide Sequences

Exemplary bufavirus variant VP1 capsid polypeptide construct sequences may be or comprise a polypeptide sequence according to SEQ ID NO: 103.

MPAIRKARGYNYLGPFNQDFSKKPTNPSDNAARKHDLEYNKLIKQGHNPY

WNYNHADEDFIKETDQATDWGGKFGNFVFRAKRALAPELAPPAKKKTKTK

HTEPEYSHKHIKAGTKRGKPFYLFVNLARKKARMTDTQDVSEQQSDQPSV

ASTSAKAGGGGGGGGSGVGHSTGNYNNRTEFYYHGDEVTIVCHSSRHIHL

NMSESEEYKIYDTDRGPTFPTDQTLQGRDTINDSYHAQVETPWFLINPNS

WGTWMNPADFQQLTTTCREVTLEHLDQTLDNIVIKTVSKQGSGAEETTQY

NNDLTALLQVALDKSNQLPWVADNMYLDSLGYIPWRPCKLKQYSYHVNFW

NTIDIISGPQQNQWQQVKKEIKWDDLQFTPIETTTEIDLLRTGDSWTSGP

YKFNTKPTQLSYHWQSTRHTGSVHPTEPPNAIGQQGRNIIDINGWQWGDR

SNPMSAATRVSNFHIGYSWPEWRIHYGSGGPAINPGAPFSQAPWSTDPQV

RLTQGASEKAIFDYNHGDDDPAHRDQWWQNNLPMTGQTDWAPKNAHQTNV

SNNIPSRQEFWTQDYHNTFGPFTAVDDVGIQYPWGAIWTKTPDTTHKPMM

SAHAPFICKDGPPGQLLVKLAPNYTENLQTDGLGNNRIVTYATFWWTGKL

VLKGKLRLPRQFNLYNLPGRPRGTEAKKFLPNEIGHFELPFMPGRCMPNY

TI

Exemplary canine parvovirus (CPV) variant VP1 capsid polypeptide construct sequences may be or comprise a polypeptide sequence according to SEQ ID NO: 104.

LAPPAKRARRGYKYLGPGNSLDQGEPTNPSDAAAKEHDEAYAAYLRSGKN

PYLYFSPADQRFIDQTKDAKDWGGKIGHYFFRAKKAIAPVLTDTPDHPST

SRPTKPTKRSKPPPHIFINLAKKKKAGAGQVKRDNLAPMSDGAVQPDGGQ

PAVRNERATGSGNGSGGGGGGGSGGVGISTGTFNNQTEFKFLENGWVEIT

ANSSRLVHLNMPESENYRRVVVNNMDKTAVNGNMALDDIHAQIVTPWSLV

DANAWGVWFNPGDWQLIVNTMSELHLVSFEQEIFNVVLKTVSESATQPPT

KVYNNDLTASLMVALDSNNTMPFTPAAMRSETLGFYPWKPTIPTPWRYYF

QWDRTLIPSHTGTSGTPTNIYHGTDPDDVQFYTIENSVPVHLLRTGDEFA

TGTFFFDCKPCRLTHTWQTNRALGLPPFLNSLPQSEGATNFGDIGVQQDK

-continued

RRGVTQMGNTNYITEATIMRPAEVGYSAPYYSFEASTQGPFKTPIAAGRG
GAQTYENQAADGDPRYAFGRQHGQKTTTTGETPERFTYIAHQDTGRYPEG
DWIQNINFNLPVTNDNVLLPTDPIGGKTGINYTNIFNTYGPLTALNNVPP
VYPNGQIWDKEFDTDLKPRLHVNAPFVCQNNCPGQLFVKVAPNLTNEYDP
DASANMSRIVTYSDFWWKGKLVFKAKLRASHTWNPIQQMSINVDNQFNYV
PSNIGGMKIVYEKSQLAPRKLY

Exemplary cutavirus variant VP1 capsid polypeptide construct sequences may be or comprise a polypeptide sequence according to SEQ ID NO: 105.

MPAIRKARGYNFLGPFNQDENKEPTNPSDNAAKQHDLEYNKLINQGHNPY
WYYNKADEDFIKATDQAPDWGGKFGNFIFRAKKHIAPELAPPAKKKSKTK
HPEPEFSHKHIKPGTKRGKPFHIFVNLARKRARMSEPAENTNDQPNDSPV
EQGAGQIGGGGGGGGSGVGHSTGDYNNRTEFIYHGDEVTIICHSTRLVHI
NMSDREDYIIYETDRGQLFPTTQDLQGRDTLNDSYHAKVETPWKLLHANS
WGCWFSPADFQQMITTCRDIAPIQMHQKIENIVIKTVSKTGTGETETTNY
NNDLTALLQIAQDNSNLLPWAADNFYIDSVGYVPWRACKLPTYCYHVDTW
NTIDINQADAPNRWREIKKGIQWDNIQFTPLETMINIDLLRTGDAWQSGN
YNFHTKPTNLAYHWQSQRHTGSCHPTVAPLVERGQGTNIQSVNCWQWGDR
NNPSSASTRVSNMHIGYSFPEWQIHYSTGGPVINPGSAFSQAPWGSTTEG
TRLTQGASEKAIYDWAHGDDQPGARETWWQNNQHVTGQTDWAPKNAHTSE
LNNNVPAATHFWKNSYHNTFSPFTAVDDHGPQYPWGAIWGKYPDTTHKPM
MSAHAPFLLHGPPGQLFVKLAPNYTDTLDNGGVTHPRIVTYGTFWWSGKL
IFKGKLRTPRQWNTYNLPSLDKRETMKNTVPNEVGHFELPYMPGRCLPNY
TL

Exemplary cutavirus variant VP1 capsid polypeptide construct sequences may be or comprise a polypeptide sequence according to SEQ ID NO: 106.

TPAIRKARGPFNQDFNKEPTNPSDNAAKQHDLEYNKLINQGHNPYWYYNK
ADEDFIKATDQAPDWGGKFGNFIFRAKKHIAPELAPPAKKKSKTKHSEPE
FSHKHIKPGTKRGKPFHIFVNLARKRARMSEPANDTNEQPDNSPVEQGAG
QIGGGGGGGGSGVGHSTGDYNNRTEFIYHGDEVTIICHSTRLVHINMSDR
EDYIIYETDRGPLFPTTQDLQGRDTLNDSYHAKVETPWKLLHANSWGCWF
SPADFQQMITTCRDIAPIKMHQKIENIVIKTVSKTGTGETETTNYNNDLT
ALLQIAQDNSNLLPWAADNFYIDSVGYVPWRACKLPTYCYHVDTWNTIDI
NQADTPNQWREIKKGIQWDNIQFTPLETMINIDLLRTGDAWESGNYNFHT
KPTNLAYHWQSQRHTGSCHPTVAPLVERGQGTNIQSVNCWQWGDRNNPSS
ASTRVSNIHIGYSFPEWQIHYSTGGPVINPGSAFSQAPWGSTTEGTRLTQ
GASEKAIYDWSHGDDQPGARETWWQNNQHVTGQTDWAPKNAHTSELNNNV
PAATHFWKNSYHNTFSPFTAVDDHGPQYPWGAIWGKYPDTTHKPMMSAHA
PFLLHGPPGQLFVKLAPNYTDTLDNGGVTHPRIVTYGTFWWSGQLIFKGK
LRTPRQWNTYNLPSLDKRETMKNTVPNEVGHFELPYMPGRCLPNYTL

Exemplary feline panleukopenia virus variant VP1 capsid polypeptide construct sequences may be or comprise a polypeptide sequence according to SEQ ID NO: 107.

LAPPAKRARRGYKYLGPGNSLDQGEPTNPSDAAAKEHDEAYAAYLRSGKN
PYLYFSPADQRFIDQTKDAKDWGGKIGHYFFRAKKAIAPVLTDTPDHPST
SRPTKPTKRSKPPPHIFINLAKKKKAGAGQVKRDNLAPMSDGAVQPDGGQ
PAVRNERATGSGNGSGGGGGGGSGGVGISTGTFNNQTEFKFLENGWVEIT
ANSSRLVHLNMPESENYKRVVVNNMDKTAVKGNMALDDIHVQIVTPWSLV
DANAWGVWFNPGDWQLIVNTMSELHLVSFEQEIFNVVLKTVSESATQPPT
KVYNNDLTASLMVALDSNNTMPFTPAAMRSETLGFYPWKPTIPTPWRYYF
QWDRTLIPSHTGTSGTPTNIYHGTDPDDVQFYTIENSVPVHLLRTGDEFA
TGTFFFDCKPCRLTHTWQTNRALGLPPFLNSLPQSEGATNFGDIGVQQDK
RRGVTQMGNTNYITEATIMRPAEVGYSAPYYSFEASTQGPFKTPIAAGRG
GAQTDENQAADGDPRYAFGRQHGQKTTTTGETPERFTYIAHQDTGRYPEG
DWIQNINFNLPVTNDNVLLPTDPIGGKTGINYTNIFNTYGPLTALNNVPP
VYPNGQIWDKEFDTDLKPRLHVNAPFVCQNNCPGQLFVKVAPNLTNEYDP
DASANMSRIVTYSDFWWKGKLVFKAKLRASHTWNPIQQMSINVDNQFNYV
PSNIGAMKIVYEKSQLAPRKLY

Exemplary minute virus of mice variant VP1 capsid polypeptide construct sequences may be or comprise a polypeptide sequence according to SEQ ID NO: 108.

TAPPAKRAKRGYKYLGPGNSLDQGEPTNPSDAAAKEHDEAYDQYIKSGKN
PYLYFSAADQRFIDQTKDAKDWGGKVGHYFFRTKRAFAPKLATDSEPGTS
GVSRAGKRTRPPAYIFINQARAKKKLTSSAAQQSSQTMSDGTSQPDSGNA
VHSAARVERAADGPGGSGGGGSGGGGVGVSTGSYDNQTHYRFLGDGWVEI
TALATRLVHLNMPKSENYCRIRVHNTTDTSVKGNMAKDDAHEQIWTPWSL
VDANAWGVWLQPSDWQYICNTMSQLNLVSLDQEIFNVVLKTVTEQDLGGQ
AIKIYNNDLTACMMVAVDSNNILPYTPAANSMETLGFYPWKPTIASPYRY
YFCVDRDLSVTYENQEGTVEHNVMGTPKGMNSQFFTIENTQQITLLRTGD
EFATGTYYFDTNSVKLTHTWQTNRQLGQPPLLSTFPEADTDAGTLTAQGS
RHGTTQMGVNWVSEAIRTRPAQVGFCQPHNDFEASRAGPFAAPKVPADIT
QGVDKEANGSVRYSYGKQHGENWASHGPAPERYTWDETSFGSGRDTKDGF
IQSAPLVVPPPLNGILTNANPIGTKNDIHFSNVFNSYGPLTAFSHPSPVY
PQGQIWDKELDLEHKPRLHITAPFVCKNNAPGQMLVRLGPNLTDQYDPNG
ATLSRIVTYGTFFWKGKLTMRAKLRANTTWNPVYQVSAEDNGNSYMSVTK
WLPTATGNMQSVPLITRPVARNTY

Exemplary tusavirus variant VP1 capsid polypeptide construct sequences may be or comprise a polypeptide sequence according to SEQ ID NO: 109.

MAPAARPRKGYNYLGPGNDLDAGEPTNKSDAAARKHDFAYSAYLKQGLDP
YWNFNKADEKFIRDTEGATDWGGRLGHWIFRAKKHILPHLKEPTLAGRKR

-continued

PAPAHIFVNLANKRKKGLPTRKDQQKDTLDSNAQQPVREADQPDGMAASS

SDSGPSSSGGGARAGGVGVSTGDFDNTTLWDFHEDGTATITCNSTRLVHL

TRPDSLDYKIIPTQNNTAVQTVGHMMDDDNHTQVLTPWSLVDCNAWGVWL

SPHDWQHIMNIGEELELLSLEQEVFNVTLKTATETGPPESRITMYNNDLT

AVMMITTDTNNQLPYTPAAIRSETLGFYPWRPTVVPRWRYYFDWDRFLSV

TSSSDQSTSIINHSSTQSAIGQFFVIETQLPIALLRTGDSYATGGYKFDC

NKVNLGRHWQTTRSLGLPPKIEPPTSESALGTINQNARLGWRWGINDVHE

TNVVRPCTAGYNHPEWFYTHTLEGPAIDPAPPTSIPSNWGGGTPPDTRAS

SHNQQRITYNYNHGNKDENLNNFSLNPNIELGSIINQGNFLSYEGNGQQI

NTTAGVGKNGETATSDPNLVRYMPNTYGVYTAVDHQGPVYPHGQIWDKQI

HTDKKPELHCLAPFTCKNNPPGQMFVRIAPNLTDTFNATPTFSEIITYAD

FWWKGTLKMKIKLRPPHQWNIATVLGAAVNIGDAARFVPNRLGQLEFPVI

NGRIVPSTVY

Exemplary rat H-1 parvovirus variant VP1 capsid polypeptide construct sequences may be or comprise a polypeptide sequence according to SEQ ID NO: 110.

TAPPAKRAKRGYKYLGPGNSLDQGEPTNPSDAAAKEHDEAYDQYIKSGKN

PYLYFSPADQRFIDQTKDAKDWGGKVGHYFFRTKRAFAPKLSTDSEPGTS

GVSRPGKRTKPPAHIFVNQARAKKKRASLAAQQRTLTMSDGTETNQPDTG

IANARVERSADGGGSSGGGGSGGGGIGVSTGTYDNQTTYKFLGDGWVEIT

AHASRLLHLGMPPSENYCRVTVHNNQTTGHGTKVKGNMAYDDTHQQIWTP

WSLVDANAWGVWFQPSDWQFIQNSMESLNLDSLSQELFNVVVKTVTEQQG

AGQDAIKVYNNDLTACMMVALDSNNILPYTPAAQTSETLGFYPWKPTAPA

PYRYYFFMPRQLSVTSSNSAEGTQITDTIGEPQALNSQFFTIENTLPITL

LRTGDEFTTGTYIFNTDPLKLTHTWQTNRHLGMPPRITDLPTSDTATASL

TANGDRFGSTQTQNVNYVTEALRTRPAQIGFMQPHDNFEANRGGPFKVPV

VPLDITAGEDHDANGAIRFNYGKQHGEDWAKQGAAPERYTWDAIDSAAGR

DTARCFVQSAPISIPPNQNQILQREDAIAGRTNMHYTNVFNSYGPLSAFP

HPDPIYPNGQIWDKELDLEHKPRLHVTAPFVCKNNPPGQLFVRLGPNLTD

QFDPNSTTVSRIVTYSTFYWKGILKFKAKLRPNLTWNPVYQATTDSVANS

YMNVKKWLPSATGNMHSDPLICRPVPHMTY iii. Exemplary VP2 Capsid Sequences

In some embodiments, constructs, compositions, virions, or populations of virions comprise a coding sequence that encodes a protoparvovirus VP2 capsid polypeptide. In some embodiments, a protoparvovirus VP2 polypeptide of a protoparvovirus is encoded by a coding sequence with at least 85%, 90%, 95%, 98% or 99% sequence identity to a coding sequence described herein. In some embodiments, a protoparvovirus VP2 capsid polypeptide of a protoparvovirus comprises a polypeptide with at least 85%, 90%, 95%, 98% or 99% sequence identity to a polypeptide of a sequence described herein.

Exemplary Bufavirus (BuV) VP2 Sequences

Exemplary bufavirus VP2 capsid polypeptide sequences may be or comprise a polypeptide sequence according to SEQ ID NO: 111.

MTDTQDVSEQQSDQPSVASTSAKAGGGGGGGGSGVGHSTGNYNNRTEFYY

HGDEVTIVCHSSRHIHLNMSESEEYKIYDTDRGPTFPTDQTLQGRDTIND

SYHAQVETPWFLINPNSWGTWMNPADFQQLTTTCREVTLEHLDQTLDNIV

IKTVSKQGSGAEETTQYNNDLTALLQVALDKSNQLPWVADNMYLDSLGYI

PWRPCKLKQYSYHVNFWNTIDIISGPQQNQWQQVKKEIKWDDLQFTPIET

TTEIDLLRTGDSWTSGPYKFNTKPTQLSYHWQSTRHTGSVHPTEPPNAIG

QQGRNIIDINGWQWGDRSNPMSAATRVSNFHIGYSWPEWRIHYGSGGPAI

NPGAPFSQAPWSTDPQVRLTQGASEKAIFDYNHGDDDPAHRDQWWQNNLP

MTGQTDWAPKNAHQTNVSNNIPSRQEFWTQDYHNTFGPFTAVDDVGIQYP

WGAIWTKTPDTTHKPMMSAHAPFICKDGPPGQLLVKLAPNYTENLQTDGL

GNNRIVTYATFWWTGKLVLKGKLRLPRQFNLYNLPGRPRGTEAKKFLPNE

IGHFELPFMPGRCMPNYTI

Exemplary Canine Parvovirus (CPV) VP2 Sequences

Exemplary canine parvovirus (CPV) VP2 capsid polypeptide sequences may be or comprise a polypeptide sequence according to SEQ ID NO: 112.

MSDGAVQPDGGQPAVRNERATGSGNGSGGGGGGGSGGVGISTGTFNNQTE

FKFLENGWVEITANSSRLVHLNMPESENYRRVVVNNLDKTAVNGNMALDD

THAQIVTPWSLVDANAWGVWFNPGDWQLIVNTMSELHLVSFEQEIFNVVL

KTVSESATQPPTKVYNNDLTASLMVALDSNNTMPFTPAAMRSETLGFYPW

KPTIPTPWRYYFQWDRTLIPSHTGTSGTPTNIYHGTDPDDVQFYTIENSV

PVHLLRTGDEFATGTFFFDCKPCRLTHTWQTNRALGLPPFLNSLPQSEGG

TNFGYIGVQQDKRRGVTQMGNTNYITEATIMRPAEVGYSAPYYSFEASTQ

GPFKTPIAAGRGGAQTDENQAADGDPRYAFGRQHGQKTTTTGETPERFTY

IAHQDTGRYPEGDWIQNINFNLPVTDDNVLLPTDPIGGKTGINYTNIFNT

YGPLTALNNVPPVYPNGQIWDKEFDTDLKPRLHVNAPFVCQNNCPGQLFV

KVAPNLTNEYDPDASANMSRIVTYSDFWWKGKLVFKAKLRASHTWNPIQQ

MSINVDNQFNYVPSNIGGMKIVYEKSQLAPRKLY

Exemplary canine parvovirus (CPV) VP2 capsid polypeptide sequences may be or comprise a coding sequence according to SEQ ID NO: 113.

ATGAGCGACGGCGCCGTGCAGCCCGACGGCGGCCAGCCCGCCGTGCGCAA

CGAGCGCGCCACCGGCAGCGGCAACGGCAGCGGCGGCGGCGGCGGCGGCG

GCAGCGGCGGCGTGGGCATCAGCACCGGCACCTTCAACAACCAGACCGAG

TTCAAGTTCCTGGAGAACGGCTGGGTGGAGATCACCGCCAACAGCAGCCG

CCTGGTGCACCTGAACATGCCCGAGAGCGAGAACTACCGCCGCGTGGTGG

TGAACAACATGGACAAGACCGCCGTGAACGGCAACATGGCCCTGGACGAC

ATCCACGCCCAGATCGTGACCCCCTGGAGCCTGGTGGACGCCAACGCCTG

GGGCGTGTGGTTCAACCCCGGCGACTGGCAGCTGATCGTGAACACCATGA

GCGAGCTGCACCTGGTGAGCTTCGAGCAGGAGATCTTCAACGTGGTGCTG

AAGACCGTGAGCGAGAGCGCCACCCAGCCCCCCACCAAGGTGTACAACAA

-continued

CGACCTGACCGCCAGCCTGATGGTGGCCCTGGACAGCAACAACACCATGC

CCTTCACCCCCGCCGCCATGCGCAGCGAGACCCTGGGCTTCTACCCCTGG

AAGCCCACCATCCCCACCCCCTGGCGCTACTACTTCCAGTGGGACCGCAC

CCTGATCCCCAGCCACACCGGCACCAGCGGCACCCCCACCAACATCTACC

ACGGCACCGACCCCGACGACGTGCAGTTCTACACCATCGAGAACAGCGTG

CCCGTGCACCTGCTGCGCACCGGCGACGAGTTCGCCACCGGCACCTTCTT

CTTCGACTGCAAGCCCTGCCGCCTGACCCACACCTGGCAGACCAACCGCG

CCCTGGGCCTGCCCCCCTTCCTGAACAGCCTGCCCCAGAGCGAGGGCGCC

ACCAACTTCGGCGACATCGGCGTGCAGCAGGACAAGCGCCGCGGCGTGAC

CCAGATGGGCAACACCAACTACATCACCGAGGCCACCATCATGCGCCCCG

CCGAGGTGGGCTACAGCGCCCCCTACTACAGCTTCGAGGCCAGCACCCAG

GGCCCCTTCAAGACCCCCATCGCCGCCGGCCGCGGCGGCGCCCAGACCTA

CGAGAACCAGGCCGCCGACGGCGACCCCCGCTACGCCTTCGGCCGCCAGC

ACGGCCAGAAGACCACCACCACCGGCGAGACCCCCGAGCGCTTCACCTAC

ATCGCCCACCAGGACACCGGCCGCTACCCCGAGGGCGACTGGATCCAGAA

CATCAACTTCAACCTGCCCGTGACCAACGACAACGTGCTGCTGCCCACCG

ACCCCATCGGCGGCAAGACCGGCATCAACTACACCAACATCTTCAACACC

TACGGCCCCCTGACCGCCCTGAACAACGTGCCCCCCGTGTACCCCAACGG

CCAGATCTGGGACAAGGAGTTCGACACCGACCTGAAGCCCCGCCTGCACG

TGAACGCCCCCTTCGTGTGCCAGAACAACTGCCCCGGCCAGCTGTTCGTG

AAGGTGGCCCCCAACCTGACCAACGAGTACGACCCCGACGCCAGCGCCAA

CATGAGCCGCATCGTGACCTACAGCGACTTCTGGTGGAAGGGCAAGCTGG

TGTTCAAGGCCAAGCTGCGCGCCAGCCACACCTGGAACCCCATCCAGCAG

ATGAGCATCAACGTGGACAACCAGTTCAACTACGTGCCCAGCAACATCGG

CGGCATGAAGATCGTGTACGAGAAGAGCCAGCTGGCCCCCCGCAAGCTGT

AC

Exemplary Cutavirus (CuV) Parvovirus VP2 Sequences

Exemplary cutavirus VP2 capsid polypeptide sequences may be or comprise a polypeptide sequence according to SEQ ID NO: 114.

MSEPANDTNEQPDNSPVEQGAGQIGGGGGGGGSGVGHSTGDYNNRTEFIY

HGDEVTIICHSTRLVHINMSDREDYIIYETDRGPLFPTTQDLQGRDTLND

SYHAKVETPWKLLHANSWGCWFSPADFQQMITTCRDIAPIKMHQKIENIV

IKTVSKTGTGETETTNYNNDLTALLQIAQDNSNLLPWAADNFYIDSVGYV

PWRACKLPTYCYHVDTWNTIDINQADTPNQWREIKKGIQWDNIQFTPLET

MINIDLLRTGDAWESGNYNFHTKPTNLAYHWQSQRHTGSCHPTVAPLVER

GQGTNIQSVNCWQWGDRNNPSSASTRVSNIHIGYSFPEWQIHYSTGGPVI

NPGSAFSQAPWGSTTEGTRLTQGASEKAIYDWSHGDDQPGARETWWQNNQ

HVTGQTDWAPKNAHTSELNNNVPAATHFWKNSYHNTFSPFTAVDDHGPQY

PWGAIWGKYPDTTHKPMMSAHAPFLLHGPPGQLFVKLAPNYTDTLDNGGV

-continued

THPRIVTYGTFWWSGQLIFKGKLRTPRQWNTYNLPSLDKRETMKNTVPNE

VGHFELPYMPGRCLPNYTL

Exemplary cutavirus VP2 capsid polypeptide sequences may be or comprise a coding sequence according to SEQ ID NO: 115.

ATGAGCGAGCCCGCCAACGACACCAACGAGCAGCCCGACAACAGCCCCGT

GGAGCAGGGCGCCGGCCAGATCGGCGGCGGCGGCGGCGGCGGCGGCAGCG

GCGTGGGCCACAGCACCGGCGACTACAACAACCGCACCGAGTTCATCTAC

CACGGCGACGAGGTGACCATCATCTGCCACAGCACCCGCCTGGTGCACAT

CAACATGAGCGACCGCGAGGACTACATCATCTACGAGACCGACCGCGGCC

CCCTGTTCCCCACCACCCAGGACCTGCAGGGCCGCGACACCCTGAACGAC

AGCTACCACGCCAAGGTGGAGACCCCCTGGAAGCTGCTGCACGCCAACAG

CTGGGGCTGCTGGTTCAGCCCCGCCGACTTCCAGCAGATGATCACCACCT

GCCGCGACATCGCCCCCATCAAGATGCACCAGAAGATCGAGAACATCGTG

ATCAAGACCGTGAGCAAGACCGGCACCGGCGAGACCGAGACCACCAACTA

CAACAACGACCTGACCGCCCTGCTGCAGATCGCCCAGGACAACAGCAACC

TGCTGCCCTGGGCCGCCGACAACTTCTACATCGACAGCGTGGGCTACGTG

CCCTGGCGCGCCTGCAAGCTGCCCACCTACTGCTACCACGTGGACACCTG

GAACACCATCGACATCAACCAGGCCGACACCCCCAACCAGTGGCGCGAGA

TCAAGAAGGGCATCCAGTGGGACAACATCCAGTTCACCCCCCTGGAGACC

ATGATCAACATCGACCTGCTGCGCACCGGCGACGCCTGGGAGAGCGGCAA

CTACAACTTCCACACCAAGCCCACCAACCTGGCCTACCACTGGCAGAGCC

AGCGCCACACCGGCAGCTGCCACCCCACCGTGGCCCCCCTGGTGGAGCGC

GGCCAGGGCACCAACATCCAGAGCGTGAACTGCTGGCAGTGGGGCGACCG

CAACAACCCCAGCAGCGCCAGCACCCGCGTGAGCAACATCCACATCGGCT

ACAGCTTCCCCGAGTGGCAGATCCACTACAGCACCGGCGGCCCCGTGATC

AACCCCGGCAGCGCCTTCAGCCAGGCCCCCTGGGGCAGCACCACCGAGGG

CACCCGCCTGACCCAGGGCGCCAGCGAGAAGGCCATCTACGACTGGAGCC

ACGGCGACGACCAGCCCGGCGCCCGCGAGACCTGGTGGCAGAACAACCAG

CACGTGACCGGCCAGACCGACTGGGCCCCCAAGAACGCCCACACCAGCGA

GCTGAACAACAACGTGCCCGCCGCCACCCACTTCTGGAAGAACAGCTACC

ACAACACCTTCAGCCCCTTCACCGCCGTGGACGACCACGGCCCCCAGTAC

CCCTGGGGCGCCATCTGGGGCAAGTACCCCGACACCACCCACAAGCCCAT

GATGAGCGCCCACGCCCCCTTCCTGCTGCACGGCCCCCCCGGCCAGCTGT

TCGTGAAGCTGGCCCCCAACTACACCGACACCCTGGACAACGGCGGCGTG

ACCCACCCCCGCATCGTGACCTACGGCACCTTCTGGTGGAGCGGCCAGCT

GATCTTCAAGGGCAAGCTGCGCACCCCCCGCCAGTGGAACACCTACAACC

TGCCCAGCCTGGACAAGCGCGAGACCATGAAGAACACCGTGCCCAACGAG

GTGGGCCACTTCGAGCTGCCCTACATGCCCGGCCGCTGCCTGCCCAACTA

CACCCTG

Exemplary Feline Panleukopenia Virus (FPV) VP2 Sequences

Exemplary feline panleukopenia virus VP2 capsid polypeptide sequences may be or comprise a polypeptide sequence according to SEQ ID NO: 116.

```
MSDGAVQPDGGQPAVRNERATGSGNGSGGGGGGGSGGVGISTGTFNNQTE

FKFLENGWVEITANSSRLVHLNMPESENYKRVVVNNMDKTAVKGNMALDD

IHVQIVTPWSLVDANAWGVWFNPGDWQLIVNTMSELHLVSFEQEIFNVVL

KTVSESATQPPTKVYNNDLTASLMVALDSNNTMPFTPAAMRSETLGFYPW

KPTIPTPWRYYFQWDRTLIPSHTGTSGTPTNIYHGTDPDDVQFYTIENSV

PVHLLRTGDEFATGTFFFDCKPCRLTHTWQTNRALGLPPFLNSLPQSEGA

TNFGDIGVQQDKRRGVTQMGNTNYITEATIMRPAEVGYSAPYYSFEASTQ

GPFKTPIAAGRGGAQTDENQAADGDPRYAFGRQHGQKTTTTGETPERFTY

IAHQDTGRYPEGDWIQNINFNLPVTNDNVLLPTDPIGGKTGINYTNIFNT

YGPLTALNNVPPVYPNGQIWDKEFDTDLKPRLHVNAPFVCQNNCPGQLFV

KVAPNLTNEYDPDASANMSRIVTYSDFWWKGKLVFKAKLRASHTWNPIQQ

MSINVDNQFNYVPSNIGAMKIVYEKSQLAPRKLY
```

Exemplary Tusavirus (TuV) VP2 Sequences

Exemplary tusavirus VP2 capsid polypeptide sequences may be or comprise a polypeptide sequence according to SEQ ID NO: 117.

```
MAASSSDSGPSSSGGGARAGGVGVSTGDFDNTTLWDFHEDGTATITCNST

RLVHLTRPDSLDYKIIPTQNNTAVQTVGHMMDDDNHTQVLTPWSLVDCNA

WGVWLSPHDWQHIMNIGEELELLSLEQEVFNVTLKTATETGPPESRITMY

NNDLTAVMMITTDTNNQLPYTPAAIRSETLGFYPWRPTVVPRWRYYFDWD

RFLSVTSSSDQSTSIINHSSTQSAIGQFFVIETQLPIALLRTGDSYATGG

YKFDCNKVNLGRHWQTTRSLGLPPKIEPPTSESALGTINQNARLGWRWGI

NDVHETNVVRPCTAGYNHPEWFYTHTLEGPAIDPAPPTSIPSNWGGGTPP

DTRASSHNQQRITYNYNHGNKDENLNNFSLNPNIELGSIINQGNFLSYEG

NGQQINTTAGVGKNGETATSDPNLVRYMPNTYGVYTAVDHQGPVYPHGQI

WDKQIHTDKKPELHCLAPFTCKNNPPGQMFVRIAPNLTDTFNATPTFSEI

ITYADFWWKGTLKMKIKLRPPHQWNIATVLGAAVNIGDAARFVPNRLGQL

EFPVINGRIVPSTVY
```

In some embodiments, a protoparvovirus capsid polypeptide comprises one or more of structural proteins of a protoparvovirus variant VP1 capsid polypeptide and/or VP2 capsid polypeptide. VP2 capsid polypeptide may be present in excess of VP1 (e.g., in ratio of VP2 capsid polypeptide to VP1 capsid polypeptide is 25:1, 20:1, 15:1, 10:1, 5:1).

iv. Expression Control Sequences

In some embodiments, a construct comprises an expression control sequence. In some embodiments, an expression control sequence comprises or is a promoter. The term "expression control sequence" or "promoter" refers to a DNA sequence recognized by enzymes/proteins that can promote and/or initiate transcription of an operably linked coding sequence. In some embodiments, a construct encoding a protoparvovirus variant VP1 capsid polypeptide can include a promoter and/or an enhancer. For example, a promoter typically refers to, e.g., a nucleotide sequence to which an RNA polymerase and/or any associated factor binds and from which it can initiate transcription. Thus, in some embodiments, a construct comprises a promoter operably linked to a non-limiting example promoter described herein. Additional examples of promoters are known in the art.

In some embodiments, a promoter comprises: (a) an immediate early promoter of an animal DNA virus, (b) an immediate early promoter of an insect virus, or (c) a host cell promoter. In some embodiments, a promoter is a polyhedrin (polh) promoter or an Immediately early 1 gene (IE-1) promoter. In some embodiments, a nucleotide sequence comprising at least one replication protein of an AAV (e.g., AAV2) comprises a nucleotide sequence encoding Rep52 and/or Rep78.

In some embodiments, an expression control sequence is a polyhedrin promoter, a P10 promoter, a CMV-b-actin promoter, an OpiE1 promoter, a JeT promoter, a Ubiquitin C promoter, or a truncated CMV enhancer and promoter. An exemplary polyhedrin promoter sequence may be or comprise a sequence according to SEQ ID NO: 118. An exemplary CMV-b-actin promoter sequence may be or comprise a sequence according to SEQ ID NO: 119. An exemplary OpiE1 promoter sequence may be or comprise a sequence according to SEQ ID NO: 120. An exemplary P10 promoter sequence may be or comprise a sequence according to SEQ ID NO: 121.

Exemplary Polyhedrin Promoter Sequence (SEQ ID NO: 118)

```
CATGGAGATAATTAAAATGATAACCATCTCGCAAATAAATAAGTATTTTA

CTGTTTTCGTAACAGTTTTGTAATAAAAAAACCTATAAA
```

```
Exemplary CMV-b-actin promoter sequence
                                     (SEQ ID NO: 119)
GGTACCTCTGGTCGTTACATAACTTACGGTAAATGGCCCGCCTGGCTGAC

CGCCCAACGACCCCCGCCCATTGACGTCAATAATGACGTATGTTCCCATAG

TAACGCCAATAGGGACTTTCCATTGACGTCAATGGGTGGAGTATTTACGG

TAAACTGCCCACTTGGCAGTACATCAAGTGTATCATATGCCAAGTACGCC

CCCTATTGACGTCAATGACGGTAAATGGCCCGCCTGGCATTATGCCCAGT

ACATGACCTTATGGGACTTTCCTACTTGGCAGTACATCTACTCGAGGCCA

CGTTCTGCTTCACTCTCCCCATCTCCCCCCCCTCCCCACCCCCAATTTTG

TATTTATTTATTTTTTAATTATTTTGTGCAGCGATGGGGGCGGGGGGGGG

GGGGGGGCGCGCGCCAGGCGGGGCGGGGCGGGGCGAGGGGCGGGGCGGGG

CGAGGCGGAGAGGTGCGGCGGCAGCCAATCAGAGCGGCGCGCTCCGAAAG

TTTCCTTTTATGGCGAGGCGGCGGCGGCGGCGGCCCTATAAAAAGCGAAG

CGCGCGGCGGGCGGGAGCGGGATCAGCCAC
```

```
Exemplary OpiE1 promoter sequence
                                     (SEQ ID NO: 120)
GCGAAACACGCACGGCGCGCGCACGCAGCTTAGCACAAACGCGTCGTTGC

ACGCGCCCACCGCTAACCGCAGGCCAATCGGTCGGCCGGCCTCATATCCG

CTCACCAGCCGCGTCCTATCGGGCGCGGCTTCCGCGCCCATTTTGAATAA

ATAAACGATAACGCCGTTGGTGGCGTGAGGCATGTAAAAGGTTACATCAT
```

-continued

TATCTTGTTCGCCATCCGGTTGGTATAAATAGACGTTCATGTTGGTTTTT

GTTTCAGTTGCAAGTTGGCTGCGGCGCGCGCAGCACCTTTGC

Exemplary P10 promoter sequence
(SEQ ID NO: 121)
GACCTTTAATTCAACCCAACACAATATATTATAGTTAAATAAGAATTATT

ATCAAATCATTTGTATATTAATTAAAATACTATACTGTAAATTACATTTT

ATTTACAATC

Exemplary JeT promoter sequence
(SEQ ID NO: 157)
GGGCGGAGTTAGGGCGGAGCCAATCAGCGTGCGCCGTTCCGAAAGTTGCC

TTTTATGGCTGGGCGGAGAATGGGCGGTGAACGCCGATGATTATATAAGG

ACGCGCCGGGTGTGGCACAGCTAGTTCCGTCGCAGCCGGGATTTGGGTCG

CGGTTCTTGTTTGTGGATCCCTGTGATCGTCACTTGACA

Exemplary Ubiquitin C promoter sequence
(SEQ ID NO: 158)
GGCCTCCGCGCCGGGTTTTGGCGCCTCCCGCGGGCGCCCCCCTCCTCA

CGGCGAGCGCTGCCACGTCAGACGAAGGGCGCAGGAGCGTTCCTGATCCT

TCCGCCCGGACGCTCAGGACAGCGGCCCGCTGCTCATAAGACTCGGCCTT

AGAACCCCAGTATCAGCAGAAGGACATTTTAGGACGGGACTTGGGTGACT

CTAGGGCACTGGTTTTCTTTCCAGAGAGCGGAACAGGCGAGGAAAAGTAG

TCCCTTCTCGGCGATTCTGCGGAGGGATCTCCGTGGGGCGGTGAACGCCG

ATGATTATATAAGGACGCGCCGGGTGTGGCACAGCTAGTTCCGTCGCAGC

CGGGATTTGGGTCGCGGTTCTTGTTTGTGGATCGCTGTGATCGTCACTTG

GT

Exemplary truncated CMV enhancer and promoter
(SEQ ID NO: 159)
GGTAAACTGCCCACTTGGCAGTACATCAAGTGTATCATATGCCAAGTAC

GCCCCCTATTGACGTCAATGACGGTAAATGGCCCGCCTGGCATTATGCCC

AGTACATGACCTTATGGGACTTTCCTACTTGGCAGTACATCTACGTATTA

GTCATCGCTATTACCATGGTGATGCGGTTTTGGCAGTACATCAATGGGCG

TGGATAGCGGTTTGACTCACGGGGATTTCCAAGTCTCCACCCCATTGACG

TCAATGGGAGTTTGTTTTGGCACCAAAATCAACGGGACTTTCCAAAATGT

CGTAACAACTCCGCCCCATTGACGCAAATGGGCGGTAGGCGTGTACGGTG

GGAGGTCTATATAAGCAGAGCTCTCTG v. Untranslated Regions (UTRs)

In some embodiments, any constructs described herein can include one or more untranslated regions. In some embodiments, a construct can include a 5' UTR and/or a 3' UTR sequence. In some embodiments, if more than one UTR is present, UTRs may come from a single gene or more than one gene.

As is understood by those of skill in the art, an untranslated region (UTR) of a gene is transcribed but not translated. In some embodiments, a 5' UTR sequence starts at a transcription start site and continues to a translation initiation sequence but does not include that translation initiation sequence. In some embodiments, a 3' UTR starts immediately following a stop codon and continues until a transcriptional termination signal. Without wishing to be bound by any particular theory, there is a growing body of evidence regarding regulatory roles played by UTRs in terms of stability of nucleic acid molecule and translation. In some embodiments, regulatory features of a UTR can be incorporated into any technologies (e.g., constructs, compositions, kits, or methods) as described herein to, e.g., enhance stability of a protein.

For example, in some embodiments, a 5' UTR sequence is included in any constructs described herein. Non-limiting examples of 5' UTR sequences including those from the following genes: albumin, serum amyloid A, Apolipoprotein A/B/E, transferrin, alpha fetoprotein, erythropoietin, and Factor VIII, can be used to enhance expression of a nucleic acid molecule, such as a mRNA. In some embodiments, 5' UTR sequences have also been known, e.g., to form secondary structures that are involved in elongation factor binding.

In some embodiments, a 5' UTR sequence from an mRNA that is transcribed by a cell can be included in any technologies (e.g., constructs, compositions, kits, and methods) described herein.

Among other things, the present example recognizes that selection of a 5' UTR sequence can improve production of a protoparvovirus VP1 capsid polypeptide. Among other things, the present example recognizes that selection of a 5' UTR sequence can reduce toxicity of a VP1 capsid polypeptide. In some embodiments, a 5'UTR is a stretch of nucleotides between an expression control sequence and a VP1 capsid coding sequence (referred to herein as "a nucleotide spacer sequence").

In some embodiments, a nucleotide spacer sequence has a length of about 1 nucleotide. In some embodiments, a nucleotide spacer sequence has a length of about 5 nucleotides. In some embodiments, a nucleotide spacer sequence has a length of about 10 nucleotides. In some embodiments, a nucleotide spacer sequence has a length of about 20 nucleotides. In some embodiments, a nucleotide spacer sequence has a length of about 30 nucleotides. In some embodiments, a nucleotide spacer sequence has a length of about 40 nucleotides. In some embodiments, a nucleotide spacer sequence has a length of about 50 nucleotides. In some embodiments, a nucleotide spacer sequence has a length of about 60 nucleotides. In some embodiments, a nucleotide spacer sequence has a length of about 70 nucleotides. In some embodiments, a nucleotide spacer sequence has a length of about 80 nucleotides. In some embodiments, a nucleotide spacer sequence has a length of about 90 nucleotides. In some embodiments, a nucleotide spacer sequence has a length of about 100 nucleotides.

In some embodiments, a nucleotide spacer sequence has a length from about 1 to about 100 nucleotides. In some embodiments, a nucleotide spacer sequence has a length from about 1 to about 75 nucleotides. In some embodiments, a nucleotide spacer sequence has a length from about 10 to about 100 nucleotides. In some embodiments, a nucleotide spacer sequence has a length from about 1 to about 50 nucleotides. In some embodiments, a nucleotide spacer sequence has a length from about 1 to about 60 nucleotides. In some embodiments, a nucleotide spacer sequence has a length from about 30 to about 60 nucleotides. In some embodiments, a nucleotide spacer sequence has a length from about 1 to about 80 nucleotides. In some embodiments, a nucleotide spacer sequence has a length from about 1 to about 55 nucleotides. In some embodiments, a nucleotide spacer sequence has a length from about 10 to about 70 nucleotides. In some embodiments, a nucleotide spacer sequence has a length from about 1 to about 90 nucleotides. In some embodiments, a nucleotide spacer sequence has a length from about 1 to about 65 nucleotides. In some embodiments, a nucleotide spacer sequence has a length from about 45 nucleotides. In some embodiments, a nucleotide spacer sequence has a length from about 20 to about 80 nucleotides. In some embodiments, a nucleotide spacer sequence has a length from about 1 to about 75 nucleotides. In some embodiments, a nucleotide spacer sequence has a length from about 40 to about 80 nucleotides.

In some embodiments, there is no nucleotide spacer sequence.

In some embodiments, a 5' UTR sequence comprises a viral 5'UTR sequence according to SEQ ID NO: 122. In some embodiments, a 5' UTR sequence comprises a nucleotide spacer sequence according to SEQ ID NO: 123. In some embodiments, a 5' UTR sequence comprises a nucleotide spacer sequence that does not comprise an alternative translation initiation sequence according to SEQ ID NO: 124.

```
Exemplary 5' viral UTR sequence
                                        (SEQ ID NO: 122)
CTCGACGAAGACTTGATCACCCGGGGGATCCCCTGTTAAG

Exemplary nucleotide spacer sequence 1
                                        (SEQ ID NO: 123)
ATTCCGGATTATTCATACCGTCCCACCATCGGGCGCGGATCT

Exemplary nucleotide spacer sequence 2
                                        (SEQ ID NO: 124)
ACTCCGGACTACTGATACCGTCCCACTTTCGGGCGCTTACCT
```

In some embodiments, 3' UTRs are known to have stretches of adenosines and uridines embedded in them. These AU-rich signatures are particularly prevalent in genes with high rates of turnover. Based on their sequence features and functional properties, AU-rich elements (AREs) can be separated into three classes (Chen et al., *Mol. Cell. Biol.* 15:5777-5788, 1995; Chen et al., *Mol. Cell Biol.* 15:2010-2018, 1995, each of which is incorporated in its entirety herein by reference): Class I AREs contain several dispersed copies of an AUUUA motif within U-rich regions. For example, c-Myc and MyOD mRNAs contain class I AREs. Class II AREs possess two or more overlapping UUAUUUA (U/A)(U/A) nonamers. GM-CSF and TNF-alpha mRNAs are examples that contain class II AREs. Class III AREs are less well defined. These U-rich regions do not contain an AUUUA motif. Two well-studied examples of this class are c-Jun and myogenin mRNAs.

Most proteins binding to AREs are known to destabilize a messenger, whereas members of the ELAV family, most notably HuR, have been documented to increase stability of mRNA. HuR binds to AREs of all three classes. Engineering HuR specific binding sites into a 3' UTR of nucleic acid molecules will lead to HuR binding and thus, stabilization of a message in vivo.

In some embodiments, introduction, removal, or modification of 3' UTR AREs can be used to modulate stability of an mRNA encoding a protein. In some embodiments, AREs can be removed or mutated to increase intracellular stability and thus increase translation and production of a protein.

In some embodiments, a UTR sequence is at least 85%, 90%, 95%, 98% or 99% identical to any UTR sequence disclosed herein (e.g., SEQ ID NOs: 122-124)

vi. Kozak Consensus Sequences

In some embodiments, a construct of the present disclosure comprises one or more Kozak consensus sequences (also herein to as Kozak consensus sequences). In some embodiments, natural 5' UTRs include a sequence that plays a role in translation initiation. For example, in some embodiments, they harbor signatures like Kozak sequences, which are commonly known to be involved in a process by which a ribosome initiates translation of many genes. Kozak sequences generally have a consensus sequence CCR(A/G) CCATGG, where R is a purine (A or G) three bases upstream of a translation initiation sequence (ATG), which is followed by another “G”. In some embodiments, Kozak sequences may be included in synthetic or additional sequence elements, such as cloning sites.

vii. Polyadenylation Sequences

In some embodiments, a construct of the present disclosure may comprise at least one poly(A) sequence. Most nascent eukaryotic mRNA possesses a poly(A) tail at its 3' end which is added during a complex process that includes cleavage of a primary transcript and a coupled polyadenylation reaction (see, e.g., Proudfoot et al., *Cell* 108:501-512, 2002, the contents of which are hereby incorporated by reference herein in its entirety). A poly(A) tail confers mRNA stability and transferability (see, e.g., Molecular Biology of the Cell, Third Edition by B. Alberts et al., Garland Publishing, 1994, the contents of which are hereby incorporated by reference herein in its entirety). In some embodiments, a poly(A) sequence is positioned 3' to a nucleic acid sequence encoding a transgene. In some embodiments, a poly(A) sequence is positioned 3' to a VP1 capsid coding sequence encoding a protoparvovirus variant VP1 capsid polypeptide.

In some embodiments, polyadenylation refers to a covalent linkage of a polyadenylyl moiety, or its modified variant, to a messenger RNA molecule. In eukaryotic organisms, most messenger RNA (mRNA) molecules are polyadenylated at a 3' end. In some embodiments, a 3' poly(A) tail is a long sequence of adenine nucleotides (often several hundred) added to pre-mRNA through enzymatic action, polyadenylate polymerase. In higher eukaryotes, a poly(A) tail is added onto transcripts that contain a specific sequence, a polyadenylation signal. In some embodiments, a poly(A) tail and a protein bound to it aid in protecting mRNA from degradation by exonucleases. As will be understood to those of skill in the art, polyadenylation is also important for transcription termination, export of mRNA from a cell’s nucleus, and translation. Polyadenylation occurs in a cell nucleus immediately after transcription of DNA into RNA, but additionally can also occur later in cytoplasm. After transcription has been terminated, an mRNA chain is cleaved through action of an endonuclease complex associated with RNA polymerase. A cleavage site is usually characterized by presence of a base sequence AAUAAA near a given cleavage site. After an mRNA has been cleaved, adenosine residues are added to a free 3' end at a cleavage site.

In some embodiments, a poly(A) signal sequence is a sequence that triggers endonuclease cleavage of an mRNA and addition of a series of adenosines to the 3' end of a cleaved mRNA. A “poly(A)” portion refers to a series of adenosines attached by polyadenylation to an mRNA. In some embodiments of for the present disclosure, such as, e.g., transient expression, a poly A is between 50 and 5000, preferably greater than 64, more preferably greater than 100, most preferably greater than 300 or 400. Poly(A) sequences can be modified chemically or enzymatically to modulate mRNA functionality such as localization, stability or efficiency of translation.

There are several poly(A) signal sequences that can be used, including those derived from bovine growth hormone (bgh) (Woychik et al., *Proc. Natl. Acad. Sci. U.S.A.* 81(13): 3944-3948, 1984; U.S. Pat. No. 5,122,458; Yew et al., *Human Gene Ther.* 8(5): 575-584, 1997; Xu et al., *Human*

Gene Ther. 12(5): 563-573, 2001; Xu et al., *Gene Ther.* 8:1323-1332, 2001; Wu et al., *Mol. Ther.* 16(2): 280-289, 2008; Gray et al., *Human Gene Ther:* 22:1143-1153, 2011; Choi et al., *Mol. Brain* 7:17, 2014, each of which is incorporated in its entirety herein by reference), mouse-β-globin, mouse-α-globin (Orkin et al., *EMBO J.* 4(2): 453-456, 1985; Thein et al., *Blood* 71(2): 313-319, 1988, each which is incorporated in its entirety herein by reference), human collagen, polyoma virus (Batt et al., *Mol. Cell Biol.* 15(9): 4783-4790, 1995, each of which is incorporated in its entirety herein by reference), Herpes simplex virus thymidine kinase gene (HSV TK), IgG heavy-chain gene polyadenylation signal (US 2006/0040354, which is incorporated in its entirety herein by reference), human growth hormone (hGH) (Szymanski et al., *Mol. Therapy* 15(7): 1340-1347, 2007; Ostegaard et al., *Proc. Natl. Acad. Sci. U.S.A.* 102(8): 2952-2957, 2005, each of which is incorporated in its entirety herein by reference), synthetic poly A (Levitt et al., *Genes Dev.* 3(7): 1019-1025, 1989; Yew et al., *Human Gene Ther.* 8(5): 575-584, 1997; Ostegaard et al., *Proc. Natl. Acad. Sci. U.S.A.* 102(8): 2952-2957, 2005; Choi et al., *Mol. Brain* 7:17, 2014, each of which is incorporated in its entirety herein by reference), HIV-1 upstream poly(A) enhancer (Schambach et al., *Mol. Ther.* 15(6): 1167-1173, 2007, each of which is incorporated in its entirety herein by reference), adenovirus (L3) upstream poly(A) enhancer (Schambach et al., *Mol. Ther.* 15(6): 1167-1173, 2007, which is incorporated in its entirety herein by reference), hTHGB upstream poly(A) enhancer (Schambach et al., *Mol. Ther.* 15(6): 1167-1173, 2007), hC2 upstream poly(A) enhancer (Schambach et al., *Mol. Ther.* 15(6): 1167-1173, 2007), the group consisting of SV40 poly(A) signal sequence, such as the SV40 late and early poly(A) signal sequence (Schek et al., *Mol. Cell Biol.* 12(12): 5386-5393, 1992; Choi et al., *Mol. Brain* 7:17, 2014; Schambach et al., *Mol. Ther.* 15(6): 1167-1173, 2007, each of which is incorporated in its entirety herein by reference). The contents of each of these references are incorporated herein by reference in its entirety.

In some embodiments, a poly(A) signal sequence can be a sequence AATAAA. In some embodiments, an AATAAA sequence may be substituted with other hexanucleotide sequences with homology to AATAAA which are capable of signaling polyadenylation, including ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, or AATAAG (see, e.g., WO 06/12414, which is incorporated in its entirety herein by reference).

In some embodiments, a poly(A) signal sequence can be a synthetic polyadenylation site (see, e.g., the pCl-neo expression construct of Promega which is based on Levitt et al, *Genes Dev.* 3(7): 1019-1025, 1989, which is incorporated in its entirety herein by reference). In some embodiments, a poly(A) signal sequence is a polyadenylation signal of soluble neuropilin-1 (sNRP) (see, e.g., WO 05/073384, which is incorporated in its entirety herein by reference). In some embodiments, a poly(A) sequence is a bovine growth hormone poly(A) sequence. Additional examples of poly(A) signal sequences are known in the art.

In some embodiments, a polyA sequence is at least 85%, 90%, 95%, 98% or 99% identical to the poly A sequence of SEQ ID NO: 125.

By way of non-limiting example, a polyadenylation sequence may be or comprise a sequence according to SEQ ID NO: 125.

```
Exemplary SV40 PolyA Sequence
                                              (SEQ ID NO: 125)
TTGTTTATTGCAGCTTATAATGGTTACAAATAAAGCAATAGCATCACAAA

TTTCACAAATAAAGCATTTTTTTCACTGCATTCTAGTTGTGGTTTGTCCA

AACTCATCAATGTATCTTATCATGTCTGGATC
```

viii. Enhancers and 5' cap

In some instances, a construct can include an expression control sequence and/or an enhancer sequence. In some embodiments, an enhancer is a nucleotide sequence that can increase a level of transcription of a nucleic acid encoding a polypeptide of interest (e.g., a protoparvovirus variant VP1 capsid polypeptide). In some embodiments, enhancer sequences (50-1500 base pairs in length) generally increase a level of transcription by providing additional binding sites for transcription-associated proteins (e.g., transcription factors). In some embodiments, an enhancer sequence is found within an intronic sequence. Unlike promoter sequences, enhancer sequences can act at much larger distance away from a transcription start site (e.g., as compared to a promoter). Non-limiting examples of enhancers include a RSV enhancer, a CMV enhancer, and a SV40 enhancer. An example of a CMV enhancer is described in, e.g., Boshart et al., Cell 41(2): 521-530, 1985, which is incorporated in its entirety herein by reference.

As described herein, a 5' cap (also termed an RNA cap, an RNA 7-methylguanosine cap or an RNA m.sup.7G cap) is a modified guanine nucleotide that has been added to a "front" or 5' end of a eukaryotic messenger RNA shortly after a start of transcription. In some embodiments, a 5' cap consists of a terminal group which is linked to a first transcribed nucleotide. Its presence is critical for recognition by a ribosome and protection from RNases. Cap addition is coupled to transcription, and occurs co-transcriptionally, such that each influences the other. Shortly after start of transcription, a 5' end of an mRNA being synthesized is bound by a cap-synthesizing complex associated with RNA polymerase. This enzymatic complex catalyzes a chemical reactions that are required for mRNA capping. Synthesis proceeds as a multi-step biochemical reaction. A capping moiety can be modified to modulate functionality of mRNA such as its stability or efficiency of translation.

ix. Exemplary Capsid Construct Sequences

In some embodiments, the present disclosure provides technologies (e.g., compositions, systems, particles, comprising protoparvovirus-related constructs). In some embodiments, such technologies comprise a single construct. In some embodiments, such technologies comprise multiple constructs. In some embodiments, the present disclosure provides compositions or systems comprising multiple virions each comprised of a single construct as described herein. In some embodiments, a single construct may deliver a polynucleotide that encodes a functional (e.g., wild type or otherwise functional, e.g., codon optimized) copy of a protoparvovirus variant VP1 gene. In some embodiments, a construct is or comprises a protoparvovirus-related construct.

In some embodiments, a single construct composition or system may comprise any or all of the exemplary construct components described herein. In some embodiments, an exemplary single construct is at least 85%, 90%, 95%, 98% or 99% identical to the sequences described herein. One skilled in the art would recognize that constructs may undergo additional modifications including codon-optimization, introduction of novel but functionally equivalent (e.g., silent mutations), addition of reporter sequences, and/or other routine modification.

Among other things, the present disclosure includes exemplary reference and protoparvovirus variant VP1 capsid polypeptide construct sequences described herein as shown in Table 4.

Table 4 shows exemplary constructs described herein.

TABLE 4

| Exemplary Construct | Sequence | SEQ ID NO: |
|---|---|---|
| Exemplary CPV Construct 1 comprising a proto-parvovirus variant VP1 capsid coding sequence Ph-v5UTR-CPV-VP1-CTG-Del-LVPPG | CATGGAGATAATTAAAATGATAACCATCTCGCAAATAAATAA GTATTTTACTGTTTTCGTAACAGTTTTGTAATAAAAAAACCT ATAAAATTCCGGATTATTCATACCGTCCCACCATCGGGCGCG GATCTCCTGTTAAGCTGGCACCTCCGGCAAAGAGAGCCAG GAGAGGATATAAATATCTTGGGCCTGGGAACAGTCTTGACC AAGGAGAACCAACTAACCCTTCTGACGCCGCTGCAAAAGA ACACGACGAAGCTTACGCTGCTTATCTTCGCTCTGGTAAAA ACCCATACTTATATTTCTCGCCAGCAGATCAACGCTTTATAG ATCAAACTAAGGACGCTAAAGATTGGGGGGGGAAAATAGG ACATTATTTTTTTAGAGCTAAAAAGGCAATTGCTCCAGTATT AACTGATACACCAGATCATCCATCAACATCAAGACCAACAA AACCAACTAAAAGAAGTAAACCACCACCTCATATTTTCATC AATCTTGCAAAAAAAAAAAAAAGCCGGTGCAGGACAAGTA AAAAGAGACAATCTTGCACCAATGAGTGATGGAGCAGTTC AACCAGACGGTGGTCAACCTGCTGTCAGAAATGAAAGAG CTACAGGATCTGGGAACGGGTCTGGAGGCGGGGGTGGTGG TGGTTCTGGGGGTGTGGGGATTTCTACGGGTACTTTCAATA ATCAGACGGAATTTAAATTTTTGGAAAACGGATGGGTGGA AATCACAGCAAACTCAAGCAGACTTGTACATTTAAATATGC CAGAAAGTGAAAATTATAGAAGAGTGGTTGTAAATAATATG GATAAAACTGCAGTTAACGGAAACATGGCTTTAGATGATAT TCATGCACAAATTGTAACACCTTGGTCATTGGTTGATGCAA ATGCTTGGGGAGTTTGGTTTAATCCAGGAGATTGGCAACTA ATTGTTAATACTATGAGTGAGTTGCATTTAGTTAGTTTTGAA CAAGAAATTTTTAATGTTGTTTTAAAGACTGTTTCAGAATC TGCTACTCAGCCACCAACTAAAGTTTATAATAATGATTTAAC TGCATCATTGATGGTTGCATTAGATAGTAATAATACTATGCC ATTTACTCCAGCAGCTATGAGATCTGAGACATTGGGTTTTTA TCCATGGAAACCAACCATACCAACTCCATGGAGATATTATTT TCAATGGGATAGAACATTAATACCATCTCATACTGGAACTAG TGGCACACCAACAAATATATACCATGGTACAGATCCAGATG ATGTTCAATTTTATACTATTGAAAATTCTGTGCCAGTACACT TACTAAGAACAGGTGATGAATTTGCTACAGGAACATTTTTT TTTGATTGTAAACCATGTAGACTAACACATACATGGCAAAC AAATAGAGCATTGGGCTTACCACCATTTCTAAATTCTTTGCC TCAATCTGAAGGAGCTACTAACTTTGGTGATATAGGAGTTC AACAAGATAAAAGACGTGGTGTAACTCAAATGGGAAATAC AAACTATATTACTGAAGCTACTATTATGAGACCAGCTGAGG TTGGTTATAGTGCACCATATTATTCTTTTGAGGCGTCTACAC AAGGGCCATTTAAAACACCTATTGCAGCAGGACGGGGGGG AGCGCAAACATATGAAAATCAAGCAGCAGATGGTGATCCA AGATATGCATTTGGTAGACAACATGGTCAAAAAACTACCAC AACAGGAGAAACACCTGAGAGATTTACATATATAGCACATC AAGATACAGGAAGATATCCAGAAGGAGATTGGATTCAAAA TATTAACTTTAACCTTCCTGTAACGAATGATAATGTATTGCT ACCAACAGATCCAATTGGAGGTAAAACAGGAATTAACTATA CTAATATATTTAATACTTATGGTCCTTTAACTGCATTAAATAA TGTACCACCAGTTTATCCAAATGGTCAAATTTGGGATAAAG AATTTGATACTGACTTAAAACCAAGACTTCATGTAAATGCA CCATTTGTTTGTCAAAATAATTGTCCTGGTCAATTATTTGTA AAAGTTGCGCCTAATTTAACAAATGAATATGATCCTGATGC ATCTGCTAATATGTCAAGAATTGTAACTTACTCAGATTTTTG GTGGAAAGGTAAATTAGTATTTAAAGCTAAACTAAGAGCCT CTCATACTTGGAATCCAATTCAACAAATGAGTATTAATGTAG ATAACCAATTTAACTATGTACCAAGTAATATTGGAGGTATGA AAATTGTATATGAAAAATCTCAACTAGCACCTAGAAAATTAT ATTAACTCGAGGCATGCGGTACCAAGCTTGTCGAGAAGTA CTAGAGGATCATAATCAGCCATACCACATTTGTAGAGGTTTT ACTTGCTTTAAAAAACCTCCCACACCTCCCCCTGAACCTGA AACATAAAATGAATGCAATTGTTGTTGTTAACTTGTTTATTG CAGCTTATAATGGTTACAAATAAAGCAATAGCATCACAAAT TTCACAAATAAAGCATTTTTTTCACTGCATTCTAGTTGTGGT TTGTCCAAACTCATCAATGTATCTTATCATGTCTGGATC | SEQ ID NO: 126 |

TABLE 4-continued

| Exemplary Construct | Sequence | SEQ ID NO: |
|---|---|---|
| Exemplary<br>CPV<br>Construct 2<br>comprising<br>a proto-<br>parvovirus<br>variant<br>VP1 capsid<br>coding<br>sequence<br>Ph-CPV-<br>VP1-CTG-<br>Del-LVPPG | CATGGAGATAATTAAAATGATAACCATCTCGCAAATAAATAA<br>GTATTTTACTGTTTTCGTAACAGTTTTGTAATAAAAAAACCT<br>ATAAACTGGCACCTCCGGCAAAGAGAGCCAGGAGAGGATA<br>TAAATATCTTGGGCCTGGGAACAGTCTTGACCAAGGAGAA<br>CCAACTAACCCTTCTGACGCCGCTGCAAAAGAACACGACG<br>AAGCTTACGCTGCTTATCTTCGCTCTGGTAAAAACCCATAC<br>TTATATTTCTCGCCAGCAGATCAACGCTTTATAGATCAAACT<br>AAGGACGCTAAAGATTGGGGGGGGAAAATAGGACATTATT<br>TTTTTAGAGCTAAAAAGGCAATTGCTCCAGTATTAACTGAT<br>ACACCAGATCATCCATCAACATCAAGACCAACAAAACCAA<br>CTAAAAGAAGTAAACCACCACCTCATATTTTCATCAATCTT<br>GCAAAAAAAAAAAAAGCCGGTGCAGGACAAGTAAAAAGA<br>GACAATCTTGCACCAATGAGTGATGGAGCAGTTCAACCAG<br>ACGGTGGTCAACCTGCTGTCAGAAATGAAAGAGCTACAGG<br>ATCTGGGAACGGGTCTGGAGGCGGGGGTGGTGGTGGTTCT<br>GGGGGTGTGGGGATTTCTACGGGTACTTTCAATAATCAGAC<br>GGAATTTAAATTTTTGGAAAACGGATGGGTGGAAATCACA<br>GCAAACTCAAGCAGACTTGTACATTTAAATATGCCAGAAAG<br>TGAAAATTATAGAAGAGTGGTTGTAAATAATATGGATAAAA<br>CTGCAGTTAACGGAAACATGGCTTTAGATGATATTCATGCA<br>CAAATTGTAACACCTTGGTCATTGGTTGATGCAAATGCTTG<br>GGGAGTTTGGTTTAATCCAGGAGATTGGCAACTAATTGTTA<br>ATACTATGAGTGAGTTGCATTTAGTTAGTTTTGAACAAGAA<br>ATTTTTAATGTTGTTTTAAAGACTGTTTCAGAATCTGCTACT<br>CAGCCACCAACTAAAGTTTATAATAATGATTTAACTGCATCA<br>TTGATGGTTGCATTAGATAGTAATAATACTATGCCATTTACTC<br>CAGCAGCTATGAGATCTGAGACATTGGGTTTTTATCCATGG<br>AAACCAACCATACCAACTCCATGGAGATATTATTTTCAATG<br>GGATAGAACATTAATACCATCTCATACTGGAACTAGTGGCA<br>CACCAACAAATATATACCATGGTACAGATCCAGATGATGTTC<br>AATTTTATACTATTGAAAATTCTGTGCCAGTACACTTACTAA<br>GAACAGGTGATGAATTTGCTACAGGAACATTTTTTTTTGAT<br>TGTAAACCATGTAGACTAACACATACATGGCAAACAAATAG<br>AGCATTGGGCTTACCACCATTTCTAAATTCTTTGCCTCAATC<br>TGAAGGAGCTACTAACTTTGGTGATATAGGAGTTCAACAAG<br>ATAAAAGACGTGGTGTAACTCAAATGGGAAATACAAACTAT<br>ATTACTGAAGCTACTATTATGAGACCAGCTGAGGTTGGTTAT<br>AGTGCACCATATTATTCTTTTGAGGCGTCTACACAAGGGCC<br>ATTTAAAACACCTATTGCAGCAGGACGGGGGGGAGCGCAA<br>ACATATGAAAATCAAGCAGCAGATGGTGATCCAAGATATGC<br>ATTTGGTAGACAACATGGTCAAAAAACTACCACAACAGGA<br>GAAACACCTGAGAGATTTACATATATAGCACATCAAGATAC<br>AGGAAGATATCCAGAAGGAGATTGGATTCAAAATATTAACT<br>TTAACCTTCCTGTAACGAATGATAATGTATTGCTACCAACAG<br>ATCCAATTGGAGGTAAAACAGGAATTAACTATACTAATATAT<br>TTAATACTTATGGTCCTTTAACTGCATTAAATAATGTACCAC<br>CAGTTTATCCAAATGGTCAAATTTGGGATAAAGAATTTGAT<br>ACTGACTTAAAACCAAGACTTCATGTAAATGCACCATTTGT<br>TTGTCAAAATAATTGTCCTGGTCAATTATTTGTAAAAGTTGC<br>GCCTAATTTAACAAATGAATATGATCCTGATGCATCTGCTAA<br>TATGTCAAGAATTGTAACTTACTCAGATTTTTGGTGGAAAG<br>GTAAATTAGTATTTAAAGCTAAACTAAGAGCCTCTCATACTT<br>GGAATCCAATTCAACAAATGAGTATTAATGTAGATAACCAA<br>TTTAACTATGTACCAAGTAATATTGGAGGTATGAAAATTGTA<br>TATGAAAAATCTCAACTAGCACCTAGAAAATTATATTAACTC<br>GAGGCATGCGGTACCAAGCTTGTCGAGAAGTACTAGAGGA<br>TCATAATCAGCCATACCACATTTGTAGAGGTTTTACTTGCTT<br>TAAAAAACCTCCCACACCTCCCCCTGAACCTGAAACATAA<br>AATGAATGCAATTGTTGTTGTTAACTTGTTTATTGCAGCTTA<br>TAATGGTTACAAATAAAGCAATAGCATCACAAATTTCACAA<br>ATAAAGCATTTTTTTCACTGCATTCTAGTTGTGGTTTGTCCA<br>AACTCATCAATGTATCTTATCATGTCTGGATC | SEQ ID<br>NO: 127 |
| Exemplary<br>CPV<br>Construct 3<br>comprising<br>a proto-<br>parvovirus<br>variant<br>VP1 capsid<br>coding<br>sequence<br>Ph-CPV-<br>VP1-ACG-<br>Del-LVPPG | CATGGAGATAATTAAAATGATAACCATCTCGCAAATAAATAA<br>GTATTTTACTGTTTTCGTAACAGTTTTGTAATAAAAAAACCT<br>ATAAAACGGCACCTCCGGCAAAGAGAGCCAGGAGAGGAT<br>ATAAATATCTTGGGCCTGGGAACAGTCTTGACCAAGGAGA<br>ACCAACTAACCCTTCTGACGCCGCTGCAAAAGAACACGAC<br>GAAGCTTACGCTGCTTATCTTCGCTCTGGTAAAAACCCATA<br>CTTATATTTCTCGCCAGCAGATCAACGCTTTATAGATCAAAC<br>TAAGGACGCTAAAGATTGGGGGGGGAAAATAGGACATTAT<br>TTTTTTAGAGCTAAAAAGGCAATTGCTCCAGTATTAACTGA<br>TACACCAGATCATCCATCAACATCAAGACCAACAAAACCA<br>ACTAAAAGAAGTAAACCACCACCTCATATTTTCATCAATCT<br>TGCAAAAAAAAAAAAAGCCGGTGCAGGACAAGTAAAAAG<br>AGACAATCTTGCACCAATGAGTGATGGAGCAGTTCAACCA | SEQ ID<br>NO: 128 |

TABLE 4-continued

| Exemplary Construct | Sequence | SEQ ID NO: |
|---|---|---|
| | GACGGTGGTCAACCTGCTGTCAGAAATGAAAGAGCTACAG<br>GATCTGGGAACGGGTCTGGAGGCGGGGGTGGTGGTGGTTC<br>TGGGGGTGTGGGGATTTCTACGGGTACTTTCAATAATCAGA<br>CGGAATTTAAATTTTTGGAAAACGGATGGGTGGAAATCAC<br>AGCAAACTCAAGCAGACTTGTACATTTAAATATGCCAGAAA<br>GTGAAAATTATAGAAGAGTGGTTGTAAATAATATGGATAAA<br>ACTGCAGTTAACGGAAACATGGCTTTAGATGATATTCATGC<br>ACAAATTGTAACACCTTGGTCATTGGTTGATGCAAATGCTT<br>GGGGAGTTTGGTTTAATCCAGGAGATTGGCAACTAATTGTT<br>AATACTATGAGTGAGTTGCATTTAGTTAGTTTTGAACAAGA<br>AATTTTTAATGTTGTTTTAAAGACTGTTTCAGAATCTGCTAC<br>TCAGCCACCAACTAAAGTTTATAATAATGATTTAACTGCATC<br>ATTGATGGTTGCATTAGATAGTAATAATACTATGCCATTTACT<br>CCAGCAGCTATGAGATCTGAGACATTGGGTTTTTATCCATG<br>GAAACCAACCATACCAACTCCATGGAGATATTATTTTCAAT<br>GGGATAGAACATTAATACCATCTCATACTGGAACTAGTGGC<br>ACACCAACAAATATATACCATGGTACAGATCCAGATGATGT<br>TCAATTTTATACTATTGAAAATTCTGTGCCAGTACACTTACT<br>AAGAACAGGTGATGAATTTGCTACAGGAACATTTTTTTTTG<br>ATTGTAAACCATGTAGACTAACACATACATGGCAAACAAAT<br>AGAGCATTGGGCTTACCACCATTTCTAAATTCTTTGCCTCA<br>ATCTGAAGGAGCTACTAACTTTGGTGATATAGGAGTTCAAC<br>AAGATAAAAGACGTGGTGTAACTCAAATGGGAAATACAAA<br>CTATATTACTGAAGCTACTATTATGAGACCAGCTGAGGTTGG<br>TTATAGTGCACCATATTATTCTTTTGAGGCGTCTACACAAGG<br>GCCATTTAAAACACCTATTGCAGCAGGACGGGGGGGAGCG<br>CAAACATATGAAAATCAAGCAGCAGATGGTGATCCAAGAT<br>ATGCATTTGGTAGACAACATGGTCAAAAAACTACCACAAC<br>AGGAGAAACACCTGAGAGATTTACATATATAGCACATCAAG<br>ATACAGGAAGATATCCAGAAGGAGATTGGATTCAAAATATT<br>AACTTTAACCTTCCTGTAACGAATGATAATGTATTGCTACCA<br>ACAGATCCAATTGGAGGTAAAACAGGAATTAACTATACTAA<br>TATATTTAATACTTATGGTCCTTTAACTGCATTAAATAATGTA<br>CCACCAGTTTATCCAAATGGTCAAATTTGGGATAAAGAATT<br>TGATACTGACTTAAAACCAAGACTTCATGTAAATGCACCAT<br>TTGTTTGTCAAAATAATTGTCCTGGTCAATTATTTGTAAAAG<br>TTGCGCCTAATTTAACAAATGAATATGATCCTGATGCATCTG<br>CTAATATGTCAAGAATTGTAACTTACTCAGATTTTTGGTGGA<br>AAGGTAAATTAGTATTTAAAGCTAAACTAAGAGCCTCTCAT<br>ACTTGGAATCCAATTCAACAAATGAGTATTAATGTAGATAA<br>CCAATTTAACTATGTACCAAGTAATATTGGAGGTATGAAAAT<br>TGTATATGAAAAATCTCAACTAGCACCTAGAAAATTATATTA<br>ACTCGAGGCATGCGGTACCAAGCTTGTCGAGAAGTACTAG<br>AGGATCATAATCAGCCATACCACATTTGTAGAGGTTTTACTT<br>GCTTTAAAAAACCTCCCACACCTCCCCCTGAACCTGAAAC<br>ATAAAATGAATGCAATTGTTGTTGTTAACTTGTTTATTGCAG<br>CTTATAATGGTTACAAATAAAGCAATAGCATCACAAATTTCA<br>CAAATAAAGCATTTTTTTCACTGCATTCTAGTTGTGGTTTGT<br>CCAAACTCATCAATGTATCTTATCATGTCTGGATC | |
| Exemplary CPV Construct 4 comprising a proto-parvovirus variant VP1 capsid coding sequence Ph-CPV-VP1-TTG-Del-LVPPG | CATGGAGATAATTAAAATGATAACCATCTCGCAAATAAATAA<br>GTATTTTACTGTTTTCGTAACAGTTTTGTAATAAAAAAACCT<br>ATAAATTGGCACCTCCGGCAAAGAGAGCCAGGAGAGGATA<br>TAAATATCTTGGGCCTGGGAACAGTCTTGACCAAGGAGAA<br>CCAACTAACCCTTCTGACGCCGCTGCAAAAGAACACGACG<br>AAGCTTACGCTGCTTATCTTCGCTCTGGTAAAAACCCATAC<br>TTATATTTCTCGCCAGCAGATCAACGCTTTATAGATCAAACT<br>AAGGACGCTAAAGATTGGGGGGGGAAAATAGGACATTATT<br>TTTTTAGAGCTAAAAAGGCAATTGCTCCAGTATTAACTGAT<br>ACACCAGATCATCCATCAACATCAAGACCAACAAAACCAA<br>CTAAAAGAAGTAAACCACCACCTCATATTTTCATCAATCTT<br>GCAAAAAAAAAAAAAGCCGGTGCAGGACAAGTAAAAAGA<br>GACAATCTTGCACCAATGAGTGATGGAGCAGTTCAACCAG<br>ACGGTGGTCAACCTGCTGTCAGAAATGAAAGAGCTACAGG<br>ATCTGGGAACGGGTCTGGAGGCGGGGGTGGTGGTGGTTCT<br>GGGGGTGTGGGGATTTCTACGGGTACTTTCAATAATCAGAC<br>GGAATTTAAATTTTTGGAAAACGGATGGGTGGAAATCACA<br>GCAAACTCAAGCAGACTTGTACATTTAAATATGCCAGAAAG<br>TGAAAATTATAGAAGAGTGGTTGTAAATAATATGGATAAAA<br>CTGCAGTTAACGGAAACATGGCTTTAGATGATATTCATGCA<br>CAAATTGTAACACCTTGGTCATTGGTTGATGCAAATGCTTG<br>GGGAGTTTGGTTTAATCCAGGAGATTGGCAACTAATTGTTA<br>ATACTATGAGTGAGTTGCATTTAGTTAGTTTTGAACAAGAA<br>ATTTTTAATGTTGTTTTAAAGACTGTTTCAGAATCTGCTACT<br>CAGCCACCAACTAAAGTTTATAATAATGATTTAACTGCATCA<br>TTGATGGTTGCATTAGATAGTAATAATACTATGCCATTTACTC<br>CAGCAGCTATGAGATCTGAGACATTGGGTTTTTATCCATGG | SEQ ID NO: 129 |

TABLE 4-continued

| Exemplary Construct | Sequence | SEQ ID NO: |
| --- | --- | --- |
| | AAACCAACCATACCAACTCCATGGAGATATTATTTTCAATG<br>GGATAGAACATTAATACCATCTCATACTGGAACTAGTGGCA<br>CACCAACAAATATATACCATGGTACAGATCCAGATGATGTTC<br>AATTTTATACTATTGAAAATTCTGTGCCAGTACACTTACTAA<br>GAACAGGTGATGAATTTGCTACAGGAACATTTTTTTTTGAT<br>TGTAAACCATGTAGACTAACACATACATGGCAAACAAATAG<br>AGCATTGGGCTTACCACCATTTCTAAATTCTTTGCCTCAATC<br>TGAAGGAGCTACTAACTTTGGTGATATAGGAGTTCAACAAG<br>ATAAAAGACGTGGTGTAACTCAAATGGGAAATACAAACTAT<br>ATTACTGAAGCTACTATTATGAGACCAGCTGAGGTTGGTTAT<br>AGTGCACCATATTATTCTTTTGAGGCGTCTACACAAGGGCC<br>ATTTAAAACACCTATTGCAGCAGGACGGGGGGGAGCGCAA<br>ACATATGAAAATCAAGCAGCAGATGGTGATCCAAGATATGC<br>ATTTGGTAGACAACATGGTCAAAAAACTACCACAACAGGA<br>GAAACACCTGAGAGATTTACATATATAGCACATCAAGATAC<br>AGGAAGATATCCAGAAGGAGATTGGATTCAAAATATTAACT<br>TTAACCTTCCTGTAACGAATGATAATGTATTGCTACCAACAG<br>ATCCAATTGGAGGTAAAACAGGAATTAACTATACTAATATAT<br>TTAATACTTATGGTCCTTTAACTGCATTAAATAATGTACCAC<br>CAGTTTATCCAAATGGTCAAATTTGGGATAAAGAATTTGAT<br>ACTGACTTAAAACCAAGACTTCATGTAAATGCACCATTTGT<br>TTGTCAAAATAATTGTCCTGGTCAATTATTTGTAAAAGTTGC<br>GCCTAATTTAACAAATGAATATGATCCTGATGCATCTGCTAA<br>TATGTCAAGAATTGTAACTTACTCAGATTTTTGGTGGAAAG<br>GTAAATTAGTATTTAAAGCTAAACTAAGAGCCTCTCATACTT<br>GGAATCCAATTCAACAAATGAGTATTAATGTAGATAACCAA<br>TTTAACTATGTACCAAGTAATATTGGAGGTATGAAAATTGTA<br>TATGAAAAATCTCAACTAGCACCTAGAAAATTATATTAACTC<br>GAGGCATGCGGTACCAAGCTTGTCGAGAAGTACTAGAGGA<br>TCATAATCAGCCATACCACATTTGTAGAGGTTTTACTTGCTT<br>TAAAAAACCTCCCACACCTCCCCCTGAACCTGAAACATAA<br>AATGAATGCAATTGTTGTTGTTAACTTGTTTATTGCAGCTTA<br>TAATGGTTACAAATAAAGCAATAGCATCACAAATTTCACAA<br>ATAAAGCATTTTTTTCACTGCATTCTAGTTGTGGTTTGTCCA<br>AACTCATCAATGTATCTTATCATGTCTGGATC | |
| Exemplary CPV Construct 5 comprising a proto-parvovirus variant VP1 capsid coding sequence | GACATTGATTATTGACTAGTTATTAATAGTAATCAATTACGG<br>GGTCATTAGTTCATAGCCCATATATGGAGTTCCGCGTTACAT<br>AACTTACGGTAAATGGCCCGCCTGGCTGACCGCCCAACGA<br>CCCCCGCCCATTGACGTCAATAATGACGTATGTTCCCATAGT<br>AACGCCAATAGGGACTTTCCATTGACGTCAATGGGTGGACT<br>ATTTACGGTAAACTGCCCACTTGGCAGTACATCAAGTGTAT<br>CATATGCCAAGTACGCCCCCTATTGACGTCAATGACGGTAA<br>ATGGCCCGCCTGGCATTATGCCCAGTACATGACCTTATGGG<br>ACTTTCCTACTTGGCAGTACATCTACGTATTAGTCATCGCTA<br>TTACCATGGTGATGCGGTTTTGGCAGTACATCAATGGGCGT<br>GGATAGCGGTTTGACTCACGGGGATTTCCAAGTCTCCACCC<br>CATTGACGTCAATGGGAGTTTGTTTTGGCACCAAAATCAAC<br>GGGACTTTCCAAAATGTCGTAACAACTCCGCCCCATTGACG<br>CAAATGGGCGGTAGGCGTGTACGGTGGGAGGTCTATATAAG<br>CAGAGCTCTCTGGCTAACTAGAGAACCCACTGCTTACTGG<br>CTTATCGAAATTAATACGACTCACTATAGGGAGACCCAAGC<br>TTGGTACCGGACTCTAGAGGATCCGGTACTCGAGGAACTG<br>AAAAACCAGAAAGTTAACTGGTAAGTTTAGTCTTTTTGTCT<br>TTTATTTCAGGTCCCGGATCCGGTGGTGGTGCAAATCAAAG<br>AACTGCTCCTCAGTGGATGTTGCCTTTACTTCTAGGCCTGT<br>ACGGAAGTGTTACTTCTGCTCTAAAAGCTGCGGAATTGTAC<br>CCGCGGAAGCTTCCTAGGCCGCCACCATGGCCCCCCCCGC<br>CAAGCGCGCCCGCCGCGGCTACAAGTACCTGGGCCCCGGC<br>AACAGCCTGGACCAGGGCGAGCCCACCAACCCCAGCGAC<br>GCCGCCGCCAAGGAGCACGACGAGGCCTACGCCGCCTACC<br>TGCGCAGCGGCAAGAACCCCTACCTGTACTTCAGCCCCGC<br>CGACCAGCGCTTCATCGACCAGACCAAGGACGCCAAGGA<br>CTGGGGCGGCAAGATCGGCCACTACTTCTTCCGCGCCAAG<br>AAGGCCATCGCCCCCGTGCTGACCGACACCCCCGACCACC<br>CCAGCACCAGCCGCCCCACCAAGCCCACCAAGCGCAGCA<br>AGCCCCCCCCCCACATCTTCATCAACCTGGCCAAGAAGAA<br>GAAGGCCGGCGCCGGCCAGGTGAAGCGCGACAACCTGGC<br>CCCCATGAGCGACGGCGCCGTGCAGCCCGACGGCGGCCA<br>GCCCGCCGTGCGCAACGAGCGCGCCACCGGCAGCGGCAA<br>CGGCAGCGGCGGCGGCGGCGGCGGCGGCAGCGGCGGCGT<br>GGGCATCAGCACCGGCACCTTCAACAACCAGACCGAGTTC<br>AAGTTCCTGGAGAACGGCTGGGTGGAGATCACCGCCAACA<br>GCAGCCGCCTGGTGCACCTGAACATGCCCGAGAGCGAGA<br>ACTACCGCCGCGTGGTGGTGAACAACATGGACAAGACCGC<br>CGTGAACGGCAACATGGCCCTGGACGACATCCACGCCCAG<br>ATCGTGACCCCCTGGAGCCTGGTGGACGCCAACGCCTGGG | SEQ ID NO: 130 |

TABLE 4-continued

| Exemplary Construct | Sequence | SEQ ID NO: |
|---|---|---|
| | GCGTGTGGTTCAACCCCGGCGACTGGCAGCTGATCGTGAA<br>CACCATGAGCGAGCTGCACCTGGTGAGCTTCGAGCAGGAG<br>ATCTTCAACGTGGTGCTGAAGACCGTGAGCGAGAGCGCCA<br>CCCAGCCCCCCACCAAGGTGTACAACAACGACCTGACCGC<br>CAGCCTGATGGTGGCCCTGGACAGCAACAACACCATGCCC<br>TTCACCCCCGCCGCCATGCGCAGCGAGACCCTGGGCTTCT<br>ACCCCTGGAAGCCCACCATCCCCACCCCCTGGCGCTACTAC<br>TTCCAGTGGGACCGCACCCTGATCCCCAGCCACACCGGCA<br>CCAGCGGCACCCCCACCAACATCTACCACGGCACCGACCC<br>CGACGACGTGCAGTTCTACACCATCGAGAACAGCGTGCCC<br>GTGCACCTGCTGCGCACCGGCGACGAGTTCGCCACCGGCA<br>CCTTCTTCTTCGACTGCAAGCCCTGCCGCCTGACCCACACC<br>TGGCAGACCAACCGCGCCCTGGGCCTGCCCCCCTTCCTGA<br>ACAGCCTGCCCCAGAGCGAGGGCGCCACCAACTTCGGCG<br>ACATCGGCGTGCAGCAGGACAAGCGCCGCGGCGTGACCC<br>AGATGGGCAACACCAACTACATCACCGAGGCCACCATCAT<br>GCGCCCCGCCGAGGTGGGCTACAGCGCCCCCTACTACAGC<br>TTCGAGGCCAGCACCCAGGGCCCCTTCAAGACCCCCATCG<br>CCGCCGGCCGCGGCGGCGCCCAGACCTACGAGAACCAGG<br>CCGCCGACGGCGACCCCCGCTACGCCTTCGGCCGCCAGCA<br>CGGCCAGAAGACCACCACCACCGGCGAGACCCCCGAGCG<br>CTTCACCTACATCGCCCACCAGGACACCGGCCGCTACCCC<br>GAGGGCGACTGGATCCAGAACATCAACTTCAACCTGCCCG<br>TGACCAACGACAACGTGCTGCTGCCCACCGACCCCATCGG<br>CGGCAAGACCGGCATCAACTACACCAACATCTTCAACACC<br>TACGGCCCCCTGACCGCCCTGAACAACGTGCCCCCCGTGT<br>ACCCCAACGGCCAGATCTGGGACAAGGAGTTCGACACCG<br>ACCTGAAGCCCCGCCTGCACGTGAACGCCCCCTTCGTGTG<br>CCAGAACAACTGCCCCGGCCAGCTGTTCGTGAAGGTGGCC<br>CCCAACCTGACCAACGAGTACGACCCCGACGCCAGCGCCA<br>ACATGAGCCGCATCGTGACCTACAGCGACTTCTGGTGGAA<br>GGGCAAGCTGGTGTTCAAGGCCAAGCTGCGCGCCAGCCA<br>CACCTGGAACCCCATCCAGCAGATGAGCATCAACGTGGAC<br>AACCAGTTCAACTACGTGCCCAGCAACATCGGCGGCATGA<br>AGATCGTGTACGAGAAGAGCCAGCTGGCCCCCCGCAAGCT<br>GTACTAATAACTCGAGCATGCATCTAGAGGTACATCTAGATA<br>GAGCTCGCTGATCAGCCTCGACTGTGCCTTCTAGTTGCCAG<br>CCATCTGTTGTTTGCCCCTCCCCCGTGCCTTCCTTGACCCT<br>GGAAGGTGCCACTCCCACTGTCCTTTCCTAATAAAATGAGG<br>AAATTGCATCGCATTGTCTGAGTAGGTGTCATTCTATTCTGG<br>GGGGGGGTGGGGCAGGACAGCAAGGGGGAGGATTGGG<br>AAGACAATAGCAGGCATGCTGGGGA | |
| Exemplary CuV Construct 1 comprising a proto-parvovirus variant VP1 capsid coding sequence Ph-v5UTR-CuV-CTG_GTC-Del-WVPPG | ATCATGGAGATAATTAAAATGATAACCATCTCGCAAATAAAT<br>AAGTATTTTACTGTTTTCGTAACAGTTTTGTAATAAAAAAAC<br>CTATAAATATTCCCTCGACGAAGACTTGATCACCCGGGGGA<br>TCCCCTGTTAAGCTGGCTCCAGCTATTAGAAAAGCCAGAG<br>GTTACAACTTCCTAGGACCCTTCAATCAAGACTTCAACAAA<br>GAACCAACTAATCCATCAGACAACGCTGCAAAACAACACG<br>ATTTGGAATACAACAAACTAATCAACCAAGGACACAATCCT<br>TATTGGTACTACAACAAAGCTGACGAAGACTTCATCAAAG<br>CAACAGATCAAGCACCAGACTGGGGAGGAAAATTTGGCA<br>ACTTCATCTTCAGAGCCAAAAAACACATCGCTCCAGAACT<br>GGCACCACCAGCAAAAAAGAAAAGCAAAACCAAACACAG<br>TGAACCAGAATTCAGCCACAAACACATCAAACCAGGCACC<br>AAAAGAGGTAAGCCTTTTCATATTTTTGTAAACCTTGCTAG<br>AAAAAGAGCCCGCATGTCAGAACCAGCTAATGATACAAAT<br>GAACAACCAGACAACTCCCCTGTTGAACAGGGTGCTGGTC<br>AAATTGGAGGAGGTGGAGGTGGAGGTGGAAGCGGTGTCG<br>GGCACAGCACTGGTGATTATAATAATAGGACTGAGTTTATTT<br>ATCATGGTGATGAAGTCACAATTATTTGCCACTCTACAAGA<br>CTGGTTCACATCAATATGTCAGACAGGGAAGACTACATCAT<br>CTATGAAACAGACAGAGGACCACTCTTTCCTACCACTCAG<br>GACCTGCAGGGTAGAGACACTCTAAATGACTCTTACCATGC<br>CAAAGTAGAAACACCATGGAAACTACTCCATGCAAACAGC<br>TGGGGCTGCTGGTTTTCACCAGCAGACTTCCAACAAATGA<br>TCACCACATGCAGAGACATAGCACCAATAAAAATGCACCA<br>AAAAATAGAAAACATTGTCATCAAAACAGTCAGTAAAACA<br>GGCACAGGAGAAACAGAAACAACCAACTACAACAATGAC<br>CTCACAGCACTCCTACAAATTGCACAAGACAACAGTAACC<br>TACTACCATGGGCTGCAGATAACTTTTATATAGACTCAGTAG<br>GTTACGTTCCATGGAGAGCATGCAAACTACCAACCTACTGC<br>TACCACGTAGACACTTGGAATACAATTGACATAAACCAAGC<br>AGACACACCAAACCAATGGAGAGAAATCAAAAAAGGCAT<br>CCAATGGGACAATATCCAATTCACACCACTAGAAACTATGA<br>TAAACATTGACTTACTAAGAACAGGAGATGCCTGGGAATCT<br>GGTAACTACAATTTCCACACAAAACCAACAAACCTAGCTT | SEQ ID NO: 131 |

TABLE 4-continued

| Exemplary Construct | Sequence | SEQ ID NO: |
|---|---|---|
| | ACCATTGGCAATCACAAAGACACACAGGCAGCTGTCACCC<br>AACAGTAGCACCTCTAGTTGAAAGAGGACAAGGAACCAA<br>CATACAATCAGTAAACTGTTGGCAATGGGGAGACAGAAAC<br>AATCCAAGCTCTGCATCAACCAGAGTATCCAATATACATATT<br>GGATACTCATTTCCAGAATGGCAAATCCACTACTCAACAGG<br>AGGACCAGTAATTAATCCAGGCAGTGCATTCTCACAAGCA<br>CCATGGGGCTCAACAACTGAAGGCACCAGACTAACCCAAG<br>GTGCATCTGAAAAAGCCATCTATGACTGGTCCCATGGAGAT<br>GACCAACCAGGAGCCAGAGAAACCTGGTGGCAAAACAAC<br>CAACATGTAACAGGACAAACTGACTGGGCACCAAAAAATG<br>CACACACCTCAGAACTCAACAACAATGTACCAGCAGCCAC<br>ACACTTCTGGAAAAACAGCTATCACAACACCTTCTCACCAT<br>TCACTGCAGTAGATGATCATGGACCACAATATCCATGGGGA<br>GCCATCTGGGGAAAATACCCAGACACCACACACAAACCAA<br>TGATGTCAGCTCACGCACCATTCCTACTTCATGGACCACCT<br>GGACAACTCTTTGTAAAACTAGCACCAAACTATACAGACA<br>CACTTGACAACGGAGGTGTAACACATCCCAGAATCGTCAC<br>ATATGGAACCTTCTGGTGGTCAGGACAACTCATCTTTAAAG<br>GAAAACTACGCACTCCAAGACAATGGAATACCTACAACCT<br>ACCAAGCCTAGACAAAAGAGAAACCATGAAAAACACAGT<br>ACCAAATGAAGTTGGTCACTTTGAACTACCATACATGCCAG<br>GAAGATGTCTACCAAACTACACATTGTAACTCGAGGCATGC<br>GGTACCAAGCTTGTCGAGAAGTACTAGAGGATCATAATCAG<br>CCATACCACATTTGTAGAGGTTTTACTTGCTTTAAAAAACC<br>TCCCACACCTCCCCCTGAACCTGAAACATAAAATGAATGCA<br>ATTGTTGTTGTTAACTTGTTTATTGCAGCTTATAATGGTTAC<br>AAATAAAGCAATAGCATCACAAATTTCACAAATAAAGCATT<br>TTTTTCACTGCATTCTAGTTGTGGTTTGTCCAAACTCATCAA<br>TGTATCTTATCATGTCTGGATC | |
| Exemplary CuV Construct 2 comprising a proto-parvovirus variant VP1 capsid coding sequence Ph-Kozak-CuV-ACG-Del-WVPPG | ATCATGGAGATAATTAAAATGATAACCATCTCGCAAATAAAT<br>AAGTATTTTACTGTTTTCGTAACAGTTTTGTAATAAAAAAAC<br>CTATAAATACTCCGGACTACTGATACCGTCCCACTTTCGGG<br>CGCTTACCTGCCGCCACGCCAGCTATTAGAAAAGCCAGAG<br>GATACAACTTCCTAGGACCCTTCAATCAAGACTTCAACAAA<br>GAACCAACTAATCCATCAGACAACGCTGCAAAACAACACG<br>ATTTGGAATACAACAAACTAATCAACCAAGGACACAATCCT<br>TATTGGTACTACAACAAAGCTGACGAAGACTTCATCAAAG<br>CAACAGATCAAGCACCAGACTGGGGAGGAAAATTTGGCA<br>ACTTCATCTTCAGAGCCAAAAAACACATCGCTCCAGAACT<br>GGCACCACCAGCAAAAAAGAAAAGCAAAACCAAACACAG<br>TGAACCAGAATTCAGCCACAAACACATCAAACCAGGCACC<br>AAAAGAGGTAAGCCTTTTCATATTTTTGTAAACCTTGCTAG<br>AAAAAGAGCCCGCATGTCAGAACCAGCTAATGATACAAAT<br>GAACAACCAGACAACTCCCCTGTTGAACAGGGTGCTGGTC<br>AAATTGGAGGAGGTGGAGGTGGAGGTGGAAGCGGTGTCG<br>GGCACAGCACTGGTGATTATAATAATAGGACTGAGTTTATTT<br>ATCATGGTGATGAAGTCACAATTATTTGCCACTCTACAAGA<br>CTGGTTCACATCAATATGTCAGACAGGGAAGACTACATCAT<br>CTATGAAACAGACAGAGGACCACTCTTTCCTACCACTCAG<br>GACCTGCAGGGTAGAGACACTCTAAATGACTCTTACCATGC<br>CAAAGTAGAAACACCATGGAAACTACTCCATGCAAACAGC<br>TGGGGCTGCTGGTTTTCACCAGCAGACTTCCAACAAATGA<br>TCACCACATGCAGAGACATAGCACCAATAAAAATGCACCA<br>AAAAATAGAAAACATTGTCATCAAAACAGTCAGTAAAACA<br>GGCACAGGAGAAACAGAAACAACCAACTACAACAATGAC<br>CTCACAGCACTCCTACAAATTGCACAAGACAACAGTAACC<br>TACTACCATGGGCTGCAGATAACTTTTATATAGACTCAGTAG<br>GTTACGTTCCATGGAGAGCATGCAAACTACCAACCTACTGC<br>TACCACGTAGACACTTGGAATACAATTGACATAAACCAAGC<br>AGACACACCAAACCAATGGAGAGAAATCAAAAAAGGCAT<br>CCAATGGGACAATATCCAATTCACACCACTAGAAACTATGA<br>TAAACATTGACTTACTAAGAACAGGAGATGCCTGGGAATCT<br>GGTAACTACAATTTCCACACAAAACCAACAAACCTAGCTT<br>ACCATTGGCAATCACAAAGACACACAGGCAGCTGTCACCC<br>AACAGTAGCACCTCTAGTTGAAAGAGGACAAGGAACCAA<br>CATACAATCAGTAAACTGTTGGCAATGGGGAGACAGAAAC<br>AATCCAAGCTCTGCATCAACCAGAGTATCCAATATACATATT<br>GGATACTCATTTCCAGAATGGCAAATCCACTACTCAACAGG<br>AGGACCAGTAATTAATCCAGGCAGTGCATTCTCACAAGCA<br>CCATGGGGCTCAACAACTGAAGGCACCAGACTAACCCAAG<br>GTGCATCTGAAAAAGCCATCTATGACTGGTCCCATGGAGAT<br>GACCAACCAGGAGCCAGAGAAACCTGGTGGCAAAACAAC<br>CAACATGTAACAGGACAAACTGACTGGGCACCAAAAAATG<br>CACACACCTCAGAACTCAACAACAATGTACCAGCAGCCAC<br>ACACTTCTGGAAAAACAGCTATCACAACACCTTCTCACCAT<br>TCACTGCAGTAGATGATCATGGACCACAATATCCATGGGGA | SEQ ID NO: 132 |

TABLE 4-continued

| Exemplary Construct | Sequence | SEQ ID NO: |
|---|---|---|
| | GCCATCTGGGGAAAATACCCAGACACCACACACAAACCAA TGATGTCAGCTCACGCACCATTCCTACTTCATGGACCACCT GGACAACTCTTTGTAAAACTAGCACCAAACTATACAGACA CACTTGACAACGGAGGTGTAACACATCCCAGAATCGTCAC ATATGGAACCTTCTGGTGGTCAGGACAACTCATCTTTAAAG GAAAACTACGCACTCCAAGACAATGGAATACCTACAACCT ACCAAGCCTAGACAAAAGAGAAACCATGAAAAACACAGT ACCAAATGAAGTTGGTCACTTTGAACTACCATACATGCCAG GAAGATGTCTACCAAACTACACATTGTAACTCGAGGCATGC GGTACCAAGCTTGTCGAGAAGTACTAGAGGATCATAATCAG CCATACCACATTTGTAGAGGTTTTACTTGCTTTAAAAAACC TCCCACACCTCCCCCTGAACCTGAAACATAAAATGAATGCA ATTGTTGTTGTTAACTTGTTTATTGCAGCTTATAATGGTTAC AAATAAAGCAATAGCATCACAAATTTCACAAATAAAGCATT TTTTTCACTGCATTCTAGTTGTGGTTTGTCCAAACTCATCAA TGTATCTTATCATGTCTGGATC | |
| Exemplary CuV Construct 3 comprising a variant VP1 capsid coding sequence CMV-codopt_CuV_VP1_delta_WVPPG | GACATTGATTATTGACTAGTTATTAATAGTAATCAATTACGG GGTCATTAGTTCATAGCCCATATATGGAGTTCCGCGTTACAT AACTTACGGTAAATGGCCCGCCTGGCTGACCGCCCAACGA CCCCCGCCCATTGACGTCAATAATGACGTATGTTCCCATAGT AACGCCAATAGGGACTTTCCATTGACGTCAATGGGTGGACT ATTTACGGTAAACTGCCCACTTGGCAGTACATCAAGTGTAT CATATGCCAAGTACGCCCCCTATTGACGTCAATGACGGTAA ATGGCCCGCCTGGCATTATGCCCAGTACATGACCTTATGGG ACTTTCCTACTTGGCAGTACATCTACGTATTAGTCATCGCTA TTACCATGGTGATGCGGTTTTGGCAGTACATCAATGGGCGT GGATAGCGGTTTGACTCACGGGGATTTCCAAGTCTCCACCC CATTGACGTCAATGGGAGTTTGTTTTGGCACCAAAATCAAC GGGACTTTCCAAAATGTCGTAACAACTCCGCCCCATTGACG CAAATGGGCGGTAGGCGTGTACGGTGGGAGGTCTATATAAG CAGAGCTCTCTGGCTAACTAGAGAACCCACTGCTTACTGG CTTATCGAAATTAATACGACTCACTATAGGGAGACCCAAGC TTGGTACCGGACTCTAGAGGATCCGGTACTCGAGGAACTG AAAAACCAGAAAGTTAACTGGTAAGTTTAGTCTTTTTGTCT TTTATTTCAGGTCCCGGATCCGGTGGTGGTGCAAATCAAAG AACTGCTCCTCAGTGGATGTTGCCTTTACTTCTAGGCCTGT ACGGAAGTGTTACTTCTGCTCTAAAAGCTGCGGAATTGTAC CCGCGGAAGCTTCCTAGGCCGCCACCATGCCCGCCATCCG CAAGGCCCGCGGCTACAACTTCCTGGGCCCCTTCAACCAG GACTTCAACAAGGAGCCCACCAACCCCAGCGACAACGCC GCCAAGCAGCACGACCTGGAGTACAACAAGCTGATCAACC AGGGCCACAACCCCTACTGGTACTACAACAAGGCCGACGA GGACTTCATCAAGGCCACCGACCAGGCCCCCGACTGGGGC GGCAAGTTCGGCAACTTCATCTTCCGCGCCAAGAAGCACA TCGCCCCCGAGCTGGCCCCCCCCGCCAAGAAGAAGAGCA AGACCAAGCACAGCGAGCCCGAGTTCAGCCACAAGCACA TCAAGCCCGGCACCAAGCGCGGCAAGCCCTTCCACATCTT CGTGAACCTGGCCCGCAAGCGCGCCCGCATGAGCGAGCCC GCCAACGACACCAACGAGCAGCCCGACAACAGCCCCGTG GAGCAGGGCGCCGGCCAGATCGGCGGCGGCGGCGGCGGC GGCGGCAGCGGCGTGGGCCACAGCACCGGCGACTACAAC AACCGCACCGAGTTCATCTACCACGGCGACGAGGTGACCA TCATCTGCCACAGCACCCGCCTGGTGCACATCAACATGAG CGACCGCGAGGACTACATCATCTACGAGACCGACCGCGGC CCCCTGTTCCCCACCACCCAGGACCTGCAGGGCCGCGACA CCCTGAACGACAGCTACCACGCCAAGGTGGAGACCCCCTG GAAGCTGCTGCACGCCAACAGCTGGGGCTGCTGGTTCAGC CCCGCCGACTTCCAGCAGATGATCACCACCTGCCGCGACA TCGCCCCCATCAAGATGCACCAGAAGATCGAGAACATCGT GATCAAGACCGTGAGCAAGACCGGCACCGGCGAGACCGA GACCACCAACTACAACAACGACCTGACCGCCCTGCTGCAG ATCGCCCAGGACAACAGCAACCTGCTGCCCTGGGCCGCCG ACAACTTCTACATCGACAGCGTGGGCTACGTGCCCTGGCG CGCCTGCAAGCTGCCCACCTACTGCTACCACGTGGACACC TGGAACACCATCGACATCAACCAGGCCGACACCCCCAACC AGTGGCGCGAGATCAAGAAGGGCATCCAGTGGGACAACAT CCAGTTCACCCCCCTGGAGACCATGATCAACATCGACCTGC TGCGCACCGGCGACGCCTGGGAGAGCGGCAACTACAACTT CCACACCAAGCCCACCAACCTGGCCTACCACTGGCAGAGC CAGCGCCACACCGGCAGCTGCCACCCCACCGTGGCCCCCC TGGTGGAGCGCGGCCAGGGCACCAACATCCAGAGCGTGA ACTGCTGGCAGTGGGGCGACCGCAACAACCCCAGCAGCG CCAGCACCCGCGTGAGCAACATCCACATCGGCTACAGCTT CCCCGAGTGGCAGATCCACTACAGCACCGGCGGCCCCGTG ATCAACCCCGGCAGCGCCTTCAGCCAGGCCCCCTGGGGCA GCACCACCGAGGGCACCCGCCTGACCCAGGGCGCCAGCG | SEQ ID NO: 133 |

TABLE 4-continued

| Exemplary Construct | Sequence | SEQ ID NO: |
| --- | --- | --- |
| | AGAAGGCCATCTACGACTGGAGCCACGGCGACGACCAGCC<br>CGGCGCCCGCGAGACCTGGTGGCAGAACAACCAGCACGT<br>GACCGGCCAGACCGACTGGGCCCCCAAGAACGCCCACAC<br>CAGCGAGCTGAACAACAACGTGCCCGCCGCCACCCACTTC<br>TGGAAGAACAGCTACCACAACACCTTCAGCCCCTTCACCG<br>CCGTGGACGACCACGGCCCCCAGTACCCCTGGGGCGCCAT<br>CTGGGGCAAGTACCCCGACACCACCCACAAGCCCATGATG<br>AGCGCCCACGCCCCCTTCCTGCTGCACGGCCCCCCCGGCC<br>AGCTGTTCGTGAAGCTGGCCCCCAACTACACCGACACCCT<br>GGACAACGGCGGCGTGACCCACCCCCGCATCGTGACCTAC<br>GGCACCTTCTGGTGGAGCGGCCAGCTGATCTTCAAGGGCA<br>AGCTGCGCACCCCCCGCCAGTGGAACACCTACAACCTGCC<br>CAGCCTGGACAAGCGCGAGACCATGAAGAACACCGTGCC<br>CAACGAGGTGGGCCACTTCGAGCTGCCCTACATGCCCGGC<br>CGCTGCCTGCCCAACTACACCCTGTAATAACTCGAGCATGC<br>ATCTAGAGGTACATCTAGATAGAGCTCGCTGATCAGCCTCG<br>ACTGTGCCTTCTAGTTGCCAGCCATCTGTTGTTTGCCCCTC<br>CCCCGTGCCTTCCTTGACCCTGGAAGGTGCCACTCCCACT<br>GTCCTTTCCTAATAAAATGAGGAAATTGCATCGCATTGTCT<br>GAGTAGGTGTCATTCTATTCTGGGGGGTGGGGTGGGGCAG<br>GACAGCAAGGGGGAGGATTGGGAAGACAATAGCAGGCAT<br>GCTGGGGA | |
| Exemplary CuV Construct 4 comprising a proto-parvovirus variant VP1 capsid coding sequence Ph-Kozak-CuV-ACG-Del-WVPPGYN FLG | ATCATGGAGATAATTAAAATGATAACCATCTCGCAAATAAAT<br>AAGTATTTTACTGTTTTCGTAACAGTTTTGTAATAAAAAAAC<br>CTATAAATACTCCGGACTACTGATACCGTCCCACTTTCGGG<br>CGCTTACCTGCCGCCACGCCAGCTATTAGAAAAGCCAGAG<br>GACCCTTCAATCAAGACTTCAACAAAGAACCAACTAATCC<br>ATCAGACAACGCTGCAAAACAACACGATTTGGAATACAAC<br>AAACTAATCAACCAAGGACACAATCCTTATTGGTACTACAA<br>CAAAGCTGACGAAGACTTCATCAAAGCAACAGATCAAGCA<br>CCAGACTGGGGAGGAAAATTTGGCAACTTCATCTTCAGAG<br>CCAAAAAACACATCGCTCCAGAACTGGCACCACCAGCAA<br>AAAAGAAAAGCAAAACCAAACACAGTGAACCAGAATTCA<br>GCCACAAACACATCAAACCAGGCACCAAAAGAGGTAAGC<br>CTTTTCATATTTTTGTAAACCTTGCTAGAAAAAGAGCCCGC<br>ATGTCAGAACCAGCTAATGATACAAATGAACAACCAGACA<br>ACTCCCCTGTTGAACAGGGTGCTGGTCAAATTGGAGGAGG<br>TGGAGGTGGAGGTGGAAGCGGTGTCGGGCACAGCACTGG<br>TGATTATAATAATAGGACTGAGTTTATTTATCATGGTGATGA<br>AGTCACAATTATTTGCCACTCTACAAGACTGGTTCACATCA<br>ATATGTCAGACAGGGAAGACTACATCATCTATGAAACAGAC<br>AGAGGACCACTCTTTCCTACCACTCAGGACCTGCAGGGTA<br>GAGACACTCTAAATGACTCTTACCATGCCAAAGTAGAAAC<br>ACCATGGAAACTACTCCATGCAAACAGCTGGGGCTGCTGG<br>TTTTCACCAGCAGACTTCCAACAAATGATCACCACATGCAG<br>AGACATAGCACCAATAAAAATGCACCAAAAAATAGAAAAC<br>ATTGTCATCAAAACAGTCAGTAAAACAGGCACAGGAGAAA<br>CAGAAACAACCAACTACAACAATGACCTCACAGCACTCCT<br>ACAAATTGCACAAGACAACAGTAACCTACTACCATGGGCT<br>GCAGATAACTTTTATATAGACTCAGTAGGTTACGTTCCATGG<br>AGAGCATGCAAACTACCAACCTACTGCTACCACGTAGACA<br>CTTGGAATACAATTGACATAAACCAAGCAGACACACCAAA<br>CCAATGGAGAGAAATCAAAAAAGGCATCCAATGGGACAAT<br>ATCCAATTCACACCACTAGAAACTATGATAAACATTGACTT<br>ACTAAGAACAGGAGATGCCTGGGAATCTGGTAACTACAAT<br>TTCCACACAAAACCAACAAACCTAGCTTACCATTGGCAATC<br>ACAAAGACACACAGGCAGCTGTCACCCAACAGTAGCACCT<br>CTAGTTGAAAGAGGACAAGGAACCAACATACAATCAGTAA<br>ACTGTTGGCAATGGGGAGACAGAAACAATCCAAGCTCTGC<br>ATCAACCAGAGTATCCAATATACATATTGGATACTCATTTCC<br>AGAATGGCAAATCCACTACTCAACAGGAGGACCAGTAATT<br>AATCCAGGCAGTGCATTCTCACAAGCACCATGGGGCTCAA<br>CAACTGAAGGCACCAGACTAACCCAAGGTGCATCTGAAAA<br>AGCCATCTATGACTGGTCCCATGGAGATGACCAACCAGGA<br>GCCAGAGAAACCTGGTGGCAAAACAACCAACATGTAACA<br>GGACAAACTGACTGGGCACCAAAAAATGCACACACCTCA<br>GAACTCAACAACAATGTACCAGCAGCCACACACTTCTGGA<br>AAAACAGCTATCACAACACCTTCTCACCATTCACTGCAGTA<br>GATGATCATGGACCACAATATCCATGGGGAGCCATCTGGGG<br>AAAATACCCAGACACCACACACAAACCAATGATGTCAGCT<br>CACGCACCATTCCTACTTCATGGACCACCTGGACAACTCTT<br>TGTAAAACTAGCACCAAACTATACAGACACACTTGACAAC<br>GGAGGTGTAACACATCCCAGAATCGTCACATATGGAACCTT<br>CTGGTGGTCAGGACAACTCATCTTTAAAGGAAAACTACGC<br>ACTCCAAGACAATGGAATACCTACAACCTACCAAGCCTAG<br>ACAAAAGAGAAACCATGAAAAACACAGTACCAAATGAAG | SEQ ID NO: 134 |

TABLE 4-continued

| Exemplary Construct | Sequence | SEQ ID NO: |
|---|---|---|
| | TTGGTCACTTTGAACTACCATACATGCCAGGAAGATGTCTA CCAAACTACACATTGTAACTCGAGGCATGCGGTACCAAGCT TGTCGAGAAGTACTAGAGGATCATAATCAGCCATACCACAT TTGTAGAGGTTTTACTTGCTTTAAAAAACCTCCCACACCTC CCCCTGAACCTGAAACATAAAATGAATGCAATTGTTGTTGT TAACTTGTTTATTGCAGCTTATAATGGTTACAAATAAAGCAA TAGCATCACAAATTTCACAAATAAAGCATTTTTTTCACTGC ATTCTAGTTGTGGTTTGTCCAAACTCATCAATGTATCTTATC ATGTCTGGATC | |
| Exemplary CuV Construct 5 comprising a proto-parvovirus variant VP1 capsid coding sequence CMV-codopt_CuV_VP1_delta_WVPPG YNFLG | GACATTGATTATTGACTAGTTATTAATAGTAATCAATTACGG GGTCATTAGTTCATAGCCCATATATGGAGTTCCGCGTTACAT AACTTACGGTAAATGGCCCGCCTGGCTGACCGCCCAACGA CCCCCGCCCATTGACGTCAATAATGACGTATGTTCCCATAGT AACGCCAATAGGGACTTTCCATTGACGTCAATGGGTGGACT ATTTACGGTAAACTGCCCACTTGGCAGTACATCAAGTGTAT CATATGCCAAGTACGCCCCCTATTGACGTCAATGACGGTAA ATGGCCCGCCTGGCATTATGCCCAGTACATGACCTTATGGG ACTTTCCTACTTGGCAGTACATCTACGTATTAGTCATCGCTA TTACCATGGTGATGCGGTTTTGGCAGTACATCAATGGGCGT GGATAGCGGTTTGACTCACGGGGATTTCCAAGTCTCCACCC CATTGACGTCAATGGGAGTTTGTTTTGGCACCAAAATCAAC GGGACTTTCCAAAATGTCGTAACAACTCCGCCCCATTGACG CAAATGGGCGGTAGGCGTGTACGGTGGGAGGTCTATATAAG CAGAGCTCTCTGGCTAACTAGAGAACCCACTGCTTACTGG CTTATCGAAATTAATACGACTCACTATAGGGAGACCCAAGC TTGGTACCGGACTCTAGAGGATCCGGTACTCGAGGAACTG AAAAACCAGAAAGTTAACTGGTAAGTTTAGTCTTTTTGTCT TTTATTTCAGGTCCCGGATCCGGTGGTGGTGCAAATCAAAG AACTGCTCCTCAGTGGATGTTGCCTTTACTTCTAGGCCTGT ACGGAAGTGTTACTTCTGCTCTAAAAGCTGCGGAATTGTAC CCGCGGAAGCTTCCTAGGCCGCCACCATGCCCGCCATCCG CAAGGCCCGCGGCCCCTTCAACCAGGACTTCAACAAGGA GCCCACCAACCCCAGCGACAACGCCGCCAAGCAGCACGA CCTGGAGTACAACAAGCTGATCAACCAGGGCCACAACCCC TACTGGTACTACAACAAGGCCGACGAGGACTTCATCAAGG CCACCGACCAGGCCCCCGACTGGGGCGGCAAGTTCGGCA ACTTCATCTTCCGCGCCAAGAAGCACATCGCCCCCGAGCT GGCCCCCCCCGCCAAGAAGAAGAGCAAGACCAAGCACAG CGAGCCCGAGTTCAGCCACAAGCACATCAAGCCCGGCACC AAGCGCGGCAAGCCCTTCCACATCTTCGTGAACCTGGCCC GCAAGCGCGCCCGCATGAGCGAGCCCGCCAACGACACCA ACGAGCAGCCCGACAACAGCCCCGTGGAGCAGGGCGCCG GCCAGATCGGCGGCGGCGGCGGCGGCGGCGGCAGCGGCG TGGGCCACAGCACCGGCGACTACAACAACCGCACCGAGTT CATCTACCACGGCGACGAGGTGACCATCATCTGCCACAGC ACCCGCCTGGTGCACATCAACATGAGCGACCGCGAGGACT ACATCATCTACGAGACCGACCGCGGCCCCCTGTTCCCCACC ACCCAGGACCTGCAGGGCCGCGACACCCTGAACGACAGC TACCACGCCAAGGTGGAGACCCCCTGGAAGCTGCTGCACG CCAACAGCTGGGGCTGCTGGTTCAGCCCCGCCGACTTCCA GCAGATGATCACCACCTGCCGCGACATCGCCCCCATCAAG ATGCACCAGAAGATCGAGAACATCGTGATCAAGACCGTGA GCAAGACCGGCACCGGCGAGACCGAGACCACCAACTACA ACAACGACCTGACCGCCCTGCTGCAGATCGCCCAGGACAA CAGCAACCTGCTGCCCTGGGCCGCCGACAACTTCTACATC GACAGCGTGGGCTACGTGCCCTGGCGCGCCTGCAAGCTGC CCACCTACTGCTACCACGTGGACACCTGGAACACCATCGA CATCAACCAGGCCGACACCCCCAACCAGTGGCGCGAGATC AAGAAGGGCATCCAGTGGGACAACATCCAGTTCACCCCCC TGGAGACCATGATCAACATCGACCTGCTGCGCACCGGCGA CGCCTGGGAGAGCGGCAACTACAACTTCCACACCAAGCCC ACCAACCTGGCCTACCACTGGCAGAGCCAGCGCCACACCG GCAGCTGCCACCCCACCGTGGCCCCCCTGGTGGAGCGCGG CCAGGGCACCAACATCCAGAGCGTGAACTGCTGGCAGTGG GGCGACCGCAACAACCCCAGCAGCGCCAGCACCCGCGTG AGCAACATCCACATCGGCTACAGCTTCCCCGAGTGGCAGA TCCACTACAGCACCGGCGGCCCCGTGATCAACCCCGGCAG CGCCTTCAGCCAGGCCCCCTGGGGCAGCACCACCGAGGGC ACCCGCCTGACCCAGGGCGCCAGCGAGAAGGCCATCTACG ACTGGAGCCACGGCGACGACCAGCCCGGCGCCCGCGAGA CCTGGTGGCAGAACAACCAGCACGTGACCGGCCAGACCG ACTGGGCCCCCAAGAACGCCCACACCAGCGAGCTGAACA ACAACGTGCCCGCCGCCACCCACTTCTGGAAGAACAGCTA CCACAACACCTTCAGCCCCTTCACCGCCGTGGACGACCAC GGCCCCCAGTACCCCTGGGGCGCCATCTGGGGCAAGTACC CCGACACCACCCACAAGCCCATGATGAGCGCCCACGCCCC | SEQ ID NO: 135 |

TABLE 4-continued

| Exemplary Construct | Sequence | SEQ ID NO: |
|---|---|---|
| | CTTCCTGCTGCACGGCCCCCCCGGCCAGCTGTTCGTGAAG CTGGCCCCCAACTACACCGACACCCTGGACAACGGCGGCG TGACCCACCCCCGCATCGTGACCTACGGCACCTTCTGGTGG AGCGGCCAGCTGATCTTCAAGGGCAAGCTGCGCACCCCCC GCCAGTGGAACACCTACAACCTGCCCAGCCTGGACAAGCG CGAGACCATGAAGAACACCGTGCCCAACGAGGTGGGCCA CTTCGAGCTGCCCTACATGCCCGGCCGCTGCCTGCCCAACT ACACCCTGTAATAACTCGAGCATGCATCTAGAGGTACATCT AGATAGAGCTCGCTGATCAGCCTCGACTGTGCCTTCTAGTT GCCAGCCATCTGTTGTTTGCCCCTCCCCCGTGCCTTCCTTG ACCCTGGAAGGTGCCACTCCCACTGTCCTTTCCTAATAAA TGAGGAAATTGCATCGCATTGTCTGAGTAGGTGTCATTCTA TTCTGGGGGGTGGGGTGGGGCAGGACAGCAAGGGGGAGG ATTGGGAAGACAATAGCAGGCATGCTGGGGA | |
| Exemplary FPV Construct 1 comprising a proto-parvovirus variant VP1 capsid coding sequence Ph-v5UTR-FPV-VP1-CTG-Del-LVPPG | CATGGAGATAATTAAAATGATAACCATCTCGCAAATAAATAA GTATTTTACTGTTTTCGTAACAGTTTTGTAATAAAAAAACCT ATAAAATTCCGGATTATTCATACCGTCCCACCATCGGGCGCG GATCTCCTGTTAAGCTGGCACCTCCGGCAAAGAGAGCCAG GAGAGGATATAAATATCTTGGGCCTGGGAACAGTCTTGACC AAGGAGAACCAACTAACCCTTCTGACGCCGCTGCAAAAGA ACACGACGAAGCTTACGCTGCTTATCTTCGCTCTGGTAAAA ACCCATACTTATATTTCTCGCCAGCAGATCAACGCTTTATAG ATCAAACTAAGGACGCTAAAGATTGGGGGGGGAAAATAGG ACATTATTTTTTTAGAGCTAAAAAGGCAATTGCTCCAGTATT AACTGATACACCAGATCATCCATCAACATCAAGACCAACAA AACCAACTAAAAGAAGTAAACCACCACCTCATATTTTCATC AATCTTGCAAAAAAAAAAAAAGCCGGTGCAGGACAAGTA AAAAGAGACAATCTTGCACCAATGAGTGATGGAGCAGTTC AACCAGACGGTGGTCAACCTGCTGTCAGAAATGAAAGAG CTACAGGATCTGGGAACGGGTCTGGAGGCGGGGGTGGTGG TGGTTCTGGGGGTGTGGGGATTTCTACGGGTACTTTCAATA ATCAGACGGAATTTAAATTTTTGGAAAACGGATGGGTGGA AATCACAGCAAACTCAAGCAGACTTGTACATTTAAATATGC CAGAAAGTGAAAATTATAAAAGAGTAGTTGTAAATAATATG GATAAAACTGCAGTTAAAGGAAACATGGCTTTAGATGATAT TCATGTACAAATTGTAACACCTTGGTCATTGGTTGATGCAA ATGCTTGGGGAGTTTGGTTTAATCCAGGAGATTGGCAACTA ATTGTTAATACTATGAGTGAGTTGCATTTAGTTAGTTTTGAA CAAGAAATTTTTAATGTTGTTTTAAAGACTGTTTCAGAATC TGCTACTCAGCCACCAACTAAAGTTTATAATAATGATTTAAC TGCATCATTGATGGTTGCATTAGATAGTAATAATACTATGCC ATTTACTCCAGCAGCTATGAGATCTGAGACATTGGGTTTTTA TCCATGGAAACCAACCATACCAACTCCATGGAGATATTATTT TCAATGGGATAGAACATTAATACCATCTCATACTGGAACTAG TGGCACACCAACAAATATATACCATGGTACAGATCCAGATG ATGTTCAATTTTATACTATTGAAAATTCTGTGCCAGTACACT TACTAAGAACAGGTGATGAATTTGCTACAGGAACATTTTTT TTTGATTGTAAACCATGTAGACTAACACATACATGGCAAAC AAATAGAGCATTGGGCTTACCACCATTTTTAAATTCTTTGCC TCAATCTGAAGGAGCTACTAACTTTGGTGATATAGGAGTTC AACAAGATAAAAGACGTGGTGTAACTCAAATGGGAAATAC AAACTATATTACTGAAGCTACTATTATGAGACCAGCTGAGG TTGGTTATAGTGCACCATATTATTCTTTTGAGGCGTCTACAC AAGGGCCATTTAAAACACCTATTGCAGCAGGACGGGGGGG AGCGCAAACAGATGAAAATCAAGCAGCAGATGGTGATCCA AGATATGCATTTGGTAGACAACATGGTCAAAAAACTACCAC AACAGGAGAAACACCTGAGAGATTTACATATATAGCACATC AAGATACAGGAAGATATCCAGAAGGAGATTGGATTCAAAA TATTAACTTTAACCTTCCTGTAACAAATGATAATGTATTGCT ACCAACAGATCCAATTGGAGGTAAAACAGGAATTAACTATA CTAATATATTTAATACTTATGGTCCTTTAACTGCATTAAATAA TGTACCACCAGTTTATCCAAATGGTCAAATTTGGGATAAAG AATTTGATACTGACTTAAAACCAAGACTTCATGTAAATGCA CCATTTGTTTGTCAAAATAATTGTCCTGGTCAATTATTTGTA AAAGTTGCGCCTAATTTAACAAATGAATATGATCCTGATGC ATCTGCTAATATGTCAAGAATTGTAACTTACTCAGATTTTTG GTGGAAAGGTAAATTAGTATTTAAAGCTAAACTAAGAGCCT CTCATACTTGGAATCCAATTCAACAAATGAGTATTAATGTAG ATAACCAATTTAACTATGTACCAAGTAATATTGGAGCTATGA AAATTGTATATGAAAAATCTCAACTAGCACCTAGAAAATTAT ATTAACTCGAGGCATGCGGTACCAAGCTTGTCGAGAAGTA CTAGAGGATCATAATCAGCCATACCACATTTGTAGAGGTTTT ACTTGCTTTAAAAAACCTCCCACACCTCCCCCTGAACCTGA AACATAAAATGAATGCAATTGTTGTTGTTAACTTGTTTATTG CAGCTTATAATGGTTACAAATAAAGCAATAGCATCACAAAT TTCACAAATAAAGCATTTTTTTCACTGCATTCTAGTTGTGGT | SEQ ID NO: 136 |

TABLE 4-continued

| Exemplary Construct | Sequence | SEQ ID NO: |
|---|---|---|
| | TTGTCCAAACTCATCAATGTATCTTATCATGTCTGGATC | |
| Exemplary MVM Construct 1 comprising a proto-parvovirus variant VP1 capsid coding sequence Ph-Kozak-MVM-VP1-ACG-Del-WVPPG | ATCATGGAGATAATTAAAATGATAACCATCTCGCAAATAAAT AAGTATTTTACTGTTTTCGTAACAGTTTTGTAATAAAAAAAC CTATAAATACTCCGGACTACTGATACCGTCCCACTTTCGGG CGCTTACCTGCCGCCACGGCGCCTCCAGCTAAAAGAGCTA AAAGAGGCTACAAGTACCTGGGACCAGGGAACAGCCTTG ACCAAGGAGAACCAACCAATCCATCTGACGCCGCTGCCAA AGAGCACGACGAGGCCTACGATCAATACATCAAATCTGGA AAAAATCCTTACCTGTACTTCTCTGCTGCTGATCAACGCTT TATTGACCAAACCAAGGACGCCAAAGACTGGGGAGGCAA GGTTGGTCACTACTTTTTTAGAACCAAGCGCGCTTTTGCAC CTAAGCTTGCTACTGACTCTGAACCTGGAACTTCTGGTGTA AGCAGAGCTGGTAAACGCACTAGACCACCTGCTTACATTTT TATTAACCAAGCCAGAGCTAAAAAAAAACTTACTTCTTCTG CTGCACAGCAAAGCAGTCAAACCATGAGTGATGGCACCAG CCAACCTGACAGCGGAAACGCTGTCCACTCAGCTGCAAGA GTTGAACGAGCAGCTGACGGCCCTGGAGGCTCTGGGGGT GGGGGCTCTGGCGGGGGTGGGGTTGGTGTTTCTACTGGGT CTTATGATAATCAAACGCATTATAGATTCTTGGGTGACGGCT GGGTAGAAATTACTGCACTAGCAACTAGACTAGTACATTTA AACATGCCTAAATCAGAAAACTATTGCAGAATCAGAGTTCA CAATACAACAGACACATCAGTCAAAGGCAACATGGCAAAA GATGATGCTCATGAGCAAATTTGGACACCATGGAGCTTGGT GGATGCTAATGCTTGGGGAGTTTGGCTCCAGCCAAGTGAC TGGCAATACATTTGCAACACCATGAGCCAGCTTAACTTGGT ATCACTTGATCAAGAAATATTCAATGTAGTGCTGAAAACTG TTACAGAGCAAGACTTAGGAGGTCAAGCTATAAAAATATAC AACAATGACCTTACAGCTTGCATGATGGTTGCAGTAGACTC AAACAACATTTTGCCATACACACCTGCAGCAAACTCAATG GAAACACTTGGTTTCTACCCCTGGAAACCAACCATAGCATC ACCATACAGGTACTATTTTTGCGTTGACAGAGATCTTTCAG TGACCTACGAAAATCAAGAAGGCACAGTTGAACATAATGT GATGGGAACACCAAAAGGAATGAATTCTCAATTTTTTACCA TTGAGAACACACAACAAATCACATTGCTCAGAACAGGGGA CGAATTTGCCACAGGTACTTACTACTTTGACACAAATTCAG TTAAACTCACACACACGTGGCAAACCAACCGTCAACTTGG ACAGCCTCCACTGCTGTCAACCTTTCCTGAAGCTGACACT GATGCAGGTACACTTACTGCTCAAGGGAGCAGACATGGAA CAACACAAATGGGGGTTAACTGGGTGAGTGAAGCAATCAG AACCAGACCTGCTCAAGTAGGATTTTGTCAACCACACAAT GACTTTGAAGCCAGCAGAGCTGGACCATTTGCTGCCCCAA AAGTTCCAGCAGATATTACTCAAGGAGTAGACAAAGAAGC CAATGGCAGTGTTAGATACAGTTATGGCAAACAGCATGGTG AAAATTGGGCTTCACATGGACCAGCACCAGAGCGCTACAC ATGGGATGAAACAAGCTTTGGTTCAGGTAGAGACACCAAA GATGGTTTTATTCAATCAGCACCACTAGTTGTTCCACCACC ACTAAATGGCATTCTTACAAATGCAAACCCTATTGGGACTA AAAATGACATTCATTTTTCAAATGTTTTTAACAGCTATGGTC CACTAACTGCATTTTCACACCCAAGTCCTGTATACCCTCAA GGACAAATATGGGACAAAGAACTAGATCTTGAACACAAAC CTAGACTTCACATAACTGCTCCATTTGTTTGTAAAAACAAT GCACCTGGACAAATGTTGGTTAGATTAGGACCAAACCTAA CTGACCAATATGATCCAAACGGAGCCACACTTTCTAGAATT GTTACATACGGTACATTTTTCTGGAAAGGAAAACTAACCAT GAGAGCAAAACTTAGAGCTAACACCACTTGGAACCCAGTG TACCAAGTAAGTGCTGAAGACAATGGCAACTCATACATGA GTGTAACTAAATGGTTACCAACTGCTACTGGAAACATGCAG TCTGTGCCGCTTATAACAAGACCTGTTGCTAGAAATACTTA CTAACTCGAGGCATGCGGTACCAAGCTTGTCGAGAAGTAC TAGAGGATCATAATCAGCCATACCACATTTGTAGAGGTTTTA CTTGCTTTAAAAAACCTCCCACACCTCCCCCTGAACCTGAA ACATAAAATGAATGCAATTGTTGTTGTTAACTTGTTTATTGC AGCTTATAATGGTTACAAATAAAGCAATAGCATCACAAATTT CACAAATAAAGCATTTTTTTCACTGCATTCTAGTTGTGGTTT GTCCAAACTCATCAATGTATCTTATCATGTCTGGATC | SEQ ID NO: 137 |
| Exemplary H-1PV Construct 1 comprising a proto-parvovirus variant VP1 capsid coding sequence | ATCATGGAGATAATTAAAATGATAACCATCTCGCAAATAAAT AAGTATTTTACTGTTTTCGTAACAGTTTTGTAATAAAAAAAC CTATAAATACTCCGGACTACTGATACCGTCCCACTTTCGGG CGCTTACCTGCCGCCACGGCACCTCCAGCTAAAAGAGCTA AAAGAGGCTACAAGTACCTGGGACCAGGGAACAGCCTTG ACCAAGGAGAACCAACCAACCCTTCTGACGCCGCTGCCAA AGAACACGACGAAGCCTACGACCAATACATCAAATCTGGA AAAAATCCTTACCTGTACTTCTCTCCTGCTGATCAACGCTT CATTGACCAAACCAAAGACGCCAAGGACTGGGGCGGCAA GGTTGGTCACTACTTTTTTAGAACCAAGCGAGCTTTTGCAC | SEQ ID NO: 138 |

TABLE 4-continued

| Exemplary Construct | Sequence | SEQ ID NO: |
|---|---|---|
| Ph-Kozak-RH1PV-VP1-ACG-Del-WVPPG | CTAAGCTTTCTACTGACTCTGAACCTGGCACTTCTGGTGTG AGCAGACCTGGTAAACGAACTAAACCACCTGCTCACATTT TTGTAAATCAAGCCAGAGCTAAAAAAAAACGCGCTTCTCT TGCTGCACAGCAGAGGACTCTGACAATGAGTGATGGCACC GAAACAAACCAACCAGACACTGGAATCGCTAATGCTAGAG TTGAGCGATCAGCTGACGGAGGTGGAAGCTCTGGGGGTGG GGGCTCTGGCGGGGGGGGATTGGTGTTTCTACTGGGACT TATGATAATCAAACGACTTATAAGTTTTTGGGAGATGGATG GGTAGAAATAACTGCACATGCTTCTAGACTTTTGCACTTGG GAATGCCTCCTTCAGAAAACTACTGCCGCGTCACCGTTCAC AATAATCAAACAACAGGACACGGAACTAAGGTAAAGGGA AACATGGCCTATGATGACACACATCAACAAATTTGGACACC ATGGAGCTTGGTAGATGCTAATGCTTGGGGAGTTTGGTTCC AACCAAGTGACTGGCAGTTCATTCAAAACAGCATGGAATC GCTGAATCTTGACTCATTGAGCCAAGAACTATTTAATGTAG TAGTCAAAACAGTCACTGAACAACAAGGAGCTGGCCAAG ATGCCATTAAAGTCTATAATAATGACTTGACGGCCTGTATGA TGGTTGCTCTGGATAGTAACAACATACTGCCTTACACACCT GCAGCTCAAACATCAGAAACACTTGGTTTCTACCCATGGA AACCAACCGCACCAGCTCCTTACAGATACTACTTTTTCATG CCTAGACAACTCAGTGTAACCTCTAGCAACTCTGCTGAAG GAACTCAAATCACAGACACCATTGGAGAGCCACAGGCACT AAACTCTCAATTTTTTACTATTGAGAACACCTTGCCTATTAC TCTCCTGCGCACAGGTGATGAGTTTACAACTGGCACCTACA TCTTTAACACTGACCCACTTAAACTTACTCACACATGGCAA ACCAACAGACACTTGGGCATGCCTCCAAGAATAACTGACC TACCAACATCAGATACAGCAACAGCATCACTAACTGCAAAT GGAGACAGATTTGGATCAACACAAACACAGAATGTGAACT ATGTCACAGAGGCTTTGCGCACCAGGCCTGCTCAGATTGG CTTCATGCAACCTCATGACAACTTTGAAGCAAACAGAGGT GGCCCATTTAAGGTTCCAGTGGTACCGCTAGACATAACAGC TGGCGAGGACCATGATGCAAACGGAGCCATACGATTTAAC TATGGCAAACAACATGGCGAAGATTGGGCCAAACAAGGAG CAGCACCAGAAAGGTACACATGGGATGCAATTGATAGTGC AGCTGGGAGGGACACAGCTAGATGCTTTGTACAAAGTGCA CCAATATCTATTCCACCAAACCAAAACCAGATCTTGCAGCG AGAAGACGCCATAGCTGGCAGAACTAACATGCATTATACTA ATGTTTTTAACAGCTATGGTCCACTTAGTGCATTTCCTCATC CAGATCCCATTTATCCAAATGGACAAATTTGGGACAAAGAA TTGGACCTGGAACACAAACCTAGACTACACGTAACTGCAC CATTTGTTTGTAAAAACAACCCACCAGGTCAACTATTTGTT CGCTTGGGGCCTAATCTGACTGACCAATTTGACCCAAACA GCACAACTGTTTCTCGCATTGTTACATATAGCACTTTTTACT GGAAGGGTATTTTGAAATTCAAAGCCAAACTAAGACCAAA TCTGACCTGGAATCCTGTATACCAAGCAACCACAGACTCTG TTGCCAATTCTTACATGAATGTTAAGAAATGGCTCCCATCTG CAACTGGCAACATGCACTCTGATCCATTGATTTGTAGACCT GTGCCTCACATGACATACTAACTCGAGGCATGCGGTACCAA GCTTGTCGAGAAGTACTAGAGGATCATAATCAGCCATACCA CATTTGTAGAGGTTTTACTTGCTTTAAAAAACCTCCCACAC CTCCCCCTGAACCTGAAACATAAAATGAATGCAATTGTTGT TGTTAACTTGTTTATTGCAGCTTATAATGGTTACAAATAAAG CAATAGCATCACAAATTTCACAAATAAAGCATTTTTTTCACT GCATTCTAGTTGTGGTTTGTCCAAACTCATCAATGTATCTTA TCATGTCTGGATC | |
| Exemplary CuV Construct 6 comprising a variant VP1 capsid coding sequence Ph-Kozak-CuV-VP1-ACG | ATCATGGAGATAATTAAAATGATAACCATCTCGCAAATAAAT AAGTATTTTACTGTTTTCGTAACAGTTTTGTAATAAAAAAAC CTATAAATACTCCGGACTACTGATACCGTCCCACTTTCGGG CGCTTACCTGCCGCCACGCCAGCTATTAGAAAAGCCAGAG GTTGGGTACCACCTGGATACAACTTCCTAGGACCCTTCAAT CAAGACTTCAACAAAGAACCAACTAATCCATCAGACAACG CTGCAAAACAACACGATTTGGAATACAACAAACTAATCAA CCAAGGACACAATCCTTATTGGTACTACAACAAAGCTGAC GAAGACTTCATCAAAGCAACAGATCAAGCACCAGACTGGG GAGGAAAATTTGGCAACTTCATCTTCAGAGCCAAAAAACA CATCGCTCCAGAACTGGCACCACCAGCAAAAAAGAAAAG CAAAACCAAACACAGTGAACCAGAATTCAGCCACAAACA CATCAAACCAGGCACCAAAAGAGGTAAGCCTTTTCATATTT TTGTAAACCTTGCTAGAAAAAGAGCCCGCATGTCAGAACC AGCTAATGATACAAATGAACAACCAGACAACTCCCCTGTT GAACAGGGTGCTGGTCAAATTGGAGGAGGTGGAGGTGGA GGTGGAAGCGGTGTCGGGCACAGCACTGGTGATTATAATA ATAGGACTGAGTTTATTTATCATGGTGATGAAGTCACAATTA TTTGCCACTCTACAAGACTGGTTCACATCAATATGTCAGAC AGGGAAGACTACATCATCTATGAAACAGACAGAGGACCAC TCTTTCCTACCACTCAGGACCTGCAGGGTAGAGACACTCTA | SEQ ID NO: 139 |

TABLE 4-continued

| Exemplary Construct | Sequence | SEQ ID NO: |
|---|---|---|
| | AATGACTCTTACCATGCCAAAGTAGAAACACCATGGAAAC<br>TACTCCATGCAAACAGCTGGGGCTGCTGGTTTTCACCAGC<br>AGACTTCCAACAAATGATCACCACATGCAGAGACATAGCA<br>CCAATAAAAATGCACCAAAAAATAGAAAACATTGTCATCA<br>AAACAGTCAGTAAAACAGGCACAGGAGAAACAGAAACAA<br>CCAACTACAACAATGACCTCACAGCACTCCTACAAATTGC<br>ACAAGACAACAGTAACCTACTACCATGGGCTGCAGATAAC<br>TTTTATATAGACTCAGTAGGTTACGTTCCATGGAGAGCATGC<br>AAACTACCAACCTACTGCTACCACGTAGACACTTGGAATAC<br>AATTGACATAAACCAAGCAGACACACCAAACCAATGGAGA<br>GAAATCAAAAAAGGCATCCAATGGGACAATATCCAATTCAC<br>ACCACTAGAAACTATGATAAACATTGACTTACTAAGAACAG<br>GAGATGCCTGGGAATCTGGTAACTACAATTTCCACACAAA<br>ACCAACAAACCTAGCTTACCATTGGCAATCACAAAGACAC<br>ACAGGCAGCTGTCACCCAACAGTAGCACCTCTAGTTGAAA<br>GAGGACAAGGAACCAACATACAATCAGTAAACTGTTGGCA<br>ATGGGGAGACAGAAACAATCCAAGCTCTGCATCAACCAGA<br>GTATCCAATATACATATTGGATACTCATTTCCAGAATGGCAA<br>ATCCACTACTCAACAGGAGGACCAGTAATTAATCCAGGCA<br>GTGCATTCTCACAAGCACCATGGGGCTCAACAACTGAAGG<br>CACCAGACTAACCCAAGGTGCATCTGAAAAAGCCATCTAT<br>GACTGGTCCCATGGAGATGACCAACCAGGAGCCAGAGAA<br>ACCTGGTGGCAAAACAACCAACATGTAACAGGACAAACTG<br>ACTGGGCACCAAAAAAATGCACACACCTCAGAACTCAACA<br>ACAATGTACCAGCAGCCACACACTTCTGGAAAAACAGCTA<br>TCACAACACCTTCTCACCATTCACTGCAGTAGATGATCATG<br>GACCACAATATCCATGGGGAGCCATCTGGGGAAAATACCC<br>AGACACCACACACAAACCAATGATGTCAGCTCACGCACCA<br>TTCCTACTTCATGGACCACCTGGACAACTCTTTGTAAAACT<br>AGCACCAAACTATACAGACACACTTGACAACGGAGGTGTA<br>ACACATCCCAGAATCGTCACATATGGAACCTTCTGGTGGTC<br>AGGACAACTCATCTTTAAAGGAAAACTACGCACTCCAAGA<br>CAATGGAATACCTACAACCTACCAAGCCTAGACAAAAGAG<br>AAACCATGAAAAACACAGTACCAAATGAAGTTGGTCACTT<br>TGAACTACCATACATGCCAGGAAGATGTCTACCAAACTACA<br>CATTGTAACTCGAGGCATGCGGTACCAAGCTTGTCGAGAA<br>GTACTAGAGGATCATAATCAGCCATACCACATTTGTAGAGG<br>TTTTACTTGCTTTAAAAAACCTCCCACACCTCCCCCTGAAC<br>CTGAAACATAAAATGAATGCAATTGTTGTTGTTAACTTGTT<br>TATTGCAGCTTATAATGGTTACAAATAAAGCAATAGCATCAC<br>AAATTTCACAAATAAAGCATTTTTTTCACTGCATTCTAGTTG<br>TGGTTTGTCCAAACTCATCAATGTATCTTATCATGTCTGGAT<br>C | |
| Exemplary MVM Construct 2 comprising a variant VP1 capsid coding sequence Ph-Kozak-MVM-VP1-ACG | ATCATGGAGATAATTAAAATGATAACCATCTCGCAAATAAAT<br>AAGTATTTTACTGTTTTCGTAACAGTTTTGTAATAAAAAAAC<br>CTATAAATACTCCGGACTACTGATACCGTCCCACTTTCGGG<br>CGCTTACCTGCCGCCACGGCGCCTCCAGCTAAAAGAGCTA<br>AAAGAGGTTGGGTGCCTCCTGGCTACAAGTACCTGGGACC<br>AGGGAACAGCCTTGACCAAGGAGAACCAACCAATCCATCT<br>GACGCCGCTGCCAAAGAGCACGACGAGGCCTACGATCAAT<br>ACATCAAATCTGGAAAAAATCCTTACCTGTACTTCTCTGCT<br>GCTGATCAACGCTTTATTGACCAAACCAAGGACGCCAAAG<br>ACTGGGGAGGCAAGGTTGGTCACTACTTTTTTAGAACCAA<br>GCGCGCTTTTGCACCTAAGCTTGCTACTGACTCTGAACCTG<br>GAACTTCTGGTGTAAGCAGAGCTGGTAAACGCACTAGACC<br>ACCTGCTTACATTTTTATTAACCAAGCCAGAGCTAAAAAAA<br>AACTTACTTCTTCTGCTGCACAGCAAAGCAGTCAAACCAT<br>GAGTGATGGCACCAGCCAACCTGACAGCGGAAACGCTGTC<br>CACTCAGCTGCAAGAGTTGAACGAGCAGCTGACGGCCCTG<br>GAGGCTCTGGGGGTGGGGGCTCTGGCGGGGGTGGGGTTG<br>GTGTTTCTACTGGGTCTTATGATAATCAAACGCATTATAGAT<br>TCTTGGGTGACGGCTGGGTAGAAATTACTGCACTAGCAACT<br>AGACTAGTACATTTAAACATGCCTAAATCAGAAAACTATTG<br>CAGAATCAGAGTTCACAATACAACAGACACATCAGTCAAA<br>GGCAACATGGCAAAAGATGATGCTCATGAGCAAATTTGGA<br>CACCATGGAGCTTGGTGGATGCTAATGCTTGGGGAGTTTGG<br>CTCCAGCCAAGTGACTGGCAATACATTTGCAACACCATGA<br>GCCAGCTTAACTTGGTATCACTTGATCAAGAAATATTCAAT<br>GTAGTGCTGAAAACTGTTACAGAGCAAGACTTAGGAGGTC<br>AAGCTATAAAAATATACAACAATGACCTTACAGCTTGCATG<br>ATGGTTGCAGTAGACTCAAACAACATTTTGCCATACACACC<br>TGCAGCAAACTCAATGGAAACACTTGGTTTCTACCCCTGG<br>AAACCAACCATAGCATCACCATACAGGTACTATTTTTGCGT<br>TGACAGAGATCTTTCAGTGACCTACGAAAATCAAGAAGGC<br>ACAGTTGAACATAATGTGATGGGAACACCAAAAGGAATGA<br>ATTCTCAATTTTTTACCATTGAGAACACACAACAAATCACA | SEQ ID NO: 140 |

TABLE 4-continued

| Exemplary Construct | Sequence | SEQ ID NO: |
|---|---|---|
| | TTGCTCAGAACAGGGGACGAATTTGCCACAGGTACTTACT<br>ACTTTGACACAAATTCAGTTAAACTCACACACACGTGGCA<br>AACCAACCGTCAACTTGGACAGCCTCCACTGCTGTCAACC<br>TTTCCTGAAGCTGACACTGATGCAGGTACACTTACTGCTCA<br>AGGGAGCAGACATGGAACAACACAAATGGGGGTTAACTG<br>GGTGAGTGAAGCAATCAGAACCAGACCTGCTCAAGTAGGA<br>TTTTGTCAACCACACAATGACTTTGAAGCCAGCAGAGCTG<br>GACCATTTGCTGCCCCAAAAGTTCCAGCAGATATTACTCAA<br>GGAGTAGACAAAGAAGCCAATGGCAGTGTTAGATACAGTT<br>ATGGCAAACAGCATGGTGAAAATTGGGCTTCACATGGACC<br>AGCACCAGAGCGCTACACATGGGATGAAACAAGCTTTGGT<br>TCAGGTAGAGACACCAAAGATGGTTTTATTCAATCAGCACC<br>ACTAGTTGTTCCACCACCACTAAATGGCATTCTTACAAATG<br>CAAACCCTATTGGGACTAAAAATGACATTCATTTTTCAAAT<br>GTTTTTAACAGCTATGGTCCACTAACTGCATTTTCACACCC<br>AAGTCCTGTATACCCTCAAGGACAAATATGGGACAAAGAA<br>CTAGATCTTGAACACAAACCTAGACTTCACATAACTGCTCC<br>ATTTGTTTGTAAAAACAATGCACCTGGACAAATGTTGGTTA<br>GATTAGGACCAAACCTAACTGACCAATATGATCCAAACGGA<br>GCCACACTTTCTAGAATTGTTACATACGGTACATTTTTCTGG<br>AAAGGAAAACTAACCATGAGAGCAAAACTTAGAGCTAACA<br>CCACTTGGAACCCAGTGTACCAAGTAAGTGCTGAAGACAA<br>TGGCAACTCATACATGAGTGTAACTAAATGGTTACCAACTG<br>CTACTGGAAACATGCAGTCTGTGCCGCTTATAACAAGACCT<br>GTTGCTAGAAATACTTACTAACTCGAGGCATGCGGTACCAA<br>GCTTGTCGAGAAGTACTAGAGGATCATAATCAGCCATACCA<br>CATTTGTAGAGGTTTTACTTGCTTTAAAAAACCTCCCACAC<br>CTCCCCCTGAACCTGAAACATAAAATGAATGCAATTGTTGT<br>TGTTAACTTGTTTATTGCAGCTTATAATGGTTACAAATAAAG<br>CAATAGCATCACAAATTTCACAAATAAAGCATTTTTTTCACT<br>GCATTCTAGTTGTGGTTTGTCCAAACTCATCAATGTATCTTA<br>TCATGTCTGGATC | |
| Exemplary H-1PV Construct 2 comprising a variant VP1 capsid coding sequence Ph-Kozak-RH1PV-VP1-ACG | ATCATGGAGATAATTAAAATGATAACCATCTCGCAAATAAAT<br>AAGTATTTTACTGTTTTCGTAACAGTTTTGTAATAAAAAAAC<br>CTATAAATACTCCGGACTACTGATACCGTCCCACTTTCGGG<br>CGCTTACCTGCCGCCACGGCACCTCCAGCTAAAAGAGCTA<br>AAAGAGGTTGGGTGCCTCCTGGCTACAAGTACCTGGGACC<br>AGGGAACAGCCTTGACCAAGGAGAACCAACCAACCCTTC<br>TGACGCCGCTGCCAAAGAACACGACGAAGCCTACGACCA<br>ATACATCAAATCTGGAAAAAATCCTTACCTGTACTTCTCTCC<br>TGCTGATCAACGCTTCATTGACCAAACCAAAGACGCCAAG<br>GACTGGGGCGGCAAGGTTGGTCACTACTTTTTTAGAACCA<br>AGCGAGCTTTTGCACCTAAGCTTTCTACTGACTCTGAACCT<br>GGCACTTCTGGTGTGAGCAGACCTGGTAAACGAACTAAAC<br>CACCTGCTCACATTTTTGTAAATCAAGCCAGAGCTAAAAAA<br>AAACGCGCTTCTCTTGCTGCACAGCAGAGGACTCTGACAA<br>TGAGTGATGGCACCGAAACAAACCAACCAGACACTGGAAT<br>CGCTAATGCTAGAGTTGAGCGATCAGCTGACGGAGGTGGA<br>AGCTCTGGGGGTGGGGGCTCTGGCGGGGGTGGGATTGGTG<br>TTTCTACTGGGACTTATGATAATCAAACGACTTATAAGTTTT<br>TGGGAGATGGATGGGTAGAAATAACTGCACATGCTTCTAGA<br>CTTTTGCACTTGGGAATGCCTCCTTCAGAAAACTACTGCCG<br>CGTCACCGTTCACAATAATCAAACAACAGGACACGGAACT<br>AAGGTAAAGGGAAACATGGCCTATGATGACACACATCAAC<br>AAATTTGGACACCATGGAGCTTGGTAGATGCTAATGCTTGG<br>GGAGTTTGGTTCCAACCAAGTGACTGGCAGTTCATTCAAA<br>ACAGCATGGAATCGCTGAATCTTGACTCATTGAGCCAAGA<br>ACTATTTAATGTAGTAGTCAAAACAGTCACTGAACAACAAG<br>GAGCTGGCCAAGATGCCATTAAAGTCTATAATAATGACTTG<br>ACGGCCTGTATGATGGTTGCTCTGGATAGTAACAACATACT<br>GCCTTACACACCTGCAGCTCAAACATCAGAAACACTTGGT<br>TTCTACCCATGGAAACCAACCGCACCAGCTCCTTACAGATA<br>CTACTTTTTCATGCCTAGACAACTCAGTGTAACCTCTAGCA<br>ACTCTGCTGAAGGAACTCAAATCACAGACACCATTGGAGA<br>GCCACAGGCACTAAACTCTCAATTTTTTACTATTGAGAACA<br>CCTTGCCTATTACTCTCCTGCGCACAGGTGATGAGTTTACA<br>ACTGGCACCTACATCTTTAACACTGACCCACTTAAACTTAC<br>TCACACATGGCAAACCAACAGACACTTGGGCATGCCTCCA<br>AGAATAACTGACCTACCAACATCAGATACAGCAACAGCATC<br>ACTAACTGCAAATGGAGACAGATTTGGATCAACACAAACA<br>CAGAATGTGAACTATGTCACAGAGGCTTTGCGCACCAGGC<br>CTGCTCAGATTGGCTTCATGCAACCTCATGACAACTTTGAA<br>GCAAACAGAGGTGGCCCATTTAAGGTTCCAGTGGTACCGC<br>TAGACATAACAGCTGGCGAGGACCATGATGCAAACGGAGC<br>CATACGATTTAACTATGGCAAACAACATGGCGAAGATTGGG<br>CCAAACAAGGAGCAGCACCAGAAAGGTACACATGGGATG | SEQ ID NO: 141 |

TABLE 4-continued

| Exemplary Construct | Sequence | SEQ ID NO: |
|---|---|---|
| | CAATTGATAGTGCAGCTGGGAGGGACACAGCTAGATGCTT<br>TGTACAAAGTGCACCAATATCTATTCCACCAAACCAAAACC<br>AGATCTTGCAGCGAGAAGACGCCATAGCTGGCAGAACTAA<br>CATGCATTATACTAATGTTTTTAACAGCTATGGTCCACTTAG<br>TGCATTTCCTCATCCAGATCCCATTTATCCAAATGGACAAAT<br>TTGGGACAAAGAATTGGACCTGGAACACAAACCTAGACTA<br>CACGTAACTGCACCATTTGTTTGTAAAAACAACCCACCAG<br>GTCAACTATTTGTTCGCTTGGGGCCTAATCTGACTGACCAA<br>TTTGACCCAAACAGCACAACTGTTTCTCGCATTGTTACATA<br>TAGCACTTTTTACTGGAAGGGTATTTTGAAATTCAAAGCCA<br>AACTAAGACCAAATCTGACCTGGAATCCTGTATACCAAGCA<br>ACCACAGACTCTGTTGCCAATTCTTACATGAATGTTAAGAA<br>ATGGCTCCCATCTGCAACTGGCAACATGCACTCTGATCCAT<br>TGATTTGTAGACCTGTGCCTCACATGACATACTAACTCGAG<br>GCATGCGGTACCAAGCTTGTCGAGAAGTACTAGAGGATCAT<br>AATCAGCCATACCACATTTGTAGAGGTTTTACTTGCTTTAAA<br>AAACCTCCCACACCTCCCCCTGAACCTGAAACATAAAATG<br>AATGCAATTGTTGTTGTTAACTTGTTTATTGCAGCTTATAAT<br>GGTTACAAATAAAGCAATAGCATCACAAATTTCACAAATAA<br>AGCATTTTTTTCACTGCATTCTAGTTGTGGTTTGTCCAAACT<br>CATCAATGTATCTTATCATGTCTGGATC | |
| Exemplary CPV Construct 6 comprising a variant VP2 capsid coding sequence CMV-opt_CPV_VP2 | GACATTGATTATTGACTAGTTATTAATAGTAATCAATTACGG<br>GGTCATTAGTTCATAGCCCATATATGGAGTTCCGCGTTACAT<br>AACTTACGGTAAATGGCCCGCCTGGCTGACCGCCCAACGA<br>CCCCCGCCCATTGACGTCAATAATGACGTATGTTCCCATAGT<br>AACGCCAATAGGGACTTTCCATTGACGTCAATGGGTGGACT<br>ATTTACGGTAAACTGCCCACTTGGCAGTACATCAAGTGTAT<br>CATATGCCAAGTACGCCCCCTATTGACGTCAATGACGGTAA<br>ATGGCCCGCCTGGCATTATGCCCAGTACATGACCTTATGGG<br>ACTTTCCTACTTGGCAGTACATCTACGTATTAGTCATCGCTA<br>TTACCATGGTGATGCGGTTTTGGCAGTACATCAATGGGCGT<br>GGATAGCGGTTTGACTCACGGGGATTTCCAAGTCTCCACCC<br>CATTGACGTCAATGGGAGTTTGTTTTGGCACCAAAATCAAC<br>GGGACTTTCCAAAATGTCGTAACAACTCCGCCCCATTGACG<br>CAAATGGGCGGTAGGCGTGTACGGTGGGAGGTCTATATAAG<br>CAGAGCTCTCTGGCTAACTAGAGAACCCACTGCTTACTGG<br>CTTATCGAAATTAATACGACTCACTATAGGGAGACCCAAGC<br>TTGGTACCGGACTCTAGAGGATCCGGTACTCGAGGAACTG<br>AAAAACCAGAAAGTTAACTGGTAAGTTTAGTCTTTTTGTCT<br>TTTATTTCAGGTCCCGGATCCGGTGGTGGTGCAAATCAAAG<br>AACTGCTCCTCAGTGGATGTTGCCTTTACTTCTAGGCCTGT<br>ACGGAAGTGTTACTTCTGCTCTAAAAGCTGCGGAATTGTAC<br>CCGCGGTTGAGGAACCTGTTAAGATGAGCGACGGCGCCGT<br>GCAGCCCGACGGCGGCCAGCCCGCCGTGCGCAACGAGCG<br>CGCCACCGGCAGCGGCAACGGCAGCGGCGGCGGCGGCGG<br>CGGCGGCAGCGGCGGCGTGGGCATCAGCACCGGCACCTTC<br>AACAACCAGACCGAGTTCAAGTTCCTGGAGAACGGCTGG<br>GTGGAGATCACCGCCAACAGCAGCCGCCTGGTGCACCTGA<br>ACATGCCCGAGAGCGAGAACTACCGCCGCGTGGTGGTGAA<br>CAACATGGACAAGACCGCCGTGAACGGCAACATGGCCCTG<br>GACGACATCCACGCCCAGATCGTGACCCCCTGGAGCCTGG<br>TGGACGCCAACGCCTGGGGCGTGTGGTTCAACCCCGGCGA<br>CTGGCAGCTGATCGTGAACACCATGAGCGAGCTGCACCTG<br>GTGAGCTTCGAGCAGGAGATCTTCAACGTGGTGCTGAAGA<br>CCGTGAGCGAGAGCGCCACCCAGCCCCCCACCAAGGTGTA<br>CAACAACGACCTGACCGCCAGCCTGATGGTGGCCCTGGAC<br>AGCAACAACACCATGCCCTTCACCCCCGCCGCCATGCGCA<br>GCGAGACCCTGGGCTTCTACCCCTGGAAGCCCACCATCCC<br>CACCCCCTGGCGCTACTACTTCCAGTGGGACCGCACCCTG<br>ATCCCCAGCCACACCGGCACCAGCGGCACCCCCACCAACA<br>TCTACCACGGCACCGACCCCGACGACGTGCAGTTCTACAC<br>CATCGAGAACAGCGTGCCCGTGCACCTGCTGCGCACCGGC<br>GACGAGTTCGCCACCGGCACCTTCTTCTTCGACTGCAAGC<br>CCTGCCGCCTGACCCACACCTGGCAGACCAACCGCGCCCT<br>GGGCCTGCCCCCCTTCCTGAACAGCCTGCCCCAGAGCGAG<br>GGCGCCACCAACTTCGGCGACATCGGCGTGCAGCAGGACA<br>AGCGCCGCGGCGTGACCCAGATGGGCAACACCAACTACAT<br>CACCGAGGCCACCATCATGCGCCCCGCCGAGGTGGGCTAC<br>AGCGCCCCCTACTACAGCTTCGAGGCCAGCACCCAGGGCC<br>CCTTCAAGACCCCCATCGCCGCCGGCCGCGGCGGCGCCCA<br>GACCTACGAGAACCAGGCCGCCGACGGCGACCCCCGCTAC<br>GCCTTCGGCCGCCAGCACGGCCAGAAGACCACCACCACC<br>GGCGAGACCCCCGAGCGCTTCACCTACATCGCCCACCAGG<br>ACACCGGCCGCTACCCCGAGGGCGACTGGATCCAGAACAT<br>CAACTTCAACCTGCCCGTGACCAACGACAACGTGCTGCTG<br>CCCACCGACCCCATCGGCGGCAAGACCGGCATCAACTACA | SEQ ID NO: 142 |

TABLE 4-continued

| Exemplary Construct | Sequence | SEQ ID NO: |
|---|---|---|
| | CCAACATCTTCAACACCTACGGCCCCCTGACCGCCCTGAA CAACGTGCCCCCCGTGTACCCCAACGGCCAGATCTGGGAC AAGGAGTTCGACACCGACCTGAAGCCCCGCCTGCACGTGA ACGCCCCCTTCGTGTGCCAGAACAACTGCCCCGGCCAGCT GTTCGTGAAGGTGGCCCCCAACCTGACCAACGAGTACGAC CCCGACGCCAGCGCCAACATGAGCCGCATCGTGACCTACA GCGACTTCTGGTGGAAGGGCAAGCTGGTGTTCAAGGCCAA GCTGCGCGCCAGCCACACCTGGAACCCCATCCAGCAGATG AGCATCAACGTGGACAACCAGTTCAACTACGTGCCCAGCA ACATCGGCGGCATGAAGATCGTGTACGAGAAGAGCCAGCT GGCCCCCCGCAAGCTGTACTAATAACTCGAGCATGCATCTA GAGATCTAGATAGAGCTCGCTGATCAGCCTCGACTGTGCCT TCTAGTTGCCAGCCATCTGTTGTTTGCCCCTCCCCCGTGCC TTCCTTGACCCTGGAAGGTGCCACTCCCACTGTCCTTTCCT AATAAAATGAGGAAATTGCATCGCATTGTCTGAGTAGGTGT CATTCTATTCTGGGGGGTGGGGTGGGGCAGGACAGCAAGG GGGAGGATTGGGAAGACAATAGCAGGCATGCTGGGGA | |
| Exemplary CuV Construct 7 comprising a variant VP2 capsid coding sequence CMV-opt_CuV_VP2 | GACATTGATTATTGACTAGTTATTAATAGTAATCAATTACGG GGTCATTAGTTCATAGCCCATATATGGAGTTCCGCGTTACAT AACTTACGGTAAATGGCCCGCCTGGCTGACCGCCCAACGA CCCCCGCCCATTGACGTCAATAATGACGTATGTTCCCATAGT AACGCCAATAGGGACTTTCCATTGACGTCAATGGGTGGACT ATTTACGGTAAACTGCCCACTTGGCAGTACATCAAGTGTAT CATATGCCAAGTACGCCCCCTATTGACGTCAATGACGGTAA ATGGCCCGCCTGGCATTATGCCCAGTACATGACCTTATGGG ACTTTCCTACTTGGCAGTACATCTACGTATTAGTCATCGCTA TTACCATGGTGATGCGGTTTTGGCAGTACATCAATGGGCGT GGATAGCGGTTTGACTCACGGGGATTTCCAAGTCTCCACCC CATTGACGTCAATGGGAGTTTGTTTTGGCACCAAAATCAAC GGGACTTTCCAAAATGTCGTAACAACTCCGCCCCATTGACG CAAATGGGCGGTAGGCGTGTACGGTGGGAGGTCTATATAAG CAGAGCTCTCTGGCTAACTAGAGAACCCACTGCTTACTGG CTTATCGAAATTAATACGACTCACTATAGGGAGACCCAAGC TTGGTACCGGACTCTAGAGGATCCGGTACTCGAGGAACTG AAAAACCAGAAAGTTAACTGGTAAGTTTAGTCTTTTTGTCT TTTATTTCAGGTCCCGGATCCGGTGGTGGTGCAAATCAAAG AACTGCTCCTCAGTGGATGTTGCCTTTACTTCTAGGCCTGT ACGGAAGTGTTACTTCTGCTCTAAAAGCTGCGGAATTGTAC CCGCGGTTGAGGAACCTGTTAAGATGAGCGAGCCCGCCAA CGACACCAACGAGCAGCCCGACAACAGCCCCGTGGAGCA GGGCGCCGGCCAGATCGGCGGCGGCGGCGGCGGCGG CAGCGGCGTGGGCCACAGCACCGGCGACTACAACAACCG CACCGAGTTCATCTACCACGGCGACGAGGTGACCATCATCT GCCACAGCACCCGCCTGGTGCACATCAACATGAGCGACCG CGAGGACTACATCATCTACGAGACCGACCGCGGCCCCCTG TTCCCCACCACCCAGGACCTGCAGGGCCGCGACACCCTGA ACGACAGCTACCACGCCAAGGTGGAGACCCCCTGGAAGCT GCTGCACGCCAACAGCTGGGGCTGCTGGTTCAGCCCCGCC GACTTCCAGCAGATGATCACCACCTGCCGCGACATCGCCC CCATCAAGATGCACCAGAAGATCGAGAACATCGTGATCAA GACCGTGAGCAAGACCGGCACCGGCGAGACCGAGACCAC CAACTACAACAACGACCTGACCGCCCTGCTGCAGATCGCC CAGGACAACAGCAACCTGCTGCCCTGGGCCGCCGACAACT TCTACATCGACAGCGTGGGCTACGTGCCCTGGCGCGCCTG CAAGCTGCCCACCTACTGCTACCACGTGGACACCTGGAAC ACCATCGACATCAACCAGGCCGACACCCCCAACCAGTGGC GCGAGATCAAGAAGGGCATCCAGTGGGACAACATCCAGTT CACCCCCCTGGAGACCATGATCAACATCGACCTGCTGCGC ACCGGCGACGCCTGGGAGAGCGGCAACTACAACTTCCACA CCAAGCCCACCAACCTGGCCTACCACTGGCAGAGCCAGCG CCACACCGGCAGCTGCCACCCCACCGTGGCCCCCCTGGTG GAGCGCGGCCAGGGCACCAACATCCAGAGCGTGAACTGC TGGCAGTGGGGCGACCGCAACAACCCCAGCAGCGCCAGC ACCCGCGTGAGCAACATCCACATCGGCTACAGCTTCCCCG AGTGGCAGATCCACTACAGCACCGGCGGCCCCGTGATCAA CCCCGGCAGCGCCTTCAGCCAGGCCCCCTGGGGCAGCACC ACCGAGGGCACCCGCCTGACCCAGGGCGCCAGCGAGAAG GCCATCTACGACTGGAGCCACGGCGACGACCAGCCCGGCG CCCGCGAGACCTGGTGGCAGAACAACCAGCACGTGACCG GCCAGACCGACTGGGCCCCCAAGAACGCCCACACCAGCG AGCTGAACAACAACGTGCCCGCCGCCACCCACTTCTGGAA GAACAGCTACCACAACACCTTCAGCCCCTTCACCGCCGTG GACGACCACGGCCCCCAGTACCCCTGGGGCGCCATCTGGG GCAAGTACCCCGACACCACCCACAAGCCCATGATGAGCGC CCACGCCCCCTTCCTGCTGCACGGCCCCCCGGCCAGCTG TTCGTGAAGCTGGCCCCCAACTACACCGACACCCTGGACA | SEQ ID NO: 143 |

TABLE 4-continued

| Exemplary Construct | Sequence | SEQ ID NO: |
|---|---|---|
| | ACGGCGGCGTGACCCACCCCCGCATCGTGACCTACGGCAC<br>CTTCTGGTGGAGCGGCCAGCTGATCTTCAAGGGCAAGCTG<br>CGCACCCCCCGCCAGTGGAACACCTACAACCTGCCCAGCC<br>TGGACAAGCGCGAGACCATGAAGAACACCGTGCCCAACG<br>AGGTGGGCCACTTCGAGCTGCCCTACATGCCCGGCCGCTG<br>CCTGCCCAACTACACCCTGTAATAACTCGAGCATGCATCTA<br>GAGATCTAGATAGAGCTCGCTGATCAGCCTCGACTGTGCCT<br>TCTAGTTGCCAGCCATCTGTTGTTTGCCCCTCCCCCGTGCC<br>TTCCTTGACCCTGGAAGGTGCCACTCCCACTGTCCTTTCCT<br>AATAAAATGAGGAAATTGCATCGCATTGTCTGAGTAGGTGT<br>CATTCTATTCTGGGGGGTGGGGTGGGGCAGGACAGCAAGG<br>GGGAGGATTGGGAAGACAATAGCAGGCATGCTGGGGA | |
| Exemplary CPV Construct comprising a variant VP1 capsid coding sequence CMV-codopt-CPV-VP1-AAV2_Rep-Kan | GACATTGATTATTGACTAGTTATTAATAGTAATCAATTACGG<br>GGTCATTAGTTCATAGCCCATATATGGAGTTCCGCGTTACAT<br>AACTTACGGTAAATGGCCCGCCTGGCTGACCGCCCAACGA<br>CCCCCGCCCATTGACGTCAATAATGACGTATGTTCCCATAGT<br>AACGCCAATAGGGACTTTCCATTGACGTCAATGGGTGGACT<br>ATTTACGGTAAACTGCCCACTTGGCAGTACATCAAGTGTAT<br>CATATGCCAAGTACGCCCCCTATTGACGTCAATGACGGTAA<br>ATGGCCCGCCTGGCATTATGCCCAGTACATGACCTTATGGG<br>ACTTTCCTACTTGGCAGTACATCTACGTATTAGTCATCGCTA<br>TTACCATGGTGATGCGGTTTTGGCAGTACATCAATGGGCGT<br>GGATAGCGGTTTGACTCACGGGGATTTCCAAGTCTCCACCC<br>CATTGACGTCAATGGGAGTTTGTTTTGGCACCAAAATCAAC<br>GGGACTTTCCAAAATGTCGTAACAACTCCGCCCCATTGACG<br>CAAATGGGCGGTAGGCGTGTACGGTGGGAGGTCTATATAAG<br>CAGAGCTCTCTGGCTAACTAGAGAACCCACTGCTTACTGG<br>CTTATCGAAATTAATACGACTCACTATAGGGAGACCCAAGC<br>TTGGTACCGGACTCTAGAGGATCCGGTACTCGAGGAACTG<br>AAAAACCAGAAAGTTAACTGGTAAGTTTAGTCTTTTTGTCT<br>TTTATTTCAGGTCCCGGATCCGGTGGTGGTGCAAATCAAAG<br>AACTGCTCCTCAGTGGATGTTGCCTTTACTTCTAGGCCTGT<br>ACGGAAGTGTTACTTCTGCTCTAAAAGCTGCGGAATTGTAC<br>CCGCGGAAGCTTCCTAGGCCGCCACCATGGCCCCCCCCGC<br>CAAGCGCGCCCGCCGCGGCCTGGTGCCCCCCGGCTACAAG<br>TACCTGGGCCCCGGCAACAGCCTGGACCAGGGCGAGCCCA<br>CCAACCCCAGCGACGCCGCCGCCAAGGAGCACGACGAGG<br>CCTACGCCGCCTACCTGCGCAGCGGCAAGAACCCCTACCT<br>GTACTTCAGCCCCGCCGACCAGCGCTTCATCGACCAGACC<br>AAGGACGCCAAGGACTGGGGCGGCAAGATCGGCCACTAC<br>TTCTTCCGCGCCAAGAAGGCCATCGCCCCCGTGCTGACCG<br>ACACCCCCGACCACCCCAGCACCAGCCGCCCCACCAAGCC<br>CACCAAGCGCAGCAAGCCCCCCCCCCACATCTTCATCAAC<br>CTGGCCAAGAAGAAGAAGGCCGGCGCCGGCCAGGTGAAG<br>CGCGACAACCTGGCCCCCATGAGCGACGGCGCCGTGCAGC<br>CCGACGGCGGCCAGCCCGCCGTGCGCAACGAGCGCGCCA<br>CCGGCAGCGGCAACGGCAGCGGCGGCGGCGGCGGCGGCG<br>GCAGCGGCGGCGTGGGCATCAGCACCGGCACCTTCAACAA<br>CCAGACCGAGTTCAAGTTCCTGGAGAACGGCTGGGTGGA<br>GATCACCGCCAACAGCAGCCGCCTGGTGCACCTGAACATG<br>CCCGAGAGCGAGAACTACCGCCGCGTGGTGGTGAACAAC<br>ATGGACAAGACCGCCGTGAACGGCAACATGGCCCTGGACG<br>ACATCCACGCCCAGATCGTGACCCCCTGGAGCCTGGTGGA<br>CGCCAACGCCTGGGGCGTGTGGTTCAACCCCGGCGACTGG<br>CAGCTGATCGTGAACACCATGAGCGAGCTGCACCTGGTGA<br>GCTTCGAGCAGGAGATCTTCAACGTGGTGCTGAAGACCGT<br>GAGCGAGAGCGCCACCCAGCCCCCCACCAAGGTGTACAA<br>CAACGACCTGACCGCCAGCCTGATGGTGGCCCTGGACAGC<br>AACAACACCATGCCCTTCACCCCCGCCGCCATGCGCAGCG<br>AGACCCTGGGCTTCTACCCCTGGAAGCCCACCATCCCCAC<br>CCCCTGGCGCTACTACTTCCAGTGGGACCGCACCCTGATCC<br>CCAGCCACACCGGCACCAGCGGCACCCCCACCAACATCTA<br>CCACGGCACCGACCCCGACGACGTGCAGTTCTACACCATC<br>GAGAACAGCGTGCCCGTGCACCTGCTGCGCACCGGCGAC<br>GAGTTCGCCACCGGCACCTTCTTCTTCGACTGCAAGCCCT<br>GCCGCCTGACCCACACCTGGCAGACCAACCGCGCCCTGGG<br>CCTGCCCCCCTTCCTGAACAGCCTGCCCCAGAGCGAGGGC<br>GCCACCAACTTCGGCGACATCGGCGTGCAGCAGGACAAGC<br>GCCGCGGCGTGACCCAGATGGGCAACACCAACTACATCAC<br>CGAGGCCACCATCATGCGCCCCGCCGAGGTGGGCTACAGC<br>GCCCCCTACTACAGCTTCGAGGCCAGCACCCAGGGCCCCT<br>TCAAGACCCCCATCGCCGCCGGCCGCGGCGGCGCCCAGAC<br>CTACGAGAACCAGGCCGCCGACGGCGACCCCCGCTACGCC<br>TTCGGCCGCCAGCACGGCCAGAAGACCACCACCACCGGC<br>GAGACCCCCGAGCGCTTCACCTACATCGCCCACCAGGACA<br>CCGGCCGCTACCCCGAGGGCGACTGGATCCAGAACATCAA | SEQ ID NO: 148 |

TABLE 4-continued

| Exemplary Construct | Sequence | SEQ ID NO: |
|---|---|---|
| | CTTCAACCTGCCCGTGACCAACGACAACGTGCTGCTGCCC<br>ACCGACCCCATCGGCGGCAAGACCGGCATCAACTACACCA<br>ACATCTTCAACACCTACGGCCCCCTGACCGCCCTGAACAA<br>CGTGCCCCCCGTGTACCCCAACGGCCAGATCTGGGACAAG<br>GAGTTCGACACCGACCTGAAGCCCCGCCTGCACGTGAACG<br>CCCCCTTCGTGTGCCAGAACAACTGCCCCGGCCAGCTGTT<br>CGTGAAGGTGGCCCCCAACCTGACCAACGAGTACGACCCC<br>GACGCCAGCGCCAACATGAGCCGCATCGTGACCTACAGCG<br>ACTTCTGGTGGAAGGGCAAGCTGGTGTTCAAGGCCAAGCT<br>GCGCGCCAGCCACACCTGGAACCCCATCCAGCAGATGAGC<br>ATCAACGTGGACAACCAGTTCAACTACGTGCCCAGCAACA<br>TCGGCGGCATGAAGATCGTGTACGAGAAGAGCCAGCTGGC<br>CCCCCGCAAGCTGTACTAATAACTCGAGCATGCATCTAGAG<br>GTACATCTAGATAGAGCTCGCTGATCAGCCTCGACTGTGCC<br>TTCTAGTTGCCAGCCATCTGTTGTTTGCCCCTCCCCCGTGC<br>CTTCCTTGACCCTGGAAGGTGCCACTCCCACTGTCCTTTCC<br>TAATAAAATGAGGAAATTGCATCGCATTGTCTGAGTAGGTG<br>TCATTCTATTCTGGGGGGTGGGGGGGGCAGGACAGCAAG<br>GGGGAGGATTGGGAAGACAATAGCAGGCATGCTGGGGA | |
| Exemplary CPV construct 8 comprising a proto-parvovirus variant VP1 capsid coding sequence Ph-Kozak-CPV-VP1-CTG-del-LVPPG | CATGGAGATAATTAAAATGATAACCATCTCGCAAATAAATAA<br>GTATTTTACTGTTTTCGTAACAGTTTTGTAATAAAAAAACCT<br>ATAAAATTCCGGATTATTCATACCGTCCCACCATCGGGCGCG<br>GATCTGCCGCCCTGGCACCTCCGGCAAAGAGAGCCAGGAG<br>AGGATATAAATATCTTGGGCCTGGGAACAGTCTTGACCAAG<br>GAGAACCAACTAACCCTTCTGACGCCGCTGCAAAAGAACA<br>CGACGAAGCTTACGCTGCTTATCTTCGCTCTGGTAAAAACC<br>CATACTTATATTTCTCGCCAGCAGATCAACGCTTTATAGATC<br>AAACTAAGGACGCTAAAGATTGGGGGGGAAAATAGGAC<br>ATTATTTTTTTAGAGCTAAAAAGGCAATTGCTCCAGTATTAA<br>CTGATACACCAGATCATCCATCAACATCAAGACCAACAAAA<br>CCAACTAAAAGAAGTAAACCACCACCTCATATTTTCATCAA<br>TCTTGCAAAAAAAAAAAAAGCCGGTGCAGGACAAGTAAA<br>AAGAGACAATCTTGCACCAATGAGTGATGGAGCAGTTCAA<br>CCAGACGGTGGTCAACCTGCTGTCAGAAATGAAAGAGCTA<br>CAGGATCTGGGAACGGGTCTGGAGGCGGGGGTGGTGGTG<br>GTTCTGGGGGTGTGGGGATTTCTACGGGTACTTTCAATAAT<br>CAGACGGAATTTAAATTTTTGGAAAACGGATGGGTGGAAA<br>TCACAGCAAACTCAAGCAGACTTGTACATTTAAATATGCCA<br>GAAAGTGAAAATTATAGAAGAGTGGTTGTAAATAATATGGA<br>TAAAACTGCAGTTAACGGAAACATGGCTTTAGATGATATTC<br>ATGCACAAATTGTAACACCTTGGTCATTGGTTGATGCAAAT<br>GCTTGGGGAGTTTGGTTTAATCCAGGAGATTGGCAACTAAT<br>TGTTAATACTATGAGTGAGTTGCATTTAGTTAGTTTTGAACA<br>AGAAATTTTTAATGTTGTTTTAAAGACTGTTTCAGAATCTG<br>CTACTCAGCCACCAACTAAAGTTTATAATAATGATTTAACTG<br>CATCATTGATGGTTGCATTAGATAGTAATAATACTATGCCATT<br>TACTCCAGCAGCTATGAGATCTGAGACATTGGGTTTTTATCC<br>ATGGAAACCAACCATACCAACTCCATGGAGATATTATTTTC<br>AATGGGATAGAACATTAATACCATCTCATACTGGAACTAGT<br>GGCACACCAACAAATATATACCATGGTACAGATCCAGATGA<br>TGTTCAATTTTATACTATTGAAAATTCTGTGCCAGTACACTT<br>ACTAAGAACAGGTGATGAATTTGCTACAGGAACATTTTTTT<br>TTGATTGTAAACCATGTAGACTAACACATACATGGCAAACA<br>AATAGAGCATTGGGCTTACCACCATTTCTAAATTCTTTGCCT<br>CAATCTGAAGGAGCTACTAACTTTGGTGATATAGGAGTTCA<br>ACAAGATAAAAGACGTGGTGTAACTCAAATGGGAAATACA<br>AACTATATTACTGAAGCTACTATTATGAGACCAGCTGAGGTT<br>GGTTATAGTGCACCATATTATTCTTTTGAGGCGTCTACACAA<br>GGGCCATTTAAAACACCTATTGCAGCAGGACGGGGGGGAG<br>CGCAAACATATGAAAATCAAGCAGCAGATGGTGATCCAAG<br>ATATGCATTTGGTAGACAACATGGTCAAAAAACTACCACAA<br>CAGGAGAAACACCTGAGAGATTTACATATATAGCACATCAA<br>GATACAGGAAGATATCCAGAAGGAGATTGGATTCAAAATAT<br>TAACTTTAACCTTCCTGTAACGAATGATAATGTATTGCTACC<br>AACAGATCCAATTGGAGGTAAAACAGGAATTAACTATACTA<br>ATATATTTAATACTTATGGTCCTTTAACTGCATTAAATAATGT<br>ACCACCAGTTTATCCAAATGGTCAAATTTGGGATAAAGAAT<br>TTGATACTGACTTAAAACCAAGACTTCATGTAAATGCACCA<br>TTTGTTTGTCAAAATAATTGTCCTGGTCAATTATTTGTAAAA<br>GTTGCGCCTAATTTAACAAATGAATATGATCCTGATGCATCT<br>GCTAATATGTCAAGAATTGTAACTTACTCAGATTTTTGGTGG<br>AAAGGTAAATTAGTATTTAAAGCTAAACTAAGAGCCTCTCA<br>TACTTGGAATCCAATTCAACAAATGAGTATTAATGTAGATAA<br>CCAATTTAACTATGTACCAAGTAATATTGGAGGTATGAAAAT<br>TGTATATGAAAAATCTCAACTAGCACCTAGAAAATTATATTA<br>ACTCGAGGCATGCGGTACCAAGCTTGTCGAGAAGTACTAG | SEQ ID NO: 149 |

TABLE 4-continued

| Exemplary Construct | Sequence | SEQ ID NO: |
|---|---|---|
| | AGGATCATAATCAGCCATACCACATTTGTAGAGGTTTTACTT GCTTTAAAAAACCTCCCACACCTCCCCCTGAACCTGAAAC ATAAAATGAATGCAATTGTTGTTGTTAACTTGTTTATTGCAG CTTATAATGGTTACAAATAAAGCAATAGCATCACAAATTTCA CAAATAAAGCATTTTTTTCACTGCATTCTAGTTGTGGTTTGT CCAAACTCATCAATGTATCTTATCATGTCTGGATC | |
| Exemplary CPV construct 9 comprising a proto-parvovirus variant VP1 capsid coding sequence Ph-Kozak-CPV-VP1-ACG-del-LVPPG | CATGGAGATAATTAAAATGATAACCATCTCGCAAATAAATAA GTATTTTACTGTTTTCGTAACAGTTTTGTAATAAAAAAACCT ATAAAATTCCGGATTATTCATACCGTCCCACCATCGGGCGCG GATCTGCCGCCACGGCACCTCCGGCAAAGAGAGCCAGGA GAGGATATAAATATCTTGGGCCTGGGAACAGTCTTGACCAA GGAGAACCAACTAACCCTTCTGACGCCGCTGCAAAAGAAC ACGACGAAGCTTACGCTGCTTATCTTCGCTCTGGTAAAAAC CCATACTTATATTTCTCGCCAGCAGATCAACGCTTTATAGAT CAAACTAAGGACGCTAAAGATTGGGGGGGGAAAATAGGAC ATTATTTTTTTAGAGCTAAAAAGGCAATTGCTCCAGTATTAA CTGATACACCAGATCATCCATCAACATCAAGACCAACAAAA CCAACTAAAAGAAGTAAACCACCACCTCATATTTTCATCAA TCTTGCAAAAAAAAAAAAAGCCGGTGCAGGACAAGTAAA AAGAGACAATCTTGCACCAATGAGTGATGGAGCAGTTCAA CCAGACGGTGGTCAACCTGCTGTCAGAAATGAAAGAGCTA CAGGATCTGGGAACGGGTCTGGAGGCGGGGGTGGTGGTG GTTCTGGGGGTGTGGGGATTTCTACGGGTACTTTCAATAAT CAGACGGAATTTAAATTTTTGGAAAACGGATGGGTGGAAA TCACAGCAAACTCAAGCAGACTTGTACATTTAAATATGCCA GAAAGTGAAAATTATAGAAGAGTGGTTGTAAATAATATGGA TAAAACTGCAGTTAACGGAAACATGGCTTTAGATGATATTC ATGCACAAATTGTAACACCTTGGTCATTGGTTGATGCAAAT GCTTGGGGAGTTTGGTTTAATCCAGGAGATTGGCAACTAAT TGTTAATACTATGAGTGAGTTGCATTTAGTTAGTTTTGAACA AGAAATTTTTAATGTTGTTTTAAAGACTGTTTCAGAATCTG CTACTCAGCCACCAACTAAAGTTTATAATAATGATTTAACTG CATCATTGATGGTTGCATTAGATAGTAATAATACTATGCCATT TACTCCAGCAGCTATGAGATCTGAGACATTGGGTTTTTATCC ATGGAAACCAACCATACCAACTCCATGGAGATATTATTTTC AATGGGATAGAACATTAATACCATCTCATACTGGAACTAGT GGCACACCAACAAATATATACCATGGTACAGATCCAGATGA TGTTCAATTTTATACTATTGAAAATTCTGTGCCAGTACACTT ACTAAGAACAGGTGATGAATTTGCTACAGGAACATTTTTTT TTGATTGTAAACCATGTAGACTAACACATACATGGCAAACA AATAGAGCATTGGGCTTACCACCATTTCTAAATTCTTTGCCT CAATCTGAAGGAGCTACTAACTTTGGTGATATAGGAGTTCA ACAAGATAAAAGACGTGGTGTAACTCAAATGGGAAATACA AACTATATTACTGAAGCTACTATTATGAGACCAGCTGAGGTT GGTTATAGTGCACCATATTATTCTTTTGAGGCGTCTACACAA GGGCCATTTAAAACACCTATTGCAGCAGGACGGGGGGGAG CGCAAACATATGAAAATCAAGCAGCAGATGGTGATCCAAG ATATGCATTTGGTAGACAACATGGTCAAAAAACTACCACAA CAGGAGAAACACCTGAGAGATTTACATATATAGCACATCAA GATACAGGAAGATATCCAGAAGGAGATTGGATTCAAAATAT TAACTTTAACCTTCCTGTAACGAATGATAATGTATTGCTACC AACAGATCCAATTGGAGGTAAAACAGGAATTAACTATACTA ATATATTTAATACTTATGGTCCTTTAACTGCATTAAATAATGT ACCACCAGTTTATCCAAATGGTCAAATTTGGGATAAAGAAT TTGATACTGACTTAAAACCAAGACTTCATGTAAATGCACCA TTTGTTTGTCAAAATAATTGTCCTGGTCAATTATTTGTAAAA GTTGCGCCTAATTTAACAAATGAATATGATCCTGATGCATCT GCTAATATGTCAAGAATTGTAACTTACTCAGATTTTTGGTGG AAAGGTAAATTAGTATTTAAAGCTAAACTAAGAGCCTCTCA TACTTGGAATCCAATTCAACAAATGAGTATTAATGTAGATAA CCAATTTAACTATGTACCAAGTAATATTGGAGGTATGAAAAT TGTATATGAAAAATCTCAACTAGCACCTAGAAAATTATATTA ACTCGAGGCATGCGGTACCAAGCTTGTCGAGAAGTACTAG AGGATCATAATCAGCCATACCACATTTGTAGAGGTTTTACTT GCTTTAAAAAACCTCCCACACCTCCCCCTGAACCTGAAAC ATAAAATGAATGCAATTGTTGTTGTTAACTTGTTTATTGCAG CTTATAATGGTTACAAATAAAGCAATAGCATCACAAATTTCA CAAATAAAGCATTTTTTTCACTGCATTCTAGTTGTGGTTTGT CCAAACTCATCAATGTATCTTATCATGTCTGGATC | SEQ ID NO: 150 |
| Exemplary CPV construct 10 comprising a proto-parvovirus | CATGGAGATAATTAAAATGATAACCATCTCGCAAATAAATAA GTATTTTACTGTTTTCGTAACAGTTTTGTAATAAAAAAACCT ATAAAATTCCGGATTATTCATACCGTCCCACCATCGGGCGCG GATCTGCCGCCTTGGCACCTCCGGCAAAGAGAGCCAGGAG AGGATATAAATATCTTGGGCCTGGGAACAGTCTTGACCAAG GAGAACCAACTAACCCTTCTGACGCCGCTGCAAAAGAACA | SEQ ID NO: 151 |

TABLE 4-continued

| Exemplary Construct | Sequence | SEQ ID NO: |
|---|---|---|
| variant VP1 capsid coding sequence Ph-Kozak-CPV-VP1-TTG-del-LVPPG | CGACGAAGCTTACGCTGCTTATCTTCGCTCTGGTAAAAACC<br>CATACTTATATTTCTCGCCAGCAGATCAACGCTTTATAGATC<br>AAACTAAGGACGCTAAAGATTGGGGGGGAAAATAGGAC<br>ATTATTTTTTTAGAGCTAAAAAGGCAATTGCTCCAGTATTAA<br>CTGATACACCAGATCATCCATCAACATCAAGACCAACAAAA<br>CCAACTAAAAGAAGTAAACCACCACCTCATATTTTCATCAA<br>TCTTGCAAAAAAAAAAAAAGCCGGTGCAGGACAAGTAAA<br>AAGAGACAATCTTGCACCAATGAGTGATGGAGCAGTTCAA<br>CCAGACGGTGGTCAACCTGCTGTCAGAAATGAAAGAGCTA<br>CAGGATCTGGGAACGGGTCTGGAGGCGGGGGTGGTGGTG<br>GTTCTGGGGGTGTGGGGATTTCTACGGGTACTTTCAATAAT<br>CAGACGGAATTTAAATTTTTGGAAAACGGATGGGTGGAAA<br>TCACAGCAAACTCAAGCAGACTTGTACATTTAAATATGCCA<br>GAAAGTGAAAATTATAGAAGAGTGGTTGTAAATAATATGGA<br>TAAAACTGCAGTTAACGGAAACATGGCTTTAGATGATATTC<br>ATGCACAAATTGTAACACCTTGGTCATTGGTTGATGCAAAT<br>GCTTGGGGAGTTTGGTTTAATCCAGGAGATTGGCAACTAAT<br>TGTTAATACTATGAGTGAGTTGCATTTAGTTAGTTTTGAACA<br>AGAAATTTTTAATGTTGTTTTAAAGACTGTTTCAGAATCTG<br>CTACTCAGCCACCAACTAAAGTTTATAATAATGATTTAACTG<br>CATCATTGATGGTTGCATTAGATAGTAATAATACTATGCCATT<br>TACTCCAGCAGCTATGAGATCTGAGACATTGGGTTTTTATCC<br>ATGGAAACCAACCATACCAACTCCATGGAGATATTATTTTC<br>AATGGGATAGAACATTAATACCATCTCATACTGGAACTAGT<br>GGCACACCAACAAATATATACCATGGTACAGATCCAGATGA<br>TGTTCAATTTTATACTATTGAAAATTCTGTGCCAGTACACTT<br>ACTAAGAACAGGTGATGAATTTGCTACAGGAACATTTTTTT<br>TTGATTGTAAACCATGTAGACTAACACATACATGGCAAACA<br>AATAGAGCATTGGGCTTACCACCATTTCTAAATTCTTTGCCT<br>CAATCTGAAGGAGCTACTAACTTTGGTGATATAGGAGTTCA<br>ACAAGATAAAAGACGTGGTGTAACTCAAATGGGAAATACA<br>AACTATATTACTGAAGCTACTATTATGAGACCAGCTGAGGTT<br>GGTTATAGTGCACCATATTATTCTTTTGAGGCGTCTACACAA<br>GGGCCATTTAAAACACCTATTGCAGCAGGACGGGGGGGAG<br>CGCAAACATATGAAAATCAAGCAGCAGATGGTGATCCAAG<br>ATATGCATTTGGTAGACAACATGGTCAAAAAACTACCACAA<br>CAGGAGAAACACCTGAGAGATTTACATATATAGCACATCAA<br>GATACAGGAAGATATCCAGAAGGAGATTGGATTCAAAATAT<br>TAACTTTAACCTTCCTGTAACGAATGATAATGTATTGCTACC<br>AACAGATCCAATTGGAGGTAAAACAGGAATTAACTATACTA<br>ATATATTTAATACTTATGGTCCTTTAACTGCATTAAATAATGT<br>ACCACCAGTTTATCCAAATGGTCAAATTTGGGATAAAGAAT<br>TTGATACTGACTTAAAACCAAGACTTCATGTAAATGCACCA<br>TTTGTTTGTCAAAATAATTGTCCTGGTCAATTATTTGTAAAA<br>GTTGCGCCTAATTTAACAAATGAATATGATCCTGATGCATCT<br>GCTAATATGTCAAGAATTGTAACTTACTCAGATTTTTGGTGG<br>AAAGGTAAATTAGTATTTAAAGCTAAACTAAGAGCCTCTCA<br>TACTTGGAATCCAATTCAACAAATGAGTATTAATGTAGATAA<br>CCAATTTAACTATGTACCAAGTAATATTGGAGGTATGAAAAT<br>TGTATATGAAAAATCTCAACTAGCACCTAGAAAATTATATTA<br>ACTCGAGGCATGCGGTACCAAGCTTGTCGAGAAGTACTAG<br>AGGATCATAATCAGCCATACCACATTTGTAGAGGTTTTACTT<br>GCTTTAAAAAACCTCCCACACCTCCCCCTGAACCTGAAAC<br>ATAAAATGAATGCAATTGTTGTTGTTAACTTGTTTATTGCAG<br>CTTATAATGGTTACAAATAAAGCAATAGCATCACAAATTTCA<br>CAAATAAAGCATTTTTTTCACTGCATTCTAGTTGTGGTTTGT<br>CCAAACTCATCAATGTATCTTATCATGTCTGGATC | |
| Exemplary CPV construct 11 comprising a proto-parvovirus variant VP1 capsid coding sequence Ph-Kozak-CPV-VP1-ATC-del-LVPPG | CATGGAGATAATTAAAATGATAACCATCTCGCAAATAAATAA<br>GTATTTTACTGTTTTCGTAACAGTTTTGTAATAAAAAAACCT<br>ATAAAATTCCGGATTATTCATACCGTCCCACCATCGGGCGCG<br>GATCTGCCGCCATCGCACCTCCGGCAAAGAGAGCCAGGAG<br>AGGATATAAATATCTTGGGCCTGGGAACAGTCTTGACCAAG<br>GAGAACCAACTAACCCTTCTGACGCCGCTGCAAAAGAACA<br>CGACGAAGCTTACGCTGCTTATCTTCGCTCTGGTAAAAACC<br>CATACTTATATTTCTCGCCAGCAGATCAACGCTTTATAGATC<br>AAACTAAGGACGCTAAAGATTGGGGGGGAAAATAGGAC<br>ATTATTTTTTTAGAGCTAAAAAGGCAATTGCTCCAGTATTAA<br>CTGATACACCAGATCATCCATCAACATCAAGACCAACAAAA<br>CCAACTAAAAGAAGTAAACCACCACCTCATATTTTCATCAA<br>TCTTGCAAAAAAAAAAAAAGCCGGTGCAGGACAAGTAAA<br>AAGAGACAATCTTGCACCAATGAGTGATGGAGCAGTTCAA<br>CCAGACGGTGGTCAACCTGCTGTCAGAAATGAAAGAGCTA<br>CAGGATCTGGGAACGGGTCTGGAGGCGGGGGTGGTGGTG<br>GTTCTGGGGGTGTGGGGATTTCTACGGGTACTTTCAATAAT<br>CAGACGGAATTTAAATTTTTGGAAAACGGATGGGTGGAAA<br>TCACAGCAAACTCAAGCAGACTTGTACATTTAAATATGCCA | SEQ ID NO: 152 |

TABLE 4-continued

| Exemplary Construct | Sequence | SEQ ID NO: |
|---|---|---|
| | GAAAGTGAAAATTATAGAAGAGTGGTTGTAAATAATATGGA<br>TAAAACTGCAGTTAACGGAAACATGGCTTTAGATGATATTC<br>ATGCACAAATTGTAACACCTTGGTCATTGGTTGATGCAAAT<br>GCTTGGGGAGTTTGGTTTAATCCAGGAGATTGGCAACTAAT<br>TGTTAATACTATGAGTGAGTTGCATTTAGTTAGTTTTGAACA<br>AGAAATTTTTAATGTTGTTTTAAAGACTGTTTCAGAATCTG<br>CTACTCAGCCACCAACTAAAGTTTATAATAATGATTTAACTG<br>CATCATTGATGGTTGCATTAGATAGTAATAATACTATGCCATT<br>TACTCCAGCAGCTATGAGATCTGAGACATTGGGTTTTTATCC<br>ATGGAAACCAACCATACCAACTCCATGGAGATATTATTTTC<br>AATGGGATAGAACATTAATACCATCTCATACTGGAACTAGT<br>GGCACACCAACAAATATATACCATGGTACAGATCCAGATGA<br>TGTTCAATTTTATACTATTGAAAATTCTGTGCCAGTACACTT<br>ACTAAGAACAGGTGATGAATTTGCTACAGGAACATTTTTTT<br>TTGATTGTAAACCATGTAGACTAACACATACATGGCAAACA<br>AATAGAGCATTGGGCTTACCACCATTTCTAAATTCTTTGCCT<br>CAATCTGAAGGAGCTACTAACTTTGGTGATATAGGAGTTCA<br>ACAAGATAAAAGACGTGGTGTAACTCAAATGGGAAATACA<br>AACTATATTACTGAAGCTACTATTATGAGACCAGCTGAGGTT<br>GGTTATAGTGCACCATATTATTCTTTTGAGGCGTCTACACAA<br>GGGCCATTTAAAACACCTATTGCAGCAGGACGGGGGGGAG<br>CGCAAACATATGAAAATCAAGCAGCAGATGGTGATCCAAG<br>ATATGCATTTGGTAGACAACATGGTCAAAAAACTACCACAA<br>CAGGAGAAACACCTGAGAGATTTACATATATAGCACATCAA<br>GATACAGGAAGATATCCAGAAGGAGATTGGATTCAAAATAT<br>TAACTTTAACCTTCCTGTAACGAATGATAATGTATTGCTACC<br>AACAGATCCAATTGGAGGTAAAACAGGAATTAACTATACTA<br>ATATATTTAATACTTATGGTCCTTTAACTGCATTAAATAATGT<br>ACCACCAGTTTATCCAAATGGTCAAATTTGGGATAAAGAAT<br>TTGATACTGACTTAAAACCAAGACTTCATGTAAATGCACCA<br>TTTGTTTGTCAAAATAATTGTCCTGGTCAATTATTTGTAAAA<br>GTTGCGCCTAATTTAACAAATGAATATGATCCTGATGCATCT<br>GCTAATATGTCAAGAATTGTAACTTACTCAGATTTTTGGTGG<br>AAAGGTAAATTAGTATTTAAAGCTAAACTAAGAGCCTCTCA<br>TACTTGGAATCCAATTCAACAAATGAGTATTAATGTAGATAA<br>CCAATTTAACTATGTACCAAGTAATATTGGAGGTATGAAAAT<br>TGTATATGAAAAATCTCAACTAGCACCTAGAAAATTATATTA<br>ACTCGAGGCATGCGGTACCAAGCTTGTCGAGAAGTACTAG<br>AGGATCATAATCAGCCATACCACATTTGTAGAGGTTTTACTT<br>GCTTTAAAAAACCTCCCACACCTCCCCCTGAACCTGAAAC<br>ATAAAATGAATGCAATTGTTGTTGTTAACTTGTTTATTGCAG<br>CTTATAATGGTTACAAATAAAGCAATAGCATCACAAATTTCA<br>CAAATAAAGCATTTTTTTCACTGCATTCTAGTTGTGGTTTGT<br>CCAAACTCATCAATGTATCTTATCATGTCTGGATC | |
| Exemplary CPV construct 12 comprising a proto-parvovirus variant VP1 capsid coding sequence CPV-OpiE1-NS2-CTG | GTATACTCCGGAATATTAATAGATGCGAAACACGCACGGCG<br>CGCGCACGCAGCTTAGCACAAACGCGTCGTTGCACGCGCC<br>CACCGCTAACCGCAGGCCAATCGGTCGGCCGGCCTCATATC<br>CGCTCACCAGCCGCGTCCTATCGGGCGCGGCTTCCGCGCC<br>CATTTTGAATAAATAAACGATAACGCCGTTGGTGGCGTGAG<br>GCATGTAAAAGGTTACATCATTATCTTGTTCGCCATCCGGTT<br>GGTATAAATAGACGTTCATGTTGGTTTTTGTTTCAGTTGCAA<br>GTTGGCTGCGGCGCGCGCAGCACCTTTGCTATTCCGGATTA<br>TTCATACCGTCCCACCATCGGGCGCGGATCTGCCTCCATGT<br>CTGGCAACCAGTATACTGAGGAAGTTATGGAGGGAGTAAA<br>TTGGTTAAAGAAACATGCAGAAAATGAAGCATTTTCGTTTG<br>TTTTTAAATGTGACAACGTCCAACTAAATGGAAAGGATGTT<br>CGCTGGAACAACTATACCAAACCAATTCAAAATGAAGAAC<br>TAACATCTTTAATTAGAGGAGCACAAACAGCAATGGATCAA<br>ACCGAAGAAGAAGAAATGGACTGGGAATCGGAAGTTGATA<br>GTCTCGCCAAAAAGTTGCAAAGACTTAGAGACACAAGCG<br>GCAAGCAATCCTCAGAGTCAAGACCAAGTTCTAACTCCTC<br>TGACTCCGGACGTAGTGGACCTTGCACTGGAACCGTGGAG<br>TACTCCAGATACGCCTATTGCAGAAACTGCAAATCAACAAT<br>CAAACCAACTTGGCGTTACTCACAAAGACGTGCAAGCGAG<br>TCCGACGTGGTCCGAAATAGAGGCAGACCTGAGAGCCATC<br>TTTACTTCCATCATCACCATCACCACTGAGAGCTCACTAGT<br>CGCGGCCGCTTTCGAATCTAGAGCCTGCAGTCTCGAGGCAT<br>GCGGTACCAAGCTTGTCGAGAAGTACTAGAGGATCATAATC<br>AGCCATACCACATTTGTAGAGGTTTTACTTGCTTTAAAAAA<br>CCTCCCACACCTCCCCCTGAACCTGAAACATAAAATGAATG<br>CAATTGTTGTTGTTAACTTGTTTATTGCAGCTTATAATGGTT<br>ACAAATAAAGCAATAGCATCACAAATTTCACAAATAAAGCA<br>TTTTTTTCACTGCATTCTAGTTGTGGTTTGTCCAAACTCATC<br>AATGTATCTTATCATGTCTGGATC | SEQ ID NO: 153 |

TABLE 4-continued

| Exemplary Construct | Sequence | SEQ ID NO: |
|---|---|---|
| Exemplary CPV construct 13 comprising a proto-parvovirus variant VP1 capsid coding sequence CPV-OpiE1-NS2-CTG | GTATACTCCGGAATATTAATAGATGCGAAACACGCACGGCG CGCGCACGCAGCTTAGCACAAACGCGTCGTTGCACGCGCC CACCGCTAACCGCAGGCCAATCGGTCGGCCGGCCTCATATC CGCTCACCAGCCGCGTCCTATCGGGCGCGGCTTCCGCGCC CATTTTGAATAAATAAACGATAACGCCGTTGGTGGCGTGAG GCATGTAAAAGGTTACATCATTATCTTGTTCGCCATCCGGTT GGTATAAATAGACGTTCATGTTGGTTTTTGTTTCAGTTGCAA GTTGGCTGCGGCGCGCGCAGCACCTTTGCTATTCCGGATTA TTCATACCGTCCCACCATCGGGCGCGGATCTGCCTCCCTGT CTGGCAACCAGTATACTGAGGAAGTTATGGAGGGAGTAAA TTGGTTAAAGAAACATGCAGAAAATGAAGCATTTTCGTTTG TTTTTAAATGTGACAACGTCCAACTAAATGGAAAGGATGTT CGCTGGAACAACTATACCAAACCAATTCAAAATGAAGAAC TAACATCTTTAATTAGAGGAGCACAAACAGCAATGGATCAA ACCGAAGAAGAAGAAATGGACTGGGAATCGGAAGTTGATA GTCTCGCCAAAAAGTTGCAAAGACTTAGAGACACAAGCG GCAAGCAATCCTCAGAGTCAAGACCAAGTTCTAACTCCTC TGACTCCGGACGTAGTGGACCTTGCACTGGAACCGTGGAG TACTCCAGATACGCCTATTGCAGAAACTGCAAATCAACAAT CAAACCAACTTGGCGTTACTCACAAAGACGTGCAAGCGAG TCCGACGTGGTCCGAAATAGAGGCAGACCTGAGAGCCATC TTTACTTCTGAGAGCTCACTAGTCGCGGCCGCTTTCGAATC TAGAGCCTGCAGTCTCGAGGCATGCGGTACCAAGCTTGTC GAGAAGTACTAGAGGATCATAATCAGCCATACCACATTTGT AGAGGTTTTACTTGCTTTAAAAAACCTCCCACACCTCCCCC TGAACCTGAAACATAAAATGAATGCAATTGTTGTTGTTAAC TTGTTTATTGCAGCTTATAATGGTTACAAATAAAGCAATAGC ATCACAAATTTCACAAATAAAGCATTTTTTTCACTGCATTCT AGTTGTGGTTTGTCCAAACTCATCAATGTATCTTATCATGTC TGGATC | SEQ ID NO: 154 |
| Exemplary CPV Construct 14 comprising a proto-parvovirus variant VP1 capsid coding sequence UBC_CPV_ VP1_del-LVPPG | CGCGTGGCCTCCGCGCCGGGTTTTGGCGCCTCCCGCGGGC GCCCCCCTCCTCACGGCGAGCGCTGCCACGTCAGACGAAG GGCGCAGGAGCGTTCCTGATCCTTCCGCCCGGACGCTCAG GACAGCGGCCCGCTGCTCATAAGACTCGGCCTTAGAACCC CAGTATCAGCAGAAGGACATTTTAGGACGGGACTTGGGTG ACTCTAGGGCACTGGTTTTCTTTCCAGAGAGCGGAACAGG CGAGGAAAAGTAGTCCCTTCTCGGCGATTCTGCGGAGGGA TCTCCGTGGGGCGGTGAACGCCGATGATTATATAAGGACGC GCCGGGTGTGGCACAGCTAGTTCCGTCGCAGCCGGGATTT GGGTCGCGGTTCTTGTTTGTGGATCGCTGTGATCGTCACTT GGTGGTACCGGACTCTAGAGGATCCGGTACTCGAGGAACT GAAAAACCAGAAAGTTAACTGGTAAGTTTAGTCTTTTTGTC TTTTATTTCAGGTCCCGGATCCGGTGGTGGTGCAAATCAAA GAACTGCTCCTCAGTGGATGTTGCCTTTACTTCTAGGCCTG TAGGGAAGTGTTACTTCTGCTCTAAAAGCTGCGGAATTGTA GCCGTTGAAGCTTCCTAGGCCGCCACCATGGCCCCCCCCG CCAAGCGCGCCCGCCGCGGCTACAAGTACCTGGGCCCCGG CAACAGCCTGGACCAGGGCGAGCCCACCAACCCCAGCGA CGCCGCCGCCAAGGAGCACGACGAGGCCTACGCCGCCTAC CTGCGCAGCGGCAAGAACCCCTACCTGTACTTCAGCCCCG CCGACCAGCGCTTCATCGACCAGACCAAGGACGCCAAGG ACTGGGGCGGCAAGATCGGCCACTACTTCTTCCGCGCCAA GAAGGCCATCGCCCCCGTGCTGACCGACACCCCCGACCAC CCCAGCACCAGCCGCCCCACCAAGCCCACCAAGCGCAGC AAGCCCCCCCCCCACATCTTCATCAACCTGGCCAAGAAGA AGAAGGCCGGCGCCGGCCAGGTGAAGCGCGACAACCTGG CCCCCATGAGCGACGGCGCCGTGCAGCCCGACGGCGGCCA GCCCGCCGTGCGCAACGAGCGCGCCACCGGCAGCGGCAA CGGCAGCGGCGGCGGCGGCGGCGGCGGCAGCGGCGGCGT GGGCATCAGCACCGGCACCTTCAACAACCAGACCGAGTTC AAGTTCCTGGAGAACGGCTGGGTGGAGATCACCGCCAACA GCAGCCGCCTGGTGCACCTGAACATGCCCGAGAGCGAGA ACTACCGCCGCGTGGTGGTGAACAACATGGACAAGACCGC CGTGAACGGCAACATGGCCCTGGACGACATCCACGCCCAG ATCGTGACCCCCTGGAGCCTGGTGGACGCCAACGCCTGGG GCGTGTGGTTCAACCCCGGCGACTGGCAGCTGATCGTGAA CACCATGAGCGAGCTGCACCTGGTGAGCTTCGAGCAGGAG ATCTTCAACGTGGTGCTGAAGACCGTGAGCGAGAGCGCCA CCCAGCCCCCCACCAAGGTGTACAACAACGACCTGACCGC CAGCCTGATGGTGGCCCTGGACAGCAACAACACCATGCCC TTCACCCCCGCCGCCATGCGCAGCGAGACCCTGGGCTTCT ACCCCTGGAAGCCCACCATCCCCACCCCCTGGCGCTACTAC TTCCAGTGGGACCGCACCCTGATCCCCAGCCACACCGGCA CCAGCGGCACCCCCACCAACATCTACCACGGCACCGACCC CGACGACGTGCAGTTCTACACCATCGAGAACAGCGTGCCC | SEQ ID NO: 155 |

TABLE 4-continued

| Exemplary Construct | Sequence | SEQ ID NO: |
|---|---|---|
| | GTGCACCTGCTGCGCACCGGCGACGAGTTCGCCACCGGCA<br>CCTTCTTCTTCGACTGCAAGCCCTGCCGCCTGACCCACACC<br>TGGCAGACCAACCGCGCCCTGGGCCTGCCCCCCTTCCTGA<br>ACAGCCTGCCCCAGAGCGAGGGCGCCACCAACTTCGGCG<br>ACATCGGCGTGCAGCAGGACAAGCGCCGCGGCGTGACCC<br>AGATGGGCAACACCAACTACATCACCGAGGCCACCATCAT<br>GCGCCCCGCCGAGGTGGGCTACAGCGCCCCCTACTACAGC<br>TTCGAGGCCAGCACCCAGGGCCCCTTCAAGACCCCCATCG<br>CCGCCGGCCGCGGCGGCGCCCAGACCTACGAGAACCAGG<br>CCGCCGACGGCGACCCCCGCTACGCCTTCGGCCGCCAGCA<br>CGGCCAGAAGACCACCACCACCGGCGAGACCCCCGAGCG<br>CTTCACCTACATCGCCCACCAGGACACCGGCCGCTACCCC<br>GAGGGCGACTGGATCCAGAACATCAACTTCAACCTGCCCG<br>TGACCAACGACAACGTGCTGCTGCCCACCGACCCCATCGG<br>CGGCAAGACCGGCATCAACTACACCAACATCTTCAACACC<br>TACGGCCCCCTGACCGCCCTGAACAACGTGCCCCCCGTGT<br>ACCCCAACGGCCAGATCTGGGACAAGGAGTTCGACACCG<br>ACCTGAAGCCCCGCCTGCACGTGAACGCCCCCTTCGTGTG<br>CCAGAACAACTGCCCCGGCCAGCTGTTCGTGAAGGTGGCC<br>CCCAACCTGACCAACGAGTACGACCCCGACGCCAGCGCCA<br>ACATGAGCCGCATCGTGACCTACAGCGACTTCTGGTGGAA<br>GGGCAAGCTGGTGTTCAAGGCCAAGCTGCGCGCCAGCCA<br>CACCTGGAACCCCATCCAGCAGATGAGCATCAACGTGGAC<br>AACCAGTTCAACTACGTGCCCAGCAACATCGGCGGCATGA<br>AGATCGTGTACGAGAAGAGCCAGCTGGCCCCCCGCAAGCT<br>GTACTAATAACTCGAGCATGCATCTAGAGGTACATCTAGATA<br>GAGCTCGCTGATCAGCCTCGACTGTGCCTTCTAGTTGCCAG<br>CCATCTGTTGTTTGCCCCTCCCCCGTGCCTTCCTTGACCCT<br>GGAAGGTGCCACTCCCACTGTCCTTTCCTAATAAAATGAGG<br>AAATTGCATCGCATTGTCTGAGTAGGTGTCATTCTATTCTGG<br>GGGGTGGGGTGGGGCAGGACAGCAAGGGGGAGGATTGGG<br>AAGACAATAGCAGGCATGCTGGGGA | |
| Exemplary CPV Construct comprising a proto-parvovirus variant VP2 capsid coding sequence CPV_VP2 | GACATTGATTATTGACTAGTTATTAATAGTAATCAATTACGG<br>GGTCATTAGTTCATAGCCCATATATGGAGTTCCGCGTTACAT<br>AACTTACGGTAAATGGCCCGCCTGGCTGACCGCCCAACGA<br>CCCCCGCCCATTGACGTCAATAATGACGTATGTTCCCATAGT<br>AACGCCAATAGGGACTTTCCATTGACGTCAATGGGTGGAG<br>TATTTACGGTAAACTGCCCACTTGGCAGTACATCAAGTGTA<br>TCATATGCCAAGTACGCCCCCTATTGACGTCAATGACGGTA<br>AATGGCCCGCCTGGCATTATGCCCAGTACATGACCTTATGG<br>GACTTTCCTACTTGGCAGTACATCTACGTATTAGTCATCGCT<br>ATTACCATGGTGATGCGGTTTTGGCAGTACATCAATGGGCG<br>TGGATAGCGGTTTGACTCACGGGGATTTCCAAGTCTCCACC<br>CCATTGACGTCAATGGGAGTTTGTTTTGGCACCAAAATCAA<br>CGGGACTTTCCAAAATGTCGTAACAACTCCGCCCCATTGAC<br>GCAAATGGGCGGTAGGCGTGTACGGTGGGAGGTCTATATAA<br>GCAGAGCTCTCTGGCTAACTAGAGAACCCACTGCTTACTG<br>GCTTATCGAAATTAATACGACTCACTATAGGGAGACCCAAG<br>CTTGGTACCGGACTCTAGAGGATCCGGTACTCGAGGAACT<br>GAAAAACCAGAAAGTTAACTGGTAAGTTTAGTCTTTTTGTC<br>TTTTATTTCAGGTCCCGGATCCGGTGGTGGTGCAAATCAAA<br>GAACTGCTCCTCAGTGGATGTTGCCTTTACTTCTAGGCCTG<br>TACGGAAGTGTTACTTCTGCTCTAAAAGCTTGATTAATTAA<br>GGCCGCCACCATGAGCGACGGCGCCGTGCAGCCCGACGG<br>CGGCCAGCCCGCCGTGCGCAACGAGCGCGCCACCGGCAG<br>CGGCAACGGCAGCGGCGGCGGCGGCGGCGGCGGCAGCGG<br>CGGCGTGGGCATCAGCACCGGCACCTTCAACAACCAGACC<br>GAGTTCAAGTTCCTGGAGAACGGCTGGGTGGAGATCACCG<br>CCAACAGCAGCCGCCTGGTGCACCTGAACATGCCCGAGAG<br>CGAGAACTACCGCCGCGTGGTGGTGAACAACATGGACAAG<br>ACCGCCGTGAACGGCAACATGGCCCTGGACGACATCCACG<br>CCCAGATCGTGACCCCCTGGAGCCTGGTGGACGCCAACGC<br>CTGGGGCGTGTGGTTCAACCCCGGCGACTGGCAGCTGATC<br>GTGAACACCATGAGCGAGCTGCACCTGGTGAGCTTCGAGC<br>AGGAGATCTTCAACGTGGTGCTGAAGACCGTGAGCGAGA<br>GCGCCACCCAGCCCCCCACCAAGGTGTACAACAACGACCT<br>GACCGCCAGCCTGATGGTGGCCCTGGACAGCAACAACACC<br>ATGCCCTTCACCCCCGCCGCCATGCGCAGCGAGACCCTGG<br>GCTTCTACCCCTGGAAGCCCACCATCCCCACCCCCTGGCGC<br>TACTACTTCCAGTGGGACCGCACCCTGATCCCCAGCCACAC<br>CGGCACCAGCGGCACCCCCACCAACATCTACCACGGCACC<br>GACCCCGACGACGTGCAGTTCTACACCATCGAGAACAGCG<br>TGCCCGTGCACCTGCTGCGCACCGGCGACGAGTTCGCCAC<br>CGGCACCTTCTTCTTCGACTGCAAGCCCTGCCGCCTGACCC<br>ACACCTGGCAGACCAACCGCGCCCTGGGCCTGCCCCCCTT<br>CCTGAACAGCCTGCCCCAGAGCGAGGGCGCCACCAACTTC | SEQ ID NO: 156 |

TABLE 4-continued

| Exemplary Construct | Sequence | SEQ ID NO: |
|---|---|---|
| | GGCGACATCGGCGTGCAGCAGGACAAGCGCCGCGGCGTG<br>ACCCAGATGGGCAACACCAACTACATCACCGAGGCCACCA<br>TCATGCGCCCCGCCGAGGTGGGCTACAGCGCCCCCTACTAC<br>AGCTTCGAGGCCAGCACCCAGGGCCCCTTCAAGACCCCCA<br>TCGCCGCCGGCCGCGGCGGCGCCCAGACCTACGAGAACCA<br>GGCCGCCGACGGCGACCCCCGCTACGCCTTCGGCCGCCAG<br>CACGGCCAGAAGACCACCACCACCGGCGAGACCCCCGAG<br>CGCTTCACCTACATCGCCCACCAGGACACCGGCCGCTACC<br>CCGAGGGCGACTGGATCCAGAACATCAACTTCAACCTGCC<br>CGTGACCAACGACAACGTGCTGCTGCCCACCGACCCCATC<br>GGCGGCAAGACCGGCATCAACTACACCAACATCTTCAACA<br>CCTACGGCCCCCTGACCGCCCTGAACAACGTGCCCCCCGT<br>GTACCCCAACGGCCAGATCTGGGACAAGGAGTTCGACACC<br>GACCTGAAGCCCCGCCTGCACGTGAACGCCCCCTTCGTGT<br>GCCAGAACAACTGCCCCGGCCAGCTGTTCGTGAAGGTGGC<br>CCCCAACCTGACCAACGAGTACGACCCCGACGCCAGCGCC<br>AACATGAGCCGCATCGTGACCTACAGCGACTTCTGGTGGA<br>AGGGCAAGCTGGTGTTCAAGGCCAAGCTGCGCGCCAGCC<br>ACACCTGGAACCCCATCCAGCAGATGAGCATCAACGTGGA<br>CAACCAGTTCAACTACGTGCCCAGCAACATCGGCGGCATG<br>AAGATCGTGTACGAGAAGAGCCAGCTGGCCCCCCGCAAGC<br>TGTACTAATGACTCGAGCATGCATCTAGAGGTACATCTAGAT<br>AGAGCTCGCTGATCAGCCTCGACTGTGCCTTCTAGTTGCCA<br>GCCATCTGTTGTTTGCCCCTCCCCCGTGCCTTCCTTGACCC<br>TGGAAGGTGCCACTCCCACTGTCCTTTCCTAATAAAATGAG<br>GAAATTGCATCGCATTGTCTGAGTAGGTGTCATTCTATTCTG<br>GGGGGTGGGGTGGGGCAGGACAGCAAGGGGGAGGATTGG<br>GAAGACAATAGCAGGCATGCTGGGGA | |

d. Exemplary Heterologous Nucleic Acid Constructs

In some embodiments, constructs of the disclosure may comprise (i) a transgene or a portion thereof and a transgene promoter sequence, and (ii) 5' and 3' AAV inverted terminal repeats (ITRs). In some embodiments, a construct may be packaged within a protoparvovirus variant VP1 capsid polypeptide to produce a virion. In some embodiments, a virion is delivered to a selected target cell. In some embodiments, a transgene is a nucleic acid sequence, heterologous to a construct sequence, which encodes a polypeptide, protein, functional RNA molecule (e.g., miRNA, miRNA inhibitor) or other gene product, of interest. A nucleic acid transgene coding sequence is operatively linked to regulatory component(s) in a manner which permits transgene transcription, translation, and/or expression in a cell of a target tissue.

Constructs as described in the present disclosure may include one or more additional elements as described herein (e.g., regulatory elements e.g., one or more of a promoter, a poly A sequence, and an IRES).

In some embodiments, constructs of the present disclosure may be at least 3 Kb, at least 3.5 Kb, at least 4.0 Kb, at least 4.1 Kb, at least 4.2 Kb, at least 4.3 Kb, at least 4.4 Kb, at least 4.5 Kb, at least 4.6 Kb, at least 4.7 Kb, at least 4.8 Kb, at least 4.9 Kb, at least 5.0 Kb, at least 5.1 Kb, at least 5.2 Kb, at least 5.3 Kb, at least 5.4 Kb, at least 5.5 Kb, at least 5.6 Kb, at least 5.7 Kb, at least 5.8 Kb, at least 5.9 Kb, at least 6.0 Kb, at least 6.1 Kb, at least 6.2 Kb, at least 6.3 Kb, at least 6.4 Kb, at least 6.5 Kb.

Methods for obtaining constructs are known in the art. For example, to produce protoparvovirus constructs, methods typically involve culturing a host cell which comprises a VP1 capsid coding sequence encoding a protoparvovirus capsid polypeptide or fragment thereof; a construct comprising an AAV inverted terminal repeats (ITRs) and a transgene; a functional capsid rep gene; a functional ITR rep gene; and/or sufficient helper functions to permit packaging of the construct into a protoparvovirus capsid polypeptide.

In some embodiments, components to be cultured in a host cell to package a construct in a protoparvovirus VP1 capsid may be provided to the host cell in trans. Alternatively, one or more components (e.g., a construct, rep sequences, cap sequences, and/or helper functions) may be provided by a stable host cell that has been engineered to contain one or more such components using methods known to those of skill in the art. In some embodiments, such a stable host cell contains such component(s) under control of an inducible promoter. In some embodiments, such component(s) may be under control of a constitutive promoter. In some embodiments, a selected stable host cell may contain selected component(s) under control of a constitutive promoter and other selected component(s) under control of one or more inducible promoters. For example, a stable host cell may be generated that is derived from HEK293T cells (which contain E1 helper functions under the control of a constitutive promoter), but that contain rep and/or cap proteins under control of inducible promoters. Other stable host cells may be generated by one of skill in the art using routine methods.

A construct, rep sequences, cap sequences, and helper functions required for producing a protoparvovirus VP1 polypeptide of the disclosure may be delivered to a packaging host cell using any appropriate genetic element (e.g., construct). A selected genetic element may be delivered by any suitable method known in the art, e.g., to those with skill in nucleic acid manipulation and include genetic engineering, recombinant engineering, and synthetic techniques (see, e.g., Sambrook et al., Molecular Cloning: A Laboratory Manual, Cold Spring Harbor Press, Cold Spring Harbor, N.Y., which is incorporated in its entirety herein by reference). Similarly, methods of generating protoparvovirus virions are well known and any suitable method can be used with the present disclosure (see, e.g., K. Fisher et al., *J. Virol.,* 70:520-532 (1993) and U.S. Pat. No. 5,478,745, each of which is incorporated in its entirety herein by reference).

i. Inverted Terminal Repeat Sequences (ITRs)

Sequences of a construct described herein may comprise a cis-acting 5' and 3' inverted terminal repeat sequences (ITRs) (See, e.g., B. J. Carter, in "Handbook of Parvoviruses," ed., P. Tijsser, CRC Press, pp. 155 168 (1990), which is incorporated in its entirety herein by reference). In some embodiments, ITR sequences are about 145 nt in length. For example, wild type AAV2 ITRs are generally about 145 nt in length. Preferably, substantially the entire sequences encoding ITRs are used in a given molecule, although some degree of minor modification of these sequences is permissible. Ability to modify ITR sequences is within the skill of the art. (See, e.g., texts such as Sambrook et al. "Molecular Cloning. A Laboratory Manual," 2d ed., Cold Spring Harbor Laboratory, New York (1989); and K. Fisher et al., J Virol., 70:520 532 (1996), each of which is incorporated in its entirety herein by reference). An example of such a molecule employed in the present disclosure is a "cis-acting" construct comprising a sequence encoding a transgene product, in which such a sequence and its associated regulatory elements are flanked by 5' or "left" and 3' or "right" AAV ITR sequences. 5' and left designations refer to a position of an ITR sequence relative to an entire construct, read left to right, in a sense direction. For example, in some embodiments, a 5' or left ITR is an ITR that is closest to a promoter (as opposed to a polyadenylation sequence) for a given construct, when a construct is depicted in a sense orientation, linearly. 3' and right designations refer to a position of an ITR sequence relative to an entire construct, read left to right, in a sense direction. For example, in some embodiments, a 3' or right ITR is an ITR that is closest to a polyadenylation sequence (as opposed to a promoter sequence) for a given construct, when a construct is depicted in a sense orientation, linearly. ITRs as provided herein are depicted in 5' to 3' order in accordance with a sense strand. Accordingly, one of skill in the art will appreciate that a 5' or "left" orientation ITR can also be depicted as a 3' or "right" ITR when converting from sense to antisense direction. Further, it is well within the ability of one of skill in the art to transform a given sense ITR sequence (e.g., a 5'/left AAV ITR) into an antisense sequence (e.g., 3'/right ITR sequence). Accordingly, based upon known AAV ITRs one of skill in the art would understand, in looking at sequences disclosed herein, whether an ITR was in a sense or antisense orientation and whether it would go on a "left" or "right" side of a construct, whether or not it is explicitly labeled as such. One of ordinary skill in the art would understand how to modify a given ITR sequence for use as either a 5'/left or 3'/right ITR, or an antisense version thereof.

ITR sequences may be obtained from any known virus. In some embodiments, an ITR is or comprises 145 nucleotides. In some embodiments an ITR is a wild-type AAV2 ITR. In some embodiments an ITR is derived from a wild-type AAV2 ITR and includes one or more modifications, e.g., truncations, deletions, substitutions or insertions as is known in the art. In some embodiments, an ITR comprises fewer than 145 nucleotides, e.g., 119, 127, 130, 134 or 141 nucleotides. For example, in some embodiments, an ITR comprises 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143 144, or 145 nucleotides.

In some embodiments, an ITR comprises (a) a dependoparvovirus ITR (b) an AAV ITR, optionally an AAV2 ITR, (c) a bocaparvovirus ITR, (d) a protoparvovirus ITR, (e) a tetraparvovirus ITR, or (f) an erythroparvovirus ITR. In certain embodiments, the ITR is a terminal palindrome with Rep binding elements and terminal resolution site (trs) that is structurally similar to the wild-type ITR. The ITR, in some embodiments, is from AAV1, 2, 3, etc. In certain embodiments, the ITR has the AAV2 RBE and trs. In some embodiments, the ITR is a chimera of different AAVs. In some embodiments, the ITR and the Rep protein are from AAV5. In some embodiments, the ITR is synthetic and is comprised of RBE motifs and terminal resolution site (trs) GGTTGG, AGTTGG, AGTTGA, RRTTRR. The typical T-shaped structure of the terminal palindrome consisting of the B/B' and C/C' stems may also be synthetically modified with substitutions and insertions that maintain the overall secondary structure based on folding prediction (available at URL (http) of unafold.rna.albany.edu/?q=mfold/DNA-Folding-Form). The stability of the ITR secondary structure is designated by the Gibbs free energy, delta G, with lower values, i.e., more negative, indicating greater stability. The full-length, 145 nt ITR has a computed ΔG=−69.91 kcal/mol. The B and C stems: GCCCGGGCAAAGCCCGGGCGTCGGGCGACCTTTGGTCGCCCG (SEQ ID NO: 144) have ΔG=−22.44 kcal/mol. Substitutions and insertions that result in a structure with ΔG=−15 kcal/mol to −30 kcal/mol are functionally equivalent and not distinct from the wild-type dependoparvovirus ITRs.

Any combination of ITRs and capsid polypeptides may be used in constructs of the present disclosure, for example, wild-type or variant AAV2 ITRs and AAV6 capsid, etc.

ii. Transgene

Among other things, the present disclosure provides that a virion described herein comprises a heterologous nucleic acid comprising a transgene. In some embodiments, a transgene encodes a receptor, toxin, a hormone, an enzyme, a marker protein encoded by a marker gene (see above), or a cell surface protein or a therapeutic protein, peptide or antibody or fragment thereof. In some embodiments, a transgene for use in construct compositions as disclosed herein encodes any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above.

In some embodiments, a transgene for use in a virion as disclosed herein encodes a polypeptide that is lacking or non-functional in the subject having a disease, including but not limited to any diseases described herein. In some embodiments, a disease is a genetic disease.

In some aspects, a transgene as described herein encodes a nucleic acid for use in methods of preventing or treating one or more genetic deficiencies or dysfunctions in a mammal, such as for example, a polypeptide deficiency or polypeptide excess in a mammal, and particularly for preventing, treating or reducing severity or extent of deficiency in a human manifesting one or more of disorders linked to a deficiency in such polypeptides in cells and tissues. In some embodiments, methods described herein involve administration of a transgene that encodes one or more therapeutic peptides, polypeptides, siRNAs, microRNAs, antisense nucleotides, etc. packaged in a virion described herein, preferably in a pharmaceutically acceptable composition, to a subject in an amount and for a period of time sufficient to prevent or treat a deficiency or disorder in a subject suffering from such a disorder.

Thus, in some embodiments, nucleic acids of interest for use in construct compositions as disclosed herein can encode one or more peptides, polypeptides, or proteins, which are useful for the treatment or prevention of a disease in a mammalian subject.

Exemplary nucleic acids of interest for use in compositions and methods as disclosed herein include but not limited to: BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16, IL-17, IL-18, VEGF, FGF, SDF-1, connexin 40, connexin 43, SCN4a, HIFia, SERCa2a, ADCYl, and ADCY6.

In some embodiments, a nucleic acid may comprise a coding sequence or a fragment thereof selected from the group consisting of a mammalian β globin gene (e.g., HBA1, HBA2, HBB, HBG1, HBG2, HBD, HBE1, and/or HBZ), alpha-hemoglobin stabilizing protein (AHSP), a B-cell lymphoma/leukemia 11A (BCL11A) gene, a Kruppel-like factor 1 (KLF1) gene, a CCR5 gene, a CXCR4 gene, a PPP1R12C (AAVS1) gene, an hypoxanthine phosphoribosyltransferase (HPRT) gene, an albumin gene, a Factor VIII gene, a Factor IX gene, a Leucine-rich repeat kinase 2 (LRRK2) gene, a Huntingtin (HTT) gene, a rhodopsin (RHO) gene, a Cystic Fibrosis Transmembrane Conductance Regulator (CFTR) gene, F8 or a fragment thereof (e.g., fragment encoding B-domain deleted polypeptide (e.g., VIII SQ, p-VIII)), a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CUT A) gene, a dystrophin gene (DMD), a glucocorticoid receptor gene (GR), an IL2RG gene, an RFX5 gene, a FAD2 gene, a FAD3 gene, a ZP15 gene, a KASII gene, a MDH gene, and/or an EPSPS gene.

In some embodiments, a transgene for use in a virion disclosed herein can be used to restore expression of genes that are reduced in expression, silenced, or otherwise dysfunctional in a subject. Similarly, in some embodiments, a transgene for use in a virion disclosed herein can also be used to knockdown expression of genes that are aberrantly expressed in a subject.

In some embodiments, a dysfunctional gene is a tumor suppressor that has been silenced in a subject having cancer. In some embodiments, a dysfunctional gene is an oncogene that is aberrantly expressed in a subject having a cancer. Exemplary genes associated with cancer (oncogenes and tumor suppressors) include but not limited to: AARS, ABCB 1, ABCC4, ABI2, ABL1, ABL2, ACK1, ACP2, ACY1, ADSL, AK1, AKR1C2, AKT1, ALB, ANPEP, ANXAS, ANXA7, AP2Ml, APC, ARHGAPS, ARHGEFS, ARID4A, ASNS, ATF4, ATM, ATPSB, ATPSO, AXL, BARDI, BAX, BCL2, BHLHB2, BLMH, BRAF, BRCA1, BRCA2, BTK, CANX, CAP1, CAPNI, CAPNS1, CAV1, CBFB, CBLB, CCL2, CCND1, CCND2, CCND3, CCNE1, CCTS, CCYR61, CD24, CD44, CD59, CDC20, CDC25, CDC25A, CDC25B, CDC2LS, CDK10, CDK4, CDK5, CDK9, CDKL1, CDKN1A, CDKN1B, CDKN1C, CDKN2A, CDKN2B, CDKN2D, CEBPG, CENPC1, CGRRF1, CHAFIA, CIB1, CKMT1, CLK1, CLK2, CLK3, CLNS1A, CLTC, COLIA1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR1, EIF5, EPHA2, ERBB2, ERBB3, ERBB4, ERCC3, ETV1, ETV3, ETV6, F2R, FASTK, FBN1, FBN2, FES, FGFR1, FGR, FKBP8, FN1, FOS, FOSL1, FOSL2, FOXG1A, FOXO1A, FRAP1, FRZB, FTL, FZD2, FZDS, FZD9, G22P1, GAS6, GCNSL2, GDF1S, GNA13, GNAS, GNB2, GNB2L1, GPR39, GRB2, GSK3A, GSPT1, GTF21, HDAC1, HDGF, HMMR, HPRT1, HRB, HSPA4, HSPAS, HSPA8, HSPB1, HSPH1, HYAL1, HYOU1, ICAM1, ID1, ID2, IDUA, IER3, IFITM1, IGF1R, IGF2R, IGFBP3, IGFBP4, IGFBPS, IL1B, ILK, ING1, IRF3, ITGA3, ITGA6, ITGB4, JAK1, JARID1A, JUN, JUNB, JUND, K-ALPHA-1, KIT, KITLG, KLK10, KPNA2, KRAS2, KRT18, KRT2A, KRT9, LAMB1, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB I, NFKB2, NFSF7, NID, NINJ1, NMBR, NME1, NME2, NME3, NOTCH 1, NOTCH2, NOTCH4, NPM1, NQO1, NRID1, NR2Fl, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PPIH, PPP1CA, PPP2RSA, PRDX2, PRDX4, PRKAR1A, PRKCBP1, PRNP, PRSS15, PSMA1, PTCH, PTEN, PTGS1, PTMA, PTN, PTPRN, RABSA, RAC1, RADSO, RAF1, RALBP1, RAP1A, RARA, RARB, RASGRF1, RB1, RBBP4, RBL2, REA, REL, RELA, RELB, RET, RFC2, RGS19, RHOA, RHOB, RHOC, RHOD, RIPK1, RPN2, RPS6 KB 1, RRM1, SARS, SELENBP1, SEMA3C, SEMA4D, SEPP1, SERPINH1, SFN, SFPQ, SFRS7, SHB, SHH, SIAH2, SIVA, SIVA TP53, SKI, SKIL, SLC16A1, SLC1A4, SLC20A1, SMO, SMPD1, SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFA, TGFB1, TGFBR1, TGFBR2, TGFBR3, THBS1, TIE, TIMP1, TIMP3, TJP1, TK1, TLE1, TNF, TNFRSF10A, TNFRSF10B, TNFRSF1A, TNFRSF1B, TNFRSF6, TNFSF7, TNK1, TOB1, TP53, TP53BP2, TP5313, TP73, TPBG, TPT1, TRADD, TRAM1, TRRAP, TSG101, TUFM, TXNRD1, TYR03, UBC, UBE2L6, UCHL1, USP7, VDAC1, VEGF, VHL, VIL2, WEE1, WNT1, WNT2, WNT2B, WNT3, WNTSA, WT1, XRCC 1, YES 1, YWHAB, YWHAZ, ZAP70, and ZNF9.

In some embodiments, a dysfunctional gene is HBB. In some embodiments, an HBB comprises at a nonsense, frameshift, or splicing mutation that reduces or eliminates β-globin production. In some embodiments, HBB comprises a mutation in a promoter region or polyadenylation signal of HBB. In some embodiments, an HBB mutation is at least one of c. 17A>T, c.-1360G, c.92+1G>A, c.92+6T>C, c.93-21G>A, c.1180T, c.316-1060G, c.25_26delAA, c.27_28insG, c.92+5G>C, c. 1180T, c. 135delC, c.315+1G>A, c.-78A>G, c.52A>T, c.59A>G, c.92+5G>C, c. 124_127delTTCT, c.316-1970T, c.-78A>G, c.52A>T, c. 124 127delTTCT, c.316-197C>T, C.-1380T, c.-79A>G, c.92+5G>C, c.75T>A, c.316-2A>G, and c.316-2A>C.

In certain embodiments, sickle cell disease is improved by gene therapy (e.g., stem cell gene therapy) that introduces an HBB variant that comprises at least one sequence variation comprising anti-sickling activity. In some embodiments, an HBB variant may be a double mutant (βAS2; T87Q and E22A). In some embodiments, an HBB variant may be a triple-mutant β-globin variant (βAS3; T87Q, E22A, and G16D). A modification at β16, glycine to aspartic acid, serves a competitive advantage over sickle globin (βS, HbS) for binding to a chain. A modification at β22, glutamic acid to alanine, partially enhances axial interaction with a20 histidine. These modifications result in anti-sickling properties greater than those of the single T87Q-modified variant and comparable to fetal globin. In a SCD murine model, transplantation of bone marrow stem cells transduced with SIN lentivirus carrying βAS3 reversed the red blood cell physiology and SCD clinical symptoms. Accordingly, this variant is being tested in a clinical trial (Identifier no: NCT02247843), Cytotherapy (2018) 20(7): 899-910.

In some embodiments, a dysfunctional gene is CFTR. In some embodiments, CFTR comprises a mutation selected from ΔF508, R553X, R74W, R668C, S977F, L997F, K1060T, A1067T, R1070Q, R1066H, T3381, R334W, G85E, A46D, I336K, H1054D, MIV, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In some embodiments, a transgene comprises a gene associated with a kidney disease.

In some embodiments, a transgene comprises a gene associated with Alport syndrome (e.g., Col4a3, Col4a4, Col4a5). In some embodiments, a transgene comprises or is Col4a3. In some embodiments, a transgene comprises or is Col4a4. In some embodiments, a transgene comprises or is Col4a5.

In some embodiments, a transgene comprises a gene associated with Fabry disease (e.g., GLA). In some embodiments, a transgene comprises or is GLA.

In some embodiments, a transgene comprises a gene associated with autosomal dominant polycystic kidney disease (PKD) (e.g., PKD1, PKD2). In some embodiments, a transgene comprises or is PKD. In some embodiments, a transgene comprises or is PKD1. In some embodiments, a transgene comprises or is PKD2.

In some embodiments, a transgene comprises a gene associated with congenital nephrotic syndrome (e.g., NPHS1 (Nephrin), NPHS2 (Podocin). In some embodiments, a transgene comprises or is NPHS1. In some embodiments, a transgene comprises or is NPHS2.

In some embodiments, a transgene comprises a gene associated with a cardiac disease (or heart disease).

In some embodiments, a transgene comprises a gene associated with hypertrophic cardiomyopathy (e.g., MYBPC3, JPH2, ALPK3). In some embodiments, a transgene comprises or is MYBPC3. In some embodiments, a transgene comprises or is JPH2. In some embodiments, a transgene comprises or is ALPK3.

In some embodiments, a transgene comprises a gene associated with dilated cardiomyopathy (e.g., RBM20). In some embodiments, a transgene comprises or is RBM20.

In some embodiments, a transgene comprises a gene associated with dilated cardiomyopathy (e.g., ALPK3, LMNA, BAG3). In some embodiments, a transgene comprises or is ALPK3. In some embodiments, a transgene comprises or is LMNA. In some embodiments, a transgene comprises or is BAG3.

In some embodiments, a transgene as defined herein encodes a small interfering nucleic acid (e.g., shRNAs, miRNAs) that inhibits the expression of a gene product associated with cancer (e.g., oncogenes) may be used to prevent or treat cancer. In some embodiments, a transgene as defined herein encodes a gene product associated with cancer (or a functional RNA that inhibits expression of a gene associated with cancer) for use, e.g., for research purposes, e.g., to study a cancer or to identify therapeutics that prevent or treat a cancer.

An ordinarily skilled artisan also appreciates that a nucleic acids of interest can comprise at least one sequence variation that result in conservative amino acid substitutions which may provide functionally equivalent variants, or homologs of a protein or polypeptide. Additionally contemplated in this disclosure is a transgene in a virion described herein, having a dominant negative mutation. For example, a transgene can encode a mutant protein that interacts with the same elements as a wild-type protein, and thereby blocks some aspects of a function of a wild-type protein.

In some embodiments, a transgene in a virion disclosed herein includes miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (de-repress the polypeptide). In some embodiments, de-repression of polypeptides encoded by mRNA targets of a miRNA is accomplished by inhibiting the miRNA activity in cells through any one of a variety of methods. For example, blocking activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, a small interfering nucleic acid that is substantially complementary to a miRNA is one that is capable of hybridizing with a miRNA, and blocking the miRNA's activity. In some embodiments, a small interfering nucleic acid that is substantially complementary to a miRNA is a small interfering nucleic acid that is complementary with the miRNA at all but 1, 2, 3, 4, 5, 6, 7, 8, 9, 10, 11, 12, 13, 14, 15, 16, 17, or 18 bases. In some embodiments, a small interfering nucleic acid sequence that is substantially complementary to a miRNA, is a small interfering nucleic acid sequence that is complementary with the miRNA at, at least, one base.

iii. Transgene Promoter Sequences

In some embodiments, a transgene promoter is an inducible promoter, a constitutive promoter, a mammalian cell promoter, a viral promoter, a chimeric promoter, an engineered promoter, a tissue-specific promoter, or any other type of promoter known in the art. In some embodiments, a promoter is a RNA polymerase II promoter, such as a mammalian RNA polymerase II promoter. In some embodiments, a promoter is a RNA polymerase III promoter, including, but not limited to, a HI promoter, a human U6 promoter, a mouse U6 promoter, or a swine U6 promoter.

In some embodiments, a transgene promoter can be a transgene promoter that, in its endogenous context, is associated with a gene in the CRISPR/Cas system. For example, in some embodiments, a promoter can be a Cas gene promoter. In some embodiments, a transgene promoter can be a Cas9 promoter.

A variety of transgene promoters is known in the art, any of which can be used herein. Non-limiting examples of transgene promoters that can be used herein include transgene promoters for: human elongation factor 1α-subunit (EF1a) (Liu et al. (2007) Exp. Mol. Med. 39(2): 170-175; Accession No. J04617.1; Gill et al., *Gene Ther.* 8(20): 1539-1546, 2001; Xu et al., Human Gene Ther. 12(5): 563-573, 2001; Xu et al., Gene Ther. 8:1323-1332; Ikeda et al., *Gene Ther.* 9:932-938, 2002; Gilham et al., *J. Gene Med.* 12(2): 129-136, 2010, each of which is incorporated in its entirety herein by reference), cytomegalovirus (Xu et al., *Human Gene Ther.* 12(5): 563-573, 2001; Xu et al., Gene Ther. 8:1323-1332; Gray et al., *Human Gene Ther.* 22:1143-1153, 2011, each of which is incorporated in its entirety herein by reference), human immediate-early cytomegalovirus (CMV) (U.S. Pat. No. 5,168,062, Liu et al. (2007) Exp. Mol. Med. 39(2): 170-175; Accession No. X17403.1 or KY490085.1, each of which is incorporated in its entirety herein by reference), human ubiquitin C (UBC) (Gill et al., *Gene Ther.* 8(20): 1539-1546, 2001; Qin et al., *PLOS One* 5(5): e10611, 2010, each of which is incorporated in its entirety herein by reference), mouse phosphoglycerate kinase 1, polyoma adenovirus, simian virus 40 (SV40), β-globin, β-actin, α-fetoprotein, γ-globin, β-interferon, γ-glutamyl transferase, mouse mammary tumor virus (MMTV), Rous sarcoma virus, rat insulin, glyceraldehyde-3-phosphate dehydrogenase, metallothionein II (MT II), amylase, cathepsin, MI muscarinic receptor, retroviral LTR (e.g., human T-cell leukemia virus HTLV, each of which is incorporated in its entirety herein by reference), AAV ITR, interleukin-2, collagenase, platelet-derived growth factor, adenovirus 5 E2, stromelysin, murine MX gene, glucose regulated proteins (GRP78 and GRP94), α-2-macroglobulin, vimentin, MHC class I gene H-2κ b, HSP70, proliferin, tumor necrosis factor, thyroid stimulating hormone α gene, immunoglobulin light chain, T-cell receptor, HLA DQα and DQβ, interleukin-2 receptor, MHC class II, MHC class II HLA-DRα, muscle creatine kinase, prealbumin (transthyretin), elastase I, albumin gene, c-fos, c-HA-ras, neural cell adhesion molecule (NCAM), H2B (TH2B) histone, rat growth hormone, human serum amyloid (SAA), troponin I (TN I), duchenne muscular dystrophy, human immunodeficiency virus, Gibbon Ape Leukemia Virus (GALV) promoters, promoter of HNRPA2β1-CBX1 (UCOE) (Powell and Gray (2015) Discov. Med. 19(102): 49-57; Antoniou et al., *Human Gene Ther.* 24(4): 363-374, 2013), β-glucuronidase (GUSB) (Husain et al., *Gene Ther.* 16:927-932, 2009), chicken β-actin (CBA) (Liu et al. (2007) Exp. Mol. Med. 39(2): 170-175; Stone et al. (2005) Mol. Ther. 11(6): 843-848; Klein et al., *Exp. Neurol.* 176(1): 66-74, 2002; Ohlfest et al., *Blood* 105:2691-2698, 2005; Gray et al., *Human Gene Ther.* 22:1143-1153, 2011, each of which is incorporated in its entirety herein by reference), a human β-actin promoter (HBA) (Accession No. Y00474.1), murine myosin VIIA (musMyo7) (Boeda et al. (2001) Hum. Mol. Genet. 10(15): 1581-1589; Accession No. AF384559.1, each of which is incorporated in its entirety herein by reference), human myosin VIIA (hsMyo7) (Boeda et al. (2001) Hum. Mol. Genet. 10(15): 1581-1589; Accession No. NG_009086.1, each of which is incorporated in its entirety herein by reference), murine poly(ADP-ribose) polymerase 2 (musPARP2) (Ame et al. (2001) J. Biol. Chem. 276(14): 11092-11099; Accession No. ΔF191547.1, each of which is incorporated in its entirety herein by reference), human poly (ADP-ribose) polymerase 2 (hsPARP2) (Ame et al. (2001) J. Biol. Chem. 276(14): 11092-11099; Accession No. X16612.1 or AF479321.1, each of which is incorporated in its entirety herein by reference), acetylcholine receptor epsilon-subunit (AChε) (Duclert et al. (1993) PNAS 90(7): 3043-3047; Accession No. S58221.1 or CR933736.12, each of which is incorporated in its entirety herein by reference), Rous sarcoma virus (RSV) (Liu et al. (2007) Exp. Mol. Med. 39(2): 170-175; Accession No. M77786.1, each of which is incorporated in its entirety herein by reference), (GFAP) (Liu et al. (2007) Exp. Mol. Med. 39(2): 170-175; Stone et al. (2005) Mol. Ther. 11(6): 843-848; Accession No. NG 008401.1 or M67446.1, each of which is incorporated in its entirety herein by reference), hAAT (Van Linthout et al., *Human Gene Ther.* 13(7): 829-840, 2002; Cunningham et al., *Mol. Ther.* 16(6): 1081-1088, 2008, each of which is incorporated in its entirety herein by reference), and a CBA hybrid (CBh) (Gray et al. (2011) Hum. Gen. Therapy 22:1143-1153; Accession No. KF926476.1 or KC152483.1, each of which is incorporated in its entirety herein by reference). Additional examples of promoters are known in the art. See, e.g., Lodish, Molecular Cell Biology, Freeman and Company, New York 2007. The contents of each of these references are incorporated by reference in its entirety.

In some embodiments, a promoter is a CMV immediate early promoter.

In some embodiments, a promoter is a CAG promoter or a CAG/CBA promoter.

The term "constitutive" transgene promoter refers to a nucleotide sequence that, when operably linked with a nucleic acid encoding a protein a nucleic acid.

Examples of constitutive transgene promoters include, without limitation, a retroviral Rous sarcoma virus (RSV) LTR promoter, a cytomegalovirus (CMV) promoter (see, e.g., Boshart et al. *Cell* 41:521-530, 1985, which is incorporated in its entirety herein by reference), an SV40 promoter, a dihydrofolate reductase promoter, a beta-actin promoter, a phosphoglycerol kinase (PGK) promoter, and an EF1-alpha promoter (Invitrogen).

In some embodiments, inducible transgene promoters allow regulation of gene expression and can be regulated by exogenously supplied compounds, environmental factors such as temperature, or presence of a specific physiological state, e.g., acute phase, a particular functional or biological state of a cell, e.g., a particular differentiation state of a cell, or in replicating cells only. Inducible promoters and inducible systems are available from a variety of commercial sources, including, without limitation, Invitrogen, Clontech, and Ariad. Additional examples of inducible promoters are known in the art.

Examples of inducible transgene promoters regulated by exogenously supplied compounds include a zinc-inducible sheep metallothionine (MT) promoter, a dexamethasone (Dex)-inducible mouse mammary tumor virus (MMTV) promoter, a T7 polymerase promoter system (WO 98/10088, which is incorporated in its entirety herein by reference); an ecdysone insect promoter (No et al. *Proc. Natl. Acad. Sci. U.S.A.* 93:3346-3351, 1996, which is incorporated in its entirety herein by reference), a tetracycline-repressible system (Gossen et al. *Proc. Natl. Acad. Sci. U.S.A.* 89:5547-5551, 1992, which is incorporated in its entirety herein by reference), a tetracycline-inducible system (Gossen et al. *Science* 268:1766-1769, 1995, see also Harvey et al. *Curr. Opin. Chem. Biol.* 2:512-518, 1998, each of which is incorporated in its entirety herein by reference), an RU486-inducible system (Wang et al. *Nat. Biotech.* 15:239-243, 1997; and Wang et al. *Gene Ther.* 4:432-441, 1997, each of which is incorporated in its entirety herein by reference), and a rapamycin-inducible system (Magari et al. *J. Clin. Invest.* 100:2865-2872, 1997, which is incorporated in its entirety herein by reference).

In some embodiments, regulatory sequences impart tissue-specific gene expression capabilities. In some cases, tissue-specific regulatory sequences bind tissue-specific transcription factors that induce transcription in a tissue-specific manner.

The term "tissue-specific" transgene promoter refers to a transgene promoter that is active only in certain specific cell types and/or tissues (e.g., transcription of a specific gene occurs only within cells expressing transcription regulatory and/or control proteins that bind to the tissue-specific promoter).

In some embodiments, provided constructs comprise a promoter sequence selected from a CAG, a CBA, a CMV, or a CB7 promoter. In some embodiments of therapeutic compositions described herein, a first or sole a construct further includes at least one promoter.

iv. Enhancers and 5' Cap

In some instances, a construct can include a transgene promoter sequence and/or an enhancer sequence. In some embodiments, an enhancer is a nucleotide sequence that can increase a level of transcription of a nucleic acid encoding a polypeptide of interest (e.g., a transgene). In some embodiments, enhancer sequences (50-1500 base pairs in length) generally increase a level of transcription by providing additional binding sites for transcription-associated proteins (e.g., transcription factors). In some embodiments, an enhancer sequence is found within an intronic sequence. Unlike promoter sequences, enhancer sequences can act at much larger distance away from a transcription start site (e.g., as compared to a promoter). Non-limiting examples of enhancers include a RSV enhancer, a CMV enhancer, and a SV40 enhancer. An example of a CMV enhancer is described in, e.g., Boshart et al., Cell 41(2): 521-530, 1985, which is incorporated in its entirety herein by reference.

As described herein, a 5' cap (also termed an RNA cap, an RNA 7-methylguanosine cap or an RNA m.sup.7G cap) is a modified guanine nucleotide that has been added to a "front" or 5' end of a eukaryotic messenger RNA shortly after a start of transcription. In some embodiments, a 5' cap consists of a terminal group which is linked to a first transcribed nucleotide. Its presence is critical for recognition by a ribosome and protection from RNases. Cap addition is coupled to transcription, and occurs co-transcriptionally, such that each influences the other. Shortly after start of transcription, a 5' end of an mRNA being synthesized is bound by a cap-synthesizing complex associated with RNA polymerase. This enzymatic complex catalyzes a chemical reactions that are required for mRNA capping. Synthesis proceeds as a multi-step biochemical reaction. A capping moiety can be modified to modulate functionality of mRNA such as its stability or efficiency of translation.

e. Reporter Sequences or Elements

Any constructs provided herein can optionally include a sequence encoding a reporter protein ("a reporter sequence"). For example, in some embodiments, a reporter sequence may be a FLAG, an eGFP, an mScarlet, a luciferase or any variant thereof. In some embodiments, a reporter sequence is visibly detectable without intervention. In some embodiments, a reporter element may be detected using a combination of fluorescent, histochemical, and/or transcript or protein analyses. Non-limiting examples of reporter sequences are described herein. Additional examples of reporter sequences are known in the art. In some embodiments, reporter sequence can be used to verify tissue-specific targeting capabilities and tissue-specific promoter regulatory activity of any constructs described herein.

f. Additional Sequences

In some embodiments, constructs of the present disclosure may comprise a T2A element or sequence. In some embodiments, constructs of the present disclosure may include one or more cloning sites. In some such embodiments, cloning sites may not be fully removed prior to manufacturing for administration to a subject.

g. Genome Editing

In some embodiments, a genome editing system targets nucleotides within a specific target site.

i. RNA-Guided Micleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a gRNA; and (b) together with gRNA, associate with, and optionally cleave or modify, a target region of a DNA that includes (i) a sequence complementary to a targeting domain of a gRNA and, optionally, (ii) an additional sequence referred to as a "protospacer adjacent motif," or "PAM," which is described in greater detail herein.

Naturally occurring CRISPR systems are organized evolutionarily into two classes and five types (Makarova et al. Nat Rev Microbiol. 2011 June; 9(6): 467-477 ("Makarova"), which is incorporated in its entirety herein by reference), and while genome editing systems of the present disclosure may adapt components of any type or class of naturally occurring CRISPR system, embodiments presented herein are generally adapted from Class 2, and type II or V CRISPR systems. Class 2 systems, which encompass types II and V, are characterized by relatively large, multidomain CRISPR proteins (e.g., Cas9 or Cpf1) and one or more gRNAs (e.g., a crRNA and, optionally, a tracrRNA) that form ribonucleoprotein (RNP) complexes that associate with (i.e., target) and cleave specific loci complementary to a targeting (or spacer) sequence of a crRNA. Genome editing systems according to the present disclosure similarly target and edit cellular DNA sequences, but differ significantly from CRISPR systems occurring in nature. For example, unimolecular gRNAs described herein do not occur in nature, and both gRNAs and CRISPR nucleases according to this disclosure may incorporate any number of non-naturally occurring modifications.

As described herein, it should be noted that a genome editing systems of the present disclosure can be targeted to a single specific nucleotide sequence, or may be targeted to—and capable of editing in parallel—two or more specific nucleotide sequences through use of two or more gRNAs. In some embodiments, use of multiple gRNAs is referred to as "multiplexing." As described herein, multiplexing can be employed, for example, to target multiple, unrelated target sequences of interest, or to form multiple SSBs or DSBs within a single target domain and, in some cases, to generate specific edits within such target domain. For example, International Patent Publication No. WO 2015/138510 by Maeder et al., which is incorporated in its entirety herein by reference; ("Maeder") describes a genome editing system for correcting a point mutation (C.2991+1655A to G) in human CEP290 that results in t creation of a cryptic splice site, which in turn reduces or eliminates function of the gene. That genome editing system of Maeder utilizes two gRNAs targeted to sequences on either side of (i.e., flanking) the point mutation, and forms DSBs that flank the mutation. This, in turn, promotes deletion of the intervening sequence, including the mutation, thereby eliminating the cryptic splice site and restoring normal gene function.

As another example, WO 2016/073990 by Cotta-Ramusino, et al. ("Cotta-Ramusino"), which is incorporated in its entirety herein by reference. Cotta-Ramusino describes a genome editing system that utilizes two gRNAs in combination with a Cas9 nickase (a Cas9 that makes a single strand nick such as *S. pyogenes* D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, WO 2015/070083 by Palestrant et al., which is incorporated in its entirety herein by reference; ("Palestrant") describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

Genome editing systems can, in some instances, form double strand breaks that are repaired by cellular DNA double-strand break mechanisms such as NHEJ or HDR. These mechanisms are described throughout the literature, for example by Davis & Maizels, PNAS, 111(10): E924-932, Mar. 11, 2014, which is incorporated in its entirety herein by reference ("Davis") (describing Alt-HDR); Frit et al. DNA Repair 17(2014) 81-97, which is incorporated in its entirety herein by reference ("Frit") (describing Alt-NHEJ); and Iyama and Wilson III, DNA Repair (Amst.) 2013-August; 12(8): 620-636, which is incorporated in its entirety herein by reference ("Iyama") (describing canonical HDR and NHEJ pathways generally).

Where genome editing systems operate by forming DSBs, such systems optionally include one or more components that promote or facilitate a particular mode of double-strand break repair or a particular repair outcome. For instance, Cotta-Ramusino also describes genome editing systems in which a single stranded oligonucleotide "donor template" is added; a donor template is incorporated into a target region of cellular DNA that is cleaved by a genome editing system, and can result in a change in a target sequence.

In some embodiments, genome editing systems modify a target sequence, or modify expression of a gene in or near a target sequence, without causing single- or double-strand breaks. For example, a genome editing system may include a CRISPR protein fused to a functional domain that acts on DNA, thereby modifying a target sequence or its expression. As one example, a CRISPR protein can be connected to (e.g., fused to) a cytidine deaminase functional domain, and may operate by generating targeted C-to-A substitutions. Exemplary nuclease/deaminase fusions are described in Komor et al. Nature 533, 420-424(19 May 2016) ("Komor"), which is incorporated in its entirety herein by reference. In some embodiments, a genome editing system may utilize a cleavage-inactivated (i.e., a "dead") nuclease, such as a dead Cas9 (dCas9), and may operate by forming stable complexes on one or more targeted regions of cellular DNA, thereby interfering with functions involving a targeted region(s) including, without limitation, mRNA transcription, chromatin remodeling, etc. In some embodiments, a genome editing system may be self-inactivating to improve a safety profile, as described by Li et al. "A Self-Deleting AAV-CRISPR System for In vivo Editing" Mol Ther Methods Clin Dev. 2019 Mar. 15; 12:111-122; published online (2018 Dec. 6), the contents of which are hereby incorporated by reference in its entirety.

As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., *S. pyogenes* vs. *S. aureus*, etc.) or variation (e.g., full-length vs. truncated or split; naturally-occurring PAM specificity vs. engineered PAM specificity, etc.) of RNA-guided nuclease. In some embodiments, a CRISPR/Cas is derived from a type II CRISPR/Cas system. In some embodiments, a CRISPR/Cas system is derived from a Cas9 protein. A Cas9 protein can be from *Streptococcus pyogenes, Streptococcus thermophilus, Staphylococcus aureus, Campylobacter jejuni*, or other species.

Administering bacterial Cas9 in humans presents immunogenicity concerns. Therefore, it is important to develop a codon-optimized CRISPR system as described herein to reduce immunogenicity. In addition, some other limitations include a need to use a two construct system (instead of a single construct system such that is used in shRNA and miRNA protocols), and determination of off-target risk.

A PAM sequence takes its name from its sequential relationship to a "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of a protospacer. Cpf1, on the other hand, generally recognizes PAM sequences that are 5' of a protospacer.

In addition to recognizing specific sequential orientations of PAMs and protospacers, RNA-guided nucleases can also recognize specific PAM sequences. *S. aureus* Cas9, for instance, recognizes a PAM sequence of NNGRRT or NNGRRV, wherein the N residues are immediately 3' of the region recognized by the gRNA targeting domain. *S. pyogenes* Cas9 recognizes NGG PAM sequences. And *F. novicida* Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from\PAM specificities of reference molecules (for instance, in the case of an engineered RNA-guided nuclease, a reference molecule may be a naturally occurring variant from which an RNA-guided nuclease is derived, or a naturally occurring variant having the greatest amino acid sequence homology to an engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154(6), 1380-1389 Sep. 12, 2013 ("Ran")), or that that do not cut at all.

The present application also recognizes that other types of CRISPR enzymes, such as Cas12a, can be used in accordance with embodiments described herein.

CRISPR Fusion Proteins

As described herein, in some embodiments, a CRISPR nuclease is part of a fusion protein comprising one or more heterologous protein domains (e.g., about or more than about 1, 2, 3, 4, 5, 6, 7, 8, 9, 10, or more domains in addition to a CRISPR nuclease). A CRISPR nuclease fusion protein may comprise any additional protein sequence, and optionally a linker sequence between any two domains. Examples of protein domains that may be fused to a CRISPR nuclease include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR nuclease are described in US20110059502, incorporated herein by reference. In some embodiments, a tagged CRISPR nuclease is used to identify a location of a target sequence. In some embodiments, a CRISPR nuclease that is part of a fusion protein has been engineered to produce only SSBs as described herein. In some embodiments, a CRISPR nuclease that is part of a fusion protein has been engineered to not cut at all as described herein.

CRISPR Variants

In general, RNA-guided nucleases comprise at least one RNA recognition and/or RNA binding domain. RNA recognition and/or RNA binding domains interact with a guiding RNA. CRISPR/Cas proteins can also comprise nuclease domains (i.e., DNase or RNase domains), DNA binding domains, helicase domains, RNAse domains, protein-protein interaction domains, dimerization domains, as well as other domains. RNA-guided nucleases can be modified to increase nucleic acid binding affinity and/or specificity, alter an enzymatic activity, and/or change another property of a protein. In some embodiments, a CRISPR/Cas-like protein of a fusion protein can be derived from a wild type Cas9 protein or fragment thereof. In some embodiments, a CRISPR/Cas can be derived from modified Cas9 protein. For example, an amino acid sequence of a Cas9 protein can be modified to alter one or more properties (e.g., nuclease activity, affinity, stability, and so forth) of a protein. Alternatively, domains of a Cas9 protein not involved in RNA-guided cleavage can be eliminated from a protein such that a modified Cas9 protein is smaller than a wild type Cas9 protein. In general, a Cas9 protein comprises at least two nuclease (i.e., DNase) domains. For example, a Cas9 protein can comprise a RuvC-like nuclease domain and a HNH-like nuclease domain. RuvC and HNH domains work together to cut single strands to make a double-stranded break in DNA (Jinek et al., 2012, Science, 337:816-821, which is incorporated in its entirety herein by reference).

In some embodiments, a Cas9-derived protein can be modified to contain only one functional nuclease domain (either a RuvC-like or a HNH-like nuclease domain). For example, a Cas9-derived protein can be modified such that one nuclease domain is deleted or mutated such that it is no longer functional (i.e., nuclease activity is absent). In some embodiments in which one nuclease domains is inactive, a Cas9-derived protein is able to introduce a nick into a double-stranded nucleic acid (such protein is termed a "nickase"), but not cleave double-stranded DNA. In any of the above-described embodiments, any or all of nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

One example of a CRISPR/Cas9 system used to inhibit gene expression, CRISPRi, is described in U.S. Publication No. US2014/0068797, which is incorporated herein by reference in its entirety. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a gRNA, a DNA recognition complex is generated that specifically interferes with transcriptional elongation, RNA polymerase binding, or transcription factor binding. This CRISPRi system efficiently represses expression of targeted genes.

ii. Guide RNAs (gRNAs)

gRNA Sequence Selection

A gRNA sequence may be specific for any gene, such as a gene that would affect (e.g., ameliorate, improve, attenuate, mitigate) a disease or disorder. In some embodiments, a gRNA sequence includes an RNA sequence, a DNA sequence, a combination thereof (a RNA-DNA combination sequence), or a sequence with synthetic nucleotides. A gRNA sequence can be a single molecule or a double molecule. In one embodiment, a gRNA sequence comprises a single guide RNA (sgRNA).

In some embodiments, a gRNA sequence is specific for a gene and targets that gene for Cas endonuclease-induced double strand breaks. A sequence of a gRNA may be within a loci of the gene. In one embodiment, a gRNA sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length. In some embodiments, a gRNA sequence is from about 18 to about 22 nucleotides in length.

As described herein, in some embodiments in the context of formation of a CRISPR complex, "target sequence" refers to a sequence to which a guide sequence is designed to have some complementarity, where hybridization between a target sequence and a guide sequence promotes formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, a target sequence may be within an organelle of a eukaryotic cell, for example, mitochondrion or nucleus. Typically, in the context of an endogenous CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) a target sequence. As with a target sequence, it is believed that complete complementarity is not needed, provided this is sufficient to be functional. In some embodiments, a tracr sequence has at least 50%, 60%, 70%, 80%, 90%, 95% or 99% of sequence complementarity along the length of a tracr mate sequence when optimally aligned.

gRNA Design

Methods for selection and validation of target sequences as well as off-target analyses have been described previously, e.g., in Mali; Hsu; Fu et al., 2014 Nat biotechnol 32(3): 279-84, Heigwer et al., 2014 Nat methods 11(2): 122-3; Bae et al. (2014) Bioinformatics 30(10): 1473-5; and Xiao A et al. (2014) Bioinformatics 30(8): 1180-1182, each of which is incorporated in its entirety herein by reference. As a non-limiting example, gRNA design may involve use of a software tool to optimize choice of potential target sequences corresponding to a user's target sequence, e.g., to minimize total off-target activity across a genome. While off-target activity is not limited to cleavage, cleavage efficiency at each off-target sequence can be predicted, e.g., using an experimentally-derived weighting scheme. These and other guide selection methods are described in detail in Maeder and Cotta-Ramusino.

For example, methods for selection and validation of target sequences as well as off-target analyses can be performed using cas-offinder (Bae S, Park J, Kim J-S. Cas-OFFinder: a fast and versatile algorithm that searches for potential off-target sites of Cas9 RNA-guided endonucleases. Bioinformatics. 2014; 30:1473-5, which is incorporated in its entirety herein by reference). Cas-offinder is a tool that can quickly identify all sequences in a genome that have up to a specified number of mismatches to a guide sequence.

As another example, methods for scoring how likely a given sequence is to be an off-target (e.g., once candidate target sequences are identified) can be performed. An exemplary score includes a Cutting Frequency Determination (CFD) score, as described by Doench J G, Fusi N, Sullender M, Hegde M, Vaimberg E W, Donovan K F, et al. Optimized sgRNA design to maximize activity and minimize off-target effects of CRISPR-Cas9. Nat Biotechnol. 2016; 34:184-91, which is incorporated in its entirety herein by reference.

gRNA Modifications

Certain exemplary modifications discussed in this section can be included at any position within a gRNA sequence including, without limitation at or near its 5' end (e.g., within 1-10, 1-5, or 1-2 nucleotides of a 5' end) and/or at or near its 3' end (e.g., within 1-10, 1-5, or 1-2 nucleotides of a 3' end). In some cases, modifications are positioned within functional motifs, such as a repeat-anti-repeat duplex of a Cas9 gRNA, a stem loop structure of a Cas9 or Cpf1 gRNA, and/or a targeting domain of a gRNA. Others types of modified nucleobases are described herein.

h. Knockdown

The present disclosure provides technologies (e.g., comprising compositions) that may, in some embodiments, reduce, suppress or otherwise decrease ("knock down") expression of one or more gene products. For example, in some embodiments, technologies of the present disclosure may achieve knockdown of a gene product (e.g., a gene, mRNA, protein, etc.).

i. Inhibitory Nucleic Acid Molecules

RNA interference (RNAi) is a process of sequence-specific post-transcriptional gene silencing by which, e.g., double stranded RNA (dsRNA) homologous to a target locus can specifically inactivate gene function (Hammond et al., Nature Genet. 2001; 2:110-119; Sharp, Genes Dev. 1999; 13:139-141, the contents of each which are hereby incorporated by reference herein in its entirety). For example, positional location of shRNAs targeting intronic-3 XmiR, poly A-3 XmiR, or both intronic-3 XmiR and PolyA-3XmiR reduced PIZ serum level (% knockdown as compared to GFP control) (Mueller et al 2012). As described herein, positional impacts of miRNAs are tested and evaluated. In some embodiments, dsRNA-induced gene silencing can be mediated by short double-stranded small interfering RNAs (siRNAs) generated from longer dsRNAs by ribonuclease III cleavage (Bernstein et al., Nature 2001; 409:363-366 and Elbashir et al., *Genes Dev.* 2001; 15:188-200, the contents of each of which are hereby incorporated by reference herein in its entirety). Without being bound by any particular theory, RNAi-mediated gene silencing is thought to occur via sequence-specific RNA degradation, where sequence specificity is determined by interaction of a siRNA with its complementary sequence within a target RNA (see, e.g., Tuschl, Chem. Biochem. 2001; 2:239-245). In some embodiments, RNAi can involve use of, e.g., siRNAs (Elbashir, et al., Nature 2001; 411:494-498, which is incorporated in its entirety herein by reference) or short hairpin RNAs (shRNAs) bearing a fold back stem-loop structure (Paddison et al., Genes Dev. 2002; 16:948-958; Sui et al., Proc. Natl. Acad. Sci. USA 2002; 99:5515-5520; Brummelkamp et al., Science 2002; 296:550-553; Paul et al., Nature Biotechnol. 2002; 20:505-508, each of which is incorporated in its entirety herein by reference).

In some embodiments an inhibitory nucleic acid is one or more of a short interfering RNA (siRNA), a short hairpin RNA (shRNA), an antisense oligonucleotide, or a ribozyme. In some embodiments, knockdown of gene expression is achieved via inhibitory nucleic acids that target a target sequence as described herein. In some such embodiments, a targeted target sequence may be a wild-type and/or pathogenic variant gene product.

siRNA or shRNA

In some embodiments, the present disclosure provides an inhibitory nucleic acid e, e.g., a chemically-modified siRNAs or a construct-driven expression of short hairpin RNA (shRNA) that are then cleaved to siRNA, e.g., within a cell. Accordingly, one of skill in the art will understand that, for purposes of sequences, an shRNA sequence is interchangeable with an siRNA sequence and that where the disclosure refers to an siRNA, an shRNA sequence may be used since the shRNA will be cleaved into siRNA. For example, in some embodiments, an inhibitory nucleic acid can be a dsRNA (e.g., siRNA) including 16-30 nucleotides, e.g., 16, 17, 18, 19, 20, 21, 22, 23, 24, 25, 26, 27, 28, 29, or 30 nucleotides in each strand, where one strand is substantially identical, e.g., at least 80% (or more, e.g., 85%, 90%, 95%, or 100%) identical, e.g., having 3, 2, 1, or 0 mismatched nucleotide(s), to a target region in an mRNA, and the other strand is complementary to the first strand. In some embodiments, dsRNA molecules can be designed using methods known in the art, e.g., Dharmacon.com (see, siDESIGN CENTER) or "The siRNA User Guide," available on the Internet at mpibpc.gwdg.de/abteilungen/100/105/sirna.html website which is incorporated in its entirety herein by reference. Without being bound by any particular theory, the present disclosure contemplates that siRNA or shRNAs are more "endogenous" (e.g., no foreign proteins) in a way that may be more recognizable to a cell compared to other available techniques that will be known to those of skill in the art. Accordingly, in some embodiments, siRNA or shRNA have lower immunogenicity and/or have less risk of off-target DNA cleavage as compared to other techniques known to those of skill in the art.

Several methods for expressing siRNA duplexes within cells from a construct to achieve long-term target gene suppression in cells are known in the art, e.g., including constructs that use a mammalian Pol III promoter system (e.g., H1 or U6/snRNA promoter systems (Tuschl, Nature Biotechnol., 20:440-448, 2002, which is incorporated in its entirety herein by reference) to express functional double-stranded siRNAs; (Bagella et al., J. Cell. Physiol., 177:206-213, 1998; Lee et al., Nature Biotechnol., 20:500-505, 2002; Paul et al., Nature Biotechnol., 20:505-508, 2002; Yu et al., Proc. Natl. Acad. Sci. U.S.A., 99(9): 6047-6052, 2002; Sui et al., Proc. Natl. Acad. Sci. U.S.A. 99(6): 5515-5520, 2002, each of which is incorporated in its entirety herein by reference). Transcriptional termination by RNA Pol III occurs at runs of four consecutive T residues in a DNA template, and can be used to provide a mechanism to end the siRNA transcript at a specific sequence. An siRNA is complementary to a sequence of a target gene in 5'-3' and 3'-5' orientations, and the two strands of a given siRNA can be expressed in the same construct or in separate constructs. Hairpin siRNAs, driven by H1 or U6 snRNA promoter and expressed in cells, can inhibit target gene expression (Bagella et al., 1998, supra; Lee et al., 2002, supra; Paul et al., 2002, supra; Yu et al., 2002, supra; Sui et al., 2002, supra).

In some embodiments, siRNAs of the present disclosure are double stranded nucleic acid duplexes (of, e.g., 15, 16, 17, 18, 19, 20, 21, 22, 23, 24, 25, 26, or 27 base pairs) comprising annealed complementary single stranded nucleic acid molecules. In some embodiments, siRNAs are short dsRNAs comprising annealed complementary single strand RNAs. In some embodiments, siRNAs comprise an annealed RNA: DNA duplex, wherein the sense strand of a duplex is a DNA molecule and the antisense strand of the same duplex is a RNA molecule.

In some embodiments, duplexed siRNAs comprise a 2 or 3 nucleotide 3' overhang on each strand of a duplex. In some embodiments, siRNAs comprise 5'-phosphate and 3'-hydroxyl groups.

In some embodiments, a siRNA molecule of the present disclosure includes one or more natural nucleobase and/or one or more modified nucleobases derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being natural degradation products). Exemplary modified nucleobases are disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, each of which is incorporated in its entirety herein by reference.

Modified nucleobases also include expanded-size nucleobases in which one or more aryl rings, such as phenyl rings, have been added. Nucleic base replacements described in the Glen Research catalog (available on the world wide web at glenresearch.com); Krueger A T et al., Acc. Chem. Res., 2007, 40, 141-150; Kool, ET, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, each of which is incorporated in its entirety herein by reference, are contemplated as useful for siRNA molecules described herein. In some embodiments, modified nucleobases also encompass structures that are not considered nucleobases but are other moieties such as, but not limited to, corrin- or porphyrin-derived rings. Porphyrin-derived base replacements have been described in Morales-Rojas, H and Kool, ET, Org. Lett., 2002, 4, 4377-4380, which is incorporated in its entirety herein by reference.

In some embodiments, modified nucleobases are of any one of the following structures, optionally substituted:

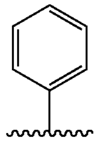
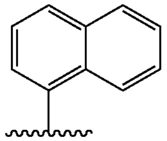
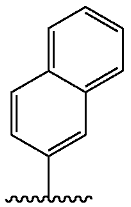
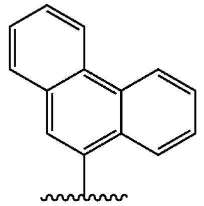
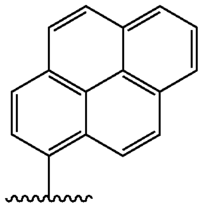
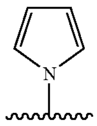
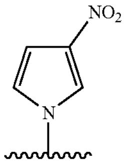
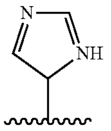

In some embodiments, a modified nucleobase is fluorescent. Exemplary such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

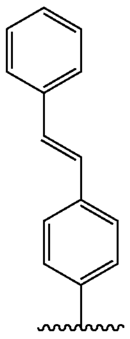
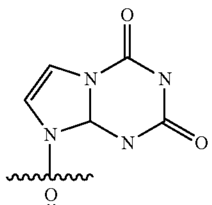
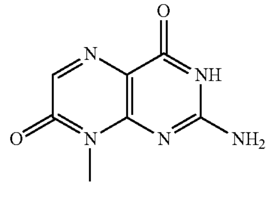

-continued

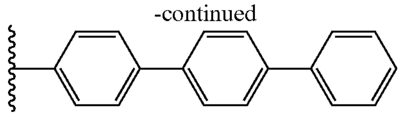

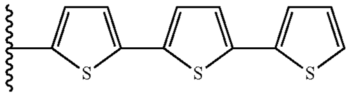

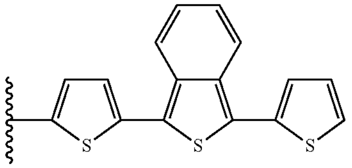

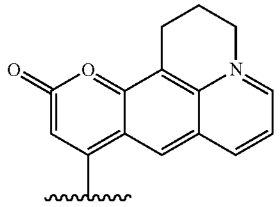

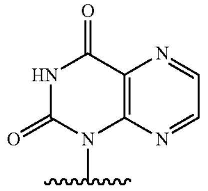

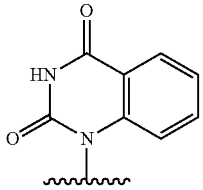

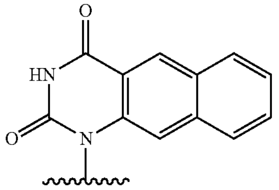

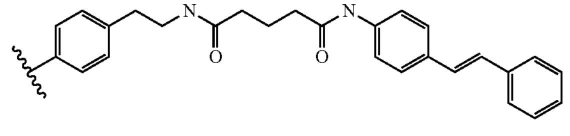

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One representative example of such a universal base is 3-nitropyrrole.

In some embodiments, siRNA molecules described herein include nucleosides that incorporate modified nucleobases and/or nucleobases covalently bound to modified sugars. Some examples of nucleosides that incorporate modified nucleobases include 4-acetylcytidine; 5-(carboxyhydroxylmethyl) uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl) carbamoyl) threonine; N-((9-beta,D-ribofuranosylpurine-6-yl)-N-methylcarbamoyl) threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or(S)-chirality at the 6'-position and include the analogs described in U.S. Pat. No. 7,399,845, which is incorporated in its entirety herein by reference. In some embodiments, nucleosides include 5'-modified bicyclic nucleoside analogs that have either (R) or (S)-chirality at the 5'-position and include the analogs described in U.S. Publ. No. 20070287831, which is incorporated in its entirety herein by reference. In some embodiments, a nucleobase or modified nucleobase is 5-bromouracil, 5-iodouracil, or 2,6-diaminopurine. In some embodiments, a nucleobase or modified nucleobase is modified by substitution with a fluorescent moiety.

Methods of preparing modified nucleobases are described in, e.g., U.S. Pat. Nos. 3,687,808; 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is incorporated in its entirety herein by reference.

In some embodiments, a siRNA molecule described herein includes one or more modified nucleotides wherein a phosphate group or linkage phosphorus in its nucleotides are linked to various positions of a sugar or modified sugar. As non-limiting examples, a phosphate group or linkage phosphorus can be linked to a 2', 3', 4' or 5' hydroxyl moiety of a sugar or modified sugar. Nucleotides that incorporate modified nucleobases as described herein are also contemplated in this context.

Other modified sugars can also be incorporated within a siRNA molecule. In some embodiments, a modified sugar contains one or more substituents at a 2' position including one of the following: —F; $CF_3$, —CN, —$N^3$, —NO, —$NO_2$, —OR', —SR', or —$N(R')_2$, wherein each R' is independently as defined above and described herein; —O—($C_1$-$C_{10}$ alkyl), —S—($C_1$-$C_{10}$ alkyl), —NH—($C_1$-$C_{10}$ alkyl), or —N($C_1$-$C_{10}$ alkyl)$_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)$_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl)$_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH ($C_1$-$C_{10}$ alkyl)$_2$, —NH-($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein the alkyl, alkylene, alkenyl and alkynyl may be substituted or unsubstituted. Examples of substituents include, and are not limited to, —$O(CH_2)_nOCH_3$, and —$O(CH_2)_nNH_2$, wherein n is from 1 to about 10, MOE, DMAOE, DMAEOE. Also contemplated herein are modified sugars described in WO 2001/088198; and Martin et al., Helv. Chim. Acta, 1995, 78, 486-504, each of which is incorporated in its entirety herein by reference. In some embodiments, a modified sugar comprises one or more groups selected from a substituted silyl group, an RNA cleaving group, a reporter group, a fluorescent label, an intercalator, a group for improving pharmacokinetic properties of a nucleic acid, a group for improving pharmacodynamic properties of a nucleic acid, or other substituents having similar properties. In some embodiments, modifications are made at one or more of a 2', 3', 4', 5', or 6' positions of a sugar or modified sugar, including a 3' position of a sugar on a 3'-terminal nucleotide or in a 5' position of a 5'-terminal nucleotide.

In some embodiments, a 2'-OH of a ribose is replaced with a substituent including one of the following: —H, —F; —$CF_3$, —CN, —$N^3$, —NO, —$NO_2$, —OR', —SR', or —$N(R')_2$, wherein each R' is independently as defined above and described herein; —O—($C_1$-$C_{10}$ alkyl), —S—($C_1$-$C_{10}$ alkyl), —NH—($C_1$-$C_{10}$ alkyl), or —N($C_1$-$C_{10}$ alkyl)$_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)$_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl)$_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH ($C_1$-$C_{10}$ alkyl)$_2$, —NH-($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein an alkyl, alkylene, alkenyl and alkynyl may be substituted or unsubstituted. In some embodiments, a 2'-OH is replaced with —H (deoxyribose). In some embodiments, a 2'-OH is replaced with —F. In some embodiments, a 2'-OH is replaced with —OR'. In some embodiments, a 2'-OH is replaced with —OMe. In some embodiments, a 2'-OH is replaced with —$OCH_2CH_2OMe$.

Modified sugars also include locked nucleic acids (LNAs). In some embodiments, a locked nucleic acid has the structure indicated below. A locked nucleic acid of the structure below is indicated, wherein Ba represents a nucleobase or modified nucleobase as described herein, and wherein $R^{2s}$ is —$OCH_2C4'$—

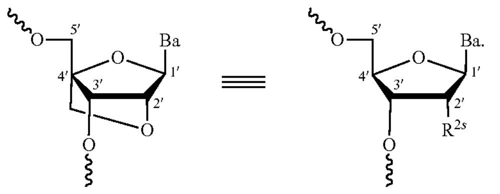

C2'$OCH_2C4'$ = LNA (Locked Nucleic Acid)

$R^{2s}$ = $OCH_2C4'$

In some embodiments, a modified sugar is an ENA such as those described in, e.g., Seth et al., J Am Chem Soc. 2010 Oct. 27; 132(42): 14942-14950, which is incorporated in its entirety herein by reference. In some embodiments, a modified sugar is any of those found in an XNA (xenonucleic acid), for instance, arabinose, anhydrohexitol, threose, 2'fluoroarabinose, or cyclohexene.

Modified sugars include sugar mimetics such as cyclobutyl or cyclopentyl moieties in place of the pentofuranosyl sugar (see, e.g., U.S. Pat. Nos. 4,981,957; 5,118,800; 5,319,080; and 5,359,044, each of which is incorporated in its entirety herein by reference). Some modified sugars that are contemplated include sugars in which an oxygen atom within a ribose ring is replaced by nitrogen, sulfur, selenium, or carbon. In some embodiments, a modified sugar is a modified ribose wherein an oxygen atom within a ribose ring is replaced with nitrogen, and wherein a nitrogen is optionally substituted with an alkyl group (e.g., methyl, ethyl, isopropyl, etc.).

Non-limiting examples of modified sugars include glycerol, which form glycerol nucleic acid (GNA) analogues. An exemplary GNA analogue is described in Zhang, R et al., J. Am. Chem. Soc., 2008, 130, 5846-5847, which is incorporated in its entirety herein by reference; see also Zhang L, et al., J. Am. Chem. Soc., 2005, 127, 4174-4175 and Tsai C H et al., PNAS, 2007, 14598-14603, each which is incorporated in its entirety herein by reference. Another example of a GNA derived analogue, flexible nucleic acid (FNA) based on mixed acetal aminal of formyl glycerol, is described in each of Joyce G F et al., PNAS, 1987, 84, 4398-4402 and Heuberger BD and Switzer C, J. Am. Chem. Soc., 2008, 130, 412-413, each of which is incorporated in its entirety herein by reference. Additional non-limiting examples of modified sugars include hexopyranosyl (6' to 4'), pentopyranosyl (4' to 2'), pentopyranosyl (4' to 3'), or tetrofuranosyl (3' to 2') sugars.

Modified sugars and sugar mimetics can be prepared by methods known in the art, including, but not limited to: A. Eschenmoser, Science (1999), 284:2118; M. Bohringer et al., Helv. Chim. Acta (1992), 75:1416-1477; M. Egli et al., J. Am. Chem. Soc. (2006), 128(33): 10847-56; A. Eschenmoser in Chemical Synthesis: Gnosis to Prognosis, C. Chatgilialoglu and V. Sniekus, Ed., (Kluwer Academic, Netherlands, 1996), p.293; K.-U. Schoning et al., Science (2000), 290:1347-1351; A. Eschenmoser et al., Helv. Chim. Acta (1992), 75:218; J. Hunziker et al., Helv. Chim. Acta (1993), 76:259; G. Otting et al., Helv. Chim. Acta (1993), 76:2701; K. Groebke et al., Helv. Chim. Acta (1998), 81:375; and A. Eschenmoser, Science (1999), 284:2118. Modifications to 2' modifications can be found in Verma, S. et al. Annu. Rev. Biochem. 1998, 67, 99-134 and all references therein, each of which is incorporated in its entirety herein by reference. Specific modifications to a ribose can be found in the following references: 2'-fluoro (Kawasaki et. al., J. Med. Chem., 1993, 36, 831-841), 2'-MOE (Martin, P. Helv. Chim. Acta 1996, 79, 1930-1938), “LNA” (Wengel, J. Acc. Chem. Res. 1999, 32, 301-310); PCT Publication No. WO2012/030683, each of which is incorporated in its entirety herein by reference.

In some embodiments, a siRNA described herein can be introduced to a target cell as an annealed duplex siRNA. In some embodiments, a siRNA described herein is introduced to a target cell as single stranded sense and antisense nucleic acid sequences that, once within a target cell, anneal to form a siRNA duplex. Alternatively, sense and antisense strands of an siRNA can be encoded by an expression construct (such as an expression construct described herein) that is introduced to a target cell. Upon expression within a target cell, transcribed sense and antisense strands can anneal to reconstitute an siRNA.

In some embodiments, an siRNA molecule as described herein can be synthesized by standard methods known in the art, e.g., by use of an automated synthesizer. Without being bound by any particular theory, RNAs produced by such methodologies tend to be highly pure and to anneal efficiently to form siRNA duplexes. In some embodiments, following chemical synthesis, single stranded RNA molecules can be deprotected, annealed to form siRNAs, and purified (e.g., by gel electrophoresis or HPLC). Alternatively, in some embodiments, standard procedures can be used for in vitro transcription of RNA from DNA templates, e.g., carrying one or more RNA polymerase promoter sequences (e.g., T7 or SP6 RNA polymerase promoter sequences). Protocols for preparation of siRNAs using T7 RNA polymerase are known in the art (see, e.g., Donze and Picard, Nucleic Acids Res. 2002; 30: e46; and Yu et al., Proc. Natl. Acad. Sci. USA 2002; 99:6047-6052, each of which is incorporated in its entirety herein by reference). In some embodiments, sense and antisense transcripts can be synthesized in two independent reactions and annealed later. In some embodiments, sense and antisense transcripts can be synthesized simultaneously in a single reaction.

In some embodiments, an siRNA molecule can also be formed within a cell by transcription of RNA from an expression construct introduced into a cell (see, e.g., Yu et al., Proc. Natl. Acad. Sci. USA 2002; 99:6047-6052, which is incorporated in its entirety herein by reference). For example, in some embodiments, an expression construct for in vivo production of siRNA molecules can include one or more siRNA encoding sequences operably linked to elements necessary for proper transcription of an siRNA encoding sequence(s), including, e.g., promoter elements and transcription termination signals. In some embodiments, preferred promoters for use in such expression constructs may include, e.g., a polymerase-III promoter, e.g., a polymerase-III HI-RNA promoter (see, e.g., Brummelkamp et al., Science 2002; 296:550-553, which is incorporated in its entirety herein by reference), a U6 polymerase-III promoter (see, e.g., Sui et al., Proc. Natl. Acad. Sci. USA 2002; Paul et al., Nature Biotechnol. 2002; 20:505-508; and Yu et al., Proc. Natl. Acad. Sci. USA 2002; 99:6047-6052, each of which is incorporated in its entirety herein by reference). In some embodiments, an siRNA expression construct can comprise one or more construct sequences that facilitate cloning of an expression construct. Standard constructs that can be used include, e.g., pSilencer 2.0-U6 construct (Ambion Inc., Austin, Tex.).

miRNA

The present disclosure provides technologies related to or comprising one or more inhibitory nucleic acid molecules such as, e.g., one or more nucleotide sequences that are, comprise, or encode, microRNAs. MicroRNAs (miRNAs) are a highly conserved class of small RNA molecules that are transcribed from DNA in genomes of plants and animals, but are not translated into protein. As is known to those in the art, animal cells express a range of noncoding RNAs of approximately 22 nucleotides termed micro RNA (miRNAs) and can regulate gene expression at a post transcriptional or translational level during animal development. miRNAs are excised from an approximately 70 nucleotide precursor RNA stem-loop. By substituting stem sequences of an miRNA precursor with miRNA sequence complementary to a target mRNA, a construct that expresses a novel miRNA can be used to produce siRNAs to initiate RNAi against specific mRNA targets in mammalian cells (Zeng, Mol. Cell, 9:1327-1333, 2002). In some embodiments, when expressed by DNA constructs containing polymerase III promoters, micro-RNA designed hairpins can silence gene expression (McManus, RNA 8:842-850, 2002).

In some embodiments, miRNAs can be synthesized and locally or systemically administered to a subject, e.g., for therapeutic purposes. In some embodiments, miRNAs can be designed and/or synthesized as mature molecules or precursors (e.g., pri- or pre-miRNAs). In some embodiments, a pre-miRNA includes a guide strand and a passenger strand that are the same length (e.g., about 15, 16, 17, 18, 19, 20, 21, 22, 23, 24, or 25 nucleotides). In some embodiments, a pre-miRNA includes a guide strand and a passenger strand that are different lengths (e.g., one strand is about 19 nucleotides, and the other is about 21 nucleotides). In some embodiments, an miRNA can target a coding region, a 5' untranslated region, and/or a 3' untranslated region, of endogenous mRNA. In some embodiments, an miRNA comprises a guide strand comprising a nucleotide sequence having sufficient sequence complementary with an endogenous mRNA of a subject to hybridize with and inhibit expression of endogenous mRNA.

Antisense Nucleic Acid

In some embodiments, an inhibitory nucleic acid molecule may be or comprise an antisense nucleic acid molecule, e.g., nucleic acid molecules whose nucleotide sequence is complementary to all or part of an mRNA encoding a protein of interest. In some embodiments, a non-coding regions ("5' and 3' untranslated regions") are 5' and 3' sequences that flank a coding region and are not translated into amino acids. Based upon sequences disclosed herein, one of skill in the art can easily choose and synthesize any of a number of appropriate antisense molecules to target a gene as described herein. For example, a "gene walk" comprising a series of oligonucleotides of 15-30 nucleotides spanning a length of a nucleic acid (e.g., an mRNA) can be prepared, followed by testing for inhibition of expression of a gene. Optionally, gaps of 5-10 nucleotides can be left between oligonucleotides to reduce numbers of oligonucleotides synthesized and tested.

In some embodiments, an antisense oligonucleotide can be, for example, about 5, 10, 15, 20, 25, 30, 35, 40, 45, or 50 nucleotides or more in length. One of skill in the art will recognize that an antisense oligonucleotide can be synthesized using various different chemistries.

Ribozymes

In some embodiments, an inhibitory nucleic acid molecule may be or comprise a ribozyme. As is known to those of skill in the art, ribozymes are catalytic RNA molecules with ribonuclease activity. In some embodiments, a ribozyme may be used as a controllable promoter. In some embodiments, ribozymes are capable of cleaving a single-stranded nucleic acid, such as an mRNA, to which they have a complementary region. Thus, in some embodiments, ribozymes (e.g., hammerhead ribozymes (described in Haselhoff and Gerlach, Nature, 334:585-591, 1988, which is incorporated in its entirety herein by reference)) can be used to catalytically cleave mRNA transcripts to thereby inhibit translation of a protein encoded by a given mRNA. Methods of designing and producing ribozymes are known in the art (see, e.g., Scanlon, 1999, Therapeutic Applications of Ribozymes, Humana Press, which is incorporated in its entirety herein by reference). In some embodiments, for example, a ribozyme having specificity for a transgene mRNA can be designed based upon nucleotide sequence of a transgene gene product cDNA (e.g., any exemplary cDNA sequences described herein). For example, a derivative of a Tetrahymena L-19 IVS RNA can be constructed in which nucleotide sequence of an active site is complementary to a nucleotide sequence to be cleaved in a transgene mRNA (Cech et al. U.S. Pat. No. 4,987,071; and Cech et al., U.S. Pat. No. 5,116,742, each of which is incorporated in its entirety herein by reference). Alternatively, an mRNA encoding a transgene protein can be used to select a catalytic RNA having a specific ribonuclease activity from a pool of RNA molecules (See, e.g., Bartel and Szostak, Science, 261:1411-1418, 1993, which is incorporated in its entirety herein by reference).

i. Pharmaceutical Compositions and Kits

Pharmaceutical compositions of the present disclosure may include constructs, as described herein. For example, in some embodiments, pharmaceutical compositions may comprise constructs and/or virions. In some such embodiments, such virions comprise one or more constructs, which comprise a nucleic acid, e.g., one or a plurality of constructs described herein. For example, a pharmaceutical composition of the present disclosure comprise as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose, or dextrans; mannitol; proteins; polypeptides or amino acids such as glycine; antioxidants; chelating agents such as EDTA or glutathione; adjuvants (e.g., aluminum hydroxide); and preservatives. In some embodiments, compositions of the present disclosure are formulated for intravenous administration.

In some embodiments, a composition includes a pharmaceutically acceptable carrier (e.g., phosphate buffered saline, saline, or bacteriostatic water). Upon formulation, solutions can be administered in a manner compatible with a dosage formulation and in such amount as is therapeutically effective. Formulations are easily administered in a variety of dosage forms such as injectable solutions, injectable gels, drug-release capsules, and the like.

Compositions provided herein can be, e.g., formulated to be compatible with their intended route of administration. A non-limiting example of an intended route of administration is local administration.

Also provided are kits including any compositions or constructs described herein. In some embodiments, a kit can include a solid composition (e.g., a lyophilized composition including at least one construct as described herein) and a liquid for solubilizing a lyophilized composition. In some embodiments, a kit can include one or more constructs described herein.

In some embodiments, a kit can include a pre-loaded syringe including any compositions described herein.

In some embodiments, a kit includes a vial comprising any of the compositions described herein (e.g., formulated as an aqueous composition, e.g., an aqueous pharmaceutical composition).

In some embodiments, a kit can include instructions for performing any methods described herein.

i. Cells

In some embodiments, the present disclosure provides a cell (e.g., an insect cell, e.g., a Sf9 cell, e.g., a mammalian cell, e.g., a human cell, e.g., a HEK293T cells, etc.) that comprises any nucleic acids, constructs (e.g., at least two different constructs described herein), compositions, etc., as described herein. As will be appreciated by one of skill in the art, nucleic acids and constructs described herein can be introduced into any cell (e.g., an insect cell, e.g., a Sf9 cell, etc.). Non-limiting examples of certain constructs and methods for introducing constructs into cells are described herein.

In some embodiments, the present disclosure provides a cell (e.g., a mammalian cell, e.g., a human cell, etc.) that comprises any nucleic acids, constructs (e.g., at least two different constructs described herein), compositions, etc., as described herein. As will be appreciated by one of skill in the art, nucleic acids and constructs described herein can be introduced into any cell (e.g., a mammalian cell, e.g., a human cell, etc.). Non-limiting examples of certain constructs and methods for introducing constructs into cells are described herein.

In some embodiments, a cell is a human cell, a mouse cell, a porcine cell, a rabbit cell, a dog cell, a rat cell, a sheep cell, a cat cell, a horse cell, a non-human primate cell, or an insect cell.

In some embodiments, a cell is a primary cell (e.g., a human primary cell). In some embodiments, a cell is a liver cell. In some embodiments, a cell is a primary hepatocyte cell (e.g., a Huh7 cell). In some embodiments, a cell is a neuron cell. In some embodiments, a cell is a kidney cell (e.g., a human renal proximal tubule (HRCE) cell, e.g., a bile duct cell, e.g., an outer medullary cell, e.g., a mixed medullary cell, e.g., renal cortical epithelial cells, e.g., renal epithelial cells). In some embodiments, a cell is an immune cell. In some embodiments, a cell is a human T cell (e.g., a CD4+ T cell, e.g., a Th2 cell). In some embodiments, a cell is a blood cell (e.g., a PBMC cell). In some embodiments, a cell is a skeletal muscle cell. In some embodiments, a cell is a differentiated skeletal muscle cell (e.g., a myotube cell). In some embodiments, a cell is a primary cardiomyocyte cell. In some embodiments, a cell is a bone marrow MSC cell. In some embodiments, a cell is a small intestine cell. In some embodiments, a cell is a muscle cell. In some embodiments, a cell is a heart cell. In some embodiments, a cell is a spleen cell. In some embodiments, a cell is a brain cell (e.g., a brain-striatum cell, e.g., a neuroblastoma cell (e.g., a SH-SY5Y cell), e.g., a CD105-positive endothelial cell, e.g., a brain cortex cell).

In some embodiments, a cell is a PymT tumor cell, a cervix cancer cell (e.g., a HeLa cell), a K562 cell, a Raji cell, a SKOV-3 cell, a breast cancer cell (e.g., a MCF-7 cell), a M07e cell, a human saphenous vascular endothelial cell (HSaVEC), a MT1-MMP cell, a primary hepatocyte cell (e.g., a Huh7 cell), an immune cell (e.g., a human T cell, e.g., a CD4+ T cell, e.g., a Th2 cell, e.g., a CAR T cell, e.g., a NK cell), a neuron cell (e.g., a LX-2 cell, e.g., a stellate cell, e.g., a primary neuron cell, e.g., a neuroblastoma cell (e.g., a SH-SY5Y cell)), a lung cell (e.g., a lung fibroblast cell), a myoblast cell, a myotube cell, a primary cardiomyocyte, a skeletal muscle cell (e.g., a differentiated skeletal muscle cell), a human vein endothelial cell, a T84 cell, a ileum cell (intestinal), a primary human airway epithelia cell), a kidney cell (e.g., a human renal proximal tubule (HRCE) cell, e.g., a bile duct cell, e.g., an outer medullary cell, e.g., a mixed medullary cell, e.g., renal cortical epithelial cells, e.g., renal epithelial cells), a bone marrow MSC cell, a blood cell (e.g., a PBMC cell), a small intestine cell, a muscle cell, a heart cell, a spleen cell, a liver cell, a brain cell (e.g., a brain-striatum cell, e.g., a CD105-positive endothelial cell, e.g., a brain cortex cell) or an ocular cell. In some embodiments, a cell is a testes cell. In some embodiments, a cell is an oocyte. In some embodiments, a cell is a medulla cell. In some embodiments, a cell is a striatum cell. In some embodiments, a cell is a spinal cord (or chord) cell. In some embodiments, a cell is a duodenum cell.

In some embodiments, a cell is in vitro. In some embodiments, a cell is in vivo or ex vivo. For example, in some embodiments, cell is present in a mammal. In some embodiments, a cell (e.g., a mammalian cell) is autologous cell obtained, e.g., from a subject (e.g., a mammal) and cultured ex vivo.

In some embodiments, cells provided by the present disclosure are transfected host cells. In some embodiments, transfection is used to refer to uptake of foreign DNA by a cell, and a cell has been "transfected" when exogenous DNA has been introduced inside a cell membrane. A number of transfection techniques are generally known in the art (see, e.g., Graham et al. (1973) Virology, 52:456; Sambrook et al. (1989) Molecular Cloning, a laboratory manual, Cold Spring Harbor Laboratories, New York, Davis et al. (1986) Basic Methods in Molecular Biology, Elsevier; and Chu et al. (1981) Gene 13:197, each of which is incorporated in its entirety herein by reference). Such techniques can be used to introduce one or more exogenous nucleic acids, such as a nucleotide integration construct and other nucleic acid molecules, into suitable host cells.

3. Methods

Among other things, the present disclosure provides methods. In some embodiments, a method comprises producing a virion described herein. In some embodiments, a method comprises purifying a virion described herein. In some embodiments, a method comprises characterizing a virion described herein. In some embodiments, a method comprises manufacturing a virion described herein.

In some embodiments, a method comprises introducing a composition as described herein into a cell of a subject. For example, provided herein are methods that in some embodiments include administering to a cell of a subject (e.g., an animal, e.g., a mammal, e.g., a primate, e.g., a human) a therapeutically effective amount of any composition described herein.

a. Methods of Making

Among other things, the present disclosure provides for methods of making constructs described herein. For example, in some embodiments, constructs are prepared using a standard dual transfection system (e.g., two plasmids/constructs, comprising (i) rep/cap genes, (ii) helper genes, and (iii) payloads (e.g., a transgene) respectively) followed by standard isolation and purification methods (e.g., CsCl gradient). For example, in some embodiments, constructs are prepared using a standard triple transfection system (e.g., three plasmids/constructs, comprising (i) rep/cap genes, (ii) helper genes, and (iii) payloads (e.g., a transgene) respectively, e.g., four plasmids/constructs, etc.) followed by standard isolation and purification methods (e.g., CsCl gradient). In some such embodiments, such preparations are formulated for delivery into a subject.

Moreover, the present disclosure provides, among other things, a method of making protoparvovirus-related compositions, preparations, constructs, virions, populations of virions, etc. In some embodiments, such methods include use of host cells.

In some embodiments, a host cell is a mammalian cell. In some embodiments, a mammalian cell is a human cell. In some embodiments, a mammalian cell is a HEK293T cell. In some embodiments, a mammalian cell is a K562 cell. In some embodiments, a mammalian cell is a HRCE cell. For example, in some embodiments, such methods include use of an exemplary CPV construct described herein (e.g., SEQ ID NO: 130, e.g., SEQ ID NO: 142) for production of compositions, preparations, constructs, virions, populations of virions, etc. in mammalian cells (e.g. HEK293T cells). For example, in some embodiments, such methods include use of an exemplary CuV construct described herein (e.g. SEQ ID NO: 133, e.g., SEQ ID NO: 143, e.g., SEQ ID NO: 148) for production of compositions, preparations, constructs, virions, populations of virions, etc. in mammalian cells (e.g., HEK293T cells). For example, in some embodiments, such methods include use of an exemplary CuV construct described herein (e.g., SEQ ID NO: 135) for production of compositions, preparations, constructs, virions, populations of virions, etc. in mammalian cells (e.g. in HEK cells). In some embodiments, a host cell is an insect cell. In some embodiments, an insect cell is an Sf9 cell. The term includes progeny of an original cell that has been transfected. Thus, a "host cell" as used herein may refer to a cell that has been transfected with an exogenous DNA sequence. It is understood that progeny of a single parental cell may not necessarily be completely identical in morphology or in genomic or total DNA complement as the original parent, due to natural, accidental, or deliberate mutation.

In some embodiments, the present disclosure provides a system in which a transgene flanked by ITRs and rep/cap genes are introduced into insect host cells by infection with insect virus (e.g., baculovirus)-based constructs. Such production systems are known in the art.

In some embodiments, provided herein are methods of producing a virion or a population of virions described herein. A number of constructs described herein may be consolidated by incorporating the structural and/or nonstructural genes into one or more constructs. In some embodiments, certain protoparvovirus genomic sequence(s) may also be integrated into a baculovirus genome to contain structural (e.g., encoding VP polypeptides(s)) and/or nonstructural genes. In some embodiments, certain protoparvovirus genomic sequences may also be integrated into a mammalian genome to contain structural (e.g., encoding VP polypeptides(s)) and/or nonstructural genes.

In some embodiments, provided herein are methods of producing a virion having a protoparvovirus variant VP1 capsid polypeptide, wherein the protoparvovirus is of a species selected from Carnivore protoparvovirus, Carnivore protoparvovirus 1, Chiropteran protoparvovirus 1, Eulipotyphla protoparvovirus 1, Primate protoparvovirus 1, Primate protoparvovirus 2, Primate protoparvovirus 3, Primate protoparvovirus 4, Rodent protoparvovirus 1, Rodent protoparvovirus 2, Rodent protoparvovirus 3, Ungulate protoparvovirus 1, and Ungulate protoparvovirus 2. In some embodiments, protoparvovirus is selected from canine parvovirus, feline panleukopenia virus, human bufavirus 1, human bufavirus 2, human bufavirus 3, human tusavirus, human cutavirus, Wuharv parvovirus, porcine parvovirus, minute virus of mice, or megabat bufavirus, or genetic variant thereof.

In some embodiments, an insect cell is derived from a species of lepidoptera, e.g., *Spodoptera frugiperda, Spodoptera littoralis, Spodoptera exigua*, or *Trichoplusiani*. In some embodiments, an insect cell is Sf9. In some embodiments, a construct is a baculoviral construct, a viral construct, or a plasmid. In some embodiments, the at least one construct is a baculoviral construct. In some embodiments, subclones of lepidopteran cell lines that demonstrate enhanced virion yield on a per cell or per volume basis are used. In some embodiments, modified lepidopteran cell lines with an integrated copy of NS1, Rep, VP, and/or construct genome, singly or in combinations, are used. The insect cell line, in some embodiments, is "cured" of endogenous or contaminating or adventitious insect viruses such as the *Spodoptera* rhabdovirus.

In some embodiments, a virion may also be produced using a mammalian cell, e.g., Grieger et al (2016) Mol Ther 24:287-297, the contents of which are incorporated by reference herein in its entirety).

b. Methods of Treatment

Among other things, in some embodiments, technologies of the present disclosure are used to treat a disease or disorder. In some embodiments, provided herein are methods of preventing or treating a disease using a virion or pharmaceutical compositions described herein. In some embodiments, a virion disclosed herein provides to a subject a transgene (e.g., those encoding a therapeutic protein or a fragment thereof) transiently, e.g., a nucleic acid transduced by a virion is eventually lost after a certain period of expression. In preferred embodiments, a nucleic acid transduced by a virion integrates stably inside cells.

In some embodiments, provided herein are methods of preventing or treating a disease, comprising administering to a subject in need thereof an effective amount of a virion or pharmaceutical composition of the present disclosure. In some embodiments, a nucleic acid encodes a polypeptide. In some embodiments, a nucleic acid decreases or eliminates expression of an endogenous gene. In some embodiments, provided herein are methods of preventing or treating a disease, comprising: (a) administering to a subject in need thereof an effective amount of a virion described herein comprising a nucleic acid that increases or restores expression of a gene whose endogenous expression is aberrantly lower than expression in a healthy subject; or (b) administering to a subject in need thereof an effective amount of a virion described herein comprising a nucleic acid that decreases or eliminates expression of a gene whose endogenous expression is aberrantly higher than expression in a healthy subject. In some embodiments, a nucleic acid comprises a transgene.

In some embodiments, provided herein are methods of preventing or treating a disease, comprising: (a) obtaining a plurality of cells from a subject with disease, (b) transducing cells with a virion described herein, optionally further selecting or screening for transduced cells, and (c) administering an effective amount of transduced cells to a subject. In some embodiments, cells are autologous to a subject. In some embodiments, cells are allogeneic to a subject. There are advantages of preparing transduced cells in vitro or ex vivo. First, existence and location of a transgene in a target cell genome can be verified before administering them to a patient, thereby avoiding interfering with cell functions or off target effects. This improves safety, even without the use of GSH. Second, transduced cells can be administered to a subject in need thereof without a virion. This can eliminate any concern for triggering immune response or inducing neutralizing antibodies that inactivate virion. Accordingly, transduced cells can be safely redosed or the dose can be titrated without any adverse effect.

Among other things, in some embodiments, provided herein are methods of preventing or treating a disease comprising standard of care measures used for gene therapies described in the art. In some embodiments, a virion or population of virions, a pharmaceutical composition, or transduced cells described herein can induce an immune response in a subject. In some embodiments, provided herein are methods of preventing or treating a disease, comprising, among other things, co-administering to a subject (1) an immune suppressant and/or a prophylactic and (2) a virion or population of virions, a pharmaceutical composition, or transduced cells described herein to mitigate an immune response. In some embodiments, a disease is an exemplary disease described herein. In some embodiments, a disease is not an ocular disease. In some embodiments, an immune suppressant and/or a prophylactic is administered to a subject prior to administering to a subject a virion or population of virions, a pharmaceutical composition, or transduced cells. In some embodiments, an immune suppressant and/or a prophylactic is administered to a subject after administering to a subject a virion or population of virions, a pharmaceutical composition, or transduced cells. In some embodiments, an immune suppressant and/or a prophylactic is administered to a subject at the same time as administering to a subject a virion or population of virions, a pharmaceutical composition, or transduced cells.

In some embodiments of any methods described herein, such methods may result in improvement in a disease described herein (e.g., any metrics for determining improvement in a disease described herein) in a subject in need thereof for at least 10 days, at least 15 days, at least 20 days, at least 25 days, at least 30 days, at least 35 days, at least 40 days, at least 45 days, at least 50 days, at least 55 days, at least 60 days, at least 65 days, at least 70 days, at least 75 days, at least 80 days, at least 85 days, at least 100 days, at least 105 days, at least 110 days, at least 115 days, at least 120 days, at least 5 months, at least 6 months, at least 7 months, at least 8 months, at least 9 months, at least 10 months, at least 11 months, or at least 12 months.

In some embodiments, a virion, pharmaceutical composition, or transduced cells of the present disclosure are administered via intravascular, intracerebral, parenteral, intraperitoneal, intravenous, epidural, intraspinal, intrasternal, intra-articular, intra-synovial, intrathecal, intra-arterial, intracardiac, intramuscular, intranasal, intrapulmonary, skin graft, or oral administration.

In some embodiments, provided herein are methods of preventing or treating a hemoglobinopathy, comprising: (a) administering to a subject in need thereof an effective amount of a virion described herein, comprising a nucleic acid that encodes a hemoglobin subunit, or (b) obtaining erythroid-lineage cells or bone marrow cells from a subject in need thereof, transducing the cells with a virion described herein, comprising a nucleic acid that encodes a hemoglobin subunit, optionally further selecting or screening for transduced cells; and administering an effective amount of cells to a subject. In some embodiments, the hemoglobinopathy is beta-thalassemia or sickle cell disease.

In some embodiments, provided herein are methods of preventing or treating a disease using a virion or pharmaceutical composition comprising a protoparvovirus variant VP1 capsid polypeptide.

As described herein, protoparvovirus transduces cells via its interaction with transferrin receptors (TfR) that are expressed on the target cells. It is an insight of the present disclosure that a mouse transferrin receptor is similar to a human transferrin receptor. In some embodiments, a target cell is a mouse cell comprising a human transferrin receptor. In some embodiments, preparations, constructs, virions, or population of virions described herein are administered to a mouse comprising a human transferrin receptor.

TfR or CD71 is expressed in brain microvascular endothelial cells (BMVECs) the major element of the blood-brain barrier (BBB) (Navone, Marfia et al. 2013 the entire contents of which are hereby incorporated by reference herein). The blood-brain barrier (BBB) constitutes a primary limitation for passage of substances, both soluble and cellular, from the blood into the brain. CD71 has become an alternative to drive receptor specific transcystosis and deliver macromolecules such as antibodies to a brain parenchyma. Thus, protoparvovirus (e.g., CPV) can exploit the use of CD71 to translocate to a brain via systemic administration and transduce brain cells to prevent or treat different neurodegenerative disorders and neuromuscular disorders including but not limited to spinal muscular atrophy type 1, Huntington's disease, Canavan's disease, and lysosomal storage diseases. TfR or CD71 is also highly expressed in erythroid progenitor cells at early stage during differentiation and B lymphoblast cells. CD71 expression transiently overlap with CD34 expression in progenitor cells, before differentiation to lymphoid or erythroid lineages. Thus, protoparvovirus (e.g., CPV) can transduce stem cells and be used for T cells, B cells or NK cells derived therapies after differentiation from stem cells. Some of these uses are in cancer therapy, antimicrobial or autoimmunity related therapies. After HSC differentiation to myeloid progenitors lineage, CD71/TfR is highly expressed in basophilic Endemic Burkitt lymphoma (EBL), polychromatic erythroblast and orthochromatic erythroblasts during erythropoiesis, before the final step to produce non-nucleated erythrocytes, therefore protoparvovirus (e.g., CPV) compositions can be used for treatment or prevention of non-malignant hemoglobinopathies such as sickle cell disease by expressing anti-sickling versions of hemoglobin genes. In some embodiments, provided herein are methods of preventing or treating a disease using a virion comprising a variant VP1 capsid polypeptide or a variant thereof of a bufavirus, cutavirus, or tusavirus. Bufavirus, cutavirus, tusavirus, or a virion comprising a variant capsid polypeptide of any one of said viruses, has broad applications for gastrointestinal disorders and other target tissues. For instance, cutavirus has been isolated from skin samples in patients with cutaneous T cells lymphomas and melanomas, showing a tropism for T and B cells. Such tropism makes cutavirus attractive for gene transfer applications in lymphoid progenitor cells and subsequent applications (i) in differentiated T cells such as CAR-T and related cancer therapies, or (ii) in differentiated B cells and their applications to express therapeutic human antibodies against invading pathogens, tumor cells (e.g., tumor antigens or neoantigens), or chronic autoimmune disease.

In some embodiments, a virion comprises a variant VP1 capsid polypeptide(s) of a cutavirus. In some embodiments, a virion or pharmaceutical composition targets a T cell, B cell, and/or a lymphoid progenitor cell. In some embodiments, a virion, pharmaceutical composition, or transduced cells prevent or treat cancer.

In some embodiments, a virion, a population of virions, a composition, or a pharmaceutical composition comprises a transgene coding sequence encoding a protein or a fragment thereof selected from a hemoglobin gene (HBA1, HBA2, HBB, HBG1, HBG2, HBD, HBE1, and/or HBZ), a gene encoding an alpha-hemoglobin stabilizing protein (AHSP), coagulation factor VIII, coagulation factor IX, von Willebrand factor, dystrophin or truncated dystrophin, micro-dystrophin, utrophin or truncated utrophin, micro-utrophin, usherin (USH2A), CEP290, glial cell line-derived neurotrophic factor (GDNF), neuturin (NTN), HTT, neuronal apoptosis inhibitory protein (NAIP), INS, F8 or a fragment thereof (e.g., fragment encoding B-domain deleted polypeptide (e.g., VIII SQ, p-VIII)), cystic fibrosis transmembrane conductance regulator (CFTR), a gene associated with Alport syndrome (e.g., Col4a3, Col4a4, Col4a5), a gene associated with Fabry disease (e.g., GLA), a gene associated with autosomal dominant polycystic kidney disease (PKD) (e.g., PKD, PKD1, PKD2), a gene associated with congenital nephrotic syndrome (e.g., NPHS1 (Nephrin), NPHS2 (Podocin), a gene associated with hypertrophic cardiomyopathy (e.g., MYBPC3, JPH2, ALPK3), a gene associated with dilated cardiomyopathy (e.g., RBM20), or a gene associated with dilated cardiomyopathy (e.g., ALPK3, LMNA, BAG3).

In some embodiments, a virion, population of virions, preparation, composition, or pharmaceutical composition transduces (a) a CD34+ stem cell, optionally transduces ex vivo; (b) a mesenchymal stem cell, optionally transduces ex vivo; (c) a liver cell, (d) a small intestinal cell, and/or (e) a lung cell.

In some embodiments, a virion, population of virions, preparation, composition, or pharmaceutical composition transduces a mammalian cell. In some embodiments, a virion, population of virions, preparation, composition, or pharmaceutical composition transduces a human cell. In some embodiments, a virion, population of virions, preparation, composition, or pharmaceutical composition transduces a human kidney cell. In some embodiments, a virion, population of virions, preparation, composition, or pharmaceutical composition transduces a myeloid cell. In some embodiments, a virion, a population of virions, a preparation, a composition, or a pharmaceutical composition transduces a cardiac cell. In some embodiments, a virion, a population of virions, a preparation, a composition, or a pharmaceutical composition transduces a brain cell.

In some embodiments, a virion, population of virions, preparation, composition, or pharmaceutical composition comprises a nucleic encoding (a) CFTR or a fragment thereof, (b) a non-coding RNA (e.g., piRNA, miRNA, shRNA, siRNA, antisense RNA) that targets an endogenous mutant form of CFTR, (c) a CRISPR/Cas system that targets an endogenous mutant form of CFTR; and/or (d) any combination of any one of a nucleic acids listed in (a) to (c). In some embodiments, a virion or pharmaceutical composition is delivered to lung via an intranasal or intrapulmonary administration. In some embodiments, a virion or pharmaceutical composition (a) increases expression of CFTR or fragment thereof; and/or (b) decreases expression of an endogenous mutant form of CFTR in a transduced cell. In some embodiments, a virion or pharmaceutical composition prevents or treats cystic fibrosis.

In some embodiments, a virion, a population of virions, a preparation, a construct, composition, or a pharmaceutical composition comprises a nucleic encoding (a) Col4a3 or a fragment thereof, (b) a non-coding RNA (e.g., piRNA, miRNA, shRNA, siRNA, antisense RNA) that targets an endogenous mutant form of Col4a3, (c) a CRISPR/Cas system that targets an endogenous mutant form of Col4a3; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of Col4a3 or fragment thereof; and/or (b) decreases expression of an endogenous mutant form of Col4a3 in a transduced cell. In some embodiments, a virion or pharmaceutical composition prevents or treats Alport syndrome.

In some embodiments, a virion, a population of virions, a preparation, a construct, composition, or a pharmaceutical composition comprises a nucleic encoding (a) Col4a4 or a fragment thereof, (b) a non-coding RNA (e.g., piRNA, miRNA, shRNA, siRNA, antisense RNA) that targets an endogenous mutant form of Col4a4, (c) a CRISPR/Cas system that targets an endogenous mutant form of Col4a4; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of Col4a4 or fragment thereof; and/or (b) decreases expression of an endogenous mutant form of Col4a4 in a transduced cell. In some embodiments, a virion or pharmaceutical composition prevents or treats Alport syndrome.

In some embodiments, a virion, a population of virions, a preparation, a construct, composition, or a pharmaceutical composition comprises a nucleic encoding (a) Col4a5 or a fragment thereof, (b) a non-coding RNA (e.g., piRNA, miRNA, shRNA, siRNA, antisense RNA) that targets an endogenous mutant form of Col4a5, (c) a CRISPR/Cas system that targets an endogenous mutant form of Col4a5; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of Col4a5 or fragment thereof; and/or (b) decreases expression of an endogenous mutant form of Col4a5 in a transduced cell. In some embodiments, a virion or pharmaceutical composition prevents or treats Alport syndrome.

In some embodiments, a virion, a population of virions, a preparation, a construct, composition, or a pharmaceutical composition comprises a nucleic encoding (a) GLA or a fragment thereof, (b) a non-coding RNA (e.g., piRNA, miRNA, shRNA, siRNA, antisense RNA) that targets an endogenous mutant form of GLA, (c) a CRISPR/Cas system that targets an endogenous mutant form of GLA; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of GLA or fragment thereof; and/or (b) decreases expression of an endogenous mutant form of GLA in a transduced cell. In some embodiments, a virion or pharmaceutical composition prevents or treats Fabry disease.

In some embodiments, a virion, a population of virions, a preparation, a construct, composition, or a pharmaceutical composition comprises a nucleic encoding (a) PKD1 or a fragment thereof, (b) a non-coding RNA (e.g., piRNA, miRNA, shRNA, siRNA, antisense RNA) that targets an endogenous mutant form of PKD1, (c) a CRISPR/Cas system that targets an endogenous mutant form of PKD1; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of PKD1 or fragment thereof; and/or (b) decreases expression of an endogenous mutant form of PKD1 in a transduced cell. In some embodiments, a virion or pharmaceutical composition prevents or treats autosomal dominant polycystic kidney disease (PKD).

In some embodiments, a virion, a population of virions, a preparation, a construct, composition, or a pharmaceutical composition comprises a nucleic encoding (a) PKD2 or a fragment thereof, (b) a non-coding RNA (e.g., piRNA, miRNA, shRNA, siRNA, antisense RNA) that targets an endogenous mutant form of PKD2, (c) a CRISPR/Cas system that targets an endogenous mutant form of PKD2; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of PKD2 or fragment thereof; and/or (b) decreases expression of an endogenous mutant form of PKD2 in a transduced cell. In some embodiments, a virion or pharmaceutical composition prevents or treats autosomal dominant polycystic kidney disease (PKD).

In some embodiments, a virion, a population of virions, a preparation, a construct, composition, or a pharmaceutical composition comprises a nucleic encoding (a) NPHS1 (nephrin) or a fragment thereof, (b) a non-coding RNA (e.g., piRNA, miRNA, shRNA, siRNA, antisense RNA) that targets an endogenous mutant form of NPHS1, (c) a CRISPR/Cas system that targets an endogenous mutant form of NPHS1; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of NPHS1 or fragment thereof; and/or (b) decreases expression of an endogenous mutant form of NPHS1 in a transduced cell. In some embodiments, a virion or pharmaceutical composition prevents or treats congenital nephrotic syndrome.

In some embodiments, a virion, a population of virions, a preparation, a construct, composition, or a pharmaceutical composition comprises a nucleic encoding (a) NPHS2 (podocin) or a fragment thereof, (b) a non-coding RNA (e.g., piRNA, miRNA, shRNA, siRNA, antisense RNA) that targets an endogenous mutant form of NPHS2, (c) a CRISPR/Cas system that targets an endogenous mutant form of NPHS2; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of NPHS2 or fragment thereof; and/or (b) decreases expression of an endogenous mutant form of NPHS2 in a transduced cell. In some embodiments, a virion or pharmaceutical composition prevents or treats congenital nephrotic syndrome.

In some embodiments, a virion, a population of virions, a preparation, a construct, composition, or a pharmaceutical composition comprises a nucleic encoding (a) MYBPC3 or a fragment thereof, (b) a non-coding RNA (e.g., piRNA, miRNA, shRNA, siRNA, antisense RNA) that targets an endogenous mutant form of MYBPC3, (c) a CRISPR/Cas system that targets an endogenous mutant form of MYBPC3; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of MYBPC3 or fragment thereof; and/or (b) decreases expression of an endogenous mutant form of MYBPC3 in a transduced cell. In some embodiments, a virion or pharmaceutical composition prevents or treats hypertrophic cardiomyopathy.

In some embodiments, a virion, a population of virions, a preparation, a construct, composition, or a pharmaceutical composition comprises a nucleic encoding (a) JPH2 or a fragment thereof, (b) a non-coding RNA (e.g., piRNA, miRNA, shRNA, siRNA, antisense RNA) that targets an endogenous mutant form of JPH2, (c) a CRISPR/Cas system that targets an endogenous mutant form of JPH2; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of JPH2 or fragment thereof; and/or (b) decreases expression of an endogenous mutant form of JPH2 in a transduced cell. In some embodiments, a virion or pharmaceutical composition prevents or treats hypertrophic cardiomyopathy.

In some embodiments, a virion, a population of virions, a preparation, a construct, composition, or a pharmaceutical composition comprises a nucleic encoding (a) ALPK3 or a fragment thereof, (b) a non-coding RNA (e.g., piRNA, miRNA, shRNA, siRNA, antisense RNA) that targets an endogenous mutant form of ALPK3, (c) a CRISPR/Cas system that targets an endogenous mutant form of ALPK3; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of ALPK3 or fragment thereof; and/or (b) decreases expression of an endogenous mutant form of ALPK3 in a transduced cell. In some embodiments, a virion or pharmaceutical composition prevents or treats hypertrophic cardiomyopathy.

In some embodiments, a virion, a population of virions, a preparation, a construct, composition, or a pharmaceutical composition comprises a nucleic encoding (a) ALPK3 or a fragment thereof, (b) a non-coding RNA (e.g., piRNA, miRNA, shRNA, siRNA, antisense RNA) that targets an endogenous mutant form of ALPK3, (c) a CRISPR/Cas system that targets an endogenous mutant form of ALPK3; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of ALPK3 or fragment thereof; and/or (b) decreases expression of an endogenous mutant form of ALPK3 in a transduced cell. In some embodiments, a virion or pharmaceutical composition prevents or treats dilated cardiomyopathy.

In some embodiments, a virion, a population of virions, a preparation, a construct, composition, or a pharmaceutical composition comprises a nucleic encoding (a) RBM20 or a fragment thereof, (b) a non-coding RNA (e.g., piRNA, miRNA, shRNA, siRNA, antisense RNA) that targets an endogenous mutant form of RBM20, (c) a CRISPR/Cas system that targets an endogenous mutant form of RBM20; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of RBM20 or fragment thereof; and/or (b) decreases expression of an endogenous mutant form of RBM20 in a transduced cell. In some embodiments, a virion or pharmaceutical composition prevents or treats dilated cardiomyopathy.

In some embodiments, a virion, a population of virions, a preparation, a construct, composition, or a pharmaceutical composition comprises a nucleic encoding (a) PKP2 or a fragment thereof, (b) a non-coding RNA (e.g., piRNA, miRNA, shRNA, siRNA, antisense RNA) that targets an endogenous mutant form of PKP2, (c) a CRISPR/Cas system that targets an endogenous mutant form of PKP2; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of PKP2 or fragment thereof; and/or (b) decreases expression of an endogenous mutant form of PKP2 in a transduced cell. In some embodiments, a virion or pharmaceutical composition prevents or treats dilated cardiomyopathy.

In some embodiments, a virion, a population of virions, a preparation, a construct, composition, or a pharmaceutical composition comprises a nucleic encoding (a) LMNA or a fragment thereof, (b) a non-coding RNA (e.g., piRNA, miRNA, shRNA, siRNA, antisense RNA) that targets an endogenous mutant form of LMNA, (c) a CRISPR/Cas system that targets an endogenous mutant form of LMNA; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of LMNA or fragment thereof; and/or (b) decreases expression of an endogenous mutant form of LMNA in a transduced cell. In some embodiments, a virion or pharmaceutical composition prevents or treats dilated cardiomyopathy.

In some embodiments, a virion, a population of virions, a preparation, a construct, composition, or a pharmaceutical composition comprises a nucleic encoding (a) BAG3 or a fragment thereof, (b) a non-coding RNA (e.g., piRNA, miRNA, shRNA, siRNA, antisense RNA) that targets an endogenous mutant form of BAG3, (c) a CRISPR/Cas system that targets an endogenous mutant form of BAG3; and/or (d) any combination of any one of a nucleic acids listed in (a) to (c). In some embodiments, a virion or pharmaceutical composition is delivered to kidney via systemic administration. In some embodiments, a virion, composition, or pharmaceutical composition (a) increases expression of BAG3 or fragment thereof; and/or (b) decreases expression of an endogenous mutant form of BAG3 in a transduced cell. In some embodiments, a virion or pharmaceutical composition prevents or treats dilated cardiomyopathy.

In some embodiments, methods of preventing or treating a disease further include re-administering an additional amount of a virion, population of virions, preparation, composition, pharmaceutical composition, or transduced cells. In some embodiments, the re-administering an additional amount is performed after an attenuation in a treatment subsequent to administering an initial effective amount of a virion, pharmaceutical composition, or transduced cells. In some embodiments, an additional amount is the same as an initial effective amount. In some embodiments, an additional amount is more than an initial effective amount. In some embodiments, an additional amount is less than an initial effective amount. In certain embodiments, an additional amount is increased or decreased based on expression of an endogenous gene and/or a nucleic acid of a virion. An endogenous gene includes a biomarker gene whose expression is, e.g., indicative of or relevant to diagnosis and/or prognosis of a disease.

In some embodiments, methods of preventing or treating a disease further comprise administering to a subject or contacting cells with an agent that modulates expression of a nucleic acid. In some embodiments, an agent is selected from a small molecule, a metabolite, an oligonucleotide, a riboswitch, a peptide, a peptidomimetic, a hormone, a hormone analog, and light. In some embodiments, an agent is selected from tetracycline, cumate, tamoxifen, estrogen, and an antisense oligonucleotide (ASO). In some embodiments, methods further comprise re-administering an agent one or more times at intervals. In some embodiments, re-administration of an agent results in pulsatile expression of a nucleic acid. In some embodiments, time between the intervals and/or amount of an agent is increased or decreased based on serum concentration and/or half-life of a protein expressed from a nucleic acid.

In some embodiments, further provided herein are methods of modulating (i) gene expression, or (ii) function and/or structure of a protein in a cell, the method comprising transducing a cell with a virion or pharmaceutical composition described herein comprising a nucleic acid that modulates gene expression, or function and/or structure of a protein in a cell. In some embodiments, such nucleic acid comprises a sequence encoding CRISPRi or CRISPRa agents. In some embodiments, gene expression, or function and/or structure of a protein is increased or restored. In some embodiments, gene expression, or function and/or structure of a protein is decreased or eliminated.

c. Methods of Delivering a Transgene to a Genomic Safe Harbor (GSH)

Among other things, in some embodiments, the present disclosure provides for a method of delivering a transgene to a genomic safe harbor (GSH).

Genomic safe harbors (GSH) are intragenic, intergenic, or extragenic regions of the human and model species genomes that are able to accommodate the predictable expression of newly integrated DNA without significant adverse effects on the host cell or organism. GSHs may comprise intronic or exonic gene sequences as well as intergenic or extragenic sequences. While not being limited to theory, a useful safe harbor must permit sufficient transgene expression to yield desired levels of the transgene-encoded protein or non-coding RNA. A GSH also should not predispose cells to malignant transformation, nor interfere with progenitor cell differentiation, nor significantly alter normal cellular functions. What distinguishes a GSH from a fortuitous good integration event is the predictability of outcome, which is based on prior knowledge and validation of a GSH.

The larger genome size of a virion described herein allows delivery of a therapeutic transgene(s) together with GSH sequences, which is otherwise not possible with virions having a limited genome size, e.g., AAV. Accordingly, virions of the present disclosure not only facilitates delivery of a larger transgene compared with e.g., AAV, but also facilitates a safe delivery of a transgene by allowing codelivery of a GSH sequences that ensures predictable expression of a transgene without adverse effects on host cells. Exemplary GSHs that have been targeted for transgene addition include (i) the adeno-associated virus site 1 (AAVS1), a naturally occurring, non-germline, site of integration of AAV virus DNA on chromosome 19; (ii) chemokine (C-C motif) receptor 5 (CCR5) gene, a chemokine receptor gene known as an HIV-1 coreceptor; (iii) human ortholog of the mouse Rosa26 locus, a locus extensively validated in the murine setting for the insertion of ubiquitously expressed transgenes; (iii) a T cell receptor locus (TCR), such as TCR alpha or TCR beta, and (iv) albumin in murine cells (see, e.g., U.S. Pat. Nos. 7,951,925; 8,771,985; 8,110,379; and 7,951,925; U.S. Patent Publication Nos. 2010/0218264; 2011/0265198; 2013/0137104; 2013/0122591; 2013/0177983; 2013/0177960; 2015/0056705 and 2015/0159172; all of which are incorporated by reference). Additional GSHs include Kif6, Pax5, collagen, HTRP, HI 1 (a thymidine kinase encoding nucleic acid at HI 1 locus), beta-2 microglobulin, GAPDH, TCR, RUNX1, KLHL7, NUPL2 or an intergenic region thereof, mir684, KCNH2, GPNMB, MIR4540, MIR4475, MIR4476, PRL32P21, LOC105376031, LOC105376032, LOC105376030, MELK, EBLN3P, ZCCHC7, RNF38, or loci meeting the criteria of a genome safe harbor as described herein (see e.g., WO 2019/169233 A1, WO 2017/079673 A1; incorporated by reference). GSHs described herein provide a non-limiting representation of GSHs that can be used with virions described herein. The present disclosure contemplates use of any GSHs that are known in the art.

In some embodiments, a GSH allows safe and targeted gene delivery that has limited off-target activity and minimal risk of genotoxicity, or causing insertional oncogenesis upon integration of foreign DNA, while being accessible to highly specific nucleases with minimal off-target activity.

In some embodiments, a GSH has any one or more of the following properties: (i) outside a gene transcription unit; (ii) located between 5-50 kilobases (kb) away from the 5' end of any gene; (iii) located between 5-300 kb away from cancer-related genes; (iv) located 5-300 kb away from any identified microRNA; and (v) outside ultra-conserved regions and long noncoding RNAs. In some embodiments, a GSH locus has any or more of the following properties: (i) outside a gene transcription unit; (ii) located >50 kilobases (kb) from the 5' end of any gene; (iii) located >300 kb from cancer-related genes; (iv) located >300 kb from any identified microRNA; and (v) outside ultra-conserved regions and long noncoding RNAs. In studies of lentiviral construct integrations in transduced induced pluripotent stem cells, analysis of over 5,000 integration sites revealed that-17% of integrations occurred in safe harbors. Virions that integrated into these safe harbors were able to express therapeutic levels of β-globin from their transgene without perturbing endogenous gene expression.

In some embodiments, a GSH is AAVS1. AAVS1 was identified as the adeno-associated virus common integration site on chromosome 19 and is located in chromosome 19 (position 19ql3.42) and was primarily identified as a repeatedly recovered site of integration of wild-type AAV in the genome of cultured human cell lines that have been infected with AAV in vitro. Integration in the AAVS1 locus interrupts the gene phosphatase 1 regulatory subunit 12C (PPP1R12C; also known as MBS85), which encodes a protein with a function that is not clearly delineated. The organismal consequences of disrupting one or both alleles of PPP1R12C are currently unknown. No gross abnormalities or differentiation deficits were observed in human and mouse pluripotent stem cells harboring transgenes targeted in AAVS1. Originally, AAV DNA integration into AAVS1 site was Rep-dependent, however, there are commercially available CRISPR/Cas9 reagents available for targeting which preserved the functionality of the targeted allele and maintained the expression of PPP1R12C at levels that are comparable to those in non-targeted cells. AAVS1 was also assessed using ZFN-mediated recombination into iPSCs or CD34+ cells.

As originally characterized, the AAVS1 locus is >4 kb and is identified as chromosome 19 nucleotides 55,113,873-55,117,983 (human genome assembly GRCh38/hg38) and overlaps with exon 1 of the PPP1R12C gene that encodes protein phosphatase 1 regulatory subunit 12C. This >4 kb region is extremely G+C nucleotide content rich and is a gene-rich region of particularly gene-rich chromosome 19 (see FIG. 1A of Sadelain et al, Nature Revs Cancer, 2012; 12; 51-58), and some integrated promoters can indeed activate or cis-activate neighboring genes, the consequence of which in different tissues is presently unknown. PPP1R12C exon 1 5'untranslated region contains a functional AAV origin of DNA synthesis indicated within a known sequence (Urcelay et al. 1995).

AAVS1 GSH was identified by characterizing an AAV provirus structure in latently infected human cell lines with recombinant bacteriophage genomic libraries generated from latently infected clonal cell lines (Detroit 6 clone 7374 IIID5) (Kotin and Berns 1989), Kotin et al, isolated non-viral, cellular DNA flanking the provirus and used a subset of "left" and "right" flanking DNA fragments as probes to screen panels of independently derived latently infected clonal cell lines. In approximately 70% of the clonal isolates, AAV DNA was detected with the cell-specific probe (Kotin et al. 1991; Kotin et al. 1990). Sequence analysis of the pre-integration site identified near homology to a portion of the AAV inverted terminal repeat (Kotin, Linden, and Beerns 1992). Although lacking the characteristic interrupted palindrome, the AAVS1 locus retained the Rep binding elements and terminal resolution sites homologous to the AAV ITR.

Selection of the exonic integration site is non-obvious, and perhaps counter-intuitive, since insertion and expression of foreign DNA likely disrupts expression of endogenous genes. Apparently, insertion of an AAV genome into this locus does not adversely affect cell viability or iPSC differentiation (DeKelver et al. 2010; Wang et al. 2012; Zou et al. 2011). AAVS1 locus is within a 5' UTR of the highly conserved PPP1R12C gene. The Rep-dependent minimal origin of DNA synthesis is conserved in a 5'UTR of a human, chimapanzee, and gorilla PPP1R12C gene. However, commercially available CRISPR/Cas9 reagents used for integrating DNA into AAVS1 target PPP1R12C intron 1 rather than an exon.

In some embodiments, a GSH is any one of Kif6, Pax5, collagen, HTRP, HI 1, beta-2 microglobulin, GAPDH, TCR, RUNX1, KLHL7, an intergenic region of NUPL2, mir684, KCNH2, GPNMB, MIR4540, MIR4475, MIR4476, PRL32P21, LOC105376031, LOC105376032, LOC105376030, MELK, EBLN3P, ZCCHC7, and RNF38.

In some embodiments, a GSH is a Pax 5 gene (also known as Paired Box 5, or "B-cell lineage specific activator protein," or BSAP). In humans PAX5 is located on chromosome 9 at 9p 13.2 and has orthologues across many vertebrate species, including, human, chimp, macaque, mouse, rat, dog, horse, cow, pig, opossum, platypus, chicken, lizard, *xenopus, C. elegans, drosophila* and zebrafish. PAX5 gene is located at Chromosome 9:36, 833,275-37,034, 185 reverse strand (GRCh38: CM000671.2) or 36,833,272-37,034,182 in GRCh37 coordinates.

Additional exemplary GSHs are listed in Table 5A and Table 5B.

TABLE 5A

Exemplary GSH loci in *Homo Sapiens* (see, e.g., WO 2019/169232; incorporated by reference)

| Gene | Chromosomal location | Accession number/location |
|---|---|---|
| PAX5 | Chromosome 9: 36,833,275-37,034,185 reverse strand | NC_000009.12 (36833274 . . . 37035949, complement) |
| MIR4540 | — | NC_000009.12 (36864254 . . . 36864308, complement) |
| MIR4475 | GRCh38.p7 (GCF_000001405.33) | NC_000009.12 (36823539 . . . 36823599, complement) |
| MIR4476 | GRCh38.p7 (GCF_000001405.33) | NC_000009.12 (36893462 . . . 36893531, complement) |
| PRL32P21 | GRCh38.p7 (GCF_000001405.33) | NC_000009.12 (37046835 . . . 37047242) |
| LOC105376031 | GRCh38.p7 (GCF_000001405.33) | NC_000009.12 (37027763 . . . 37031333) |
| LOC105376032 | GRCh38.p7 (GCF_000001405.33) | NC_000009.12 (37002697 . . . 37007774) |
| LOC105376030 | GRCh38.p7 (GCF_000001405.33) | NC_000009.12 (36779475 . . . 36830456) |
| MELK | GRCh38.p7 (GCF_000001405.33) | NC_000009.12 (36572862 . . . 36677683) |
| EBLN3P | GRCh38.p7 (GCF_000001405.33) | NC_000009.12 (37079896 . . . 37090401) |
| ZCCHC7 | GRCh38.p7 (GCF_000001405.33) | NC_000009.12 (37120169 . . . 37358149) |
| RNF38 | GRCh38.p7 (GCF_000001405.33) | NC_000009.12 (36336398 . . . 36487384, complement) |

TABLE 5B

Exemplary GSH loci (see, e.g., WO 2019/169232; incorporated by reference)

| Taxonomic Rank | Brief description | Species | Chromosomal location |
|---|---|---|---|
| | | Intergenic Loci | |
| Macropodidae (taxonomic rank: Family) | mAAV_eve integration between cadherin (cdh) 8 and cdh 16. Because the macropod genome is poorly annotated, another marsupial Mondelphis domestica with a more completely assemble genome is used as a substitute genome. | *M. domestica* | chromosome 1:<br>cdh 8: 674,639,xxx - 675,163,xxx<br>cdh 10: 680,370,7xx - 680,581, xxx<br>Intergenic distance= 5.2 Mb<br>Empty EVE locus in *M. domestica* 674,422,470-675,422,729 |
| | | *Mouse* | ch: 9<br>cdh: 8 99,028,769 - 99,416-471<br>cdh 11: 192,632,095 - 102,785,111<br>Intergenic distance = 3.2 Mb |
| | | *Homo sapiens* | Chromosome 16<br>cdh 8: 61,647,242 - 62,036,835<br>cdh 11: 64,943,753 - 65,122,198<br>Intergenic distance: 2.9 Mb |

TABLE 5B-continued

| Exemplary GSH loci (see, e.g., WO 2019/169232; incorporated by reference) | | | |
|---|---|---|---|
| Taxonomic Rank | Brief description | Species | Chromosomal location |
| Leporidae (Family) - the Family Leporidae are rabbits and hares species of the Lagomorph Order. | Laporidae EVE located between NupL 2 and GPNMD The gene order is: <-Fam126A- - KLH7->------NUPL2->---EVE--------GPNMB->--<IGF28P3-MALSU1 | *H. Sapiens*<br>*M. mus* | Chromosome 7: --KLH7->--NUPL2→GPNMB<br>--KLH L7->--NUPL2→mir684-KCNH2 |
| Intergenic loci | | | |
| Cetacea (Order) | EVE integrated into an intron on PAX5 | *H. sapiens*<br>*M. mus* | Chromosome 9: (Pax5) 36,833,275 - 37,034,185<br>Chromosome 4: (Pax5) 44,531,506 - 44,710,440 |
| (Family-Vespertilionidae, Order - Chiroptera). Myotis (Genus), Myotinae (Subfamily) | Myotis EVE integrated into the Kif6 gene, intronic or exonic | *H. sapiens* | Chromosome 6 (Kif6) 39,329,990 - 39,725,405<br>Chromosome 17 (Kif6) 49,754,497 - 50,049,172 |

d. Methods of Integration into a Target Genome

Among other things, in some embodiments, the present disclosure provides for a method of integration into a target genome.

Integration to a target genome may be driven by cellular processes, such as homologous recombination or non-homologous end-joining (NHEJ). Integration may also be initiated and/or facilitated by an exogenously introduced nuclease. In preferred embodiments, a nucleic acid packaged within a virion described herein is integrated to a specific locus within a genome, e.g., a GSH. In some embodiments, a GSH is any locus that permits sufficient transgene expression to yield desired levels of the transgene-encoded protein or non-coding RNA. A GSH also should not predispose cells to malignant transformation nor significantly alter normal cellular functions. Site-specific integration to a GSH may be mediated by a nucleic acid homologous to a GSH that is placed 5' and 3' to a nucleic acid to be integrated. Such homologous donor sequences may provide a template for homology-dependent repair that allows integration at the desired locus.

In preferred embodiments, a virion described herein comprises a nucleic acid comprising a nucleic acid sequence that is at least about 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to a nucleic acid sequence of a genomic safe harbor (GSH) of a target cell. In some embodiments, said nucleic acid that is at least about 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to a GSH is placed 5' and 3' (homology arms) to a nucleic acid to be integrated, thereby allowing insertion (of a nucleic acid located between homology arms) to a specific locus in a target genome by homologous recombination. In some embodiments, a nucleic acid to be integrated is any one of a nucleic acids operably linked to a promoter described herein. In some embodiments, a GSH is AAVS1, ROSA26, CCR5, Kif6, Pax5, an intergenic region of NUPL2, collagen, HTRP, HI 1 (a thymidine kinase encoding nucleic acid at HI 1 locus), beta-2 microglobulin, GAPDH, TCR, RUNX1, KLHL7, mir684, KCNH2, GPNMB, MIR4540, MIR4475, MIR4476, PRL32P21, LOC105376031, LOC105376032, LOC105376030, MELK, EBLN3P, ZCCHC7, or RNF38. In some embodiments, a GSH is AAVS1, ROSA26, CCR5, Kif6, Pax5, or an intergenic region of NUPL2.

In certain embodiments, a coding sequence of a virion is integrated into a genome of a target cell upon transduction. In some embodiments, a nucleic acid is integrated into a GSH or EVE. In some embodiments, a GSH is AAVS1, ROSA26, CCR5, Kif6, Pax5, an intergenic region of NUPL2, collagen, HTRP, HI 1 (a thymidine kinase encoding nucleic acid at HI 1 locus), beta-2 microglobulin, GAPDH, TCR, RUNX1, KLHL7, mir684, KCNH2, GPNMB, MIR4540, MIR4475, MIR4476, PRL32P21, LOC105376031, LOC105376032, LOC105376030, MELK, EBLN3P, ZCCHC7, or RNF38. In some embodiments, a GSH is AAVS1, ROSA26, CCR5, Kif6, Pax5, or an intergenic region of NUPL2. In some embodiments, a nucleic acid is integrated into a target genome by homologous recombination followed by a DNA break formation induced by an exogenously-introduced nuclease. In some embodiments, a nuclease is TALEN, ZEN, a meganuclease, a megaTAL, or a CRISPR endonuclease (e.g., a Cas9 endonuclease or a variant thereof). In some embodiments, a CRISPR endonuclease is in a complex with a guide RNA.

In some embodiments, provided herein are methods of integrating a heterologous nucleic acid into a GSH in a cell, comprising: (a) transducing a cell with one or more virions described herein comprising a heterologous nucleic acid flanked at the 5' end and 3' end by a donor nucleic acid sequence that is at least about 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to the target GSH nucleic acid; or (b) transducing the cell with one or more virions described herein comprising (i) a heterologous nucleic acid flanked at a 5' end and 3' end by a donor nucleic acid sequence that is at least about 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to the target GSH nucleic acid, and (ii) a nucleic acid encoding a nuclease (e.g., Cas9 or a variant thereof, ZFN, TALEN) and/or a guide RNA, wherein a nuclease or the nuclease/gRNA complex makes a DNA break at a GSH, which is repaired using a donor nucleic acid, thereby integrating a heterologous nucleic acid at GSH. In some embodiments, (i) a heterologous nucleic acid flanked by a donor nucleic acid that is at least about 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to a target GSH nucleic acid and (ii) a nucleic acid encoding a nuclease and/or the gRNA are transduced in separate virions. In some embodiments, a GSH is AAVS1, ROSA26, CCR5, Kif6, Pax5, an intergenic region of NUPL2, collagen, HTRP, HI 1 (a thymidine kinase encoding nucleic acid at HI 1 locus), beta-2 microglobulin, GAPDH, TCR, RUNX1, KLHL7, mir684, KCNH2, GPNMB, MIR4540, MIR4475, MIR4476, PRL32P21, LOC105376031, LOC105376032, LOC105376030, MELK, EBLN3P, ZCCHC7, or RNF38. In some embodiments, a GSH is AAVS1, ROSA26, CCR5, Kif6, Pax5, or an intergenic region of NUPL2.

For integration of a nucleic acid located between the 5' and 3' homology arms, the 5' and 3' homology arms should be long enough for targeting to a GSH and allow (e.g., guide) integration into a genome by homologous recombination. To increase the likelihood of integration at a precise location and enhance probability of homologous recombination, the 5' and 3' homology arms may include a sufficient number of nucleic acids. In some embodiments, the 5' and 3' homology arms may include at least 10 base pairs but no more than 5,000 base pairs, at least 50 base pairs but no more than 5,000 base pairs, at least 100 base pairs but no more than 5,000 base pairs, at least 200 base pairs but no more than 5,000 base pairs, at least 250 base pairs but no more than 5,000 base pairs, or at least 300 base pairs but no more than 5,000 base pairs. In some embodiments, the 5' and 3' homology arms include about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 base pairs. Detailed information regarding length of homology arms and recombination frequency is art-known, see e.g., Zhang et al. "Efficient precise knock in with a double cut HDR donor after CRISPR/Cas9-mediated double-stranded DNA cleavage." Genome biology 18.1 (2017): 35, which is incorporated herein in its entirety by reference.

5' and 3' homology arms may be any sequence that is homologous with a GSH target sequence in a genome of a host cell. In some embodiments, 5' and 3' homology arms may be homologous to portions of a GSH described herein. Furthermore, 5' and 3' homology arms may be non-coding or coding nucleotide sequences.

In some embodiments, a 5' and/or 3' homology arms can be homologous to a sequence immediately upstream and/or downstream of the integration or DNA cleavage site on the chromosome. Alternatively, the 5' and/or 3' homology arms can be homologous to a sequence that is distant from the integration or DNA cleavage site, such as at least 1, 2, 5, 10, 15, 20, 25, 30, 50, 75,100,125, 150, 175, 200, 225, 250, 275, 300, 325, 350, 375, 400, 425, 450, 475, 500 or more base pairs away from the integration or DNA cleavage site, or partially or completely overlapping with a DNA cleavage site (e.g., can be a DNA break induced by an exogenously-introduced nuclease). In some embodiments, a 3' homology arm of the nucleotide sequence is proximal to an ITR.

4. Administration

Provided herein are technologies comprising, among other things, therapeutic delivery systems for treating a disease or disorder. In some embodiments the present disclosure provides compositions that are part of or comprise at least one construct, e.g., viral construct, e.g., a protoparvovirus variant VP1 construct. In some such embodiments, a composition comprises a virion. In some embodiments, a virion comprises a protoparvovirus variant VP1 capsid polypeptide.

a. Routes of Administration

In some embodiments, the present disclosure provides various routes of and formulations for administration. As will be known to one of skill in the art, pharmaceutical forms suitable for injectable use include sterile aqueous solutions or dispersions and sterile powders for extemporaneous preparation of sterile injectable solutions or dispersions. Dispersions may also be prepared in glycerol, liquid polyethylene glycols, and mixtures thereof and in oils.

Under ordinary conditions of storage and use, these preparations contain a preservative to prevent growth of microorganisms. In many cases the form is sterile and fluid to the extent that easy syringability exists. It must be stable under conditions of manufacture and storage and must be preserved against contaminating action of microorganisms, such as bacteria and fungi. In some embodiments, a carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by use of a coating, such as lecithin, by maintenance of the required particle size in the case of dispersion and by use of surfactants. Prevention of action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of injectable compositions can be brought about use in compositions of agents delaying absorption, for example, aluminum monostearate and gelatin. For administration of an injectable aqueous solution, for example, a solution may be suitably buffered, if necessary, and a liquid diluent first rendered isotonic with sufficient saline or glucose. Aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at a proposed site of infusion, (see for example, "Remington's Pharmaceutical Sciences" 15th Edition, pages 1035-1038 and 1570-1580, which is incorporated in its entirety herein by reference). Some variation in dosage will necessarily occur depending on condition of a host. A person responsible for administration will, in any event, determine an appropriate dose for an individual host.

In some embodiments, sterile injectable solutions are prepared by incorporating active virion in a required amount in an appropriate solvent with various other ingredients enumerated herein, as required, followed by filtered sterilization. Generally, dispersions are prepared by incorporating various sterilized active ingredients into a sterile vehicle which contains basic dispersion medium and required other ingredients from those enumerated above. In the case of sterile powders for preparation of sterile injectable solutions, in some embodiments, preferred methods of preparation are vacuum-drying and freeze-drying techniques which yield a powder of active ingredient plus any additional desired ingredient from a previously sterile-filtered solution thereof.

In some embodiments, virion compositions disclosed herein may also be formulated in a neutral or salt form. Pharmaceutically-acceptable salts, include acid addition salts (formed with free amino groups of a given protein) and which are formed with inorganic acids such as, for example, hydrochloric or phosphoric acids, or such organic acids as acetic, oxalic, tartaric, mandelic, and the like. Salts formed with free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions can be administered in a manner compatible with the dosage formulation and in such amount as is therapeutically effective. Formulations are easily administered in a variety of dosage forms such as injectable solutions, drug-release capsules, and the like.

Delivery vehicles such as liposomes, nanocapsules, microparticles, microspheres, lipid particles, vesicles, and the like, may be used for introduction of compositions of the present disclosure into suitable host cells. In particular, in some embodiments, virion-construct delivered transgenes may be formulated for delivery either encapsulated in a lipid particle, a liposome, a vesicle, a nanosphere, or a nanoparticle or the like.

Such formulations may be preferred for introduction of pharmaceutically acceptable formulations of nucleic acids or virion constructs disclosed herein. Formation and use of liposomes is generally known to those of skill in the art. Recently, liposomes were developed with improved serum stability and circulation half-times (U.S. Pat. No. 5,741,516, which is incorporated in its entirety herein by reference). Further, various methods of liposome and liposome like preparations as potential drug carriers have been described (U.S. Pat. Nos. 5,567,434; 5,552,157; 5,565,213; 5,738,868 and 5,795,587, each of which is incorporated in its entirety herein by reference).

Liposomes have been used successfully with a number of cell types that are normally resistant to transfection by other procedures. In addition, liposomes are free of DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining efficacy of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 Tm. Sonication of MLVs results in formation of small unilamellar vesicles (SUVs) with diameters in a range of approximately 200 to 500.ANG., containing an aqueous solution in the core.

Alternatively, nanocapsule formulations of a virion may be used. Nanocapsules can generally entrap substances in a stable and reproducible way. To avoid side effects due to intracellular polymeric overloading, such ultrafine particles (sized around 0.1 Tm) should be designed using polymers able to be degraded in vivo. Biodegradable polyalkyl-cyanoacrylate nanoparticles that meet these requirements are contemplated for use.

In addition to methods of delivery described above, the following techniques are also contemplated as alternative methods of delivering a virion to a host. Sonophoresis (i.e., ultrasound) has been used and described in U.S. Pat. No. 5,656,016, which is incorporated in its entirety herein by reference, as a device for enhancing the rate and efficacy of drug permeation into and through a circulatory system. Other drug delivery alternatives contemplated are intraosseous injection (U.S. Pat. No. 5,779,708, which is incorporated in its entirety herein by reference), microchip devices (U.S. Pat. No. 5,797,898, which is incorporated in its entirety herein by reference), ophthalmic formulations (Bourlais et al., 1998, which is incorporated in its entirety herein by reference), transdermal matrices (U.S. Pat. Nos. 5,770,219 and 5,783,208, each of which is incorporated in its entirety herein by reference) and feedback-controlled delivery (U.S. Pat. No. 5,697,899, which is incorporated in its entirety herein by reference).

In some embodiments, administration of any compositions of the present disclosure may be carried out in any convenient manner, including by aerosol inhalation, injection, ingestion, transfusion, implantation or transplantation. Compositions described herein may be administered to a patient trans arterially, subcutaneously, intradermally, intranodally, intramedullary, intramuscularly, by intravenous (i.v.) injection, or intraperitoneally. In some embodiments, a nucleic acid composition of the present disclosure is administered to a patient by intradermal or subcutaneous injection. In some embodiments, a nucleic composition of the present disclosure is administered by i.v. injection.

b. Dosing

In some embodiments, any of the methods disclosed herein comprise a dose-escalation study to assess safety and tolerability in subjects, e.g., mammals, e.g., humans, e.g., patients, with a disease described herein. In some embodiments, a preparation, a construct(s), a virion, a population of virions, a composition, or a pharmaceutical composition disclosed herein is administered at a dosing regimen disclosed herein. In some embodiments, the dosing regimen comprises either unilateral or bilateral intracochlear administrations of a dose, e.g., as described herein, of a preparation, a construct(s), a virion, a population of virions, a composition, or a pharmaceutical composition disclosed herein. In some embodiments, a dosing regimen comprises delivery in a volume of at least 0.001 mL, 0.005 mL, 0.01 mL, at least 0.02 mL, at least 0.03 mL, at least 0.04 mL, at least 0.05 mL, at least 0.06 mL, at least 0.07 mL, at least 0.08 mL, at least 0.09 mL, at least 0.10 mL, at least 0.11 mL, at least 0.12 mL, at least 0.13 mL, at least 0.14 mL, at least 0.15 mL, at least 0.16 mL, at least 0.17 mL, at least 0.18 mL, at least 0.19 mL, or at least 0.20 mL per cochlea. In some embodiments, the dosing regimen comprises delivery in a volume of at most 0.30 mL, at most 0.25 mL, at most 0.20 mL, at most 0.15 mL, at most 0.14 mL, at most 0.13 mL, at most 0.12 mL, at most 0.11 mL, at most 0.10 mL, at most 0.09 mL, at most 0.08 mL, at most 0.07 mL, at most 0.06 mL, at most 0.05 mL, at most 0.01 mL, at most 0.005 mL, or at most 0.001 mL per cochlea. In some embodiments, the dosing regimen comprises delivery in a volume of about 0.001 mL, 0.005 mL, 0.01 mL, 0.05 mL, about 0.06 mL, about 0.07 mL, about 0.08 mL, about 0.09 mL, about 0.10 mL, about 0.11 mL, about 0.12 mL, about 0.13 mL, about 0.14 mL, or about 0.15 mL per cochlea, depending on the population. In some embodiments, the dosing regimen comprises delivery in a volume of at least 0.001 mL, 0.005 mL, 0.01 mL, at least 0.02 mL, at least 0.03 mL, at least 0.04 mL, at least 0.05 mL, at least 0.06 mL, at least 0.07 mL, at least 0.08 mL, at least 0.09 mL, at least 0.10 mL, at least 0.11 mL, at least 0.12 mL, at least 0.13 mL, at least 0.14 mL, at least 0.15 mL, at least 0.16 mL, at least 0.17 mL, at least 0.18 mL, at least 0.19 mL, or at least 0.20 mL per cochlea. In some embodiments, the dosing regimen comprises delivery in a volume of at most 0.30 mL, at most 0.25 mL, at most 0.20 mL, at most 0.15 mL, at most 0.14 mL, at most 0.13 mL, at most 0.12 mL, at most 0.11 mL, at most 0.10 mL, at most 0.09 mL, at most 0.08 mL, at most 0.07 mL, at most 0.06 mL, at most 0.05 mL, at most 0.01 mL, at most 0.005 mL, or at most 0.001 mL per cochlea. In some embodiments, the dosing regimen comprises delivery in a volume of about 0.001 mL, about 0.005 mL, about 0.01 mL, 0.05 mL, about 0.06 mL, about 0.07 mL, about 0.08 mL, about 0.09 mL, about 0.10 mL, about 0.11 mL, about 0.12 mL, about 0.13 mL, about 0.14 mL, or about 0.15 mL per cochlea, depending on the population.

In some embodiments, a dosing regimen comprises delivery in a concentration of about 1.0e13 VG/kg, about 1.1 e13 VG/kg, about 1.2e13 VG/kg, about 1.3e13 VG/kg, about 1.4e13 VG/kg, about 1.5e13 VG/kg, about 1.6e13 VG/kg, about 1.7e13 VG/kg, about 1.8e13 VG/kg, about 1.9e13 VG/kg, about 2.0e13 VG/kg, about 2.1e13 VG/kg, about 2.2e13 VG/kg, about 2.3e13 VG/kg, about 2.4e13 VG/kg, about 2.5e13 VG/kg, about 2.6e13 VG/kg, about 2.7e13 VG/kg, about 2.8e13 VG/kg, about 2.9e13 VG/kg, about 3.0e13 VG/kg, about 3.1e13 VG/kg, about 3.2e13 VG/kg, about 3.3e13 VG/kg, about 3.4e13 VG/kg, about 3.5e13 VG/kg, about 3.6e13 VG/kg, about 3.7e13 VG/kg, about 3.8e13 VG/kg, about 3.9e13 VG/kg, about 4.0e13 VG/kg, about 4.1e13 VG/kg, about 4.2e13 VG/kg, about 4.3e13 VG/kg, about 4.4e13 VG/kg, about 4.5e13 VG/kg, about 4.6e13 VG/kg, about 4.7e13 VG/kg, about 4.8e13 VG/kg, about 4.9e13 VG/kg, about 5.0e13 VG/kg, about 1.0e14 VG/kg, about 1.le14 VG/kg, about 1.2e14 VG/kg, about 1.3e14 VG/kg, about 1.4e14 VG/kg, about 1.5e14 VG/kg, about 1.6e14 VG/kg, about 1.7e14 VG/kg, about 1.8e14 VG/kg, about 1.9e14 VG/kg, about 2.0e14 VG/kg.

In some embodiments, a method disclosed herein evaluates safety and tolerability of escalating doses of a preparation, a construct(s), a virion, a population of virions, a composition, or a pharmaceutical composition disclosed herein administered via systemic administration to a subject, e.g., 1 to 80 years of age, with a disease described herein.

In some embodiments, any of the methods disclosed herein comprise an evaluation of safety and tolerability of a preparation, a construct(s), a virion, a population of virions, a composition, or a pharmaceutical composition disclosed herein. In some embodiments, evaluation of the efficacy of a preparation, a construct(s), a virion, a population of virions, a composition, or a pharmaceutical composition disclosed herein to treat a disease described herein, is performed in a randomized, controlled setting (using a concurrent, non-intervention observation arm).

5. Exemplary Diseases

In some embodiments, compositions, preparations, constructs, virions, population of virions, host cells, and/or pharmaceutical compositions described herein may be used for prevention and/or treatment of various diseases.

In some embodiments, a disease is selected from endothelial dysfunction, cystic fibrosis, cardiovascular disease, kidney disease, renal disease, ocular disease, cancer, hemoglobinopathy, anemia, hemophilia, myeloproliferative disorder, coagulopathy, sickle cell disease, alpha-thalassemia, beta-thalassemia, hemophilia (e.g., hemophilia A), Fanconi anemia, familial intrahepatic cholestasis, epidermolysis bullosa, Fabry, Gaucher, Nieman-Pick A, Nieman-Pick B, GM1 Gangliosidosis, Mucopolysaccharidosis (MPS) I (Hurler, Scheie, Hurler/Scheie), MPS II (Hunter), MPS VI (Maroteaux-Lamy), hematologic cancer, hemochromatosis, hereditary hemochromatosis, juvenile hemochromatosis, cirrhosis, hepatocellular carcinoma, pancreatitis, diabetes mellitus, cardiomyopathy, arthritis, hypogonadism, cardiac (or heart) disease, heart attack, hypothyroidism, glucose intolerance, arthropathy, liver fibrosis, Wilson's disease, ulcerative colitis, Crohn's disease, Tay-Sachs disease, neurodegenerative disorder, Spinal muscular atrophy type 1, Huntington's disease, Canavan's disease, lysosomal storage diseases, rheumatoid arthritis, inflammatory bowel disease, psoriatic arthritis, juvenile chronic arthritis, psoriasis, and ankylosing spondylitis, and autoimmune disease, neurodegenerative disease (e.g., Alzheimer's disease, Parkinson's disease, Huntington's disease, ataxias), inflammatory disease, inflammatory bowel disease, Crohn's disease, rheumatoid arthritis, lupus, multiple sclerosis, chronic obstructive pulmony disease/COPD, pulmonary fibrosis, Sjogren's disease, hyperglycemic disorders, type I diabetes, type II diabetes, insulin resistance, hyperinsulinemia, insulin-resistant diabetes (e.g. Mendenhall's Syndrome, Werner Syndrome, leprechaunism, and lipoatrophic diabetes), dyslipidemia, hyperlipidemia, elevated low-density lipoprotein (LDL), depressed highdensity lipoprotein (HDL), elevated triglycerides, metabolic syndrome, liver disease, renal disease, cardiovascular disease, ischemia, stroke, complications during reperfusion, muscle degeneration, atrophy, symptoms of aging (e.g., muscle atrophy, frailty, metabolic disorders, low grade inflammation, atherosclerosis, stroke, age-associated dementia and sporadic form of Alzheimer's disease, pre-cancerous states, and psychiatric conditions including depression), spinal cord injury, arteriosclerosis, infectious diseases (e.g., bacterial, fungal, viral), AIDS, tuberculosis, defects in embryogenesis, infertility, lysosomal storage diseases, activator deficiency/GM2 gangliosidosis, alpha-mannosidosis, aspartylglucoaminuria, cholesteryl ester storage disease, chronic hexosaminidase A deficiency, cystinosis, Danon disease, Farber disease, fucosidosis, galactosialidosis, Gaucher Disease (Types I, II and III), GM1 Gangliosidosis, (infantile, late infantile/juvenile and adult/chronic), Hunter syndrome (MPS II), I-Cell disease/Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Neuronal ceroid lipofuscinoses, CLN6 disease, Jansky-Bielschowsky disease, Pompe disease, pycnodysostosis, Sandhoff disease, Schindler disease, and Wolman disease.

In some embodiments, a disease is a kidney disease. In some embodiments, a disease is Alport syndrome. In some embodiments, a disease is Fabry disease. In some embodiments, a disease is autosomal dominant polycystic kidney disease (PKD). In some embodiments, a disease is congenital nephrotic syndrome.

In some embodiments, a disease is a cardiac (or heart) disease. In some embodiments, a cardiac (or heart) disease is hypertrophic cardiomyopathy. In some embodiments, a disease is dilated cardiomyopathy.

In some embodiments, compositions, preparations, constructs, virions, population of virions, host cells, and/or pharmaceutical compositions comprising a protoparvovirus variant VP1 capsid polypeptide are useful for transducing a hematopoietic cells, hematopoietic progenitor cell, hematopoietic stem cells, erythroid lineage cell, megakaryocyte, erythroid progenitor cell (EPC), CD34+ cell, CD36+ cell, mesenchymal stem cell, nerve cell, intestinal cells, intestinal stem cell, gut epithelial cell, endothelial cells, lung cells, enterocyte, liver cell (e.g., hepatocyte, hepatic stellate cells (HSCs), Kupffer cells (KCs), liver sinusoidal endothelial cells (LSECs)), brain microvascular endothelial cell (BMVECs), erythroid progenitor cell, lymphoid progenitor cells, B lymphoblast cell, T cells, B cells, basophilic Endemic Burkitt Lymphoma (EBL), polychromatic erythroblast, orthochromatic erythroblast, kidney cells, or cardiac (or heart) cells. In some embodiments, compositions, preparations, constructs, virions, population of virions, host cells, and/or pharmaceutical compositions comprising a protoparvovirus variant VP1 capsid polypeptide are useful for transducing a testes cell, an oocyte, a medulla cell, a striatum cell, a spinal cord (or chord) cell, or a duodenum cell. In some embodiments, compositions, preparations, constructs, virions, population of virions, host cells, and/or pharmaceutical compositions comprising a protoparvovirus variant VP1 capsid polypeptide are useful for transducing kidney cells. In some embodiments, compositions, preparations, constructs, virions, population of virions, host cells, and/or pharmaceutical compositions comprising a protoparvovirus variant VP1 capsid polypeptide are useful for transducing cardiac (or heart) cells. In some embodiments, compositions, preparations, constructs, virions, population of virions, host cells, and/or pharmaceutical compositions comprising a protoparvovirus variant VP1 capsid polypeptide are useful for transducing brain cells.

In addition, in some embodiments, compositions, preparations, constructs, virions, population of virions, host cells, and/or pharmaceutical compositions described herein are particularly useful in delivering a nucleic acid (e.g., a therapeutic nucleic acid, e.g., a transgene) in vivo (e.g., administering directly to a subject, e.g., targeting a specific tissue via viral tropism), as well as in vitro or ex vivo (obtaining a plurality of cells from a subject, transducing said cells using virions, and administering the subject an effective number of transduced cells).

In some embodiments, an exemplary disease is hemochromatosis as described by "Protoparvovirus and tetraparvovirus compositions and methods for gene therapy" published as WO2022140683A1 on Jun. 30, 2022, the entire contents of which are hereby incorporated by reference herein.

In some embodiments, an exemplary disease includes inflammatory bowel disease (IBD) as described by "Protoparvovirus and tetraparvovirus compositions and methods for gene therapy" published as WO2022140683A1 on Jun. 30, 2022, the entire contents of which are hereby incorporated by reference herein.

In some embodiments, an exemplary disease includes autophagy-related diseases as described by "Protoparvovirus and tetraparvovirus compositions and methods for gene therapy" published as WO2022140683A1 on Jun. 30, 2022 the entire contents of which are hereby incorporated by reference herein.

In some embodiments, an exemplary disease includes inflammatory disorders as described by "Protoparvovirus and tetraparvovirus compositions and methods for gene therapy" published as WO2022140683A1 on Jun. 30, 2022, the entire contents of which are hereby incorporated by reference herein.

In some embodiments, an exemplary disease includes cancer as described by "Protoparvovirus and tetraparvovirus compositions and methods for gene therapy" published as WO2022140683A1 on Jun. 30, 2022 the entire contents of which are hereby incorporated by reference herein.

In some embodiments, an exemplary disease includes familial intrahepatic cholestasis as described by "Protoparvovirus and tetraparvovirus compositions and methods for gene therapy" published as WO2022140683A1 on Jun. 30, 2022 the entire contents of which are hereby incorporated by reference herein.

In some embodiments, an exemplary disease includes Wilson disease as described by "Protoparvovirus and tetraparvovirus compositions and methods for gene therapy" published as WO2022140683A1 on Jun. 30, 2022, the entire contents of which are hereby incorporated by reference herein.

In some embodiments, an exemplary disease includes lysosomal Storage Disorders as described by "Protoparvovirus and tetraparvovirus compositions and methods for gene therapy" published as WO2022140683A1 on Jun. 30, 2022, the entire contents of which are hereby incorporated by reference herein.

In some embodiments, an exemplary disease includes epidermolysis bullosa as described by "Protoparvovirus and tetraparvovirus compositions and methods for gene therapy" published as WO2022140683A1 on Jun. 30, 2022, the entire contents of which are hereby incorporated by reference herein.

In some embodiments, an exemplary disease includes hematologic diseases as described by "Protoparvovirus and tetraparvovirus compositions and methods for gene therapy" published as WO2022140683A1 on Jun. 30, 2022, the entire contents of which are hereby incorporated by reference herein.

In some embodiments, an exemplary disease includes type I diabetes as described by "Protoparvovirus and tetraparvovirus compositions and methods for gene therapy" published as WO2022140683A1 on Jun. 30, 2022, the entire contents of which are hereby incorporated by reference herein.

In some embodiments, an exemplary disease includes hemophilia A as described by "Protoparvovirus and tetraparvovirus compositions and methods for gene therapy" published as WO2022140683A1 on Jun. 30, 2022, the entire contents of which are hereby incorporated by reference herein.

In some embodiments, an exemplary disease includes neurodegenerative disorders and neuromuscular disorders including but not limited to spinal muscular atrophy type 1, Huntington's disease, Canavan's disease, and lysosomal storage diseases as described herein.

In some embodiments, an exemplary disease includes ocular disorders.

The disclosure is further described in detail by reference to the following experimental examples. These examples are provided for purposes of illustration only, and are not intended to be limiting unless otherwise specified. Thus, the disclosure should in no way be construed as being limited to the following examples, but rather should be construed to encompass any and all variations that become evident as a result of the teaching provided herein.

For example, other assays, including those described in the Example section herein as well as those that are known in the art, can also be used in accordance with the present disclosure.

EXAMPLES

Example 1: Alignments of Protoparvovirus VP1 Capsid Amino Acid Sequences Across Exemplary Protoparvovirus Species Showed Significant Conservation of a Splice Variant that Eliminates a Stretch of Amino Acid Residues within a Protoparvovirus VP1 Capsid Polypeptide The present example identifies significantly conserved characteristic sequence elements within a protoparvovirus VP1 capsid polypeptide (e.g., within a VP1 unique region (VP1u)).

Expression of protoparvovirus capsid polypeptides in host cell systems, including baculovirus-Sf9 systems, is challenging due to cell toxicity. Without wishing to be bound to any theory, cell toxicity may be due to protoparvovirus VP1 capsid polypeptide retention in cell cytoplasm, which can result in protein aggregation and subsequent toxicity as described herein.

Figure 2:
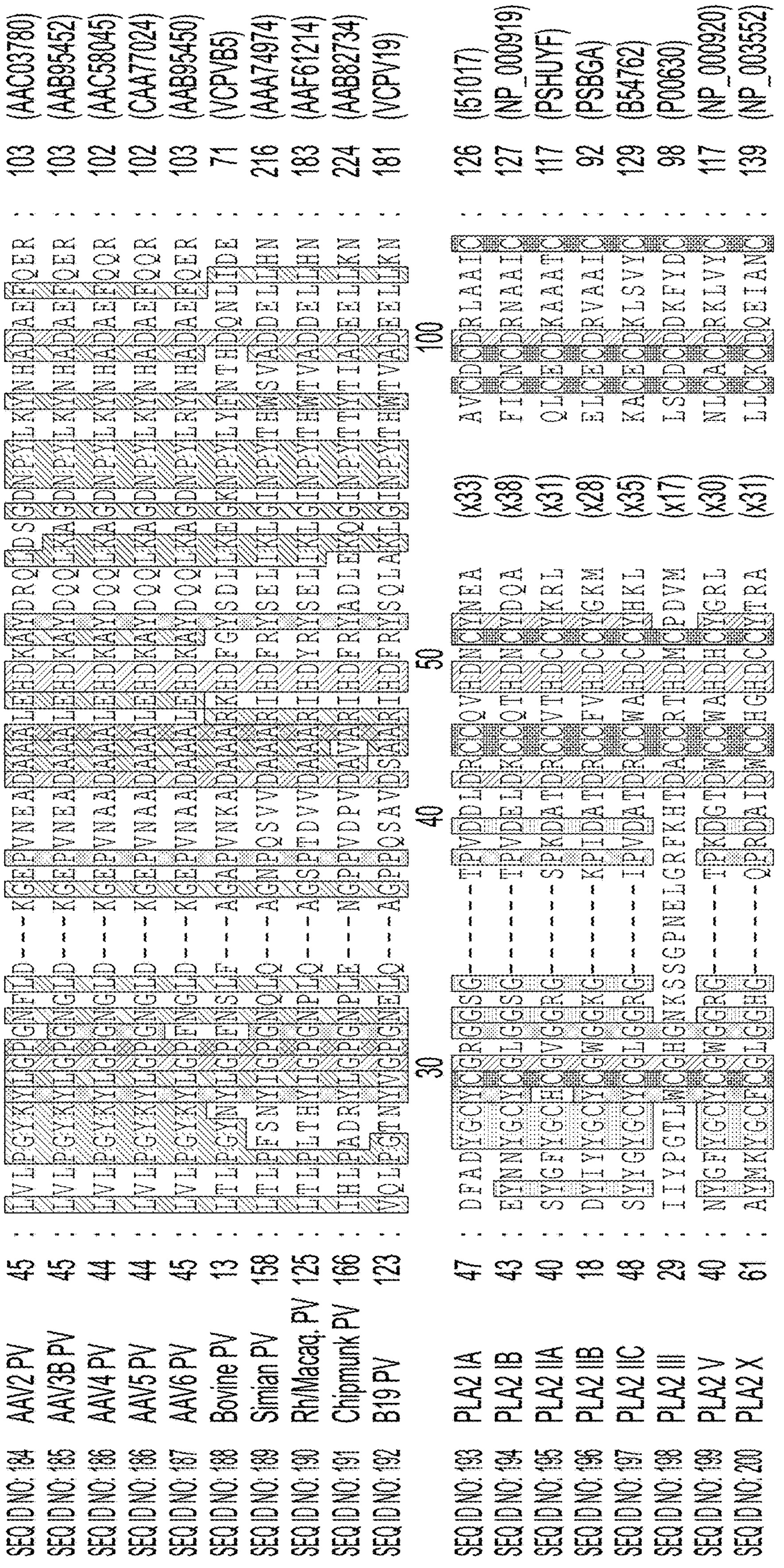
FIG. 2 shows alignments of highly conserved parvovirus PLA2 motif residues.

FIG. 1 shows alignments of an N-terminus region of exemplary protoparvovirus VP1u within a VP1 capsid polypeptide. Alignments depicted by FIG. 1 reveal significant conservation of a stretch of amino acid residues ("aa_del" motif) within exemplary protoparvovirus species including bufavirus (BuV), cutavirus (CuV), tusavirus (TuV), minute virus of mice (MVM), canine parvovirus (CPV), and feline panleukopenia virus (FPV). Alignments depicted by FIG. 1 also show significant conservation of a putative nuclear localization signal sequence (NLS) upstream of a five amino acid motif. Alignments depicted by FIG. 1 also show highly conserved PLA2 motif residues downstream of an aa_del motif (see FIG. 2).

Figure 3:
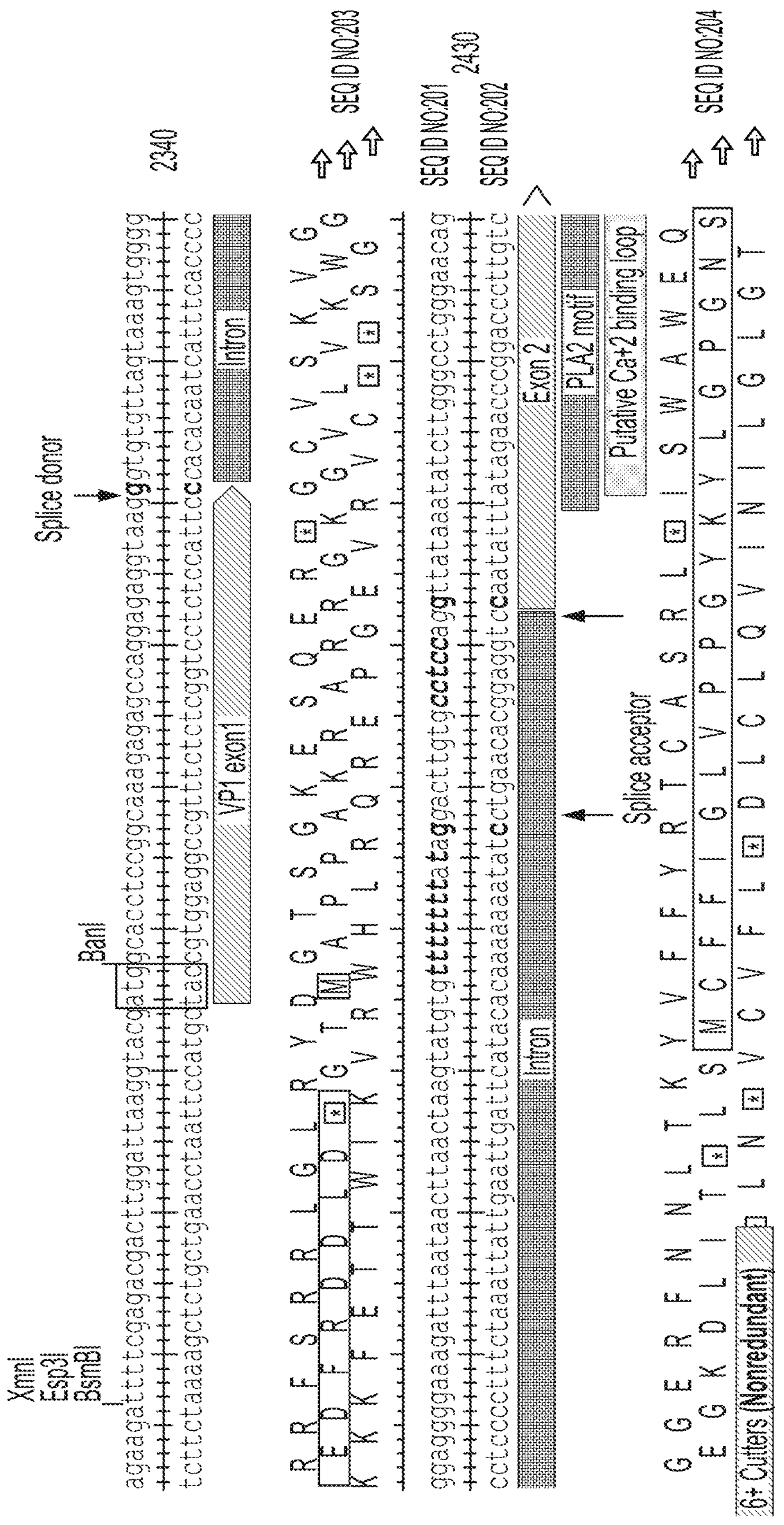
FIG. 3 shows an image depicting adjacent splice donor/acceptor sequences between a NLS (KRARRG-SEQ ID NO: 145) and initiation of a PLA2 motif that results in deletion of a five amino acid motif in a reference canine parvovirus (CPV) VP1 capsid polypeptide sequence, according to an embodiment of the present disclosure.
Figure 4:
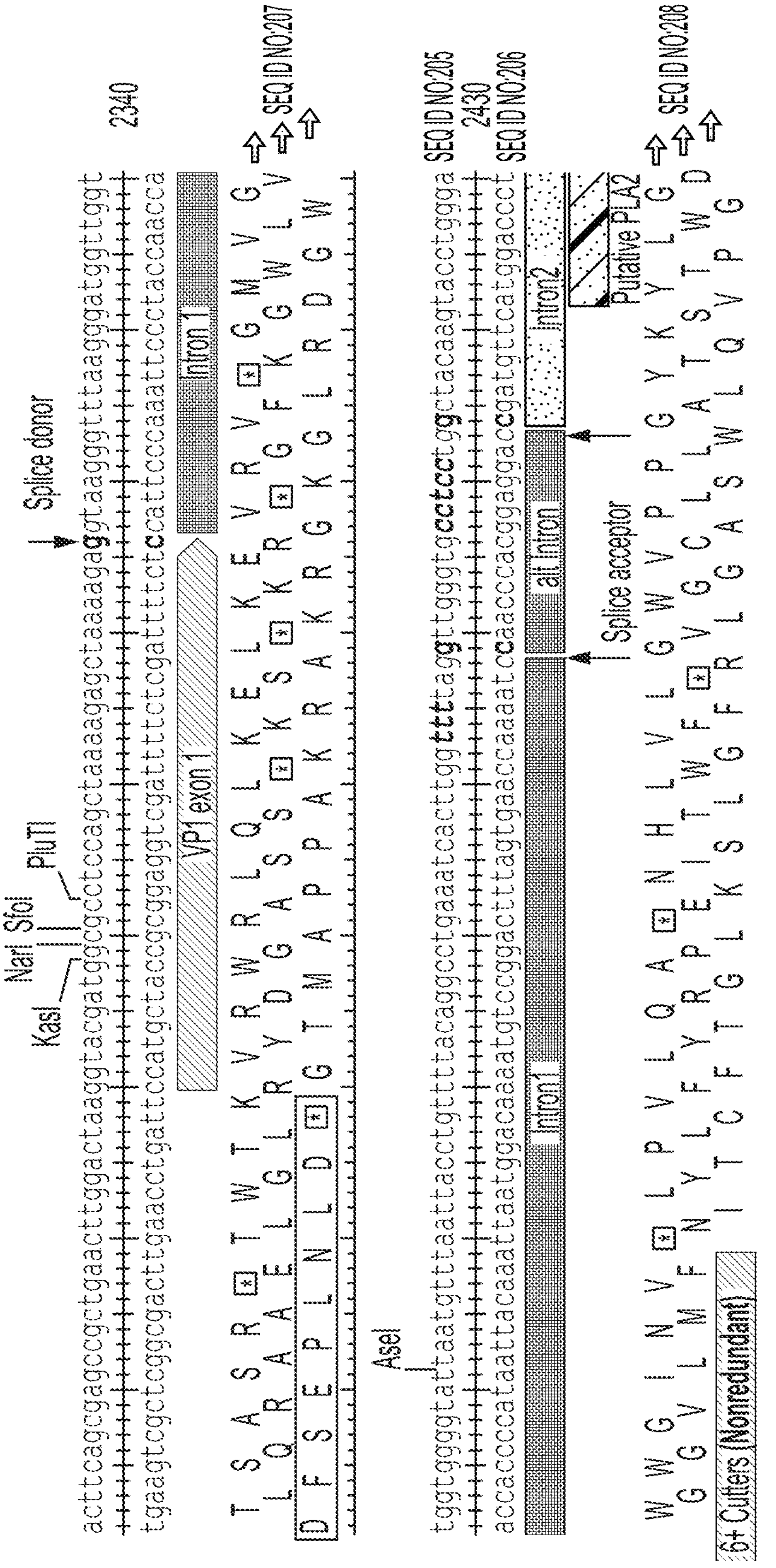
FIG. 4 shows an image depicting two adjacent donor/acceptor sequences between a NLS (KRAKRG-SEQ ID NO: 146) and a PLA2 motif that can result in deletion of a five amino acid motif in a reference minute virus of mice (MVM) VP1 capsid polypeptide sequence, according to an embodiment of the present disclosure.
Figure 5:
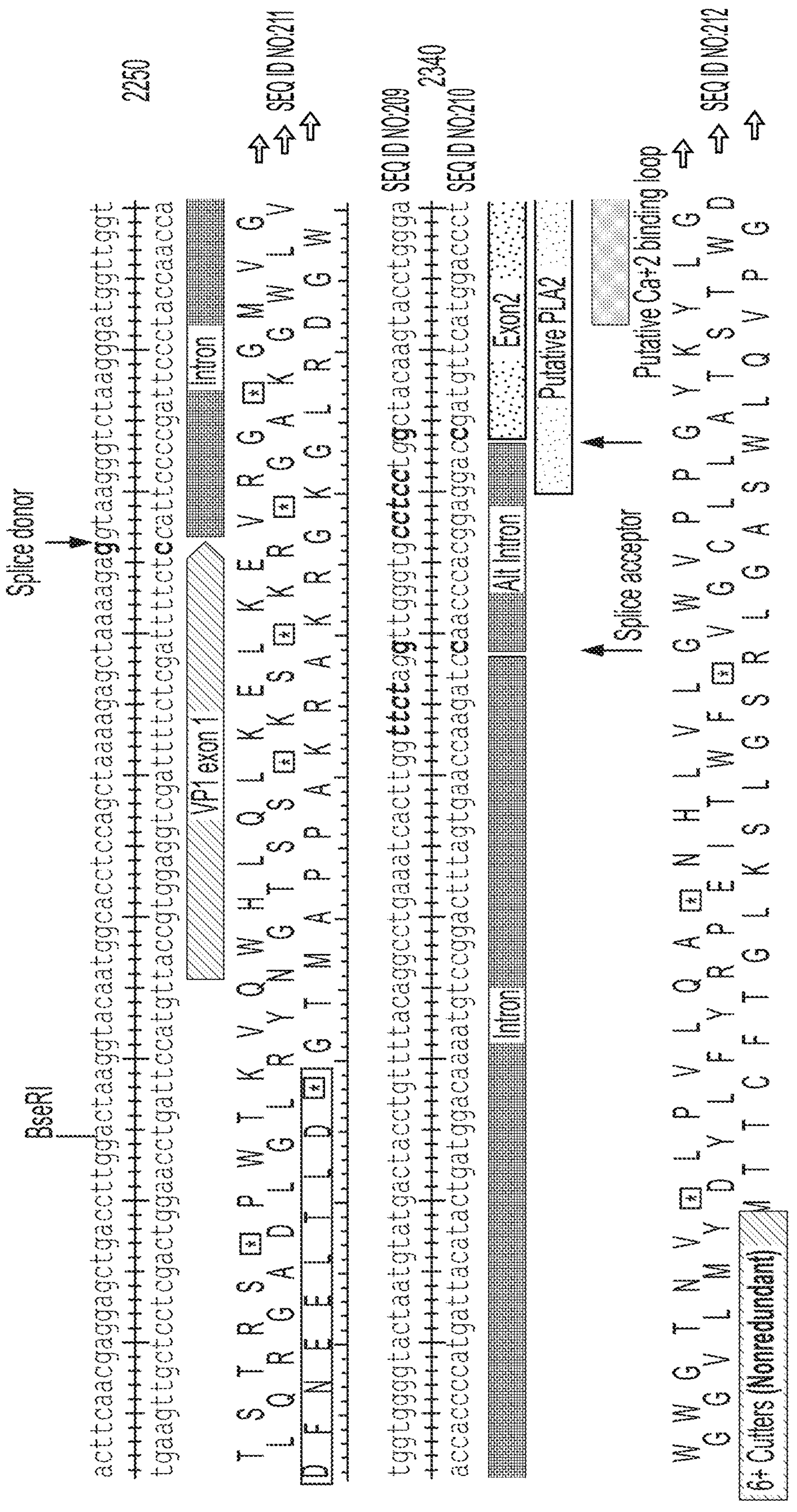
FIG. 5 shows an image depicting adjacent splice acceptor/donor sequences between a NLS (KRAKRG-SEQ ID NO: 146) and a PLA2 motif that can result in deletion of a five amino acid motif in a reference rat H-1 parvovirus (H-1PV) VP1 capsid polypeptide sequence, according to an embodiment of the present disclosure.
Figure 6:
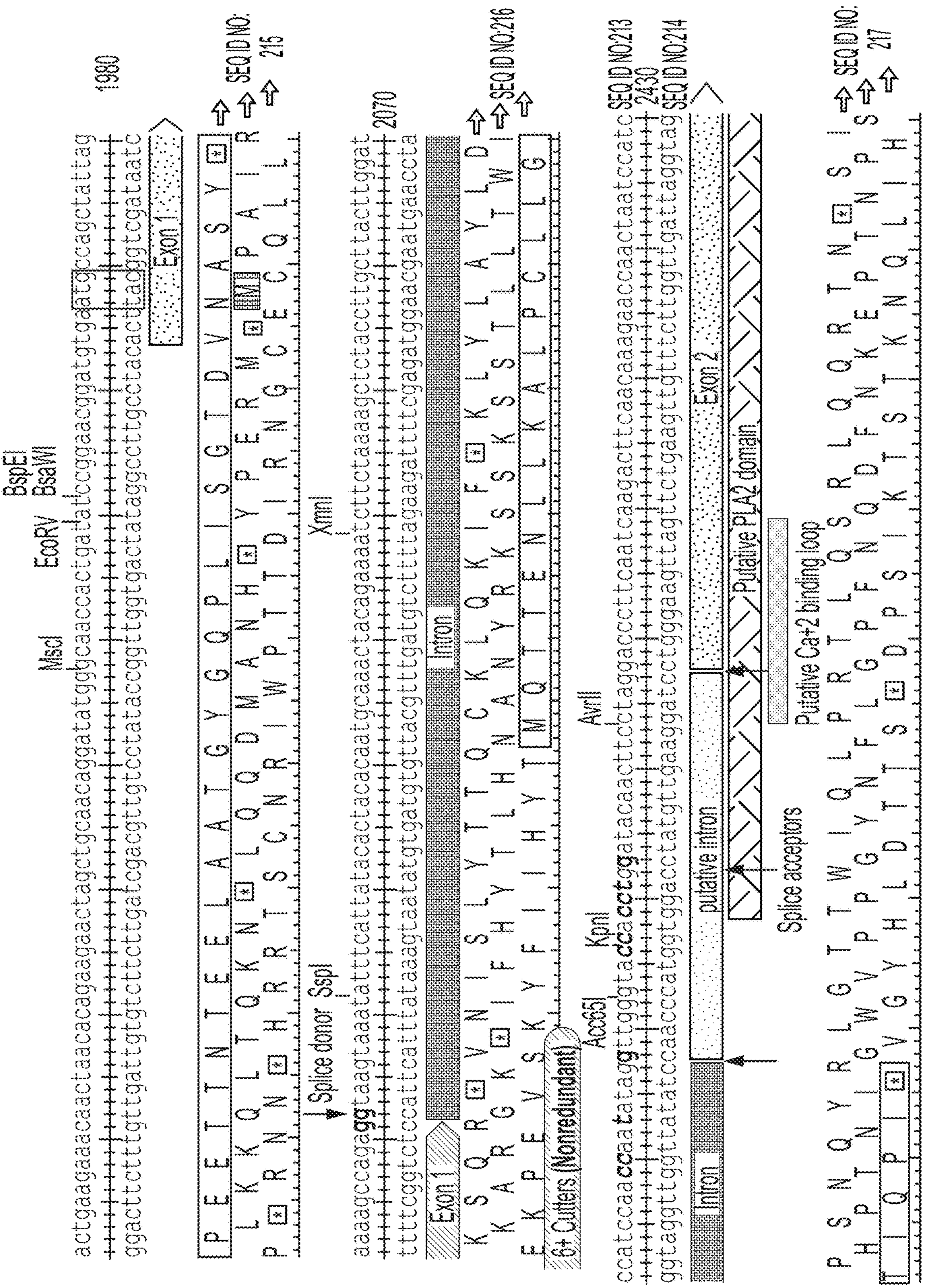
FIG. 6 shows an image depicting adjacent donor/acceptor sequences between a NLS (KARG-SEQ ID NO: 147) and a PLA2 motif that can result in deletion or partial deletion of a five amino acid motif in a reference cutavirus (CuV) VP1 capsid polypeptide sequence, according to an embodiment of the present disclosure.
Figure 7:
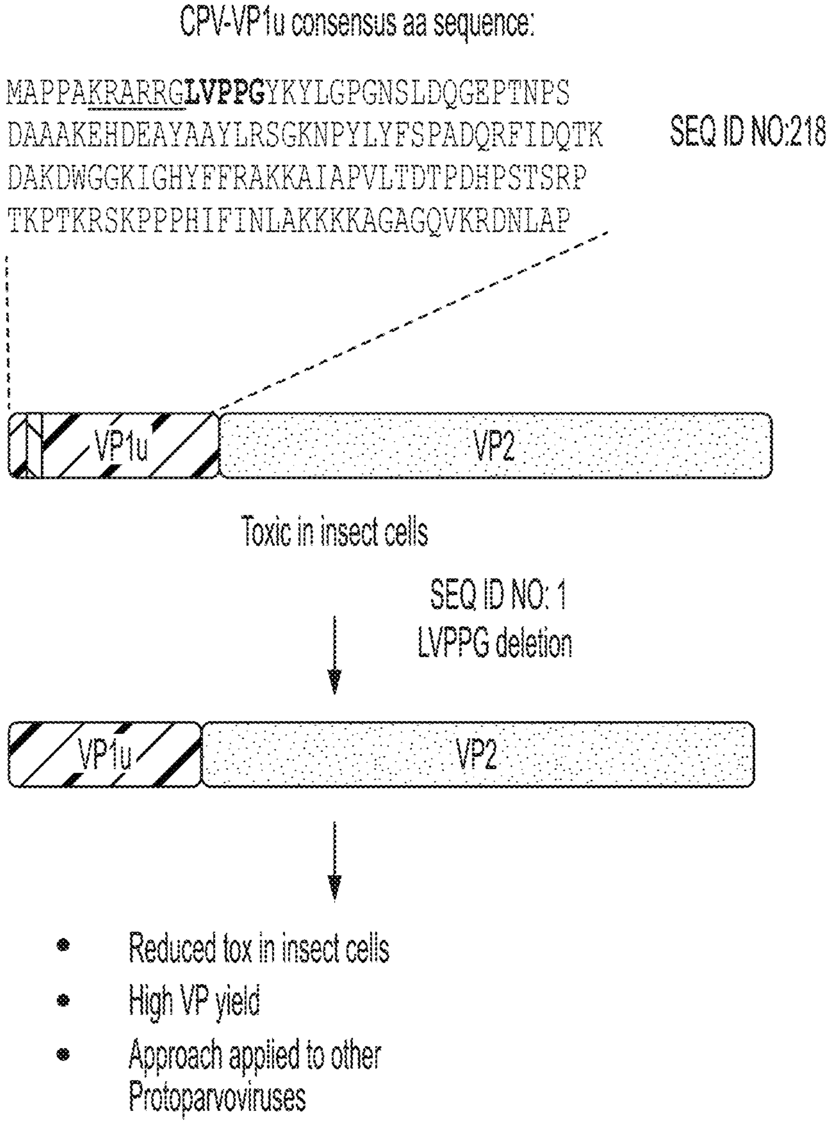
FIG. 7 shows a schematic depicting deletion of a five amino acid motif in a VP1u region of a canine parvovirus (CPV) VP1 capsid polypeptide, according to an embodiment of the present disclosure. In some embodiments, such a deletion leads to reduced toxicity in insect cells, high capsid yield. Moreover, the present disclosure describes that this approach can be applied to other protoparvoviruses.

The present disclosure recognizes that an adjacent splice donor sequence and a splice acceptor sequence occurs downstream of a conserved NLS and upstream of a conserved PLA2 within this region that results in deletion of a conserved amino acid motif (see FIG. 7). The present disclosure also recognizes that this splice variant can reduce VP1 capsid polypeptide toxicity. The present disclosure also recognizes that this splice variant can increase virion potency. It is an insight of the present disclosure that a splice variant does not necessarily occur in host cells as described herein. Moreover, as described herein, it is an insight of the present disclosure that adjacent splice donor/acceptor sequences between a NLS and initiation of a PLA2 motif are conserved across a variety of protoparvovirus species. For example, canine parvovirus (CPV) sequence analysis depicted in FIG. 3 shows adjacent splice donor/acceptor sequences between a NLS (KRARRG) and initiation of a PLA2 motif that results in deletion of a five amino acid motif. As another example, FIG. 4 shows two adjacent donor/acceptor sequences between a NLS (KRAKRG) and a PLA2 motif that can result in deletion of a five amino acid motif in a reference minute virus of mice (MVM) VP1 capsid polypeptide sequence. Moreover, FIG. 5 shows adjacent splice acceptor/donor sequences between a NLS (KRAKRG) and a PLA2 motif that can result in deletion of a five amino acid motif in a reference rat H-1 parvovirus (H-1PV) VP1 capsid polypeptide sequence. As another example, FIG. 6 shows adjacent donor/acceptor sequences between a NLS (KARG) and a PLA2 motif that can result in deletion or partial deletion of a five amino acid motif in a reference cutavirus (CuV) VP1 capsid polypeptide sequence.

Accordingly, without wishing to be bound to any theory, it is an insight of the present example that protoparvovirus VP1 capsid polypeptide toxicity can be reduced by engineering compositions, preparations, constructs, virions, population of virions, and host cells comprising a protoparvovirus variant VP1 capsid polypeptide as described herein.

Example 2: A Protoparvovirus Variant VP1 Capsid Polypeptide in Host Cells Exhibited Increased Potency and Reduced Toxicity in Host Cells The present example provides exemplary compositions, preparations, constructs, virions, population of virions, and host cells for gene therapy and related methods that show increased potency and reduced toxicity in host cells as described herein.

Figure 8:
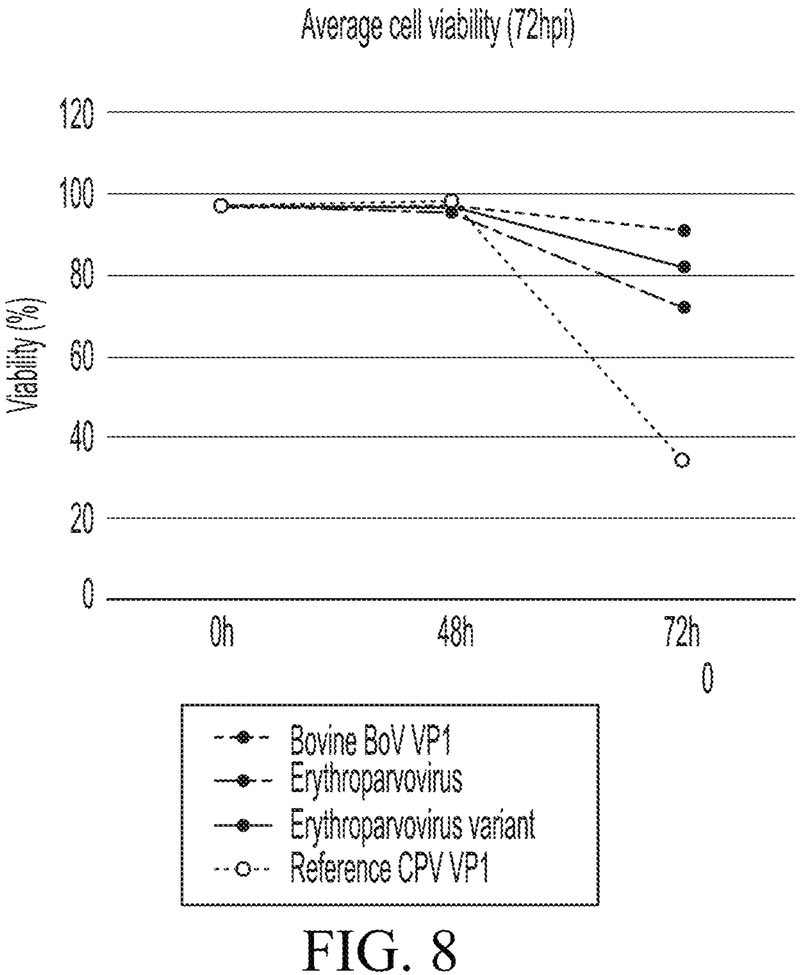
FIG. 8 shows a graph demonstrating that a canine parvovirus (CPV) reference VP1 capsid polypeptide (1) exhibited elevated toxicity in insect cells at 72 hours post-infection (hpi), and (2) affected VP1 capsid polypeptide yield, compared to other genuses in family parvovirinae (such as bocavirus or erythroparvovirus), according to an embodiment of the present disclosure.

Virions comprising a CPV reference VP1 capsid polypeptide encoded by a CPV reference VP1 capsid coding sequence according to SEQ ID NO: 126) were generated and tested in host cells according to standard protocols. As shown in FIG. 8, a CPV reference VP1 capsid polypeptide showed elevated toxicity in insect cells at 72 hours post-infection (hpi), affecting VP1 capsid polypeptide yield, compared to other genuses in family parvovirinae (such as bocavirus or erythroparvovirus).

Figure 9:
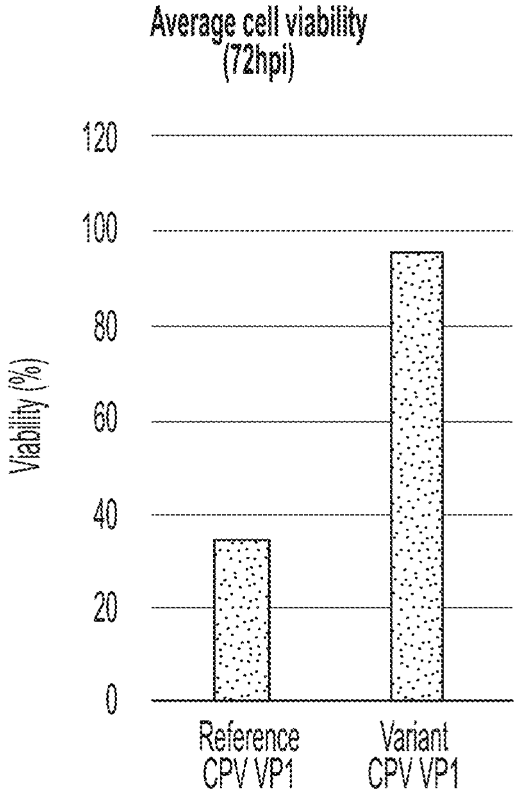
FIG. 9 shows a graph demonstrating that a canine parvovirus (CPV) variant VP1 capsid polypeptide exhibited more than double the average percent cell viability at 72 hpi compared to a CPV reference VP1 capsid polypeptide, according to an embodiment of the present disclosure.
Figure 10:
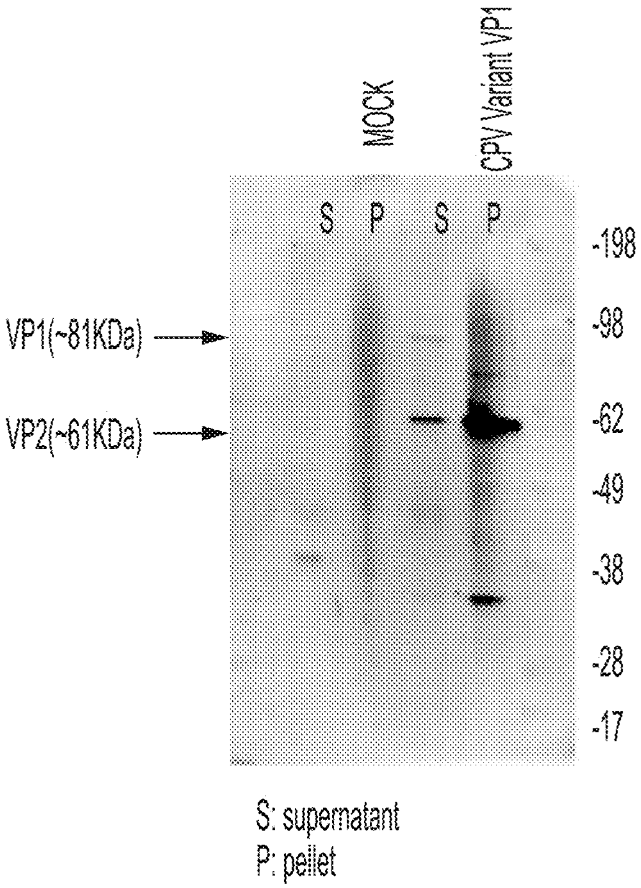
FIG. 10 shows a Western Blot that measured levels of canine parvovirus (CPV) VP1 capsid polypeptide and VP2 capsid polypeptide in the supernatant and pellet of insect (Sf9) cells infected with a baculovirus construct (BEV) comprising a CPV variant VP1 capsid coding sequence, according to an embodiment of the present disclosure.

An exemplary construct comprising deletion of a five amino acid motif (LVPPG-SEQ ID NO: 1) immediately downstream of a NLS within the CPV VP1 capsid polypeptide (e.g., a construct according to SEQ ID NO: 121) was designed and tested in host cells according to standard protocols. As described by Example 1, this deleted region is conserved across other protoparvovirus species. As shown in FIG. 9, a CPV variant VP1 capsid polypeptide construct showed more than double the average percent cell viability at 72 hpi compared to a CPV reference VP1 capsid polypeptide. Further, FIG. 10 depicts detection of CPV VP1 and VP2 capsid polypeptides by Western Blot in the supernatant and pellet of insect (Sf9) cells infected with a baculovirus construct (BEV) expressing a CPV variant VP1 construct. The present disclosure recognizes that other exemplary protoparvovirus variant VP1 capsid polypeptides described herein can be used.

Accordingly, in some embodiments, the present example demonstrates a protoparvovirus variant VP1 capsid polypeptides described herein increases potency and reduces toxicity of exemplary virions comprising a protoparvovirus variant VP1 capsid polypeptide in host cells.

Example 3: Exemplary Constructs Comprising a Protoparvovirus Variant VP1 Capsid Polypeptide in a Host Cell Increased VP1 Initiation Relative to a Protoparvovirus Reference VP1 Capsid Polypeptide The present example demonstrates that modifications and/or selections of components of constructs encoding a protoparvovirus VP1 capsid polypeptide or protoparvovirus variant VP1 capsid polypeptide described herein, can increase VP1 initiation in host cells. Moreover, the present example demonstrates that modifications and/or selections of components of constructs encoding a protoparvovirus VP1 capsid polypeptide or protoparvovirus variant VP1 capsid polypeptide described herein, can increase potency in host cells.

FIG. 11 depicts exemplary protoparvovirus construct elements that can improve production and/or reduce toxicity of protoparvovirus variant VP1 capsid polypeptides in host cells, according to an embodiment of the present disclosure. In some embodiments, a construct element includes one or more of an expression control sequence, a 5' UTR, a VP1 translation initiation sequence, or a combination thereof.

In some embodiments, selection of an expression control sequence having certain components can improve production of a protoparvovirus VP1 capsid polypeptide. In some embodiments, selection of an expression control sequence having certain characteristics can reduce toxicity of a protoparvovirus VP1 capsid polypeptide. In some embodiments a characteristic is strong expression. In some embodiments a characteristic is weak expression. In some embodiments a characteristic is delayed expression. In some embodiments a characteristic is early expression.

For example, polyhedrin is an exemplary expression control sequence that can initiate strong and/or late expression of a VP1 capsid polypeptide. As another example, P10 is an exemplary expression control sequence that can initiate strong and/or late expression of a VP1 capsid polypeptide. Moreover, OpiE1 is an exemplary expression control sequence that can initiate weak and/or early expression of a VP1 capsid polypeptide.

Among other things, the present example recognizes that selection of a 5' UTR sequence can improve production and/or reduce toxicity of a VP1 capsid polypeptide. In some embodiments, a 5'UTR sequence is a stretch of nucleotides between an expression control sequence and a VP1 capsid coding sequence (referred to herein as "a nucleotide spacer sequence").

In some embodiments, a 5'UTR sequence comprises a nucleotide spacer sequence. In some embodiments, a 5' UTR sequence comprises a nucleotide spacer sequence that does not comprise an alternative translation initiation sequence (e.g., so translation does not start before a VP1 capsid coding sequence). In some embodiments, a 5' UTR sequence comprises a nucleotide spacer sequence and a Kozak consensus sequence. In some embodiments, a 5' UTR sequence does not comprise a nucleotide spacer sequence. In some embodiments, there is no nucleotide spacer sequence between an expression control sequence and a VP1 capsid coding sequence.

In some embodiments, a 5' UTR sequence comprises a nucleotide spacer sequence as shown in Table 6.

TABLE 6

| Sequence Name | Sequence | SEQ ID NO: |
|---|---|---|
| Exemplary Nucleotide Spacer Sequence 1 | ATTCCGGATTATTCATACCGT CCCACCATCGGGCGCGGATCT | SEQ ID NO: 123 |
| Exemplary Nucleotide Spacer Sequence 2 (without alternative translation initiation sequences) | ACTCCGGACTACTGATACCGT CCCACTTTCGGGCGCTTACCT | SEQ ID NO: 124 |

In some embodiments, a Kozak sequence comprises a eukaryotic (GCCGCC - - - G), viral-derived (CCTGT-TAAG), or alternate sequence (AAA).

In some embodiments, a protoparvovirus variant VP1 capsid polypeptide construct comprises an alternative translation initiation sequence such as CTG, ATC, TTG and ACG.

Figure 12:
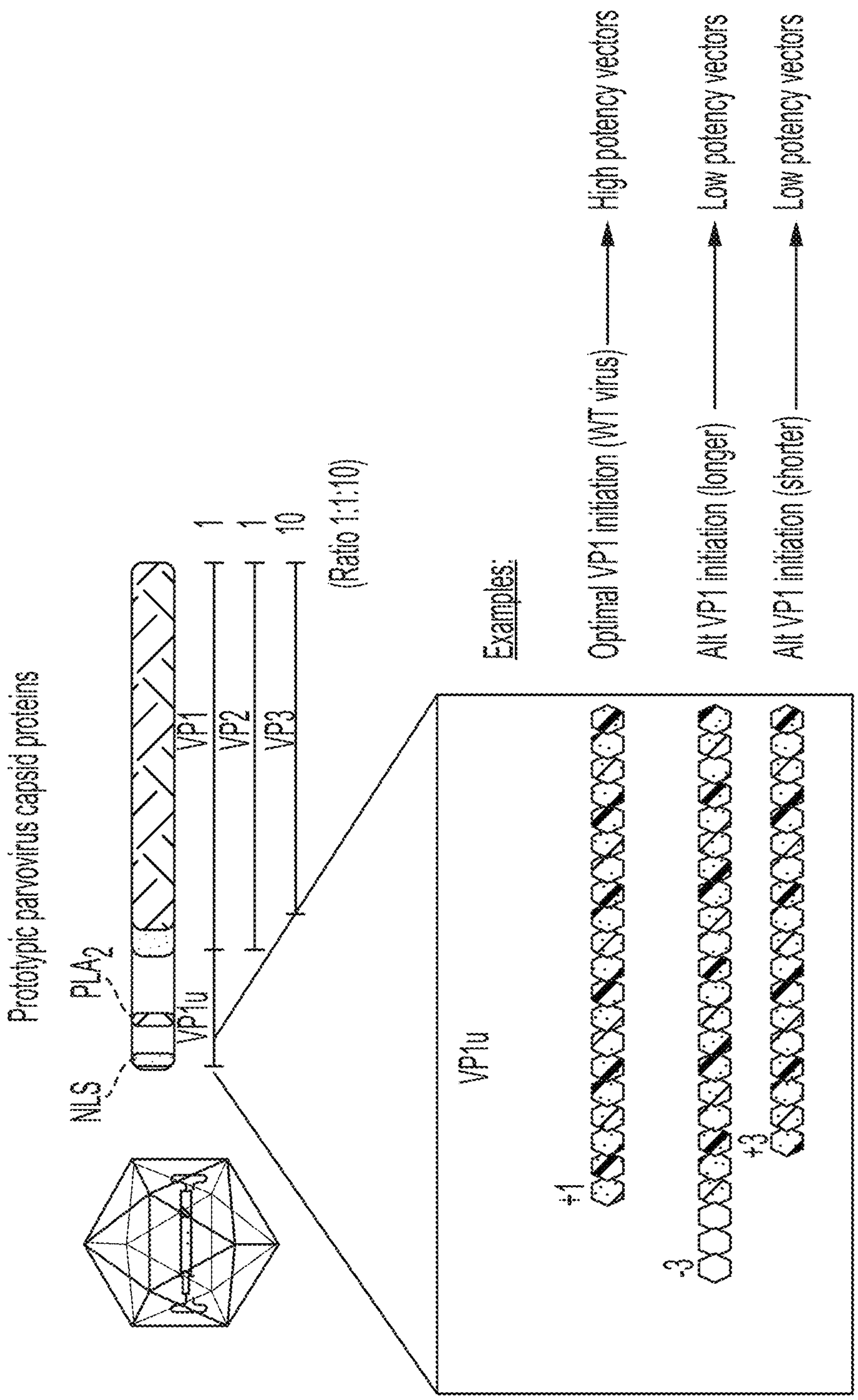
FIG. 12 shows a schematic that depicts alternative initiation of a VP1 capsid polypeptide leads to a longer or shorter VP1 capsid polypeptide which can negatively impact virion potency, according to an embodiment of the present disclosure.

Moreover, the present example describes that leaky scanning of an mRNA sequence for expression of VP1, VP2, and VP3 capsid polypeptides in a suitable ratio, for example, a VP1: VP2: VP3 ratio of 1:1:10, can result in alternate initiation of a VP1 capsid polypeptide. As described by this Example, alternative initiation of a VP1 capsid polypeptide leads to a longer or shorter VP1 capsid polypeptide which can negatively impact virion potency, as shown in FIG. 12. Appropriate VP1 capsid polypeptide initiation leads to high potency virions.

Accordingly, in some embodiments, the present disclosure describes compositions, preparations, constructs, virions, population of virions, and host cells comprising a protoparvovirus variant VP1 capsid polypeptide can exhibit increased VP1 initiation relative to a reference VP1 capsid polypeptide.

Example 4: Increased AAV Genome Trans-Encapsidation Generates a High Filled/Empty Capsid Ratio in a Host System The present example demonstrates that modifications and/or selections of components of constructs encoding a protoparvovirus VP1 capsid polypeptide or protoparvovirus variant VP1 capsid polypeptide described herein, can increase AAV genome trans-encapsidation within a protoparvovirus variant VP1 capsid polypeptide in host cells.

Figure 13:
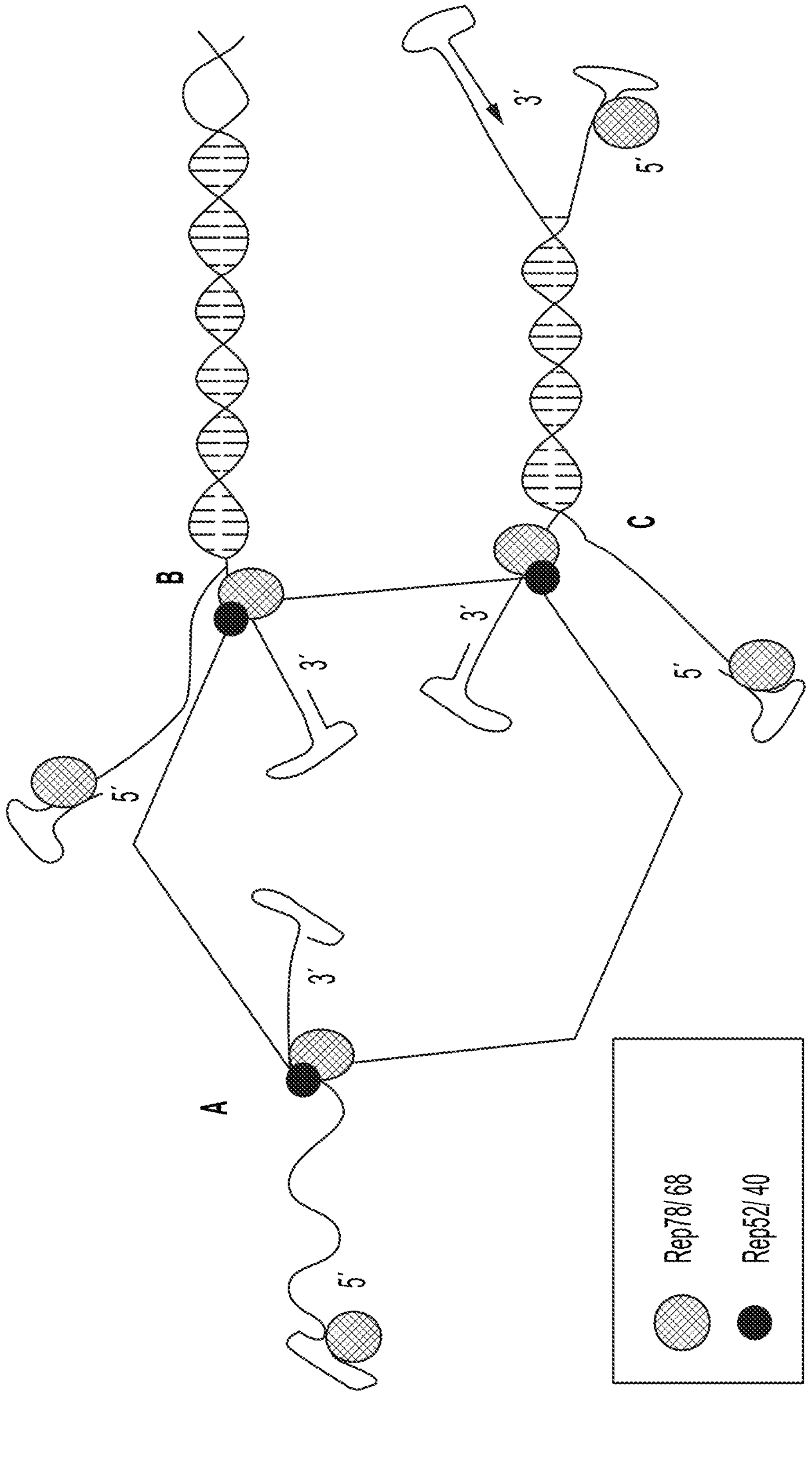
FIG. 13 shows a schematic depicting models for involvement of AAV Rep helicases as motors to incorporate a viral genome into a preformed capsid, as (A) a single-stranded molecule using the initial 'scanning' function before the first duplexed base pairs are encountered or (B) by unwinding a double-stranded dimer or multimer genome on a capsid surface at the same time or (C) simultaneous replication (arrow) of a double-stranded monomer genome being packaged, according to an embodiment of the present disclosure.

Parvovirus non-structural proteins play a key role in different steps of a virus life cycle, from DNA replication and transcription regulation to genome packaging. While an N-terminus region of a full-length NS (e.g., Rep78 in AAVs or NS1 in autonomous parvoviruses) participates in genome replication, recognizing the viral genome in a sequence-specific manner, a C-terminus region (e.g., Rep 52/40 in AAVs) contains an SF3 helicase domain. A SF3 helicase domain acts as a motor to incorporate a viral genome into a preformed capsid, as shown in FIG. 13 (see also King et al. EMBO J. 2001 Jun. 15; 20(12): 3282-91, doi: 10.1093/emboj/20.12.3282, the entire contents of which are hereby incorporated by reference herein). In some embodiments, without wishing to be bound to any theory, the present disclosure describes that an SF3 helicase domain of a NS1 of a protoparvovirus can apply a force to incorporate an AAV genome into a protoparvovirus variant VP1 capsid polypeptide in an ATP-dependent manner. Without wishing to be bound to any theory, this function is believed to take place via an AAV packaging complex comprising an immobilized helicase complex, composed of large and small Rep proteins, on a capsid surface. As shown in FIG. 13, a genome is translocated through an AAV packaging complex and into a capsid either (A) as a single-stranded molecule using the initial 'scanning' function before the first duplexed base pairs are encountered or (B) by unwinding a double-stranded dimer or multimer genome on a capsid surface at the same time or (C) simultaneous replication (arrow) of a double-stranded monomer genome being packaged.

In view of functional co-evolution of parvovirus NS proteins and respective capsids, it is an insight of the present disclosure that co-expression of the C-terminus region of a NS protein from a cognate autonomous protoparvovirus provides a more efficient NS-capsid interaction, thus improving packaging of an AAV-derived genome (e.g., a transgene) into a respective capsid via a helicase domain, in a sequence-independent manner.

Accordingly, in some embodiments, the present disclosure describes compositions, preparations, constructs, virions, population of virions, and host cells can exhibit increased encapsidation via co-expression of NS1.

Example 5: Exemplary Virions Comprising a Parvovirus VP1 Capsid Polypeptide Produced in Host HEK293 Cells The present Example confirms that exemplary compositions, preparations, nucleotide sequences, and methods described herein can be used to produce virions comprising a protoparvovirus VP1 capsid polypeptide in mammalian host cells e.g., HEK293 cells.

Figure 14:
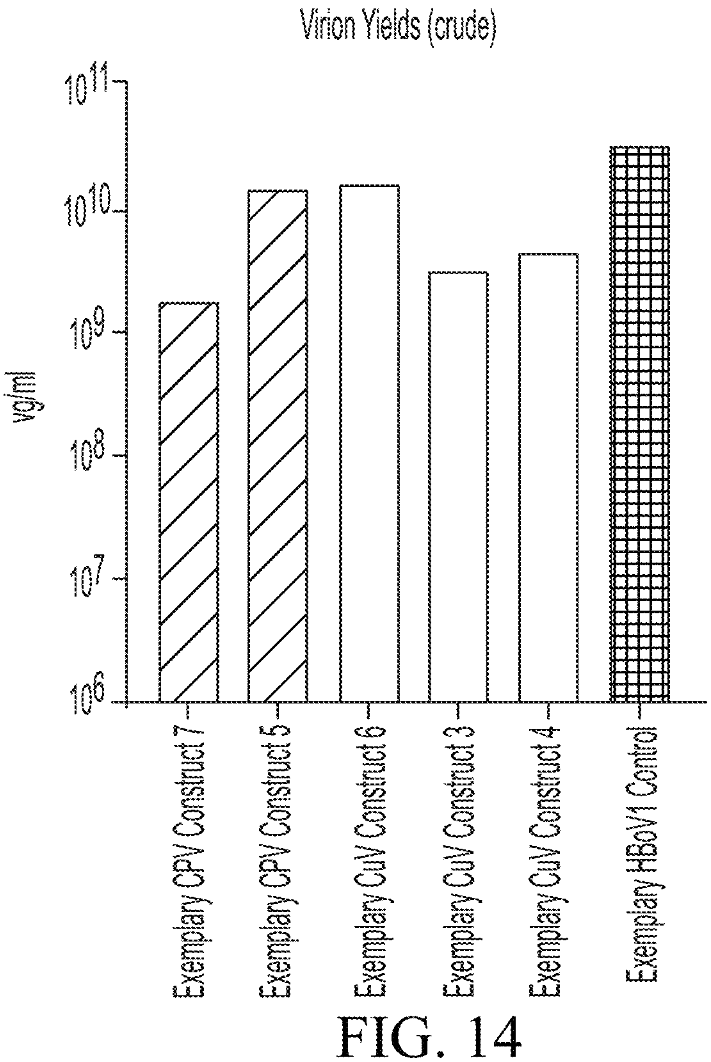
FIG. 14 shows virion yields (vg/mL) of virions comprising a CPV VP1 capsid polypeptide encoded by a VP1 capsid coding sequence according to SEQ ID NO: 148 (Exemplary CPV Construct 7) produced in host HEK293 cells, virions comprising a CPV VP1 capsid polypeptide encoded by a VP1 capsid coding sequence according to SEQ ID NO: 130 (Exemplary CPV Construct 5) produced in host HEK293 cells, virions comprising a CuV VP1 capsid polypeptide encoded by a VP1 capsid coding sequence according to SEQ ID NO: 139 (Exemplary CuV Construct 6) produced in host HEK293 cells, virions comprising a CuV VP1 capsid polypeptide encoded by a VP1 capsid coding sequence according to SEQ ID NO: 133 (Exemplary CuV Construct 3) produced in host HEK293 cells, virions comprising a CuV VP1 capsid polypeptide encoded by a VP1 capsid coding sequence according to SEQ ID NO: 134 (Exemplary CuV Construct 4) produced in host HEK293 cells, and virions comprising an exemplary control HBoV1 capsid polypeptide produced in host HEK293 cells.
Figure 21:
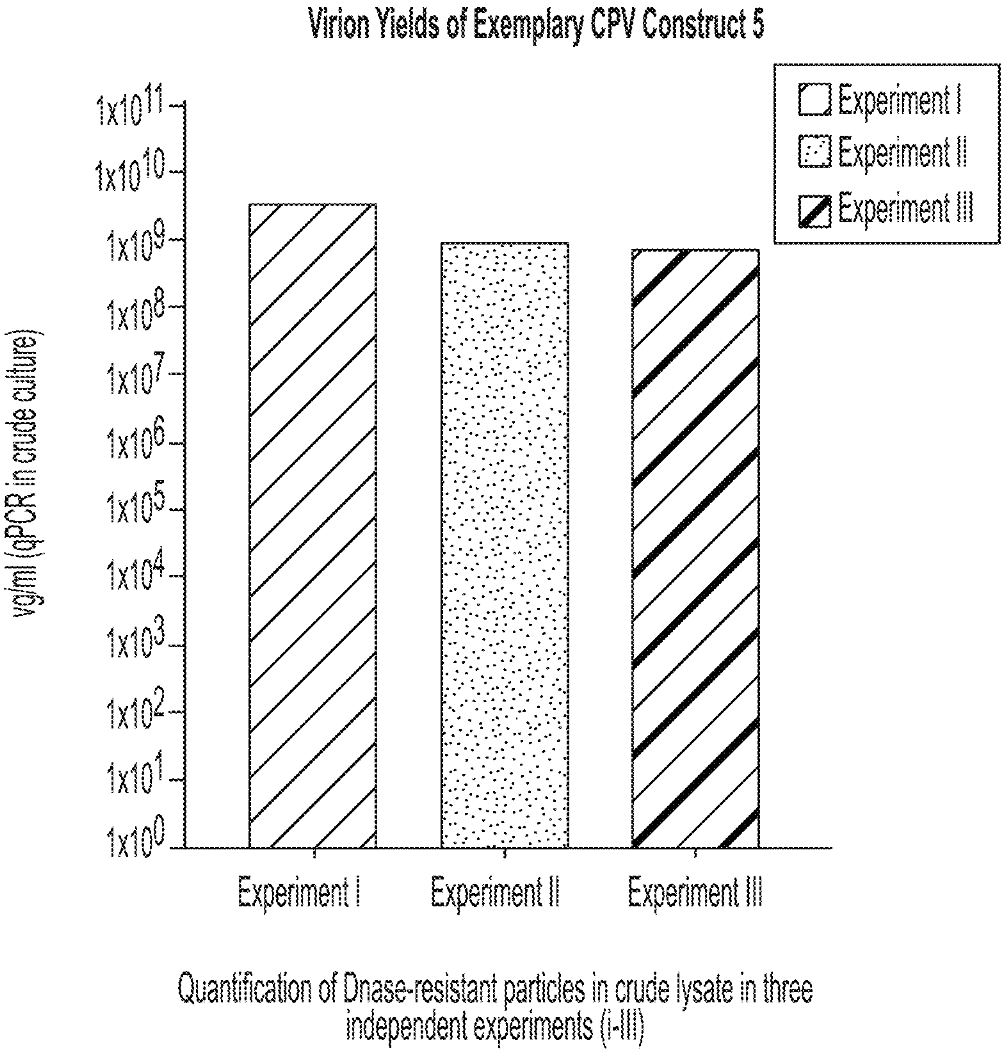
FIG. 21 shows a bar graph depicting virion yields (vg/mL) of virions comprising a CPV VP1 capsid polypeptide encoded by a VP1 capsid coding sequence according to SEQ ID NO: 130 (Exemplary CPV Construct 5) produced in host HEK293T cells, across three independent experiments.
Figure 22:
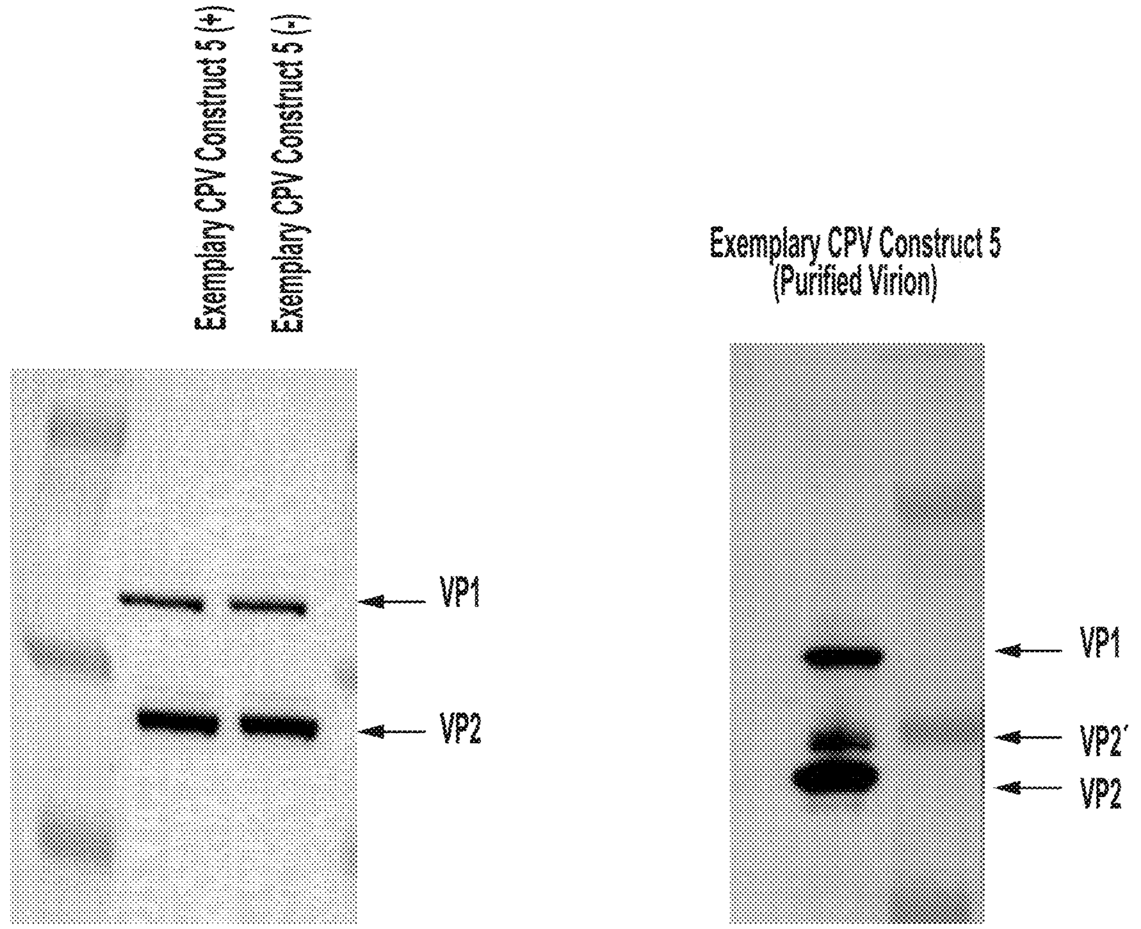
FIG. 22 shows (left) a western blot analysis of capsid composition and amounts of VP1 and VP2 capsid polypeptides of virions comprising a CPV VP1 capsid polypeptide encoded by a VP1 capsid coding sequence according to SEQ ID NO: 130 (Exemplary CPV Construct 5) with (+) and without (−) trypsin treatment conditions, produced in host HEK293 cells and (right) a western blot analysis of capsid composition and amounts of VP1, a VP2 cleavage product (VP2'), and VP2 capsid polypeptides of virions comprising a CPV VP1 capsid polypeptide encoded by a VP1 capsid coding sequence according to SEQ ID NO: 130 (Exemplary CPV Construct 5).

As shown in FIG. 14, (1) virions comprising a CPV VP1 capsid polypeptide encoded by a VP1 capsid coding sequence according to SEQ ID NO: 130 (Exemplary CPV Construct 5) and (2) virions comprising a CuV VP1 capsid polypeptide encoded by a VP1 capsid coding sequence according to SEQ ID NO: 139 (Exemplary CuV Construct 6) produced similar virion yields (vg/mL) in host HEK293 cells relative to virions comprising an exemplary control HBoV1 capsid polypeptide. Moreover, as shown in FIG. 14, (3) virions comprising a CPV VP1 capsid polypeptide encoded by a VP1 capsid coding sequence according to SEQ ID NO: 148 (Exemplary CPV Construct 7), (4) virions comprising a CuV VP1 capsid polypeptide encoded by a VP1 capsid coding sequence according to SEQ ID NO: 133 (Exemplary CuV Construct 3), and (5) virions comprising a CuV VP1 capsid polypeptide encoded by a VP1 capsid coding sequence according to SEQ ID NO: 134 (Exemplary CuV Construct 4) generated reasonable quantities of virion yields (vg/mL) in host HEK293 cells, despite being an order magnitude less than quantities of virion yields (vg/mL) of (6) virions comprising an exemplary control HBoV1 capsid polypeptide in host HEK293 cells. FIG. 21 shows comparable virion yields (vg/mL) of virions comprising a CPV VP1 capsid polypeptide encoded by a VP1 capsid coding sequence according to SEQ ID NO: 130 (Exemplary CPV Construct 5) produced in host HEK293T cells across three independent experiments.

Figure 15A:
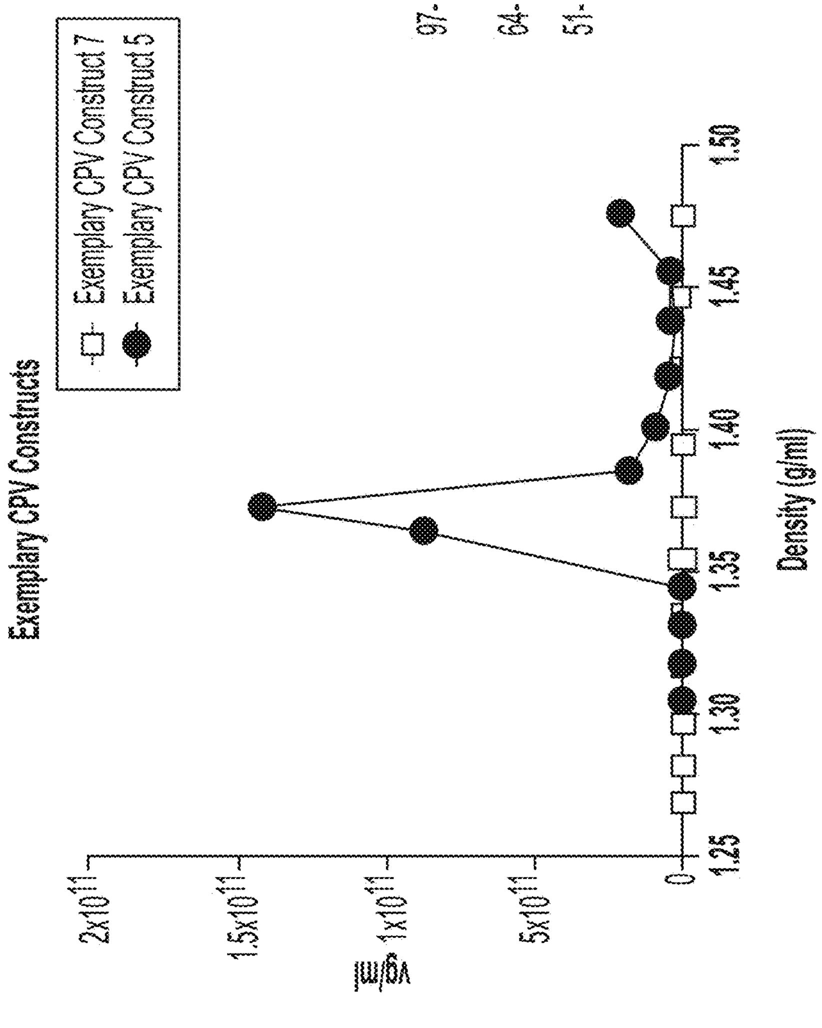
FIG. 15A shows virion density of virions (or particles) that were detected and isolated via ultracentrifugation in CsCl of virions comprising a CPV VP1 capsid polypeptide encoded by a VP1 capsid coding sequence according to SEQ ID NO: 148 (Exemplary CPV Construct 7), and virions comprising a CPV VP1 capsid polypeptide encoded by a VP1 capsid coding sequence according to SEQ ID NO: 130 (Exemplary CPV Construct 5).
Figure 15B:
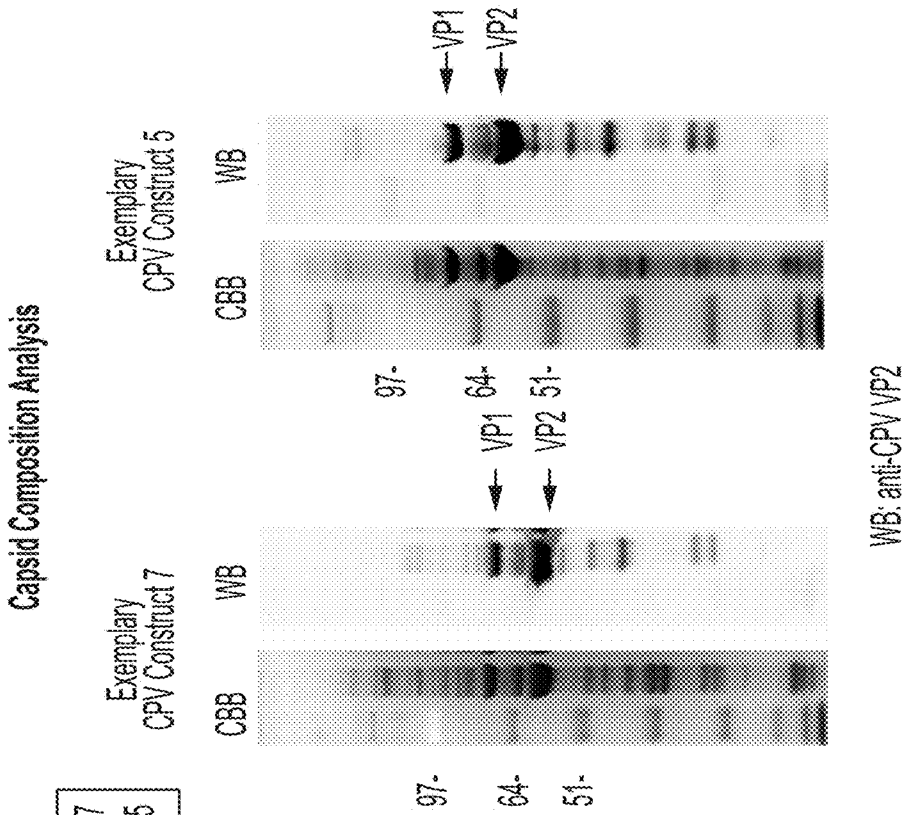
FIG. 15B shows a western blot analysis of capsid composition and amounts of VP1 and VP2 capsid polypeptides of virions comprising a CPV VP1 capsid polypeptide encoded by a VP1 capsid coding sequence according to SEQ ID NO: 148 (Exemplary CPV Construct 7), and virions comprising a CPV VP1 capsid polypeptide encoded by a VP1 capsid coding sequence according to SEQ ID NO: 130 (Exemplary CPV Construct 5) produced in host HEK293 cells.

FIG. 15A shows fractions comprising filled virions (or particles) that were detected and isolated via ultracentrifugation in CsCl of virions comprising a CPV VP1 capsid polypeptide encoded by a VP1 capsid coding sequence according to SEQ ID NO: 148 (Exemplary CPV Construct 7) and virions comprising a CPV VP1 capsid polypeptide encoded by a VP1 capsid coding sequence according to SEQ ID NO: 130 (Exemplary CPV Construct 5). FIG. 15B shows a western blot analysis of capsid composition and amounts of VP1 and VP2 capsid polypeptides of virions comprising a CPV VP1 capsid polypeptide encoded by a VP1 capsid coding sequence according to SEQ ID NO: 148 (Exemplary CPV Construct 7), and virions comprising a CPV VP1 capsid polypeptide encoded by a VP1 capsid coding sequence according to SEQ ID NO: 130 (Exemplary CPV Construct 5) produced in host HEK293 cells.

Figure 16A:
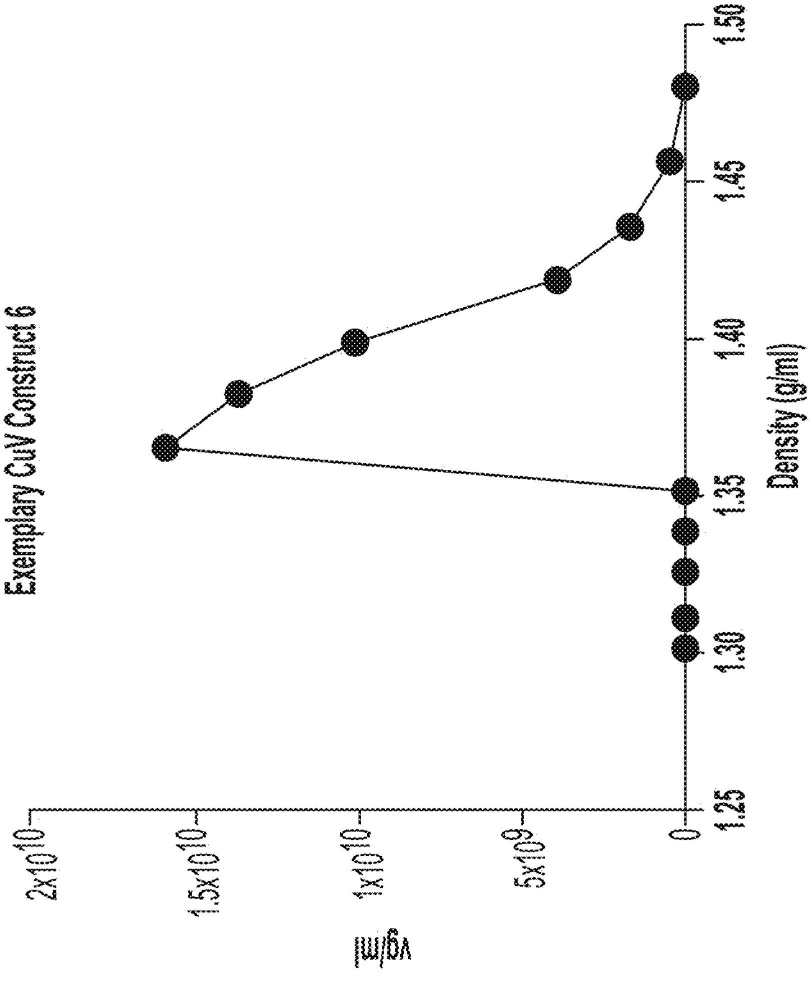
FIG. 16A shows virion density of virions (or particles) that were detected and isolated via ultracentrifugation in CsCl of virions comprising a CuV VP1 capsid polypeptide encoded by a VP1 capsid coding sequence according to SEQ ID NO: 139 (Exemplary CuV Construct 6) produced in HEK293 cells.
Figure 16B:
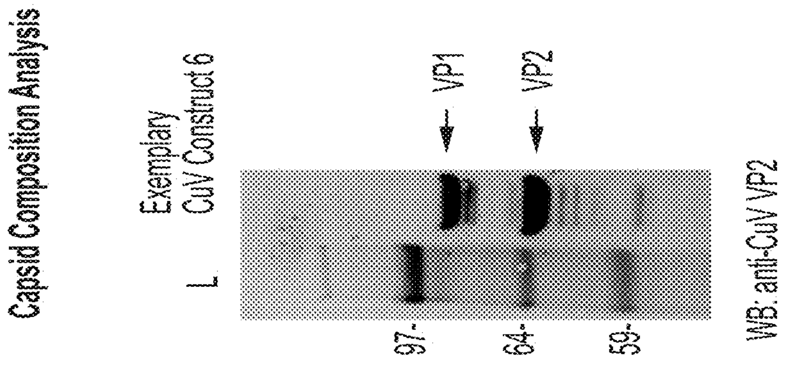
FIG. 16B shows a western blot analysis of capsid composition and amounts of VP1 and VP2 capsid polypeptides of virions comprising a CuV VP1 capsid polypeptide encoded by a VP1 capsid coding sequence according to SEQ ID NO: 139 (Exemplary CuV Construct 6) produced in host HEK293 cells.

FIG. 16A shows fractions comprising filled virions (or particles) that were detected and isolated via ultracentrifugation in CsCl of virions comprising a CuV VP1 capsid polypeptide encoded by a VP1 capsid coding sequence according to SEQ ID NO: 139 (Exemplary CuV Construct 6) produced in HEK293 cells. FIG. 16B shows a western blot analysis of capsid composition and amounts of VP1 and VP2 capsid polypeptides of virions comprising CuV VP1 capsid polypeptide encoded by a VP1 capsid coding sequence according to SEQ ID NO: 139 (Exemplary CuV Construct 6) produced in host HEK293 cells.

Figure 17A:
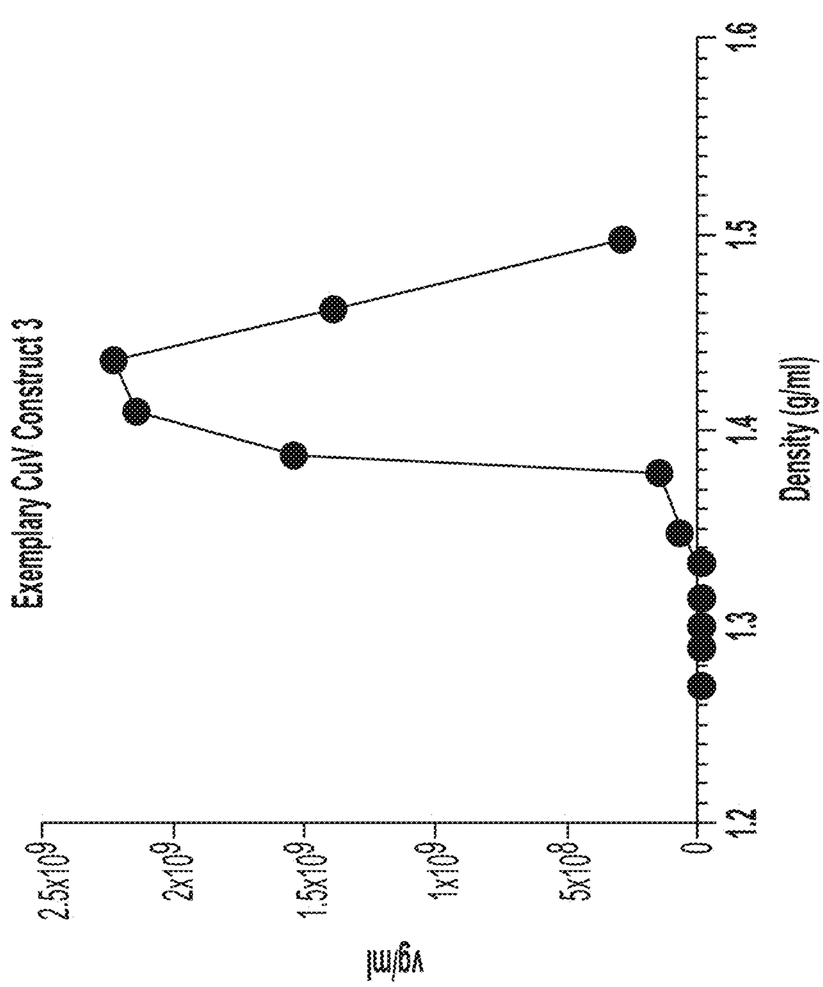
FIG. 17A shows virion density of virions (or particles) that were detected and isolated via ultracentrifugation in CsCl of virions, a CuV VP1 capsid polypeptide encoded by a VP1 capsid coding sequence according to SEQ ID NO: 133 (Exemplary CuV Construct 3) produced in HEK293 cells.
Figure 17B:
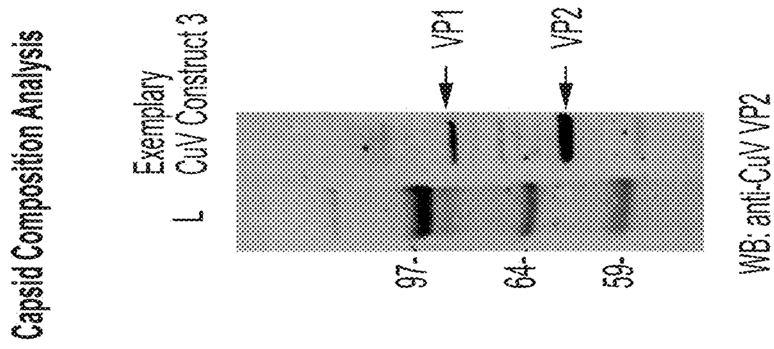
FIG. 17B shows a western blot analysis of capsid composition and amounts of VP1 and VP2 capsid polypeptides of virions comprising a CuV VP1 capsid polypeptide encoded by a VP1 capsid coding sequence according to SEQ ID NO: 133 (Exemplary CuV Construct 3) produced in host HEK293 cells.

FIG. 17A shows fractions comprising filled virions (or particles) that were detected and isolated via ultracentrifugation in CsCl of virions a CuV VP1 capsid polypeptide encoded by a VP1 capsid coding sequence according to SEQ ID NO: 133 (Exemplary CuV Construct 3) produced in HEK293 cells. FIG. 17B shows a western blot analysis of capsid composition and amounts of VP1 and VP2 capsid polypeptides of virions comprising a CuV VP1 capsid polypeptide encoded by a VP1 capsid coding sequence according to SEQ ID NO: 133 (Exemplary CuV Construct 3) produced in host HEK293 cells.

Figure 18B:
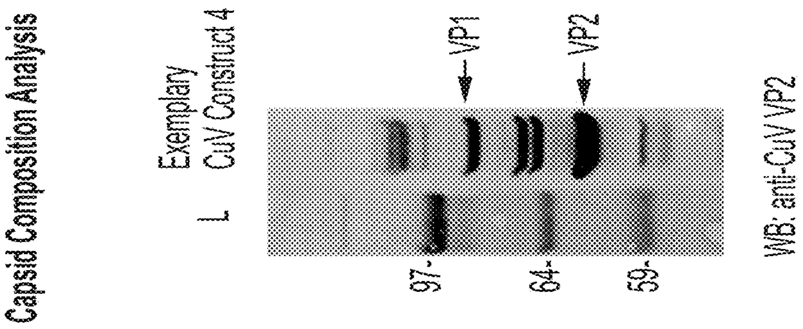
FIG. 18B shows a western blot analysis of capsid composition and amounts of VP1 and VP2 capsid polypeptides of virions comprising a CuV VP1 capsid polypeptide encoded by a VP1 capsid coding sequence according to SEQ ID NO: 134 (Exemplary CuV Construct 4) produced in host HEK293 cells.
Figure 18A:
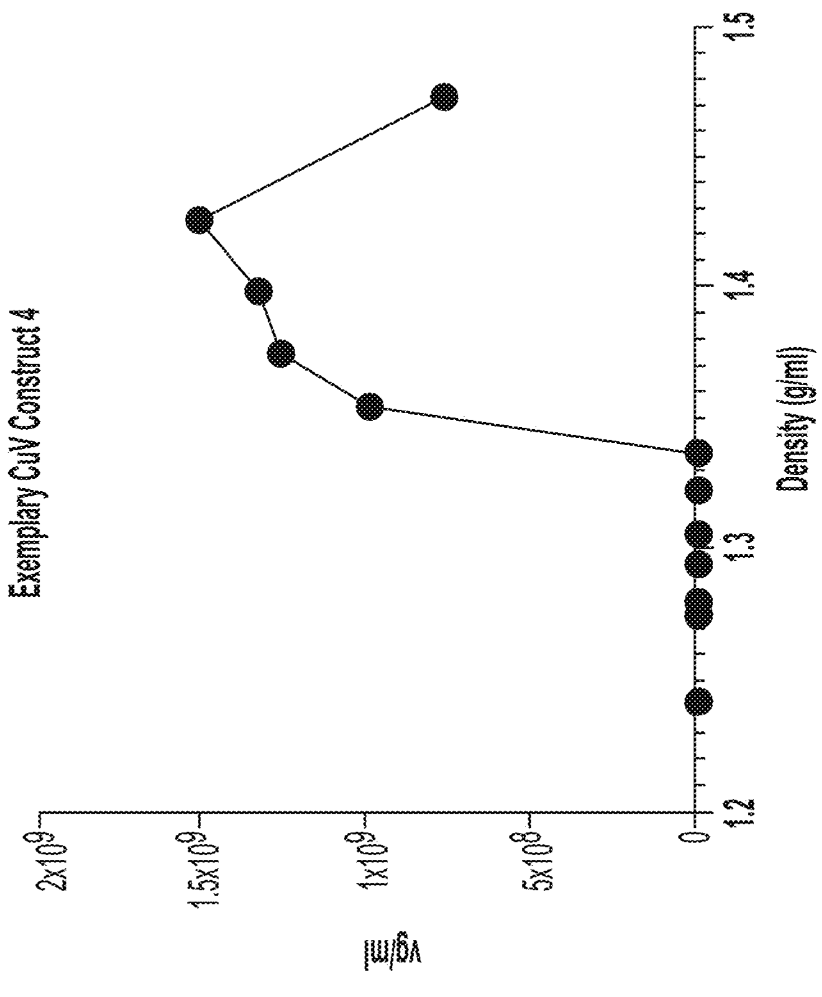
FIG. 18A shows virion density of virions (or particles) that were detected and isolated via ultracentrifugation in CsCl of virions comprising a CuV VP1 capsid polypeptide encoded by a VP1 capsid coding sequence according to SEQ ID NO: 134 (Exemplary CuV Construct 4) produced in HEK293 cells.

FIG. 18A shows fractions comprising filled virions (or particles) that were detected and isolated via ultracentrifugation in CsCl of virions comprising a CuV VP1 capsid polypeptide encoded by a VP1 capsid coding sequence according to SEQ ID NO: 134 (Exemplary CuV Construct 4) produced in HEK293 cells. FIG. 18B shows a western blot analysis of capsid composition and amounts of VP1 and VP2 capsid polypeptides of virions comprising a CuV VP1 capsid polypeptide encoded by a VP1 capsid coding sequence according to SEQ ID NO: 134 (Exemplary CuV Construct 4) produced in host HEK293 cells.

Therefore, the data shown in FIGS. 14-18B confirm efficient and robust production of virions comprising a CPV or CuV VP1 capsid polypeptide in mammalian cells. Moreover, the data also confirm that construct component design can influence virion production in host cells.

The present Example can be used with other protoparvovirus capsid polypeptides beyond CPV and CuV capsid polypeptides as described herein.

Accordingly, the present Example confirms that exemplary compositions, preparations, nucleotide sequences, and methods described herein can be used to produce virions comprising a protoparvovirus VP1 capsid polypeptide in mammalian host cells. Moreover, the present Example confirms that virions comprising an exemplary CPV VP1 capsid polypeptide as described herein can be produced in mammalian cells. Moreover, the present Example confirms that virions comprising an exemplary CuV VP1 capsid polypeptide as described herein can be produced in mammalian cells.

Example 6: Exemplary Virions Comprising a CPV Capsid Interact with a Transferrin Receptor The present Example provides exemplary compositions, preparations, constructs, virions, population of virions, which can interact with a transferrin receptor (TfR). In particular, for instance, the present Example demonstrates that a protoparvovirus VP1 capsid coding sequence encoding a VP1 capsid polypeptide sequence as described herein produced virions that were efficiently transduced into human neuroblastoma (e.g., SH-SY-5Y) cells and human kidney (e.g., HEK293T) cells.

Figure 20:
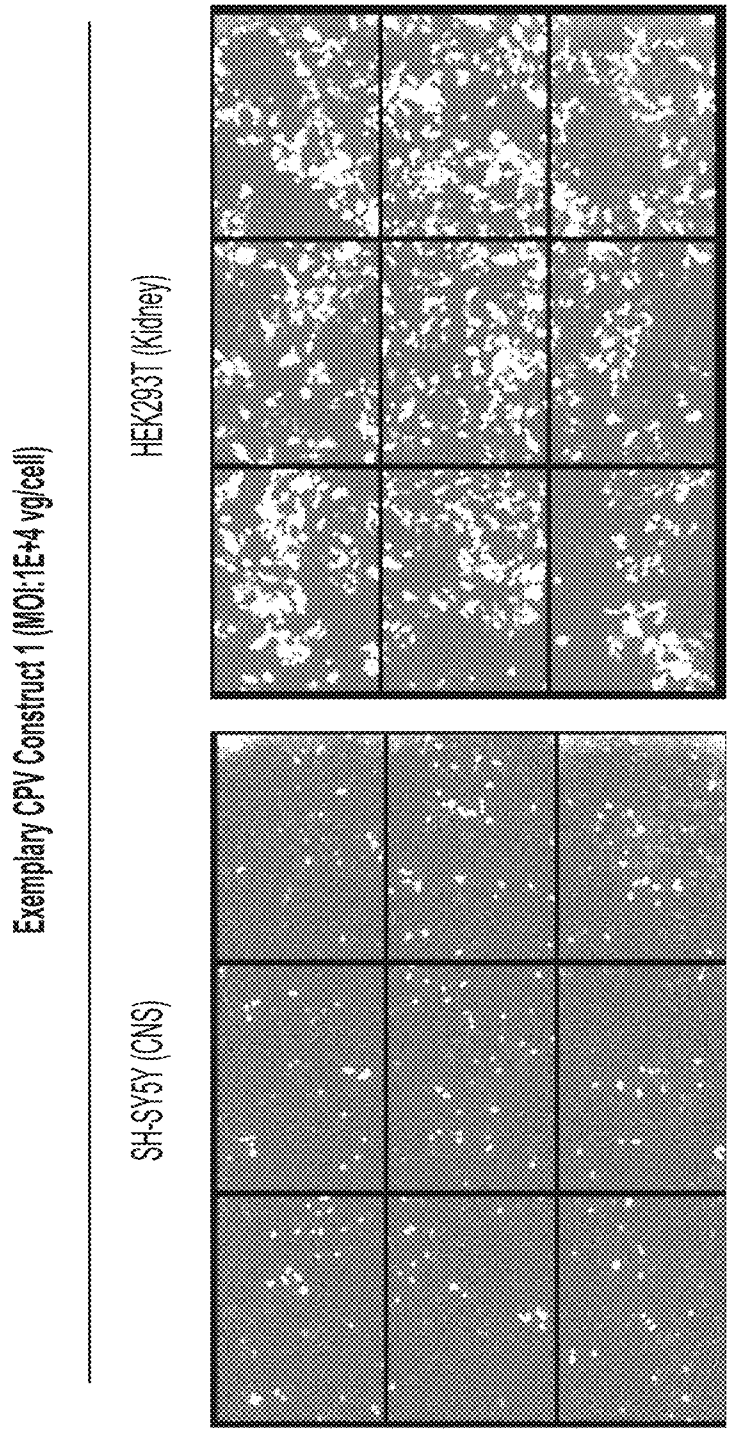
FIG. 20 shows fluorescence imaging of human neuroblastoma cell line SH-SY5Y cells (left) and kidney cell line HEK293 cells (right) transduced with MOI 1E+4 vg/cell of virions comprising a CPV VP1 capsid polypeptide encoded by a VP1 capsid coding sequence according to SEQ ID NO: 126 (Exemplary CPV Construct 1).
Figure 23:
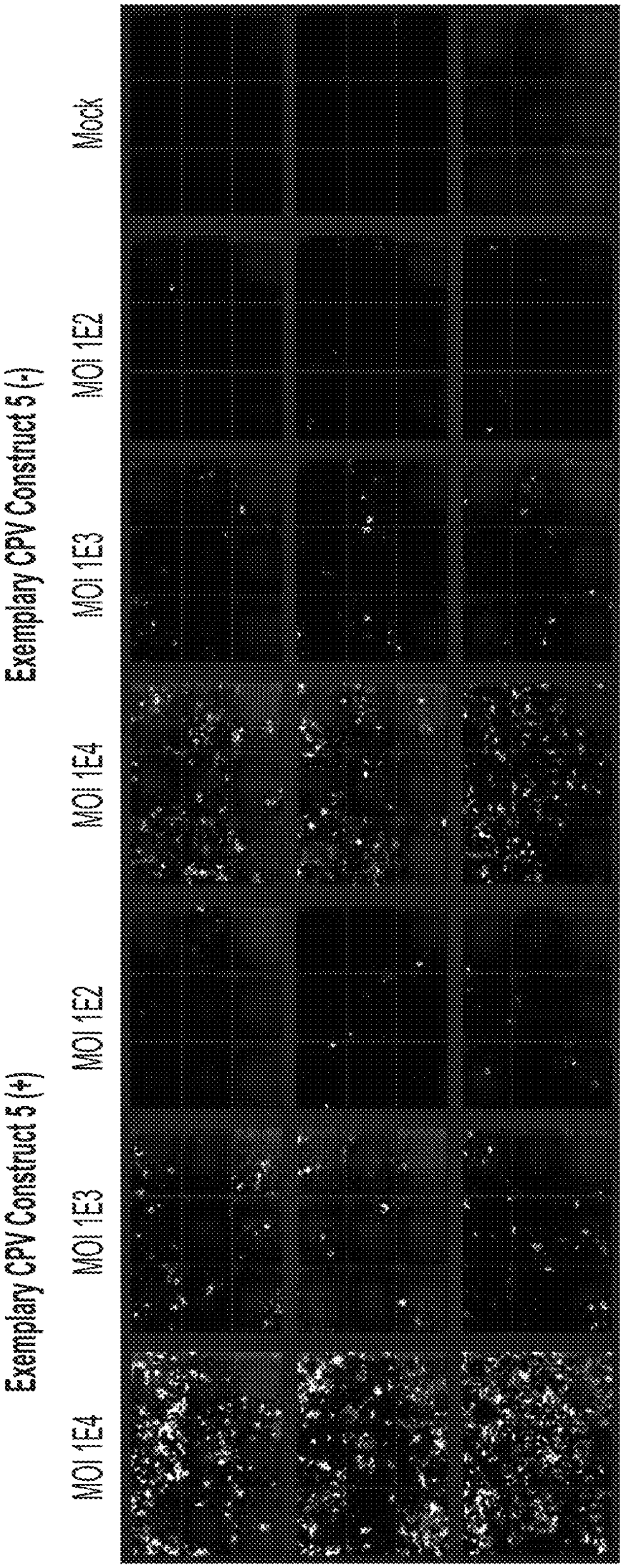
FIG. 23 shows fluorescence imaging of kidney cell line HEK293T cells transduced with MOI 1E4, 1E3, 1E2 vg/cell of virions comprising a CPV VP1 capsid polypeptide encoded by a VP1 capsid coding sequence according to SEQ ID NO: 130 (Exemplary CPV Construct 5) with (+) and without (−) trypsin treatment conditions. Imaging was performed at 2 days and 6 hours.
Figure 24:
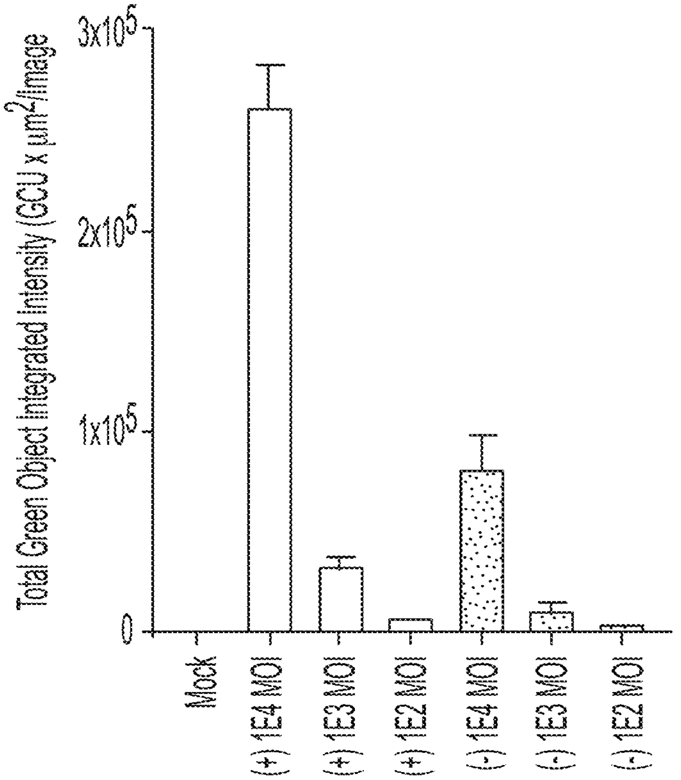
FIG. 24 shows a bar graph depicting GFP transgene expression as measured by GCU×μm2 per image of HEK293T cells transduced with MOI 1E4 vg/cell, 1E3 vg/cell, and 1E2 vg/cell of virions comprising a CPV VP1 capsid polypeptide encoded by a VP1 capsid coding sequence according to SEQ ID NO: 130 (Exemplary CPV Construct 5) with (+) and without (−) trypsin treatment conditions. Measurements were quantified via Incucyte.

Virions comprising a CPV VP1 capsid polypeptide encoded by a VP1 capsid coding sequence according to SEQ ID NO: 126 (Exemplary CPV Construct 1) produced in HEK293T cells via triple transfection showed transduction of human neuroblastoma cell line SH-SY5Y cells and kidney cell line HEK293T cells, as shown in FIG. 20. Initial manufacturability shows titers of about 1E9 vg/ml in crude (data not shown). FIG. 23 shows fluorescence imaging of kidney cell line HEK293T cells transduced with MOI 1E4 vg/cell, 1E3 vg/cell, and 1E2 vg/cell of virions comprising a CPV VP1 capsid polypeptide encoded by a VP1 capsid coding sequence according to SEQ ID NO: 130 (Exemplary CPV Construct 5) with (+) and without (−) trypsin conditions. FIG. 24 shows a bar graph depicting GFP transgene expression as measured by GCU×μm2 per image of HEK293T cells transduced with MOI 1E4 vg/cell, 1E3 vg/cell, and 1E2 vg/cell of virions comprising a CPV VP1 capsid polypeptide encoded by a VP1 capsid coding sequence according to SEQ ID NO: 130 (Exemplary CPV Construct 5) with (+) and without (−) trypsin conditions. As shown in FIGS. 23-24, virions comprising a CPV VP1 capsid polypeptide encoded by a VP1 capsid coding sequence according to SEQ ID NO: 130 (Exemplary CPV Construct 5) showed robust transduction of HEK293T cells at MOI 1E4 vg/cell.

Accordingly, the present Example confirms that exemplary compositions, preparations, constructs, virions, and population of cells comprising recombinant virions can be produced in mammalian host cells. Moreover, the present Example confirms transduction of the described virions in human cells. The present Example also confirms that virions comprising an exemplary CPV VP1 capsid polypeptide as described herein can transduce mammalian cells as described herein.

The present Example can be used with other protoparvovirus capsid polypeptides beyond CPV capsid polypeptides as described herein.

EXEMPLARY EMBODIMENTS

Embodiment 1. A construct comprising a VP1 capsid coding sequence operably linked to an expression control sequence, wherein the VP1 capsid coding sequence encodes a protoparvovirus variant VP1 capsid polypeptide having an amino acid sequence that:

(i) shows at least 70% overall sequence identity with that of a protoparvovirus reference VP1 capsid polypeptide selected from the group consisting of those in Table 3B, which reference polypeptide includes an amino acid sequence element as set forth in SEQ ID NOs: 1-3 or both; and (ii) includes at least one sequence variation (e.g., otherwise functional, e.g., codon optimized) relative to any such protoparvovirus reference VP1 capsid polypeptide.

Embodiment 2. The construct of embodiment 1, wherein the at least one sequence variation reduces toxicity in a host cell, relative to the protoparvovirus reference VP1 capsid polypeptide.

Embodiment 3. The construct of embodiment 1 or 2, wherein the at least one sequence variation increases virion production in a host cell, relative to the protoparvovirus reference VP1 capsid polypeptide.

Embodiment 4. The construct of any one of the preceding embodiments, wherein the at least one sequence variation increases capsid polypeptide yield, relative to the protoparvovirus reference VP1 capsid polypeptide.

Embodiment 5. The construct of any one of embodiments 2-4, wherein the host cell is an insect cell.

Embodiment 6. The construct of any one of embodiments 2-4, wherein the host cell is a mammalian cell.

Embodiment 7. The construct of any one of the preceding embodiments, wherein the construct comprises a nuclear localization signal (NLS) sequence.

Embodiment 8. The construct of any one of the preceding embodiments, wherein the at least one sequence variation is downstream (e.g., immediately downstream) of the NLS sequence.

Embodiment 9. The construct of any one of the preceding embodiments, wherein the at least one sequence variation is at the 3' end of the NLS sequence.

Embodiment 10. The construct of any one of the preceding embodiments, wherein the at least one sequence variation comprises a deletion of one or more amino acid residues downstream of the NLS sequence.

Embodiment 11. The construct of any one of the preceding embodiments, wherein the at least one sequence variation comprises a deletion of two or more amino acid residues downstream of the NLS sequence.

Embodiment 12. The construct of any one of the preceding embodiments, wherein the at least one sequence variation comprises a deletion of three or more amino acid residues downstream of the NLS sequence.

Embodiment 13. The construct of any one of the preceding embodiments, wherein the at least one sequence variation comprises a deletion of four or more amino acid residues downstream of the NLS sequence.

Embodiment 14. The construct of any one of the preceding embodiments, wherein the at least one sequence variation comprises a deletion of five or more amino acid residues downstream of the NLS sequence.

Embodiment 15. The construct of any one of the preceding embodiments, wherein the at least one sequence variation comprises a deletion of five or more amino acid residues upstream of a phospholipase A2 (PLA2) motif.

Embodiment 16. The construct of any one of the preceding embodiments, wherein the at least one sequence variation comprises a deletion of five or more amino acid residues between the NLS sequence and the PLA2 motif.

Embodiment 17. The construct of any one of the preceding embodiments, wherein the at least one sequence variation comprises deletion of LVPPG (SEQ ID NO: 1), WVPPG (SEQ ID NO: 2), or WVPPGYNFLG (SEQ ID NO: 3).

Embodiment 18. The construct of any one of the preceding embodiments, wherein the protoparvovirus variant VP1 capsid polypeptide comprises an amino acid sequence with at least 60% identity to SEQ ID NO: 90 (GenBank accession number AXQ00350).

Embodiment 19. The construct of embodiment 18, wherein the protoparvovirus variant VP1 capsid polypeptide comprises an amino acid sequence that is at least about 60% identical to SEQ ID NO: 104 (GenBank accession number AXQ00350).

Embodiment 20. The construct of any one of embodiments 1-17, wherein the at least one sequence variation comprises deletion of residues 12-16 of the protoparvovirus variant VP1 capsid polypeptide.

Embodiment 21. The construct of any one of embodiments 1-17 or 20, wherein the protoparvovirus variant VP1 capsid polypeptide comprises an amino acid sequence with at least 60% identity to SEQ ID NO: 89 (GenBank accession number M19296.1).

Embodiment 22. The construct of any one of embodiments 1-17 or 20, wherein the protoparvovirus variant VP1 capsid polypeptide comprises an amino acid sequence with at least 60% identity to SEQ ID NO: 93 (GenBank accession number ACD37389.1).

Embodiment 23. The construct of any one of embodiments 1-17 or 20, wherein the protoparvovirus variant VP1 capsid polypeptide comprises an amino acid sequence with at least 60% identity to SEQ ID NO: 94 (GenBank accession number AKI88071).

Embodiment 24. The construct of any one of embodiments 1-17 or 20, wherein the protoparvovirus variant VP1 capsid polypeptide comprises an amino acid sequence with at least 60% identity to SEQ ID NO: 95 (GenBank accession number J02275.1).

Embodiment 25. The construct of any one of embodiments 1-17, wherein the at least one sequence variation comprises deletion of residues 10-14 of the protoparvovirus variant VP1 capsid polypeptide.

Embodiment 26. The construct of any one of embodiments 1-17 or 25, wherein the protoparvovirus variant VP1 capsid polypeptide comprises an amino acid sequence with at least 60% identity to SEQ ID NO: 91 (GenBank accession number AQN78782.1).

Embodiment 27. The construct of any one of embodiments 1-17 or 25, wherein the protoparvovirus variant VP1 capsid polypeptide comprises an amino acid sequence with at least 60% identity to SEQ ID NO: 92 (GenBank accession number YP_009508805).

Embodiment 28. The construct of any one of embodiments 1-17 or 25, wherein the protoparvovirus variant VP1 capsid polypeptide comprises an amino acid sequence with at least 60% identity to SEQ ID NO: 88 (GenBank accession number AFN44271).

Embodiment 29. The construct of any one of embodiments 1-17, wherein the at least one sequence variation comprises deletion of residues 11-15 of the protoparvovirus variant VP1 capsid polypeptide.

Embodiment 30. The construct of any one of embodiments 1-17 or 29, wherein the protoparvovirus variant VP1 capsid polypeptide comprises an amino acid sequence with at least 60% identity to SEQ ID NO: 96 (GenBank accession number AIT18930).

Embodiment 31. The construct of any of the preceding embodiments, wherein the at least one sequence variation diminishes human humoral immune response against a virion, and/or reduces neutralization of a virion by human antibodies.

Embodiment 32. The construct of any one of the preceding embodiments, further comprising a sequence that encodes a protoparvovirus VP2 capsid polypeptide.

Embodiment 33. The construct of embodiment 32, wherein the construct includes sequences that direct transcription and/or translation start such that the protoparvovirus VP2 capsid polypeptide is present in excess of the protoparvovirus variant VP1 capsid polypeptide (e.g., wherein the ratio of protoparvovirus VP2 capsid polypeptide to VP1 capsid polypeptide is 25:1, 20:1, 15:1, 10:1, 5:1).

Embodiment 34. The construct of embodiment 33, wherein the VP1 capsid coding sequence comprises fewer translation initiation sequence(s) (e.g., ATG sequence(s)) across the length of the VP1 capsid coding sequence (e.g., in frame or out of frame) that encodes the protoparvovirus variant VP1 capsid polypeptide relative to the reference protoparvovirus VP1 capsid coding sequence.

Embodiment 35. The construct of embodiment 34, wherein the VP1 capsid coding sequence comprises fewer translation initiation sequence(s) (e.g., ATG sequence(s)) across the length of the VP1 capsid coding sequence (e.g., in frame or out of frame) that encodes the protoparvovirus variant VP1 capsid polypeptide due to a deletion in one or more translation initiation sequence(s) relative to the protoparvovirus reference VP1 capsid coding sequence.

Embodiment 36. The construct of embodiment 34, wherein the VP1 capsid coding sequence comprises fewer translation initiation sequence(s) (e.g., ATG sequence(s)) across the length of the VP1 capsid coding sequence (e.g., in frame or out of frame) that encodes the protoparvovirus variant VP1 capsid polypeptide due to a substitution in one more translation initiation sequence(s) relative to the protoparvovirus reference VP1 capsid coding sequence.

Embodiment 37. The construct of embodiment 34, wherein the VP1 capsid coding sequence comprises an alternative translation initiation sequence (e.g., CTG, TTG, ACG, ATC).

Embodiment 38. The construct of embodiment 37, wherein the alternative translation initiation sequence improves potency relative to a construct comprising an ATG initiation sequence.

Embodiment 39. The construct of any one of the preceding embodiments, further comprising a heterologous peptide tag.

Embodiment 40. The construct of embodiment 39, wherein the heterologous peptide tag allows affinity purification using an antibody, an antigen-binding fragment of an antibody, or a nanobody.

Embodiment 41. The construct of embodiment 39 or 40, wherein the heterologous peptide tag comprises an epitope/tag selected from hemagglutinin, His (e.g., 6X-His), FLAG, E-tag, TK15, Strep-tag II, AU1, AU5, Myc, Glu-Glu, KT3, and IRS.

Embodiment 42. The construct of any one of the preceding embodiments, wherein the construct further comprises a nucleic acid sequence that encodes one or more heterologous peptides having a length from about 10 amino acids to 20 amino acids (e.g., according to SEQ ID NOs: 5-84) (e.g., wherein the one or more heterologous peptides comprises or is a heterologous targeting peptide).

Embodiment 43. The construct of embodiment 42, wherein the one or more heterologous peptides are inserted into one or more residues of a protoparvovirus variant VP1 capsid polypeptide corresponding to one or more residues within a variable region of a parvovirus (e.g., AAV) capsid (e.g., wherein the one or more residues of a protoparvovirus variant VP1 capsid polypeptide map(s) onto a structural overlay of one or more residues within a variable region of a parvovirus VP1 capsid (e.g., AAV capsid)).

Embodiment 44. The construct of embodiment 42, wherein the one or more heterologous peptides are inserted into one or more residues along the 3-fold axis of symmetry of a common VP3 region of the protoparvovirus variant VP1 capsid polypeptide.

Embodiment 45. The construct of embodiment 42, wherein the one or more heterologous peptides are inserted into one or more residues along the 3-fold axis of symmetry of a common VP2 region of the protoparvovirus variant VP1 capsid polypeptide.

Embodiment 46. The construct of embodiment 42, wherein the one or more heterologous peptides targets a cell (e.g., a PymT tumor cell, a cervix cancer cell (e.g., a HeLa cell), a K562 cell, a Raji cell, a SKOV-3 cell, a breast cancer cell (e.g., a MCF-7 cell), a M07e cell, a human saphenous vascular endothelial cell (HSaVEC), a MT1-MMP cell, a primary hepatocyte cell (e.g., a Huh7 cell), an immune cell (e.g., a human T cell, e.g., a CD4+ T cell, e.g., a Th2 cell, e.g., a CAR T cell, e.g., a NK cell), a neuron cell (e.g., a LX-2 cell, e.g., a stellate cell, e.g. a primary neuron cell, e.g., neuroblastoma cell (e.g., a SH-SY5Y cell)), a lung cell (e.g., a lung fibroblast cell), a myoblast cell, a myotube cell, a primary cardiomyocyte, a skeletal muscle cell, (e.g., a differentiated skeletal muscle cell), a human vein endothelial cell, a T84 cell, a ileum cell (intestinal), a primary human airway epithelia cell), a kidney cell (e.g., a human renal proximal tubule (HRCE) cell, e.g., a bile duct cell, e.g., an outer medullary cell, e.g., a mixed medullary cell, e.g., renal cortical epithelial cells, e.g., renal epithelial cells), a bone marrow MSC cell, a blood cell (e.g., hematopoietic stem cell (HSC), e.g., a PBMC cell), a small intestine cell, a muscle cell, a heart cell, a spleen cell, a liver cell, a brain cell (e.g., a brain-striatum cell, e.g., a CD105-positive endothelial cell, e.g., a brain cortex cell), an ocular cell, a testes cell, an oocyte, a medulla cell, a striatum cell, a spinal cord (or chord) cell, or a duodenum cell) (e.g., wherein the one or more heterologous peptides comprises or is a heterologous targeting peptide).

Embodiment 47. The construct of any one of the preceding embodiments, wherein the protoparvovirus variant VP1 capsid polypeptide confers increased infectivity, relative to the protoparvovirus reference VP1 capsid polypeptide.

Embodiment 48. The construct of any one of embodiments 42 to 47, wherein the one or more heterologous peptides increases cell specificity and/or viral transduction efficiency and/or increases virion performance.

Embodiment 49. The construct of any one of the preceding embodiments, wherein the expression control sequence comprises a promoter.

Embodiment 50. The construct of embodiment 49, wherein the promoter is a polyhedrin promoter, a P10 promoter, a CMV-b-actin promoter, an OpiE1 promoter, a JeT promoter, a Ubiquitin C promoter, or a truncated CMV enhancer and promoter.

Embodiment 51. The construct of any one of the preceding embodiments, wherein the construct further comprises a 5' untranslated region (UTR) sequence.

Embodiment 52. The construct of embodiment 51, wherein the 5' UTR further comprises either a (i) nucleotide spacer sequence or (ii) a Kozak consensus sequence or both.

Embodiment 53. The construct of embodiment 52, wherein the nucleotide spacer sequence comprises a nucleotide sequence according to SEQ ID NO: 121.

Embodiment 54. The construct of embodiment 52, wherein the nucleotide spacer sequence comprises a nucleotide sequence according to SEQ ID NO: 122.

Embodiment 55. The construct of embodiment 52, wherein the Kozak consensus sequence comprises or is a eukaryotic conventional Kozak consensus sequence (GCCGCC - - - G), Viral-derived Kozak consensus sequence (CCTGTTAAG), or alternative Kozak consensus sequence (AAA).

Embodiment 56. The construct of any one of the preceding embodiments, wherein the construct does not comprise a 5' UTR sequence.

Embodiment 57. The construct of any one of embodiments 1-56, wherein the VP1 capsid coding sequence comprises or is single-stranded deoxyribonucleic acid (ssDNA).

Embodiment 58. The construct of any one of embodiments 1-56, wherein the VP1 capsid coding sequence comprises or is double stranded DNA (dsDNA).

Embodiment 59. The construct of any one of embodiments 1-56, wherein the VP1 capsid coding sequence comprises or is RNA (e.g., an mRNA).

Embodiment 60. The construct of any one of the preceding embodiments, wherein the VP1 capsid coding sequence comprises a sequence according to CTG, TTG, ACG, or ATC.

Embodiment 61. A construct comprising a sequence having at least 70% identity (e.g., 80%, 85%, 90%, 95%, 100% identity) to a sequence shown in Table 4.

Embodiment 62. A protoparvovirus variant VP1 capsid polypeptide having an amino acid sequence that:

(i) shows at least 70% overall sequence identity with that of a protoparvovirus reference VP1 capsid selected from the group consisting of those in Table 3B, which reference polypeptide includes an amino acid sequence element as set forth in SEQ ID NOs: 1-3 or both; and (ii) includes at least one sequence variation relative to any such protoparvovirus reference VP1 capsid polypeptide.

Embodiment 63. The protoparvovirus variant VP1 capsid polypeptide of embodiment 62, wherein the protoparvovirus variant VP1 capsid polypeptide is characterized by reduced toxicity in a host cell relative to the protoparvovirus reference VP1 capsid polypeptide.

Embodiment 64. The protoparvovirus variant VP1 capsid polypeptide of embodiment 63, wherein the protoparvovirus variant VP1 capsid polypeptide is characterized by improved production of VP1 capsid polypeptide in a host cell relative to the protoparvovirus reference VP1 capsid polypeptide.

Embodiment 65. A virion comprising the protoparvovirus variant VP1 capsid polypeptide of any one of embodiments 1-64.

Embodiment 66. The virion of embodiment 65, wherein the protoparvovirus variant VP1 capsid polypeptide diminishes human humoral immune response against the virion, and/or reduces neutralization of the virion by human antibodies.

Embodiment 67. The virion of embodiment 65 or 66, wherein the protoparvovirus variant VP1 capsid polypeptide increases affinity and/or specificity of the virion to at least one cellular receptor involved in internalization of the virion.

Embodiment 68. The virion of any one of embodiments 65-67, wherein the protoparvovirus variant VP1 capsid polypeptide comprises an insertion of one or more heterologous peptides having a length of from 10 amino acids to 20 amino acids (e.g., wherein the insertion of one or more heterologous peptides is at one or more residues along the 3-fold axis of symmetry of a VP1 capsid polypeptide).

Embodiment 69. The virion of embodiment 68, wherein the one or more heterologous peptides targets a cell (e.g., a PymT tumor cell, a cervix cancer cell (e.g., a HeLa cell), a K562 cell, a Raji cell, a SKOV-3 cell, a breast cancer cell (e.g. a MCF-7 cell), a M07e cell, a human saphenous vascular endothelial cell (HSaVEC), a MT1-MMP cell, a primary hepatocyte cell (e.g., a Huh7 cell), an immune cell (e.g., a human T cell, e.g., a CD4+ T cell, e.g., a Th2 cell, e.g., a CAR T cell, e.g., a NK cell), a neuron cell (e.g., a LX-2 cell, e.g., a stellate cell, e.g. a primary neuron cell, e.g., neuroblastoma cell (e.g., a SH-SY5Y cell), a lung cell (e.g., a lung fibroblast cell), a myoblast cell, a myotube cell, a primary cardiomyocyte, a skeletal muscle cell, (e.g., a differentiated skeletal muscle cell), a human vein endothelial cell, a T84 cell, a ileum cell (intestinal), a primary human airway epithelia cell), a kidney cell (e.g., a human renal proximal tubule (HRCE) cell, e.g., a bile duct cell, e.g., an outer medullary cell, e.g., a mixed medullary cell, e.g., renal cortical epithelial cells, e.g., renal epithelial cells), a bone marrow MSC cell, a blood cell (e.g., hematopoietic stem cell (HSC), e.g., a PBMC cell), a small intestine cell, a muscle cell, a heart cell, a spleen cell, a liver cell, a brain cell (e.g., a brain-striatum cell, e.g., a CD105-positive endothelial cell, e.g., a brain cortex cell), an ocular cell, a testes cell, an oocyte, a medulla cell, a striatum cell, a spinal cord (or chord) cell, or a duodenum cell.

Embodiment 70. The virion of any one of embodiments 65-69, wherein the protoparvovirus variant VP1 capsid polypeptide confers increased infectivity, relative to the protoparvovirus reference VP1 capsid polypeptide.

Embodiment 71. The virion of any one of embodiments 65-70, wherein the one or more heterologous peptides increases cell specificity and/or viral transduction efficiency and/or increases virion performance.

Embodiment 72. The virion of any one of embodiments 65-71, further comprising a heterologous nucleic acid sequence.

Embodiment 73. The virion of embodiment 72, wherein the heterologous nucleic acid comprises a nucleic acid sequence that is at least about 60% identical to a nucleic acid sequence of a target cell.

Embodiment 74. The virion of embodiment 72 or 73, wherein the heterologous nucleic acid is at least about 60% identical to a nucleic acid of a mammal, preferably wherein the mammal is a human.

Embodiment 75. The virion of any one of embodiments 72-74, wherein the heterologous nucleic acid sequence comprises at least one inverted terminal repeat (ITR).

Embodiment 76. The virion of embodiment 75, wherein the at least one ITR comprises one or more of the following:

(a) a dependoparvovirus ITR,
(b) a bocaparvovirus ITR
(c) a protoparvovirus ITR,
(d) a tetraparvovirus ITR, or
(e) an erthythroparvovirus ITR.

Embodiment 77. The virion of any one of embodiments 72-76, wherein the heterologous nucleic acid sequence is deoxyribonucleic acid (DNA).

Embodiment 78. The virion of embodiment 77, wherein the DNA is single-stranded or self-complementary duplex.

Embodiment 79. The virion of any one of embodiments 72-78, wherein the heterologous nucleic acid sequence comprises a Rep protein-dependent origin of replication (ori).

Embodiment 80. The virion of any one of embodiments 72-79, wherein the heterologous nucleic acid sequence comprises a transgene coding sequence.

Embodiment 81. The virion of any one of embodiments 72-80, wherein the transgene coding sequence is operably linked to a transgene promoter, optionally placed between two ITRs.

Embodiment 82. The virion of embodiment 80, wherein the transgene coding sequences comprises one or more of:

(a) a gene encoding a protein or a fragment thereof, preferably a human protein or a fragment thereof;
(b) a nucleic acid encoding a nuclease, optionally a Transcription Activator-Like Effector Nuclease (TALEN), a zinc-finger nuclease (ZFN), a meganuclease, a megaTAL, or a CRISPR endonuclease, (e.g., a Cas9 endonuclease or a variant thereof);
(c) a nucleic acid encoding a reporter, e.g., luciferase or GFP; or
(d) a nucleic acid encoding a drug resistance protein, e.g., neomycin resistance.

Embodiment 83. The virion of embodiment 81 or 82, wherein the transgene coding sequence is codon-optimized for expression in a target cell.

Embodiment 84. The virion of embodiment 83, wherein the target cell is or comprises a PymT tumor cell, a cervix cancer cell (e.g., a HeLa cell), a K562 cell, a Raji cell, a SKOV-3 cell, a breast cancer cell (e.g. a MCF-7 cell), a M07e cell, a human saphenous vascular endothelial cell (HSaVEC), a MT1-MMP cell, a primary hepatocyte cell (e.g., a Huh7 cell), an immune cell (e.g., a human T cell (e.g., a CD4+ T cell, e.g., a Th2 cell, e.g., a CAR T cell), e.g., a NK cell), a neuron cell (e.g., a LX-2 cell, e.g., a stellate cell, e.g. a primary neuron cell, e.g., neuroblastoma cell (e.g., a SH-SY5Y cell)), a human vein endothelial cell, a T84 cell, a ileum cell (intestinal), a primary human airway epithelia cell, a kidney cell (e.g., a human renal proximal tubule (HRCE) cell, e.g., a bile duct cell, e.g., an outer medullary cell, e.g., a mixed medullary cell, e.g., renal cortical epithelial cells, e.g., renal epithelial cells), a bone marrow MSC cell, a blood cell (e.g., hematopoietic stem cell (HSC)), a small intestine cell, a spleen cell, a liver cell, a heart cell (e.g., a myoblast cell, e.g., a myotube cell, e.g., a primary cardiomyocyte), a lung cell (e.g., a lung fibroblast cell), a brain cell (e.g., a brain-striatum cell, e.g., CD105-positive endothelial cells, e.g., a brain cortex cell), a muscle cell (e.g., a skeletal muscle cell, e.g., a differentiated skeletal muscle cell), a testes cell, an oocyte, a medulla cell, a striatum cell, a spinal cord (or chord) cell, or a duodenum cell).

Embodiment 85. The virion of any one of embodiments 80-84, wherein the transgene coding sequence comprises a hemoglobin gene (HBA1, HBA2, HBB, HBG1, HBG2, HBD, HBE1, and/or HBZ), a gene encoding an alpha-hemoglobin stabilizing protein (AHSP), coagulation factor VIII, coagulation factor IX, von Willebrand factor, dystrophin or truncated dystrophin, micro-dystrophin, utrophin or truncated utrophin, micro-utrophin, usherin (USH2A), CEP290, glial cell line-derived neurotrophic factor (GDNF), neuturin (NTN), HTT, neuronal apoptosis inhibitory protein (NAIP), cystic fibrosis transmembrane conductance regulator (CFTR), F8 or a fragment thereof (e.g., fragment encoding B-domain deleted polypeptide (e.g., VIII SQ, p-VIII)), T cell receptor (e.g., TCR alpha or TCR beta), a gene associated with lysosomal storage diseases, a gene associated with Alport syndrome (e.g., Col4a3, Col4a4, Col4a5), a gene associated with Fabry disease (e.g., GLA), a gene associated with autosomal dominant polycystic kidney disease (PKD) (e.g., PKD, PKD1, PKD2), a gene associated with congenital nephrotic syndrome (e.g., NPHS1 (Nephrin), NPHS2 (Podocin), a gene associated with hypertrophic cardiomyopathy (e.g., MYBPC3, JPH2, ALPK3), a gene associated with dilated cardiomyopathy (e.g., RBM20), or a gene associated with dilated cardiomyopathy (e.g., ALPK3, LMNA, BAG3).

Embodiment 86. The virion of any one of embodiments 72-85, wherein the heterologous nucleic acid sequence comprises a non-coding sequence.

Embodiment 87. The virion of embodiment 86, wherein the non-coding sequence comprises or is RNA.

Embodiment 88. The virion of embodiment 87, wherein the RNA comprises or is lncRNA, miRNA, shRNA, siRNA, antisense RNA, and/or guide RNA.

Embodiment 89. The virion of embodiment 86, wherein the non-coding sequence comprises or is DNA.

Embodiment 90. The virion of embodiment 89, wherein the DNA comprises or is:

(a) a transcription regulatory element (e.g., an enhancer, a transcription termination sequence, an untranslated region (5' or 3' UTR), a proximal promoter element, a locus control region, a polyadenylation signal sequence), and/or (b) a translation regulatory element (e.g., Kozak sequence, woodchuck hepatitis virus post-transcriptional regulatory element).

Embodiment 91. The virion of embodiment 90, wherein the DNA comprises or is a transcription regulatory element, and wherein the transcription regulatory element is a locus control region, optionally a β-globin LCR or a DNase hypersensitive site (HS) of β-globin LCR.

Embodiment 92. The virion of any one of embodiments 80-91, wherein the transgene coding sequence (or the protein translated therefrom) or the non-coding sequence increases or restores the expression of an endogenous gene of the target cell.

Embodiment 93. The virion of any one of embodiments 80-91, wherein the transgene coding sequence (or the protein translated therefrom) or the non-coding sequence decreases or eliminates the expression of an endogenous gene of the target cell.

Embodiment 94. The virion of any one of embodiments 81-93, wherein the transgene promoter is selected from:

(a) a promoter heterologous to a nucleic acid;

(b) a promoter that facilitates the tissue-specific expression of a nucleic acid, preferably wherein the transgene promoter facilitates hematopoietic cell-specific expression or erythroid lineage-specific expression;

(c) a promoter that facilitates the constitutive expression of a nucleic acid; and (d) a promoter that is inducibly expressed, optionally in response to a metabolite or small molecule or chemical entity.

Embodiment 95. The virion of any one of embodiments 81-94, wherein the transgene promoter is selected from the CMV promoter, β-globin promoter, CAG promoter, AHSP promoter, MND promoter, Wiskott-Aldrich promoter, and PKLR promoter.

Embodiment 96. The virion of any one of embodiments 65-95, wherein the virion is icosahedral.

Embodiment 97. The virion of any one of embodiments 65-95, wherein the protoparvovirus variant VP1 capsid polypeptide is phosphorylated.

Embodiment 98. A population of virions according to any one of embodiments 65-97, wherein the population is characterized as having reduced toxicity in a host cell, improved virion production in a host cell, increased capsid polypeptide yield, or any combination thereof, relative to a population of virions comprising the protoparvovirus reference VP1 capsid polypeptide.

Embodiment 99. A system comprising a construct of any one of embodiments 1-61 and/or a second construct comprising a sequence that encodes a protoparvovirus VP2 capsid polypeptide, wherein the protoparvovirus VP2 capsid polypeptide is present in excess of the protoparvovirus variant VP1 capsid polypeptide (e.g., wherein the ratio of protoparvovirus VP2 capsid polypeptide to VP1 capsid polypeptide is 25:1, 20:1, 15:1, 10:1, 5:1).

Embodiment 100. A system comprising a protoparvovirus variant VP1 capsid polypeptide of any one of embodiments 62-64 and a protoparvovirus VP2 capsid polypeptide, wherein the protoparvovirus VP2 capsid polypeptide is present in excess of the protoparvovirus variant VP1 capsid polypeptide (e.g., wherein the ratio of protoparvovirus VP2 capsid polypeptide to VP1 capsid polypeptide is 25:1, 20:1, 15:1, 10:1, 5:1).

Embodiment 101. A composition comprising a construct of any one of embodiments 1-61.

Embodiment 102. A composition comprising a virion of any one of embodiments 65-97.

Embodiment 103. A composition comprising a population of virions of embodiment 98.

Embodiment 104. A composition comprising a protoparvovirus variant VP1 capsid polypeptide of any one of embodiments 62-64.

Embodiment 105. The composition of any one of embodiments 101-104, wherein the composition is a pharmaceutical composition.

Embodiment 106. The composition of embodiment 105, further comprising a pharmaceutically acceptable carrier.

Embodiment 107. A kit comprising a construct of any one of embodiments 1-61 and a construct comprising a codon sequence encoding a least one capsid replication protein (e.g., NS1) of a protoparvovirus operably linked to an expression control sequence for expression in a host cell.

Embodiment 108. A host cell comprising a construct of any one of embodiments 1-61.

Embodiment 109. A host cell comprising a protoparvovirus variant VP1 capsid polypeptide of any one of embodiments 62-64.

Embodiment 110. A host cell comprising a virion of any one of embodiments 65-97.

Embodiment 111. A host cell comprising a population of virions of embodiment 98.

Embodiment 112. A host cell comprising a composition of any one of embodiments 101-106.

Embodiment 113. The host cell of embodiment 108, further comprising a second construct comprising a polynucleotide comprising at least one ITR nucleotide sequence.

Embodiment 114. The host cell of embodiment 113, wherein the at least one ITR comprises a parvovirus ITR.

Embodiment 115. The host cell of embodiment 113, wherein the at least one ITR comprises one or more of the following:

(a) a dependoparvovirus ITR, (b) a bocaparvovirus ITR (c) a protoparvovirus ITR, (d) a tetraparvovirus ITR, or (e) an erthythroparvovirus ITR.

Embodiment 116. The host cell of embodiment 115, wherein the at least one ITR comprises a dependoparvovirus ITR, wherein the at least one dependoparvovirus ITR comprises an AAV ITR, optionally an AAV2 ITR.

Embodiment 117. The host cell of any one of claims 108-116, further comprising a third construct comprising a polynucleotide comprising:

(1) at least one capsid replication protein (e.g., NS1) of a protoparvovirus operably linked to an expression control sequence for expression in a host cell, (2) (i) at least one ITR replication protein of a protoparvovirus, bocaparvovirus, dependoparvovirus, tetraparvovirus, or erythroparvovirus, or (ii) at least one ITR replication protein of an AAV, optionally wherein the at least one ITR replication protein of an AAV comprises (a) a Rep52 or a Rep40 coding sequence operably linked to an expression control sequence for expression in a host cell, and/or (b) a Rep78 or a Rep68 coding sequence operably linked to an expression control sequence for expression in a host cell, or (3) a combination of (1) and (2i) or (1) and (2ii).

Embodiment 118. The host cell of any one of embodiments 108-117, wherein at least the first construct, the second construct, or the third construct is stably integrated in the host cell genome.

Embodiment 119. The host cell of any one of embodiments 108-118, wherein the at least one capsid replication protein of a protoparvovirus is an NS1 protein (e.g., having at least 30% identity to SEQ ID NO: 4).

Embodiment 120. The host cell of any one of embodiments 108-118, wherein the host cell is an insect cell.

Embodiment 121. The host cell of any one of embodiments 108-118, wherein the host cell is a mammalian cell.

Embodiment 122. The host cell of embodiment 120, wherein the host cell is derived from a species of lepidoptera.

Embodiment 123. The host cell of embodiment 122, wherein the species of lepidoptera is *Spodoptera frugiperda, Spodoptera littoralis, Spodoptera exigua*, or *Trichoplusiani.*

Embodiment 124. The host cell of embodiment 120, wherein the insect cell is Sf9.

Embodiment 125. The host cell of any one of embodiments 111-124, wherein the construct is a baculoviral construct, a viral construct, or a plasmid.

Embodiment 126. The host cell of any one of embodiments 111-125, wherein the construct is a baculoviral construct.

Embodiment 127. The host cell of any one of embodiments 113-126, wherein the expression control sequence for expression in a host cell comprises a promoter.

Embodiment 128. The host cell of embodiment 127, wherein the promoter comprises:

(a) an immediate early promoter of an animal DNA virus, (b) an immediate early promoter of a host virus, or (c) a host cell promoter.

Embodiment 129. The host cell of embodiment 128, wherein the animal DNA virus is cytomegalovirus (CMV), parvovirus, or AAV.

Embodiment 130. The host cell of embodiment 128, wherein the host virus is a lepidopteran virus or a baculovirus, optionally wherein the baculovirus is *Autographa californica* multicapsid nucleopolyhedrovirus (AcMNPV).

Embodiment 131. The host cell of any one of embodiments 127-130, wherein the promoter is a polyhedrin (polh) promoter, a Immediately early 1 gene (IE-1) promoter, a P10 promoter, a CMV-b-actin promoter, an OpiE1 promoter, a JeT promoter, a Ubiquitin C promoter, or a truncated CMV enhancer and promoter.

Embodiment 132. The host cell of any one of embodiments 113-131, wherein the heterologous nucleic acid sequence comprises at least one ITR replication protein of an AAV comprises a nucleotide sequence encoding Rep52 and/or Rep78.

Embodiment 133. The host cell of any one of embodiments 113-131, wherein the AAV is AAV2.

Embodiment 134. A method of producing a virion according to any one of embodiments 65-91 or a population of virions according to embodiment 98, comprising:

(1) providing one or more of the following:

(i) a first construct comprising at least one ITR nucleotide sequence, optionally further comprising a heterologous nucleic acid operably linked to a promoter for expression in a target cell, (ii) a second construct comprising a construct according to any one of embodiments 1-61 and/or a construct comprising a VP1 capsid coding sequence linked to an expression control sequence, wherein the VP1 capsid coding sequence encodes a protoparvovirus variant VP1 capsid polypeptide, wherein the expression control sequence comprises or is an expression control sequence for expression in a host cell, and (2) introducing the first construct and/or the second construct into a host cell, and (3) maintaining said host cell under conditions such that a virion according to any one of embodiments 65-97 or a population of virions according to embodiment 98 is produced.

Embodiment 135. The method of embodiment 134, further comprising (4) providing a third construct comprising:

(A) at least one capsid replication protein (e.g., NS1) of protoparvovirus operably linked to an expression control sequence for expression in a host cell (e.g., wherein the at least one capsid replication protein of a protoparvovirus enhances encapsidation, relative to encapsidation without the at least one capsid replication protein of a protoparvovirus), (B) at least one ITR replication protein of an AAV, optionally wherein the at least one ITR replication protein of an AAV comprises (a) a Rep52 or a Rep40 coding sequence operably linked to an expression control sequence for expression in a host cell, and/or (b) a Rep78 or a Rep68 coding sequence operably linked to an expression control sequence for expression in a host cell, or (C) a combination of (A) and (B).

Embodiment 136. The method of embodiment 134, wherein the host cell achieves a cell viability of greater than 50% (e.g., of greater than 60%, 70%, or 80%).

Embodiment 137. A method of producing a virion according to any one of embodiments 65-97 or a population of virions according to embodiment 98 in a host cell, the method comprising:

(1) providing a host cell comprising (i) a first construct comprising at least one ITR nucleotide sequence, optionally further comprising a heterologous nucleic acid operably linked to a promoter for expression in a target cell, (ii) a second construct comprising a construct according to any one of embodiments 1-65 and/or a construct comprising a VP1 capsid coding sequence linked to an expression control sequence, wherein the VP1 capsid coding sequence encodes a protoparvovirus variant VP1 capsid polypeptide, wherein the expression control sequence comprises or is an expression control sequence for expression in a host cell, and (iii) a third construct comprising (A) at least one capsid replication protein (e.g., NS1) of protoparvovirus operably linked to an expression control sequence for expression in a host cell (e.g., wherein the at least one capsid replication protein of a protoparvovirus enhances encapsidation, relative to encapsidation without the at least one capsid replication protein of a protoparvovirus), (B) at least one ITR replication protein of an AAV, optionally wherein the at least one ITR replication protein of an AAV comprises (a) a Rep52 or a Rep40 coding sequence operably linked to an expression control sequence for expression in a host cell, and/or (b) a Rep78 or a Rep68 coding sequence operably linked to an expression control sequence for expression in a host cell, or (C) a combination of (A) and (B), optionally, a fourth construct, wherein at least one of (i), (ii), (iii) (A), (iii) (B), and (iii) (C) is/are stably integrated in the host cell genome, and the fourth construct, when present, comprises the remainder of the (i), (ii), (iii) (A), (iii) (B), and (iii) (C) nucleotide sequences which is/are not stably integrated in the host cell genome, and (2) maintaining the host cell under conditions such that a virion according to any one of embodiments 65-97 or a population of virions according to embodiment 98 is produced.

Embodiment 138. The method of embodiment 137, wherein the host cell achieves a cell viability of greater than 50% (e.g., of greater than 60%, 70%, or 80%).

Embodiment 139. The method of any one of embodiment 137 or 138, wherein the host cell is derived from a species of lepidoptera.

Embodiment 140. The method of embodiment 139, wherein the species of lepidoptera is *Spodoptera frugiperda, Spodoptera littoralis, Spodoptera exigua*, or *Trichoplusiani.*

Embodiment 142. The method of any one of embodiments 137-139, wherein the host cell is Sf9.

Embodiment 143. The method of embodiment 137 or 138, wherein the host cell is a mammalian cell.

Embodiment 144. The method of any one of embodiments 137-143, wherein the at least one construct is a baculoviral construct, a viral construct, or a plasmid.

Embodiment 145. The method of any one of embodiments 137-144, wherein the at least one construct is a baculoviral construct.

Embodiment 146. The method of any one of embodiments 137-145, wherein the at least one ITR comprises one or more of the following:

(a) a dependoparvovirus ITR, (b) a bocaparvovirus ITR (c) a protoparvovirus ITR, (d) a tetraparvovirus ITR, or (e) an erthythroparvovirus ITR.

Embodiment 147. The method of any one of embodiments 137-146, wherein the expression control sequence for expression in a host cell comprises:

(a) a promoter, and/or (b) a Kozak consensus sequence.

Embodiment 148. The method of any one of embodiments 137-147, wherein the nucleotide sequence comprising at least one ITR replication protein of an AAV comprises a nucleotide sequence encoding Rep52 and/or Rep78.

Embodiment 149. The method of any one of embodiments 137-148, wherein the AAV is AAV2.

Embodiment 150. A method of purifying a virion according to any one of embodiments 65-97 or a population of virions according to embodiment 98, wherein the virion or the population of virions is purified using an antibody, an antigen-binding fragment of an antibody, or a nanobody that binds the virion.

Embodiment 151. The method of embodiment 150, wherein the antibody, an antigen-binding fragment of an antibody, or a nanobody binds the heterologous peptide tag in the capsid of the virion.

Embodiment 152. The method of embodiment 151, wherein the heterologous peptide tag comprises an epitope/tag selected from hemagglutinin, His (e.g., 6X-His), FLAG, E-tag, TK15, Strep-tag II, AU1, AU5, Myc, Glu-Glu, KT3, and IRS.

Embodiment 153. A method of preventing or treating a disease, comprising: administering to a subject in need thereof an effective amount of virion according to any one of embodiments 65-97 or a population of virions according to embodiment 98 or a pharmaceutical composition of embodiment 105.

Embodiment 154. A method of preventing or treating a disease, comprising:

(a) obtaining a plurality of cells;

(b) transducing the cells with a virion according to any one of embodiments 65-97 or a population of virions according to embodiment 98 or the pharmaceutical composition of embodiment 105, optionally further selecting or screening for the transduced cells; and (c) administering an effective amount of the transduced cells to a subject in need thereof.

Embodiment 155. The method of embodiments 153 and 154, further comprising co-administering an immune suppressant and/or a prophylactic to mitigate an immune response.

Embodiment 156. A method of characterizing a virion according to any one of embodiments 65-97 or a population of virions according to embodiment 98 or the pharmaceutical composition of embodiment 105.

Embodiment 157. A method of manufacturing an intermediate (e.g., any intermediate that can be stored or shipped) of a virion according to any one of embodiments 65-97 or a population of virions according to embodiment 98 or the pharmaceutical composition of embodiment 105.

Embodiment 158. A method of providing a virion according to any one of embodiments 65-97 or a population of virions according to embodiment 98 or the pharmaceutical composition of embodiment 105, comprising assessing one or more characteristics of the virion or the population of virions and establishing one or more characteristics of the virion or population of virions (e.g., compared to a reference sample).

Embodiment 159. A system comprising a host cell according to any one of embodiments 108-133.

Embodiment 160. A method comprising contacting a cell with a construct of any one of embodiments 1-61.

Embodiment 161. A virion according to any one of embodiments 65-97 or a population of virions according to embodiment 98 or the pharmaceutical composition of embodiment 105 for use in the treatment of a disease or disorder.

Embodiment 162. Use of a construct of any one of embodiments 1-61 for the manufacture of a medicament to treat a disease or disorder.

Embodiment 163. Use of a virion of any one of embodiments 65-97 for the manufacture of a medicament to treat a disease or disorder.

Embodiment 164. Use of a population of virions of embodiment 98 for the manufacture of a medicament to treat a disease or disorder.

Embodiment 165. A kit comprising a construct of any one of embodiments 1-61, a protoparvovirus variant VP1 capsid polypeptide of any one of embodiments 62-64, a virion of any one of embodiments 65-97, a population of virions of embodiment 98, a composition of any one of embodiments 101-106, or a host cell of any one of embodiments 108-133.

EQUIVALENTS

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

It is to be understood that while the disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

We claim:

1. A construct comprising a VP1 capsid coding sequence operably linked to an expression control sequence, wherein the VP1 capsid coding sequence encodes a protoparvovirus variant VP1 capsid polypeptide having an amino acid sequence that:

(i) shows at least 98% sequence identity to SEQ ID NO: 104, or (ii) shows at least 98% sequence identity to SEQ ID NO: 107, wherein the protoparvovirus variant VP1 capsid polypeptide lacks an amino acid sequence as set forth in SEQ ID NO: 1.

2. The construct of claim 1, further comprising a sequence that encodes a protoparvovirus VP2 capsid polypeptide.

3. The construct of claim 2, wherein the construct includes sequences that direct transcription and/or translation start such that the protoparvovirus VP2 capsid polypeptide is present in excess of the protoparvovirus variant VP1 capsid polypeptide.

4. The construct of claim 3, wherein the VP1 capsid coding sequence comprises fewer translation initiation sequence(s) across the length of the VP1 capsid coding sequence that encodes the protoparvovirus variant VP1 capsid polypeptide relative to the protoparvovirus reference VP1 capsid coding sequence.

5. The construct of claim 1, wherein the construct further comprises a nucleic acid sequence that encodes one or more heterologous peptides having a length from about 10 amino acids to 20 amino acids.

6. The construct of claim 1, wherein the expression control sequence comprises a promoter.

7. The construct of claim 1, wherein the construct further comprises a 5' untranslated region (UTR) sequence.

8. The construct of claim 7, wherein the 5' UTR further comprises either a (i) nucleotide spacer sequence or (ii) a Kozak consensus sequence or both.

9. A kit comprising the construct of claim 1 and a construct comprising a coding sequence encoding a least one capsid replication protein of a protoparvovirus operably linked to an expression control sequence for expression in a host cell.

10. A nucleic acid construct comprising a sequence that encodes a protoparvovirus variant VP1 capsid polypeptide, wherein the protoparvovirus variant VP1 capsid polypeptide has an amino acid sequence having at least 98% identity to SEQ ID NOs: 104 or 107, and wherein the protoparvovirus variant VP1 capsid polypeptide lacks an amino acid sequence as set forth in SEQ ID NO: 1.

11. A protoparvovirus variant VP1 capsid polypeptide having an amino acid sequence that:

(i) shows at least 98% sequence identity to SEQ ID NO: 104, or (ii) shows at least 98% sequence identity to SEQ ID NO: 107, wherein the protoparvovirus variant VP1 capsid polypeptide lacks an amino acid sequence as set forth in SEQ ID NO: 1.

12. A virion comprising:

(1) a protoparvovirus variant VP1 capsid polypeptide having an amino acid sequence that:

(i) shows at least 98% sequence identity to SEQ ID NO: 104, or (ii) shows at least 98% sequence identity to SEQ ID NO: 107, wherein the protoparvovirus variant VP1 capsid polypeptide lacks an amino acid sequence as set forth in SEQ ID NO: 1; and (2) a heterologous nucleic acid sequence comprising:

(i) a transgene coding sequence, and (ii) at least one inverted terminal repeat (ITR).

13. The virion of claim 12, wherein the protoparvovirus variant VP1 capsid polypeptide comprises an insertion of one or more heterologous peptides having a length of from 10 amino acids to 20 amino acids.

14. The virion of claim 12, wherein the transgene coding sequence is operably linked to a transgene promoter, optionally placed between two ITRs.

15. The virion of claim 12, wherein the protoparvovirus variant VP1 capsid polypeptide is phosphorylated.

16. A composition comprising the virion of claim 12.

17. The composition of claim 16, wherein the composition is a pharmaceutical composition.

18. A host cell comprising the virion of claim 12.

19. A method of preventing or treating a disease, comprising:

administering to a subject in need thereof an effective amount of virion according to claim 12.

20. A method of producing the virion according to claim 12, comprising:

(1) providing one or more of the following:

(i) a first construct comprising at least one ITR nucleotide sequence, optionally further comprising a heterologous nucleic acid operably linked to a promoter for expression in a target cell, (ii) a second construct comprising a construct comprising a VP1 capsid coding sequence operably linked to an expression control sequence, wherein the VP1 capsid coding sequence encodes a protoparvovirus variant VP1 capsid polypeptide having an amino acid sequence that:

(a) shows at least 98% sequence identity to SEQ ID NO: 104, or (b) shows at least 98% sequence identity to SEQ ID NO: 107, wherein the protoparvovirus variant VP1 capsid polypeptide lacks an amino acid sequence as set forth in SEQ ID NO: 1; and (2) introducing the first construct and/or the second construct into a host cell, and (3) maintaining said host cell under conditions such that the virion is produced.

21. The method of claim 20, further comprising (4) providing a third construct comprising:

(A) at least one capsid replication protein of protoparvovirus operably linked to an expression control sequence for expression in a host cell, (B) at least one ITR replication protein of an AAV, optionally wherein the at least one ITR replication protein of an AAV comprises (a) a Rep52 or a Rep40 coding sequence operably linked to an expression control sequence for expression in a host cell, and/or (b) a Rep78 or a Rep68 coding sequence operably linked to an expression control sequence for expression in a host cell, or (C) a combination of (A) and (B).

* * * * *